US007444011B2

(12) United States Patent
Pan et al.

(10) Patent No.: US 7,444,011 B2
(45) Date of Patent: Oct. 28, 2008

(54) IMAGING SYSTEM PERFORMING SUBSTANTIALLY EXACT RECONSTRUCTION AND USING NON-TRADITIONAL TRAJECTORIES

(75) Inventors: Xiaochuan Pan, Chicago, IL (US); Yu Zou, Naperville, IL (US); Lifeng Yu, Chicago, IL (US); Chien-Min Kao, Wilmette, IL (US); Martin King, Chicago, IL (US); Maryellen Giger, Elmhurst, IL (US); Dan Xia, Chicago, IL (US); Howard Halpern, Chicago, IL (US); Charles Pelizzari, Chicago, IL (US); Emil Y. Sidky, Chicago, IL (US); Seungryong Cho, Chicago, IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 11/410,594

(22) Filed: Apr. 24, 2006

(65) Prior Publication Data

US 2007/0036418 A1 Feb. 15, 2007

Related U.S. Application Data

(63) Continuation-in-part of application No. 11/054,788, filed on Feb. 10, 2005.

(60) Provisional application No. 60/677,222, filed on May 2, 2005, provisional application No. 60/674,116, filed on Apr. 22, 2005, provisional application No. 60/630, 624, filed on Nov. 24, 2004, provisional application No. 60/543,331, filed on Feb. 10, 2004.

(51) Int. Cl.
*G06K 9/46* (2006.01)

(52) U.S. Cl. .......................................... 382/131; 378/4

(58) Field of Classification Search ................. 382/131; 250/455.11; 378/4
See application file for complete search history.

(56) References Cited

U.S. PATENT DOCUMENTS 5,038,285 A * 8/1991 Jouandet ..................... 382/131

(Continued)

OTHER PUBLICATIONS

Sidky et al., Volume reconstruction from a straight-line source trajectory, Oct. 29, 2005, IEEE, 2005 IEEE Nuclear Science Symposium Conference Record, pp. 2441-2444.*

(Continued)

*Primary Examiner*—Vikkram Bali
*Assistant Examiner*—Thomas M Redding
(74) *Attorney, Agent, or Firm*—Brinks Hofer Gilson & Lione

(57) ABSTRACT

A method and apparatus for reconstruction of a region of interest (ROI) for an object using an imaging system is provided. The imaging system may substantially exactly reconstruct the ROI with a straight line trajectory. In the straight line trajectory, the ROI is not bounded or encircled by the actual trajectory of the source (e.g., no chords that are composed from two points on the source trajectory intersect or fill the ROI to be imaged). However, the ROI may be substantially reconstructed by using “virtual” chords to reconstruct the ROI. The virtual chords are such that no point on the trajectory is included in the virtual chord (such as one that is parallel to the straight line trajectory). These virtual chords may intersect and fill the ROI, thus enabling substantially exact reconstruction. Further, in reconstructing the image, the straight line trajectory may be assumed to be infinite in length.

23 Claims, 151 Drawing Sheets

U.S. PATENT DOCUMENTS

| | | | | |
|---|---|---|---|---|
| 5,165,100 | A | 11/1992 | Hsieh et al. | |
| 5,225,980 | A | 7/1993 | Hsieh et al. | |
| 6,324,249 | B1 * | 11/2001 | Fazzio | 378/22 |
| 6,535,821 | B2 | 3/2003 | Wang et al. | |
| 2003/0058994 | A1 | 3/2003 | Sambritzki | |
| 2006/0140335 | A1 | 6/2006 | Heuscher et al. | |

OTHER PUBLICATIONS

Bleuet et al., An Adapted Fan Volume Sampling Scheme for 3D Algebraic Reconstruction in Linear Tomosynthesis, Nov. 2001, 2001 IEEE Nuclear Sicience Symposium Conference Record, vol. 3 4-10 Nov. 2001, pp. 1720-1724.*

Matsuo et al., Three-Dimensional Image Reconstruction by Digital Tomo-Synthesis Using Inverse Filtering, Jun. 1993, IEEE, IEEE Transactions on Medical Imaging, vol. 12, No. 2, pp. 307-313.*

Ye, Y., et al., "Exact reconstruction for cone-beam scanning along nonstandard spirals and other curves," *Developments in X-Ray Tomography IV*, edited by Ulrich Bonse, Proc. Of SPIE vol. 5535 (SPIE, Bellingham, WA, 2004), pp. 293-300.

Ye, Y., et al., "Filtered backprojection formula for exact image reconstruction from cone-beam data along a general scanning curve," *Med. Phys.*, vol. 32, No. 1, Jan. 2005, Am. Assoc. Phys. Med., pp. 42-48.

Danielsson, P.E., et al., "Towards Exact 3D-reconstruction for Helical Cone-Beam scanning of Long Objects. A New Detector Arrangement and a New Completeness Condition," Proceedings of the 1997 International Meeting on Fully-Three-dimensional Image Reconstruction in Radiology and Nuclear Medicine, Jun. 25-28, 1997, Pittsburgh, PA, 4 pages.

Palamodov, V.P., "Reconstruction from ray integrals with sources on a curve," 2004 IOP Publishing Ltd., UK, pp. 239-242.

Zou, Y., et al., "Exact image reconstruction on PI-lines from minimum data in helical cone-beam CT," 2004 IOP Publishing Ltd., UK, pp. 941-959.

* cited by examiner

Fig. 76B
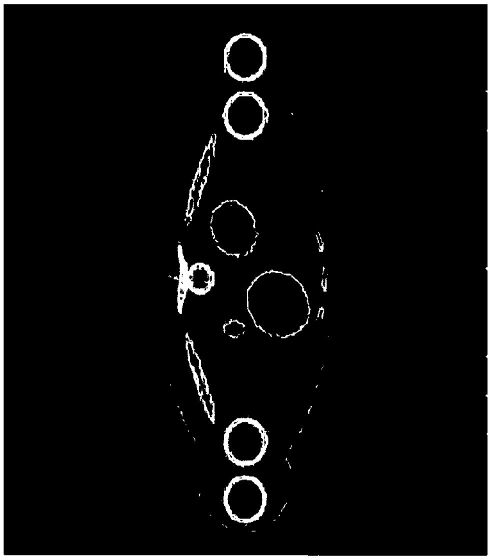
Fig. 76A
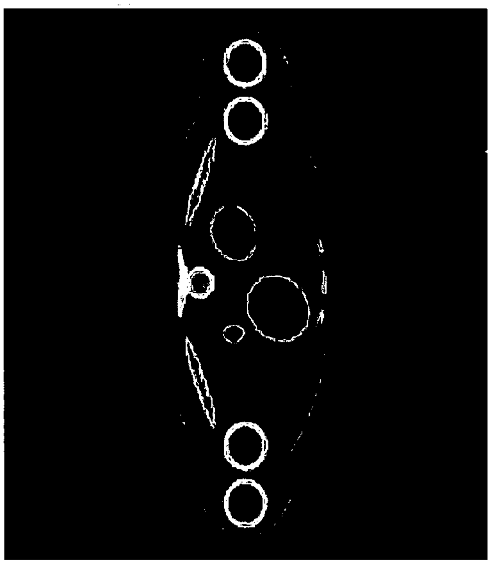
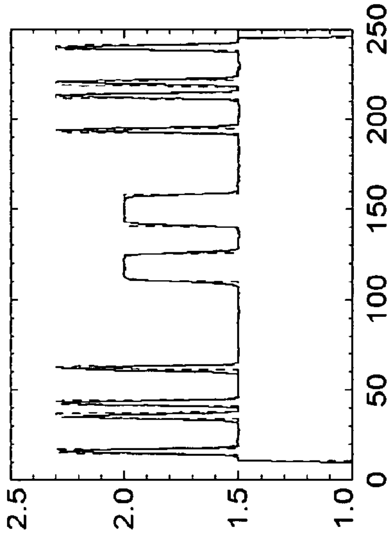
Fig. 76C

Bracket Scan

| Point | $PFSD$ | Gating | $\overline{T}_{ROI}$ (ms) | Algorithm | Figure |
|---|---|---|---|---|---|
| A | 64.5% | No | 234 | FFBP/WBPF | 14(a)-(d) |
| B | 45% | No | 173 | WBPF | 15(b) |
| C | 64.5% | Yes | 121 | FFBP/WBPF | 16(c)-(d) |
| D | 45% | Yes | 111 | WBPF | 16(f) |

| Label | Width | Pattern | Redundancy | *PFSD*(%) |
|---|---|---|---|---|
| MS | Thick | Dashed | None | 46.5 |
| RS1 | Thin | Solid | Reduced-scan | 48.5 |
| RS2 | Thin | Solid | Reduced-scan | 51.5 |
| RS3 | Thin | Solid | Reduced-scan | 56.0 |
| SS | Thick | Dashed | Short-scan | 64.5 |

IMAGING SYSTEM PERFORMING SUBSTANTIALLY EXACT RECONSTRUCTION AND USING NON-TRADITIONAL TRAJECTORIES

REFERENCE TO RELATED APPLICATIONS

This application claims the benefit of U.S. Provisional Patent Application No. 60/674,116, filed Apr. 22, 2005, pending, claims the benefit of U.S. Provisional Patent Application No. 60/677,222, filed May 2, 2005, pending, is a continuation-in-part of U.S. patent application Ser. No. 11/054,788, filed Feb. 10, 2005, pending, which claims the benefit of U.S. Provisional Patent Application No. 60/543,331, filed on Feb. 10, 2004, and which claims the benefit of U.S. Provisional Patent Application No. 60/630,624 filed on Nov. 24, 2004, pending. The contents of U.S. Provisional Patent Application No. 60/674,116, U.S. Provisional Patent Application No. 60/677,222, U.S. patent application Ser. No. 11/054,788, U.S. Provisional Patent Application No. 60/543,331, and U.S. Provisional Patent Application No. 60/674,116 are incorporated by reference herein in their entirety.

GOVERNMENT LICENSE RIGHTS

This invention was made with government support under EB000225, EB002765, EB003913 awarded by the National Institutes of Health. The government has certain rights in the invention.

FIELD OF THE INVENTION

The present invention relates to a method and apparatus for imaging an object. More particularly, the present invention relates to a method and apparatus for imaging an interior of a part, or all, of a living or non-living object.

BACKGROUND

Imaging techniques typically comprise detecting a signal from an object and constructing an image based on the detected signal. The detected signal may include any detectable datum from the sample, such as an electromagnetic signal from any frequency range, a magnetic signal, an ionization signal, heat, particles (electron, proton, neutron, etc.), or the like.

The imaged object may comprise any portion of a living organism (e.g., human or animal) or a non-living object. For example, the portion may comprise an internal or an external portion, or may comprise the entire internal or external portion of the object. There are a wide variety of techniques for imaging of the object. Examples of imaging techniques include, but are not limited to: computed tomography (CT), positron emission tomography (PET), single-photon emission computed tomography (SPECT), magnetic resonance imaging (MRI), electron paramagnetic resonance imaging (EPRI), wave imaging (such as phase contrast imaging, thermacoustic imaging, and thermoptical imaging), and particle imaging. Further, various imaging techniques may be combined. For example, CT imaging and PET imaging may be combined to generate an image.

CT is an X-ray procedure in which the X-ray beam may move around the object, taking pictures from different angles. These images may be combined by a computer to produce a cross-sectional picture of the inside of the object. PET is a diagnostic imaging procedure that may assess the level of metabolic activity and perfusion in various organ systems of an object, such as a human body. A positron camera (tomograph) may be used to produce cross-sectional tomographic images, which may be obtained from positron emitting radioactive tracer substances (radiopharmaceuticals), such as 2-[F-18] Fluoro-D-Glucose (FDG), that may be administered intravenously to the object. SPECT scans and PET scans are part of the nuclear imaging family. The SPECT scan is capable of revealing information about the object, such as blood flow to tissue. For example, radionuclide may be given intravenously, with the tissues absorbing the radionuclides (diseased tissue absorbs at a different rate), and the rotating camera picking up images of these particles, which may then be transferred to a computer. The images may be translated onto film as cross sections and can be viewed in a 3-D format. Moreover, MRI and EPRI are imaging techniques that use a magnetic field and radiofrequency radiation to generate information, such as anatomical information.

To create an exact reconstruction of an image, prior systems have used a filtration-backprojection (FBP) methodology. This methodology requires that data be acquired for an entire section of an object and that all the acquired data be processed, even if an image of only a subsection of the object is sought. For example, if a CT image is sought of a single breast, the FBP methodology required scanning of the entire chest region, including not only the single breast, but the second breast, torso, etc. This is shown in FIG. 1*a*, which is a cross section of a portion of the scan with a source, an object and a detector. The FBP methodology required that data be acquired sufficient to image the entire section (such as the entire cross-section of the chest region). Thus, the beam of the source must be wide enough to expose the entire torso to X-rays, as shown in FIG. 1*a*. Further, as shown in FIG. 1*a*, the detector used in the prior systems must be large enough to obtain the data for the entire chest region. For a 3-dimensional image, the object must be scanned to acquire data for the entire section of the object, even though only image of a subsection is sought. This is shown in FIG. 1*b*, which includes a second cross-section of portion of the scan with a source, an object, and a detector at an angle different from that shown in FIG. 1*a*. Prior systems using the FBP methodology also required the data from the entire section (such as an entire chest region) be subject to data processing for reconstruction of the image. Specifically, the data from the entire chest region was subject to filtration. These requirements of the prior FBP methodology made data acquisition and data processing difficult.

SUMMARY

The invention comprises a method and apparatus for acquiring data for an imaging system. The imaging system may reconstruct images, including substantially exactly reconstructing images, using a variety of source trajectories. With regard to the source trajectory, the source and/or object may move relative to one another to generate the source trajectory. The imaging system may substantially exactly reconstruct a region of interest with a straight line trajectory. In the straight line trajectory, the region of interest is not bounded or encircled by the actual trajectory of the source. Specifically, since the trajectory is a straight line, no chords that are composed from two points on the source trajectory intersect or fill the region of interest to be imaged. However, the region of interest may be substantially reconstructed by using "virtual" chords to reconstruct the region of interest. The virtual chords are such that no point on the trajectory is included in the virtual chord. An example of a virtual chord is one that is parallel to the straight line trajectory. These virtual chords may intersect and fill the region of interest, thus enabling substantially exact reconstruction. Further, in reconstructing the image, the straight line trajectory may be assumed to be infinite in length. For example, for a 60 cm trajectory, it may be assumed that the trajectory is infinite; however the values outside of the 60 cm trajectory may be altered (such as assumed to be zero) in order to reconstruct the image.

The imaging system may also substantially exactly reconstruct a region of interest in a plane that is outside of the plane defined by the source trajectory. Specifically, a source trajectory may comprise a piecewise continuous trajectory (such as a trajectory include kinks) and/or may comprise a non-closed trajectory (such as a trajectory that is not a circle). An example of a source trajectory that is both piecewise continuous and non-closed is a trajectory in the form of a bracket. The source trajectory may define a plane. The imaging system may substantially reconstruct an image in an off-plane (e.g., a plane the is parallel to but not coincident with the plane defined by the source trajectory). Further, the imaging system may use chords to reconstruct the image in the off-plane.

The imaging system may also exactly (or substantially exactly) reconstruct a region of interest for a trajectory that may go through the region of interest to be imaged. Chords may be used to reconstruct the image for the region of interest.

In addition, the imaging system may exactly (or substantially exactly) reconstruct a region of interest for motion contaminated data. Data may be contaminated based on motion that occurs during acquiring the data. Based on weighting of the data, including weighting of the motion contaminated data, the imaging system may still reconstruct the image of the region of interest.

The imaging system may further use chords to reconstruct the image regardless of the type of detector used, including a partially curved, completely curved, partially flat, or completely flat detector, etc.

BRIEF DESCRIPTION OF THE DRAWINGS

FIGS. 56*a-d* represent images within planes at x=0 (FIG. 56*a*), y=25 mm (FIG. 56*b*), z=0 (FIG. 56*c*), and z=6.4 mm (FIG. 56*d*), respectively.

FIGS. 58*a-d* represent images within planes at x=0 (FIG. 58*a*), y=25 mm (FIG. 58*b*), z=0 (FIG. 58*c*), z=6.4 mm (FIG. 58*d*).

FIGS. 60*a-c* represent images within planes at x=0 (FIG. 60*a*), y=25 mm (FIG. 60*b*), z=0 (FIG. 60*c*), z=6.4 mm (FIG. 60*d*).

FIGS. 62*a-d* represent images within planes at x=0 (FIG. 62*a*), y=25 mm (FIG. 62*b*), z=0 (FIG. 62*c*), z=6.4 mm (FIG. 62*d*).

FIGS. 63*a-d* show the images within planes specified by x=0 (FIG. 63*a*), y=0 (FIG. 63*b*), z=0 (FIG. 63*c*), and z=−33.8 mm (FIG. 63*d*).

FIGS. 65*a-d* show the images within planes specified by x=0 (FIG. 65*a*), y=0 (FIG. 65*b*), z=0 (FIG. 65*c*), and z=−33.8 mm (FIG. 65*d*).

FIGS. 76*a-c* display the images within the plane of the circle-trajectory component reconstructed by use of the BPF methodology without noise and with noise for a curved detector.

and $$s_b \in \left[-\frac{\pi}{3}, \frac{\pi}{3}\right],$$

obtained by use of the BPF (FIG. 79*a*), MDFBP (FIG. 79*b*), and FBP (FIG. 79*c*) methodologies, respectively.

Figure 79A:
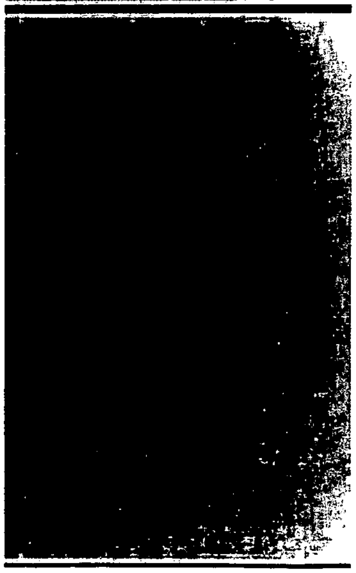
FIGS. 79*a-c* display the image variances on a set of chords, specified by $$s_a = -\pi$$
Figure 79B:
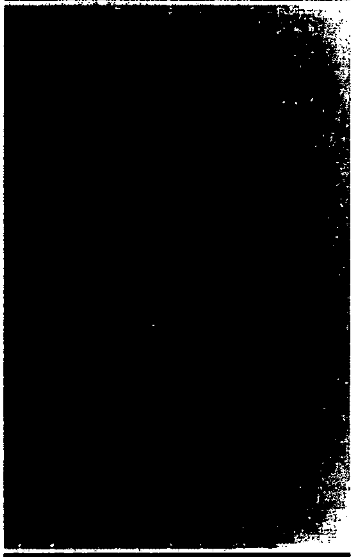
Figure 79C:
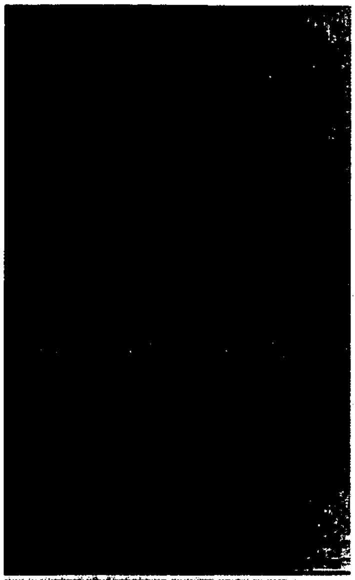
Figure 80A:
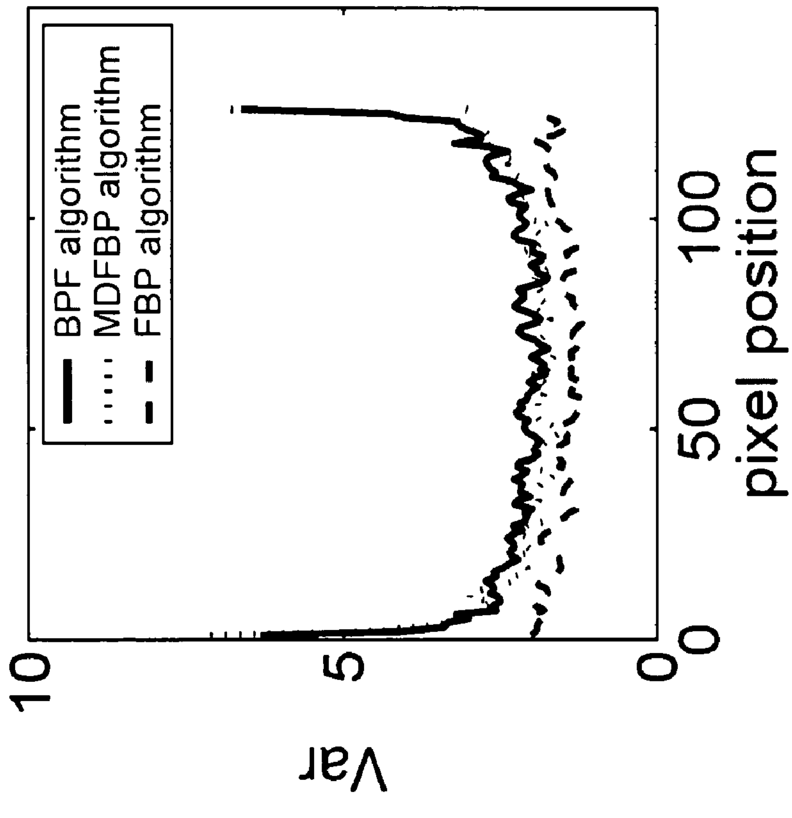

FIG. 80*a* shows the image variances on a chord represented by the central horizontal line from FIGS. 79*a-c* obtained by use of the BPF (solid), MDFBP (dotted), and FBP (dashed) methodologies, respectively.

Figure 80B:
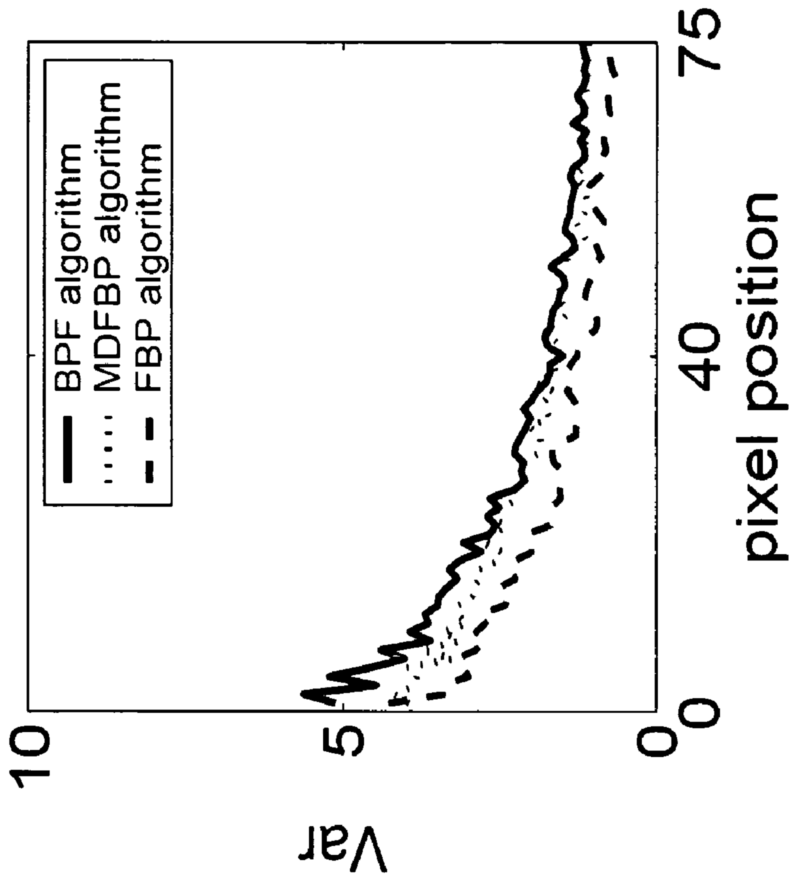

FIG. 80*b* shows the image variances across the different chords (i.e., along the central vertical line in FIGS. 79*a-c*) obtained by use of the BPF (solid), MDFBP (dotted), and FBP (dashed) methodologies, respectively.

Figures 81A, 81B, 81C:
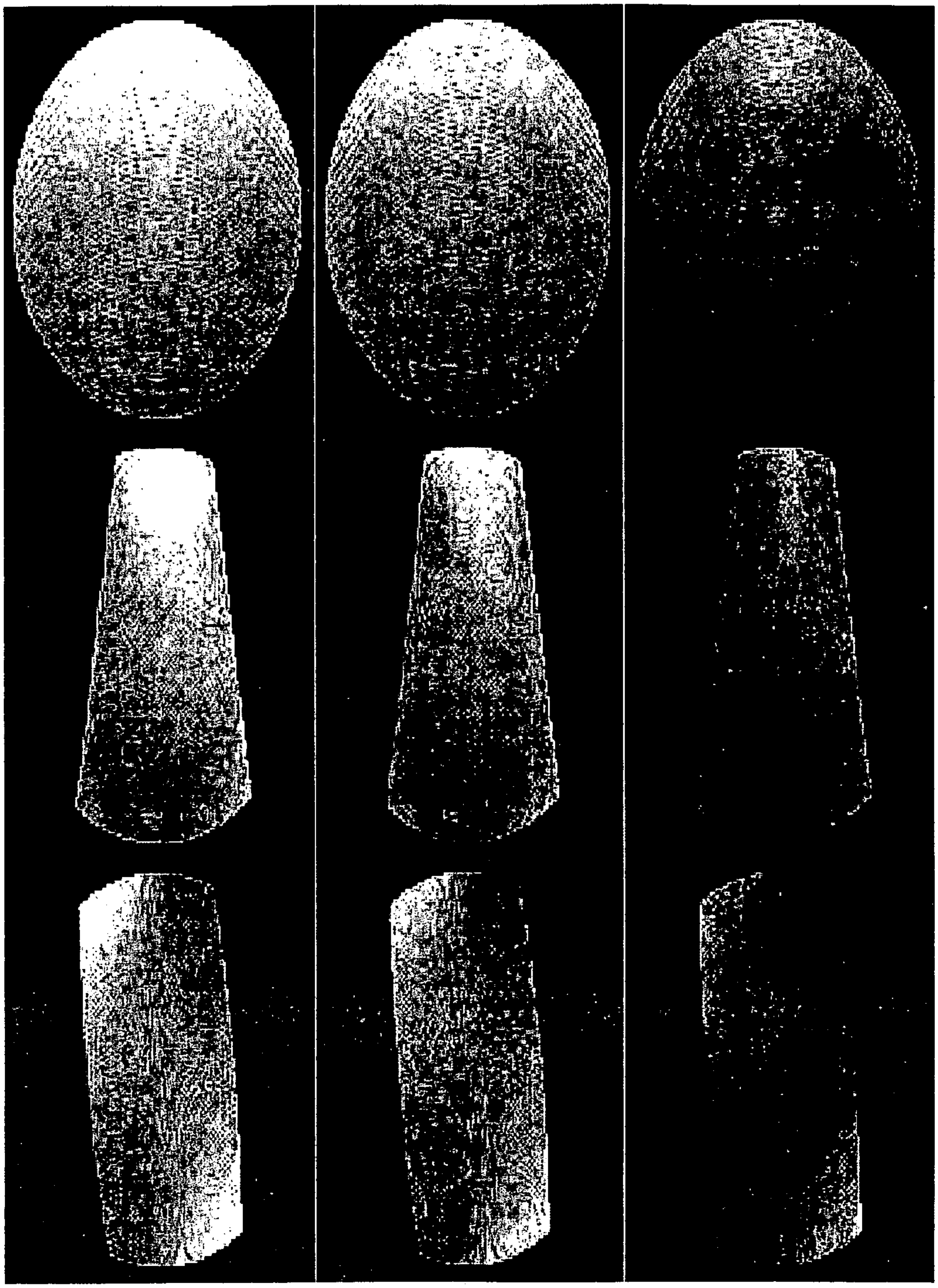

FIGS. 81*a-c* show image variances computed from images on the Cartesian grid converted from chord images by use of the first interpolation scheme.

Figure 82C:
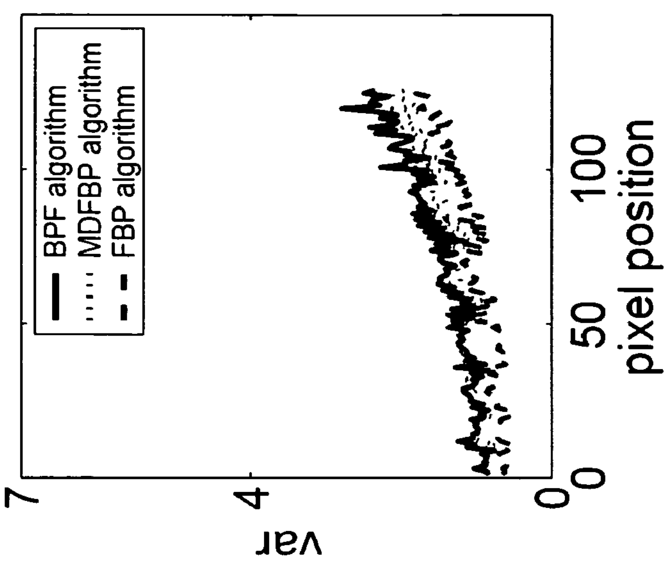
Figure 82B:
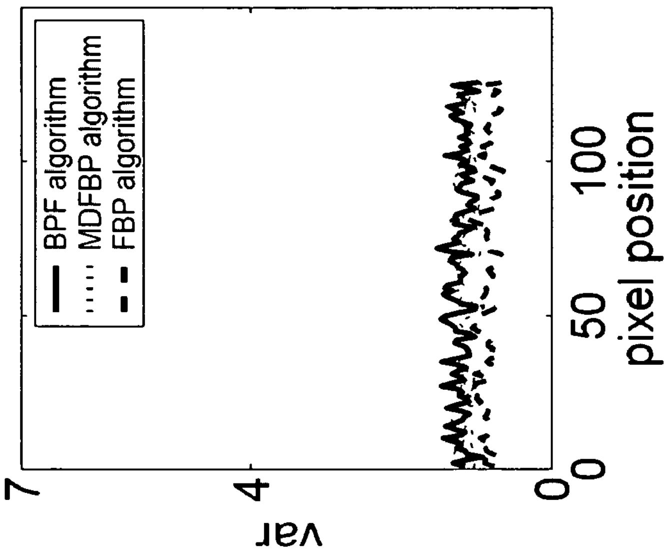
Figure 82A:
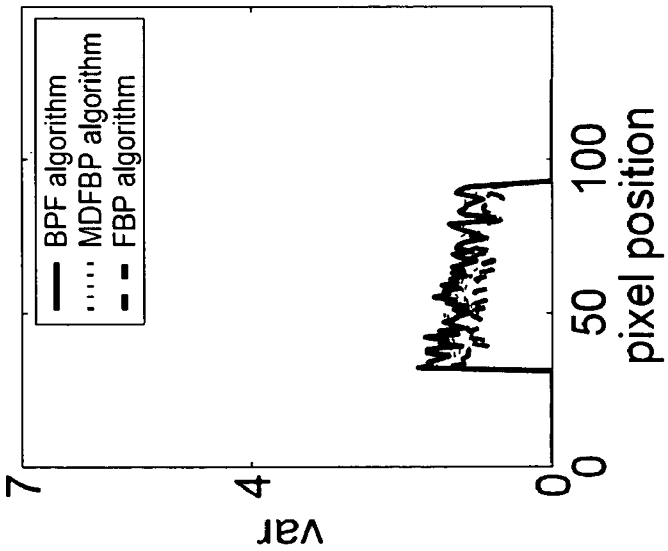

FIGS. 82*a-c* display image variances obtained by using the BPF (solid), MDFBP (dotted), and FBP (dashed) methodologies on lines (in FIGS. 81*a-c*) specified by x=−2.2 cm and y=−4.4 cm (FIG. 82*a*), x=−2.2 cm and z=0 cm (FIG. 82*b*), and y=−4.4 cm and z=0 cm (FIG. 82*c*).

Figures 83A, 83B, 83C:
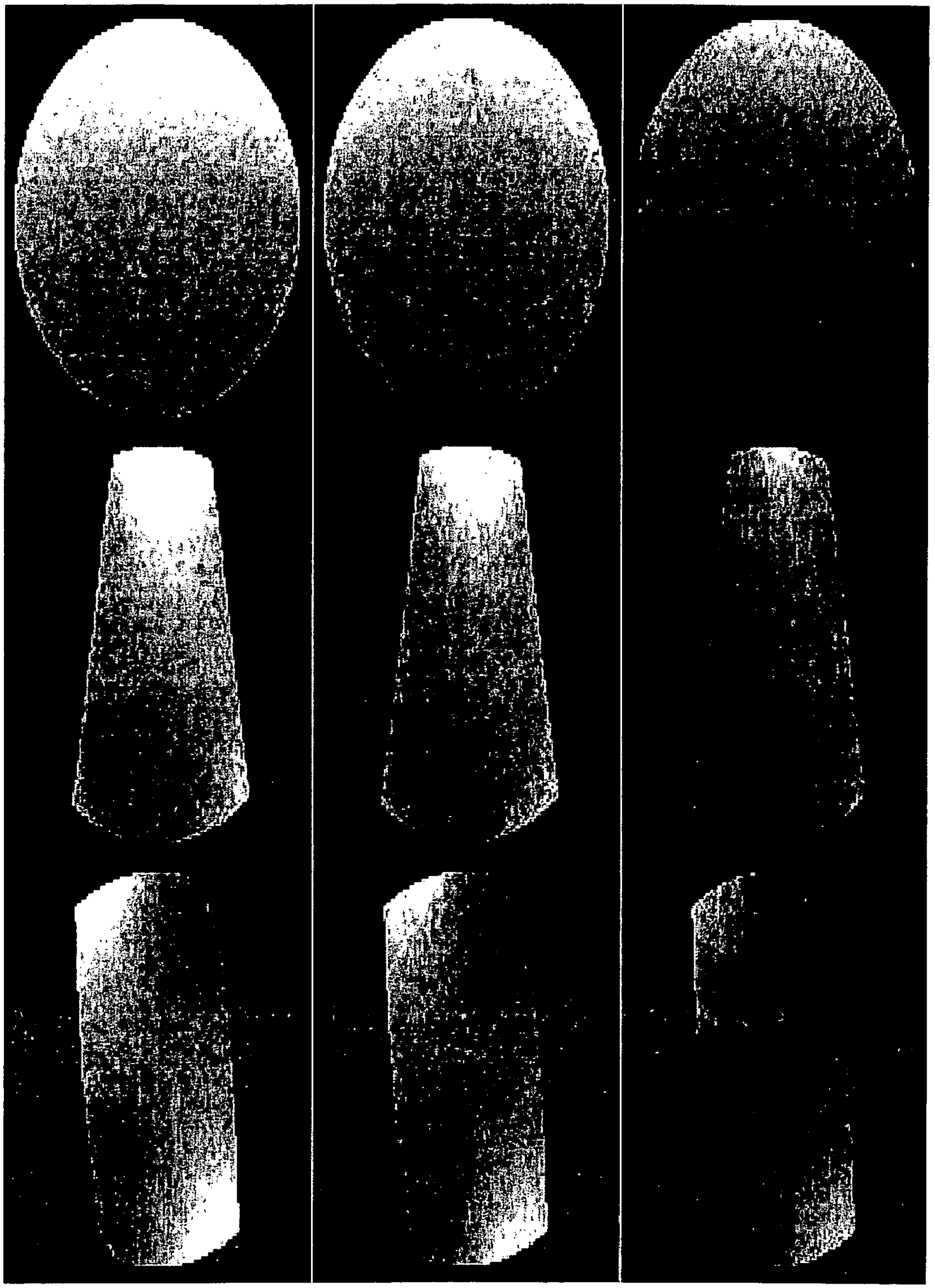

FIGS. 83*a-c* show image variances computed from images on the Cartesian grid converted from chord images by use of the second interpolation scheme.

Figure 84A:
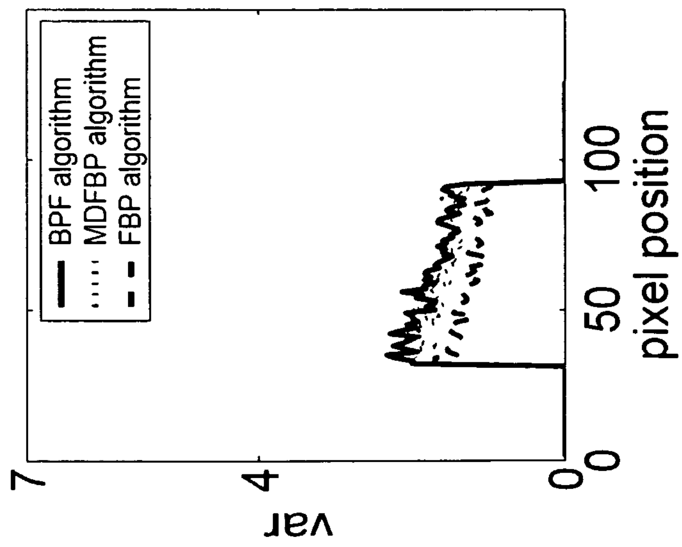
Figure 84B:
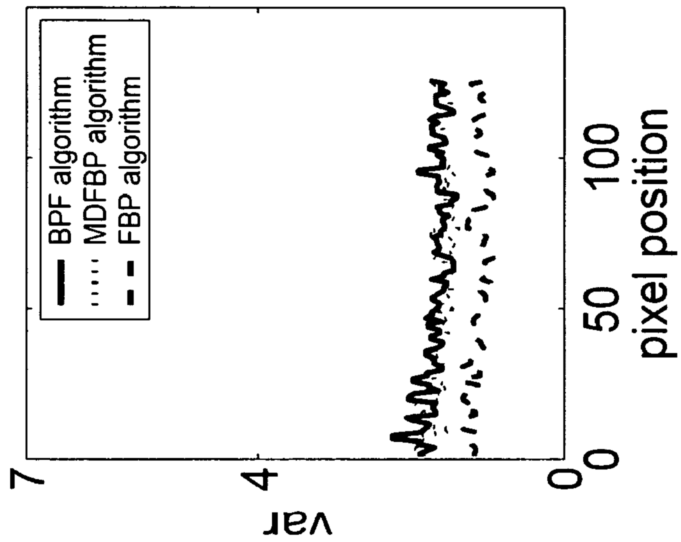
Figure 84C:
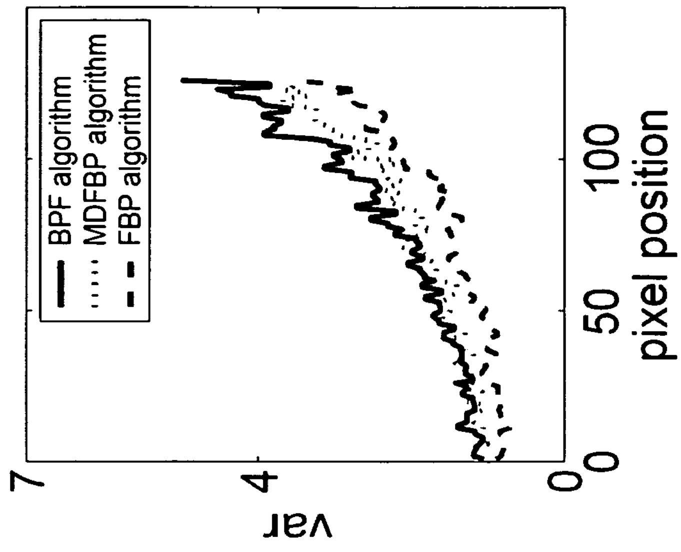

FIGS. 84*a-c* depict image variances obtained by using the BPF (solid), MDFBP (dotted), and FBP (dashed) methodologies on lines (in FIGS. 83*a-c*) specified by x=−2.2 cm and y=−4.4 cm (FIG. 84*a*), x=−2.2 cm and z=0 cm (FIG. 84*b*), and y=−4.4 cm and z=0 cm (FIG. 84*c*).

Figure 85C:
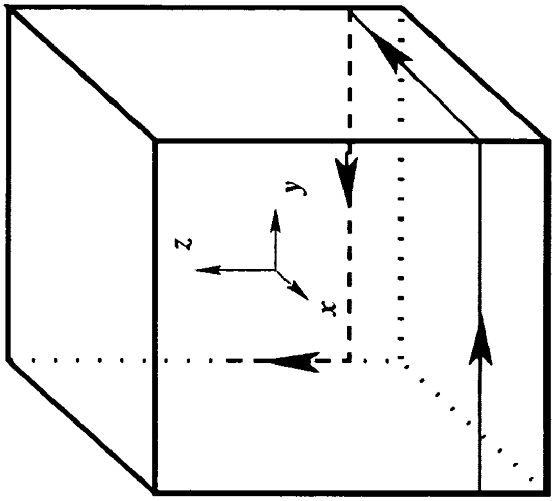
Figure 85B:
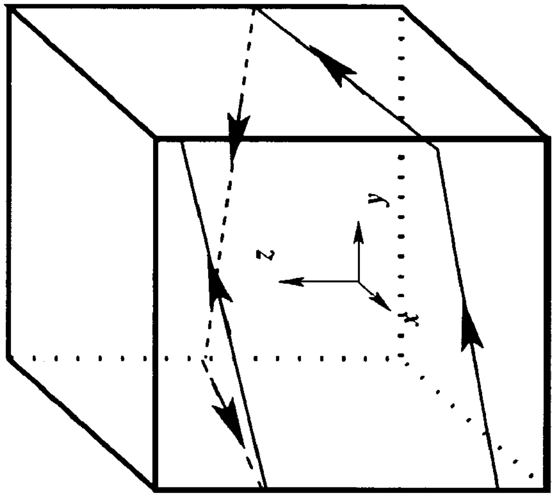
Figure 85A:
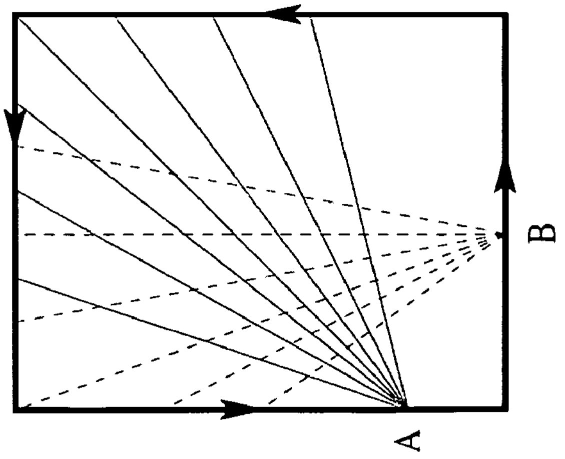

FIGS. 85*a-c* illustrate the reformulation of PET data into XCBT data.

FIGS. 86*a-b* and 87*a-c* show the images of the Shepp-Logan phantom reconstructed by use of the chord-based BFP methodology from noiseless data (FIG. 86*a*) and from noisy data (FIG. 86*b*) for the square helical trajectory.

Figures 88A, 88B:
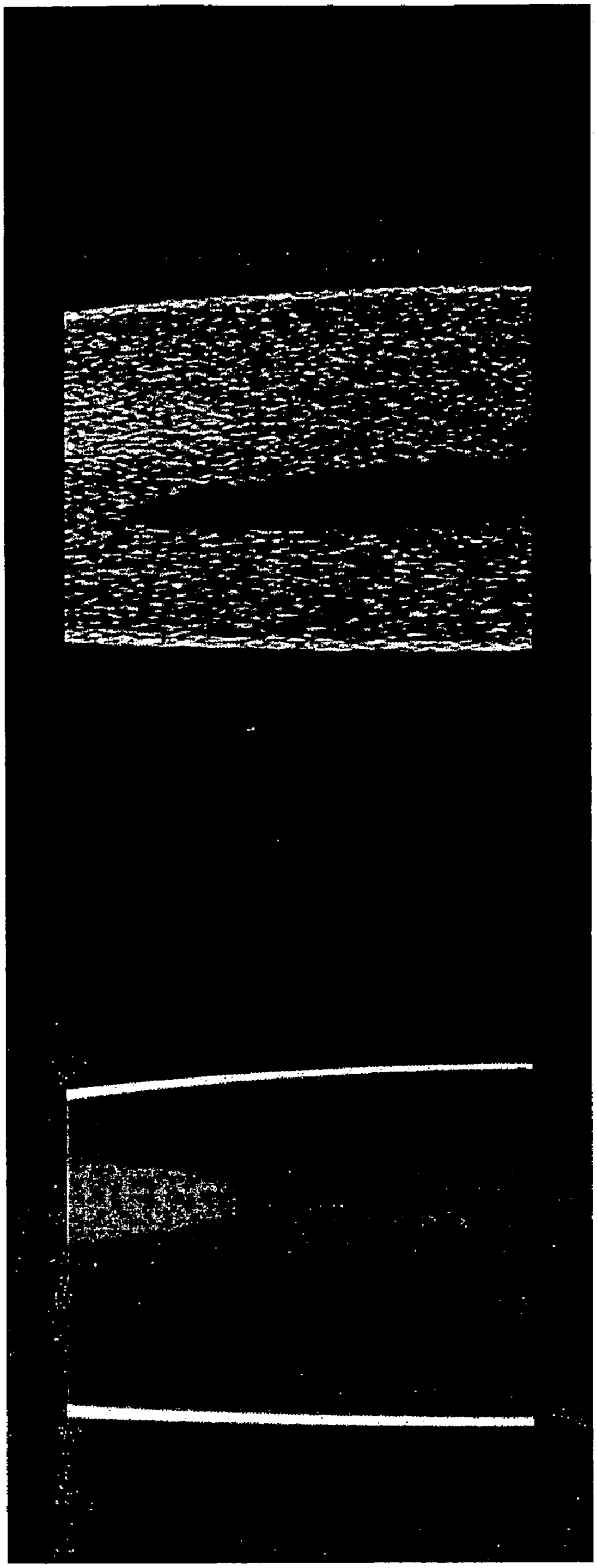

In FIGS. 88*a-b*, images of the numerical Shepp-Logan phantom on a set of chords reconstructed by use of the BPF algorithm from noiseless data (FIG. 88*a*) and noisy data (FIG. 88*b*) derived for the 3h1v trajectory are shown.

Figures 89A, 89B, 89C:
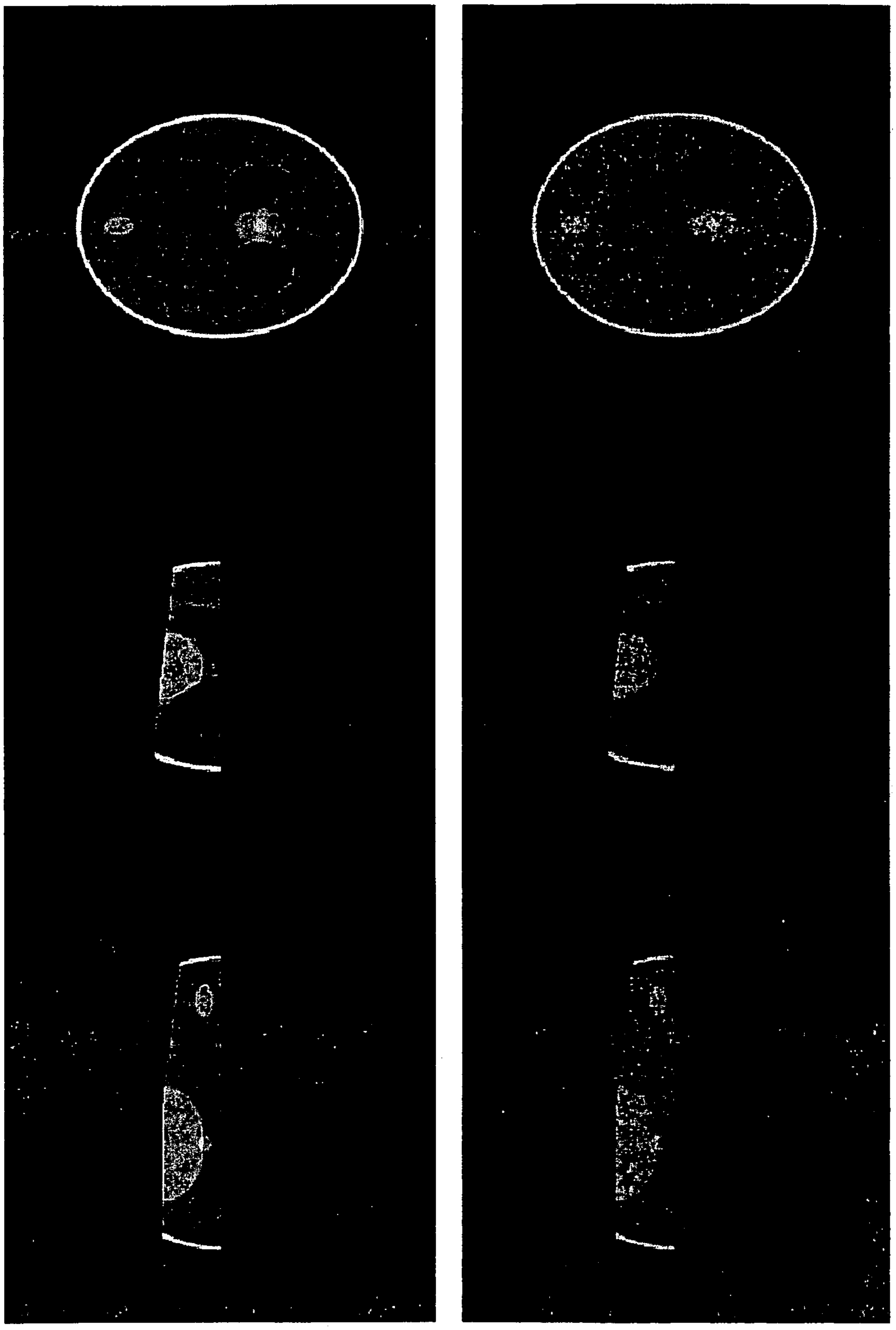

FIGS. 89*a-c* illustrate images of a numerical Shepp-Logan phantom reconstructed by use of the BPF algorithm from noiseless (upper row) and noisy (lower row) data with the 3h1v trajectory.

Figure 90:
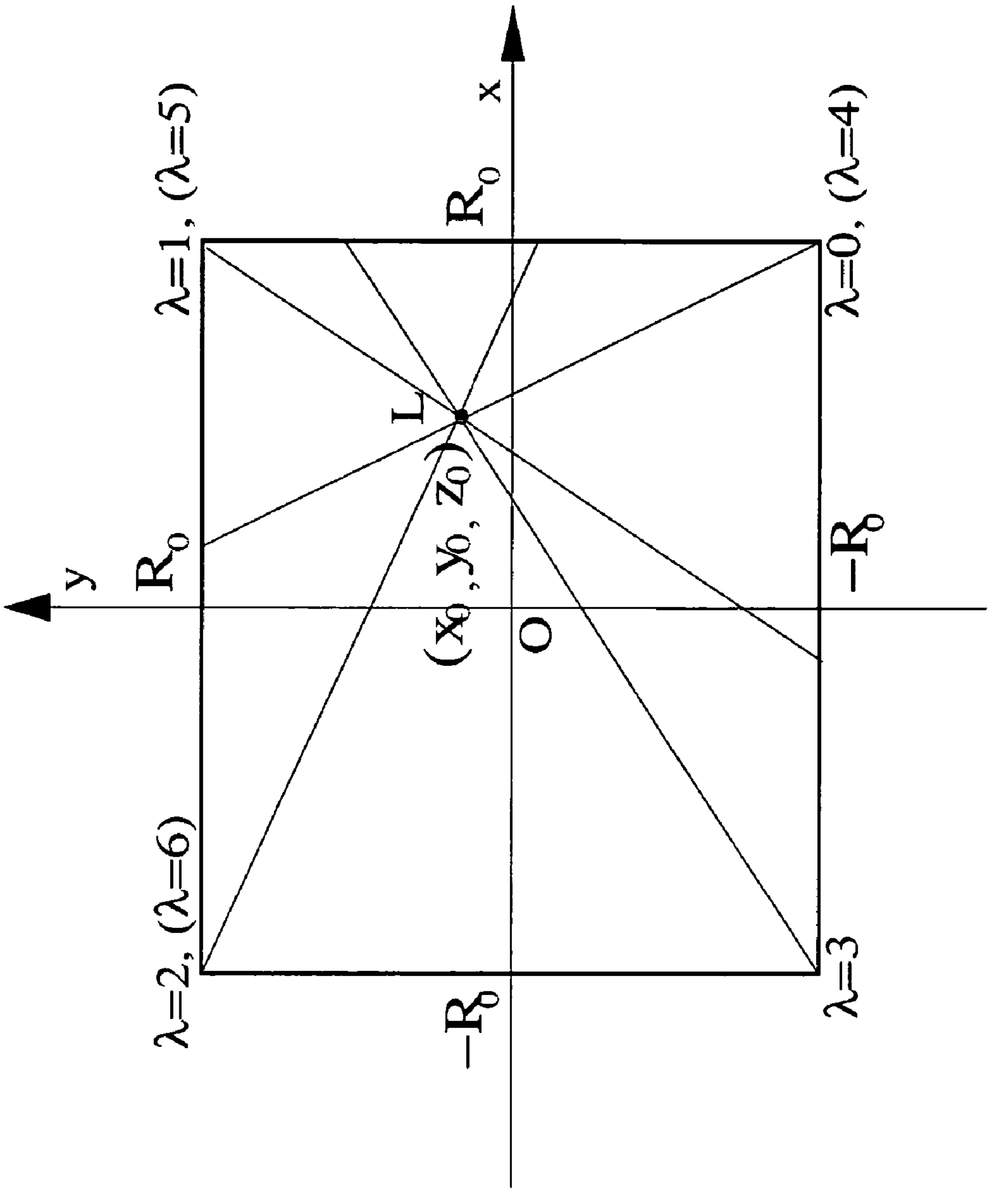

FIG. 90 illustrates a transverse section of the square prism. Line L, shown as a solid dot with coordinates ($x_0$, $y_0$) within the x-y plane, is parallel to the central axis of the square prism and is closest to the flat-panel detector at x=$R_0$.

Figure 91:
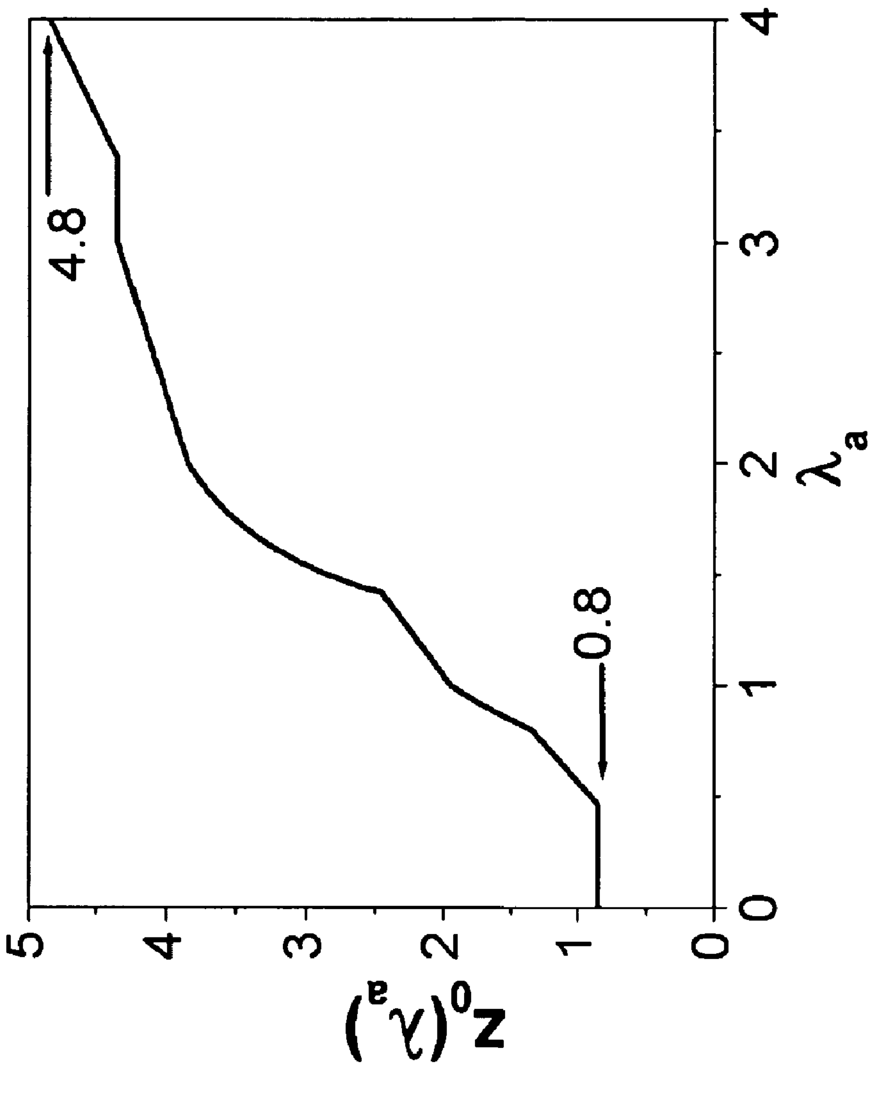

FIG. 91 is a plot of $z_0(\lambda_a)$ for $0<\lambda_a<4$.

Figure 92:
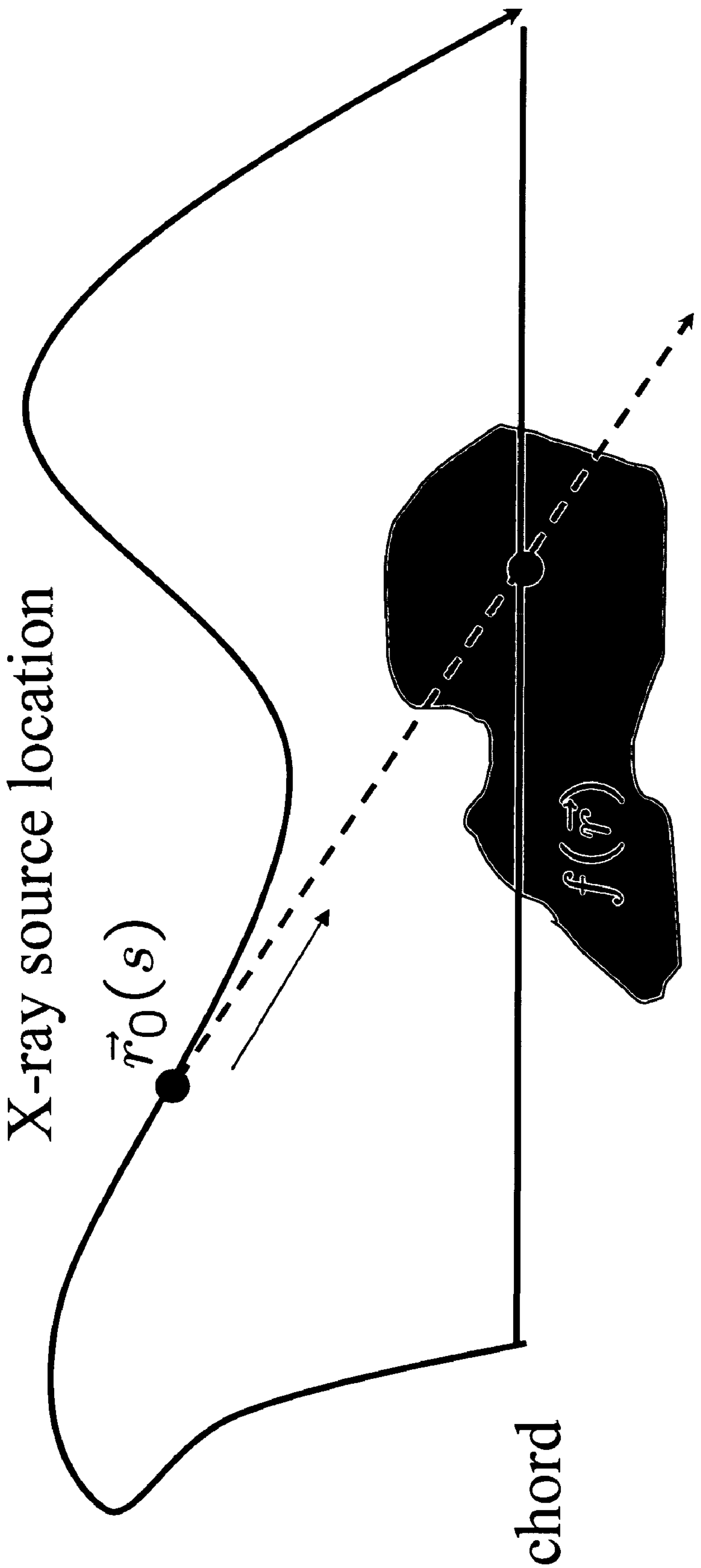

FIG. 92 shows one type of non-straight source trajectory (shown as the curved line in FIG. 92).

Figure 93:
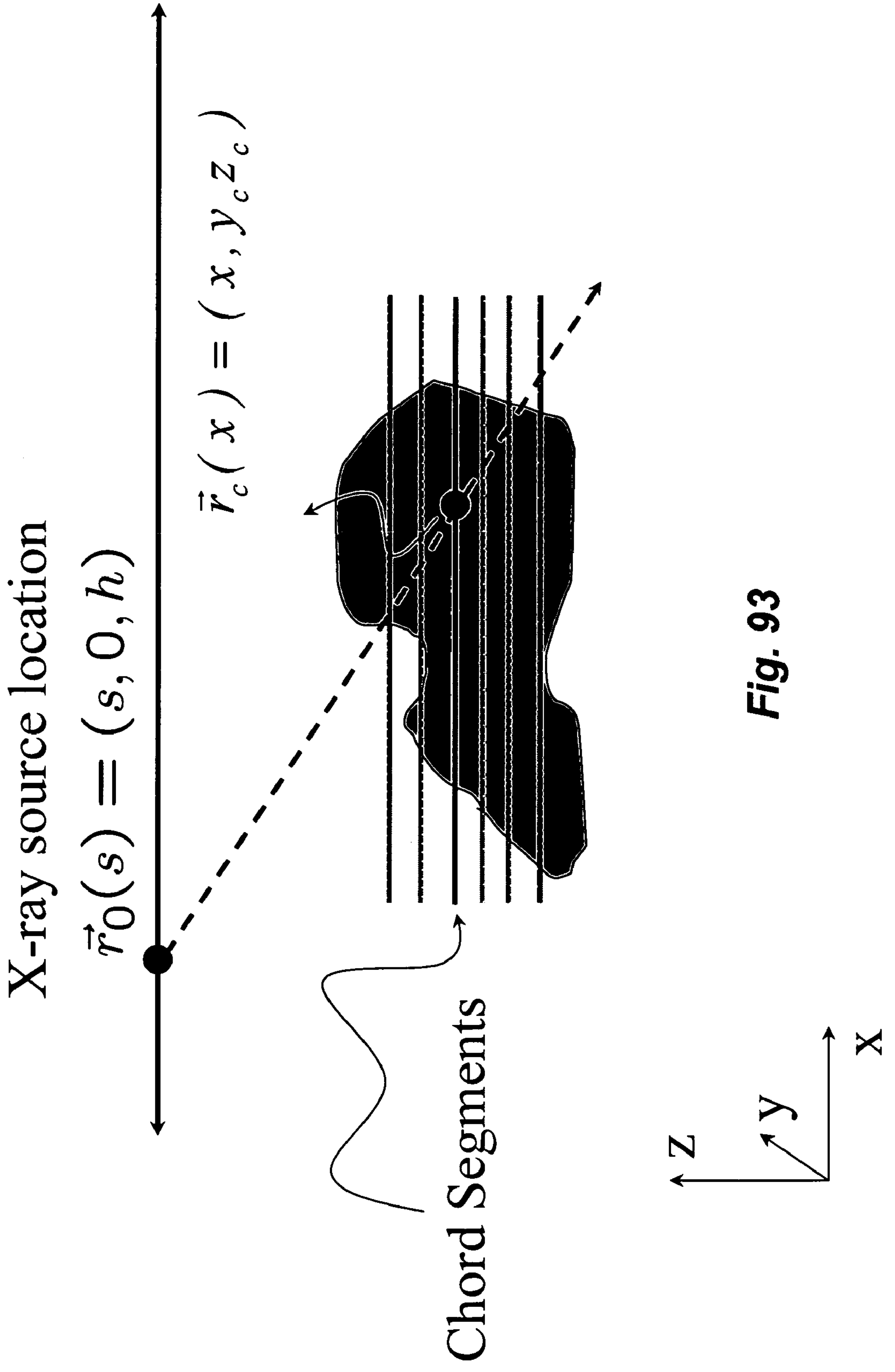

FIG. 93 shows a straight source trajectory (the straight line in FIG. 93) with $\vec{r}_0$.

Figure 94:
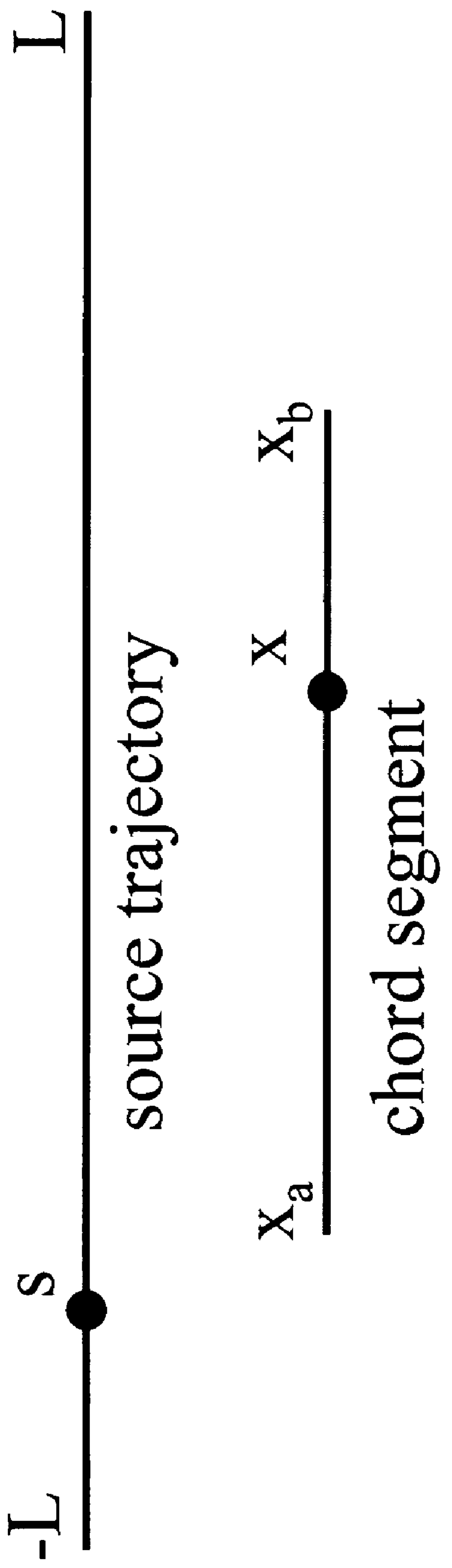

FIG. 94 shows a chord segment $x_a$ to $x_b$, with a point along the chord designated as x.

Figure 95A:
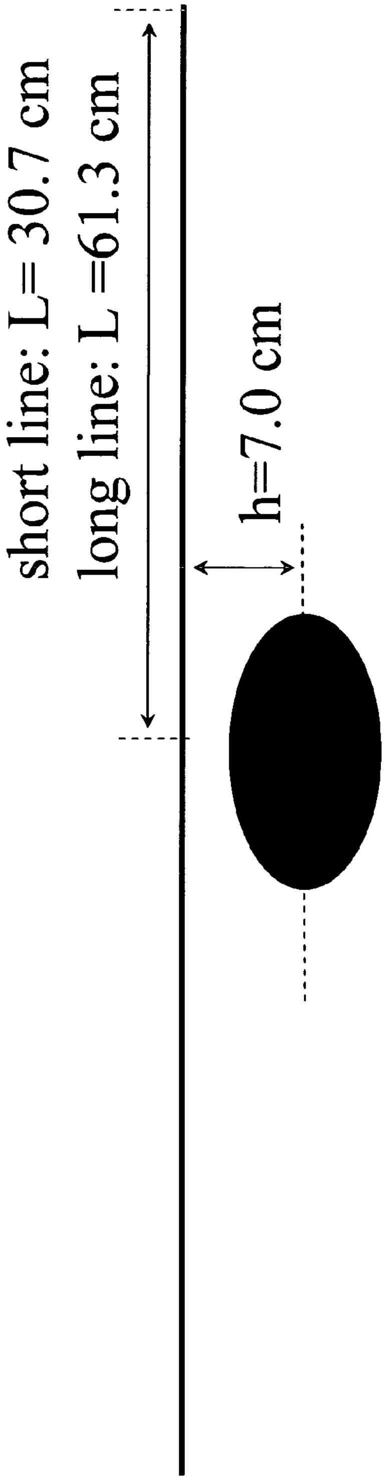

FIG. 95*a* depicts the dimensions of a long and short line trajectory, with L=61.3 cm for the long line trajectory and L=30.7 cm for the short line trajectory.

Figure 95B:
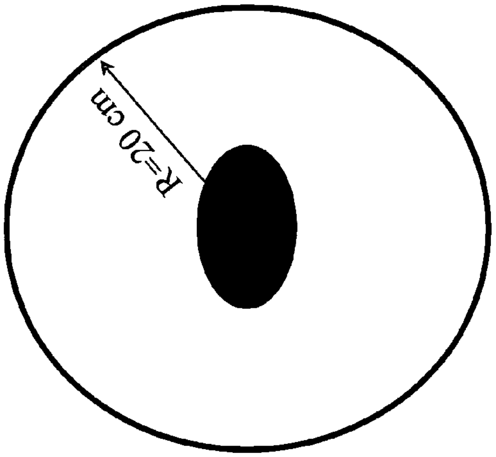

FIG. 95B is a circular cone-beam scan, with a radius of 20 cm, so that the circumference of the circle shown in FIG. 95B is the same length as the long line scan depicted in FIG. 95A.

FIGS. 96*a-d* displays the "in" plane slice, labeled a, "off"-plane slice, b, and a trans-axial slice c.

Figure 97A:
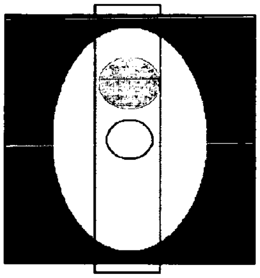
Figure 97B:
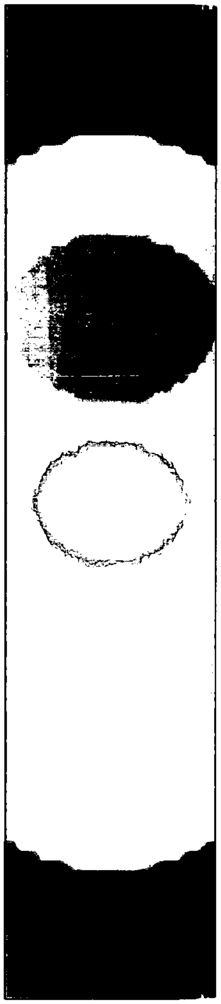
Figure 97C:
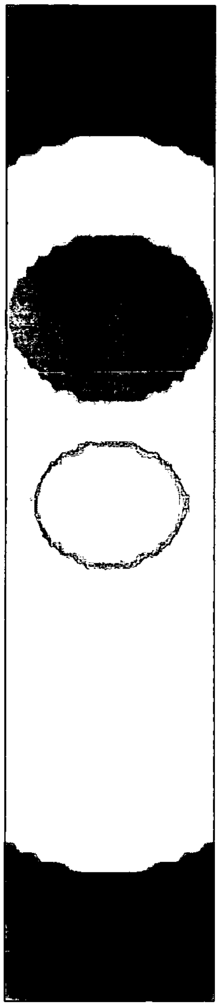
Figure 97D:
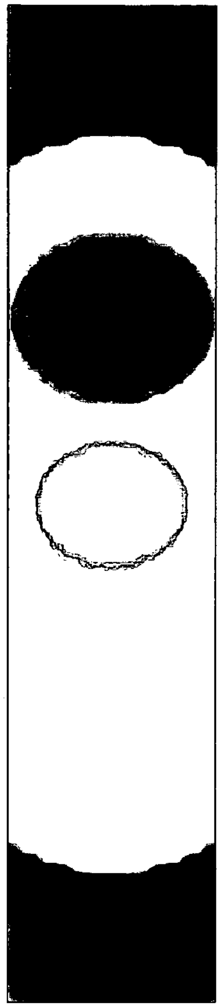

FIGS. 97*a-d* show the mid-plane results, with FIG. 97*a* being the true reconstructed slice, and FIGS. 97*b*, 97*c*, and 97*d* being the reconstructed slices based on the short line trajectory, long line trajectory, and circular scan trajectory, respectively.

Figure 98A:
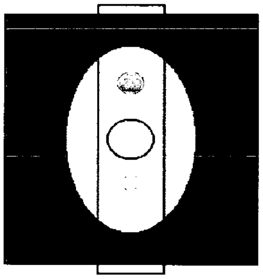
Figure 98B:
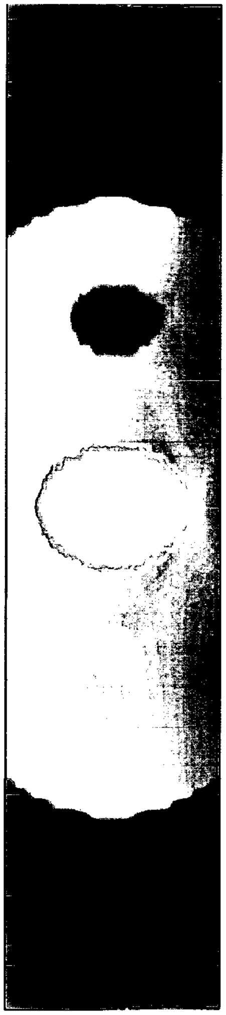
Figure 98C:
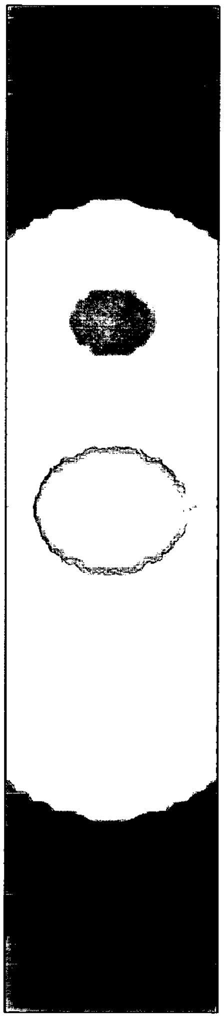
Figure 98D:
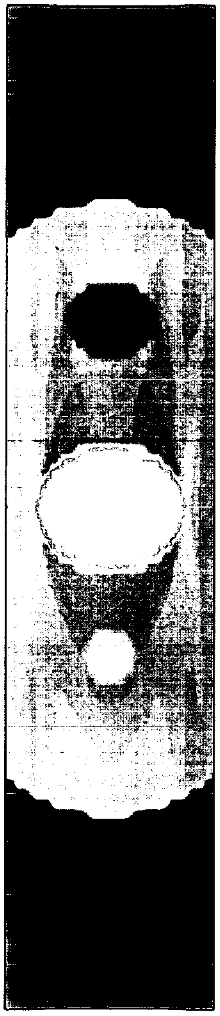

FIGS. 98*a-d* show the off mid-plane results, with FIG. 98*a* being the true reconstructed slice, and FIGS. 98*b*, 98*c*, and 98*d* being the reconstructed slice based on the short line trajectory, long line trajectory, and circular scan trajectory respectively.

Figure 99A:
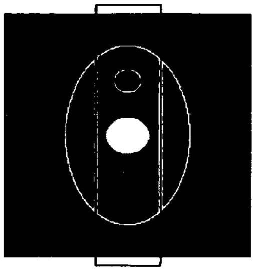

FIG. 99*a* is a true reconstructed slice for the off mid-plane profile (identical to FIG. 98A).

Figure 99B:
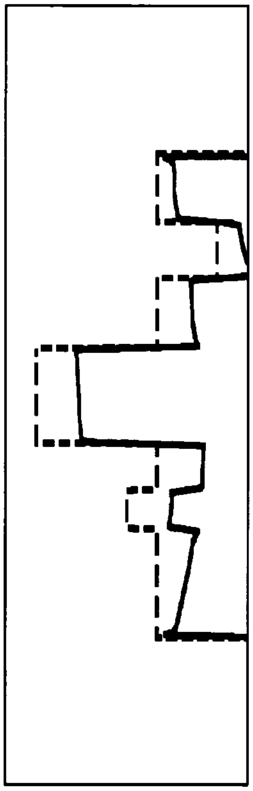
Figure 99C:
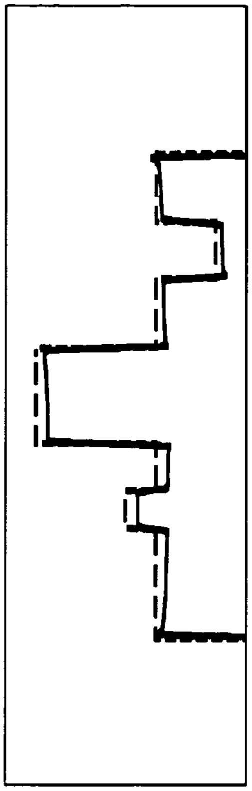
Figure 99D:
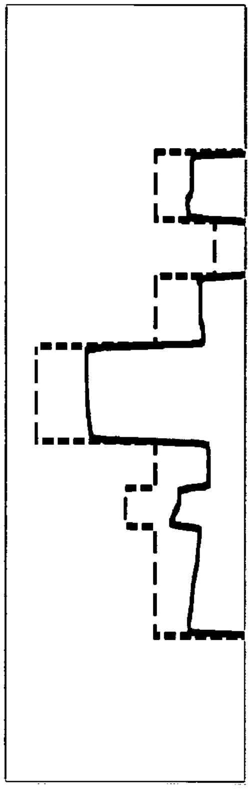

FIGS. 99*b-d* represent the corresponding profiles for the short line trajectory, long line trajectory, and circular scan trajectory, respectively, for a horizontal line in the middle of the images, y=0, z=0.

Figures 100A, 100B, 100C:
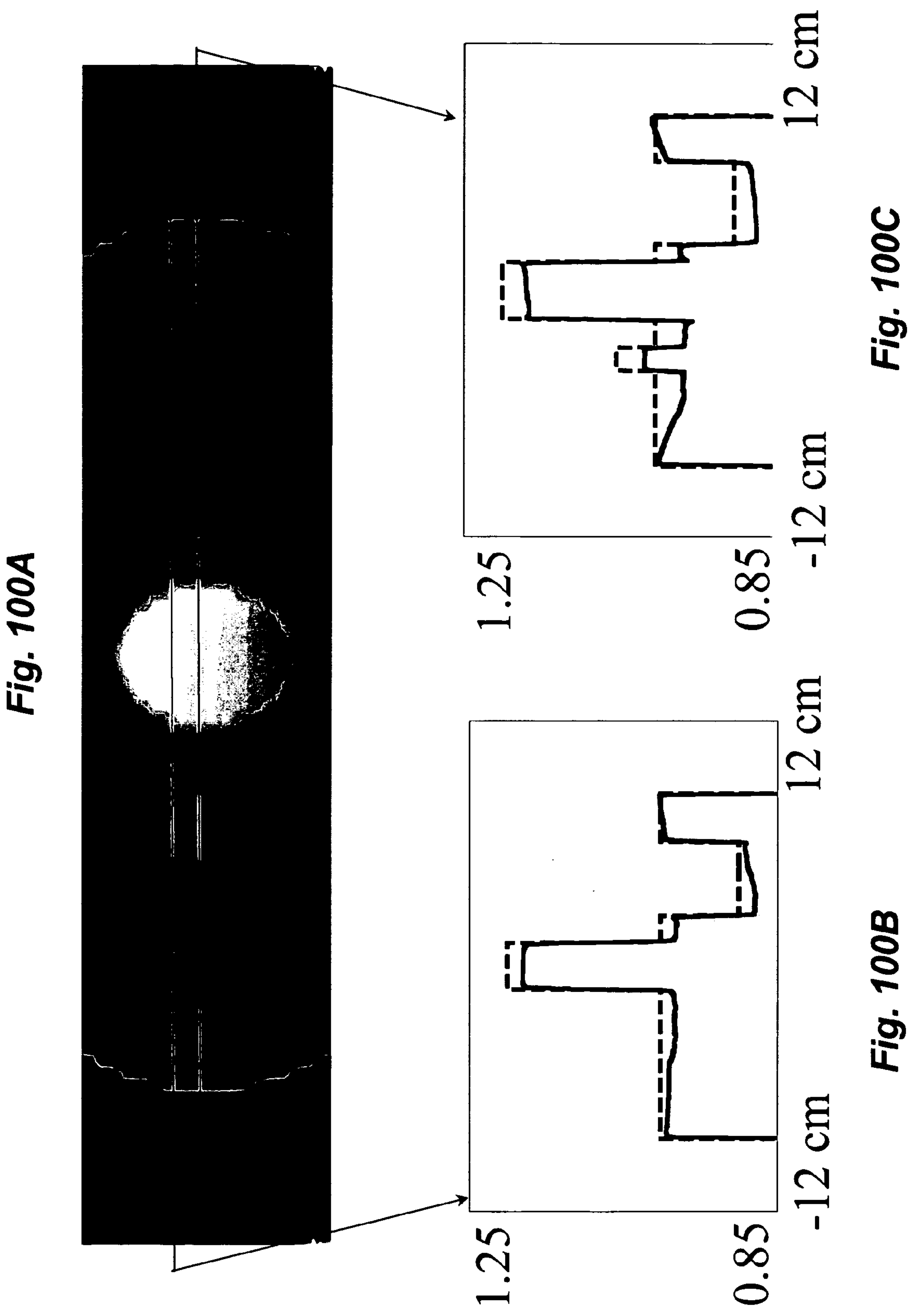

FIG. 100*a-c* shows the short scan, mid-plane, with an additional upper and a lower horizontal line through the images, and corresponding profiles for the lines in FIG. 100*b* and FIG. 100*c*, respectively.

Figures 101A, 101B, 101C:
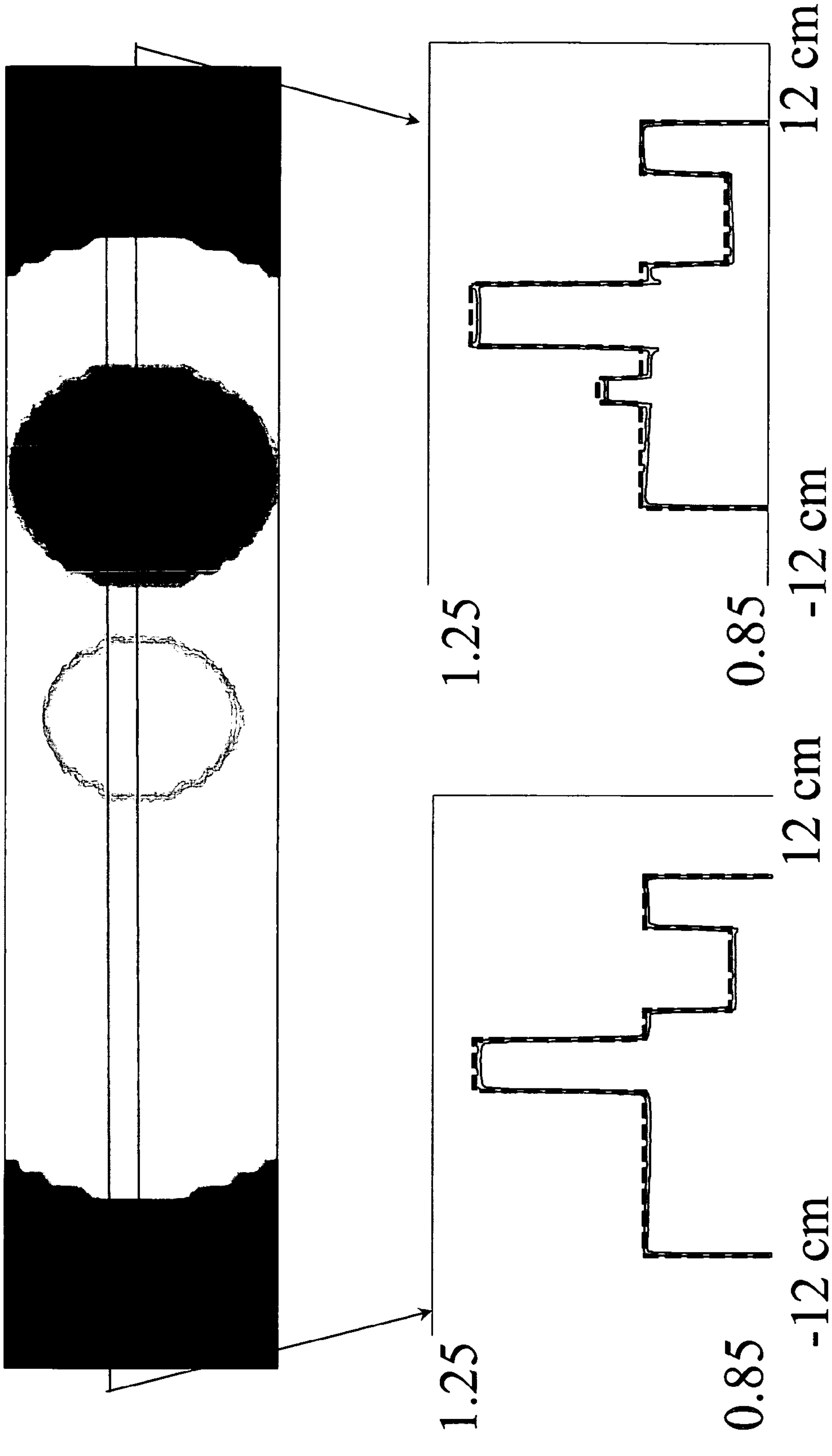

FIG. 101*a-c* shows the long scan, mid-plane, with an additional upper and a lower horizontal line through the images, and corresponding profiles for the lines in FIG. 101*b* and FIG. 101*c*, respectively.

Figure 102A:
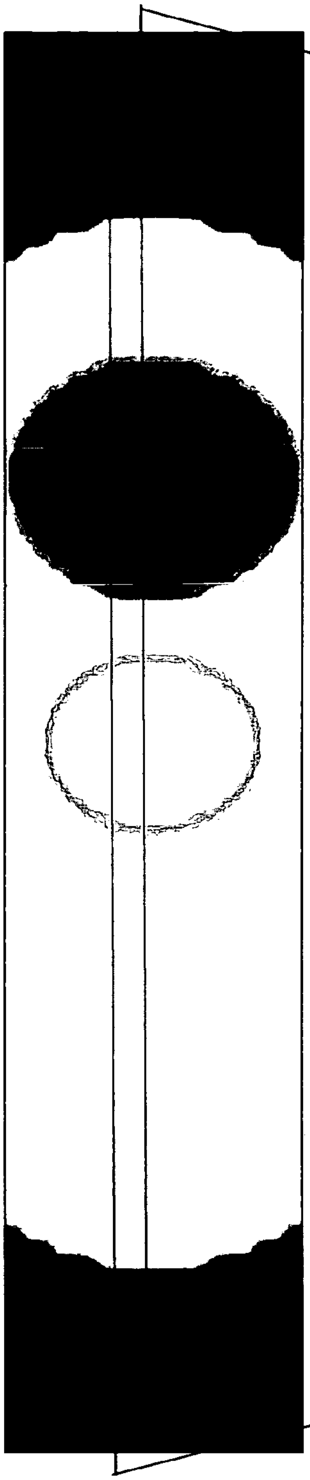
Figure 102C:
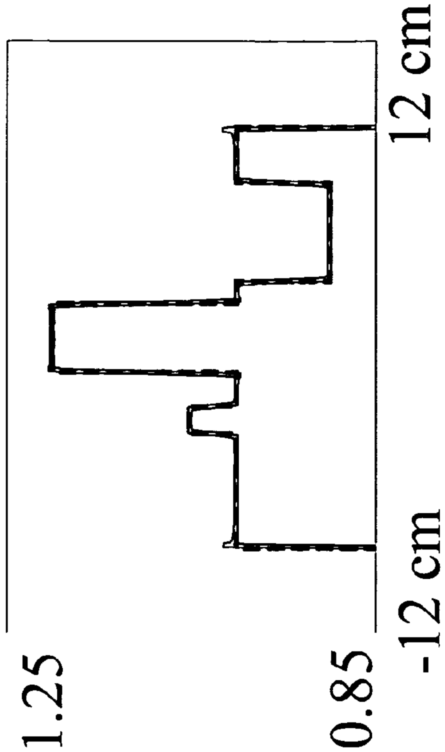
Figure 102B:
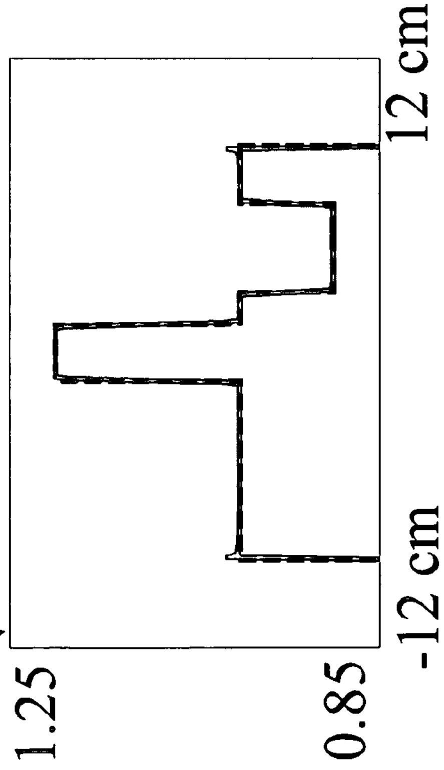

FIG. 102*a-c* shows the circular scan, mid-plane, with an additional upper and a lower horizontal line through the images, and corresponding profiles for the lines in FIG. 102*b* and FIG. 102*c*, respectively.

FIG. 103$a$-$c$ shows the short scan, off-plane, with an additional upper and a lower horizontal line through the images, and corresponding profiles for the lines in FIG. 103$b$ and FIG. 103$c$, respectively.

FIG. 104$a$-$c$ shows the long scan, off-plane, with an additional upper and a lower horizontal line through the images, and corresponding profiles for the lines in FIG. 104$b$ and FIG. 104$c$, respectively.

FIG. 105$a$-$c$ shows the circular scan, off-plane, with an additional upper and a lower horizontal line through the images, and corresponding profiles for the lines in FIG. 105$b$ and FIG. 105$c$, respectively.

Figure 106:
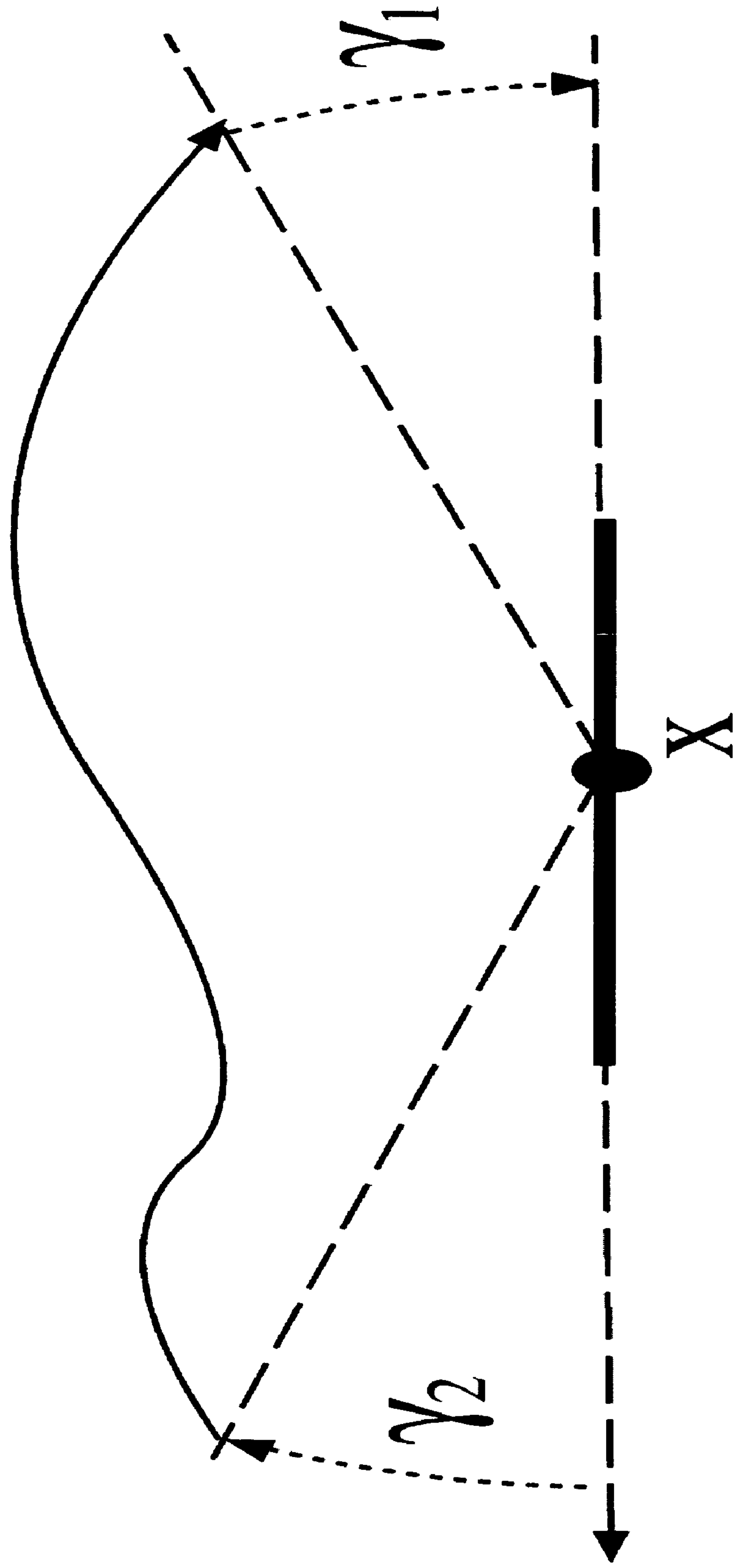

FIG. 106 shows a diagram of approximation made by the chord reconstruction methodologies for "incomplete" trajectories.

Figure 107:
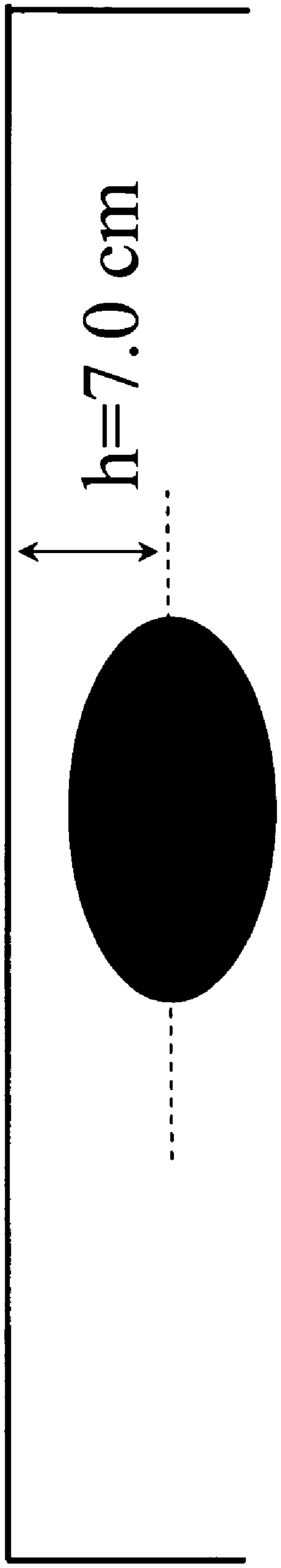

FIG. 107 depicts one example of the bracket scan.

Figures 108A, 108B, 108C:
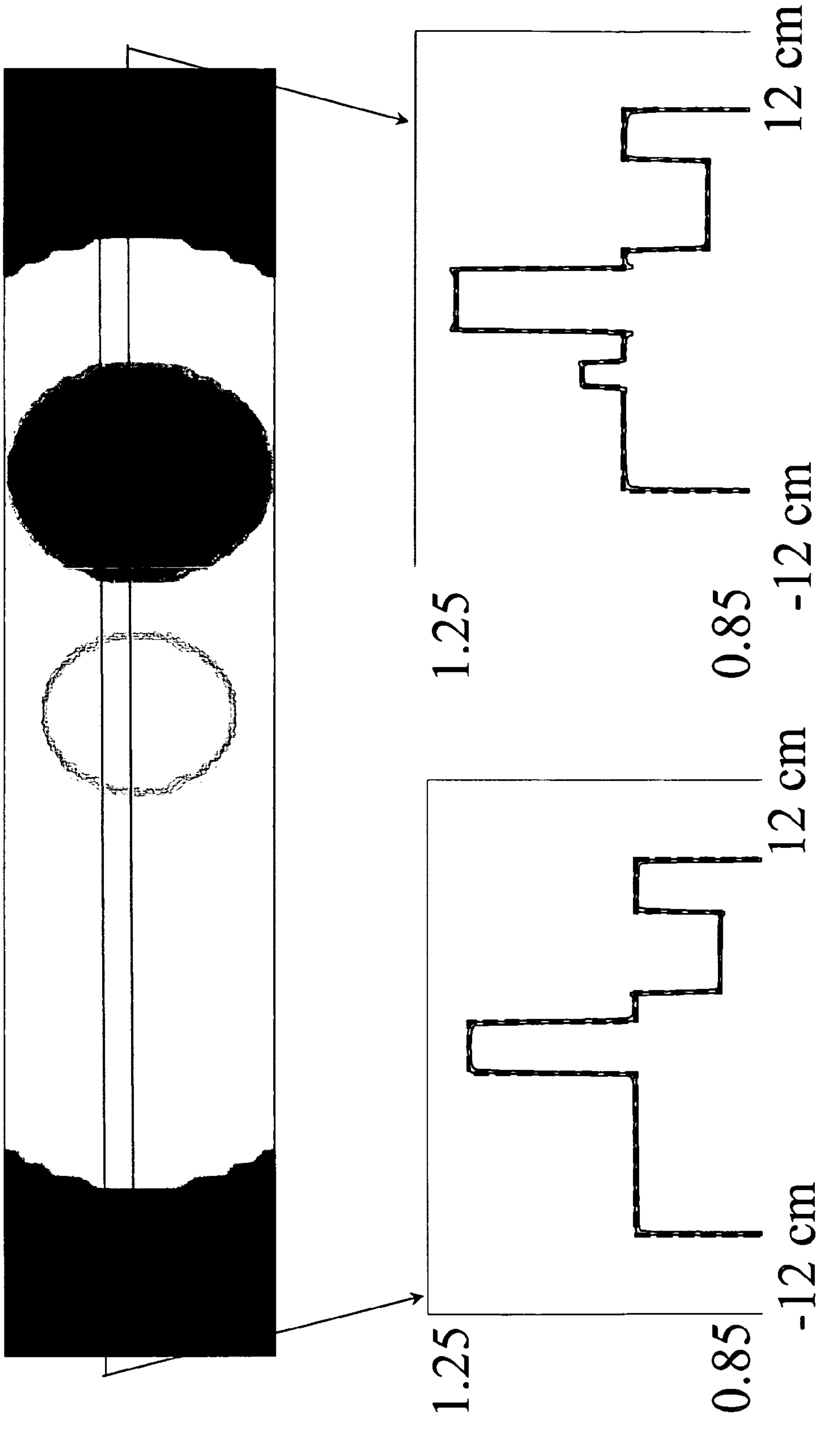

FIG. 108$a$ shows the reconstructed slice based on the bracket line trajectory, with an additional upper and a lower horizontal line through the images, and corresponding profiles for the lines in FIG. 108B and FIG. 108C, respectively.

Figure 109A:
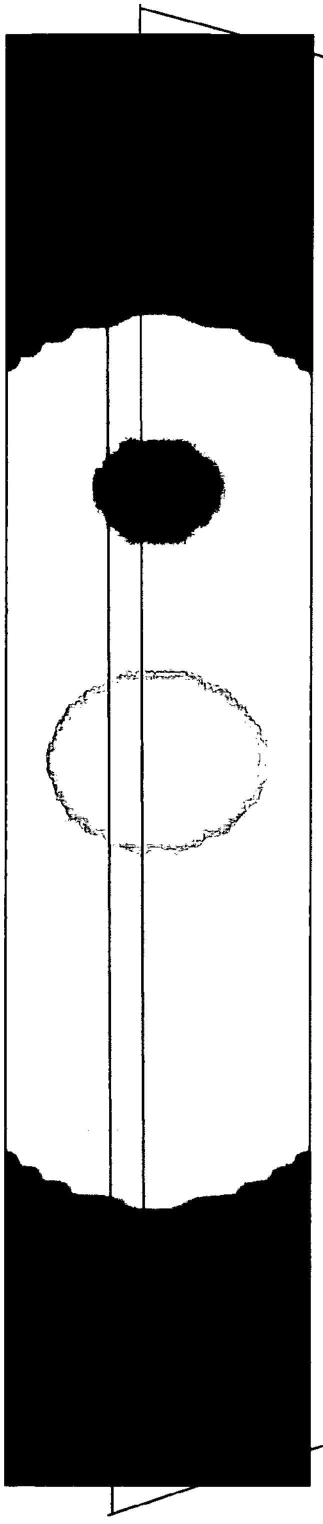
Figure 109B:
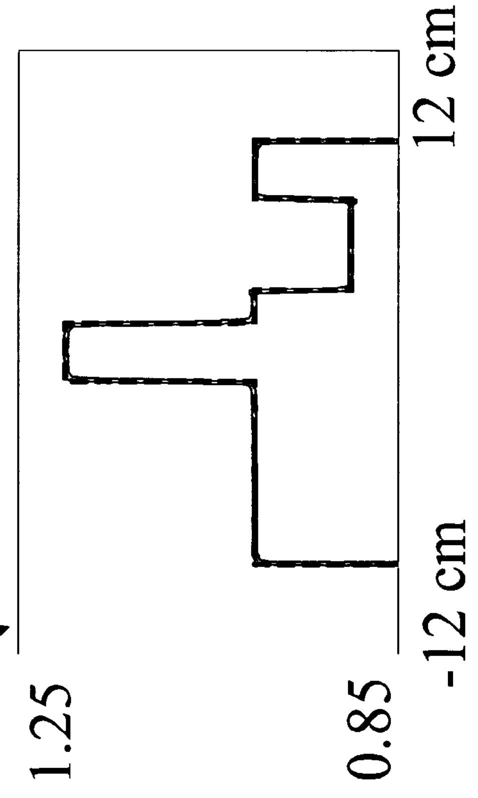
Figure 109C:
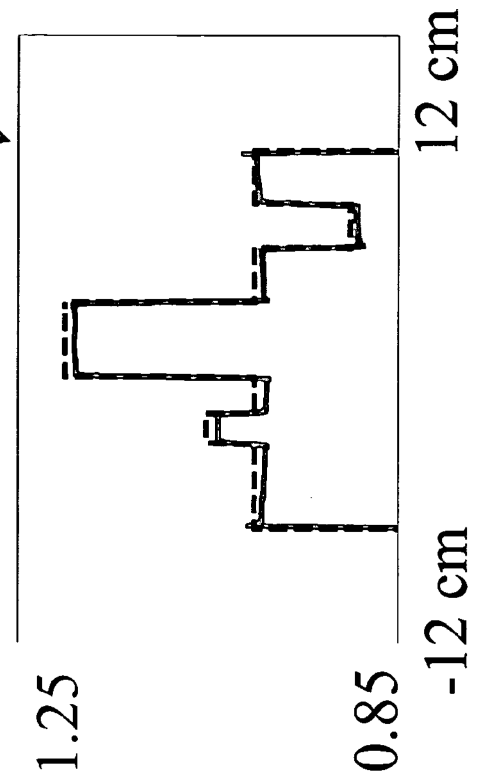

FIG. 109$a$ shows the reconstructed slice based on the bracket line trajectory, with an additional upper and a lower horizontal line through the images, and corresponding profiles for the lines in FIG. 109B and FIG. 109C, respectively.

FIGS. 110$a$-$b$ illustrate the fan-beam geometry with a circular source trajectory.

FIGS. 111$a$-$d$ illustrate PI-line segments.

FIGS. 112$a$-$b$ illustrate ROI reconstruction using redundant data, depicting two different angular reconstruction intervals used by the WBPF methodology for reconstructing ROI images containing the solid rectangle (which may act as an object).

Figure 113:
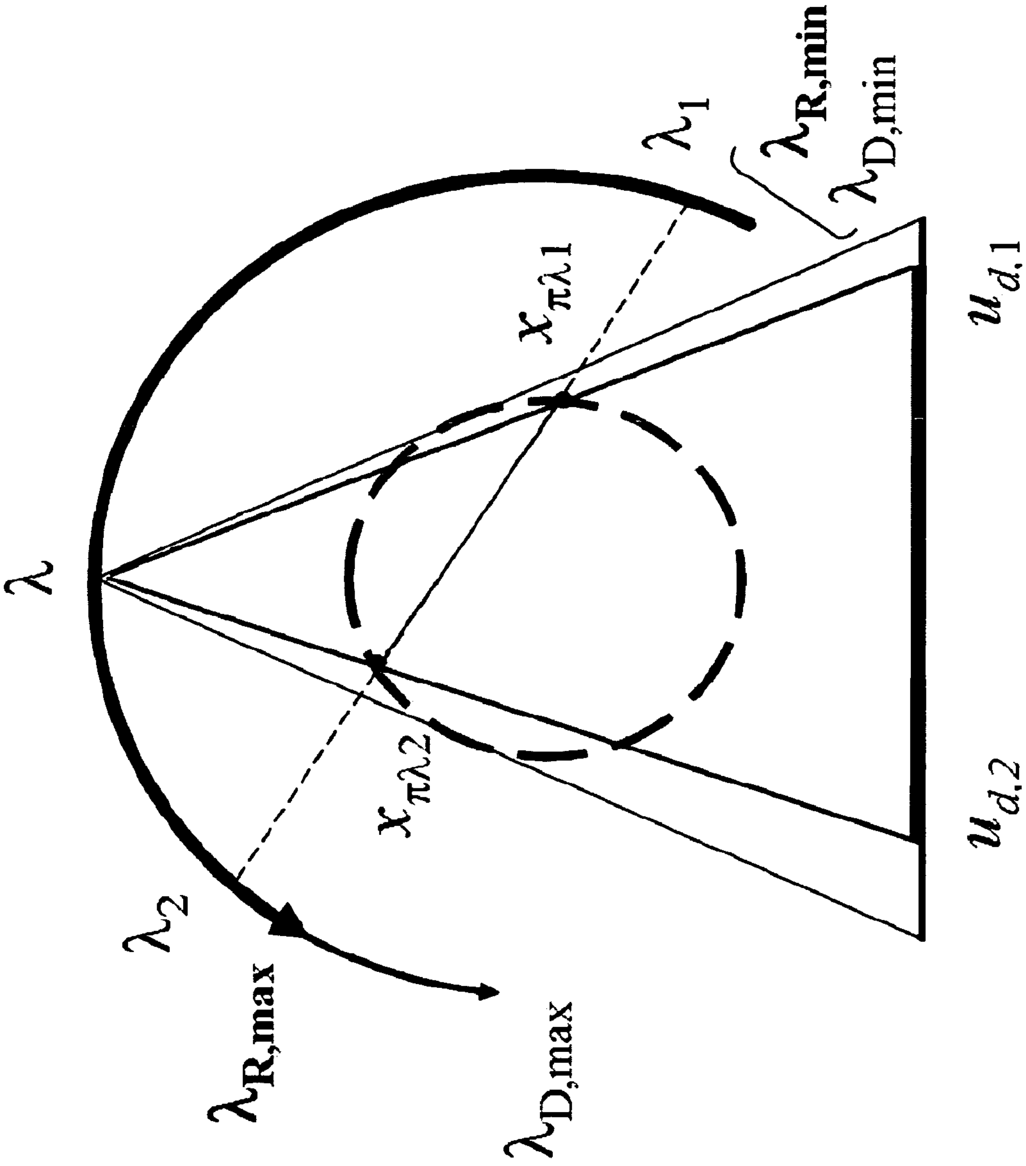

FIG. 113 is a schematic illustrating the data sufficiency conditions for obtaining an exact reconstruction of an image on a PI-line segment specified by $\lambda_1$ and $\lambda_2$ using the WBPF methodology.

FIGS. 114$a$-$b$ illustrate the effect of off-center positioning on the angular range $\Delta\lambda_R$.

FIG. 115$a$ illustrates a modified FORBILD phantom with dynamic cardiac insert.

FIG. 115$b$ illustrates a temporal phase profile for the radius of the entire cardiac insert.

Figure 116:

FIG. 116 depicts an attenuation map generated from the NCAT phantom at mid-to-late diastole ($\phi$=0.75).

Figure 117:
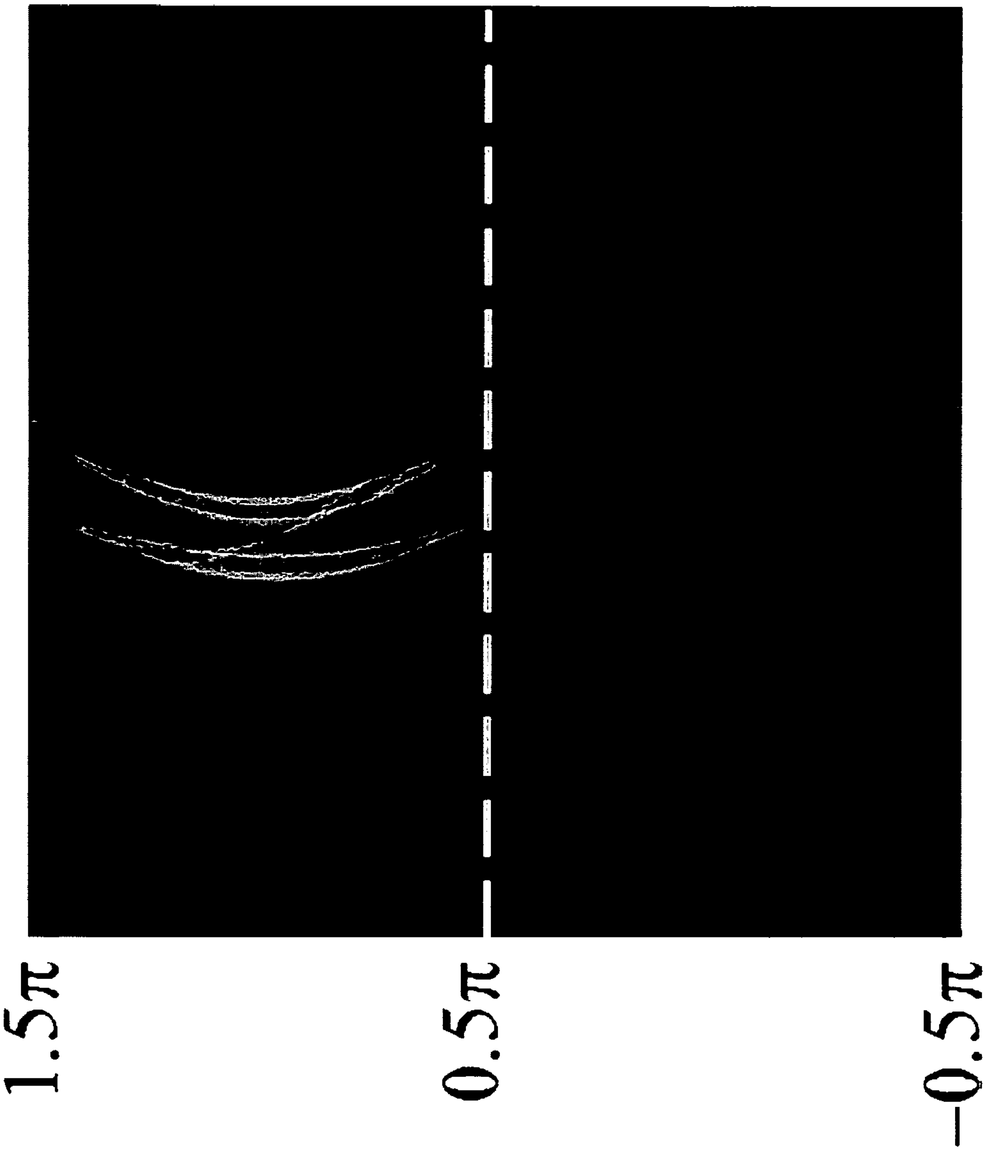

FIG. 117 illustrates a difference sinogram (scanning angle $\lambda$ versus detector bin $u_d$) highlighting regions of motion-induced inconsistencies in the data acquired from the modified FORBILD phantom.

FIGS. 118$a$-$d$ illustrate the phase-interval image reconstruction for the modified FORBILD phantom.

FIGS. 119$a$-$d$ illustrates the results of four phase-interval ROI reconstructions for the modified FORBILD phantom using the WBPF methodology that were performed.

FIGS. 120$a$-$b$ depict phase-interval ROI reconstruction with off-center positioning using non-truncated data.

FIGS. 121$a$-$b$ illustrate the phase-interval ROI reconstruction with off-center positioning using truncated data.

FIGS. 122$a$-$d$ illustrate morphology of motion artifacts in reconstructions from truncated data.

FIGS. 123$a$-$d$ illustrate phase-interval image reconstruction for the NCAT phantom.

FIGS. 124$a$-$b$ illustrate phase-interval ROI reconstruction with off-center positioning using non-gated data with truncations.

FIGS. 125$a$-$f$ illustrate phase-interval ROI reconstruction using gated data.

FIGS. 126$a$-$b$ illustrate $\bar{T}_{ROI}$ calculations for ungated and gated reconstructions.

Figure 127C:
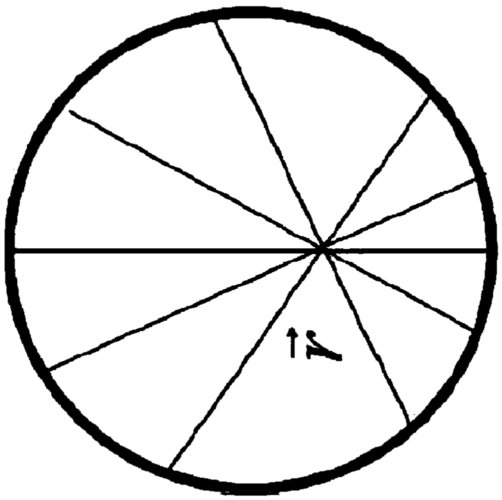
Figure 127B:
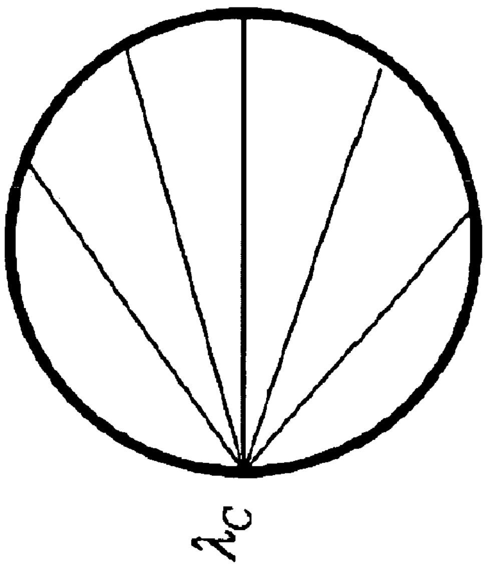
Figure 127A:
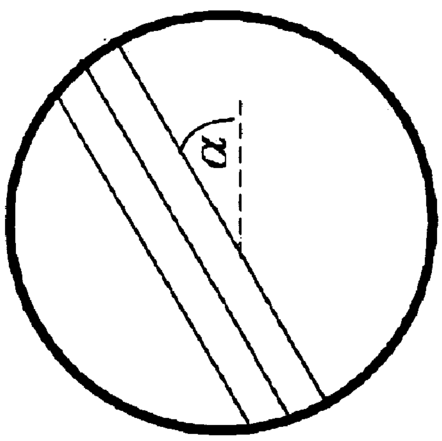

FIGS. 127$a$-$c$ illustrate definitions of chords for the circular fan-beam case using various configurations: ($a$) parallel (angular orientation); ($b$) the converging (angle of convergence); and ($c$) the intersecting configurations (point).

FIGS. 128$a$-$b$ illustrate ($a$) the temporal trajectory for a uniform circular phantom (L: 1 HU/W: 1 HU) and ($b$) a plot of a sample temporal phase profile for the diameter of the inner circle, which undergoes sinusoidal contractile motion with an amplitude of −6 cm.

FIGS. 129$a$-$b$ illustrate ($a$) a modified FORBILD phantom with dynamic cardiac insert. The white arrow in points to an added high contrast circle representing a coronary plaque or calcification within the cardiac insert (L: 50 HU/W: 400 HU), and ($b$) a sample temporal trajectory of the diameter of the entire cardiac insert over one complete temporal phase for the diameter of the entire cardiac insert.

Figure 130:
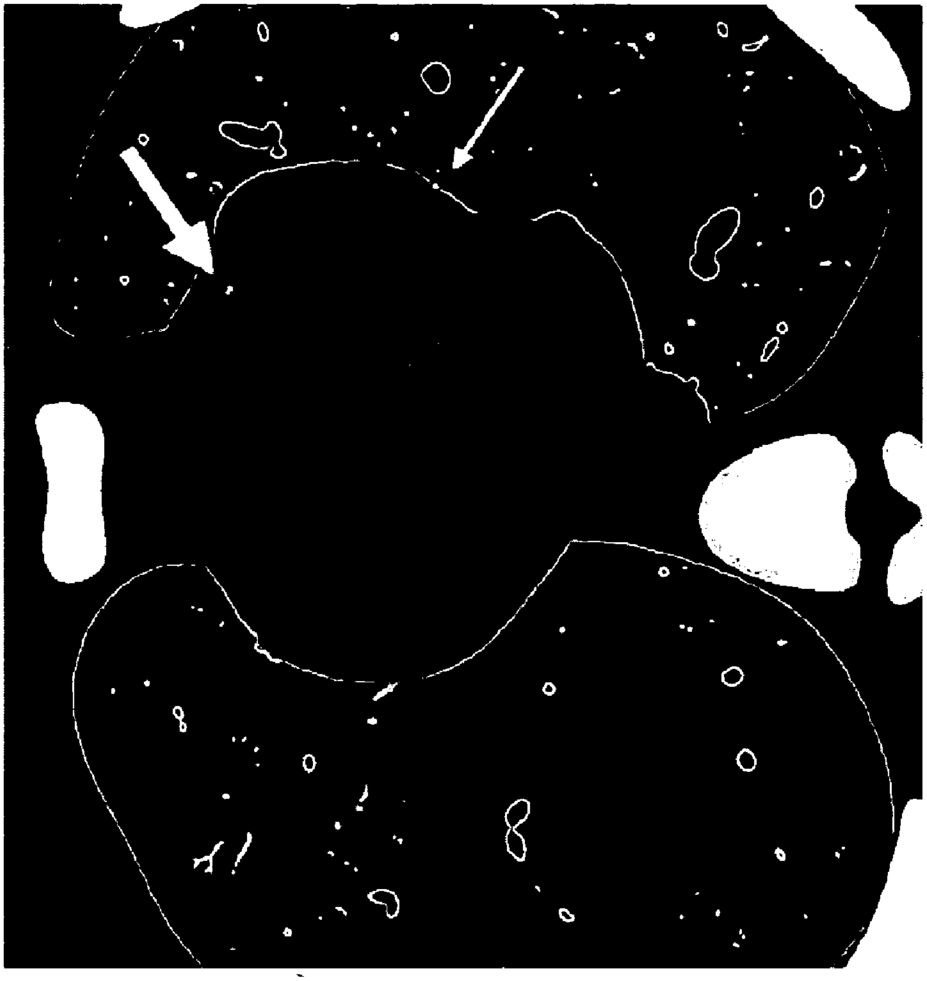

FIG. 130 illustrates an example of the NCAT phantom with coronary plaques in the left anterior descending (LAD) and left circumflex (LCX).

FIGS. 131$a$-$b$ illustrate minimum data and full-scan reconstructions of the uniform circular phantom contracting at an amplitude of −6 cm diameter using a vertical chord orientation. Arrows point to chords whose profiles are plotted in FIGS. 132$a$-$b$ (L: 1 HU/W: 2 HU). ($b$) depicts corresponding backprojection images for the images shown in ($a$).

FIGS. 132$a$-$b$ depict profiles involving vertical chord-based reconstructions obtained from datasets A and B.

FIGS. 133$a$-$b$ depict reduced-scan and short-scan chord-based FBP reconstructions of the uniform circular phantom using vertical chords from full-scan datasets A ($\phi\epsilon[0, 0.25]$) and B ($\phi\epsilon[0, 0.50]$).

FIGS. 134$a$-$d$ depict minimum data and full-scan reconstructions of the NCAT phantom from noisy data acquired during early systole. Chord-based FBP reconstructions are shown using ($a$) minimum standard data, ($b$) minimum opposing data, and ($d$) full-scan data. ($d$) depicts conventional FFBP reconstruction using full-scan data.

FIGS. 135$a$-$d$ depict reduced-scan and short-scan reconstructions of the NCAT phantom from noisy data acquired during early systole. Chord-based FBP reconstruction are shown using ($a$) reduced-scan data with PFSD=48.5%, ($b$) reduced-scan data with PFSD=51.5%, and ($c$) short-scan data (PFSD=64.5%) ($d$) depicts conventional FFBP reconstruction using short-scan data.

FIGS. 136$a$-$f$ illustrate the dependency of motion-induced streak artifacts on cardiac phase. ($a$)-($c$) depict profiles along oblique chords ($\alpha$=26.1°) tangent to the anterior edge of the left ventricle from full-scan data acquired during ($a$) systolic temporal phases $\phi\epsilon[0.0, 0.4]$, ($b$) diastolic phases $\phi\epsilon[0.6, 1.0]$, ($c$) and a stationary phase $\phi$=0.7. ($d$)-($f$) depict difference profiles obtained by subtracting the short-scan profiles labeled as SS from the other respective profiles for data acquired during ($d$) systolic phases, ($e$) diastolic phases, and a ($f$) stationary temporal phase.

FIGS. 137$a$-$c$ illustrate a helical cone-beam reconstruction of the dynamic NCAT phantom by use of the BPF methodology. ($a$) illustrates profiles along two chords tangent to the left ventricle of the heart. ($b$) depicts reconstructed images on converging chords. ($c$) depicts reconstructed image at a transverse slice through the heart (L: 50 HU/W: 400 HU).

FIGS. 138$a$-$b$ shows ($a$) how actual and virtual chords may be defined for circular cone-beam scans, and ($b$) virtual chords for a fragmented helical cone-beam configuration.

Figure 139C:
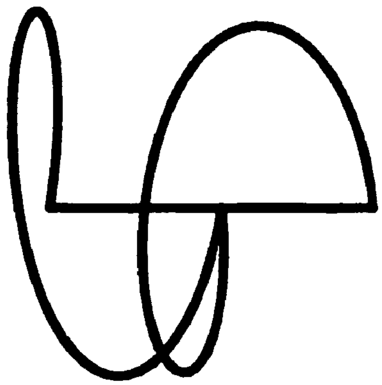
Figure 139B:
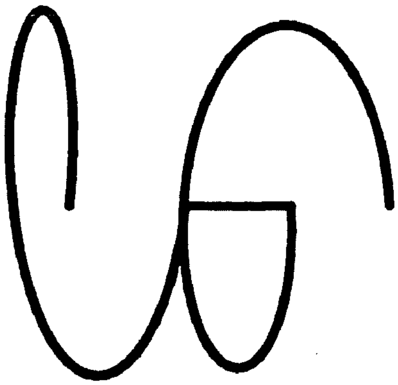
Figure 139A:

FIGS. 139A-C illustrate the reconstructible volume by PI-line based algorithm for a single-turn helical trajectory viewed at an angle of 0° (FIG. 139A), 45° (FIG. 139B), and 90° (FIG. 139C) are shown. The ellipsoid represents an object to be imaged.

Figure 140C:
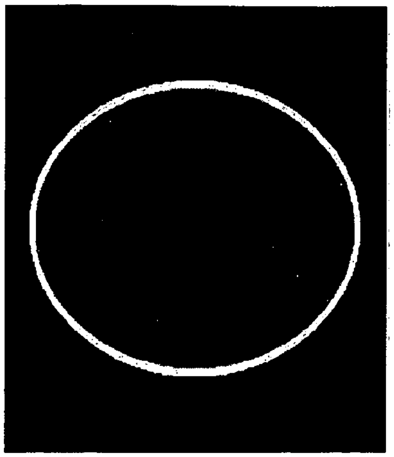
Figure 140B:
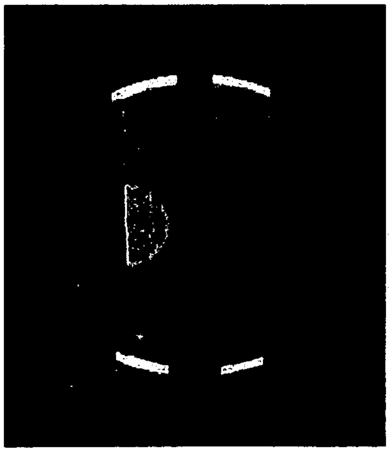
Figure 140A:
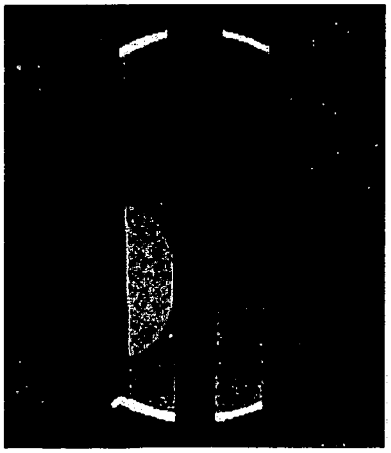

FIGS. 140A-C illustrate reconstructions from a helical cone-beam scan.

Figure 141C:
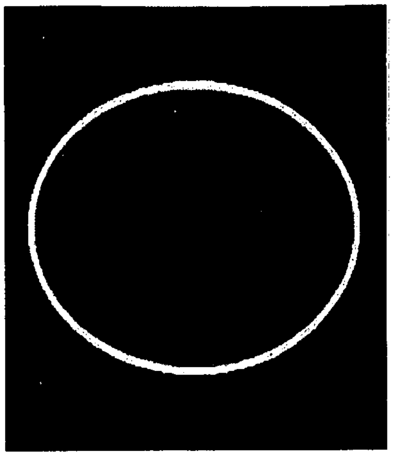
Figure 141B:
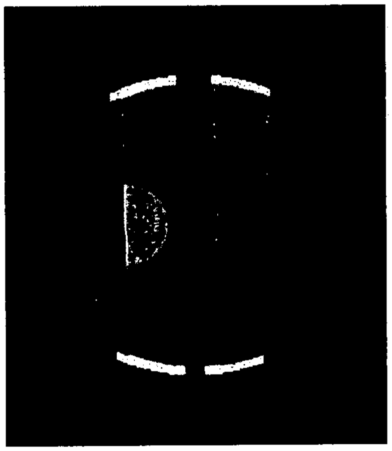
Figure 141A:
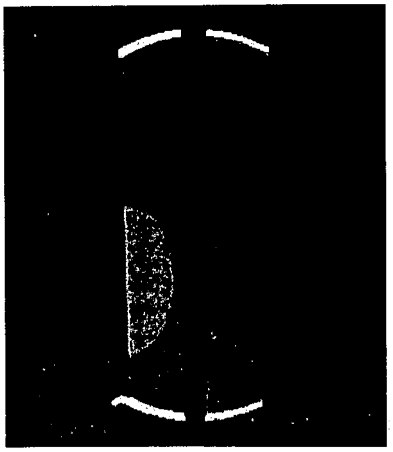

FIGS. 141A-C illustrate reconstructions from a helical cone-beam scan.

Figure 142C:
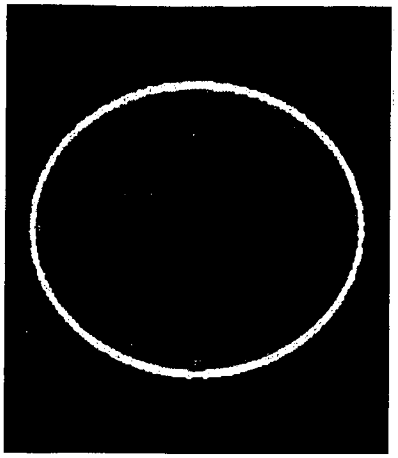
Figure 142B:
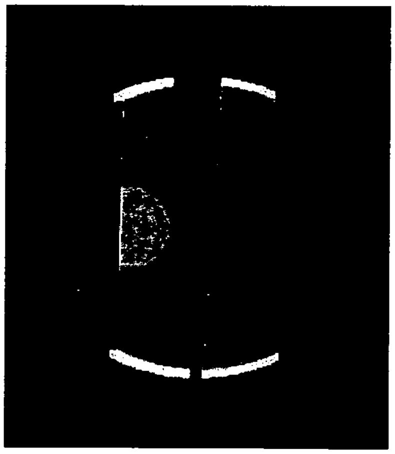
Figure 142A:
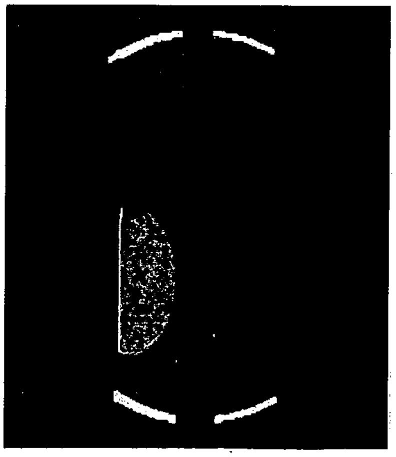

FIGS. 142A-C show slices of the reconstructed volume obtained for the line plus reverse helical trajectory I.

Figure 143C:
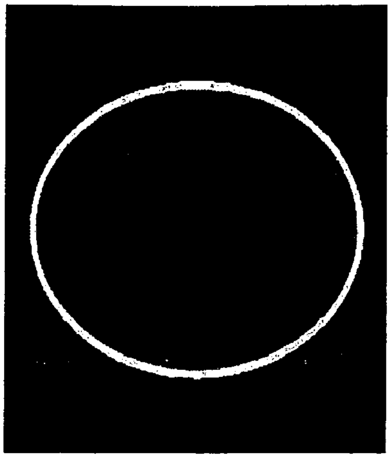
Figure 143B:
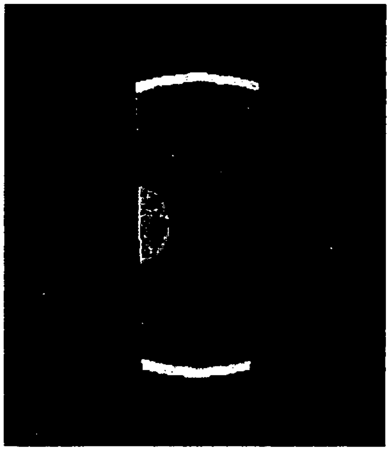
Figure 143A:
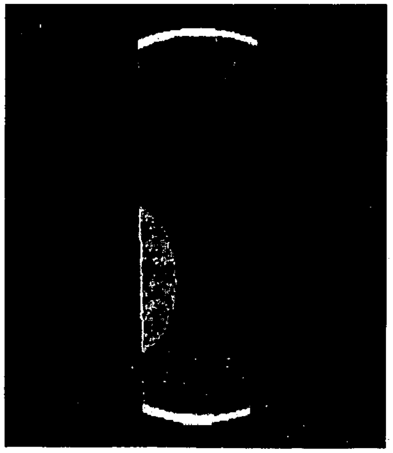

FIGS. 143A-C show slices of the reconstructed volume obtained for the line plus reverse helical trajectory II.

Figure 144C:
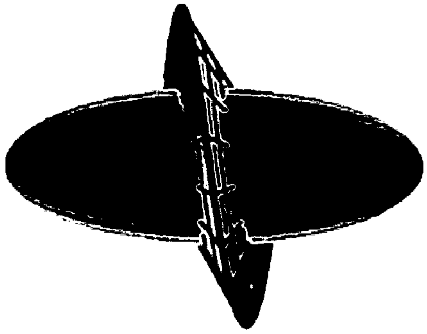
Figure 144B:
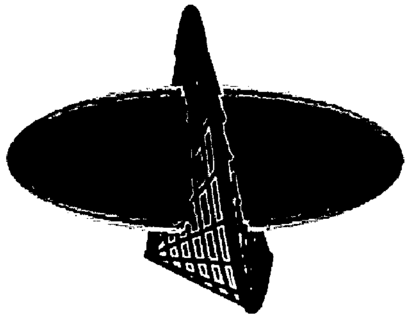
Figure 144A:
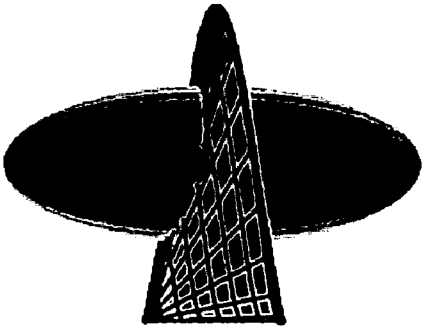

FIG. 144 illustrate reconstructible volume by PI-line based algorithm for a single-turn helical trajectory at an angle of 0° (FIG. 144A), 45° (FIG. 144B), and 90° (FIG. 144C).

Figure 145B:
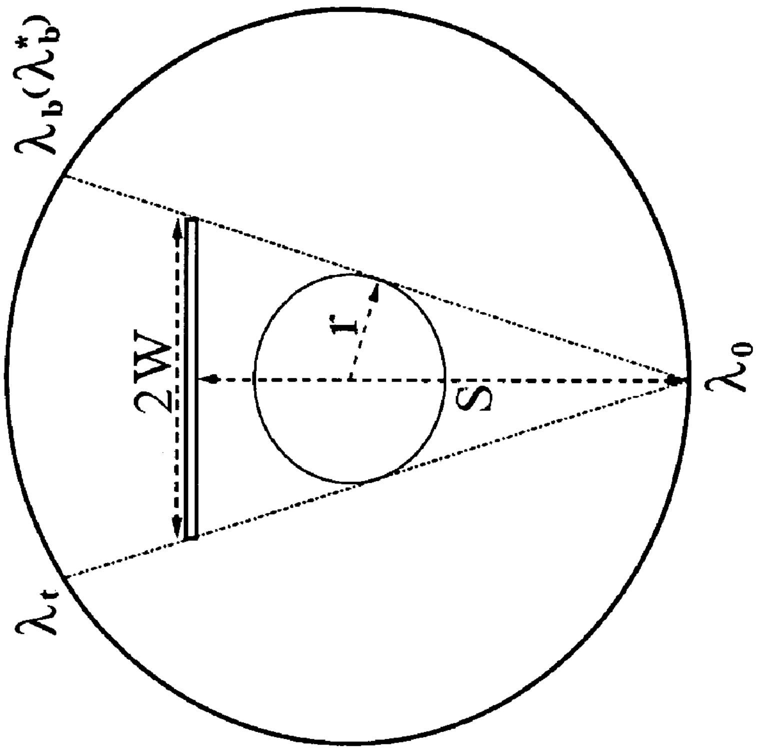
Figure 145A:
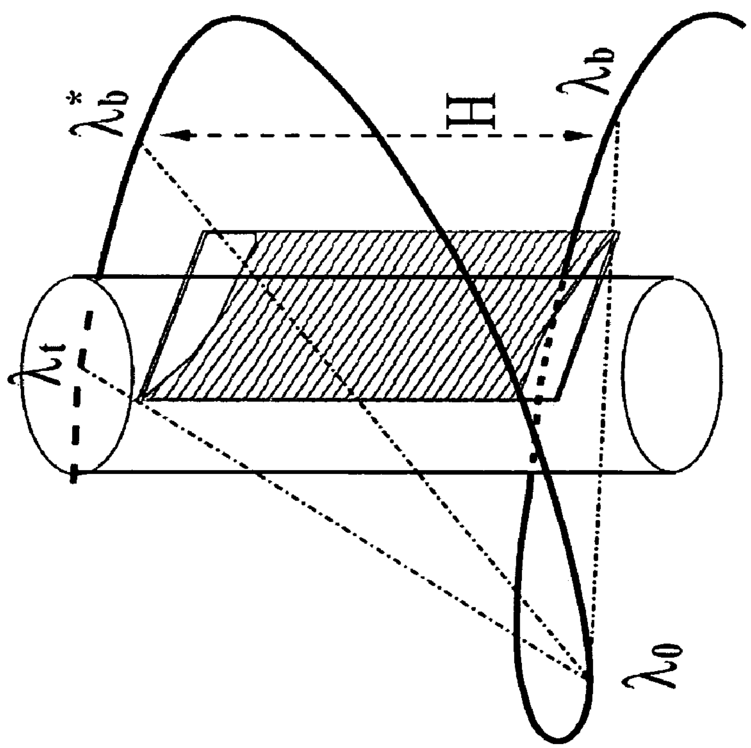

FIGS. 145A-B illustrate how the maximum pitch is determined from a given geometry.

Figure 146B:
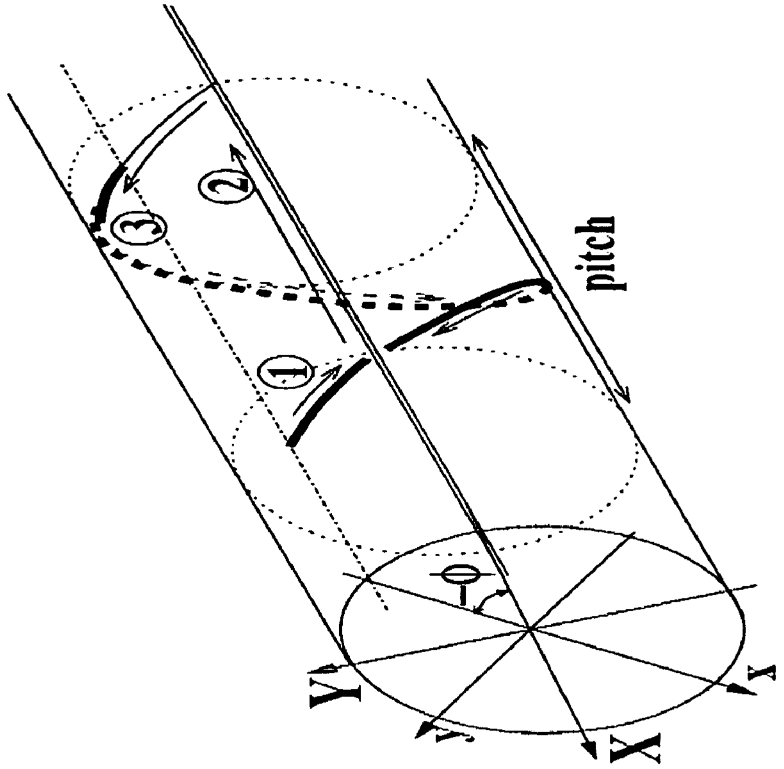
Figure 146A:
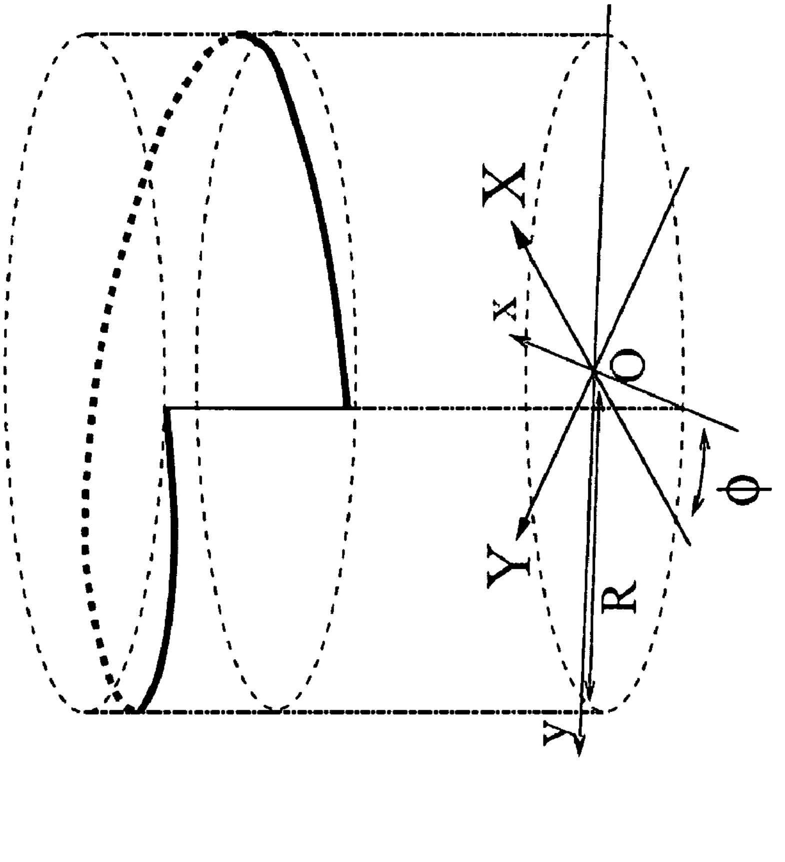

FIG. 146A illustrates how phase angle is defined as the angle between the fixed X-Y frame and the moving x-y frame in which the helical scan starts from its negative x-axis.

FIG. 146B illustrates the gantry rotation is physically limited to a single turn with fixed angular boundaries.

Figure 147D:
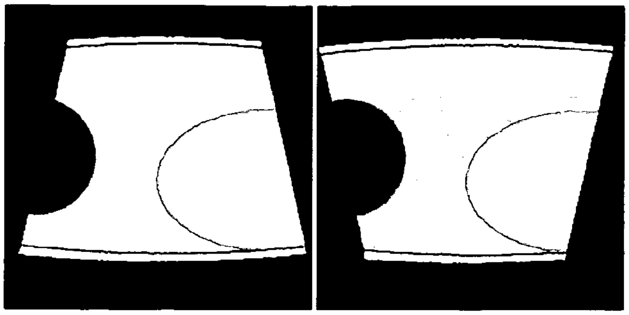
Figure 147C:
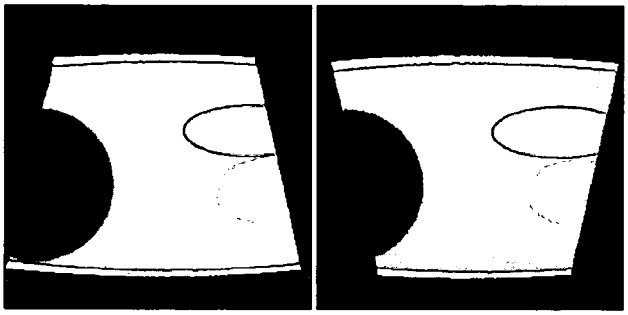
Figure 147B:
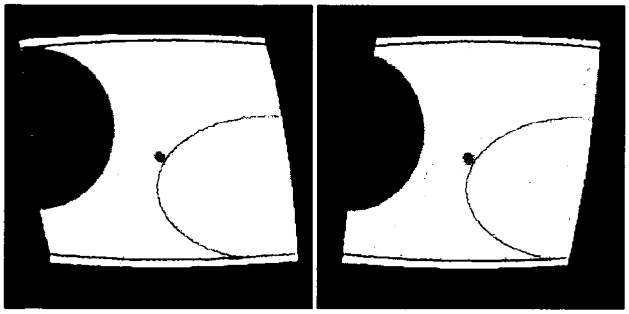
Figure 147A:
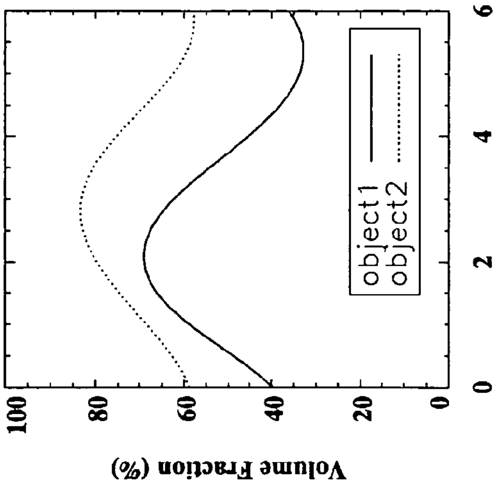

FIG. 147A shows the fraction of the reconstructible volumes of two targeted ROI's as a function of phase angle.

FIGS. 147B-D show 2D slices of the reconstructed volumes; top row for the optimized phase angle and bottom row for the phase angle giving the minimum reconstructible volumes.

DETAILED DESCRIPTION OF THE PRESENTLY PREFERRED EMBODIMENTS

In order to address the deficiencies of the prior art, a method and apparatus is described below for imaging of an object. The imaging of an object may be based on chords that fill at least a portion (such as all, or more than all) of a region of interest (ROI). The ROI may be 2-dimensional, 3-dimensional, or n-dimensional. The chords used for reconstruction may be a connection between two points, such as a straight line or a section of a curve. The points which define the chords may be based on any aspect related to imaging, examples of which may include, without limitation, the trajectory of the source or the Cartesian coordinate system, as described in more detail below. By decomposing at least a portion of the ROI, such as the entire ROI, into chords, the image may be reconstructed based on the set of chords. For example, various methodologies, such as may use the chords to reconstruct a 2-dimensional or 3-dimensional ROI, include backprojection-filtration (BPF), Minimum-data Filtration Backprojection (MFBP), and Filtration Backprojection (FBP). For example, the various points along the chords which fill at least a portion (or all) of the ROI may be exactly reconstructed to image the ROI.

One application of using the chord reconstruction methodology allows for reducing the amount of data acquired and/or processed in order to reconstruct a substantially exact image of the ROI. For example, an ROI which is less than an object support may be substantially exactly reconstructed by acquiring data which is less than required to substantially reconstruct the entire object support, and without requiring processing of data acquired from the entire object support. An object support may be defined as a domain in space within which the object function could be non-zero, and outside of which is certainly zero. As discussed in more detail below, an example of a 2-dimensional object support comprises a cross section of a chest, with the region inside the cross-section of the chest comprising the object support (which may have non-zero data values) and the section outside of the cross-section being outside of the object support (which certainly has a non-zero value). If the ROI comprises a portion of the object support, such as a cross-section of one of the breasts in the section of the torso, data may be acquired and processed which is less than that for the entire object support in order to substantially exactly reconstruct the cross-section of the breast. For example, data associated with support segments which define the ROI may be used to exactly reconstruct the cross-section of the breast. Support segments may be defined as chords with values on the segments that may be non-zero, and values for the object function outside the segments that are certainly zero. Therefore, unlike previous methodologies, data related to the support segments, rather than data for the entire object support, need only be acquired in order to substantially exactly reconstruct the ROI. Similarly, an example of a 3-dimensional object support comprises a section of the torso, such as a volume from the stomach to the neck. If the ROI comprises a sub-volume of the object support, such as a volume of one of the breasts in the section of the torso, data may be acquired and processed which is less than that for the entire object support in order to substantially exactly reconstruct the volume of the breast. In the 3-dimensional example, data may be acquired which is less than the entire torso in order to image the volume of a single breast. For example, data associated with support segments that define the volume of the breast may be obtained in order to image the single breast.

Chords may be used to define at least a part (all, or more than all) of the ROI. Further, the chords may be used to define less than the entire object support. Using various parameters of data acquisition, such as the source trajectory or control of the source or detector, data may be acquired which is less than the data required to image the entire object support. For example, when seeking to create a substantially exact reconstruction of a 2-dimensional cross-section, the method and apparatus in one aspect of the invention does not require data acquisition for the entire contiguous cross-section when only an image of a portion of the cross-section is sought. Similarly, when seeking to create a substantially exact reconstruction of a 3-dimensional volume, the method and apparatus in one aspect of the invention does not require data acquisition for an entire volume when only a portion of the object support is sought to be imaged.

Figure 2A:
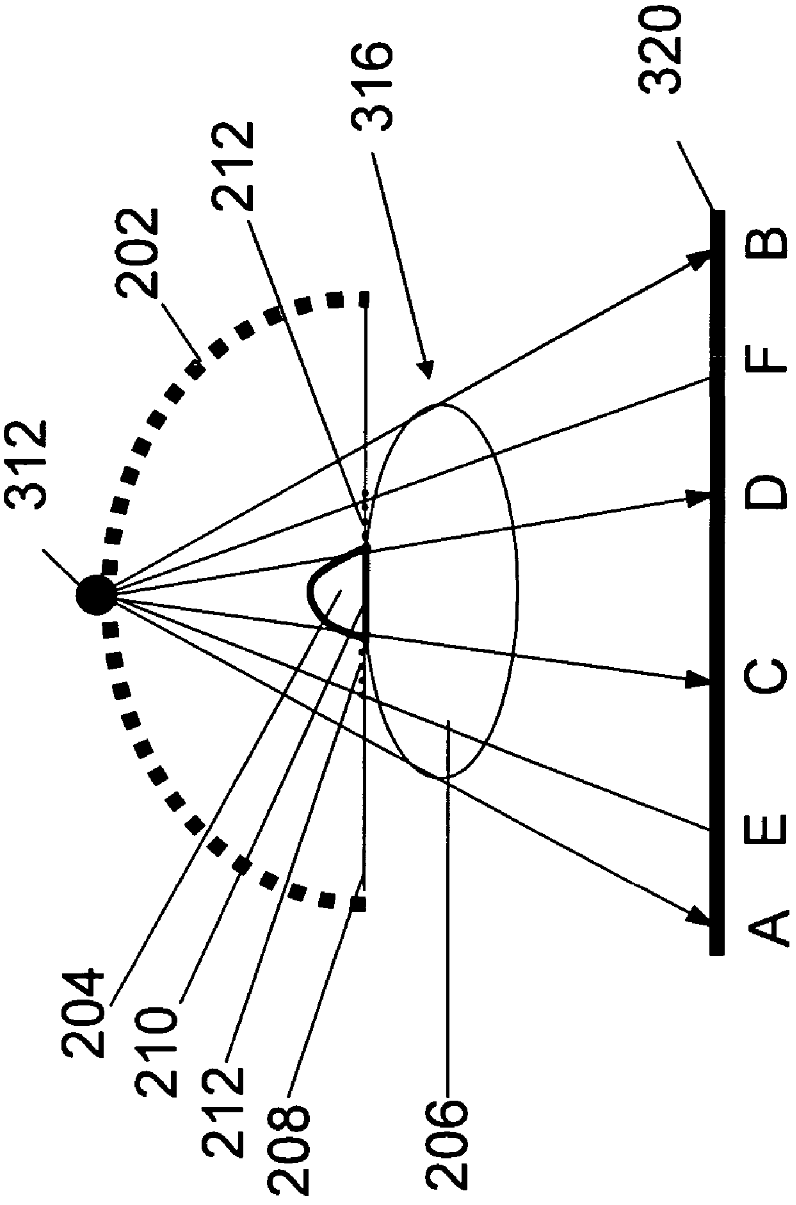
FIGS. 2*a-c* show three cross-sections of a source, object, and detector when scanning a torso to acquire data for use in imaging wherein the data obtained is less than that required to reconstruct a substantially exact image of the entire object support.

In the drawings, where like reference numerals refer to like elements, FIG. 2*a* shows one illustration of a cross section of a source 312, object 316, and detector 320. As discussed in more detail below, the source may travel relative to the object via a trajectory, designated by the dashed line in FIG. 2*a*. A portion 204 of the entire cross-section 206 is sought to be substantially exactly reconstructed (as shown in a bold outline). In prior imaging systems, it was required to obtain a sufficient amount of data to image the entire cross-section 206. Thus, the source trajectory had to be sufficient to obtain data for the entire cross-section, such as a trajectory which encircled cross-section 206. At the various points in the trajectory, the source 312 was required to have a beam wide enough to cover the entire cross-section 206. Further, the detector 320 had to be large enough so that data from point "A" to point "B" was registered. Moreover, the data from point "A" to point "B" had to be processed, at least in part, if only portion 204 was sought to be exactly reconstructed.

By contrast, in one aspect of the invention, if portion 204 is sought to be substantially reconstructed, data less than that sufficient to image the entire cross-section 206 (which includes portion 204 and an additional section) may be obtained. As discussed in more detail below, various methodologies, such as backprojection-filtration (BPF), and Minimum-data Filtration Backprojection (MFBP), do not require data sufficient to image the entire cross-section 206 if portion 204 is sought to be imaged. Rather, data less than that sufficient to image the entire cross-section 206 may be used. For example, data sufficient to image only portion 204 may be used, such as data for support segments which define portion 204.

Because data less than that sufficient to image the entire cross-section is required, various aspects of the data acquisition, such as selection of the trajectory, control of the source or detector, etc. may be modified and may be different from that used in previous imaging systems. For example, the relative trajectory of the source may be selected which acquires data that is less than that sufficient to image the entire cross-section. As shown in FIG. 2*a*, the trajectory is semi-circular in order to generate a set of chords to fill the portion 204 (as discussed in more detail below). These set of chords may be defined as support segments since beyond the support segments, the object function is zero. This is in contrast to a prior art trajectory which would completely encircle cross-section 206. The trajectory shown in FIG. 2*a* is merely an example. Other trajectories may be used, as discussed in more detail below. For example, trajectories which are greater than the semi-circular trajectory shown in FIG. 2*a* but are less than a 360° trajectory may be used. In this manner, data which is less than that sufficient to image the entire cross-section may be obtained. Similarly, if a 3-dimensional image is sought, data which is less than that sufficient to image the entire 3-dimensional volume may be obtained if the sought image is less than the entire 3-dimensional volume.

As another example, the source may be modified so that data acquired by the detector is less than that sufficient to image the entire cross-section. For example, the characteristics of the source may be modified such that data may be acquired at least sufficient to image the ROI, but less than that sufficient to image the entire cross-section. Any characteristic of the source may be modified to affect the data which is detected by the detector. Example characteristics, discussed in more detail below, include illumination coverage (e.g., aperture setting of beam, width of beam, modification of cone beam coverage, etc.); intensity of beam; and spectral distribution of beam. For example, the width of the beam of the source may be modified so that the beam covers the entire portion 204. The detector 320 thus may acquire data between points "C" and "D". Alternatively, the beam width of the source may be in a range that is less than the entire cross-section (e.g., less than from points "A" and "B") to a range that includes portion 204 (e.g., greater than or equal to points "C" and "D.") For example, the beam width may be such that data is acquired at the detector 320 between points "E" and "F."

Figure 2B:
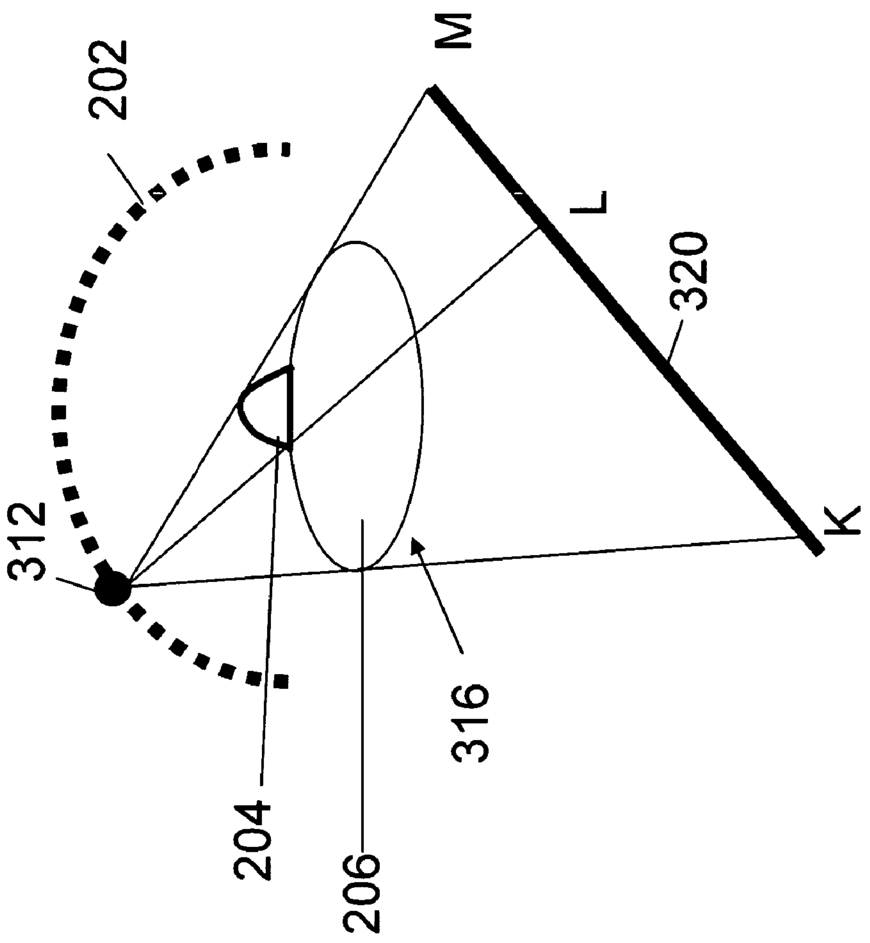

As the source travels relative to the object, the characteristics of the source may remain constant or may change. For example, the characteristics of the source may remain constant such that data may be acquired at least sufficient to image the ROI, but less than that sufficient to image the entire cross-section. Or, the characteristics of the source may change at least once during the trajectory such that data may be acquired at least sufficient to image the ROI, but less than that sufficient to image the entire cross-section. FIG. 2*b* shows a cross section of a source 312, object 316, and detector 320, where source 312 is at a different position than that shown in FIG. 2*a*. As discussed in more detail below, the characteristics of the source selected may depend on the ROI selected. As shown in FIG. 2*b*, the beam width may change such that it may be widened or narrowed such that at least the ROI is included in the beam. Or, the beam width may be selected so that it includes the ROI but is not wide enough to cover the entire cross-section 206. Controlling any aspect of the source may reduce illumination of the object, while still allowing for sufficient illumination of portion 204 for imaging. For example, controlling the source may still allow for data acquisition of support segments which may include portion 204.

Figure 2C:
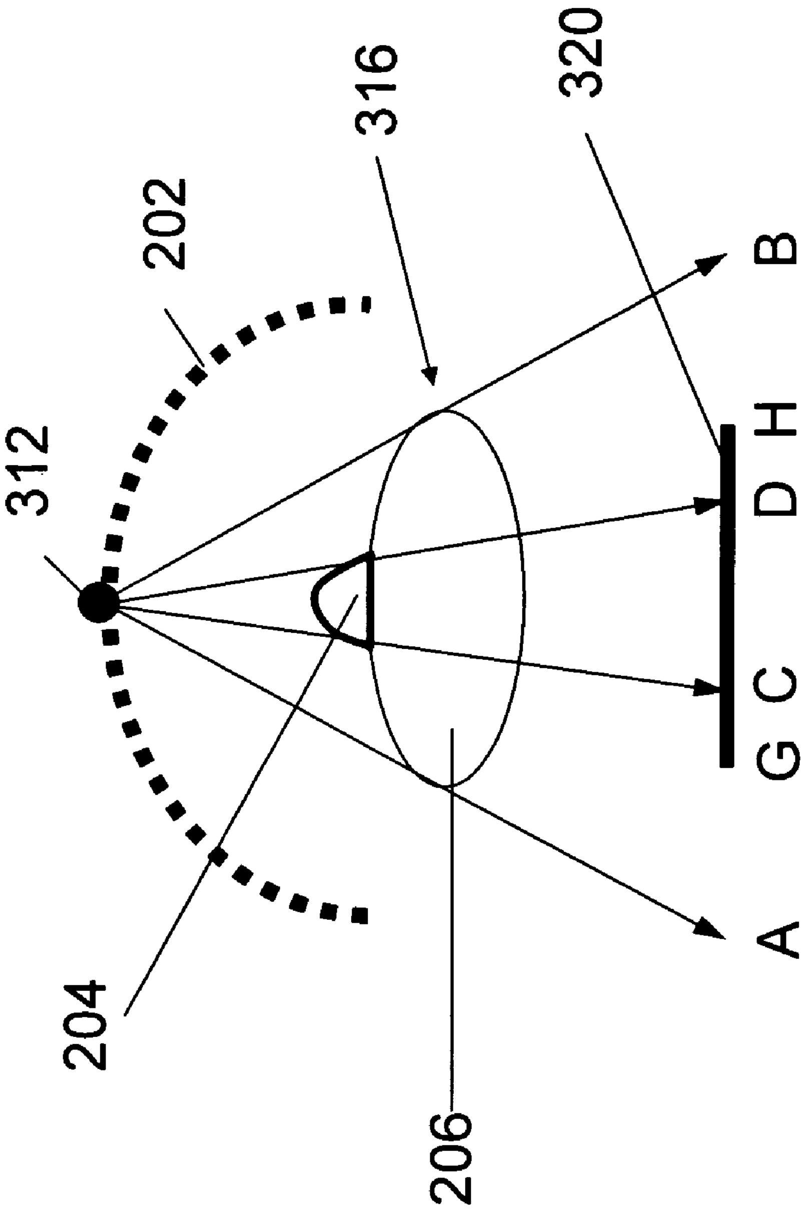

Because the methodologies do not require data sufficient to image the entire cross-section or an entire volume, truncated data (e.g., data which is less than that sufficient to image the entire cross-section or which may image a truncated portion) may be obtained. For example, as shown in FIG. 2*c*, the detector is shown as spanning from point "G" to point "H," which includes data regarding the ROI, between points "C" and "D." Under the prior art methodologies, the detector 320 had to be larger to be able to obtain data sufficient to image the entire cross-section. By contrast, the detector 320 shown in FIG. 2*c* may be smaller, and may be such that a truncated portion of the cross-section is imaged. Further, reduced data (e.g., data which is less than that sufficient to image the entire cross-section) may be obtained. A smaller detector may be advantageous as it may be less expensive to manufacture, and/or, if it is designed to move during data acquisition, may require less energy to move.

As discussed above, prior methodologies acquired additional data which was not required to substantially exactly reconstruct an ROI. This additional data may not improve the reconstruction of the ROI, and may reduce the quality of the reconstruction. For example, if there is motion or noise in the data related to the object support which is outside of the ROI, this data may degrade the image if used to reconstruct the ROI.

Another aspect of the invention is a method and apparatus for processing data to generate an image, such as a substantially exact image. In one embodiment, the image is reconstructed based at least in part on chords. A part, all, or more than all of the ROI may be decomposed into chords. The chords may be defined by two points, with a connection between the two points, such as a straight line or a curve. For example, an entire 2-dimensional or 3-dimensional ROI may be defined by a set of chords. The ROI may be reconstructed based on the chords, such as by a point by point reconstruction along segments of the chords.

The chords used for reconstruction may be defined by any aspect related to imaging. For example, the two endpoints which may define a chord may be based on the source trajectory, as discussed in more detail below. As another example, chords may be defined by the Cartesian coordinate system. Various methodologies may be used to reconstruct the image based on chords defined by the source trajectory including FBP, BPF, and MFBP. In another embodiment, the image may be reconstructed based on data which is less than that sufficient to image an entire portion (e.g., in imaging a portion of a cross-section, data which is less than that sufficient to image the entire cross-section may be used). Various methodologies may be used to reconstruct an image using data which is less than that sufficient to image an entire portion including, without limitation, BPF and MFBP.

Figure 3:
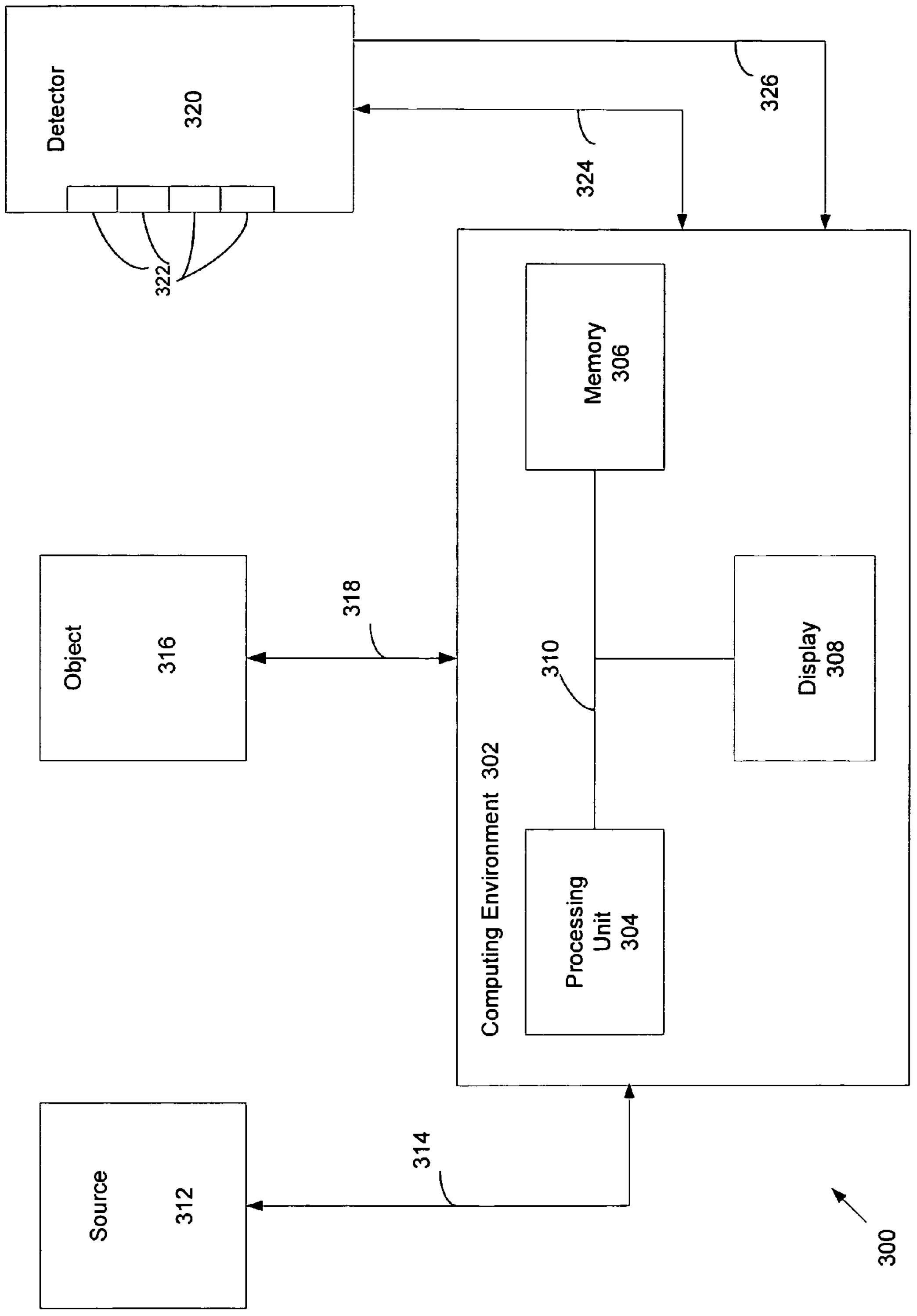
FIG. 3 shows a block diagram of an exemplary imaging system.

FIG. 3 shows a block diagram of an imaging system 300 according to an embodiment of the present invention. The system may include any type of imaging system. Examples of types of imaging systems include, but are not limited to: computed tomography (CT), positron emission tomography (PET), single-photon emission computed tomography (SPECT), magnetic resonance imaging (MRI), electron paramagnetic resonance imaging (EPRI), tomosynthesis (such as if a trajectory is used which creates chords which pass through the portion to be imaged, as discussed below), and wave imaging (such as phase contrast imaging, thermacoutic imaging, and thermoptical imaging). Moreover, the imaging systems may include a single type of imaging, or multiple types of imaging. For example, the imaging system may comprise CT imaging. Alternatively, the imaging system may comprise multiple modality imaging, such as CT and PET imaging in combination. Further, the imaging system may be used in combination with another system. For example, the imaging system may be integrated with a therapeutic system, such as a radiation therapy delivery system. The two systems may work in combination with the imaging system providing imaging for guidance (such as CT imaging) and radiation therapy for treatment.

With reference to FIG. 3, an exemplary imaging system 300 for implementing the invention includes a general purpose computing device in the form of a computing environment 302, including a processing unit 304, a system memory 306, and display 308. A system bus, 310, may couple various system components of the computing environment 302, including the processing unit, 304, the system memory 306, and the display 308. The processing unit 304 may perform arithmetic, logic and/or control operations by accessing system memory 306. For example, the processing unit 304 may control the various system components to acquire data for imaging and may process the acquired data to generate an image. Alternatively, different system processors, or different devices may control the various system components to acquire data for imaging and may process the acquired data to generate an image.

The system memory 306 may store information and/or instructions for use in combination with processing unit 304. For example, the system memory 306 may store computer readable instructions, data structures, program modules or the like for operation of the imaging system 300, including, for example, control of movement of any of the source, object, and detector and control of the functionality of the source and the detector, as discussed below. Further, the system memory 306 may store data obtained from detector 320 and may process the data for display on the display 308, as discussed in more detail below. The system memory 306 may include volatile and non-volatile memory, such as random access memory (RAM) and read only memory (ROM). It should be appreciated by those skilled in the art that other types of computer readable media which can store data that is accessible by a computer, such as magnetic cassettes, flash memory cards, random access memories, read only memories, and the like, may also be used in the exemplary computer environment. A user may enter commands and/or information, as discussed below, into the computing environment 302 through input devices such as a mouse and keyboard, not shown. The commands and/or information may be used to control operation of the imaging system, including acquisition of data and processing of data.

FIG. 3 further shows source 312 communicating with computing environment 302 via line 314. Line 314 may comprise a control line whereby the processing unit may control at least one characteristic of source 312. Characteristics of the source which may be controlled comprise any aspect of the source including, but not limited to: illumination coverage (e.g., aperture setting of beam, width of beam, modification of cone beam coverage, etc.); intensity of beam; and spectral distribution of beam. Source 312 may be stationary or may move relative to any one, or both, of object 316 and detector 320. Line 314 may also control movement of source 312, such as by sending commands to a motor (not shown) to move all or a part of source 312. For example, if the source 312 is an X-ray tube, the motor may move the entire X-ray tube relative to one, or both of, object 316 and detector 320. Alternatively, the X-ray tube may remain stationary with a reflector revolving using the motor. In this manner, the beam emanating from the X-ray tube may be moved by bouncing the beam off the revolving reflector.

The source 312 may comprise any device which generates any signal that may be received from detector 320. The source 312 selected for imaging system 300 may depend on the type of imaging performed by imaging system 300. For example, source 312 may generate electromagnetic radiation in any frequency range, such as gamma rays, x-rays, visible light, microwaves, and radio/tv waves. Specifically, source 312 may comprise an X-ray source and generate X-rays or may comprise a radio frequency (RF) source and generate radio waves. Source 312 may also generate other types of signals such as magnetic fields, mechanical waves (e.g., sound waves), heat, particle (e.g., electron, proton, neutron), or the like. Though depicted in imaging system 300, certain types of imaging systems do not require a source (such as source 312). For example, PET scanning does not require an external source, as discussed in more detail below.

FIG. 3 also shows object 316. Object 316 may comprise anything which is capable of being scanned, such as a living organism (e.g., human or animal) or a non-living object (e.g., a piece of luggage, a cargo container, food, an ocean, underground the earth, etc.). The position of the object may be stationary or may move relative to any one, or both, of source 312 and detector 320. Line 318 may control movement of object 316, such as by sending commands to a motor (not shown) to move object 316. Any part, or all, of object 316 may be imaged using imaging system 300. Further, the object may ingest or be injected with a substance, such as a contrast agent, which may assist in imaging a part or all of object 316. As shown in FIG. 3, source 312 is external to object 316. Alternatively, source 312 may be internal to object 316.

FIG. 3 further shows detector 320 communicating with computing environment 302 via lines 324 and 326. Line 324 may comprise a control line whereby the processing unit may control at least one characteristic of detector 320. Characteristics of the detector which may be controlled include any aspect of the detector including, but not limited to activation/deactivation of sections 322 of the detector or sensitivity of the detector. Line 326 may comprise a data line whereby data sensed from the detectors may be sent to computing environment 302 for processing by processing unit 304, as discussed below. Detector 320 may comprise any type of detector which senses any datum, such as electromagnetic radiation from any frequency range (such as X-rays), magnetic fields, sound waves, heat, or the like. For example, for a 2-dimensional detector (flat-panel imager), detector 320 may comprise one row of detectors for fan beam geometry, four rows of detectors for quasi-fan-beam geometry, or more than four rows of detectors for cone-beam geometry. Detector 320 may be stationary or may move relative to any one, or both, of source 312 and object 316. Line 324 may control movement of detector 320, such as by sending commands to a motor (not shown) to move all or a part of detector 320. As shown in FIG. 3, detector 320 is external to object 316. Alternatively, detector 320 may be internal to object 316. Thus, both source 312 and detector 320 may be internal or external to the object. Moreover, source 312 may be internal and detector 320 may be external to object 316, or source 312 may be external and detector 320 may be internal to object 316. For example a dental image of a patient may be acquired with an external source and a detector held in the mouth of a patient.

Various scans of the object may be generated based on the movement of one, some or all of source 312, object 316, and detector 320. For example, a line scan may be generated by subjecting object 316 to translational movement while keeping source 312 and detector 320 stationary. As another example, a circular scan may be generated by rotating source 312 and detector 320 in synch while keeping object 316 stationary. In still another example, a helical scan may be generated by rotating source 312 and detector 320 in synch while subjecting object 316 to translational movement. Line, circular and helical scans are merely exemplary. Other scans may be generated, as discussed in more detail below.

The object 316 may include a region of interest (ROI) for imaging by imaging system 300. The ROI may include a 2-dimensional cross-section or may be a 3-dimensional volume of the object. For example, a 2-dimensional image may comprise a projection or a transverse image. As another example, a 3-dimensional image may comprise a sagittal or a coronal image. Further, the ROI may be a single portion, multiple portions, or all of object 316. For example, the ROI may be an entire volume of a single breast (either right or left breast) or may be an entire volume of both the right and left breast. Alternatively, the ROI may be a cross-section of a single breast.

Selecting a Trajectory for Imaging

As discussed above, typical imaging systems required that data be acquired for an entire object support and that all the acquired data be processed, even if an image of only a subsection of the object support is sought. In one aspect of the invention, if an image of a subpart of an object support is sought (such as an ROI which is a part of a cross section or a volume), the relative trajectory of the source may be selected which acquires data that is less than that sufficient to image the entire object support (such as the entire cross-section or entire volume), but which acquires data that is at least sufficient to image the ROI. For example, using a typical imaging system, if the ROI were a single breast, a trajectory would be selected which would completely encircle the entire chest region. For example, if a helical scan were used, the source would rotate an entire 360° around the chest region in order to obtain data regarding a single breast. This results in a significant amount of over-scanning of the object and in unnecessary over-exposure of the object to source 312. This over-exposure may be problematic if one seeks to limit the amount of exposure to source 312, such as may be the case with an X-ray source. Over-scanning may also be undesirable if the speed of acquisition is a priority.

In one aspect of the invention, a suitable trajectory (or multiple suitable trajectories) of the source relative to the object may be selected based on the ROI. A suitable trajectory (or multiple suitable trajectories) may include one wherein a set of support segments of chords defined by the trajectory fills the ROI. If multiple trajectories are suitable, an optimal trajectory may be selected from the multiple trajectories depending on certain factors, as discussed below.

Figure 4A:
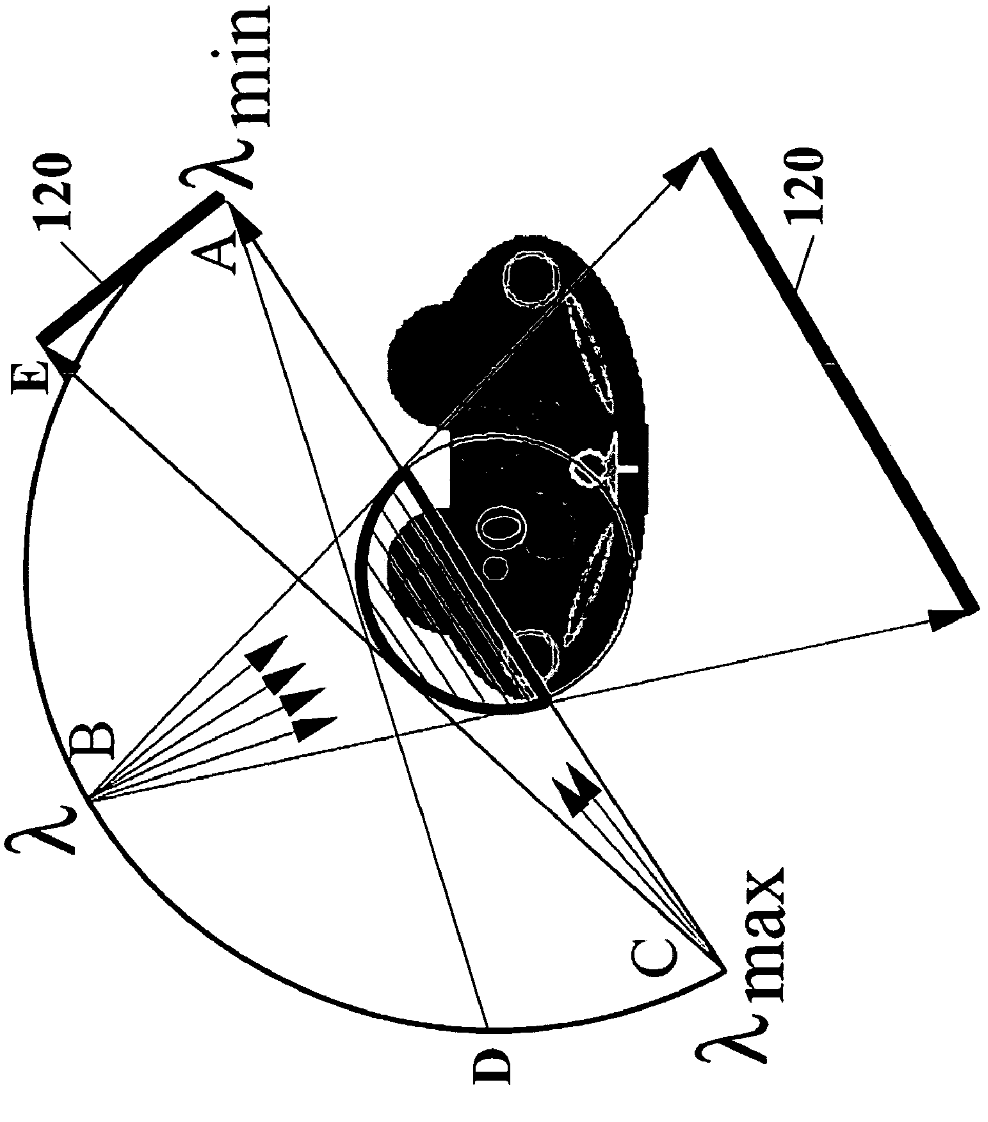
FIG. 4*a* shows a cross-section of a chest including breasts with a trajectory from "A" to "C."

The ROI may be 2-dimensional or 3-dimensional. One example of a 2-dimensional ROI (a cross-section of a single breast) and a suitable trajectory from point "A" to point "C" is shown in FIG. 4*a*. FIG. 4*a* shows a diagram of a chest cross-section including breasts. The region enclosed by the thick curve indicates the peripheral ROI for imaging. The parallel line segments in the ROI depict the support-segments, which are the portions of the parallel PI-line segments within the ROI. As shown in FIG. 4*a*, the values of the object function along the supports segments may be non-zero, whereas the values outside the supports segments are certainly zero. Points on the "A" to "C" trajectory may define chords. Specifically, a chord may be defined as a straight line connecting two points along the trajectory. In the example shown in FIG. 4*a*, one chord is defined by points "A" and "C" on the trajectory. As shown on this "A-C" chord, at least a part of the chord (in bold in FIG. 4*a*) is a segment of the chord that passes through the object to be scanned. A specific trajectory is suitable for imaging if segments of chords defined by the trajectory fill the ROI.

Multiple sets of chords may define a single ROI. In the 2-dimensional example shown in FIG. 4*a*, the "A" to "C" trajectory is suitable since there is a set of support segments, defined by chords from the trajectory, which fill the area of the region of interest. For example, a set of chords, each parallel to the "A" to "C" chord may fill the area of interest, as shown in FIG. 4*a*. Another example is a set of chords with the first point of each chord being defined by point "A" on the trajectory and the second point of each chord being defined in a range from point "C" to point "D." Another example of a set of chords that fills the area of interest is with the first point of each chord being defined by point "C" on the trajectory and the second point of each chord being defined in a range from point "A" to point "E." Thus, multiple sets of chords may fill an area of interest, depending on the points selected along the trajectory.

Figure 4B:
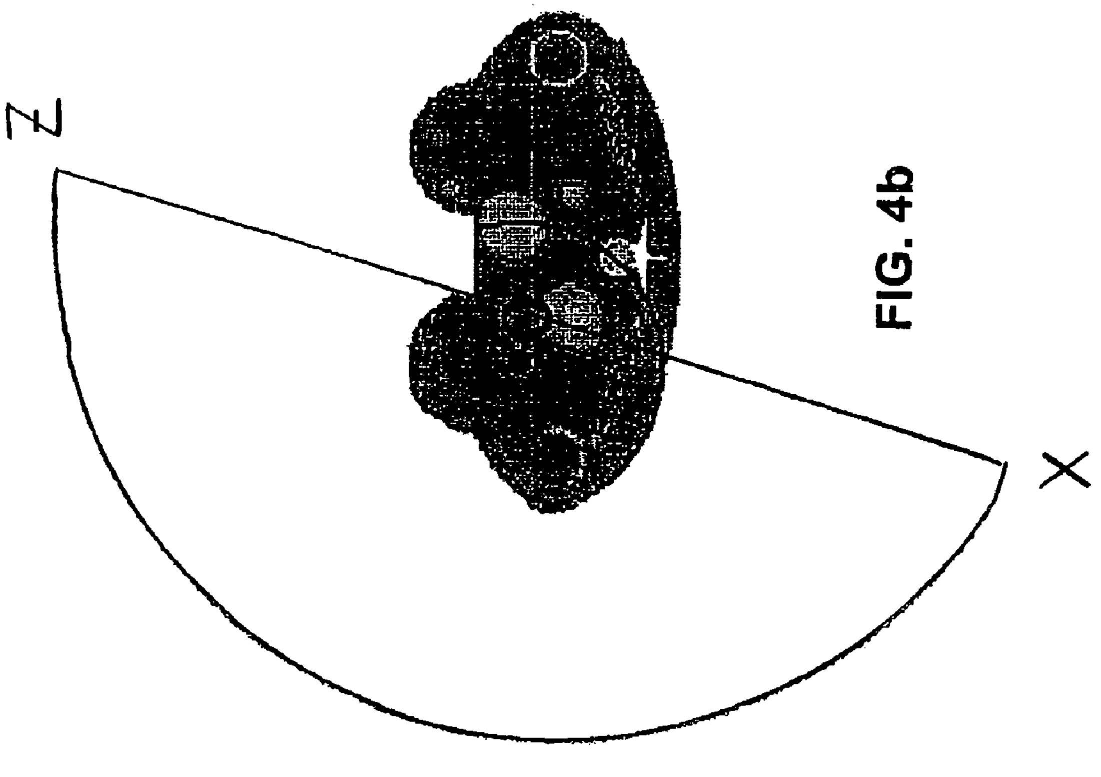
FIG. 4*b* shows a cross-section of a chest including breasts with a trajectory from "X" to "Z."

Further, more than one trajectory may be suitable for an ROI. Another example of an ROI of the single breast, with a suitable trajectory from point "X" to point "Z," is shown in FIG. 4*b*. Similar to the trajectory shown in FIG. 4*a*, the "X" to "Z" trajectory may define a set of segments of chords that fills the ROI of the single breast.

One may select a preferred trajectory from the multiple suitable trajectories based on a single criterion or multiple criteria. Examples of criteria include, but are not limited to: (1) reducing or minimizing exposure to non-ROI portions from the source; and (2) reducing imaging effort. First, there are instances where exposure from the source should be reduced or minimized. For example, in CT scanning which uses an X-ray source, the trajectory may be selected so that the exposure of the source's X-rays to the regions outside of the region of interest (non-ROI) is reduced or minimized. FIGS. 4*a* and 4*b* provide examples of trajectories that are suitable for an ROI of a single breast. One manner in which to evaluate the multiple suitable trajectories is to determine the amount of exposure of the source to non-ROI. In the 2-dimensional examples of FIGS. 4*a* and 4*b*, the amount of exposure may be determined by calculating the area outside of the ROI which is exposed to source (i.e., the non-ROI which is subjected to the source). Comparing the figures, trajectory "X" to "Z" exposes more non-ROI area to the source than trajectory "A" to "C." Therefore, trajectory "A" to "C" is considered a better trajectory than trajectory "X" to "Z" based on this single criterion.

The 2-dimensional examples shown in FIGS. 4*a* and 4*b* are merely for illustrative purposes. In a 3-dimensional region of interest, exposure of the source to a volume (as opposed to an area) of the object may be calculated. A trajectory with a smaller non-ROI volume may be preferred over a trajectory with a greater non-ROI volume. Further, in the example given for FIGS. 4*a* and 4*b*, the non-ROI areas are given equal weight. Though, if a part of an object may be considered particularly sensitive to exposure by the source, exposure of the source to that sensitive part of the object may be accounted for by assigning a greater weight. For example, a part of the object which is more sensitive to exposure to the source may be weighted greater than other less sensitive parts of the objects.

Further, a trajectory may be selected from multiple suitable trajectories based on imaging effort. Examples of imaging effort include, but are not limited to, imaging time and ability to image. For example, a trajectory which requires a greater time to obtain the data may be less desirable than a trajectory which may obtain the data quicker. As another example, depending on the configuration of the object, certain trajectories may be more difficult to image.

Trajectories may be selected to scan for an ROI for a specific object or may be selected to scan for an ROI for a generalized object. For example, a trajectory may be selected to scan a right breast for a specific patient. The trajectory may thus be tailored for the shape of the right breast of the specific patient to meet certain factors, such as minimizing exposure to source. Alternatively, a trajectory may be selected for scanning a single breast of any patient (or a group of patients with a certain weight, height, etc.). Thus, logic may be used to determine a preferred trajectory for an ROI for a generalized object, and the trajectory may thereafter be programmed into imaging system 300 so that the trajectory need not be re-calculated for every patient. In another embodiment, if a trajectory is fixed, the method and system may determine which ROI may be imaged using the fixed trajectory. Specifically, an ROI or multiple ROIs may be determined that may be imaged from data generated with a source traveling via the fixed trajectory. For example, for a fixed trajectory, portions of an object which allows for support segments to fill a region may be identified so that the region may be imaged.

The following is an example of trajectories which may be used for imaging. Let the support of the image function $f(\vec{r})$ under consideration be confined within a cylinder of a radius $\rho_s$ and height $z_s$, and let the central axis of this cylinder coincide with the z-axis of the fixed-coordinate system. One may use $\vec{r}$ to denote a spatial vector, which may be written as $\vec{r}=(x, y, z)$ in the fixed-coordinate system. Therefore, one may assume that:

$$f(\vec{r})=0 \quad x^2+y^2>\rho_s^2,\ z<0,\ \text{or}\ z>z_s. \tag{1}$$

Consider a general scanning trajectory displayed in FIGS. 4*a* and 4*b*, which is assumed to be characterized by a vector $\vec{r}_0(s)$ that is a function of the path length s, defined implicitly by:

$$\left|\frac{d\vec{r}_0(s)}{ds}\right| = 1. \tag{2}$$

The path length provides one parameter with which points along the trajectory can be identified. The reconstruction theory discussed in detail below may make use of derivatives of the source position along the trajectory, and employing the path length as a parameter, may avoid coordinate singularities and multivaluedness. In the fixed, Cartesian coordinate system, one may write $\vec{r}_0(s)=(x_o(s), y_0(s), z_0(s))$. The distance between a point on the trajectory and the z-axis is thus given by:

$$\rho(s)=\sqrt{x_0^2(s)+y_0^2(s)} \tag{3}$$

and the distance from the origin to a point on the trajectory may be given by:

$$R(s)=\sqrt{x_0^2(s)+y_0^2(s)+z_0^2(s)} \tag{4}$$

The detector, identified as element 320 in FIG. 3, is specified with a flat-panel geometry and assumed to rotate and translate so that the line from the source spot to the midpoint of the detector remains perpendicular to the detector plane. As discussed above, detector 320 and source 312 may rotate and translate with one another. Though the detector has a flat-panel geometry in the present example, detector 320 may be curved, or may comprise sections 322 which may move independently of one another. Further, the distance S(s) between the source spot and the detector plane may vary with path length.

Figure 5B:
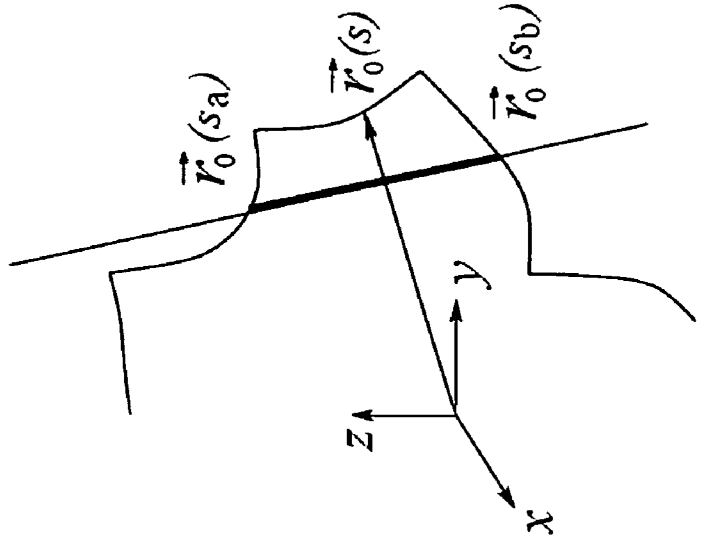
FIG. 5*b* is a side view of the general trajectory $\vec{r}_0(s)$ shown in FIG. 5*a* with a chord-line shown.
Figure 5A:
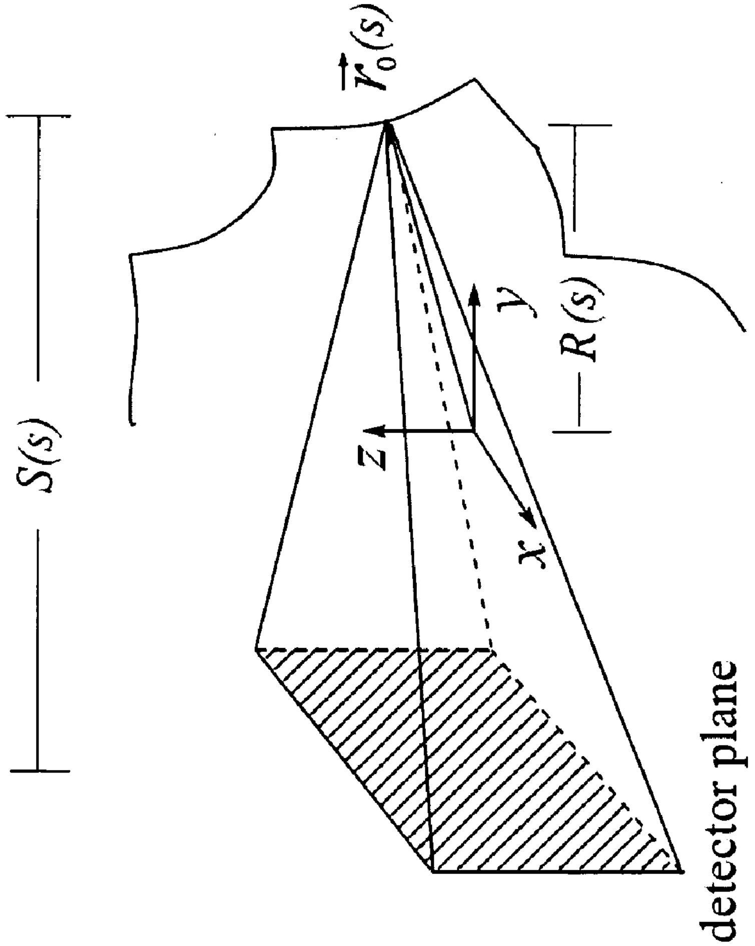
FIG. 5*a* is a side view of a general trajectory $\vec{r}_0(s)$ and a detector plane.

Referring to FIG. 5*a*, there is shown a general trajectory characterized by $\vec{r}_0(s)$. R(s) (or S(s)), shown in FIG. 5*a*, may denote the distance between point s on the trajectory and the z-axis (or the detector plane). Referring to FIG. 5*b*, there is shown a straight line (in bold) intersecting the trajectory at $s_a$ and $s_b$. This straight line is an example of a chord-line, and the portion of the chord-line between $\vec{r}_0(s_a)$ and $\vec{r}_0(s_b)$, which is indicated as the bold thick line segment, may be referred to as the chord. The general trajectory shown in FIGS. 5*a* and 5*b* includes a finite number of kinks at which it may not differentiable. Without the loss of generality, it is assumed that $s_a \leqq s_b$. The segment of the trajectory, $s\in[s_a, s_b]$ may be referred to as a trajectory segment. One may use the following equation to denote the direction of the chord-line:

$$\hat{e}_c = \frac{\vec{r}_0(s_b) - \vec{r}_0(s_a)}{\left|\vec{r}_0(s_b) - \vec{r}_0(s_a)\right|} \tag{5}$$

Any point $\vec{r}$ on the chord-line may be expressed as:

$$\vec{r} = \frac{1}{2}\left[\vec{r}_0(s_a) + \vec{r}_0(s_b)\right] + x_c\hat{e}_c, \quad x_c \in \mathbb{R} \tag{6}$$

Further, one may refer to the segment on the chord-line between points $\vec{r}_0(s_a)$ and $\vec{r}_0(s_b)$ as the chord. A point $\vec{r}$ on the chord may thus be expressed as:

$$\vec{r}=\tfrac{1}{2}[\vec{r}_0(s_a)+\vec{r}_0(s_b)]+x_c\hat{e}_c,\ x_c\in[-l,l], \tag{7}$$

where $l=\tfrac{1}{2}|\vec{r}_0(s_b)-\vec{r}_0(s_a)|$ denotes one half of the chord length. In the example of a helical trajectory, the path length s is proportional to the rotation angle λ, and when the $s_a$ and $s_b$ are within one turn, the chord-line and the chord can be understood as a PI-line and PI-line segment, respectively. Though, other types of trajectories may be used. And, other types of chords, such as multiple PI-lines, may be used.

Figure 6:
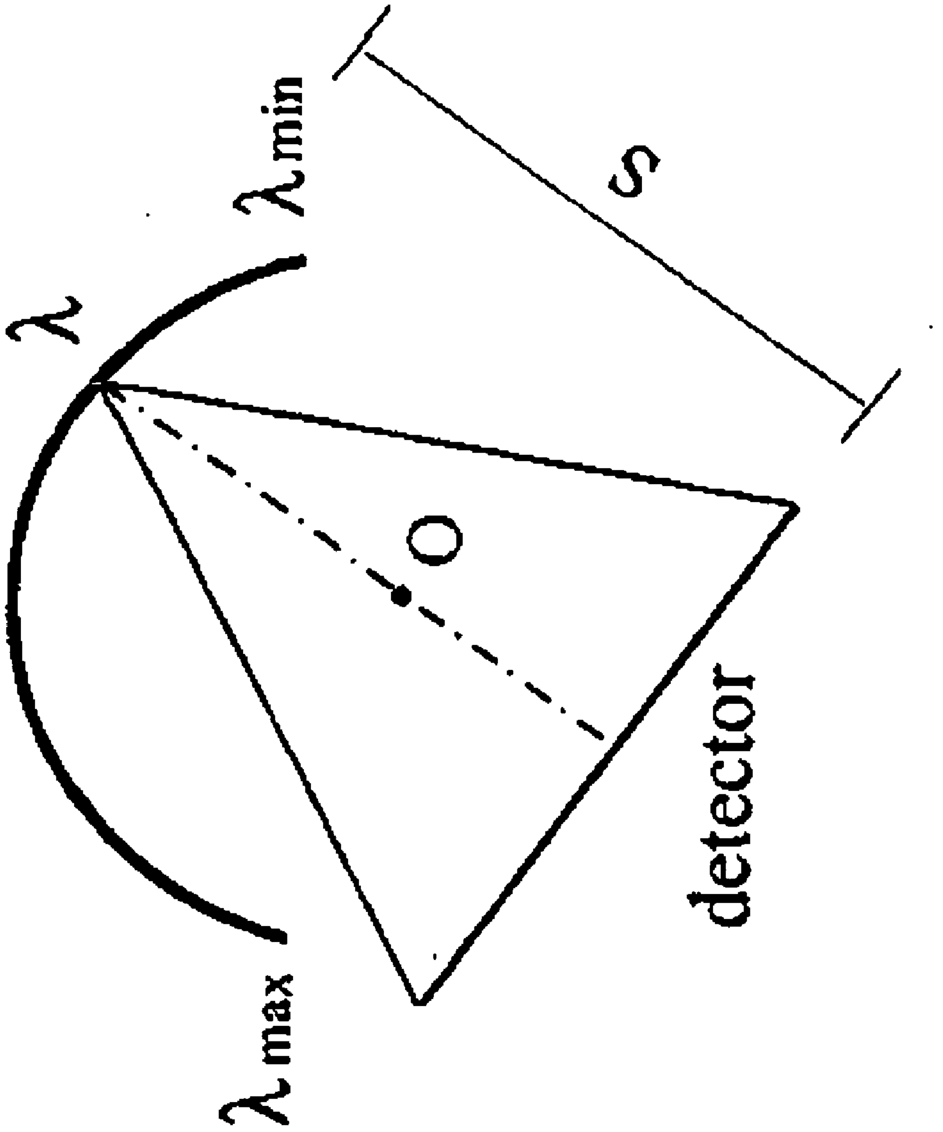
FIG. 6 is a schematic of a fan-beam configuration with the middle line of the fan-beam passing through a center of rotation O.

The concept of chords may be applied to specific trajectories. For example, PI-lines may be used for image reconstruction of a fan-beam scan over a portion of a circular source trajectory, as shown in FIG. 6. Specifically, FIG. 6 shows a schematic of a fan-beam configuration. The starting angle for the source trajectory is designated as $\lambda_{min}$ and the ending angle as $\lambda_{max}$. The middle line of the fan beam, shown in FIG. 6, passes through a center of rotation O and the distance between the source and the detector is designated as S.

Figure 7A:
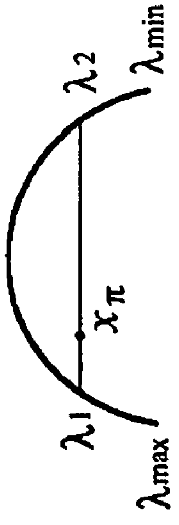
FIG. 7*a* shows a chord-segment joining two points, labeled $\lambda_1$ and $\lambda_2$ on the source trajectory with a starting angle of $\lambda_{min}$ and an ending angle of $\lambda_{max}$.

The PI-line segment is a straight line segment joining two points labeled by the scanning angles $\lambda_1$ and $\lambda_2$, as shown in FIG. 7*a*. $x_\pi$ is used to denote the coordinate of a point on the PI-line segment with $(x_\pi, \lambda_1, \lambda_2)$ as the PI-line coordinates. The region $\Omega_R$ enclosed by the source trajectory and the PI-line segment specified by $\lambda_{min}$ and $\lambda_{max}$, shown in FIG. 7*b*, may be completely filled by non-intersecting PI-line segments. One example of non-intersecting PI-line segments which completely fill region $\Omega_R$ is displayed as a set of parallel lines in FIG. 7*b*. Therefore, each point within region $\Omega_R$ may belong to one and only one of these parallel PI-line segments. Further, the relationship between the fixed coordinates (x, y) and the PI-line coordinates ($x_\pi$, $\lambda_1$, $\lambda_2$) is determined by:

$$x=R[(1-t)\cos\lambda_1+t\cos\lambda_2] \quad (8)$$

$$y=R[(1-t)\sin\lambda_1+t\sin\lambda_2] \quad (9)$$

where $t\in[0, 1]$ is related to $x_\pi$ through:

$$x_\pi=(t-\tfrac{1}{2})|\vec{r}_0(\lambda_1)-\vec{r}_0(\lambda_2)| \quad (10)$$

Therefore, $x_\pi=0$ indicates the middle point of the PI-line segment. In the fixed-coordinate system, the source trajectory $\vec{r}_0(\lambda)$ may be expressed as:

$$\vec{r}_0(\lambda)=(R\cos\lambda, R\sin\lambda)^T \quad (11)$$

It may also be beneficial to introduce a rotation-coordinate system {u, w} for the present example, for characterizing data on the detector. It may be assumed that $\vec{r}_0(\lambda)$ is the origin of the rotation-coordinate system. Referring to FIG. 7*c*, there is shown a fixed-coordinate system (x, y) with its origin on the center of rotation of the source, the rotation-coordinate system {u, w} with its origin on the source point, and a radius R of the source trajectory. For a rotation angle λ in the fixed-coordinate system, as shown in FIG. 7*c*, the unit vectors along the u- and w-axis may be written as $\hat{e}_u(\lambda)=(-\sin\lambda, \cos\lambda)^T$ and $\hat{e}_w(\lambda)=(\cos\lambda, \sin\lambda)^T$. Furthermore, the fixed and rotation coordinates, (x, y) and {u, w}, of a point within $\Omega_R$ are related through:

$$x=-u\sin\lambda+(w+R)\cos\lambda. \quad (12)$$

$$y=u\cos\lambda+(w+R)\sin\lambda. \quad (13)$$

Without loss of generality, considering a line detector that is always parallel to $\hat{e}_u(\lambda)$ and that is at a distance S from the source, $u_d$ as the coordinate of a point on the detector may be expressed as:

$$u_d=-(S/w)u \quad (14)$$

Referring back to the general trajectory example shown in FIGS. 5*a*-*b*, one may assume that the trajectory satisfies two conditions: (1) $\rho(s)>\rho_s$ or $R(s)>R_s$; and (2) $\vec{r}_0(s)$ is continuous and piece-wise (first order) differentiable with respect to the arc length s. Condition (1) indicates that the trajectory never intersects with the support cylinder (or, equivalently, the image support). Moreover, using path length to parameterize the source trajectory avoids coordinate singularities in evaluating the derivative along the source trajectory. Condition (2) is rather general in that it may be satisfied by a wide variety of trajectories, including those that may be potentially usefully in imaging, such as practical CT-imaging applications. One example of a trajectory which satisfies condition (2) is shown in FIG. 5*b*.

As discussed above, many trajectories may be suitable for imaging. One possible family of source trajectories includes generalizations of the helical trajectory described as follows:

$$\vec{r}_0(s[\lambda])=(R(\lambda)\cos\lambda, R(\lambda)\sin\lambda, Z(\lambda)) \quad (15)$$

where λ denotes the rotation angle, and the path length s(λ) is related to the rotation angle λ through $$s(\lambda)=\int_0^\lambda\left|\frac{d\vec{r}_0(\lambda')}{d\lambda'}\right|d\lambda' \quad (16)$$

With this parameterization, the helical trajectory has a variable radius R(λ) and a variable pitch $$\frac{dZ(\lambda)}{d\lambda}.$$

As long as $d\vec{r}_0(s)/ds=d\vec{r}_0((s[\lambda])/d\lambda\, d\lambda/ds)$ exists almost everywhere, the chord reconstruction methodology, discussed below, may be applied to reconstructing the image on chords from data acquired with this trajectory. When $R(\lambda)=R_0$ and $$Z(\lambda)=\frac{h}{2\pi}\lambda,$$

the equation for $\vec{r}_0(s[\lambda])$ specifies the conventional helical trajectory with a constant radius $R_0$ and constant pitch length h. Also, both saddle and tilted helical trajectories may fit within this general helix parameterization. In particular, the saddle trajectory may be determined by:

$$\vec{r}_0(s[\lambda])=(R_0\cos\lambda, R_0\sin\lambda, h\cos 2\lambda) \quad (17)$$

and the tilted helical trajectory can be expressed as:

$$\vec{r}_0(s[\lambda])=\left(R_0\cos\lambda,\ R_0\sin\lambda,\ \cos\mu,\ R_0\sin\lambda\sin\mu+\frac{h}{2\pi}\lambda\right) \quad (18)$$

where μ is a constant indicating the angle between the z-axis and the actual rotation axis of the tilted CT gantry. For both saddle and tilted helical trajectories, $$\frac{d\vec{r}_0(s)}{ds}$$

exists. Therefore, the reconstruction methodology may be applied to reconstructing the image on chords from data acquired with these trajectories.

Figure 8C:
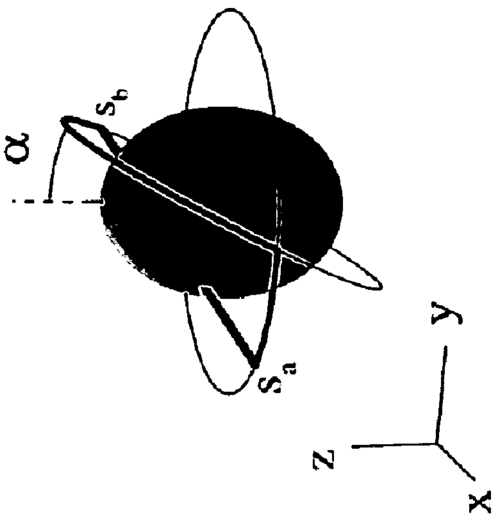
FIGS. 8*a-c* shows examples of different possible source trajectories, including, respectively, a generalized helix trajectory, a circle-line trajectory, and a two-circle line trajectory.
Figure 8B:
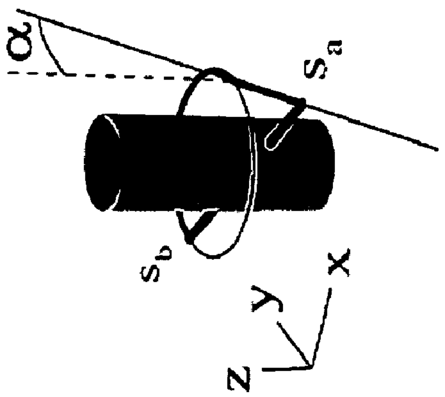
Figure 8A:
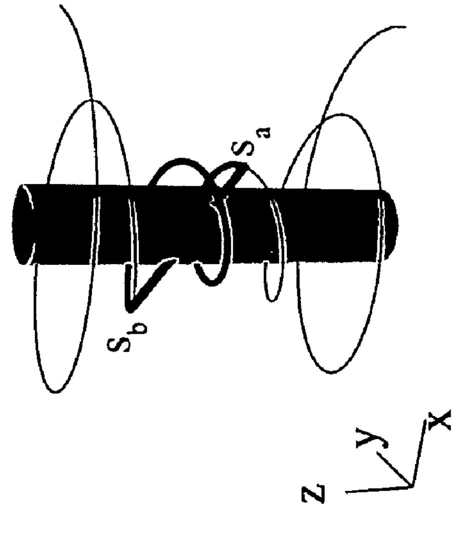

Referring to FIGS. 8*a*-*c*, there are shown examples of different possible source trajectories for the chord reconstruction discussed below. FIG. 8*a* shows a generalized helix trajectory, FIG. 8*b* shows a circle-line trajectory, and FIG. 8*c* shows a two-circle trajectory. The trajectories in FIGS. 8*b* and 8*c* are only piecewise differentiable. The chord reconstruction methodology, discussed in more detail below, may support trajectories that have a finite number of kinks in them. Specifically, these are trajectories where $dr_0(s)/ds$ does not exist at a finite number of isolated points on the trajectories. The source may traverse the trajectory segment (the thick curve shown in the figures) in order to obtain the image on the chord (thick line).

The circle-line trajectory can be expressed in terms of path length as follows:

$$\vec{r}_0(s) = \begin{cases} (0, s\sin(\alpha), s\cos(\alpha)) & s \le 0 \\ \rho_{cl}\left(\cos\frac{S}{\rho_{cl}} - 1, \sin\frac{S}{\rho_{cl}}, 0\right) & 0 < s < 2\pi\rho_{cl} \\ (0, (s - 2\pi\rho_{cl})\sin(\alpha), (s - 2\pi\rho_{cl})\cos(\alpha)) & 2\pi\rho_{cl} < s \end{cases} \quad (19)$$

where $\rho_{cl}$ may indicate the radius of the circle, and the line is $\alpha$ radians from vertical in the y-z plane. Similarly the two-circle trajectory may be expressed as:

$$\vec{r}_0(s) = \begin{cases} \rho_{cc}\left(\cos\frac{S}{\rho_{cc}}, \sin\frac{S}{\rho_{cc}}, 0\right) & -2\pi\rho_{cc} < s < 0 \\ \rho_{cc}, \left(\cos\frac{S}{\rho_{cc}}, \sin(\alpha)\sin\frac{S}{\rho_{cc}}, \cos(\alpha)\sin\frac{S}{\rho_{cc}}\right) & 0 \le s < 2\pi\rho_{cc} \end{cases} \quad (20)$$

where $\rho_{cc}$ denotes the radius of the circles. In each case, the indicated chord may be reconstructed when the source follows the corresponding trajectory segment. Moreover, there maybe more than one path that connects the endpoints of the chord in which case either path may be utilized to reconstruct the chord. For the circle-line trajectory shown in FIG. 8*b*, the derivative with respect to path length does not exist where the circle and line join, but as long as the trajectory is continuous at that point, the chord reconstruction methodology discussed below may be applied. The situation is the same for the two-circles trajectory, shown in FIG. 8*c*, at the joint of both circles.

Modifying the Source During Data Acquisition

As discussed above, typical imaging systems require that data be acquired for an entire section of an object and that all the acquired data be processed, even if an image of only a subsection of the object is sought. In one aspect of the invention, if an ROI is a portion of an object support, such as a part of a contiguous cross-section or a part of a volume, at least one characteristic of the source may be selected which acquires data that is less than that sufficient to image the entire object support, but which acquires data that is at least sufficient to image the ROI. For example, the control of the at least one characteristic of the source may enable illumination of support segments which fill the ROI.

As discussed above, source 312 may comprise any device which generates a signal (or a combination of signals) that may be received from detector 320. Characteristics of the source that may be controlled include any aspect of the source which may affect the signal received by the detector including, but not limited to: illumination coverage (e.g., aperture setting of beam, width of beam, modification of cone beam coverage, etc.); intensity of beam; and spectral distribution of beam. Typically, the characteristics of the source, such as the illumination coverage, remain fixed during imaging.

In another aspect of the invention, at least one characteristic of the source may be modified so that the data generated is less than that sufficient to image an object support. The characteristic may be changed so that it is constant as the source moves relative to the object. Or, the characteristic may be changed at least once as the source moves relative to the object. In one embodiment, the characteristic or characteristics of the source may be modified based on the ROI. For example, the characteristic of the source which is modified may comprise illumination coverage of the source. Specifically, the illumination coverage of the source may be modified so that the coverage is substantially directed to the ROI and substantially reduced for the non-ROI (or substantially not directed to the non-ROI). In this manner, exposure of the source to non-ROI may be reduced or minimized and exposure of the source to the ROI is sufficient to image the object (such as by generating support segments). This is advantageous when one may wish to reduce or limit exposure to the source, such as an x-ray source. Modification of the illumination coverage enables reduction of exposure to non-ROI areas or volumes while still maintaining illumination coverage to ROI areas or volumes.

As a general matter, illumination coverage may be modified based on the type of source used in the imaging system. If the source generates a fan beam, the aperture setting of source may be modified to change the angle of the fan beam, as discussed in more detail below. If the source generates a parallel beam, the width of beam may be modified. If the source generates a cone beam, the spread of the cone beam may be modified.

Moreover, modification of the characteristic or characteristics of the source may be dynamic, changing at any one or multiple points as the source travels relative to the object (e.g., the source moving with the object stationary, the source stationary and the object moving, or the source and object moving relative to one another). For example, an initial illumination coverage of the source may be selected as the source is initially directed at the object. The initial illumination coverage may be selected so that illumination to non-ROI areas is reduced or minimized. As the source travels relative to the object, the characteristic of the source (such as the illumination coverage) may be modified. The modification may be performed at discrete points along the trajectory. Or, the modification may be performed so that the characteristic is constant as the source travels relative to the object.

The following is an example of modifying a characteristic of the source during CT image scanning. Fan beam scanning is widely used in clinical CT systems for data acquisition. However, other types of scanning may be used for CT systems. As merely one example, cone-beam scanning (such as helical cone-bean scanning) may also be used in CT systems. In fan beam scanning, when the fan beam scan covers an angular range of $2\pi$ or $\pi$ plus the fan-beam angle, it is referred to as the full- or short-scan, respectively. A fan-beam scan over an angular range smaller than that in a short scan may be referred to as a reduced scan.

The fan-beam geometry with a circular trajectory is most widely used configuration in practice. However, other configurations may be used. In this configuration, the field of view (FOV) is determined by the open-angle of the fan beam and the radius R of the trajectory. Because certain image reconstruction methodologies for an ROI reconstruction, such as filtered-backprojection (FBP) discussed below, do not allow data truncations at any of the scanned views, the entire support of the image must be within the FOV. The following presents two situations in which data truncations occur in the data acquisition, and show that other image reconstruction methodologies, such as the backprojection-filtration (BPF) methodology discussed below, can exactly reconstruct images within an ROI in both situations in which data truncations occur. It is assumed that the scan includes a suitable trajectory over an angular range $\lambda_{min}$ and $\lambda_{max}$. As discussed above, a suitable trajectory may include one wherein a set of segments of chords defined by the trajectory fills the ROI. It is also assumed that at each view, $\lambda \epsilon [\lambda_{min}$ and $\lambda_{max}]$ data are available on and only on the projection range of the support section, discussed in more detail below.

In the first situation, the open-angle of the fan-beam, and thus the FOV, remains fixed, whereas, in the second situation, the open-angle of the fan-beam at different views over the scanning angular range can change. As shown below, both situations generate sufficient data to satisfy $\lambda \in [\lambda_{min}$ and $\lambda_{max}]$ data are available on and only on the projection range of the support section. In the first situation, the open-angle of the fan-beam at the scanned views remains fixed. Because the fan-beam has a fixed open-angle, data in $[-u_{dm}, u_{dm}]$ can always be collected, where $\pm u_{dm}$ depict the points at which the two out-most rays in the fan-beam intersect with the detector array. It is assumed that the ROI is covered completely by the FOV and that a set of PI-lines exists, which fill the ROI and do not intersect the support outside the ROI. Under this assumption, it can be seen that, for all of the support-sections on the PI-lines within the ROI, their projection ranges on the detector satisfy $[u_{d1}, u_{d2}] \subseteq [-u_{dm}, u_{dm}]$. Therefore, for each of the support-sections, data are available in $[u_{d1}, u_{d2}]$ and thus sufficient data are generated. Even if the image support is larger than the FOV, meaning that measurements contain truncations, data in $[-u_{dm}, u_{dm}]$ and thus in $[u_{d1}, u_{d2}]$ are always available. Consequently, the image on the PI-line segment can exactly be reconstructed from data containing truncations by use of the fan-beam BPF methodology. Because this can be done for each of the selected PI-line segments that fill the ROI, the image within the ROI can thus be obtained. The following are two examples to illustrate a sufficient trajectory and sufficient amount of data.

Figure 9C:
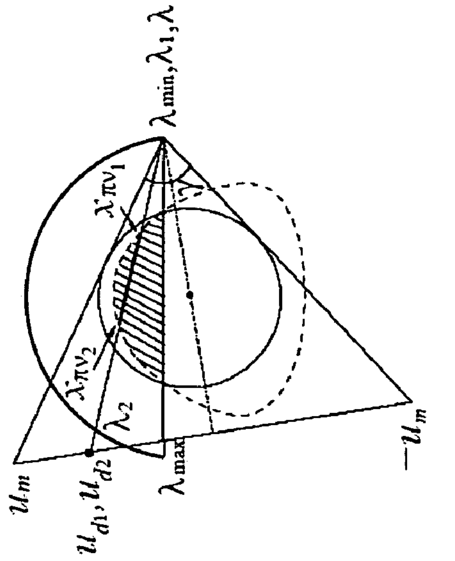
FIGS. 9*a-c* illustrate three views of data acquisition in a fan-beam scan with a fixed open angle.
Figure 9B:
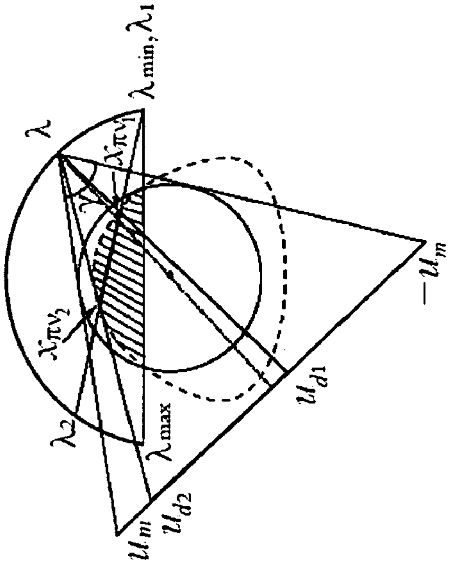
Figure 9A:
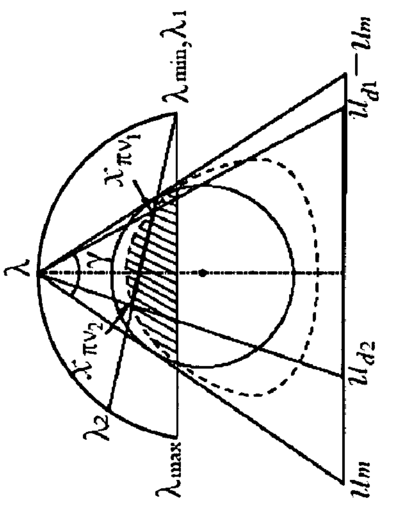

Referring to FIGS. 9*a-c*, a fan-beam scan is shown over $[\lambda_{min}, \lambda_{max}]$ in which the open-angle of the fan-beam remains fixed and the FOV is enclosed by the solid circle. The scanned trajectory over $[\lambda_{min}, \lambda_{max}]$ is indicated by the thick curve, with the regions enclosed by the solid circle and by the dashed curve showing the FOV and the image support, respectively. The ROI considered is depicted as the shadow region and the support-section $[x_{\pi^1}, x_{\pi^2}]$, shown as the thick line segment between $x_{\pi^1}$ and $x_{\pi^2}$, denotes the intersection between the image support and a PI-line segment, specified by $\lambda_1$ and $\lambda_2$, that intersects with the image support. FIGS. 9*a-c* display, at three views $\lambda \in [\lambda_1, \lambda_2]$, the projection ranges of the support-section onto the detector, which are the thick segments between $[u_{d1}, u_{d2}]$ on the detector. $\pm u_m$ depict the points at which the two outmost rays in the fan-beam intersect with the detector, and the open-angle is formed by the two lines connecting $-u_m$ and $u_m$ respectively, to the source at $\lambda$.

As shown in FIGS. 9*a-c*, the entire support of the image, indicated by the dashed curve, is larger than the FOV. Therefore, projection data acquired at most of the views $\lambda \in [\lambda_{min}, \lambda_{max}]$ would contain truncations. Consider image reconstruction in the ROI, indicated as shaded region, that is confined within the FOV. A set of PI-line segments may be selected, each of which is specified by $\lambda_1$ and $\lambda_2$, where $\lambda_1 = \lambda_{min}$ and $\lambda_2 = \in [\lambda_{min}, \lambda_{max}]$. Therefore, the ROI can completely be filled by these PI-line segments, and is thus a suitable trajectory. Specifically, for a PI-line segment specified by $\lambda_1$ and $\lambda_2$ in the set, it is observed that, for image reconstruction on this PI-line segment, $[\lambda_1, \lambda_2] \in [\lambda_{min}, \lambda_{max}]$ and thus that the scanning angular range is suitable.

In FIGS. 9*a-c*, displayed are the support-section of the PI-line segment specified by $\lambda_1$ and $\lambda_2$ and its projection ranges at three different views $\lambda \in [\lambda_1, \lambda_2]$. It can be seen that, despite the fact that the projections of the full image at these views contain truncations, data collected in $[-u_{dm}, u_{dm}]$ contain the necessary data in $[u_{d1}, u_{d2}]$ (i.e., on the projection range of the support-section) because $[u_{d1}, u_{d2}] \subseteq [-u_{dm}, u_{dm}]$. This means that an exact image may be reconstructed on the support-section (or, equivalently, on its PI-line segment) by use of the fan-beam BPF methodology. The above analysis also applies to all of the PI-line segments that fill completely the ROI. Therefore, images on these PI-line segments and, consequently, in the ROI can be reconstructed exactly by use of the fan-beam BPF methodology.

In the second situation, the open-angle of the fan beam may change at different views. As discussed above, a characteristic of the source, such as the open angle of the fan-beam, may be modified as the source travels relative to the object. It is assumed that the support-sections on the selected PI-line segments are within the ROI and that the open-angle of the fan beam changes in such a way that the fan-beam at each view contains (or substantially contains) only rays that intersect with the ROI. This assumption allows data to be collected on and only on the projection ranges (i.e., in and only in $[u_{d1}, u_{d2}]$) of the support-sections of the PI-line segments that fill completely the ROI. Therefore, even though data so collected may contain severe truncations, they contain the necessary data to support exact reconstruction. Consequently, the image on the PI-line segment can be reconstructed exactly from these data by use of the fan-beam BPF methodology.

Figure 10C:
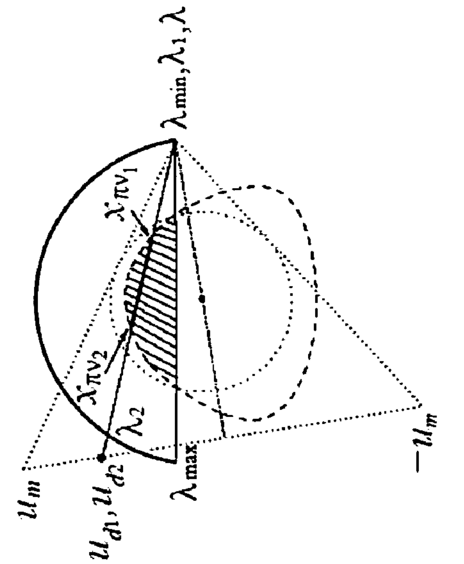
FIGS. 10*a-c* illustrate three views of data acquisition in a fan-beam scan, similar to the views shown in FIGS. 9*a-c*, with a varying open angle.
Figure 10B:
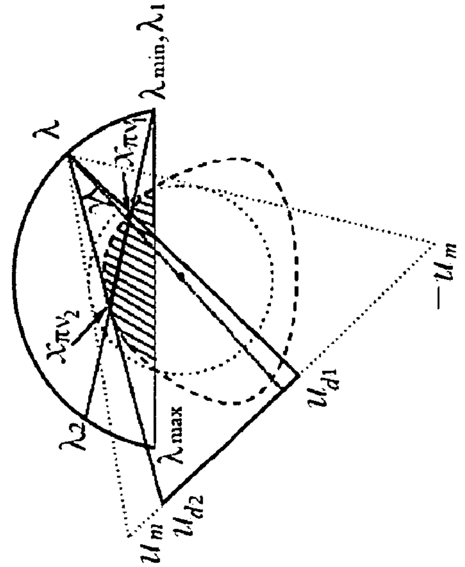
Figure 10A:
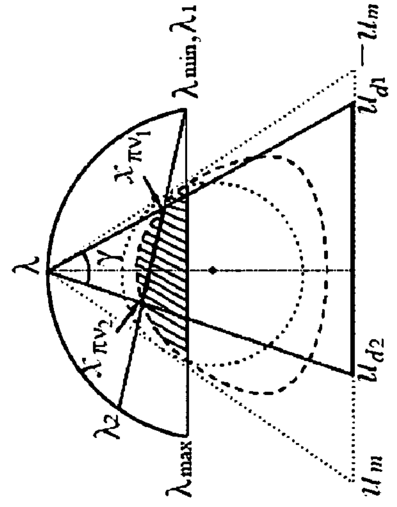

Referring to FIGS. 10*a-c*, there is shown data acquisition in a fan-beam scan, similar to FIGS. 9*a-c*. The notations and symbols are identical to those in FIGS. 9*a-c* except that the open-angle of the fan-beam can vary at different views $\lambda \in [\lambda_1, \lambda_2]$. In particular, the open-angle is now formed by the two lines connecting $u_{d1}$ and $u_{d2}$, respectively, to the source at $\lambda$. The original FOV and fan-beam are indicated by the dotted curves. As shown in FIGS. 10*a-c*, displayed are the projection ranges of the support-section on a PI-line segment, specified by $[\lambda_1, \lambda_2]$, at three different views $\lambda \in [\lambda_1, \lambda_2]$. The open-angles at the three views: (1) are smaller than the open-angle covering the FOV; (2) are substantially different than the three open-angles shown in FIGS. 9*a-c*, and (3) cover the support-section completely. For example, the open-angle in FIG. 10*c* is zero because only one ray is needed to cover the support-section on this PI-line segment at this view. Consequently, data can be collected at $u_d \in [u_{d1}, u_{d2}]$ (i.e., on the projection ranges of the support-section of the PI-line segment). Therefore, even in limiting the output of the source, such as by narrowing the fan beam, sufficient data may be collected to reconstruct an exact image on the PI-line segment by use of the fan-beam BPF methodology. Moreover, the above analysis applies to all of the PI-line segments in the selected set of PI-line segments covering the ROI. Therefore, the image on these PI-line segments and, consequently, in the ROI can be reconstructed exactly by use of the fan-beam BPF methodology. The varying open-angle in FIGS. 10*a-c* was shown for a single support-section. When the entire ROI (i.e., the shaded region in FIGS. 10*a-c*) is considered, the open-angle may be varied so that the fan-beam only covers the ROI at all of the views $\lambda \in [\lambda_1, \lambda_2]$.

Figure 11B:
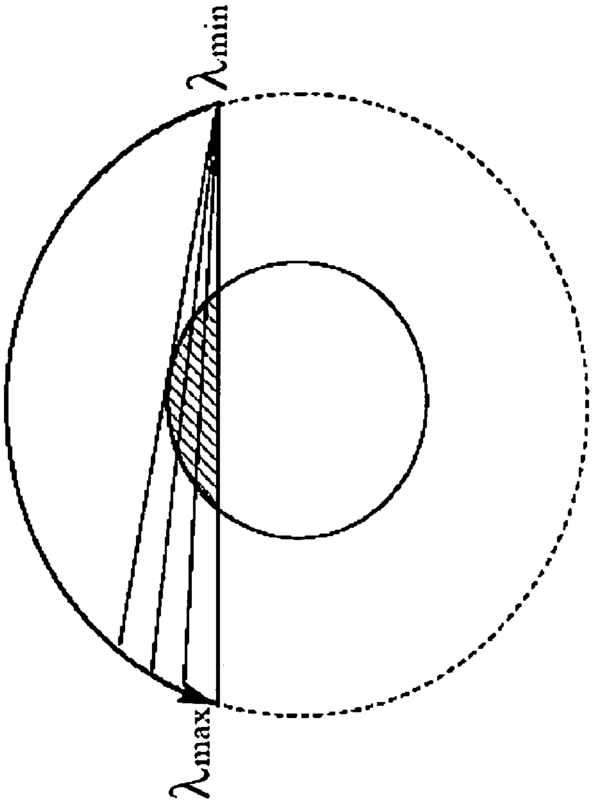
FIGS. 11*a-b* illustrate two scanning trajectories that cover angular ranges [π, 2π] and [1.2π, 1.8π], with the shaded areas designating the regions of interest to be reconstructed.
Figure 11A:
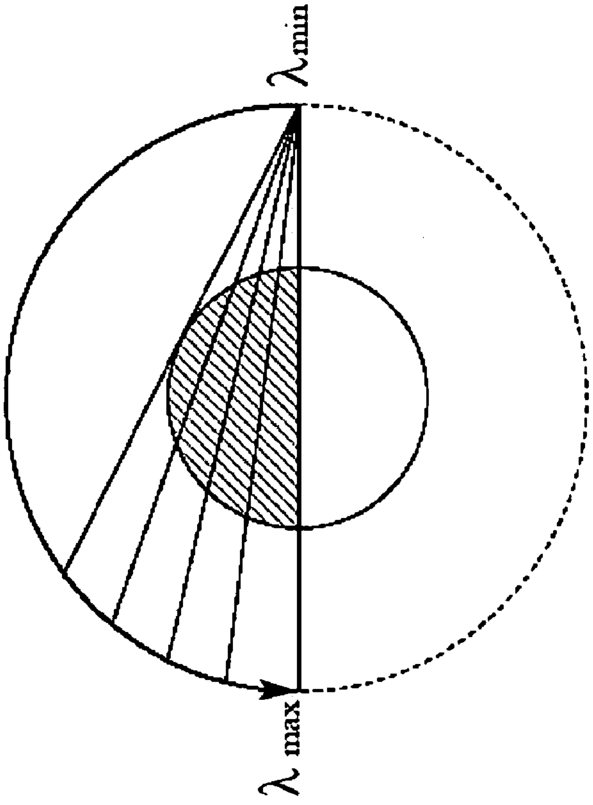
Figure 12A:
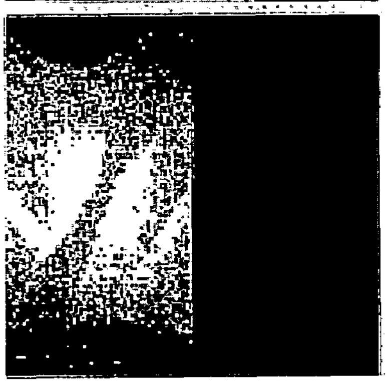
FIG. 12*a* illustrates data collected over [π, 2π] in FIG. 11*a* by use of a fan-beam with a fixed open angle.
Figure 12B:
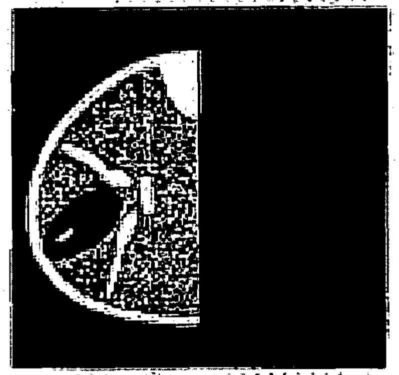
FIG. 12*b* illustrates an image reconstructed on PI-line segments using the data illustrated in FIG. 12*a* and a filtered-backprojection methodology.
Figure 12C:
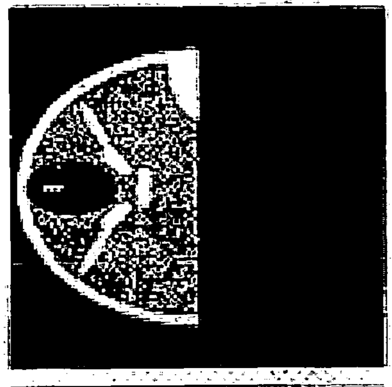
FIG. 12*c* illustrates a reconstructed image displayed in terms of fixed coordinates, which is converted from the image reconstructed in FIG. 12*b*.
Figure 12D:
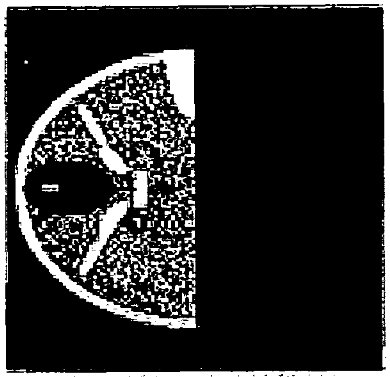
FIG. 12*d* illustrates a reconstructed noisy image for the image reconstructed in FIG. 12*c*.
Figure 13A:
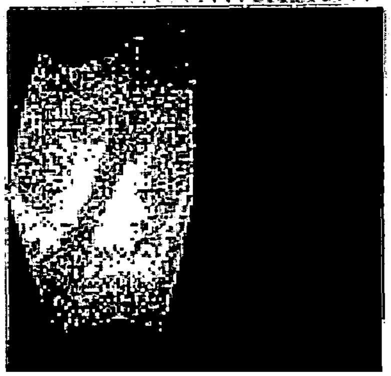
FIG. 13*a* illustrates data collected over [π, 2π] in FIG. 11*a* by use of a fan-beam with a varying open angle.
Figure 13B:
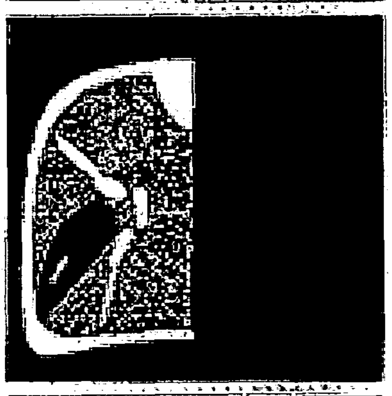
FIG. 13*b* illustrates an image reconstructed on PI-line segments using the data illustrated in FIG. 13*a* and a backprojection-filtration methodology.
Figure 13C:
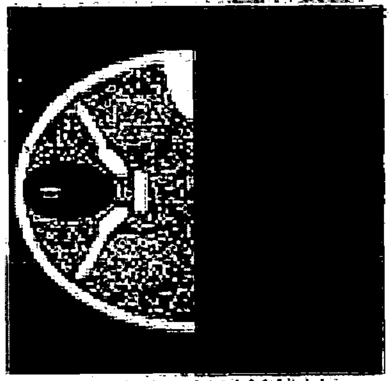
FIG. 13*c* illustrates a reconstructed image displayed in terms of fixed coordinates, which is converted from the image reconstructed in FIG. 13*b*.
Figure 13D:
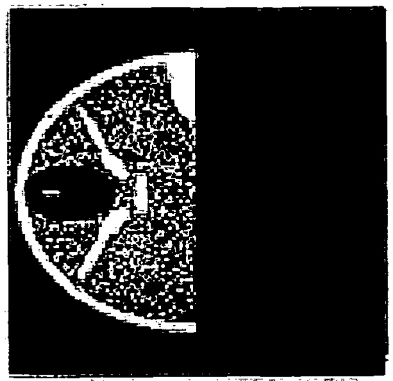
FIG. 13*d* illustrates a reconstructed noisy image for the image reconstructed in FIG. 13*c*.
Figure 14A:
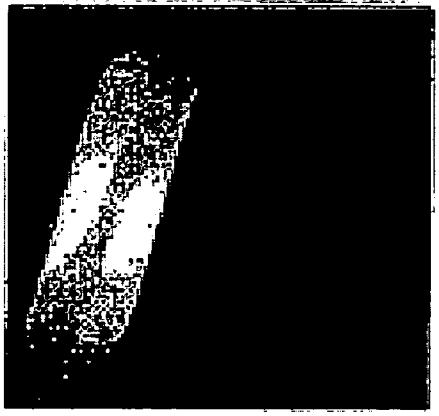
FIG. 14*a* illustrates data collected over [1.097π, 1.91π] in FIG. 11*a* by use of a fan-beam with a varying open angle.
Figure 14B:
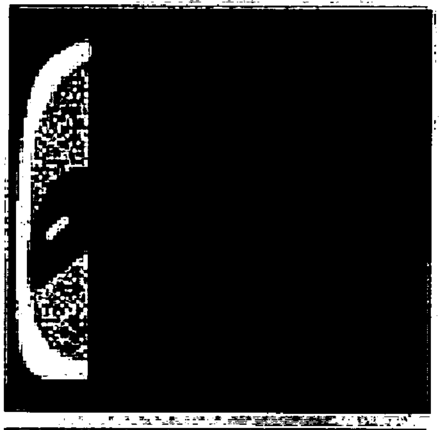
FIG. 14*b* illustrates an image reconstructed on PI-line segments using the data illustrated in FIG. 14*a* and a backprojection-filtration methodology.
Figure 14C:
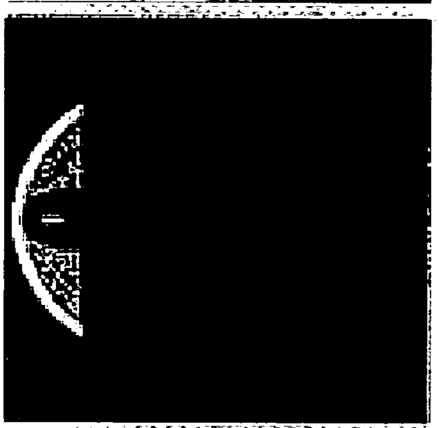
FIG. 14*c* illustrates a reconstructed image displayed in terms of fixed coordinates, which is converted from the image reconstructed in FIG. 14*b*.
Figure 14D:
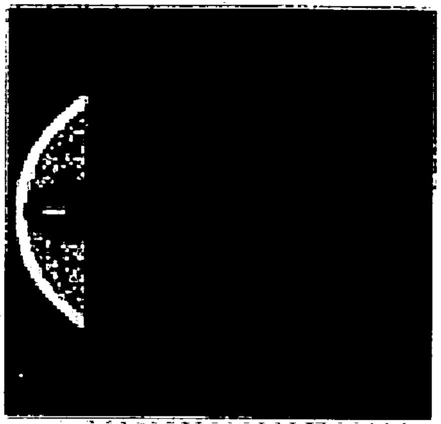
FIG. 14*d* illustrates a reconstructed noisy image for the image reconstructed in FIG. 14*c*.

The following is a computer-simulation study to demonstrate and verify quantitatively the proposed fan-beam BPF methodology. In the numerical study, a circular fan-beam configuration is considered in which the trajectory has a radius of R=27.0 cm and the (virtual) one-dimensional (1-D) detector array is at the center of rotation. In this case, S=R=27.0 cm. The 1D detector array consists of 512 square-shape elements each of which has a size of 0.55 mm. The fan-beam configuration thus admits a FOV with a radius of 12.5 cm when the open-angle of the fan-beam remains fixed for all projection views. The 2D head phantom is used, having an elliptical support with half axes of 9.6 cm and 12.0 cm, along the x- and y-axis, respectively. Two scanning trajectories are considered, shown in FIGS. 11$a$ and 11$b$. Specifically, FIG. 11$a$ covers an angular range of [$\pi$, $2\pi$] and FIG. 11$b$ covers an angular range of [$1.2\pi$, $1.8\pi$]. The shaded areas in FIGS. 11$a$-$b$ are the ROIs to be reconstructed. Further, as shown in FIGS. 11$a$-$b$, a converging set of PI-line segments is used to fill the ROI. Each PI-line segment in the set is specified by $\lambda_1$ and $\lambda_2$, where $\lambda_1=\lambda_{min}$ and $\lambda_2 \in [\lambda_{min}, \lambda_{max}]$.

For the scanning trajectory in FIG. 11$a$, using the fan-beam configuration with a fixed open-angle and the head phantom described above, data is generated at 512 projection views uniformly distributed over [$\pi$, $2\pi$], which are shown in FIG. 12$a$. In this case, it is assumed that data contain no truncations at each view. Because data contain no truncations, the FBP-based methodology may be used for reconstructing an exact image within the ROI on the PI-line segments intersecting with the ROI. This reconstructed image is shown in FIG. 12$b$ in which each horizontal line represents a PI-line segment. Using the relationship between the PI-line coordinates ($x_{\square}$, $\lambda_1$, $\lambda_2$) and the fixed coordinates (x, y) which is discussed above, the image presented in terms of the PI-line coordinates in FIG. 12$b$ can be converted to an image presented in terms of the fixed coordinates, as shown in FIG. 12$c$. In an attempt to demonstrate how the FBP-based algorithm respond to data noise, Gaussian noise is added to the generated noiseless data. The standard deviation of the Gaussian noise is 2% of the maximum value of the fan-beam data. From the noisy data, a "noisy" image is reconstructed within the ROI, which is shown in FIG. 12$d$. Images similar to those in FIGS. 12$c$ and 12$d$ may also be reconstructed from data displayed in FIG. 12$a$ by use of the fan-beam BPF methodology. Moreover, data in FIG. 12$a$ contain more information than what is needed for exact image reconstruction in that ROI by use of the fan-beam BPF algorithm.

For the scanning trajectory in FIG. 11$a$, using the fan-beam configuration with a varying open-angle and the head phantom described above, data is generated at 512 projection views uniformly distributed over [$\pi$, $2\pi$], which are displayed in FIG. 13$a$. The open-angle was varied such that data were acquired at and only at $u_d \in [u_{d1}, u_{d2}]$ (i.e., on the projection range of the support-section on the PI-line segments) for the scanned views. Therefore, this set of data is sufficient to reconstruct the image. Comparison of FIGS. 13$a$ and 13$b$ indicates that data acquired with the varying open-angle contain truncations. Therefore, the FBP-based methodologies cannot reconstruct exactly an image within the ROI from this set of truncated data. However, as mentioned above, an image on PI-line segments that intersect with the ROI can exactly (or substantially exactly) be reconstructed by use of the fan-beam BPF methodology or the MFBP methodology. FIG. 13$b$ displays the reconstructed image on PI-line segments. The PI-line coordinate is normalized to the length of each PI-line segment. Again, using the relationship between the PI-line coordinates and the fixed coordinates, discussed in more detail below, the image presented in terms of the PI-line coordinates in FIG. 13$b$ is converted to an image presented in terms of the fixed coordinates, which is shown in FIG. 13$c$. The fan-beam BPF algorithm was also used to reconstruct an image from data containing Gaussian noise, and the reconstructed noisy image is displayed in FIG. 13$d$.

For the scanning trajectory in FIG. 11$b$, using the fan-beam configuration with a varying open-angle and the head phantom described above, data is also generated data at 416 projection views uniformly distributed over [$1.09\pi$, $1.91\pi$], which are displayed in FIG. 14$a$. Again, the open-angle was varied such that data were acquired at and only at $u_d \in [u_{d1}, u_{d2}]$ (i.e., on the projection range of the support-section on the PI-line segments) for the scanned views. Therefore, this set of data is sufficient to reconstruct an image. Comparison of FIGS. 12$a$ and 14$a$ clearly indicates that this set of data contains severe truncations. In fact, data at all of the scanned views in [$1.09\pi$, $1.91\pi$] contain truncations. The truncations occur only on one end of the detector array for some views such as the views near $\lambda_{min}=1.09\square$. However, data truncations take place on both ends of the detector array for the rest of the scanned views. The FBP-based methodologies cannot reconstruct exactly an image within the ROI from this set of severely truncated data. However, as mentioned above, an exact image on PI-line segments that intersect with the ROI can be reconstructed by use of the fan-beam BPF methodology or the MFBP methodology. FIG. 14$b$ demonstrates the reconstructed image on such PI-line segments. Based upon the relationship between the PI-line and fixed coordinates, discussed below, the image in FIG. 14$b$ may be converted to an image in FIG. 14$c$, which is presented in terms of the fixed coordinates. The fan-beam BPF algorithm was also used to reconstruct an image from data containing Gaussian noise, and the reconstructed noisy image is displayed in FIG. 14$d$.

Modifying the Detector During Data Acquisition

As discussed above, detector 320 may comprise any device which senses a signal (or a combination of signals). The signal may originate from source 312 or may originate from object 316. In another aspect of the invention, at least one characteristic of the detector may be modified during acquisition of the data for imaging. In one embodiment, the characteristic or characteristics of the detector may be modified based on the ROI. For example, the characteristic of the detector that is modified may comprise activation or deactivation of sections of the detector. Sections 322 of detector 320 may be enabled or disabled so that data sensed by detector 320 is substantially for the ROI and substantially not for non-ROI. In this manner, extraneous data may be reduced or minimized. In another embodiment, the data generated by the detector may be accepted or rejected based on the ROI. Data generated by sections 322 of detector 320 may be accepted or rejected so that data sensed by detector 320 is substantially for the ROI and substantially not for non-ROI. In this manner, extraneous data may be reduced or minimized. Detector 320 may determine whether data from a section is accepted or rejected. Alternatively, processing unit 304 may determine whether data from a section is accepted or rejected.

Generating an Image Based on Chords

After data acquisition, the data may be processed to generate a reconstructed image of a portion, or all, of the object. The reconstruction may be based on chords that fill at least a portion (such as all) of a region of interest (ROI). The chords used for reconstruction may be a connection between two points, such as a straight line or a section of a curve.

The chords may be based on any aspect of imaging, such as a non-fixed coordinate system. One such non-fixed coordinate system may be defined, at least in part, by the source trajectory or how the source travels relative to the object (e.g., the source moving with the object stationary, the source stationary and the object moving, or the source and object moving relative to one another). After the image is reconstructed on the non-fixed coordinate system, the image may be converted into a fixed coordinate system, such as a Cartesian coordinate system. Alternatively, the chords may be based on a fixed coordinate system, such as the Cartesian coordinate system.

For example, image reconstruction may be based, at least in part, on chords defined by the source trajectory. As discussed above, two points along the source trajectory may define a chord. Points along the chord may further be defined by a third point. Thus, the chords may be defined with a first point along the source path, a second point along the source path which is different from the first point, and a third point on a chord formed between the first point and the second point. The first and second points may be defined by scalars or may be defined by arc lengths along the source path. The entire ROI, either for a 2-Dimensional or 3-Dimensional ROI, may be defined by points along the chords defined by the source trajectory. Further, the image may be reconstructed using the chords. As merely one example, discussed in more detail below, the image may be reconstructed by identifying a set of chords that connect pairs of points along the source path, wherein the set of chords fill a volume for a region of interest in the body, calculating image densities on the chords from the collected data, and constructing a three-dimensional image based on the image densities and on the source path. Therefore, when using chords for reconstruction defined by the source trajectory, the reconstruction of the image may be based on a coordinate system defined by the source trajectory.

Figure 15C:
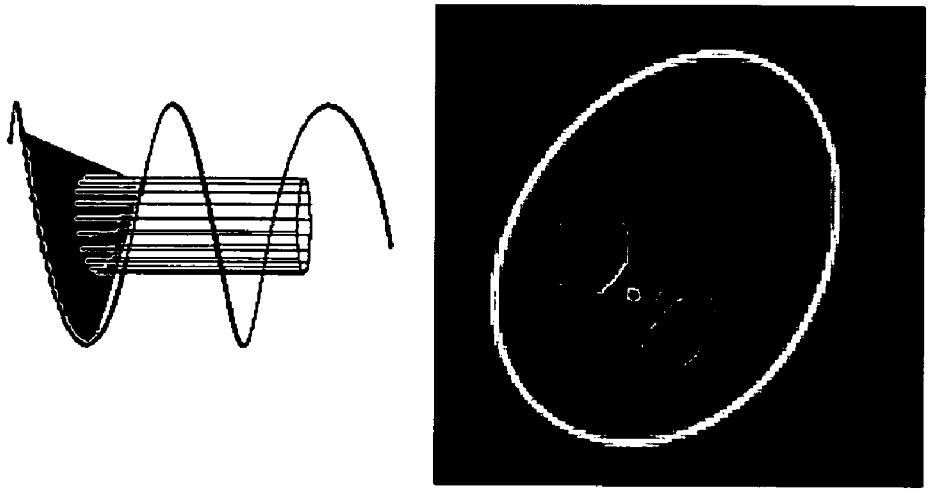
FIGS. 15*a-c* show an object which is cylindrical in shape being scanned with a helical source trajectory and corresponding reconstructed images.
Figure 15B:
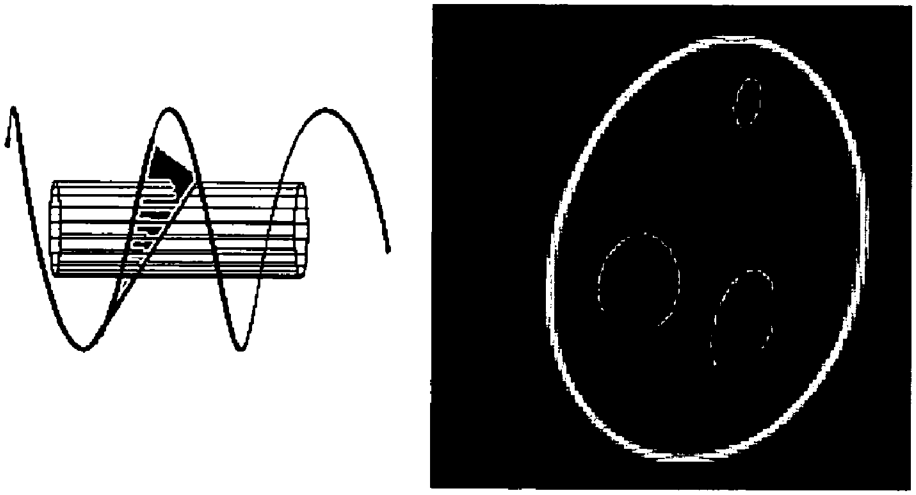
Figure 15A:
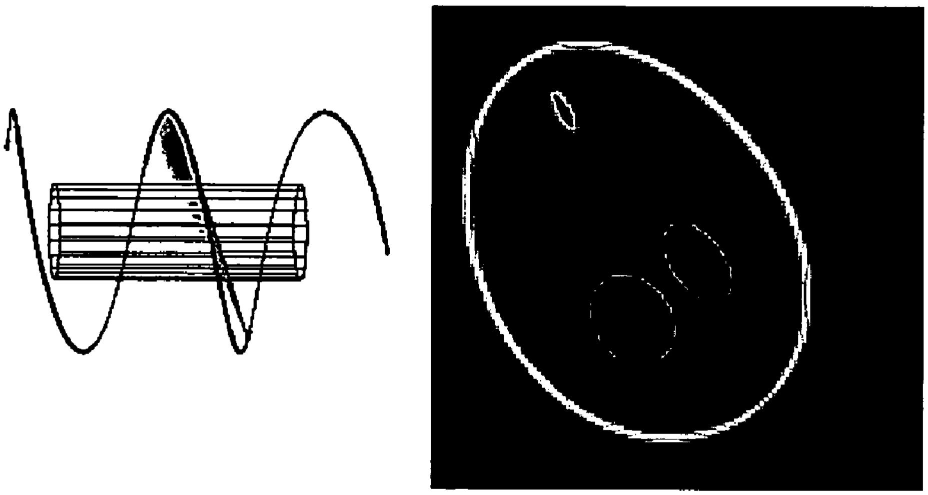

For example, FIGS. 4_a_ and 4_b_, discussed above, define points along the chords for an entire area of an ROI. As another example, FIGS. 15_a-c_ show an object which is cylindrical in shape being scanned with a helical source trajectory. The shape of the object and the type of trajectory are merely exemplary. Other objects may be scanned, and other trajectories may be used. Each point within an object may be defined by points on chords. For example, the chords defined by the source trajectory in FIGS. 15_a-c_ may fill the entire volume of the cylindrical object by defining a series of planes which fill the object. Three of the planes are shown in FIGS. 15_a-c_ with corresponding reconstructed images.

Since an ROI may be defined by at least a part of the chords, the image may therefore be reconstructed using the chords. Specifically, the image may be reconstructed on at least a part of the chords to generate the image for the ROI. In the example shown in FIGS. 4_a_ and 4_b_, the image may be constructed on a segment of the chord which overlaps the ROI, or may be constructed over the entire chord. In the example shown in FIGS. 15_a-c_, the image may be constructed over surface areas which make up the volume of the ROI, or may be constructed over the entire surface area defined by the chords. Alternatively, the image may be constructed point by point to make up the volume of the ROI. A variety of methodologies may be used to reconstruct the image based on chords. Three methodologies, including filtered-backprojection (FBP), backprojection-filtration (BPF), and Minimum-data Filtration Backprojection (MFBP), are described in the following example to reconstruct the image. However, other methodologies may be used. Further, the example uses a cone-beam projection. Other projections may be used, including a fan-beam projection. Or, a projection may not be needed at all, such as in the case of PET scanning.

A cone-beam projection of the object function or density distribution may be defined as:

$$D(\vec{r}_0(s),\hat{\beta})=\int_0^{\infty}dt f(\vec{r}_0(s)+t\hat{\beta}) \tag{21}$$

where the unit vector $\hat{\beta}$, indicating the projection direction of an individual x-ray passing through the point $\vec{r}'$, may be written as:

$$\hat{\beta}=\frac{\vec{r}'-\vec{r}_0(s)}{|\vec{r}'-\vec{r}_0(s)|} \tag{22}$$

and $\vec{r}'\in R^3$. $D(\vec{r}_0(s),\hat{\beta})$ may be referred to as physical data because they are assumed to be measurable. Assume that $\vec{r}$ is on a chord determined by $s_a$ and $s_b$ (two points on the source trajectory). For a generalized trajectory, suppose that there are N−1 kinks on the trajectory segment specified by $s\in[s_a, s_b]$, dividing it into N connected pieces. The N−1 kinks may be denoted by $s_i$, $i\in[2, N]$, and $s_1=s_a$ and $s_{N+1}=s_b$. For $\vec{r}$ on a chord-line, the object function $f(\vec{r})$ may be reconstructed exactly as:

$$f(\vec{r})=\int_{R^3}d\vec{r}'K(\vec{r},\vec{r}')g(\vec{r}') \tag{23}$$

where the integral kernel $K(\vec{r},\vec{r}')$ in the above equation may be represented by:

$$K(\vec{r},\vec{r}')=\frac{1}{2\pi j}\int_{R^3}d\vec{v}\,\mathrm{sgn}[\vec{v}\cdot\hat{e}_c]e^{2\pi j\vec{v}\cdot(\vec{r}-\vec{r}')} \tag{24}$$

the generalized backprojection $g(\vec{r}')$ may be expressed as:

$$\begin{aligned} g(\vec{r}') &= \int_{s_a}^{s_b}\frac{ds}{|\vec{r}'-\vec{r}_0(s)|}\frac{\partial}{\partial q}\bar{D}(\vec{r}_0(q),\hat{\beta})\Big|_{q=s} \\ &= \sum_{i=1}^{N}\int_{s_i}^{s_{i+1}}\frac{ds}{|\vec{r}'-\vec{r}_0(s)|}\frac{\partial}{\partial q}\bar{D}(\vec{r}_0(q),\hat{\beta})\Big|_{q=s} \end{aligned} \tag{25}$$

and the extended data function may be defined as:

$$\bar{D}(\vec{r}_0(s),\hat{\beta})=D(\vec{r}_0(s),\hat{\beta})-D(\vec{r}_0(s),-\hat{\beta}) \tag{26}$$

As discussed above, reconstruction of an image using chords may be achieved in a variety of manners. As shown below, exact reconstruction of the object functions $f(\vec{r})$ may be performed based on filtered-backprojection (FBP), backprojection-filtration (BPF), and Minimum-data Filtration Backprojection (MFBP). Other methodologies may also be used to reconstruct the image based on chords.

The explicit form of a reconstruction algorithm may depend generally upon the selection of the coordinate systems. For each point s on the trajectory, let {u, v, w} denote the rotation-coordinate system. It is assumed that its origin is at $\vec{r}_0(s)$ and that its unit vectors are given by:

$$\hat{e}_u(s)=(-\sin(s),\cos(s),0),\ \hat{e}_v(s)=(0,0,1),\ \hat{e}_w(s)=(\cos(s),\sin(s),0) \tag{27}$$

Let (x, y, z) and (u, v, w) denote the coordinates of a point within the support cylinder in the fixed- and rotation-coordinate systems, respectively, which can be shown to satisfy:

$$\begin{aligned} x&=-u\sin(s)+w\cos(s)+x_0(s)\\ y&=u\cos(s)+w\sin(s)+y_0(s)\\ z&=v+z_0(s) \end{aligned} \tag{28}$$

It can be seen that the u-w plane and the v-axis of the rotation-coordinate system are parallel to the x-y plane and to the z-axis, respectively, of the fixed-coordinate system.

One may use a two-dimensional (2D) detector that has a normal vector $\hat{e}_w(s)$ and is at a distance S(s)>0 from a point $\vec{r}_0(s)$ on the trajectory. On the detector plane, $\{u_d, v_d\}$ may be used to denote the cone-beam projection of the 2D coordinate system $\{u, v\}$. Therefore, the $u_d$- and $v_d$-axes are along $\hat{e}_u(s)$ and $\hat{e}_v(s)$, respectively, and the origin of the detector-coordinate system $\{u_d, v_d\}$ is at the projection of $\vec{r}_0(s)$ onto the detector plane. Any point on the detector plane can now be specified completely in terms of $(u_d, v_d)$. It can readily be shown that:

$$u = -\frac{w}{S(s)}u_d \text{ and } v = -\frac{w}{S(s)}v_d \tag{29}$$

In the context of CT scanning, because an individual x-ray within the cone-beam from a source point at $\vec{r}_0(s)$ can be specified completely by the detector coordinates $u_d$ and $v_d$, we can also use $P(u_d, v_d, s)$ to denote the data $D(\vec{r}_0(s), \hat{\beta})$:

$$P(u_d, v_d, s) = D(\vec{r}_0(s), \hat{\beta}) \text{ and } \frac{\partial}{\partial_q}D(\vec{r}_0(q), \hat{\beta})\Big|_{q=s} = \frac{dP(u_d, v_d, s)}{ds}\Big|_{\hat{\beta}} \tag{30}$$

where $\hat{\beta}$ also satisfies:

$$\hat{\beta} = \frac{1}{A(u_d, v_d)}[u_d\hat{e}_u(s) + v_d\hat{e}_v(s) - S(s)\hat{e}_w(s)] \tag{31}$$

$$A(u_d, v_d) = \sqrt{u_d^2 + v_d^2 + S^2(s)} \tag{32}$$

One existing methodology for reconstructing images is called filtered-backprojection (FBP). FBP-based methodologies reconstruct images by performing a shift-invariant filtering of the modified data followed by a weighted backprojection of the filtered data. The following reconstructs the image on a chord using the FBP methodology by exploiting data on the cone-beam projection of the chord-line onto the detector plane.

Under conditions (1) and (2) discussed above, Equation (23), in combination with Equations (24)-(26), yields an exact image function on an entire chord-line, and thus on the chord as well. The following provides an exact expression of the image $f(\vec{r})$, $$f_R(\vec{r}) = \int_{R^3} d\vec{v}\,\text{sgn}[\vec{v}\cdot\hat{e}_c] \sum_{i=1}^{N}\int_{s_i}^{s_{i+1}} ds\left[\vec{v}\cdot\frac{d\vec{r}_0(s)}{ds}\right]F(\vec{v})e^{2\pi j\vec{v}\cdot\vec{r}_0(s)}\delta(\vec{v}\cdot\vec{r} - \vec{v}\cdot\vec{r}_0(s)). \tag{33}$$

in which the δ-function implies the condition $\vec{v}\cdot(\vec{r} - \vec{r}_0(s))=0$, where $\vec{r}$ is on the chord-line. Further, $\hat{e}'_c$ may be defined as:

$$\hat{e}'_c = \frac{1}{a}[\hat{e}_c \times (\vec{r} - \vec{r}_0(s))] \times \hat{e}_w \text{ and } \vec{v}_d = \hat{e}_w \times [\vec{v} \times \hat{e}_w] \tag{34}$$

where $a=|[\hat{e}_c\times(\vec{r} - \vec{r}_0(s))]\times\hat{e}_w|$ is the normalization factor. Unit vector $\hat{e}'_c$ indicates the direction of the cone-beam projection of the chord-line onto the detector plane.

For $\vec{r}$ on the chord-line, one can readily conclude that $\hat{e}_w\cdot(\vec{r} - \vec{r}_0(s))<0$. Using this result and $\vec{v}\cdot(\vec{r} - \vec{r}_0(s))=0$, it may be shown that:

$$sgn[\vec{v}\cdot\hat{e}_c]=sgn[\vec{v}_d\cdot\hat{e}'_c]=sgn[v'_c] \tag{35}$$

where $v'_c=\vec{v}_d\cdot\hat{e}'_c$. Therefore, a portion of Equation (24) may be rewritten as:

$$K(\vec{r}, \vec{r}\,') = \frac{1}{2\pi j}\frac{S^2(s)}{w^2}\int_R dv'_c\,\text{sgn}[v'_c]e^{2\pi j(u_c-u'_c)v'_c}\delta(u_\perp - u'_\perp)\delta(w-w') \tag{36}$$

where $u_c$ and $u'_c$ denote the coordinates on the conebeam projection of the chord-line onto the detector plane, and the $u_\perp$-axis is perpendicular to the $u_c$-axis. For $\vec{r}$ on the chord-line, $u_\perp=0$. Therefore, one can express this portion of the equation as:

$$K(\vec{r}, \vec{r}\,') = \frac{1}{2\pi^2}\frac{S^2(s)}{w^2}\frac{1}{(u_c - u'_c)}\delta(u'_\perp)\delta(w-w') \tag{37}$$

Because of the δ(w−w') function in Equation (37), only the first term (i.e., the physical data $D(\vec{r}_0(s), \hat{\beta})$) of the extended data function in Equation (26) contributes to the backprojection image $g_c(x_c, s_a, s_b)$. Therefore, the derivation below considers the contribution only from the physical data term $D(\vec{r}_0(s), \hat{\beta})$.

Since $$d\vec{r}\,' = \frac{w'^2}{S^2(a)}du'_c du'_\perp dw',$$

substituting Equations (26) and (37) into Equation (23), and changing the orders of the integrations over $u'_c$ and s, one obtains:

$$f(x_c, s_a, s_b) = \frac{1}{2\pi^2}\int_{s_a}^{s_b} ds \int_R \frac{du'_c}{u_c - u'_c}\frac{1}{|\vec{r}\,' - \vec{r}_0(s)|^2}\frac{dP(u'_d, v'_d, s)}{ds}\Big|_{\hat{\beta}} \tag{38}$$

Equation (38) is referred to as the filtered backprojection (FBP) algorithm because it performs a 1D Hilbert transform (i.e., the integration over $u'_c$) before backprojecting the filtered data (i.e., the integration over s) onto the chord. Non-truncated data are necessary when the FBP algorithm is used for reconstructing the image on a chord because the filtration in the FBP algorithm requires knowledge of data over $u'_c \in R$.

Reconstructing an Image Based on Back-Projection Filtration

Another methodology for reconstructing images is the backprojection-filtration (BPF) methodology. Unlike the existing FBP-based methodology, the BPF methodology reconstructs an image within an ROI by first backprojecting the data (such as weighted data) and then performing filtering (such as shift-invariant filtering) of the backprojection. Generally speaking, backprojection involves transforming measured data from data space into image space. When backprojecting, the data may further be modified. For example, the data may be weighted or the derivative of the data may be taken. However, modifying the data when backprojecting is not necessarily required.

When backprojecting, the measured data may first be selected, and then transformed from data space into image space. With backprojecting using chords, one may select the data on the projection of the segment of the chord in the ROI onto the detector. Referring to FIG. 2*a* as an example, if the segment of the chord (shown as line 208) in the ROI for reconstruction is the flat line at the bottom of portion 204 (shown as line 210), the projection of that segment onto the detector is the data from point "C" to point "D." These data in the range from "C" to "D" may be backprojected onto the segment of the chord. Alternatively, if the segment of the chord is longer than segment 208 (such as a segment which includes 208 and additional segments 212, the projection of this segment onto the detector is the data from point "E" to point "F." These data in the range from "E" to "F" may be backprojected onto the segment of the chord. Thus, data corresponding to any segment of the chord, or the entire chord, may be backprojected onto the segment. The backprojection may be performed for all of the views onto that specific segment. After backprojection, filtration may be performed on the backprojections onto the specific segment. The segments used to reconstruct the ROI using the BPF methodology may comprise support segments. Depending on the type of image sought to be reconstructed, various filtration methodologies may be used. For example, if a substantially exact reconstruction is sought, one example of a filtration methodology is using a Hilbert transform. As another example, if a substantially exact reconstruction is not sought, other filtration methodologies may be used.

A variety of data acquisition methodologies may be used to generate data for the BPF methodology. The BPF methodology may exactly reconstruct an image within a given ROI directly from reduced-scan data that contain truncations or from data that does not contain truncations. For example, the data acquisition methodology discussed above wherein at least one characteristic of the source is modified (such as the illumination coverage of the source) may be used to generate data for the BPF methodology.

The following is an example using the BPF methodology in the context of reconstructing an image based on chords. However, the BPF methodology is not limited to reconstructing an image using chords, and may reconstruct images generally. For example, the BPF methodology may be used in traditional reconstruction outside of the chord context.

For a given chord specified by $s_a$ and $s_b$ (points on the source trajectory), a coordinate system $\{x_c, y_c, z_c\}$ is considered that has its origin at the middle point of the chord. In this system, the $x_c$-axis coincides with the chord-line and has a unit vector $\hat{e}_c$, whereas the $y_c$- and $z_c$-axes are perpendicular to the $x_c$-axis. Therefore, any point on the chord-line specified by $s_a$ and $s_b$ can be denoted as $(x_c, s_a, s_b)$, and $f(x_c, s_a, s_b)$ and $g_c(x_c, s_a, s_b)$ may be used to denote the image function and the backprojection on the chord-line, which satisfy:

$$f(\vec{r})=f_c(x_c,s_a,s_b) \text{ and } g(\vec{r})=g_c(x_c,s_a,s_b) \tag{39}$$

where $\vec{r}$ and $x_c$ are related through Equation (6). In terms of $P(u_d, v_d\, s)$, the backprojection image on a chord specified by $s_a$ and $s_b$ is:

$$g_c(x_c, s_a, s_b) = \int_{s_a}^{s_b} \frac{\operatorname{sgn}(-\hat{\beta}\cdot\hat{e}_w)ds}{|\vec{r}(x_c)-\vec{r}_0(s)|}\frac{\partial}{\partial s}P(u_d, v_d, s)\Big|_{\hat{\beta}} \tag{40}$$

The signum factor in the integral derives from the extension of the data function in Equation (26). For $\vec{r}$ on the chord-line, the kernel $K(\vec{r}, \vec{r}\,')$ in Equation (24) may be rewritten as:

$$\begin{aligned} K(\vec{r}, \vec{r}\,') &= \frac{1}{2\pi j}\int_R d\nu_c \operatorname{sgn}[\nu_c]e^{2\pi j\nu_c(x_c-x_c')}\delta(y_c')\delta(z_c') \\ &= \frac{1}{2\pi^2(x_c-x_c')}\delta(y_c')\delta(z_c') \end{aligned} \tag{41}$$

where $\vec{r}\,'\epsilon R^3$, and $v_c$, denotes the spatial frequency with respect to $x_c$. Applying Equation (34) to Equation (23) yields:

$$f_c(x_c, s_a, s_b) = \frac{1}{2\pi^2}\int_R \frac{dx_c'}{x_c - x_c'} g_c(x_c', s_a, s_b) \tag{42}$$

where $x_c \epsilon R$. Therefore, the image $f_c(x_c, s_a, s_b)$ on the chord-line is the Hilbert transform, along the chord-line, of the backprojection image $g_c(x_c, s_a, s_b)$. The result in Equation (42) provides a methodology for reconstructing the image on a chord from knowledge of the backprojection image over the entire chord-line. As discussed in more detail below, by exploiting the condition that the image support is confined on the chord, it is shown that the image on the chord can be reconstructed from knowledge of the backprojection image only on the chord.

Figure 16:
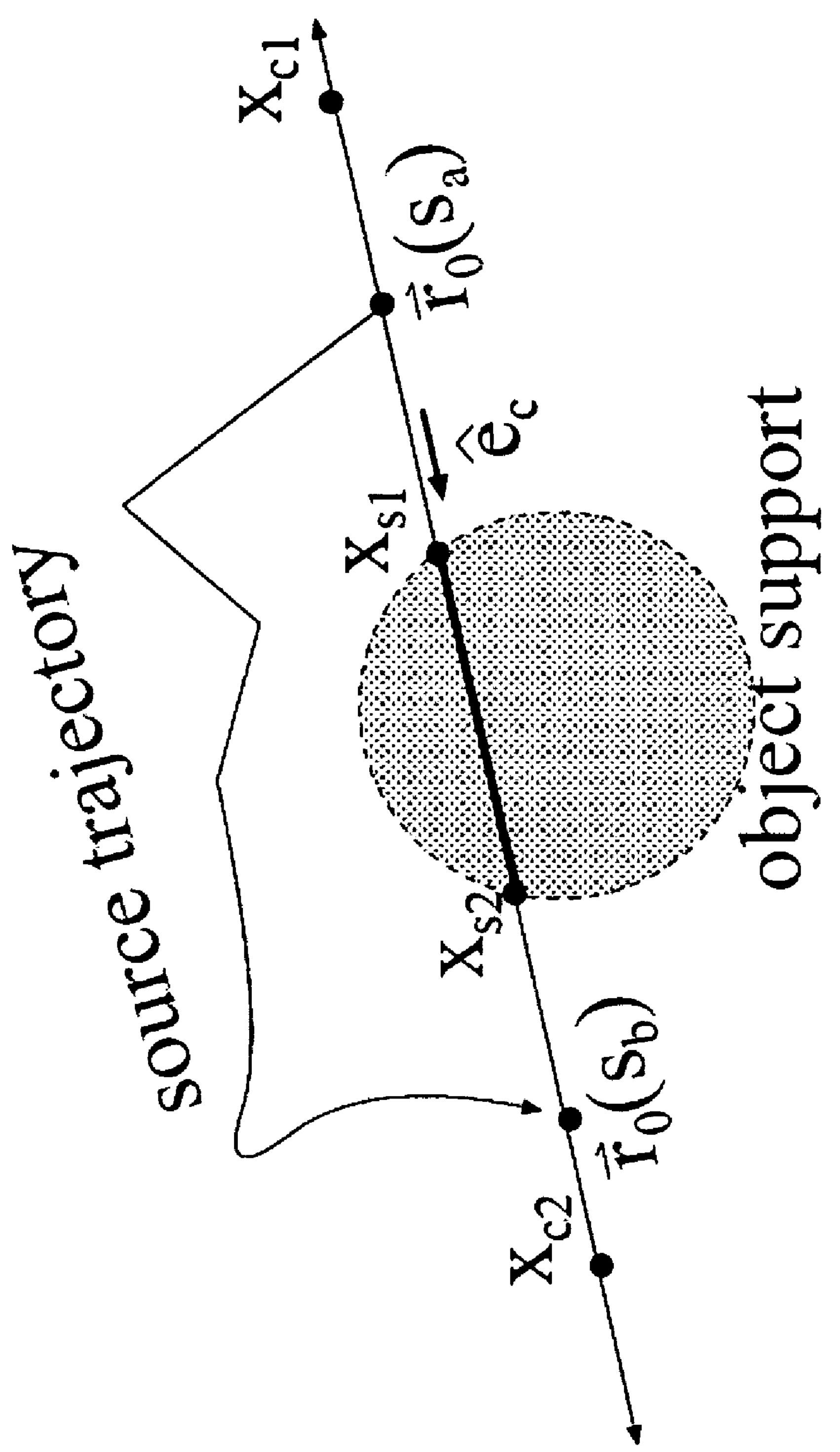
FIG. 16 illustrates an object support and source trajectory, illustrating the support segment ($x_c \in [x_{s1}, x_{s2}]$) and backprojection segment ($x_c \in [x_{c1}, x_{c2}]$).

$x_{s1}$ and $x_{s2}$ are denoted as the endpoints of the intersection of the chord with the support cylinder, and referred to as the support segment on the chord. Without loss of generality, it is assumed that $x_{s1} \leqq x_{s2}$. Considering condition (1) on the trajectory, $[x_{s1}, x_{s2}] \epsilon [-l, l]$, i.e., the support segment is always within the chord as shown in FIG. 16. Specifically, FIG. 16 depicts an object support and source trajectory, illustrating the support segment $(x_c \epsilon [x_{s1}, x_{s2}])$ and backprojection segment $(x_c \epsilon [x_{c1}, x_{c2}])$. Performing the Hilbert transform with respect to $x_c$ on both sides of Equation (42), results in:

$$\begin{aligned} g_c(x_c, s_a, s_b) &= 2\int_R \frac{dx_c'}{x_c' - x_c} f_c(x_c', s_a, s_b) \\ &= 2\int_{x_{c1}}^{x_{c2}} \frac{dx_c'}{x_c' - x_c} f_c(x_c', s_a, s_b), \end{aligned} \tag{43}$$

where $x_c \epsilon R$, and parameters $x_{c1}$ and $x_{c2}$ satisfy $x_{c1} \epsilon (-\infty, x_{s1}]$ and $x_{c2} \epsilon [x_{s2}, \infty)$, respectively. $[x_{c1}, x_{c2}]$ is referred to as the backprojection segment. The last part of Equation (43) is determined by observing that $f_c(x_c, s_a, s_b)=0$ for $x_c \notin [x_{s1}, x_{s2}]$.

The result in Equation (43) represents a Hilbert transform on a finite interval, and its inversion can be obtained as:

$$f_c(x_c, s_a, s_b) = \frac{1}{2\pi^2}\frac{1}{\sqrt{(x_{c2}-x_c)(x_c-x_{c1})}} \times \left[\int_{x_{c1}}^{x_{c2}} \frac{dx'_c}{x'_c - x_c} \sqrt{(x_{c2}-x'_c)(x'_c-x_{c1})}\, g_c(x'_c, s_a, s_b) + C\right], \tag{44}$$

where $x_c \in [x_{s1}, x_{s2}]$, the relationship between $x_c$ and $\vec{r}$ is determined by Equation (6), and the constant C is given by:

$$C = 2\pi\int_{x_{c1}}^{x_{c2}} f_c(x_c, s_a, s_b)\,dx_c = 2\pi D(\vec{r}_0(s_a), \hat{e}_c) \tag{45}$$

Because the second term in Equation (44) is only a constant that can readily be obtained directly from data, the computation load required for reconstructing the image on a chord is determined by the compilation load required by the first term in Equation (44).

By modifying the form of the first term, Equation (44) may be rewritten as:

$$f_c(x_c, s_a, s_b) = \frac{1}{2\pi}\frac{1}{\sqrt{(x_{c2}-x_c)(x_c-x_{c1})}}\left[\int_R \frac{dx'_c}{x_c - x'_c}\, g_\pi(x'_c, s_a, s_b) + 2\pi D(\vec{r}_0(s_a), \hat{e}_c)\right] \tag{46}$$

where $$g_\pi(x'_c, s_a, s_b) = \prod_c (x'_c)\sqrt{(x_{c2}-x'_c)(x'_c-x_{c1})}\, g_c(x'_c, s_a, s_b) \tag{47}$$

and $\Pi_c(x'_c)=1$ if $x'_c \in [x_{c1}, x_{c2}]$ and 0 if $x'_c \notin [x_{c1}, x_{c2}]$. Unlike the first term (i.e., the Hilbert transform over a finite interval) in Equation (44) that does not appear to represent explicitly a shift-invariant filtration on the $x'_c$-axis, Equation (46) indicates explicitly a shift-invariant filtering (i.e., the Hilbert transform) over the entire $x'_c$-axis. Such a change may have practical significance in terms of performing the calculations because the Hilbert transform may now be calculated efficiently by use of the fast-Fourier-transform (FFT) technique.

Analyzing Equation (47), it is observed that the image on the chord may be obtained exactly from knowledge of the backprojection image on a support segment, specified by $x_c \in [x_{s1}, x_{s2}]$, on the chord. This provides the basis for exact image reconstruction on a chord possibly from projections containing transverse truncation. Equation (47) is referred to as the backprojection-filtration (BPF) algorithm because it backprojects the modified data (i.e., the integration over s in obtaining $g_c(x'_c, s_a, s_b)$) before performing the 1D Hilbert transform of the weighted backprojection image (i.e., the integration over $x'_c$).

Generating an Image Based on Minimum-Data Filtration Backprojection

Still another methodology for reconstructing images is the minimum-data filtration backprojection (MFBP) methodology. The MFBP methodology differs fundamentally from existing FBP methodologies because, like the BPF methodology, the MFBP methodology admits reconstruction from minimum data. Specifically, the MFBP methodology may exactly reconstruct an image within a given ROI directly from reduced-scan data that contain truncations. The data acquisition methodology discussed above wherein at least one characteristic of the source is modified (such as the illumination coverage of the source) may be used to generate data for the MFBP methodology. The MFBP methodology may also exactly reconstruct an image from data that does not contain truncations.

When using the MFBP methodology with chords, filtration may be performed on data based on a projection of the segment or chord onto the detector. Any segment of the chord, or the entire chord, may be used. Using the example shown in FIG. 2*a*, the projection of segment 210 corresponds to the data from point "C" to point "D" on the detector. Filtration may be performed on this data. Then, the filtered data may be backprojected onto the segment 210. As discussed above, the type of filtration may depend on the image sought, such as a Hilbert transform if a substantially exact image is sought, or other methodologies if a substantially exact image is not sought. Similarly, segments other than segment 210 may be used. For example, a segment which includes segment 210 and additional segments 212 may be used. The segments used to reconstruct the ROI using the MFBP methodology may comprise support segments.

The following is an example using the MFBP methodology in the context of reconstructing an image based on chords. However, the MFBP methodology is not limited to reconstructing an image using chords, and may reconstruct images generally. For example, the MFBP methodology may be used in traditional reconstruction outside of the chord context.

The BPF methodology described in the above example reconstructs the image on a chord by performing a 1D filtration of the backprojection along the chord-line. It is also possible to reconstruct the image on a chord by performing the ID-data-filtration on the detector prior to their backprojection onto the chord. The MFBP algorithm described below may reconstruct images on chords for any general trajectory. Therefore, the below MFBP methodology may be applied to any of the exemplary trajectories discussed herein.

Using Equations (26), (30), and (47) in Equation (46) and changing the order of the integrations over $x'_c$ and s, we obtain $$f_c(x_c, s_a, s_b) = \frac{1}{\pi^2}\frac{1}{\sqrt{(x_{c2}-x_c)(x_c-x_{c1})}} \times \left[\int_{s_a}^{s_b} ds \int_R \frac{dx'_c}{x_c - x'_c}\frac{\sqrt{(x_{c2}-x'_c)(x'_c-x_{c1})}}{|\vec{r}' - \vec{r}_0(s)|}\, \mathrm{sgn}[-\hat{\beta}\cdot\hat{e}_w]\frac{dP(u'_d, v'_d, s)}{ds}\bigg|_{\hat{\beta}} + C\right], \tag{48}$$

where $\vec{r}$ and $x_c$, are related through Equation (6); the relationship between $\vec{r}'$ and $x'_c$ can be obtained from Equation (6) by simply replacing $\vec{r}$ and $x_c$ with $\vec{r}'$ and $x'_c$, respectively; and C is given by Equation (45).

For a given $s \in [s_a, s_b]$, letting $u_c$ denote the cone-beam projection of $x_c \in [x_{c1}, x_{c2}]$ onto the detector, it can then be shown that:

$$u_c = \frac{w_2(x_c - x_{c1})}{w_1(x_{c2}-x_c) + w_2(x_c - x_{c1})} \tag{49}$$

where $w_1=-[\vec{r}_0(s_a)-\vec{r}_0(s_a)]\cdot\hat{e}_w$, and $w_2=-[\vec{r}_0(s_b)-\vec{r}_0(s)])]\cdot\hat{e}_w$. In particular, $u_{c1}$ and $u_{c2}$ is used to denote the values of $u_c$ that are obtained when using $x_c=x_{c1}$ and $x_{c2}$ in Equation (49), respectively. Replacing $x_c$ by $u_c$ in Equation (48) yields:

$$f_c(x_c, s_a, s_b) = \int_{s_a}^{s_b} ds[w_2(x_{c2}-u_c) + w_1(u_c - x_{c1})]\left[\int_R \frac{du'_c}{u_c - u'_c} P_n(u'_c, s_a, s_b) + C\right] \quad (50)$$

where, for a given $u'_c$, one determines $x'_c$ by use of Equation (49), $\vec{r}\,'$ and $x'_c$ are related through Equation (30), $x'_c$ and $u'_c$ are related through Equation (49), and $$(u'_d, v'_d, -S(s)) = \vec{r}_0(s) - \left(\vec{r}\,' - \vec{r}_0(s)\right)\frac{S(s)}{\left(\vec{r}\,' - \vec{r}_0(s)\right)\cdot\hat{e}_w} \quad (51)$$

$$P_\pi(u'_c, s_a, s_b) = \frac{\sqrt{(x_{c2}-x'_c)(x'_c - x_{c1})}}{w_2(x_{c2}-u'_c) + w_1(u'_c - x_{c1})}\frac{\Pi_c(x'_c)}{\left|\vec{r}\,' - \vec{r}_0(s)\right|}\mathrm{sgn}\left[-\hat{\beta}\cdot\hat{e}_w\right]\frac{dP(u'_d, v'_d, s)}{ds}\bigg|_{\hat{\beta}} \quad (52)$$

It can be seen that the first term in Equation (50) represents a Hilbert transform over the $u'_c$-axis, thus allowing an efficient computation of the data filtering in Equation (50) by use of the FFT technique. Therefore, the algorithm expressed in Equation (50) may reconstruct the image on a chord by performing a filtering of the weighted data (i.e., the 1D Hilbert transform) over $u'_c$-axis on the detector followed by the backprojection of the filtered data (i.e., the integration over s) onto the chord. Because this new methodology was derived from the BPF methodology, it may also exactly reconstruct the image on a chord from truncated data, similar to the BPF methodology. This is unlike the FBP methodology which cannot reconstruct exactly the image on a chord from truncated data.

Numerical Studies Applying BPF, MFBP, and FBP

Figure 17A:
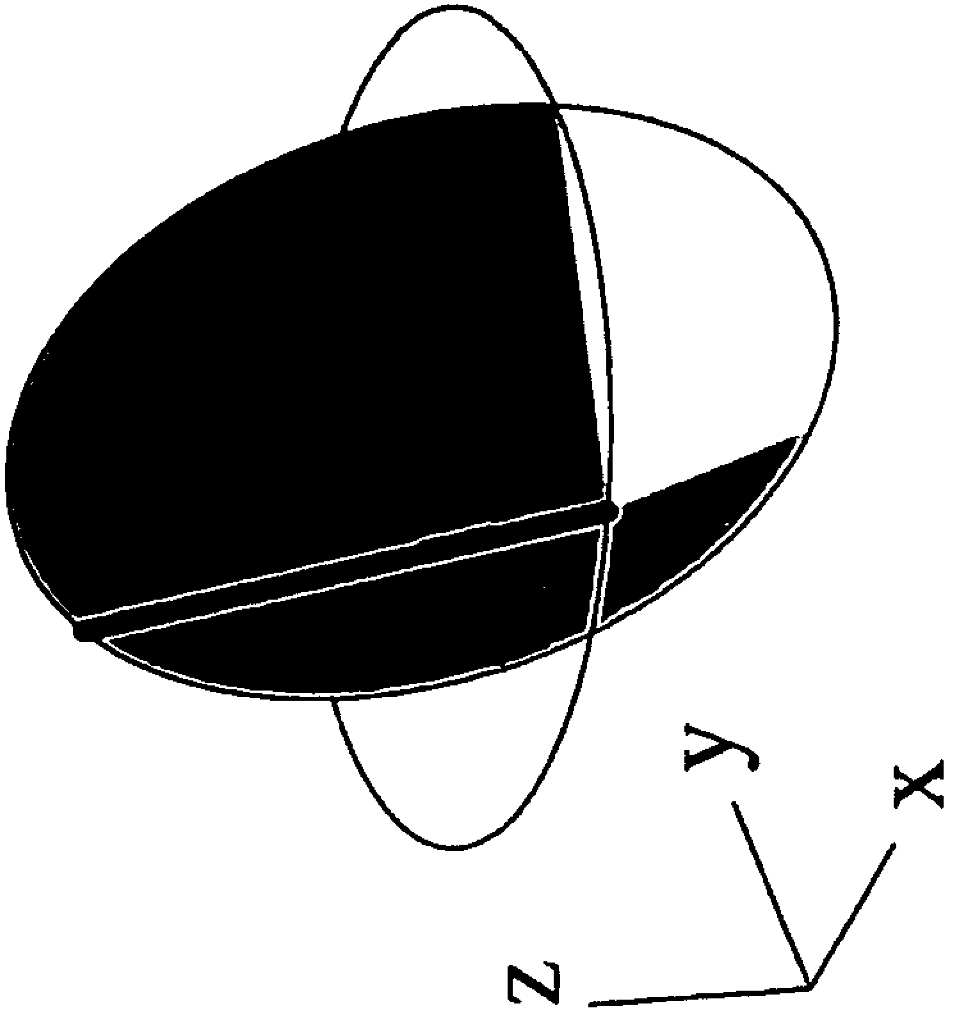
FIG. 17*a* illustrates the two-circle trajectory with the surface being generated by fixing $s_a = 0.04\pi p_{cc}$ and by sweeping $s_b$ through the interval $[0.3\pi p_{cc}/2]$.

Quantitative results of the numerical studies are presented for demonstrating the theory and methodologies developed above. First, image reconstruction is performed on individual chords from data acquired with a two-circle trajectory, as shown in FIGS. 8*c* and 17*a*. Subsequently, image reconstruction is conducted within a 3D region of interest (ROI) from n-PI data acquired with a helical trajectory.

The three methodologies described above, FBP in Equation (38), BPF in Equation (46), MFBP in Eq. (50), involve determining the data derivative:

$$\frac{\partial}{\partial q} D\left(\vec{r}_0(q), \hat{\beta}\right)\bigg|_{q=s} \quad (53)$$

or equivalently, $$\frac{dP(u_d, v_d, s)}{ds}\bigg|_{\hat{\beta}} \quad (54)$$

For a helical scan, the direct computation of the data derivative with respect to λ (or, equivalently, s) may be susceptible to aliasing artifacts due to the relatively sparse angular sampling. Instead, an alternative expression for computation of the data derivative may be derived:

$$\frac{\partial}{\partial q} D\left(\vec{r}_0(q), \hat{\beta}\right)\bigg|_{q=s} = \frac{dP(u_d, v_d, s)}{ds}\bigg|_{\hat{\beta}} = \left[\frac{d\vec{r}_0(s)}{ds}\cdot\hat{e}_u(s) + \frac{u_d}{S(s)}\frac{d\vec{r}_0(s)}{ds}\cdot\hat{e}_w(s)\right]\frac{A(u_d, v_d)}{\vec{r}\,' - \vec{r}_0(s)}\frac{\partial P(u_d, v_d, s)}{\partial u_d} + \left[\frac{d\vec{r}_0(s)}{ds}\cdot\hat{e}_v(s) + \frac{v_d}{S(s)}\frac{d\vec{r}_0(s)}{ds}\cdot\hat{e}_w(s)\right]\frac{A(u_d, v_d)}{\vec{r}\,' - \vec{r}_0(s)}\frac{\partial P(u_d, v_d, s)}{\partial u_d} + \frac{dP(u_d, v_d, s)}{ds}\bigg|_{\vec{r}\,'}, \quad (55)$$

where $A(u_d, v_d)$ is defined in Equation (32). In practical cone-beam imaging, data are measured generally on discrete grids uniformly distributed on axes $u_d$ and $v_d$. Therefore, using the expression in Equation (55), data derivatives with respect to $u_d$ and $v_d$ may be computed directly from the measured data without invoking additional interpolation, whereas the data derivative in the last term of Equation (55) may be computed analytically through the integration over s in the backprojection step, yielding the boundary terms at $s_a$ and $s_b$, respectively.

In the present numerical study, the scanning of the Shepp-Logan phantom is considered by use of two trajectories. The central point of the largest ellipsoid of the Shepp-Logan phantom is assumed to be on the origin of the fixed-coordinate system. For scan one, the two-circles trajectory described with respect to FIG. 6*c* is employed in which the two circles are perpendicular to each other ($\alpha=\pi/2$) and the trajectory segment is $s\in[-p_{cc}\pi/2, 3\,p_{cc}\pi/2]$. For scan two, the standard helical trajectory is used and images are reconstructed on chords that correspond to the so-called 3-PI lines; namely, $s_a\in[-2\pi R_0, 0]$ and $s_b\in[s_a+2\pi R_1, s_a+4\pi R_1]$ and $R_1^2=R_0^2+(h/2\pi)^2$. Condition (2) is satisfied by the two trajectories considered. From the Shepp-Logan phantom, the two trajectories are used to generate two sets of cone-beam data. For the two-circles trajectory, the arc length interval of $2\pi p_{cc}$ is divided into 1024 points, where $p_{cc}$ is taken to be 570 mm. The spacing along the helical trajectory is $2\pi R_1/1200$, where $R_0$ is 570 mm and the pitch h is 40 mm per turn. The source-detector distance is taken to be constant at S=1005 mm. A 2D detector plane is used consisting of 512×256 square detector-elements. The short side of the rectangle detector plane is along the z-axis, and the size of square detector element is 0.78 mm by 0.78 mm.

Figure 17B:
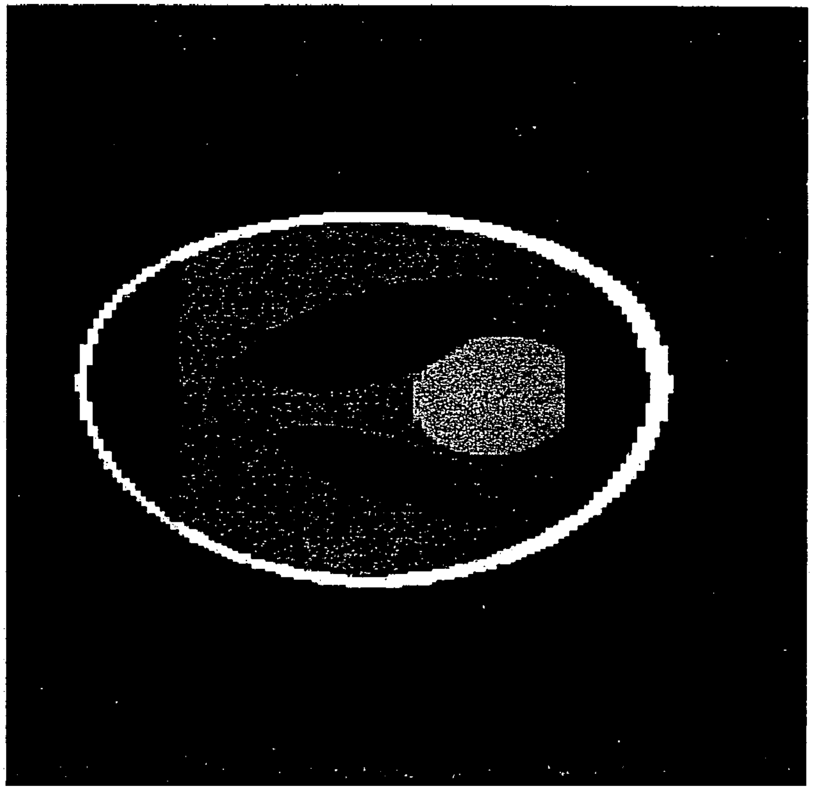
FIG. 17*b* illustrates a reconstruction image of the Shepp-Logan phantom on chords comprising the surface shown in FIG. 17*a*.
Figure 17C:
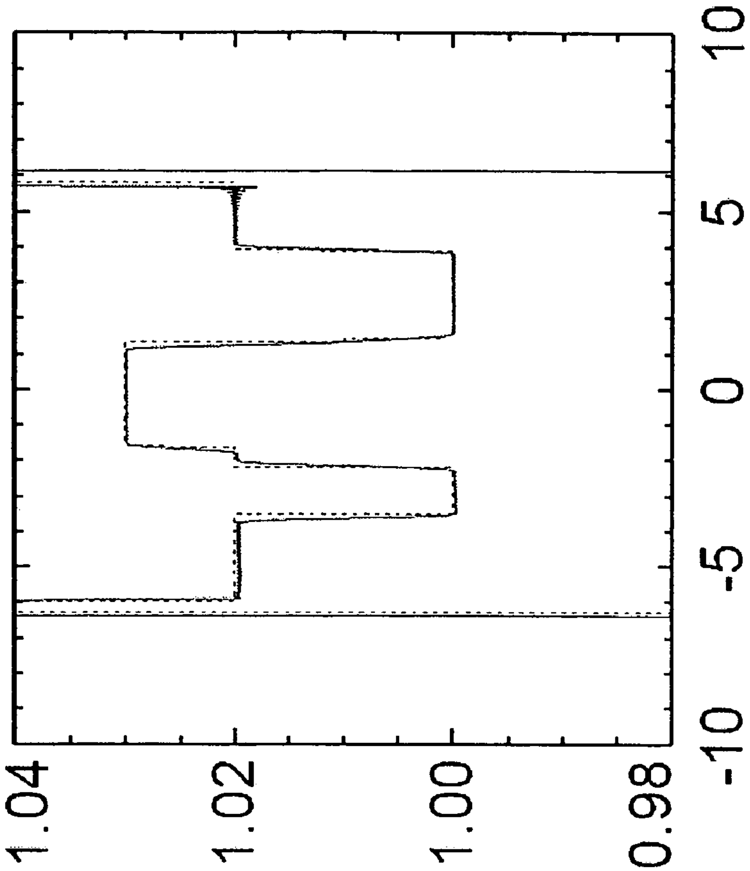
FIG. 17*c* shows a profile of the reconstructed (solid line) and true (dashed line) images along the chord indicated in FIG. 17*a*.

To demonstrate the flexibility of the chord reconstruction methodology, the two-circle source trajectory is used. For this example, only the results obtained by employing the BPF methodology are shown. Similar results may also be obtained by use of the MFBP and FBP methodologies. FIG. 17*a* shows the two-circle trajectory with the surface being generated by fixing $s_a=0.04\pi p_{cc}$ and by sweeping $s_b$ through the interval $[0.3\pi p_{cc}/2]$. The thick line segment in FIG. 17*a* depicts the chord specified by $s_a=-0.04\pi p_{cc}$ and $s_b=0.98\pi p_{cc}$. FIG. 17*b* is the reconstruction image of the Shepp-Logan phantom on chords comprising the surface shown in FIG. 17*a*. Quantitative agreement is shown in FIG. 17*c*. Specifically, FIG. 17*c* shows a profile of the reconstructed (solid line) and true (dashed line) images of the chord indicated in FIG. 17*a*, comparing the reconstructed image with the corresponding true image on a chord and demonstrating the accuracy of the proposed methodologies for image reconstruction on chords.

An ROI within any three dimensional object, such as a support cylinder, may be decomposed into a family of straight line segments. When these line segments are on chords of a trajectory satisfying conditions (1) and (2), the reconstruction methodologies may be used for exactly reconstructing images on the chords and, consequently, for reconstructing an exact image within the ROI. For the conventional helical trajectory, chords are the n-PI-line segments specified by $(n-1)\pi R_1 \leqq s_b - s_a \leqq (n+1)\pi R_1$, where n is an odd integer. In particular, for n=1, the chords become the PI-line segments.

As an example, the image reconstruction within an ROI is illustrated below using the BPF and MFBP methodologies from 3-PI data acquired with a conventional helical trajectory. To simulate the 3-PI reconstruction problem, the cone-beam data were sampled at 2400 views along the source trajectory within two turns. Noisy data is also generated by adding Gaussian noise to the noiseless data. The standard deviation of the Gaussian noise is chosen to be 0.1% of the maximum value of the noiseless data so that the very low contrast structures within the Shepp-Logan phantom are not completely overwhelmed by data noise.

Figure 18A:
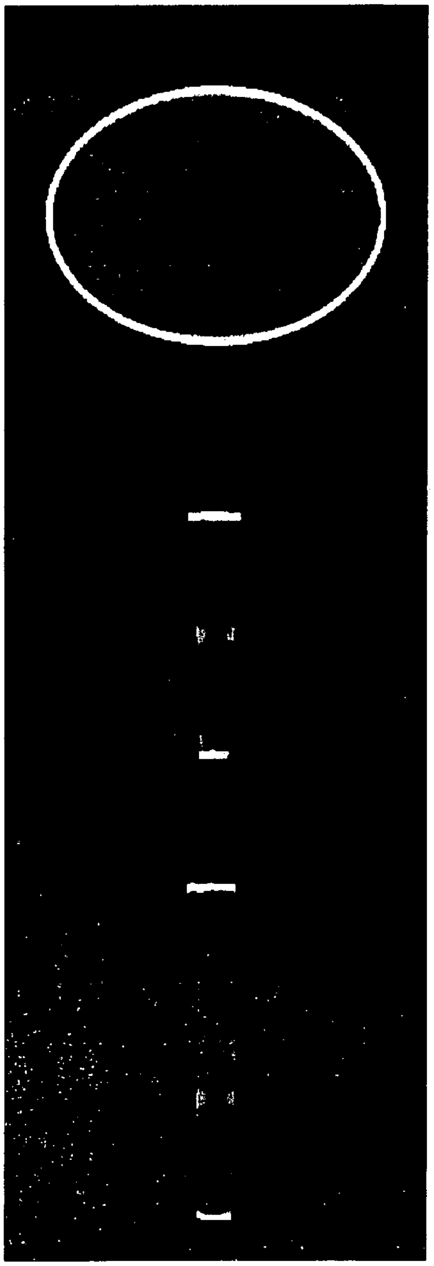
FIGS. 18*a-b* illustrate images of the Shepp-Logan phantom reconstructed using a backprojection-filtration methodology from the generated noiseless (in FIG. 18*a*) and noisy (in FIG. 18*b*) 3-PI data using chords, respectively.
Figure 18B:
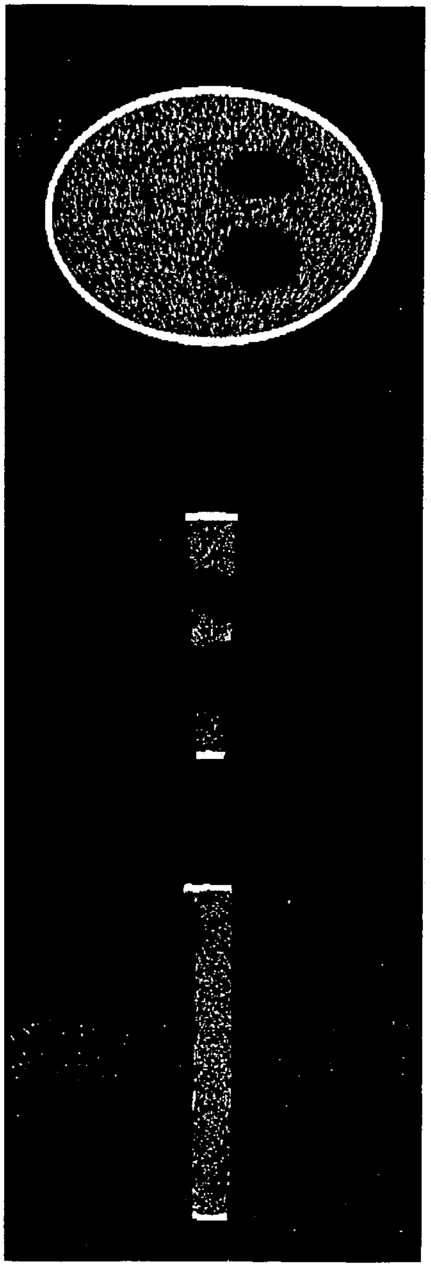
Figure 19A:
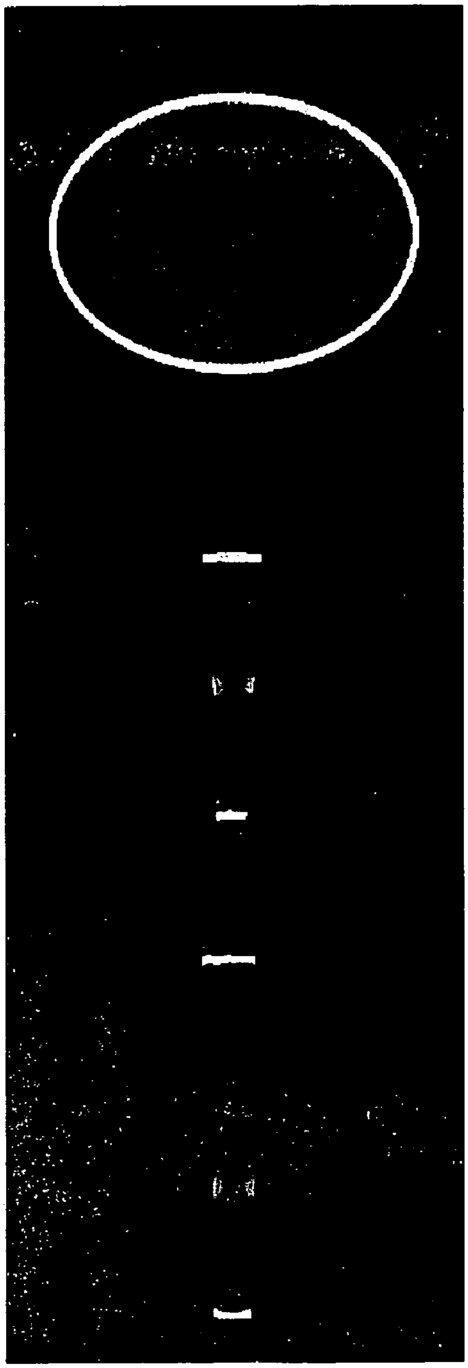
FIGS. 19*a-b* illustrate images of the Shepp-Logan phantom reconstructed using the minimum-data filtration backprojection methodology from the generated (in FIG. 19*a*) and noisy (in FIG. 19*b*) 3-PI data using chords, respectively.
Figure 19B:
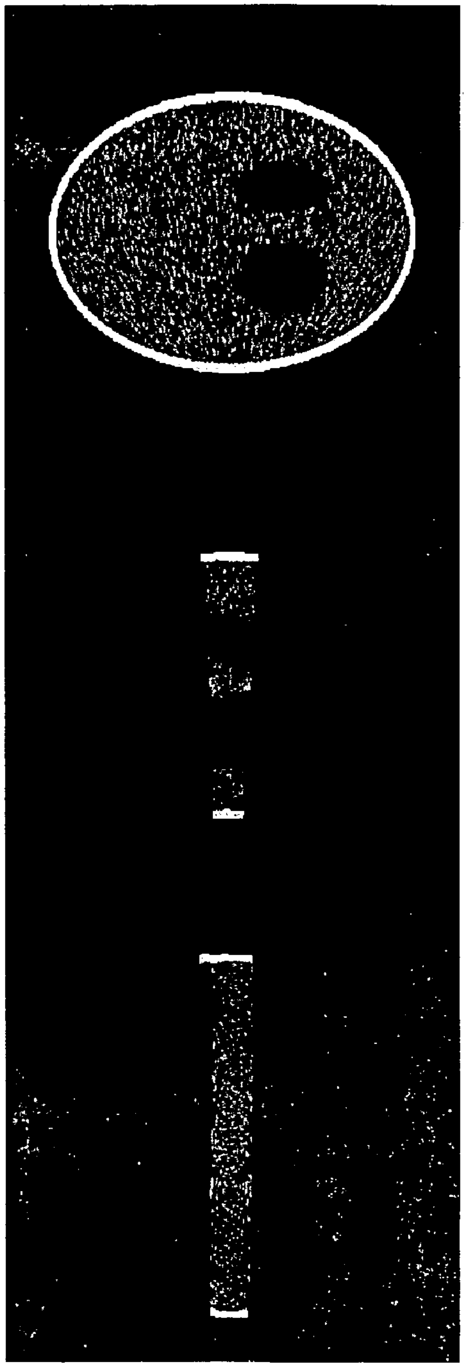

Referring to FIGS. 18*a-b*, there are shown images of the Shepp-Logan phantom reconstructed using the BPF methodology from the generated noiseless (in FIG. 18*a*) and noisy (in FIG. 18*b*) 3-PI data using chords, respectively. Images in the left, middle, and right columns in FIGS. 18*a* and 18*b* are on 2D slices specified by x=0 cm, y=−2.7 cm, and z=0 cm, respectively. The display window is [1.0, 1.05]. Referring to FIGS. 19*a-b*, there are shown images of the Shepp-Logan phantom reconstructed using the MFBP methodology from the generated (in FIG. 19*a*) and noisy (in FIG. 19*b*) 3-PI data using chords, respectively. Images in the left, middle, and right columns in (a) and (b) are on 2D slices specified by x=0 cm, y=−2.7 cm, and z=0 cm, respectively. The display window is [1.0, 1.05]. Similar results, though not shown here, may also be obtained using the FBP methodology. These results indicate that the proposed methodologies can accurately reconstruct images on 3-PI-lines (i.e., chords).

Figure 20A:
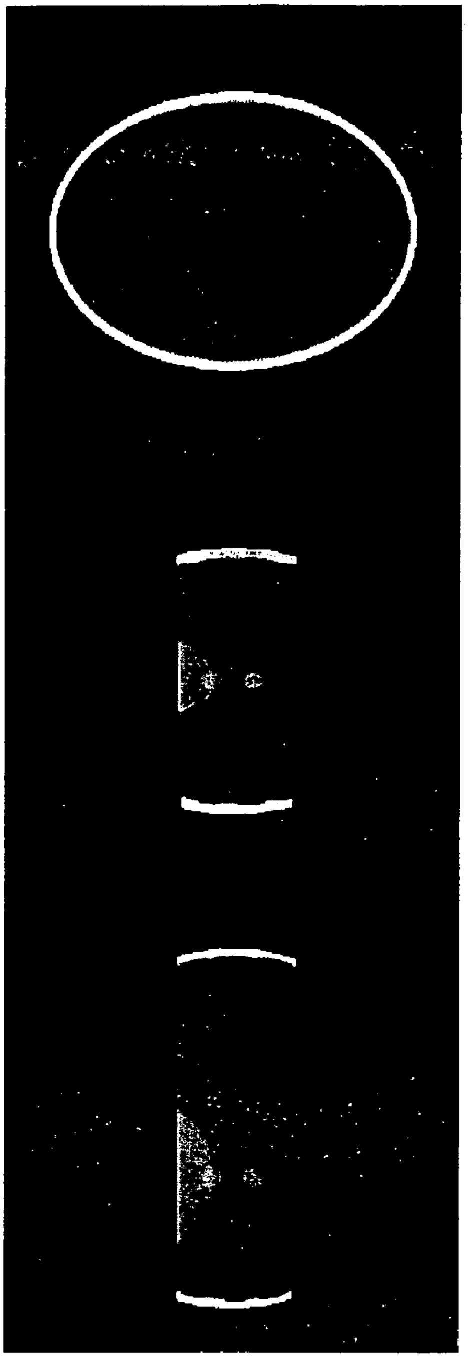
FIGS. 20*a-b* illustrate images of the Shepp-Logan phantom reconstructed using the backprojection-filtration methodology from the generated (in FIG. 20*a*) and noisy (in FIG. 20*b*) data on PI-line segments, respectively.
Figure 20B:
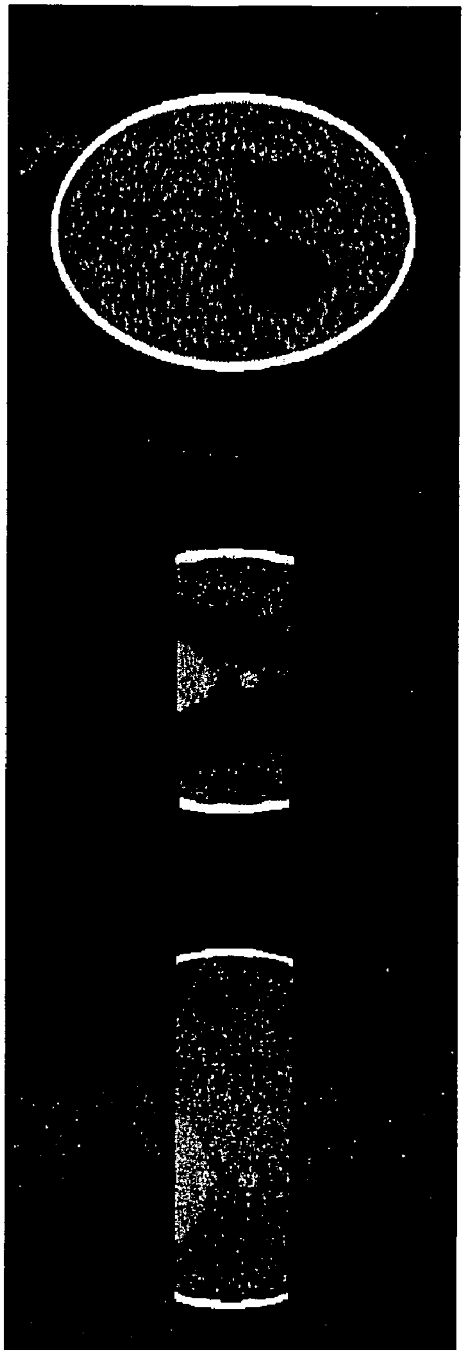
Figure 21B:
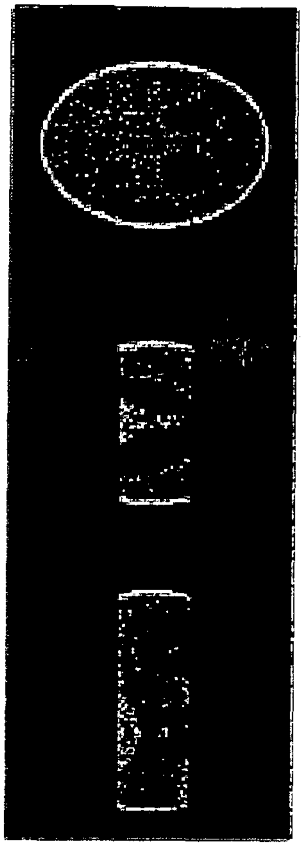
FIGS. 21*a-b* illustrate images of the Shepp-Logan phantom reconstructed using the minimum-data filtration backprojection methodology from the generated (in FIG. 21*a*) and noisy (in FIG. 21*b*) data on PI-line segments, respectively.
Figure 21A:
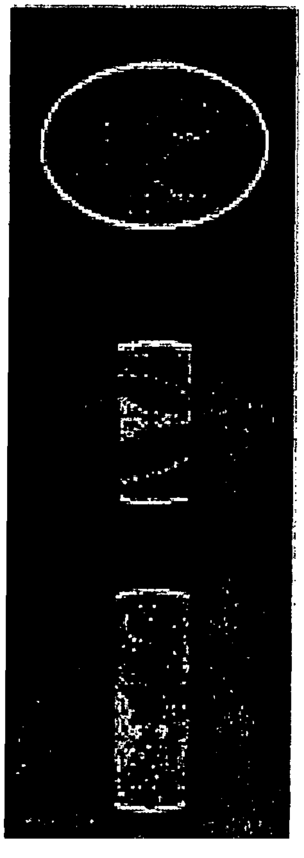

For comparison, the BPF and MFBP methodologies are also applied to reconstructing images on PI-line segments from the generated data over two turns, which are displayed in FIGS. 20*a-b* and 21*a-b*, respectively. Again, the images in FIGS. 20*a* and 21*a* and FIGS. 20*b* and 21*b* were obtained from the noiseless and noisy data, respectively. Images in the left, middle, and right columns in FIGS. 20*a* and 20*b* are on 2D slices specified by x=0 cm, y=−2.7 cm, and z=0 cm, respectively. The display window is [1.0, 1.05]. Images in the left, middle, and right columns in FIGS. 21*a* and 21*b* are on 2D slices specified by x=0 cm, y=−2.7 cm, and z=0 cm, respectively. The display window is [1.0, 1.05]. Reviewing the figures, it is apparent that the methodologies can accurately reconstruct images on PI-line segments (i.e., chords). For a fixed number of turns, it appears the 3D ROI that is reconstructable based only upon the 3-PI-line segments is smaller than that reconstructable based upon the PI-line segments. This may be understood by recognizing that more 3-PI-line segments (i.e., more turns) than the PI-line segments are generally required to fill a given ROI.

PET Imaging

As discussed above, PET imaging is a diagnostic imaging procedure that may assess the level of metabolic activity and perfusion in various organ systems of an object, such as a human body. Some present PET imaging systems adopt a cylindrical configuration in which discrete detection elements are employed and arranged to form a stack of circular detector rings. Analytic PET reconstruction methods are also designed to work with this geometry. However, configurations other than a cylindrical configuration may be used.

PET systems based on detector panels have also been investigated and developed. For example, the PENN-PET systems consist of six hexagonally arranged flat, single-crystal NaI(Tl) detectors. In an exemplary C-PET scanner, these flat panels are replaced with curved NaI(Tl) plates. Other types of detectors may also be used. In addition, coincidence imaging by use of conventional gamma cameras have been considered. Detector panels may be used in small-animal and application-specific PET imagers. For example, dedicated PEM (positron emission mammography) systems and prostate imagers are often based on using two opposite flat or curved detector panels.

One advantage to using detector panels in a PET system is its cost-effectiveness. Large-area panels having high packing fraction can be built at a relatively low cost for obtaining PET systems with considerable axial extensions and hence increased detection sensitivity and imaging-volume coverage. The use of detector panels also allows for modular PET system designs, thereby offering flexible configurations that can be exploited for achieving optimal imaging under varying imaging conditions. Large-area detector panels may be used for providing high-performance imaging of objects, such as small-animal and application-specific PET imaging.

Image reconstruction for panel-based PET systems is accomplished by use of either iterative techniques or conventional analytic methodologies. Iterative techniques for 3D PET imaging are typically computationally extensive; on the other hand, analytic methodologies are generally more efficient. However, the conventional analytic methodologies are developed for working with cylindrical PET systems; therefore, it is necessary to interpolate the acquired data onto cylindrical coordinates before reconstruction for panel-based systems. This process can result in significant resolution loss in high-resolution imagers, such as in small-animal PET systems. Furthermore, the effectiveness and accuracy of existing analytical methodologies rely on the satisfaction of considerable restrictive imaging conditions. These conditions are often difficult to satisfy by panel-based PET systems. (For example, significant gaps may often exist between adjacent panels, resulting in missing data in the sinogram and leading to streak artifacts in images.)

Chord-based reconstruction may improve PET imaging. For example, for cone-beam reconstruction, the methodologies disclosed above allow for the use of general source trajectories and permit exact or substantially exact ROI reconstructions from reduced data. This ROI imaging capability may be useful for application-specific imaging in which small field-of-view scanners are used for acquiring data at various positions and views. Conversely, with these general reconstruction methods, one can study imaging configurations for producing images of certain prescribed ROIs while reducing radiation dose or avoiding exposure to critical organs.

The reconstruction methods discussed above, such as the x-ray cone-beam reconstruction techniques, may be extended to PET systems for producing an entirely new class of analytic reconstruction methods. Because the source trajectory may be any continuous path that is piecewise $C^1$ smooth, these techniques may be applied to work with the native data coordinates of PET systems, such as panel-based PET systems, without requiring interpolation of the data onto certain preferred coordinates. Therefore, one source of resolution loss in the conventional analytic PET reconstruction may be eliminated. In addition, because the methodologies allow for exact ROI reconstruction from reduced data that satisfy certain conditions, the reconstruction problems due to failed detection elements and detector gaps may be avoided for certain ROIs. The performance of these methods, such as image noise characteristics and spatial resolution, is discussed below.

Furthermore, the new techniques may be used to investigate the idea of modular design in which a PET system's configuration is flexible for yielding optimized performance under varying imaging conditions. For example, the reconstruction methodology may allow one to examine whether a given configuration can generate exact reconstructions for prescribed ROIs before reconstruction is performed. Given an imaging task, one can therefore develop suitable configurations for use and select among them those that can meet certain conditions, such as maximized sensitivity.

In PET, every pair of detection elements may define a line of response (LOR), which is conventionally defined as the line connecting the center of the front faces of the two detection elements. Assuming ideal spatial resolution, the expected coincidence counts measured by a PET scanner are equal to the line integrals of the activity distribution along the scanner's LORs. In comparison, the line integrals generated in x-ray cone-beam imaging are defined by the lines connecting the x-ray source to x-ray detectors. Therefore, every detection element in a PET system may be treated as the "source" or a virtual source in the cone-beam geometry, with the others as the detectors. By making this connection, which is discussed in more detail below, the reconstruction techniques discussed above may be readily extended to generate an entirely new class of analytic 3D PET reconstruction methodologies.

Figure 22B:
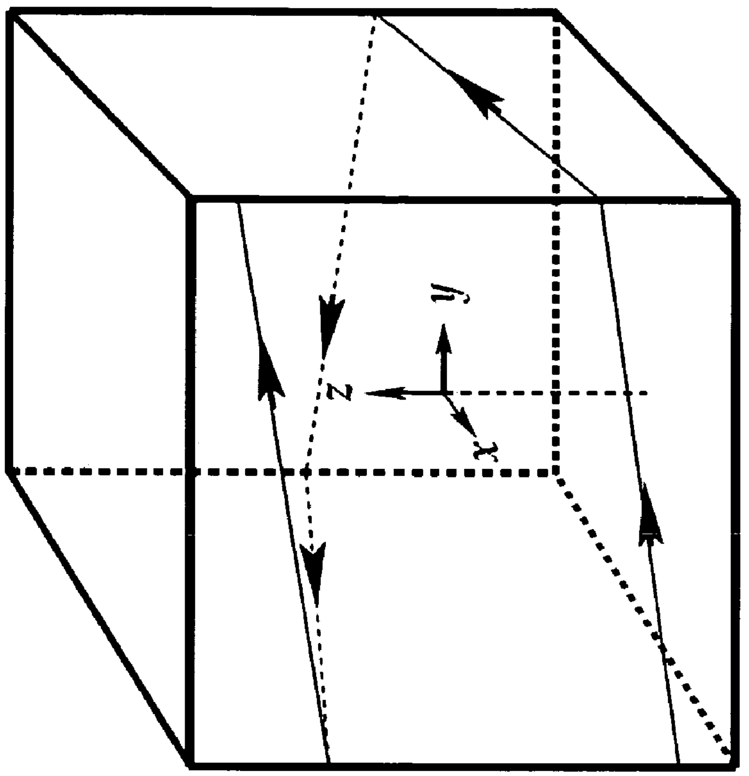
FIG. 22*b* illustrates a trajectory obtained by projecting a helical path onto the detector faces of a PET system.

As merely one example, the x-ray cone-beam reconstruction methods discussed above may be extended to work with any PET scanner configuration. As a specific example, however, a PET system that consists of four flat detector panels is considered, as shown in FIG. 22*b*. The LORs generated by this scanner configuration do not provide convenient sampling on the native coordinates assumed in analytic methods developed for reconstructing data generated by cylindrical PET systems. Although data can be rebinned, the process can be quite involved in order to avoid resolution degradation.

Figure 22A:
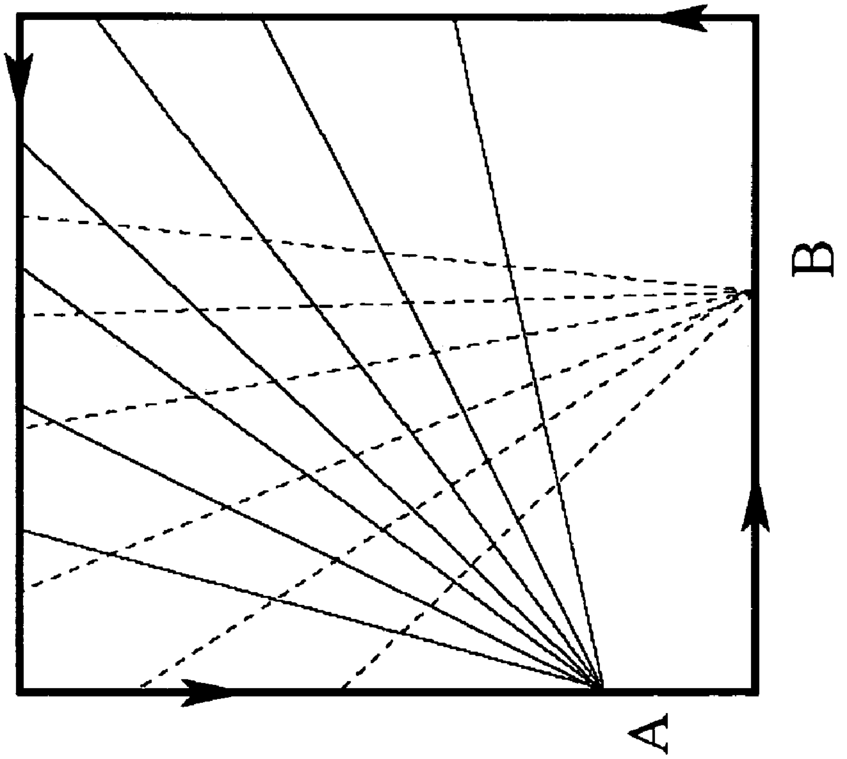
FIG. 22*a* illustrates two examples of fan-beam data generated by grouping the lines of response (LORs) associated with a given detection element (A or B) in a 2D rectangular PET system.

FIG. 22*a* illustrates an example of fan-beam data generated by grouping the LORs associated with a given detection element (A or B) in a 2D rectangular PET system. By advancing the detection element along the detector faces (indicated by arrows), an effective virtual source trajectory may be obtained. In this case, there is a unique non-trivial source trajectory. Thus, FIG. 22*a* illustrates how 2D PET data may be regrouped or organized into fan-beam data. The LORs associated with a given detection element form the fan-beam data with the detection element acting as the "source." A "source trajectory" or a virtual source trajectory can be obtained by advancing the source position on the detector faces. With the 2D rectangular system the only non-trivial trajectory consists of the four connected straight lines. When extending to 3D four-panel rectangular PET systems, the LORs associated with a given detection element may now form the cone-beam data. In this case, however, the source trajectory is no longer unique. In fact, any continuous path defined on the four detector panels is a valid path. FIG. 22*b* illustrates a virtual source trajectory obtained by projecting a helical path onto the detector panels. The pitch of the helical path may be varied for defining different trajectories. Different trajectories of this kind may also be generated by translating a trajectory along the scanner's axis. Trajectories as shown in FIG. 22*b* are different from the usual helical trajectories that are widely considered in x-ray cone-beam imaging: they contain connected linear segments with kinks. Regardless, the analytic cone-beam reconstruction techniques discussed above may be directly applied to work with such trajectories.

With the cone-beam reconstruction techniques, different paths result in different reconstruction algorithms and in general yield different regions that permit exact reconstruction (up to statistical uncertainties). For example, algorithms obtained with large-pitch helical trajectories may correspond to reconstructions obtained by including larger ring-difference coincidence data. Conversely, exact reconstruction for a given ROI may be obtained by employing different source trajectories, and hence from non-identical subsets of the acquired data. By appropriately defining multiple virtual source trajectories and averaging results generated by using these trajectories, all measured data may be considered in reconstruction for reducing noise. As shown below, reconstructions with the trajectory are illustrated in FIG. 22*b*. However, the reconstruction algorithm is applicable for general trajectories.

Chord-based reconstruction may be used for image reconstruction. For example, backprojection filtration (BPF) and the minimum-data filtered backprojection (MFBP) methodologies may be used for image reconstruction from cone-beam data acquired with a general trajectory. These methodologies may accommodate projection data collected with a trajectory with kinks. As FIGS. 22 *a* and *b* above show, data acquired with a panel-based PET system may be interpreted as cone-beam data acquired with a virtual trajectory with singularities. Therefore, the methodologies for image reconstruction from cone-beam data may readily be applied to image reconstruction in the panel-based PET system.

As shown in FIG. 22*b*, an effective virtual trajectory $\vec{r}_0(\lambda)$ may be designed for a four-panel PET system. Such an effective virtual trajectory is a piecewise smooth function of λ with multiple singularities at the junctions of two neighboring panels. For the designed trajectory, a chord-line may be defined as a straight line intersecting with the effective virtual trajectory at two points $\vec{r}_0(\lambda_a)$ and $\vec{r}_0(\lambda_b)$. Alternatively, a chord may be defined as a curve intersecting with the effective virtual trajectory at two points $\vec{r}_0(\lambda_a)$ and $\vec{r}_0(\lambda_b)$. As discussed above, the segment on the chord-line with $\vec{r}_0(\lambda_a)$ and $\vec{r}_0(\lambda_b)$ as the ending points may be a type of chord. One can use:

$$\hat{e}_c = \frac{\vec{r}_0(\lambda_b) - \vec{r}(\lambda_a)}{|\vec{r}_0(\lambda_b) - \vec{r}(\lambda_a)|} \quad (56)$$

to denote the direction of the chord-line. Equation (56) is similar to equation (5). The cone-beam projection of an object function $f(\vec{r})$ may be expressed mathematically as:

$$P(u_d, v_d, \lambda) = \int_0^\infty dt f(\vec{r}_0(\lambda) + t\hat{\beta}) \quad (57)$$

where the unit vector $\hat{\beta}$ denotes the direction of a specific x-ray intersecting with the detector plane at $(u_d, v_d)$. The distance between the source and the projection point $(u_d, v_d)$ can be calculated by $A(u_d, v_d) = \sqrt{u_d^2 + v_d^2 + S^2}$ where S is the distance from the source to the detector.

Methodologies discussed above may reconstruct an image on a chord. Examples of the methodologies comprise BPF and MFBP. Similar to the discussion above for the BPF methodology, let $x_{c1}$ and $x_{c2}$ denote two ending points of a chord, and let $[x_A, x_B] \supseteq [x_{c1}, x_{c2}]$. Further, the modified data function may be defined as:

$$P'(u'_d, v'_d, \lambda) = -\left[\frac{d\vec{r}_0}{d\lambda}\cdot\hat{\beta}\right]P(u'_d, v'_d, \lambda) + A(u'_d, v'_d)\frac{d\vec{r}_0}{d\lambda}\nabla_{u_d v_d}P(u'_d, v'_d, \lambda) \quad (58)$$

The BPF methodology may be given mathematically by:

$$f(\vec{r}) = \frac{f_{bp}(\vec{r}) + f_{bc}(\vec{r})}{2\pi^2\sqrt{(x_B - x_c)(x_c - x_A)}} \quad (59)$$

where $$f_{bp}(\vec{r}) = \int_{xA}^{xB}\frac{dx'_c}{x_c - x'_c}\sqrt{(x_B - x'_c)(x'_c - x_A)} \times \int_{\lambda_1}^{\lambda_2}\frac{1}{|\vec{r}\,' - \vec{r}_0|^2}P'(u'_d, v'_d, \lambda), \quad (60)$$

$$f_{bc}(\vec{r}) = P(u_{d0}, v_{d0}, \lambda_1)\times\left[\frac{\pi\sqrt{(2l - x_B)(2l - x_A)}}{2l - x_c} + \frac{\pi\sqrt{x_B x_A}}{x_c}\right] \quad (61)$$

$$l = |\vec{r}(\lambda_b) - \vec{r}(\lambda_a)|/2, \quad (62)$$

with $$\vec{r}\,' = \vec{r}_0(\vec{r}) + x'_c\hat{e}_c,\ x'_c \in [0, 2l],$$

denoting the point on the chord identified by the coordinate $x'_c$, and $u_{do}$ and $v_{do}$ denote the location on the detector the cone-beam projection of the point $\vec{r}$ at the rotation angle $\lambda_1$. Equation (59) may be valid for any point $\vec{r}$ satisfying $x_c \in (x_A, x_B)$.

Moreover, Similar to the discussion above for the MFBP methodology, the methodology may be expressed as:

$$f(\vec{r}) = \int_{\lambda_1}^{\lambda_2} d\lambda[(1 - u_c)w_2 + u_c w_1] \times \int_{x_A}^{x_B}\frac{du'_c}{u_c - u'_c}\frac{\sqrt{(x_B - x'_c)(x'_c - x_A)}}{(1 - u'_c)w_2 + u'_c w_1} \times \frac{1}{|\vec{r}\,' - \vec{r}_0|^2} P'(u'_d, v'_d, \lambda) + \frac{1}{2\pi^2}\frac{1}{\sqrt{(x_B - x_c)(x_c - x_A)}}f_{bc}(\vec{r}), \quad (63)$$

where $u_c$ denotes the cone-beam projection of $x_c$ onto the detector, and it can be related to $x_c$ by $$u_c = \frac{w_2 x_c}{w_1(1 - x_c) + w_2 x_c},$$

with $w_1 = -[\vec{r}_0(\lambda_1) - \vec{r}_0(\lambda)]\cdot\hat{e}_w$ and $w_2 = -[\vec{r}_0(\lambda_2) - \vec{r}_0(\lambda)]\cdot\hat{e}_w$. The unit vector $\hat{e}_w$ indicates the direction from the source pointing to the middle point of the detector.

The following are numerical studies to demonstrate the ROI-image reconstruction in a four-panel PET system by use of the BPF and MFBP methodologies. Other types of PET systems and other types of methodologies may be used. For a PET system with four panels, as shown in FIG. 22*b*, one can devise a "square" virtual helical trajectory. This effective virtual trajectory may be parameterized as:

$$\vec{r}_0(\lambda) = \begin{cases} (R_0, 2R_0\lambda - R_0, h\lambda)^t & \lambda \in [0, 1], \\ (-2R_0\lambda + 3R_0, R_0, h\lambda)^t & \lambda \in [1, 2], \\ (-R_0, -2R_0\lambda + 5R_0, h\lambda)^t & \lambda \in [2, 3], \\ (2R_0\lambda - 7R_0, -R_0 h\lambda)^t & \lambda \in [3, 4], \end{cases} \quad (64)$$

where $R_0$ is the distance from a plane to the z-axis and h is similar to the pitch in a helical trajectory that determines the increase rate of the trajectory along the z-axis. With this trajectory, cone-beam projection data may be generated for the Shepp-Logan phantom for 1024 views uniformly distributed in $\lambda \in [0, 4]$ by using $R_0$=26.5 cm and h=12.8 cm.

Figure 23B:
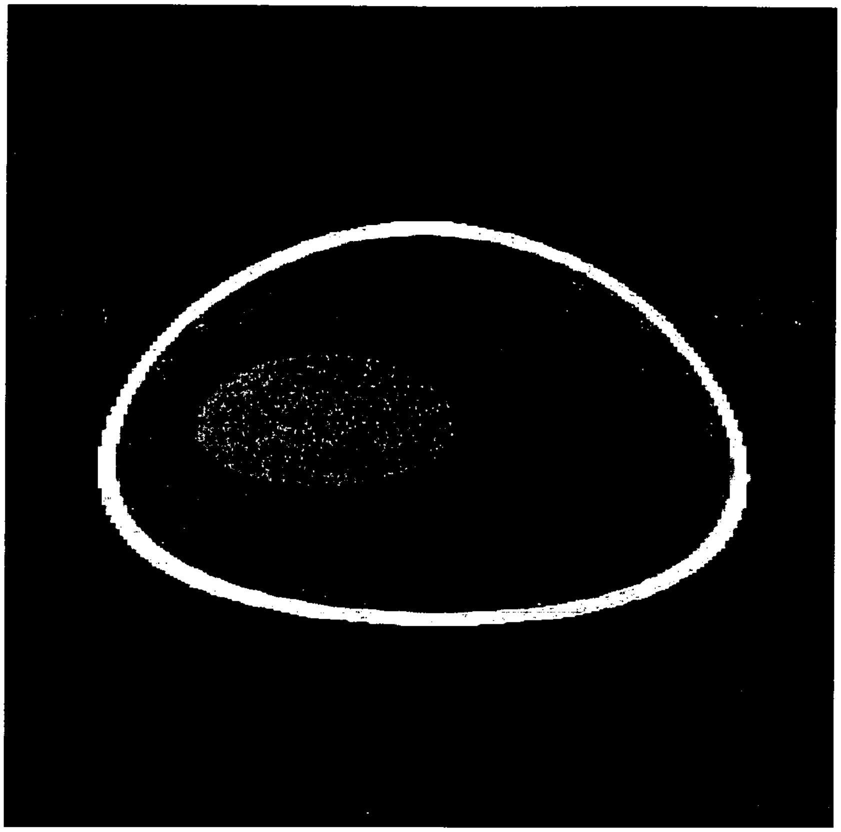
FIG. 23*b* illustrates a reconstructed image of the Shepp-Logan phantom on chords specified by $s_1=0.5$ and $s_2 \in (2, 3)$, with a display window of [1.0, 1.05].
Figure 23A:
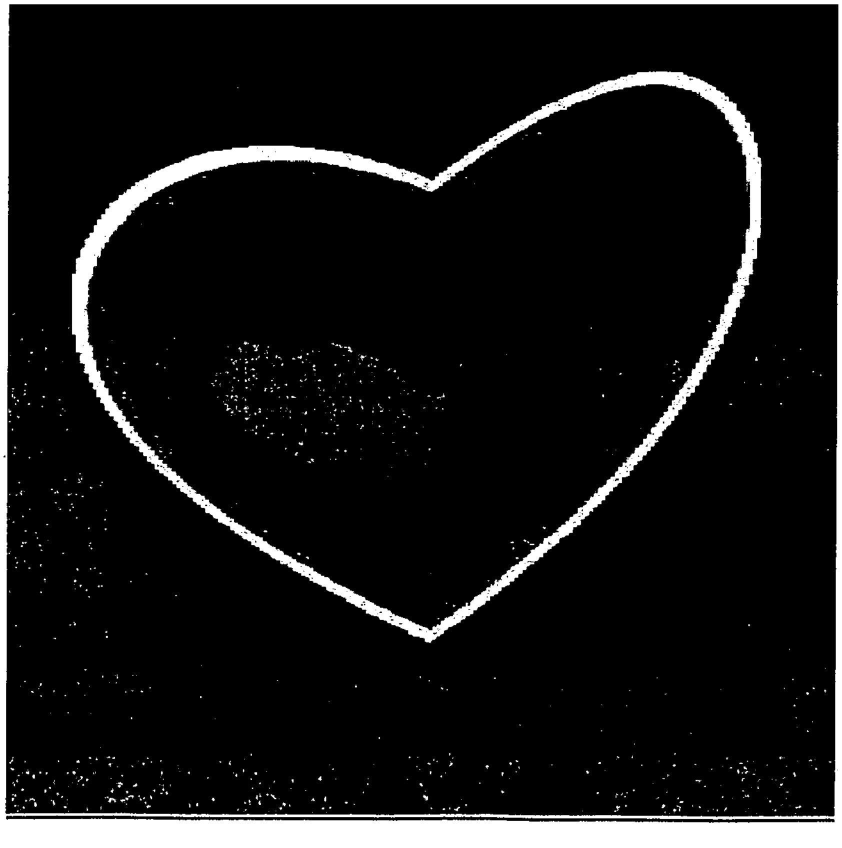
FIG. 23*a* illustrates a reconstructed image of the Shepp-Logan phantom on chords specified by $s_1=0$ and $s_2 \in (1, 3)$, with a display window of [1.0, 1.05].
Figures 24A, 24B, 24C:
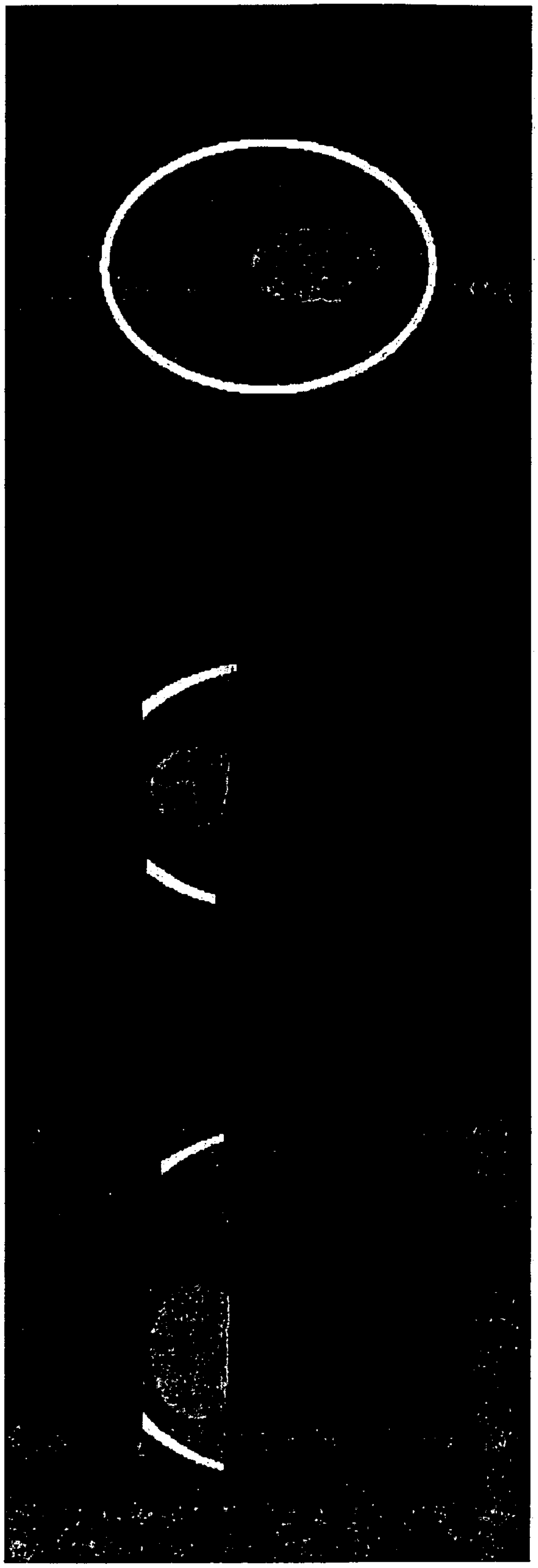
FIGS. 24*a-c* illustrate images in the planes at x=0 cm, y=−2.7 cm, and z=2.5 cm, respectively, with a display window of [1.0, 1.05].

From the simulated data, by use of the "square" virtual helical trajectory, images may be reconstructed using the BPF and MFBP methodologies. The following only displays results generated by the BPF methodology; however, the MFBP methodology may similarly be used. FIGS. 23 *a* and *b* display images obtained on two selected sets of chords of the "square" virtual helical trajectory. In these images, the horizontal axis denotes the coordinate on each chord, $x'_c$ in Equation (62), whereas the vertical axis indicates different chords. When displaying results on these native chord coordinates, the images may appear substantially different from the original phantom defined on the Cartesian coordinates. In FIG. 23*a*, the image on the set of chords specified by $\lambda_1$=0 and $\lambda_2 \in (1, 3)$ is shown. The image appears to consist of two distinct parts. By inspecting the trajectory in FIG. 22*b*, it is observed that there is a kink at $\lambda$=2, which forms the boundary of the two apparently distinct parts in the image. FIG. 23*b* also shows the image on the set of chords specified by $\lambda_1$=0.5 and $\lambda_2 \in (2, 3)$. Because the effective trajectory is smooth for $\lambda \in (2, 3)$, the image does not show distinct parts as observed in the previous case. Images obtained on the native chord coordinates may be readily transformed to obtain images on the Cartesian coordinates. FIGS. 24*a-c* shows the reconstructed images on the Cartesian coordinates. Specifically, FIGS. 24*a-c* represent the images in the planes at x=0 cm, y=−2.7 cm, and z=2.5 cm, respectively, with a display window of [1.0, 1.05].

Redundant Information

As discussed above, trajectories may be selected so that there are sufficient data generated to image the ROI. There are instances where data may be redundant in that the data are duplicative of other data already obtained. Data may be considered redundant if the source trajectory generates chords which are unnecessary to reconstruct the ROI (e.g., chords that do not fill the region of interest). Instead of simply discarding the redundant data, the redundant data may be used to modify, such as improve, a selected characteristic of the image. Any characteristic of the image may be modified using the redundant data including, but not limited to: noise, bias, texture, resolution, and variance.

The redundant information may first be identified, either qualitatively or quantitatively. For example, the redundant information may be identified qualitatively to determine whether the chords overfill the region of interest. Specifically, if a set of chords may be compiled which not only fill the ROI, but additional regions, redundant data may be present. Once it is determined that redundant data are present, the redundant data may be factored into modifying the at least one characteristic. For example, weights may be used to factor in the redundant data, as discussed in more detail below. Alternatively, the redundant data may be discarded if one wishes to accelerate the processing of the image.

Figure 7B:
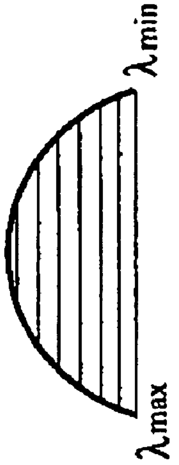
FIG. 7*b* shows the region $\Omega_R$ enclosed by the source trajectory and the PI-line segment specified by $\lambda_{min}$ and $\lambda_{max}$ shown in FIG. 6*a*.
Figure 7C:
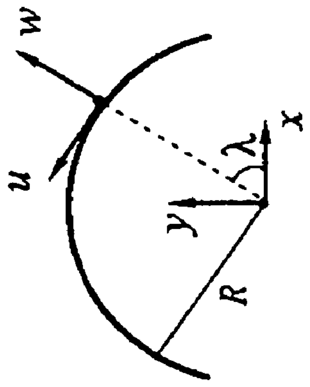
FIG. 7*c* shows a fixed-coordinate system (x, y) with its origin on the center of rotation of the source, the rotation-coordinate system {u, w} with its origin on the source point, and a radius R of the source trajectory.
Figure 25B:
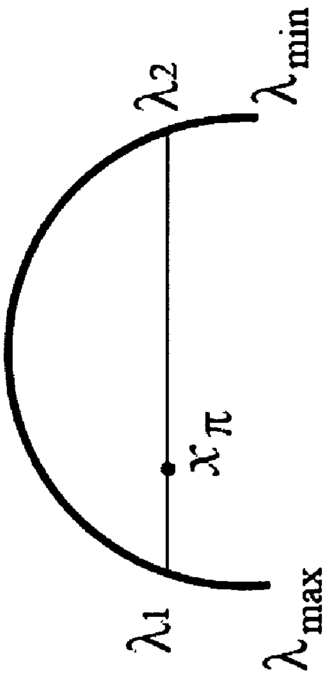
FIG. 25*b* illustrates an actual scanning angular range of $\lambda_{min}$ to $\lambda_{max}$ indicating redundant information.
Figure 25A:
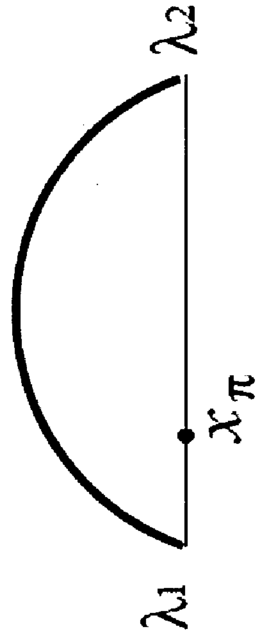
FIG. 25*a* illustrates a scanning angular range of $\lambda_1$ to $\lambda_2$ necessary for exact reconstruction of an image.

The following is an example using the scan from FIGS. 7*a-c*. Though a 2-dimensional ROI is used in the example, redundant information may likewise be used when imaging a 3-dimensional ROI. If the ROI may be contained within the region bounded by the PI-line segment specified by $\lambda_1$ and $\lambda_2$ and the fan beam scan, the necessary scanning angular range is $[\lambda_1, \lambda_2]$, as shown in FIG. 25*a*. Considering an actual scanning angular range $[\lambda_{min}, \lambda_{max}]$, as shown in FIG. 25*b*, if $[\lambda_1, \lambda_2]$□$[\lambda_{min}, \lambda_{max}]$, data acquired over the angular ranges $[\lambda_{min}, \lambda_1)$ and $(\lambda_2, \lambda_{max}]$ contain redundant information with respect to the image reconstruction on the PI-line segment specified by $\lambda_1$ and $\lambda_2$.

The chord reconstruction methodology may reconstruct the image on this PI-line segment by use of data only over $[\lambda_1, \lambda_2]$. Data over $[\lambda_{min}, \lambda_1)$ and $(\lambda_2, \lambda_{max}]$ need not be utilized.

Such redundant information may readily be incorporated into the reconstruction methodology. To factor in the redundant information, data acquired over the actual scanning angular range $[\lambda_{min}, \lambda_{max}]$ may be appropriately weighted so that the contribution to the image on the PI-line segment from the redundant portions of the acquired data may be adequately normalized.

The backprojection that exploits the redundant information inherent in data may be given by:

$$g_\pi^{(w)}(x'_\pi, \lambda_1, \lambda_2) = \int_{\lambda min}^{\lambda max} \frac{d\lambda}{\left|\vec{r}' - \vec{r}_0(\lambda)\right|^2} \left\{ -\left[ \frac{d\vec{r}_0(\lambda)}{d\lambda} \cdot \hat{\beta}(u'_d, \lambda) \right) \right] \quad (65)$$

$$[w(u'_d, \lambda)P(u'_d, \lambda)] + \left[ \frac{d\vec{r}_0(\lambda)}{d\lambda} \right] \cdot \hat{e}_u(\lambda) \sqrt{u'^2_d + S^2}$$

$$\left. \frac{\partial[w(u'_d, \lambda)P(u_d^{1,\lambda})]}{\partial_d^{u'}} \right\} + \frac{[w(u'_d\lambda)P(u'_d, \lambda)]}{\left|\vec{r}' - \vec{r}_0(\lambda)\right|} \Big|_{\lambda min}^{\lambda max}$$

where the weighting function $w(u_d, \lambda)$ is given by:

$$\omega(u_d,\lambda)-\omega(u'_d,\lambda')=1.0 \quad (66)$$

$$\omega(u_d,\lambda)=0 \text{ if } \lambda<\lambda_{min} \text{ or } \lambda<\lambda_{max} \quad (67)$$

Therefore, Equation (65) comprises a new methodology capable of exploiting the data redundancy. As shown in Equation (65), the integration is from $\lambda_{min}$ to $\lambda_{max}$. Further, the choice of ω depends on the characteristic sought to be modified. For example, if variance is sought to be improved, one may take the derivative of Equation (65) with respect to ω, set it to zero, and solve for ω. As another example, if bias may be represented as a function of ω, the bias may be improved by taking the derivative of the bias function with respect to ω, set it to zero and solve for ω.

As discussed above, there are numerous ways in which to reconstruct the image based on the collected data. One method and apparatus of imaging an ROI in an object support, with the ROI being a portion of the object support, comprises collecting data which is less than that sufficient to substantially exactly reconstruct an image for the object support, and generating a substantially exact reconstruction of the ROI based on the collected data. The object support, as discussed above, may comprise a domain in space within which the object may be non-zero and outside of which is certainly zero. For example, the data collected may comprise truncated data for the object support. Further, to collect the data, a source may be moved in a trajectory relative to the object support so that data less than that sufficient to substantially reconstruct an image for the object support is collected. The trajectory may be one in which a set of segments of chords defined by the trajectory fill the ROI. Moreover, to collect the data, a source may be controlled so that the data, which is less than that sufficient to substantially reconstruct an image for the object support, is collected. For example, controlling the source may comprise moving the source relative to the object support, and modifying at least one characteristic of the source as the source moves relative to the object support. The modifying of the source may be based on the ROI, such as reducing illumination of the object support outside of the ROI. Moreover, modifying of the source may change the illumination coverage of the source so that the ROI is substantially illuminated and outside of the ROI illumination is reduced, such as not substantially illuminated. Generating a substantially exact reconstruction of the ROI may comprise filtering the collected data, and backprojecting the filtered data to generate a density distribution. Backprojecting may comprise backprojecting onto at least a portion of a chord defined by a path of a source used for collecting data on the ROI. Alternatively, generating a substantially exact reconstruction of the ROI may comprise backprojecting based on the collected data to generate an intermediate density distribution, and filtering the intermediate density distribution to create a substantially exact image of the ROI, such as a volume filling image.

Another method and apparatus for imaging a region of an object may comprise irradiating the region with a radiation source traveling along a source path relative to the object, collecting data on radiation transmitted through the region of interest, and constructing an image of the region from the collected data based at least in part on a coordinate system defined by the source path. Constructing the image of the region from the collected data may comprise identifying a set of chords that connect pairs of points along the source path, wherein the set of chords fill a volume for a region of interest in the object, calculating image densities on the chords from the collected data, and constructing a three-dimensional image based on the image densities and on the source path. The coordinate system may be defined by a first point relating to the source path, a second point relating to the source path which is different from the first point, and a third point on a chord formed between the first point and the second point. An additional step may include transforming the constructed image into Cartesian coordinates. Or, the constructed image may already be in Cartesian coordinates.

Another method and apparatus for imaging a region of an object may comprise irradiating the region with a radiation source traveling along a source path relative to the object, collecting data on radiation transmitted through the object, and constructing an image on a plurality of chords defined by the source path. The chords may comprise PI-lines. And the construction of the image may include identifying a set of chords that connect pairs of points along the source path, where the set of chords fill a volume for a region of interest in the object, calculating image densities on the chords from the collected data, and constructing a three-dimensional image based on the image densities and on the source path.

Still another method and apparatus for imaging a region of an object comprises collecting data on radiation emitted from the object and organizing the data according to detection locations that form a path, where the path defines chords with segments that fill a volume of the region of the object. Any type of radiation may be emitted, such as positron emission. Moreover, a method and apparatus for imaging an ROI using positron emission tomography may include collecting data emitted from the object and organizing the data in order to reconstruct the ROI based on chords. The organizing of the data may be based on selecting a virtual source external to the object traveling along a virtual source trajectory. Further, reconstructing the ROI may include identifying a set of chords that connect pairs of points along the virtual source trajectory, wherein the set of chords fill a volume for the ROI, calculating image densities on the chords from collected data; and constructing a three-dimensional image based on the image densities.

Still another method and apparatus for imaging a region of interest for an object may include collecting data on the region of interest, backprojecting based on the data to generate an intermediate object function, and filtering the intermediate object function to create a substantially exact image of the region of interest. The backprojecting may include backprojecting onto at least a portion of a chord defined by a path of a source used for collecting data on the region of interest. And, the filtering may comprise using a Hilbert transform. Further, backprojecting may be based on modified data (such as weighted data) to generate the intermediate object function or may be based on unmodified data.

Another method and apparatus for imaging a region of interest in an object may include collecting truncated data on the region of interest and generating a substantially exact reconstruction of an image based on the truncated data. There are various methods for generating the substantially exact reconstruction, such as filtering the truncated data and backprojecting the filtered truncated data to generate a density distribution, or such as backprojecting the data to generate an intermediate object function and filtering the intermediate object function to create a substantially exact image of the region of interest. Further, the backprojection may include backprojecting onto at least a portion of a chord defined by a path of a source used for collecting data on the region of interest.

As discussed above, the above disclosure may be applied to a variety of situations including:

1. Chord-Based Reconstruction with Non-Traditional Trajectories

As discussed above, the chord-based reconstruction may be applied to any trajectory, including helical trajectory and circular trajectory, widely used in clinical cone-beam (CB) computed tomography (CT), as well as other trajectories, such as tilted helix, saddle, circle-circle, and circle-line trajectories, which are of practical interest in certain applications. The following analysis details the application of the chord-based reconstruction to various non-traditional trajectories.

Exact image reconstruction from data acquired with these trajectories is not only practically important but also theoretically challenging. Furthermore, in some applications of cone-beam CT, the x-ray source trajectory may not be smooth and has a finite number of kinks (e.g., singularities). Examples of such trajectories include the circle-circle and circle-line trajectories. Further, other trajectories may be used. Previously, there has been no methodology for tomographic reconstruction from truncated cone-beam projections; therefore, those trajectories were analyzed on a case-per-case basis.

Tilted helical trajectories are used in routine head scans to reduce radiation exposure to the eyes and to visualize the bone image without metal artifacts due to teeth fillings. Previously methodologies used for image reconstruction from tilted helical CB data were basically approximate, and a unified method was developed to extend the application of any helical CB methodology, including exact and quasiexact methods, to tilted data by rebinning tilted helical CB data into nontilted helical CB data. Saddle trajectories have attractive features for cardiac imaging in modern C-arm systems or in multislice CT scanners. The saddle trajectory was generalized and investigated using an approach based on Katsevich's formula. Recently, the reconstruction methodology was applied using the backprojection of locally filtered projections to a saddle trajectory, and an exact shift-invariant filtered backprojection (FBP) methodology for a saddle was proposed. Circle-line and circle-circle trajectories are readily achievable in an on-board imager mounted on a linear accelerator treatment system, and the circle-circle trajectory may have important applications with the C-arm systems. An exact shift-invariant FBP methodology was applied for circle-line and circle-arc trajectories to reconstruct the image from CB data. The present chord-based methodology may be applied to all four-trajectories discussed above (tilted helical, saddle, circle-circle, and circle-line) to reconstruct the ROI-image. Moreover, the present chord-based methodology may be used to reconstruct any region-of-interest with the source trajectory that satisfies Tuy's condition.

As discussed above, an image may be reconstructed on a chord of a general source trajectory (such as a general cone-beam trajectory), which can be either a smooth trajectory or a trajectory with a finite number of kinks. Two reconstruction methodologies, backprojection filtration (BPF) and minimum-data filtered backprojection (MD-FBP), may be used for image reconstruction on a chord. As discussed above, the BPF methodology may reconstruct an image by performing a backprojection followed by filtering the backprojection data along the chord in image space. The MD-FBP methodology may reconstruct an image by first filtering data along the projection of a chord on the detector plane and by subsequently performing a backprojection of the filtered data. These two methodologies differ fundamentally from the FBP-based methodology because they may admit projection data containing both longitudinal and transverse truncations. As discussed below, ROI reconstruction may be performed on chords using a variety of methodologies, such as the BPF and MD-FBP methodologies, from data collected with the tilted helix, saddle, circle-circle, and circle-line trajectories. Thus, a single methodology may be used for various trajectories, such as clinically important trajectories, to perform image reconstruction (such as for truncated cone-beam computed tomography).

The following discusses the BPF and MDFBP methodologies for image reconstruction on chords in cone-beam CT from data acquired with a general trajectory. Other methodologies may be used.

The subject to be imaged may be confined in a cylinder of radius $R_s$. Therefore, the support of the object function $f(\vec{r})$ may satisfy:

$$f(\vec{r})=0\ x^2+y^2>R_s^2, \tag{A-1}$$

where $\vec{r}=(x, y, z)^T$, and the central axis of the support cylinder coincides with the z-axis.

The x-ray source trajectory may be characterized by a vector $\vec{r}_0(\lambda)$ that is a continuous function of a parameter $\lambda$, which can be a scanning angle or the path length. In the fixed-coordinate system, $\vec{r}_0(\lambda)=(x_0(\lambda), y_0(\lambda), z_0(\lambda))^T$, and the distance between a point on the trajectory and the z-axis may thus be given by:

$$R(\lambda)=\sqrt{x_0^2(\lambda)+y_0^2(\lambda)}. \quad \text{(A-2)}$$

One may assume that $R(\lambda)>R_s$. Therefore, the trajectory may not pass through the support cylinder and thus may not intersect the support of the object function. The line connecting the source spot and the central point of the detector plane may remain perpendicular to the flat-panel detector and the distance S between the source spot and the detector plane may be fixed during the scanning.

The trajectory considered may be a smooth or piecewise smooth function of λ. As mentioned above, the BPF and MDFBP methodologies may reconstruct images on a chord. A chord-line may be defined as a straight line connecting two points $\vec{r}_0(\lambda_a)$ and $\vec{r}_0(\lambda_b)$ on the trajectory, whereas a chord indicates the line segment between $\vec{r}_0(\lambda_a)$ and $\vec{r}_0(\lambda_b)$ on the chord-line. One can use $$\hat{e}_c = \frac{\vec{r}_0(\lambda_b) - \vec{r}_0(\lambda_a)}{|\vec{r}_0(\lambda_b) - \vec{r}_0(\lambda_a)|} \quad \text{(A-3)}$$

to denote the direction of the chord. Without loss of generality, one may assume that $\lambda_a<\lambda_b$.

The cone-beam projection of the object function may be defined as:

$$D(\vec{r}_0(\lambda),\hat{\beta})=\int_0^{\infty}dt f(\vec{r}_0(\lambda)+t\hat{\beta}), \quad \text{(A-4)}$$

where the unit vector $\hat{\beta}$ indicates the projection direction of an individual x-ray passing through the point $\vec{r}\,'\in R^3$ and may be written as:

$$\hat{\beta} = \frac{\vec{r}\,' - \vec{r}_0(\lambda)}{|\vec{r}\,' - \vec{r}_0(\lambda)|}. \quad \text{(A-5)}$$

As defined above, a chord may be the segment between points $\vec{r}_0(\lambda_a)$ and $\vec{r}_0(\lambda_b)$ on the chord-line. A point $\vec{r}$ on a chord determined by $\lambda_a$ and $\lambda_b$, may comprise:

$$\vec{r} = \frac{1}{2}[\vec{r}_0(\lambda_a) + \vec{r}_0(\lambda_b)] + x_c\hat{e}_c, \quad x_c \in [-l, l], \quad \text{(A-6)}$$

where $$l = \frac{1}{2}|\vec{r}_0(\lambda_b) - \vec{r}_0(\lambda_a)|$$

denotes one half of the chord length. For a helical trajectory and for $|\lambda_b-\lambda_a|\leqq 2\pi$, the chord-line and the chord may become the conventional PI-line and PI-line segment, respectively.

The trajectory may be specified by $\vec{r}_0(\lambda)$, where $\lambda\in[\lambda_a, \lambda_b]$. The trajectory may be continuous and may also contain a finite number of points at which $$\frac{d\vec{r}_0(\lambda)}{d\lambda}$$

does not exist. These non-differential points on the trajectory may be referred to as the kinks. Suppose that there are N−1 kinks on the trajectory of $\vec{r}_0(\lambda)$, where $\lambda\in[\lambda_a, \lambda_b]$, which consequently divide the trajectory into N differentiable pieces. Let $\lambda_i$, $i\in[2, N]$ denote the locations of the N−1 kinks, and let $\lambda_1=\lambda_a$ and $\lambda_{N+1}=\lambda_b$.

For $\vec{r}$ on a chord-line, the image function $f(\vec{r})$ may be reconstructed exactly as:

$$f(\vec{r}) = \int_{R^3} d\vec{r}\,' K(\vec{r}, \vec{r}\,')g(\vec{r}\,'), \quad \text{(A-7)}$$

where $$K(\vec{r}, \vec{r}\,') = \frac{1}{2\pi j}\int_{R^3} d\vec{v}\,\mathrm{sgn}[\vec{v}\cdot\hat{e}_c]e^{2\pi j\vec{v}\cdot(\vec{r}-\vec{r}\,')}, \quad \text{(A-8)}$$

$$g(\vec{r}\,') = \int_{\lambda_a}^{\lambda_b} \frac{d\lambda}{|\vec{r}\,' - \vec{r}_0(\lambda)|}\frac{\partial}{\partial q}\overline{D}(\vec{r}_0(q), \hat{\beta})\bigg|_{q=\lambda} = \sum_{i=1}^{N}\int_{\lambda_1}^{\lambda_{i+1}} \frac{d\lambda}{|\vec{r}\,' - \vec{r}_0(\lambda)|}\frac{\partial}{\partial q}\overline{D}(\vec{r}_0(q), \hat{\beta})\bigg|_{q=\lambda}, \quad \text{(A-9)}$$

and $$\overline{D}(\vec{r}_0(\lambda), \hat{\beta}) = D(\vec{r}_0(\lambda), \hat{\beta}) - D(\vec{r}_0(\lambda), -\hat{\beta}). \quad \text{(A-10)}$$

$g(\vec{r}\,')$ may be referred to as the generalized backprojection and $\overline{D}(\vec{r}_0(\lambda), \hat{\beta})$ may be referred to as the extended data function.

The methodology may be applied to a 2D detector plane with a 2D coordinate system $\{u_d, v_d\}$. Greater dimensional detector planes may be used. Any point on the detector plane may thus be specified by the coordinates $u_d$ and $v_d$. The object function may be between the source and detector plane, the distance S between the source and the central point of detector plane may remains a constant, and the orientation $\hat{e}_w$ of the detector may be perpendicular to $$\frac{d\vec{r}_0(\lambda)}{d\lambda}.$$

The cone-beam projection of an object function $f(\vec{r})$ may be rewritten as:

$$P(u_d,v_d,\lambda)=D(\vec{r}_0(\lambda),\hat{\beta})=\int_0^{\infty}dt f(\vec{r}_0(\lambda)+t\hat{\beta}), \quad \text{(A-11)}$$

where λ indicates the projection view, and $\hat{\beta}$ denotes the direction of a specific x-ray intersecting the detector plane at $(u_d, v_d)$. Therefore, the distance between the source and the projection point $(u_d, v_d)$ may be given by $A(u_d, v_d)=\sqrt{u_d^2+v_d^2+S^2}$. Based upon the formula in Equations (A-7)-(A-10), two methodologies have been derived for reconstruction of images on chords. Likewise, other methodologies may be used to reconstruct images on chords.

For the BPF methodology, $[x_{c1}, x_{c2}]$ may be used denote the intersection of the chord and the support of the object function. Because the trajectory may not intersect the object support, $[x_{c1}, x_{c2}] \subset [-1, 1]$. The BPF methodology may be written as:

$$f(\vec{r}) = \frac{1}{2\pi^2} \frac{1}{\sqrt{(x_B - x_c)(x_c - x_A)}} [f_{bp}(\vec{r}) + f_{bc}(\vec{r})], \quad \text{(A-12)}$$

where $\vec{r}$ and $x_c$ are related through Eq. (A-6), and parameters $x_A$ and $x_B$ satisfy that $[x_{c1}, x_{c2}] \subseteq [x_A, x_B] \subset [-1, 1]$. Eq. (A-12) may be valid only for points $\vec{r}$ satisfying $x_c \in (x_A, x_B)$. Furthermore, the term $f_{bp}(\vec{r})$ in Eq. (A-12) may be given by:

$$f_{bp}(\vec{r}) = \int_{x_A}^{x_B} \frac{dx'_c}{x_c - x'_c} \sqrt{(x_B - x'_c)(x'_c - x_A)} \int_{\lambda_1}^{\lambda_2} d\lambda \frac{1}{|\vec{r}' \vec{r}_0|^2} P'(u'_d, v'_d, \lambda), \quad \text{(A-13)}$$

where $$P'(u'_d, v'_d, \lambda) = -\left[\frac{d\vec{r}_0}{d\lambda} \cdot \beta\right] P(u'_d, v'_d, \lambda) + A \frac{d\vec{r}_0}{d\lambda} \cdot \nabla_{u_d, v_d} P(u'_d, v'_d, \lambda), \quad \text{(A-14)}$$

whereas the second term $f_{bc}(\vec{r})$ may be expressed as:

$$f_{bc}(\vec{r}) = P(u_{d0}, v_{d0}, \lambda_1) \times \left[\frac{\pi\sqrt{(l - x_B)(l - x_A)}}{l - x_c} + \frac{\pi\sqrt{(x_B + l)(x_A + l)}}{x_c + l}\right] \quad \text{(A-15)}$$

where $(u_{d0}, v_{d0})$ denotes the cone-beam projection of point $\vec{r}$ from the view $\lambda_1$.

2. The MDFBP Methodology

The MDFBP methodology may also formally be written as $$f(\vec{r}) = \frac{1}{2\pi^2} \frac{1}{\sqrt{(x_B - x_c)(x_c - x_A)}} [f_{bp}(\vec{r}) + f_{bc}(\vec{r})]. \quad \text{(A-16)}$$

where $\vec{r}$ and $x_c$ are related through Eq. (A-6), and parameters $x_A$ and $x_B$ satisfy that $[x_{c1}, x_{c2}] \subseteq [x_A, x_B] \subset [-1, 1]$. However, the first term $f_{bp}(\vec{r})$ may have a form different from that in the Eq. (A-13) and may be given by:

$$f_{bp}(\vec{r}) = \int_{\lambda_1}^{\lambda_2} d\lambda[(1 - u_c)w_2 + u_c w_1] \times \int_{x_A}^{x_B} \frac{du'_c}{u_c - u'_c} \quad \text{(A-17)}$$

-continued $$\frac{\sqrt{(x_B - x'_\pi)(x'_c - x_A)}}{(1 - u'_c)w_2 + u'_c w_1} \times \frac{1}{|\vec{r}' - \vec{r}_0|^2} P'(u'_d, v'_d, \lambda),$$

where $u_c$ denotes the cone-beam projection of $x_c$ onto the detector, and it is related to $x_c$ through $$u_c = \frac{w_2 x_c}{w_1(1 - x_c) + w_2 x_c},$$

with $w_1 = -[\vec{r}_0(\lambda_1) - \vec{r}_0(\lambda)] \cdot \hat{e}_w$ and $w_2 = -[\vec{r}_0(\lambda_2) - \vec{r}_0(\lambda)] \cdot \hat{e}_w$. Again, the Eq. (A-16) may be valid only for points $\vec{r}$ satisfying $x_c \in (x_A, x_B)$.

Computer-simulation studies are presented below in which the chord-based BPF and MDFBP methodologies have been applied to reconstructing images from data acquired by use of the tilted helical, saddle, circle-circle, and circle-line trajectories.

A tilted helical trajectory may be parameterized as $$\vec{r}_0(\lambda) = \left(R_0\cos\lambda,\ R_0\sin\lambda\cos\mu,\ R_0\sin\lambda\sin\mu + \frac{h}{2\pi}\lambda\right), \quad \text{(A-18)}$$

where $R_0$ and h indicate the radius and the pitch length, respectively, μ is a constant indicating the angle between the z-axis and the actual rotation axis of the tilted CT gantry, and parameter λ denotes the rotation angle. When μ=0, the tilted helical trajectory may become the conventional helical trajectory, and the chords may become the PI-line segments. Image reconstruction on chords specified by $\lambda_a$ and $\lambda_b$ may satisfy $|\lambda_b - \lambda_a| \leqq 2\pi$.

Figure 26B:
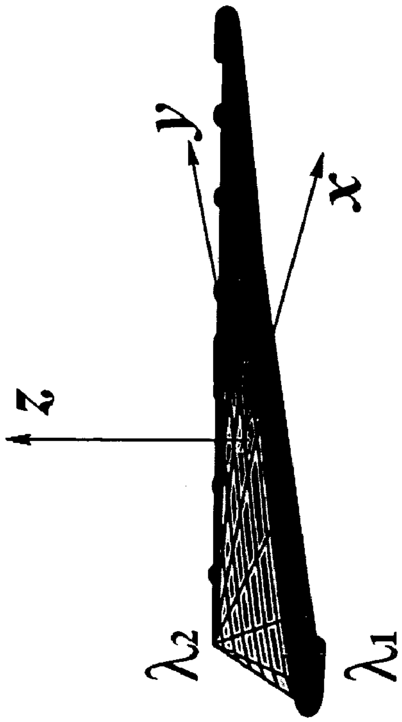
FIG. 26*b* illustrates a section of the ROI filled by the chords specified by $\lambda_1 \leqq \lambda_a < \lambda_b \leqq \lambda_2$ on this tilted helical trajectory.
Figure 26A:
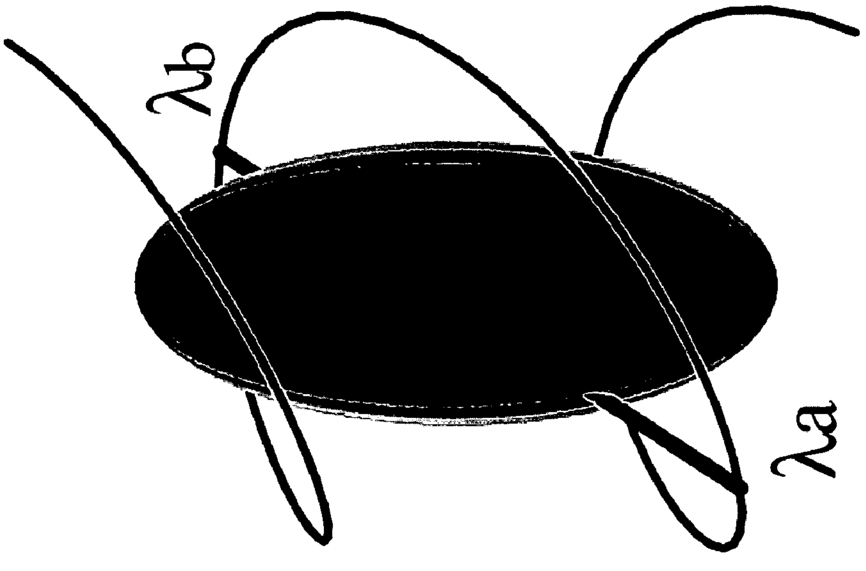
FIG. 26*a* depicts a tilted helical trajectory (thin line curve) and a chord (thick line segment labeled by $\lambda_a$ and $\lambda_b$).
Figure 27C:
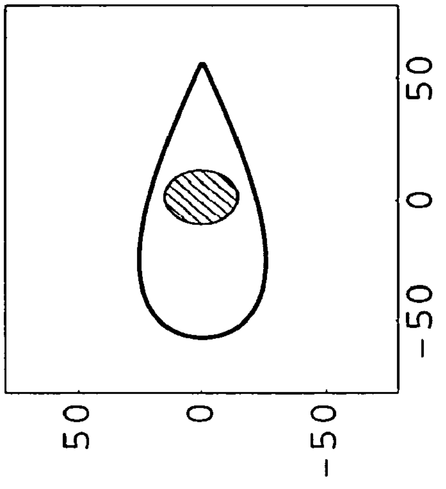
FIG. 27*a-c* shows the intersections of the ROI of FIG. 26B with three planes at x=0 cm, y=0 cm, and z=0 cm, respectively.
Figure 27B:
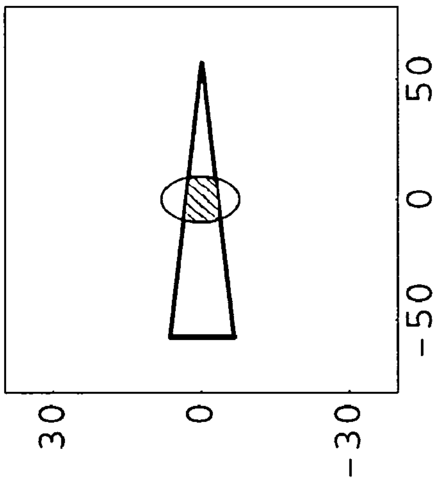
Figure 27A:
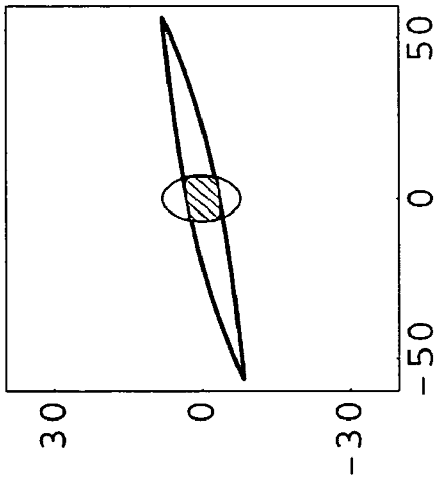

FIG. 26A depicts a tilted helical trajectory (thin line curve) and a chord (thick line segment labeled by $\lambda_a$ and $\lambda_b$). For a scan performed from $\lambda_1$ to $\lambda_2$, the 3D ROI, which is formed by the chords on this piece of trajectory, is shown in FIG. 26B. Specifically, FIG. 26B illustrates a section of the ROI filled by the chords specified by $\lambda_1 \leqq \lambda_a < \lambda_b \leqq \lambda_2$ on this tilted helical trajectory. In the numerical studies below, $\lambda_1 = -\pi$ and $\lambda_2 = \pi$ are used. FIGS. 27A-C also depict the intersections of this ROI with three planes at x=0 cm, y=0 cm, and z=0 cm, respectively. In particular, the solid curves show the intersections of the two curved surfaces in FIG. 26B with planes at x=0 cm (FIG. 27A), y=0 cm (FIG. 27B), and z=0 cm (FIG. 27C), respectively. Similarly to a helical trajectory, the 3D ROI filled by a set of chords specified by $\lambda_1 \leqq \lambda_a < \lambda_b \leqq \lambda_2$ on a tilted helical trajectory is the 3D volume sandwiched between two curved surfaces, which are formed by the chords converging to $\lambda_1$ and to $\lambda_2$.

Figure 28B:
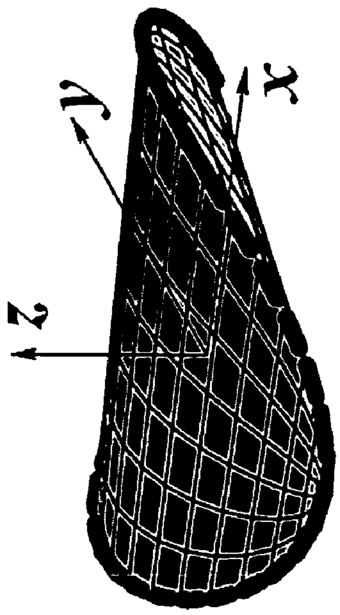
FIG. 28*b* shows the ROI filled by the chords on this trajectory may be the 3D volume sandwiched between the two curved surfaces.
Figure 28A:
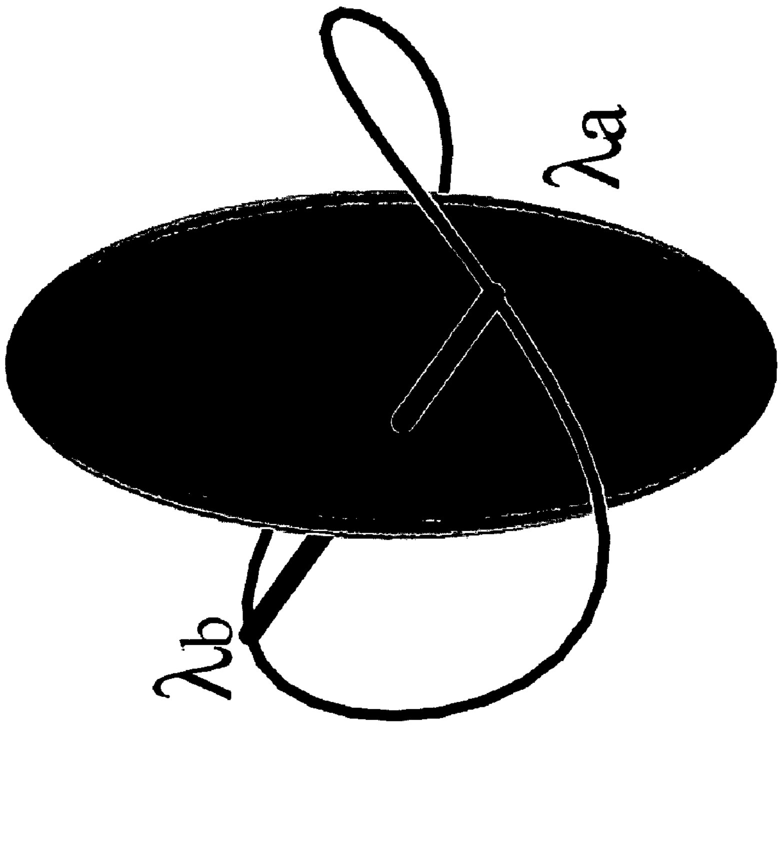
FIG. 28*a* illustrates a saddle trajectory (denoted by the thin curve), and the thick line segment labeled by $\lambda_a$ and $\lambda_b$ indicates a chord.

A saddle trajectory, as shown in FIG. 28A, may be determined by:

$$\vec{r}_0(\lambda) = (R_0 \cos\lambda, R_0 \sin\lambda, h \cos 2\lambda), \quad \text{(A-19)}$$

where λ denotes the polar angle within the x-y plane, and $R_0$ and h are the radius and the height of the saddle. As shown in FIG. 28A, the thin curve denotes the saddle trajectory, and the thick line segment labeled by $\lambda_a$ and $\lambda_b$ indicates a chord. The 3D volume that may be filled by the chords is the region confined by the following two surfaces:

$$z_{upper}(x,y)=h(1-2y^2/R_0^2)$$

$$z_{lower}(x,y)=h(2x^2/R_0^2-1), \quad \text{(A-20)}$$

under the condition $x^2+y^2 \leqq R_0^2$.

Figure 29C:
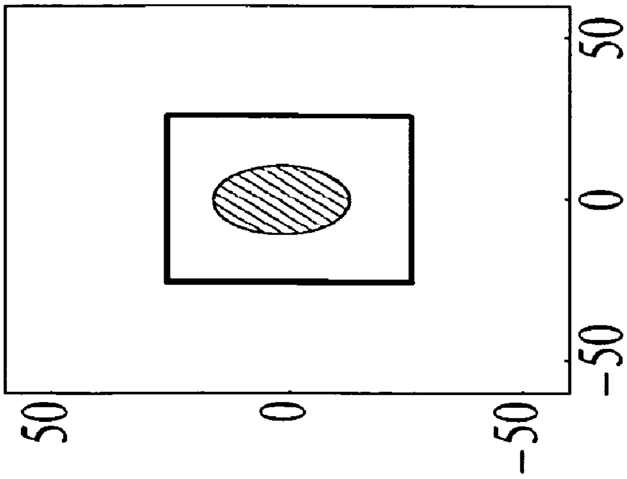
FIGS. 29*a-c* depict the intersections of the curved surfaces in the ROI in FIG. 28*b* as solid curves with three planes at x=0 cm, y=0 cm, and z=0 cm, respectively, with the solid curves showing the intersections of the two curved surfaces in FIG. 28*b*.
Figure 29B:
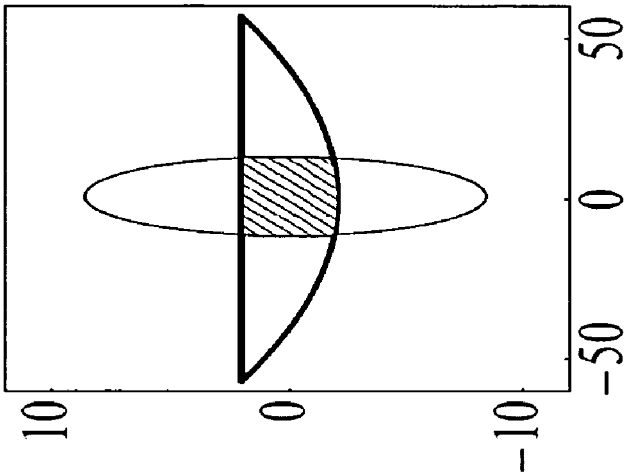
Figure 29A:
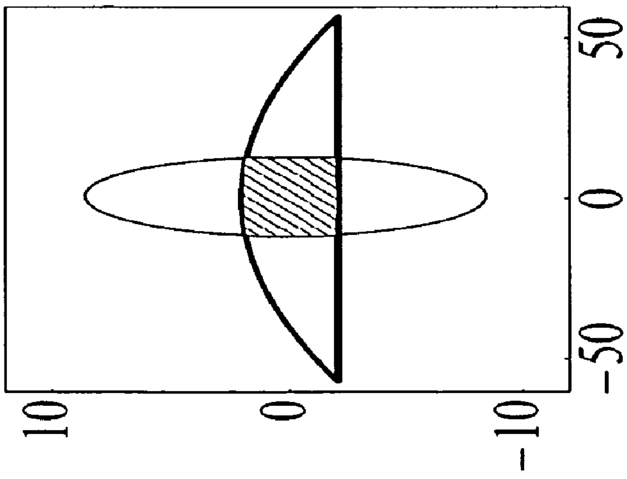

The ROI filled by the chords on this trajectory may be the 3D volume sandwiched between the two curved surfaces, as shown in FIG. 28B. FIGS. 29A-C also depict the intersections of the curved surfaces in FIG. 28B of this ROI as solid curves with three planes at x=0 cm (FIG. 29A), y=0 cm (FIG. 29B), and z=0 cm (FIG. 29C), with the solid curves showing the intersections of the two curved surfaces in FIG. 28B. The intersection of the 3D ROI and the plane parallel to the x-y plane may have a rectangular shape. In particular, the intersection of the ROI and the plane z=0 may be a square. In addition, the saddle data acquisition has another feature: there may exist more than one chord intersecting a point within the ROI. This property may be exploited for noise reduction.

Figure 30A:
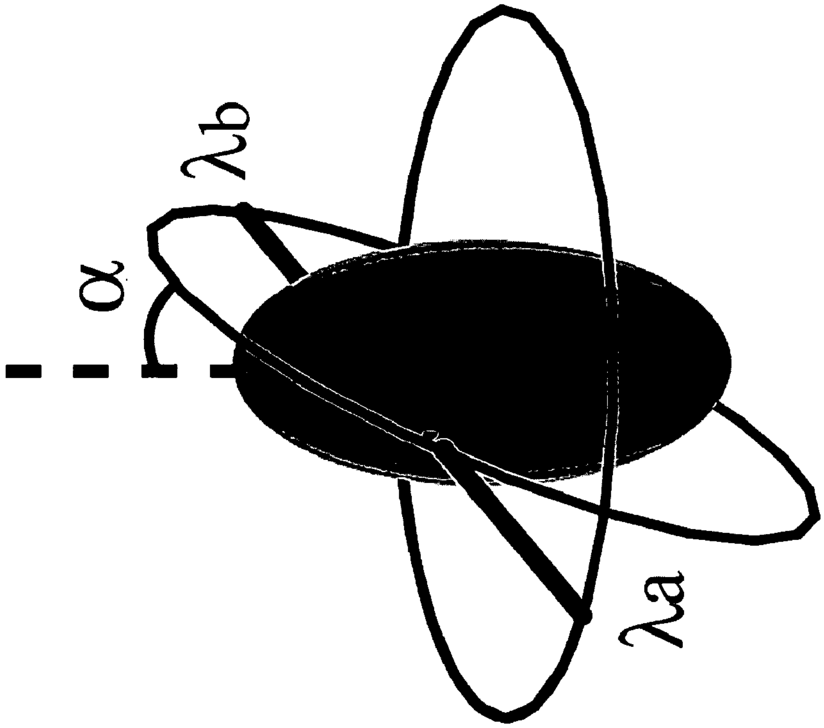
FIG. 30*a* illustrates the circle-circle trajectory, and the thick line segments labeled by $\lambda_a$ and $\lambda_b$ indicate a chord.
Figure 30B:
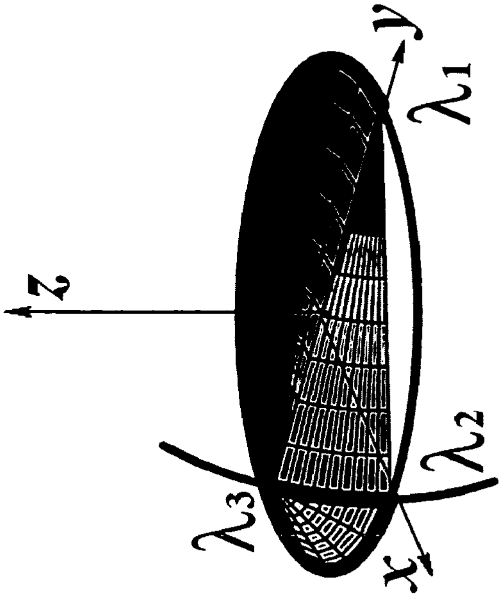
FIG. 30*b* depicts the ROI formed by the chords on the circle-circle trajectory.

The circle-circle trajectory in FIG. 30A may be mathematically be written as:

$$\vec{r}_0(\lambda)=(R_0\cos\lambda,\ R_0\sin\lambda,\ 0) \qquad \lambda\in\left[-\frac{3\pi}{2},\ 0\right) \quad \text{(A-21)}$$

$$\vec{r}_0(\lambda)=(R_0\cos\lambda,\ R_0\sin\lambda\sin\alpha,\ R_0\sin\lambda\cos\alpha) \qquad \lambda\in\left[0,\ \frac{\pi}{2}\right),$$

where $\lambda$ is an angular parameter denoting the polar angle within the planes occupied by these two circles, and $R_0$ is the radius of these two circles. The thin curves depicted in FIG. 30A denote the circle-circle trajectory, and the thick line segments labeled by $\lambda_a$ and $\lambda_b$ indicate a chord. For the chord specified by $\lambda_a$ and $\lambda_b$, data acquired over the thick portions on the trajectories between $\lambda_a$ and $\lambda_b$ may be used. If $\alpha$=0, the first circle is in the x-y plane, whereas the second circle is in the x-z plane and a kink appears at $\lambda$=0. FIG. 30B depicts the ROI formed by the chords specified by $\lambda_a\in[\lambda_1, \lambda_2)$ and $\lambda_b\in[\lambda_2, \lambda_3)$ on the circle-circle trajectory. In the numerical studies discussed below, $$\alpha=0,\ \ \lambda_1=-\frac{3}{2}\pi,\ \ \lambda_2=0,\ \text{and}\ \ \lambda_3=\frac{\pi}{2}$$

are used. FIG. 30B thus depicts a 3D ROI formed by a set of chords specified by $$\lambda_a\in\left[-\frac{3\pi}{2},\ 0\right)\ \text{and}\ \ \lambda_b\in\left[0,\ \frac{\pi}{2}\right).$$

Figure 31C:
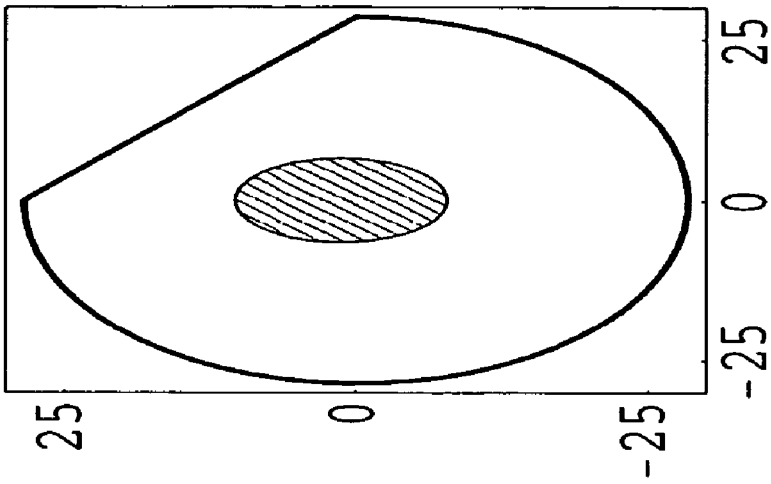
FIGS. 31*a-c* depicts the intersections of the curved surfaces in FIG. 30*b* of the ROI as solid curves with three planes at x=0 cm, y=0 cm, and z=0 cm, respectively.
Figure 31B:
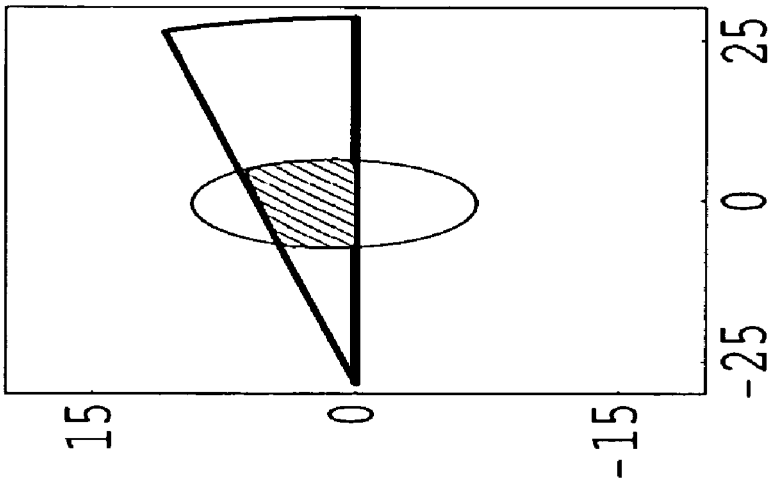
Figure 31A:
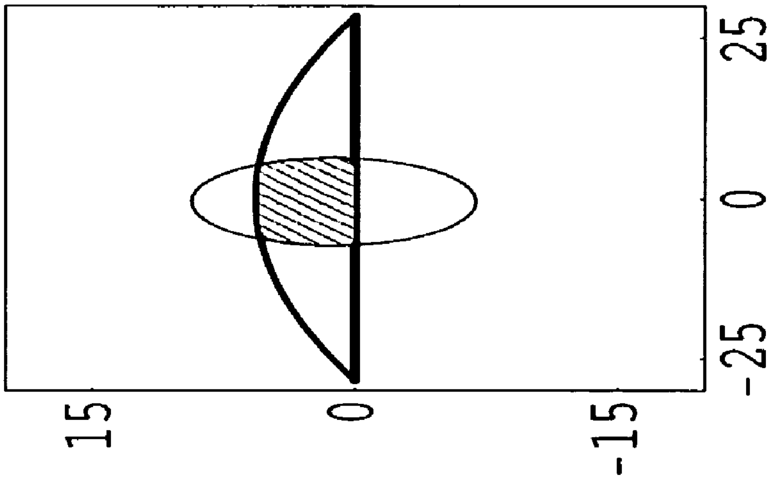

FIGS. 31A-C depict the intersections of the curved surfaces in FIG. 30B of the ROI as solid curves with three planes at x=0 cm (FIG. 31A), y=0 cm (FIG. 31B), and z=0 cm (FIG. 31C).

Figure 32A:
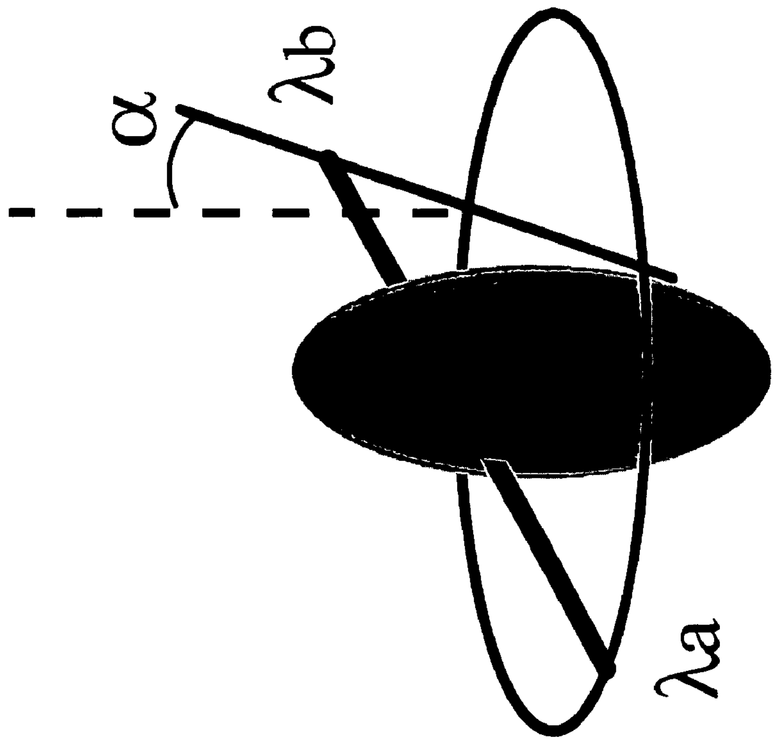
FIG. 32*a* shows the thin line and curve denote the circle-line trajectory, and the thick line segments labeled by $\lambda_a$ and $\lambda_b$ indicate a chord.

The circle-line trajectory in FIG. 32A is described as $$\vec{r}_0(\lambda)=(R_0\cos\lambda,\ R_0\sin\lambda,\ 0) \qquad \lambda\in\left[-\frac{3\pi}{2},\ 0\right) \quad \text{(A-22)}$$

$$\vec{r}_0(\lambda)=(R_0,\ h\lambda\sin\alpha,\ h\lambda\cos\alpha) \qquad \lambda\in\left[0,\ \frac{\pi}{2}\right)$$

where $\lambda$ is a parameter which represents the polar angle within the x-y plane when the source is on the circle trajectory and is linearly proportional to the path length when the source is on the line trajectory. $R_0$ denotes the radius of the circle trajectory, and h indicates the ratio between the path length of the line trajectory and the parameter $\lambda$. As shown in FIG. 32A, the thin line and curve denote the circle-line trajectory, and the thick line segments labeled by $\lambda_a$ and $\lambda_b$ indicate a chord. For the chord specified by $\lambda_a$ and $\lambda_b$, data acquired over the thick portions on the trajectories between $\lambda_a$ and $\lambda_b$ is used. From the definition above, if $\alpha$=0, the line trajectory is perpendicular to the plane containing the circle trajectory and yields a kink at $\lambda$=0. The ROI may be formed by the chords specified by $\lambda_a\in[\lambda_1, \lambda_2)$ and $\lambda_b\in[\lambda_2, \lambda_3)$ on the circle-circle trajectory. In the numerical studies discussed below, $$\alpha=0,\ \ \lambda_1=-\frac{3}{2}\pi,\ \ \lambda_2=0,\ \text{and}\ \ \lambda_3=\frac{\pi}{2}$$

are used. Therefore, FIG. 32B shows a 3D ROI formed by a set of chords specified by $$\lambda_a\in\left[-\frac{3\pi}{2},\ 0\right)\ \text{and}\ \ \lambda_b\in\left[0,\ \frac{\pi}{2}\right).$$

Figure 32B:
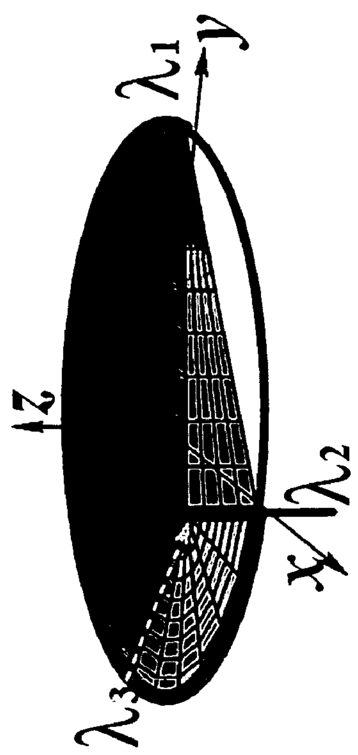
FIG. 32B shows a 3D ROI formed by a set of chords specified by $\lambda_a \in [-3\pi/2, 0)$ and $\lambda_b \in [0, \pi/2)$ where $\lambda_1=-3/2\pi$, $\lambda_2=0$ and $\lambda_3=\pi/2$.
Figure 33C:
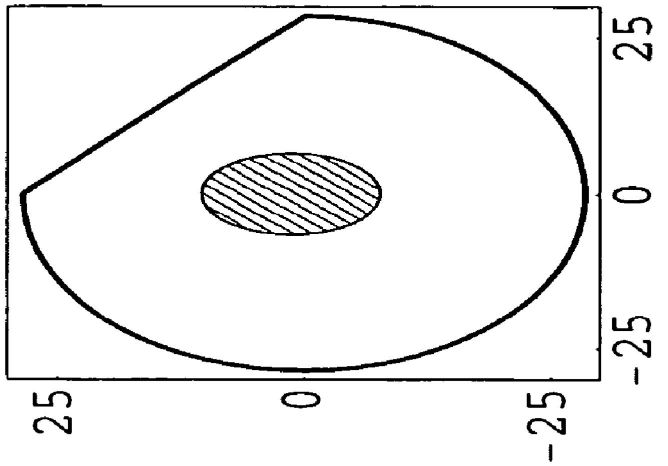
FIGS. 33*a-c* show the intersections of the curved surfaces in FIG. 32*b* as solid curves with three planes at x=0 cm, y=0 cm, and z=0 cm, respectively.
Figure 33B:
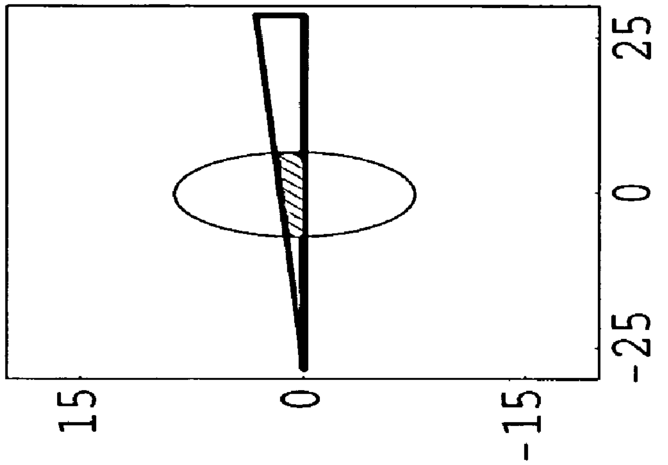
Figure 33A:
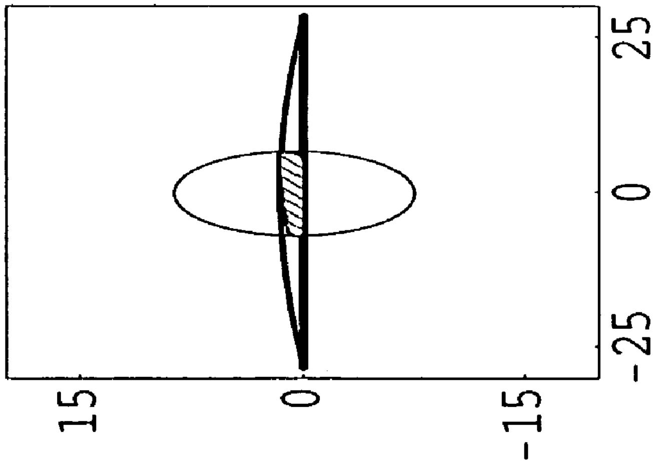

FIGS. 33A-C also show the intersections of the curved surfaces in FIG. 32B as solid curves with three planes at x=0 cm (FIG. 33A), y=0 cm (FIG. 33B), and z=0 cm (FIG. 33C).

The following is a computer-simulation study to demonstrate reconstruction of ROI images by use of the chord-based BPF and MDFBP methodologies from data acquired with the tilted helical, saddle, circle-circle, and circle-line trajectories. This computer-simulation is for illustrative purposes only. Because the quantitative results obtained by use of the two methodologies are virtually identical, the results obtained only with the BPF methodology are presented. In these studies, the 3D Shepp-Logan phantom is used to generate cone-beam data.

The chord-based BPF and MDFBP methodologies may be used to reconstruct images from data acquired with the tilted helical and saddle trajectories, which are smooth trajectories. In these studies, the tilted helical trajectory was determined by use of parameters $R_0$=57.0 cm, h=12.8 cm, and $\mu$=5° in Eq. (A-18), whereas the saddle trajectory was specified by use of $R_0$=57.0 cm and h=2.04 cm in Eq. (A-19). The square detector plane is placed at a distance S=100.5 cm from the source point. The detector may comprise 256×256 detection bins each of which has a size of 1.5×1.5 mm$^2$. Noiseless cone-beam data were generated at 1024 projection views over $\lambda\in[-\pi, \pi]$. Moreover, using the noiseless data as the means, Poisson data is generated at a noise level simulating the situation in which $10^6$ photos are incident on the object over a solid angle subtended by one detector bin. Such a noise level is slightly lower than the smallest contrast level in the Shepp-Logan phantom.

Figures 34A, 34B, 34C:
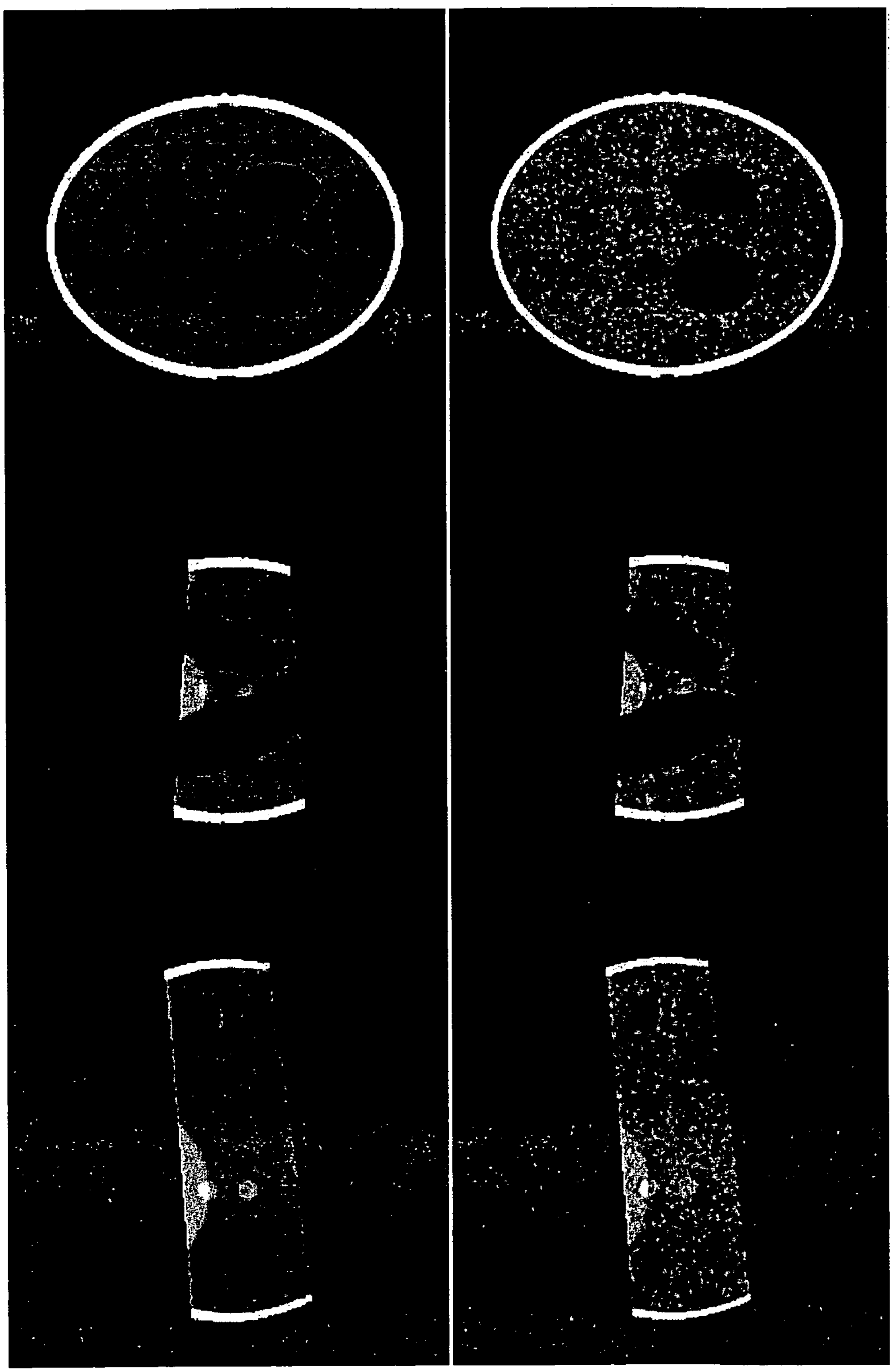
FIGS. 34*a-c* shows reconstructed ROI images. The upper rows depict the reconstructed ROI images from noiseless data within 2D slices at x=0 cm (FIG. 34*a*), y=−2.7 cm (FIG. 34*b*), and z=0 cm (FIG. 34*c*). The lower row depicts the reconstructed ROI noisy images within 2D slices at x=0 cm (FIG. 34*a*), y=−2.7 cm (FIG. 34*b*), and z=0 cm (FIG. 34*c*).
Figures 35A, 35B, 35C, 35D:
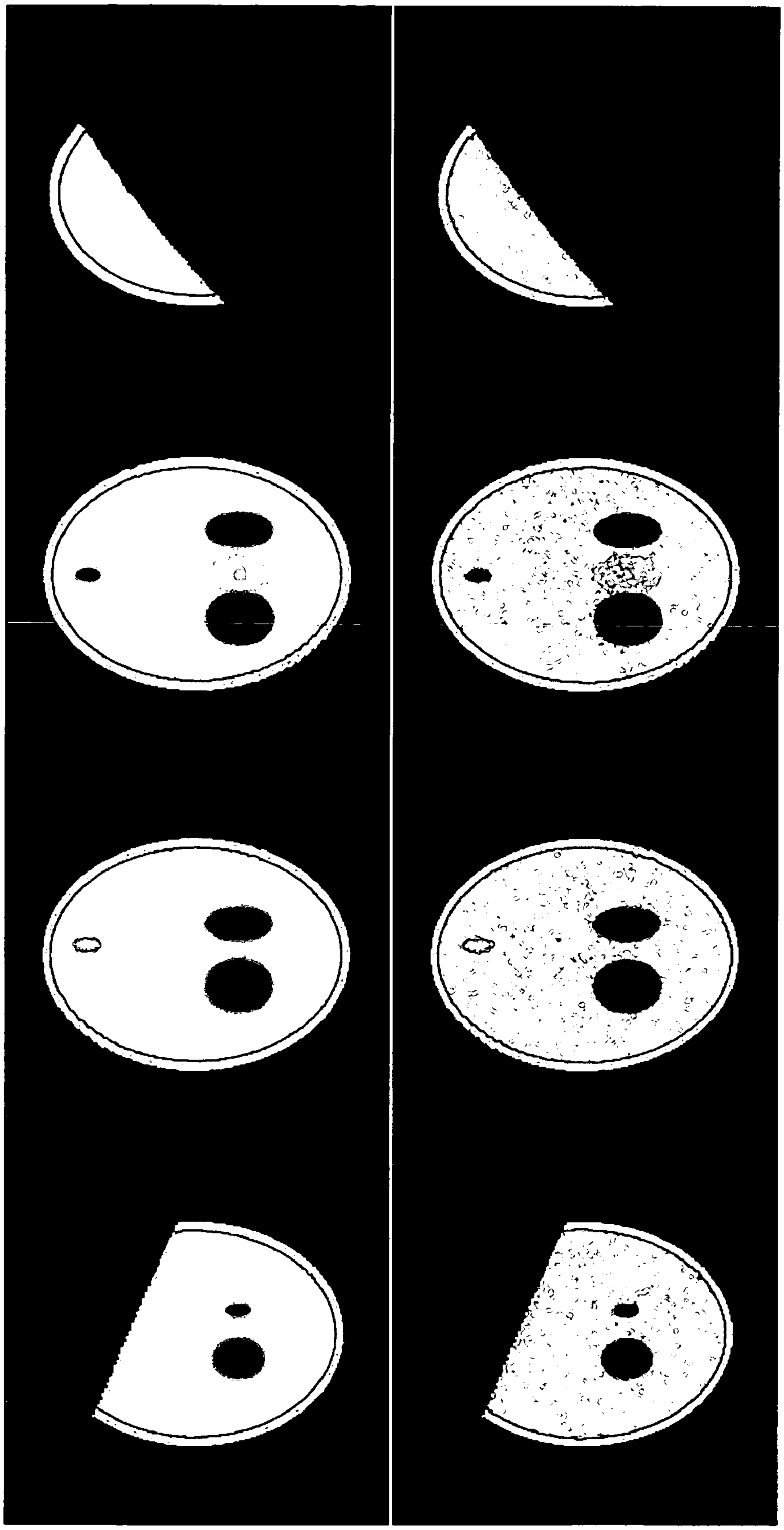
FIGS. 35*a-d* illustrate reconstructed ROI images. The upper rows depict the reconstructed noiseless ROI images from the data acquired from the tilted helical trajectory within 2D transverse slices specified by z=−2.7 cm (FIG. 35*a*), z=−1.35 cm (FIG. 35*b*), z=1.35 cm (FIG. 35*c*), and z=2.7 cm (FIG. 35*d*). The lower row depicts the reconstructed, noisy 2D images at transverse slices specified by z=−2.7 cm (FIG. 35*a*), z=−1.35 cm (FIG. 35*b*), z=1.35 cm (FIG. 35*c*), and z=2.7 cm (FIG. 35*d*).

ROI images are first reconstructed from noiseless data acquired with the tilted helical trajectory. The upper row of FIGS. 34A-C depict the reconstructed ROI images from noiseless data within 2D slices at x=0 cm (FIG. 34A), y=−2.7 cm (FIG. 34B), and z=0 cm (FIG. 34C). The display gray scale for FIGS. 34A-C, as well as for FIGS. 35-39, is [1.0, 1.04]. Moreover, FIGS. 35A-D depict the reconstructed noiseless ROI images from the data acquired from the tilted helical trajectory within 2D transverse slices specified by z=−2.7 cm (FIG. 35A), z=−1.35 cm (FIG. 35B), z=1.35 cm (FIG. 35C), and z=2.7 cm (FIG. 35D). Having performed a quantitative comparison of these reconstructed images and the true phantom, the comparative results indicate that the reconstruction agrees well with the true values within the Shepp-Logan phantom.

The analysis described above may be repeated by using noisy data acquired with the tilted helical trajectory. For example, the lower row of FIGS. 34A-C depict the reconstructed ROI noisy images within 2D slices at x=0 cm (FIG. 34A), y=−2.7 cm (FIG. 34B), and z=0 cm (FIG. 34C). Also, the lower row of FIGS. 35A-D depict the reconstructed, noisy 2D images at transverse slices specified by z=−2.7 cm (FIG. 35A), z=−1.35 cm (FIG. 35B), z=1.35 cm (FIG. 35C), and z=2.7 cm (FIG. 35D).

Figures 36A, 36B, 36C:
FIGS. 36*a-c* illustrate reconstructed ROI images. Specifically, the upper rows depict the reconstructed ROI images within 2D slices at x=0 cm (FIG. 36*a*), y=−2.7 cm (FIG. 36*b*), and z=0 cm (FIG. 36*c*), from noiseless data. The lower row depicts the reconstructed ROI noisy images within 2D slices at x=0 cm (FIG. 36*a*), y=−2.7 cm (FIG. 36*b*), and z=0 cm (FIG. 36*c*).
Figures 37A, 37B, 37C, 37D:
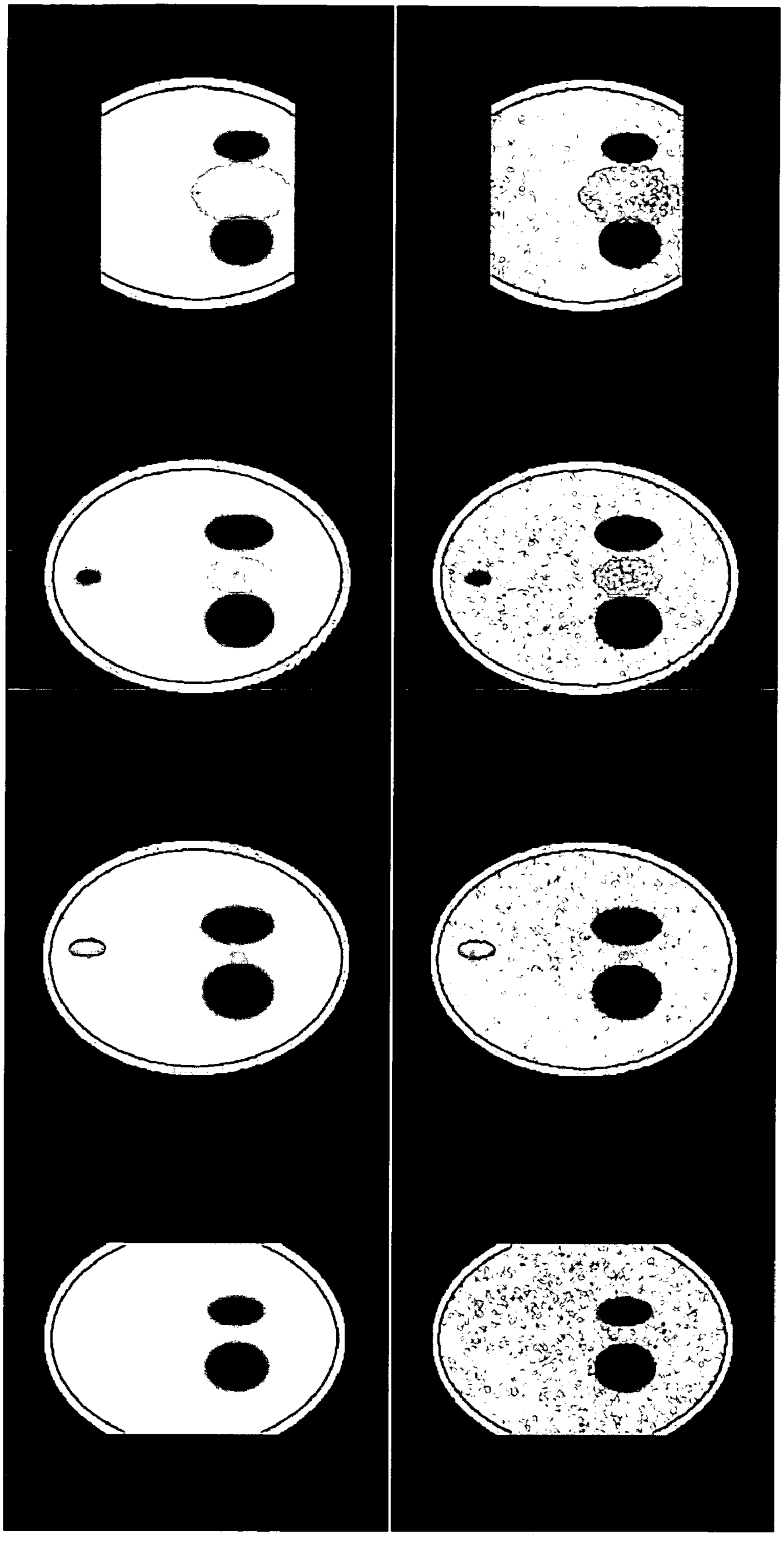
FIGS. 37*a-d* illustrate reconstructed ROI images. The upper rows depict the reconstructed, noiseless 2D images at transverse slices specified by z=−2.7 cm (FIG. 37*a*), z=−1.35 cm (FIG. 37*b*), z=1.35 cm (FIG. 37*c*), and z=2.7 cm (FIG. 37*d*). The lower row of FIGS. 37*a-d* depict the reconstructed, noisy 2D images at transverse slices specified by z=−2.7 cm (FIG. 37*a*), z=−1.35 cm (FIG. 37*b*), z=1.35 cm (FIG. 37*c*), and z=2.7 cm (FIG. 37*d*).

The ROI images may also be reconstructed from noiseless data acquired with the saddle trajectory. The upper row of FIGS. 36A-C depict the reconstructed ROI images within 2D slices at x=0 cm (FIG. 36A), y=−2.7 cm (FIG. 36B), and z=0 cm (FIG. 36C), from noiseless data. Moreover, the upper row of FIGS. 37A-D depicts the reconstructed, noiseless 2D images at transverse slices specified by z=−2.7 cm (FIG. 37A), z=−1.35 cm (FIG. 37B), z=1.35 cm (FIG. 37C), and z=2.7 cm (FIG. 37D). A quantitative comparison of these reconstructed images and the true phantom may also be performed. The quantitative comparison results may indicate the reconstruction agrees well with the true values within the Shepp-Logan phantom. Thus, as noted above, the ROIs in FIG. 37A and FIG. 37D may be confined within rectangular regions.

The analysis described above may be repeated by using noisy data acquired with the saddle trajectory. For example, the lower row of FIGS. 36A-C depict the reconstructed ROI noisy images within 2D slices at x=0 cm (FIG. 36A), y=−2.7 cm (FIG. 36B), and z=0 cm (FIG. 36C). Also, the lower row of FIGS. 37A-D depict the reconstructed, noisy 2D images at transverse slices specified by z=−2.7 cm (FIG. 37A), z=−1.35 cm (FIG. 37B), z=1.35 cm (FIG. 37C), and z=2.7 cm (FIG. 37D).

The chord-based methodologies have been used to reconstruct images from data acquired with the circle-circle (FIG. 30) and circle-line (FIG. 32) trajectories, which are non-smooth trajectories containing kinks where the two different trajectory segments meet. One may assume a constant distance S=50.25 cm between the source and detector plane. Other constant distances may be used. The 2D rectangular detector plane may comprise 512×256 detection bins, each of which has a size of 0.78 mm. The detector plane may include more or fewer detector bins of different size. The short side of the rectangle detector plane may be along the z-axis. In this analysis, the circle-circle trajectory was determined by use of parameters $R_0$=28.5 cm and α=0 in Eq. (A-21), whereas the circle-line trajectory was specified by $R_0$=28.5 cm, α=0, and h=128 mm/radian (A-22). In both trajectories, $$\lambda \in \left[-\frac{3\pi}{2}, \frac{\pi}{2}\right],$$

and a kink occurs at λ=0 on the circle-circle trajectory and on the circle-line trajectory, respectively. Noiseless cone-beam data were generated at 1024 projection views uniformly distributed over $$\lambda \in \left[-\frac{3\pi}{2}, \frac{\pi}{2}\right].$$

Using the noiseless data as the means, Poisson data is generated at a noise level simulating the situation in which $10^6$ photos are incident on the object over a solid angle subtended by one detector bin.

Figures 38A, 38B, 38C:
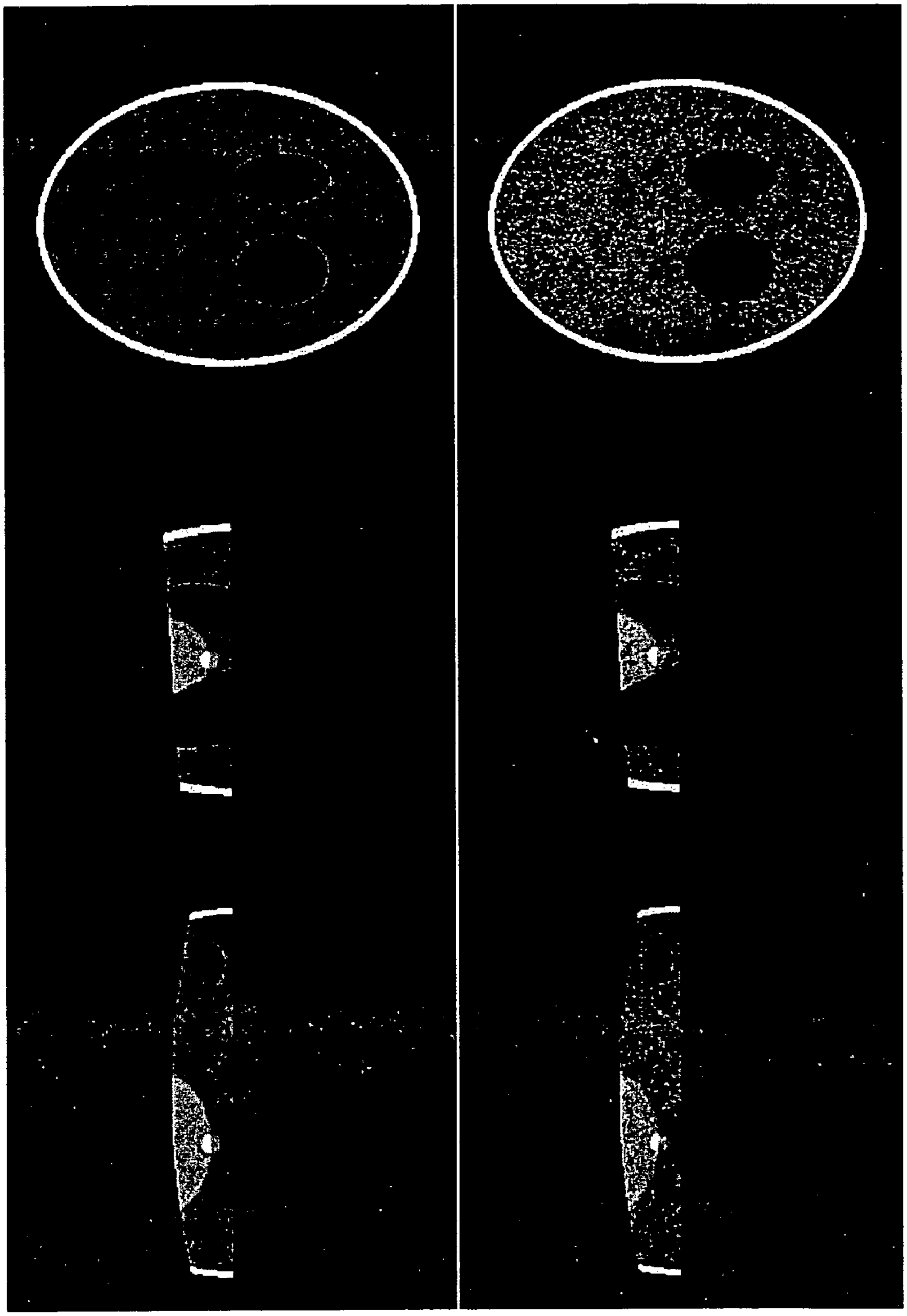
FIGS. 38*a-c* illustrate reconstructed ROI images. The upper row of FIGS. 38*a-c* depicts the reconstructed ROI images within 2D slices at x=0 cm (FIG. 38*a*), y=−2.7 cm (FIG. 38*b*), and z=0 cm (FIG. 38*c*), from noiseless data. In the lower row of FIG. 38*a-c*, the reconstructed, noisy images within 2D slices are depicted at x=0 cm (FIG. 38*a*), y=−2.7 cm (FIG. 38*b*), and z=0 cm (FIG. 38*c*).

The ROI images have been reconstructed from noiseless data acquired with the circle-circle trajectory. The upper row of FIGS. 38A-C depicts the reconstructed ROI images within 2D slices at x=0 cm (FIG. 38A), y=−2.7 cm (FIG. 38B), and z=0 cm (FIG. 38C), from noiseless data. A quantitative comparison of these reconstructed images and the true phantom has been performed. The quantitative comparison results indicate the reconstruction agrees well with the true values within the Shepp-Logan phantom. The analysis described above was repeated by using noisy data acquired with the circle-circle trajectory. In the lower row of FIG. 38A-C, the reconstructed, noisy images within 2D slices are depicted at x=0 cm (FIG. 38A), y=−2.7 cm (FIG. 38B), and z=0 cm (FIG. 38C).

Figures 39A, 39B, 39C:
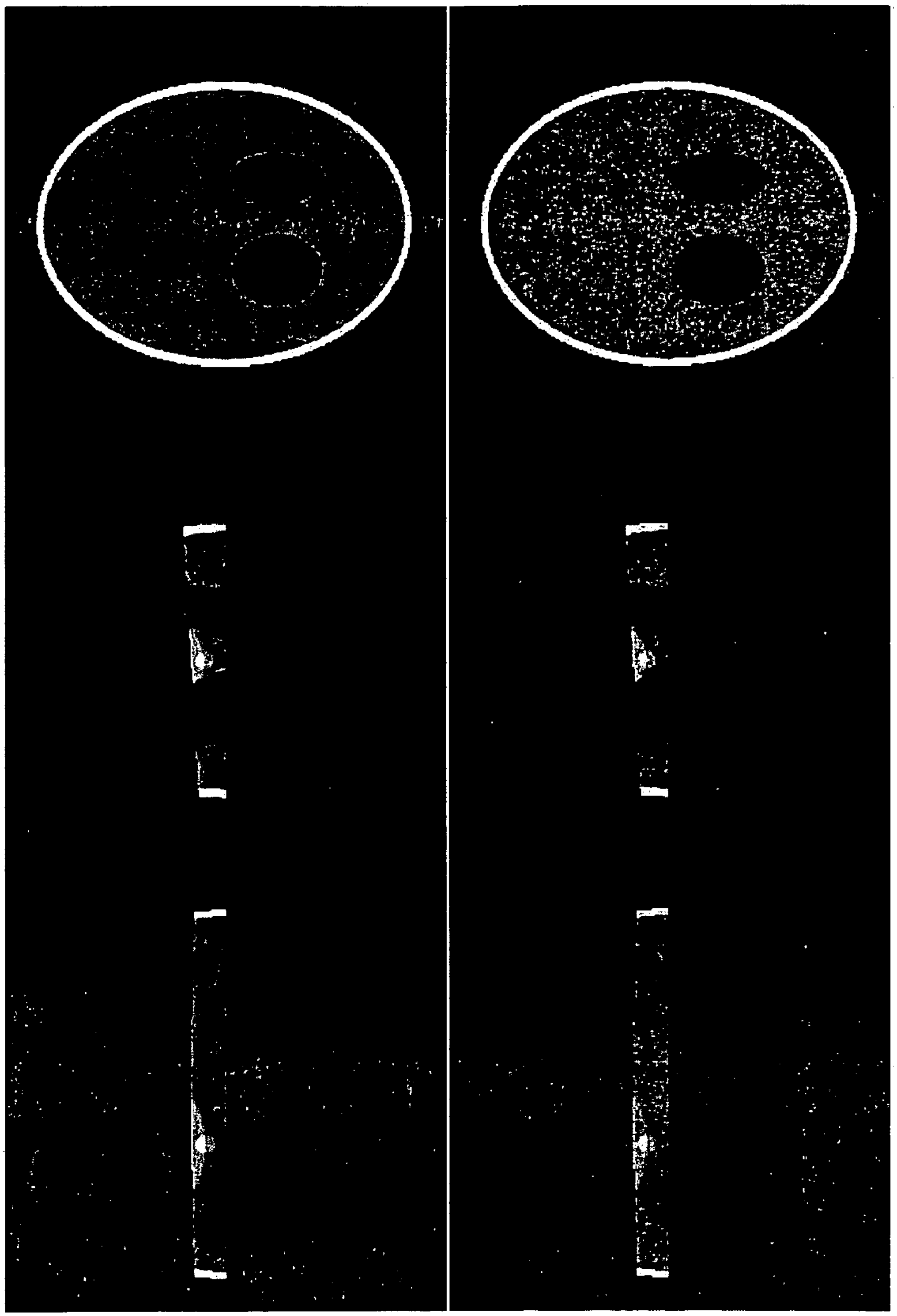
FIGS. 39*a-c* illustrate reconstructed ROI images. In the upper row of FIG. 39*a-c*, the reconstructed images are displayed within 2D slices at x=0 cm (FIG. 39*a*), y=−2.7 cm (FIG. 39*b*), and z=0 cm (FIG. 39*c*) from noiseless data. In the lower row of FIG. 39*a-c*, the reconstructed, noisy images are depicted within 2D slices at x=0 cm (FIG. 39*a*), y=−2.7 cm (FIG. 39*b*), and z=0 cm (FIG. 39*c*).

The ROI images are also reconstructed from noiseless data acquired with the circle-line trajectory. In the upper row of FIG. 39A-C, the reconstructed images are displayed within 2D slices at x=0 cm (FIG. 39A), y=−2.7 cm (FIG. 39B), and z=0 cm (FIG. 39C) from noiseless data. Again, a quantitative comparison of these reconstructed images and the true phantom is performed. The quantitative comparison results indicate the reconstruction agrees well with the true values within the Shepp-Logan phantom. The analysis described above is repeated by using noisy data acquired with the circle-line trajectory. In the lower row of FIG. 39A-C, the reconstructed, noisy images are depicted within 2D slices at x=0 cm (FIG. 39A), y=−2.7 cm (FIG. 39B), and z=0 cm (FIG. 39C).

As discussed above, 3D ROI image reconstruction from cone-beam data acquired with a general scanning trajectory may be of practical significance and are theoretically challenging. The image may be reconstructed by use of chord-based methodologies from data acquired with a number of practically useful scanning trajectories, including the tilted helical, saddle, circle-circle, and circle-line trajectories. In particular, images may be reconstructed using the BPF and MDFBP methodologies because of their capability of exactly reconstructing ROI images from data containing truncations. An interesting flexibility offered by the chord-based methodologies is that one can determine explicit scanning conditions on both trajectory design and x-ray illumination coverage for exact reconstruction of an ROI image. The numerical studies discussed above also verify that the chord-based methodologies may reconstruct images exactly for a variety of general, continuous scanning trajectories, including trajectories that contain a finite number of kinks. The chord-based BPF and MDFBP methodologies may find applications in diagnostic imaging, radiation-therapy imaging, security scanning, and animal imaging where different, non-conventional scanning configurations may be necessary. Furthermore, the capability of the chord-based BPF and MDFBP methodologies for reconstructing ROI images from truncated data may be used to reduce x-ray illumination coverage, and, consequently, reduce radiation dose to the imaged subject and possibly motion artifacts in the resulting image. Thus, the above demonstrates the ability of the methodology for image reconstruction from CB data and also in visualizing the reconstructible regions-of-interest (ROIs) for those general trajectories so that one may setup the scanning parameters with an appropriate guide.

2. ROI-Image Reconstruction from Data Acquired with an Arbitrary Trajectory Passing Through the Imaged Object One of the goals of micro-CT is to obtain extremely high resolution, perhaps even imaging subjects on cellular length scales. The resolution in CT can be increased by reducing the x-ray source focal spot size and by bring the focal spot close to the desired region of interest within the imaged subject. Given the reconstruction methodologies discussed above, the x-ray focal spot may pass through the imaged object. Technologically, such a source may be accomplished through high-harmonic generation with high-power lasers. By bringing the focal spot within the imaged subject, a tremendous jump in magnification may be possible. The methodologies discussed above may obtain images in a volume ROI for focal spot trajectories that pass through the imaged subject.

3. Analysis of Overscan Data when Performing Chord-Based Image Reconstruction

As discussed above, exact methodologies have been developed for directly reconstructing the volume image from helical cone-beam data. Oftentimes, the data generated may be more than is necessary to reconstruct using chord-based methodologies. These methodologies may thus allow for reduced or minimal angular scanning for volume regions-of-interest (ROIs), thereby reducing the necessary x-ray exposure. Methodologies were discussed above for reconstructing images on "of π-lines" from a reduced or minimal set of data on the detector in helical cone-beam CT, allowing ROI reconstruction from projection data with both longitudinal and transverse truncations. These methodologies were generalized to reconstruct images on chords for a general trajectory. The introduction of the M-line concept and reconstruction provides additional flexible means to cover volume ROIs.

Little effort has been directed at investigating the noise properties of these methodologies discussed above. With the methodology development for reconstruction of ROI images, it has been tacitly assumed that the reduction in the necessary scanning angle and in projection data may lead to ROI images from less radiation exposure. This conclusion may, however, depend on the noise properties of reconstruction methodologies. If reconstructing ROIs from the minimal (or reduced) data set leads to noisier ROI images than reconstruction of the same ROI from a larger data set, it may be necessary to increase the x-ray source intensity for the ROI-data set to attain the same image quality as images reconstructed from larger data sets. Such an increase may offset the fact that reduced or minimum projection data are needed for ROI reconstruction.

The following discussion investigates and compares the noise properties of image reconstruction from minimal data set and large data sets by use of chord-based methodologies. It is demonstrated that the minimal data set may indeed lead to actual reduction of radiation exposure for attaining comparable image quality, defined in terms of image variance, as that obtained with a larger data set.

A continuous source trajectory may be specified by $\vec{r}_0(s)=(x(s), y(s), z(s))$, where $x(s)$, $y(s)$, and $z(s)$ denote the x-, y-, and z-components of $\vec{r}_0(s)$ in the fixed-coordinate system, and s is a curve parameter indicating the position of the x-ray source on the trajectory. A rotation-coordinate system $\{u, v, w\}$ is also introduced whose origin is fixed on the source point and whose unit vectors can be written as $\hat{e}_u(\lambda)=(-\sin\lambda, \cos\lambda, 0)^T$, $\hat{e}_v(\lambda)=(0, 0, 1)^T$ and $\hat{e}_w(\lambda)=(\cos\lambda, \sin\lambda, 0)^T$ where $$\sin\lambda = \frac{y(s)}{\sqrt{x(s)^2 + y(s)^2}}.$$

The projection data of the object function $f(\vec{r})$ may be expressed as:

$$D(\vec{r}_0(s),\hat{\beta})=\int_0^\infty dt f(\vec{r}_0(s)+t\hat{\beta}), \tag{B-1}$$

where the unit vector $\hat{\beta}$ denotes the direction of a specific x-ray passing through the point $\vec{r}$:

$$\hat{\beta} = \frac{\vec{r} - \vec{r}_0(s)}{|\vec{r} - \vec{r}_0(s)|}. \tag{B-2}$$

A chord may be a line segment connecting two points $\vec{r}_0(s_a)$ and $\vec{r}_0(s_b)$ on the trajectory. Any point $\vec{r}$ on the chord may be expressed as:

$$\vec{r} = \frac{\vec{r}_0(s_a) + \vec{r}_0(s_b)}{2} + x_c \hat{e}_c, \quad x_c \in [-l, l], \tag{B-3}$$

where $$\hat{e}_c = \frac{\vec{r}_0(s_b) - \vec{r}_0(s_a)}{|\vec{r}_0(s_b) - \vec{r}_0(s_a)|}$$

denotes the direction of the chord, and $$l = \frac{1}{2}|\vec{r}_0(s_b) - \vec{r}_0(s_a)|$$

is one half of the chord length. For a helical trajectory, the path length s may be linearly related to the rotation angle $\lambda$, and in the current analysis, $s=\lambda$. When $s_a$ and $s_b$ are within one turn, the chord becomes the conventional PI-line segment. The intersection between a chord and the object may be referred to as a support segment. Further, $x_{c1}$ and $x_{c2}$ may represent the end points of a support segment. Because the trajectory under consideration may not intersects the object, $[x_{c1}, x_{c2}] \subset [-l, l]$. Therefore, one can use $(x_c, a s_a, s_b)$ and $f_c(x_c, s_a, s_b)$ to denote a point and the corresponding image on the chord. Several methodologies, including three methodologies, referred to as the BPF, MDFBP, and FBP methodologies, may be used for exact image reconstruction on a chord of a general trajectory.

The BPF methodology may reconstruct the image on a chord specified by $s_a$ and $s_b$ as $$f_c(x_c, s_a, s_b) = \hat{f}(x_c, s_a, s_b) + \frac{1}{\pi}\frac{D(\vec{r}_0(s_a), \hat{e}_c)}{\sqrt{(x_B - x_c)(x_c - x_A)}}, \quad \text{(B-4)}$$

where $x_A$ and $x_B$ are two points on the chord satisfying $[x_{c1}, x_{c2}] \subseteq [x_A, x_B] \subset [-1, 1]$, and $D(\vec{r}_0(s_a), \hat{e}_c)$ denotes the projection along the chord. The filtered image $\hat{f}(x_c, s_a, s_b)$ is given by $$\hat{f}(x_c, s_a, s_b) = \frac{1}{2\pi^2}\frac{1}{\sqrt{(x_B - x_c)(x_c - x_A)}} \int_R \frac{dx'_c}{x_c - x'_c}\sqrt{(x_B - x_c)(x'_c - x_A)}\, g(x'_c, s_a, s_b), \quad \text{(B-5)}$$

where the backprojection image on the chord is given by $$g(x'_c, s_a, s_b) = \Pi_c(x'_c)\int_{s_a}^{s_b} ds \frac{\text{sgn}(-\hat{\beta}\cdot\hat{e}_w)}{|\vec{r}' - \vec{r}_0(s)|}\frac{\partial}{\partial q}D(\vec{r}_0(q), \hat{\beta})\Big|_{q=s}, \quad \text{(B-6)}$$

and the square function $\Pi_c(x'_c)=1$ if $x'_c \in [x_A, x_B]$ and 0 otherwise. It may be observed in Eq. (B-4) that the chord image may be obtained exactly from knowledge of the backprojection image $g(x'_c, s_a, s_b)$ for $x'_c \in [x_A, x_B]$, which is referred to as the reconstruction segment because it determines the actual reconstruction interval on the chord. In particular, because the reconstruction segment $[x_A, x_B]$ may be chosen as small as the support segment $[x_{c1}, x_{c2}]$, the chord image may be reconstructed from knowledge of $g(x'_c, s_a, s_b)$ only on the support segment. This interesting property of the Hilbert transform may form the basis for exact image reconstruction on a chord from projections containing longitudinal and/or transverse truncations. The Hilbert transform is discussed below.

The BPF methodology may reconstruct the chord image by performing a 1D filtration (e.g., the integration over $x'_c$ in Eq. (B-4)) of the backprojection image (e.g., the integration over s in Eq. (B-6)). On the other hand, the MDFBP methodology may reconstruct the chord image by performing a 1D data filtration (e.g., the integration over $u'_c$) prior to their backprojection (e.g., the integration over s) onto the chord:

$$f_c(x_c, s_a, s_b) = \frac{1}{2\pi^2}\frac{1}{\sqrt{(x_B - x_c)(x_c - x_A)}} \int_{s_a}^{s_b} ds\,[w_2(1 - u_c) + w_1 u_c]\int_R \frac{du'_c}{u_c - u'_c}P_\Pi + \frac{1}{\pi}\frac{D(\vec{r}_0(s_a))}{\sqrt{(x_B - x_c)(x_c - x_A)}}, \quad \text{(B-7)}$$

where $$P_\Pi = \Pi_c(x'_c)\frac{\sqrt{(x_B - x'_c)(x'_c - x_A)}}{w_2(1 - u'_c) + w_1 u'_c}\frac{\text{sgn}(-\hat{\beta}\cdot\hat{e}_w)}{|\vec{r}' - \vec{r}_0(s)|}\frac{\partial}{\partial q}D(\vec{r}_0(q), \hat{\beta})\Big|_{q=s}, \quad \text{(B-8)}$$

$w_1=-[\vec{r}_0(s_a)-\vec{r}_0(s)]\cdot\hat{e}_w$, and $w_2=-[\vec{r}_0(s_b)-\vec{r}_0(s)]\cdot\hat{e}_w$. For a source position s, the variables $u_c$ and $u_c$ may denote the cone-beam projections of $x_c$ and $x'_c$ onto the detector and can be obtained, respectively, by replacing x with $x_c$ and $x_c$ in $$u = \frac{w_2(x + l)}{w_1(l - x) + w_2(x + l)} \quad \text{(B-9)}$$

The square function $\Pi_c(x'_c)$ in Eq. (B-8) indicates that the MDFBP methodology can reconstruct a chord image from knowledge of data only on the cone-beam projection of the reconstruction segment $[x_A, x_B]$, which can be as small as the support segment. Therefore, similar to the BPF methodology, the MDFBP methodology may also reconstruct a chord image from data containing truncations.

The chord-based FBP methodology may be expressed as $$f_c(x_c, s_a, s_b) = \frac{1}{2\pi^2}\int_{s_a}^{s_b} ds \frac{A}{|\vec{r} - \vec{r}_0(s)|}\int_{-\infty}^{\infty}\frac{du'_c}{u_c - u'_c}\frac{1}{|\vec{r}' - \vec{r}_0(s)|}\frac{\partial}{\partial q}D(\vec{r}_0(q), \hat{\beta})\Big|_{q=s}, \quad \text{(B-10)}$$

where $u_c$ indicates the cone-beam projection of $x_c$ onto the detector and is determined by using $x_c$ to replace x in Eq. (B-9), and A denotes the distance from the source point $\vec{r}_0(s)$ to a point on the detector at which the ray connecting $\vec{r}$ and $\vec{r}_0(s)$ intersects the detector. As the filtering (e.g., the integration over $u_c$) is carried out over the projection of the straight line containing the chord, similar to other existing FBP-based methodologies, the chord-based FBP methodology may not be able to exactly reconstruct ROI images from data containing transverse truncations.

As shown in Eq. (B-10), a data-sufficiency condition for the FBP methodology is: (a) data are available over the trajectory segment $s \in [s_a, s_b]$, and (b) for each s, data on the cone-beam projection of the chord are non-truncated. The condition is similar to that for other FBP-based methodologies. On the other hand, from Eqs. (B-4) and (B-7), a data-sufficiency condition for the chord-based BPF and MDFBP methodologies is: (a) data are collected over the trajectory segment $[s_a, s_b]$, and (b) at each s, data only on the cone-beam projection of the reconstruction segment $[x_a, x_B]$ on the chord are available. It follows that, because the reconstruction segment $[x_A, x_B]$ may be chosen to be as small as the support segment $[x_{c1}, x_{c2}]$, the BPF and MDFBP methodologies may require, at each s, data only on the cone-beam projection of the support segment $[x_{c1}, x_{c2}]$ (instead of the entire chord as the chord-based FBP methodology requires). Different selections of the reconstruction segment $[x_A, x_B]$ imply that different amounts of data at each s can be used for reconstructing the chord image. Under the ideal continuous conditions, different selections of $[x_A, x_B]$ yield identical chord images. However, when data contain noise and other inconsistencies, and when different selections of $[x_A, x_B]$ are used, the BPF and MDFBP methodologies in their discrete forms may yield different chord images. This is one of the issues discussed below.

The BPF, MDFBP, and FBP methodologies described above may be applied to reconstructing chord images from a variety of data, such as parallel-, fan-, and cone-beam data. The noise properties of chord-based reconstruction are analyzed below by use of these methodologies in their discrete forms. As mentioned above, the BPF and MDFBP methodologies may reconstruct the image on the reconstruction segment $[x_A, x_B]$ if it covers the support segment $[x_{c1}, x_{c2}]$. Therefore, theoretical image-noise properties are investigated on the reconstruction segments of different lengths. As shown below, the BPF and MDFBP methodologies yield chord-based reconstructions with very similar noise properties. Therefore, the analysis focuses only on the noise properties of the BPF reconstruction, and the analysis may be extended to analyze the noise properties of the MDFBP reconstruction.

In the presence of data noise, the measured projection $D(\vec{r}_0(s), \hat{\beta})$ may be interpreted as a stochastic process. Boldface and normal letters are used to denote a stochastic process and its mean. As shown in Eq. (B-4), because $g(x_c, s_a, s_b)$, $\hat{f}(x_c, s_a, s_b)$, and $f_c(x_c, s_a, s_b)$ are computed from $D(\vec{r}_0(s), \hat{\beta})$, they may also be considered as stochastic processes. From Eq. (B-6), one may estimate the noise properties of the backprojection image $g(x_c, s_a, s_b)$. Since Eq. (B-6) involves only data derivative and backprojection, for uncorrelated data noise, $g(x_c, s_a, s_b)$ may be approximately uncorrelated:

$$Cov\{g(x_c,s_a,s_b),g(x'_c,s_a,s_b)\}\approx c(x'_c)\delta(x_c-x_c), \quad \text{(B-11)}$$

where $c(x_c)$ can be determined empirically from knowledge of data-noise variance for different x-ray illumination configurations.

Using Eq. (B-4), one can write the variance of the reconstructed chord image as $$\mathrm{Var}\{f_c(x_c, s_a, s_b)\} \approx \mathrm{Var}\{\hat{f}(x_c, s_a, s_b)\} + \frac{\mathrm{Var}\{D(\vec{r}_0(s), \hat{e}_c)\}}{\pi^2(x_B - x_c)(x_c - x_A)}, \quad \text{(B-12)}$$

where the correlation between the two terms in Eq. (B-4) has been disregarded. Assuming that the backprojection image is band limited to $v_m$, the discussion below shows that:

$$\mathrm{Var}\{\hat{f}(x_c, s_a, s_b)\} = \frac{1}{(x_B - x_c)(x_c - x_A)}\int_{x_A}^{x_B} dx'_c(x_B - x'_c)(x'_c - x_A)c(x'_c)h^2(x_c - x'_c). \quad \text{(B-13)}$$

where $$h(x) = \frac{2\sin^2(\pi v_m x)}{x}.$$

In the numerical implementation of Eq. (B-13) below, $$v_m = \frac{1}{2\Delta x},$$

where Δx denotes the sampling interval on the reconstruction segment. Therefore, for a given reconstruction segment $[x_A, x_B]$ and the determined backprojection variance $c(x_c)$, Eq. (B-13) may provide a theoretical formula for computing the chord-image variance. Finally, substituting Eq. (B-13) into (B-12), a relation for computing the variances of a chord image may be obtained.

Figure 40A:
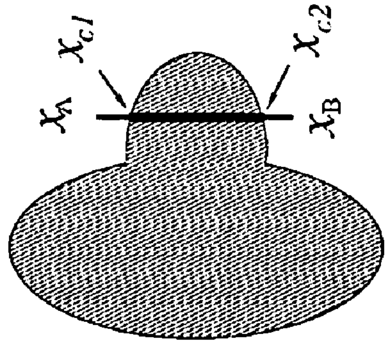
FIG. 40*a-c* depicts numerical phantom, parallel-beam configuration, and fan-beam configuration, respectively.
Figure 40B:
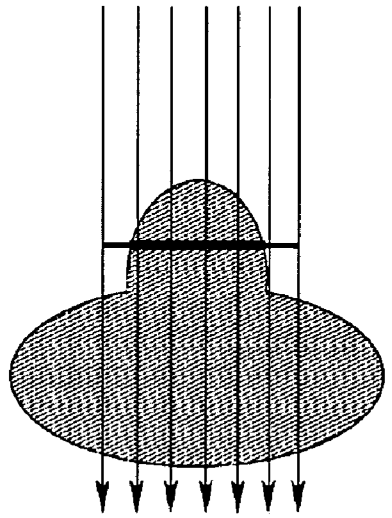

Using the numerical phantom depicted in FIG. 40A and the parallel-beam configuration in FIG. 40B, noiseless, 2D projection data at 512 views is determined uniformly distributed over $$[-\frac{\pi}{2}, \frac{\pi}{2}].$$

Each projection contains 256 bins spanning 28.3 cm. Fewer or greater view and bins may be used. 10,000 sets of noisy data may be subsequently generated by adding to the noiseless data uncorrelated Gaussian noise, whose standard deviation is 1.74% of the maximum value in the noiseless data. Four reconstruction segments with different lengths $L_{AB}=|x_B-x_A|$: 7.8 cm, 10.0 cm, 14.1 cm, and 20.0 cm are investigated. As shown in FIG. 40B, the length of the support segment, 5.5 cm in length, may be shorter than the four reconstruction segments considered. Therefore, the image on this chord may be reconstructed exactly by use of data determined by these reconstruction segments, respectively. One may also conclude from FIG. 40B that data determined by the first three reconstruction segments, which are shorter than the maximum dimension (about 15.6 cm) of the object support, are truncated.

From the 10,000 sets of noisy data, Eqs. (B-4), (B-5), and (B-6) may be used to calculate 10,000 noisy $f_c(x_c, s_a, s_b)$, $\hat{f}(x_c, s_a, s_b)$, and $g(x_c, s_a, s_b)$, respectively. Based upon these reconstructions, the corresponding empirical variances may be computed, which are shown in the upper row of FIGS. 41A-C. Specifically, FIGS. 41A-C depict the empirical (upper row) and theoretical (lower row) variances of $g(x_c, s_a, s_b)$ (FIG. 41A), $\hat{f}(x_c, s_a, s_b)$ (FIG. 41B), and $f_c(x_c, s_a, s_b)$ (FIG. 41C) obtained on four reconstruction segments with $L_{AB}$=7.8 cm, 10.0 cm, 14.1 cm, and 20.0 cm, respectively, from parallel-beam data.

The result of the empirical variances of $g(x_c, s_a, s_b)$ in the upper row of FIG. 41A suggests that $c(x_c)\approx 0.04$ on the reconstruction segments, which, as shown in the lower row of FIG. 41A (depicting the theoretical variances), are subsequently used in Eqs. (B-12) and (B-13) for computing the theoretical variances of $\hat{f}_c(x_c, s_a, s_b)$ and $f(x_c, s_a, s_b)$. Specifically, the lower row of FIGS. 41A-C depicts the theoretical results for the four reconstruction segments described above. It can be seen that the theoretical and empirical results agree very well with each other, indicating that Eq. (B-12) provides sufficient theoretical description of the image variance on the chord.

Figure 41C:
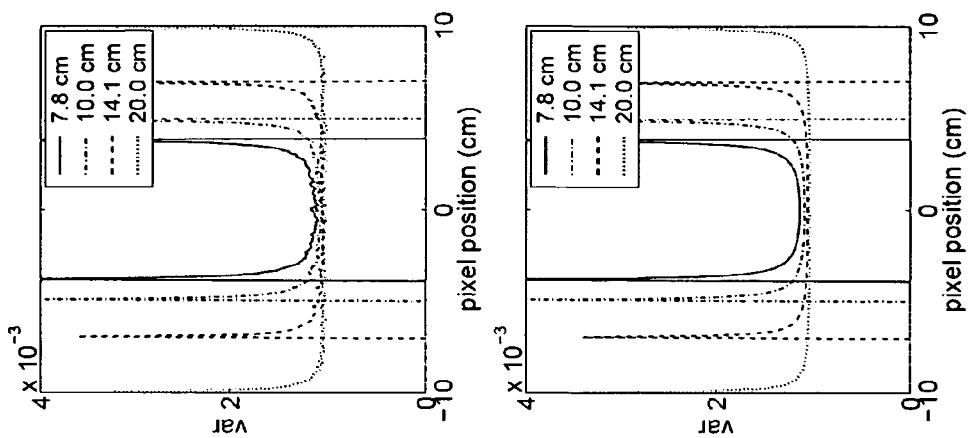
FIGS. 41*a-c* depict the empirical (upper row) and theoretical (lower row) variances of $g(x_c, s_a, s_b)$ (FIG. 41*a*), $\tilde{f}(x_c, s_a, s_b)$ (FIG. 41*b*), and $f_c(x_c, s_a, s_b)$ (FIG. 41*c*) obtained on four reconstruction segments with $L_{AB}$=7.8 cm, 10.0 cm, 14.1 cm, and 20.0 cm, respectively, from parallel-beam data.
Figure 41B:
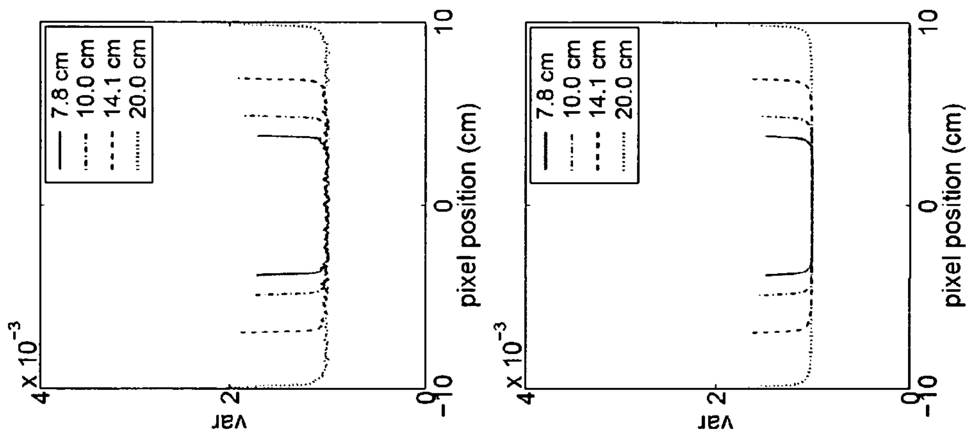
Figure 41A:
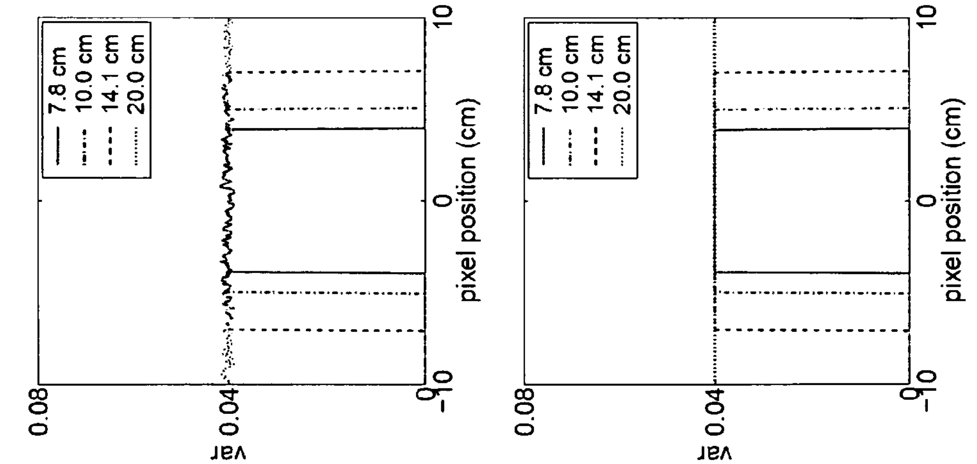

It may also be observed in FIG. 41C that the shorter the reconstruction segment, the higher the chord-image variances. This is because the second term in Eq. (B-12) increases as $L_{AB}$ (i.e., $(x_A-x_c)(x_c-x_B)$) decreases. However, the difference of the chord-image variances in the central part of the support segment is quite small among these reconstruction segments. The implication of this result is that there may be a real gain in terms of dose reduction by using a short reconstruction segment, because data required to reconstruct an image on this reconstruction segment is less than that required by using a longer reconstruction segment, thus resulting in the reduction of dose delivery to the object. For similar x-ray intensities, which are directly related to the data noise level, the reconstruction using a short reconstruction segment appears to yield image variance within the support segment that is comparable to that obtained with a longer reconstruction segment.

Figure 42B:
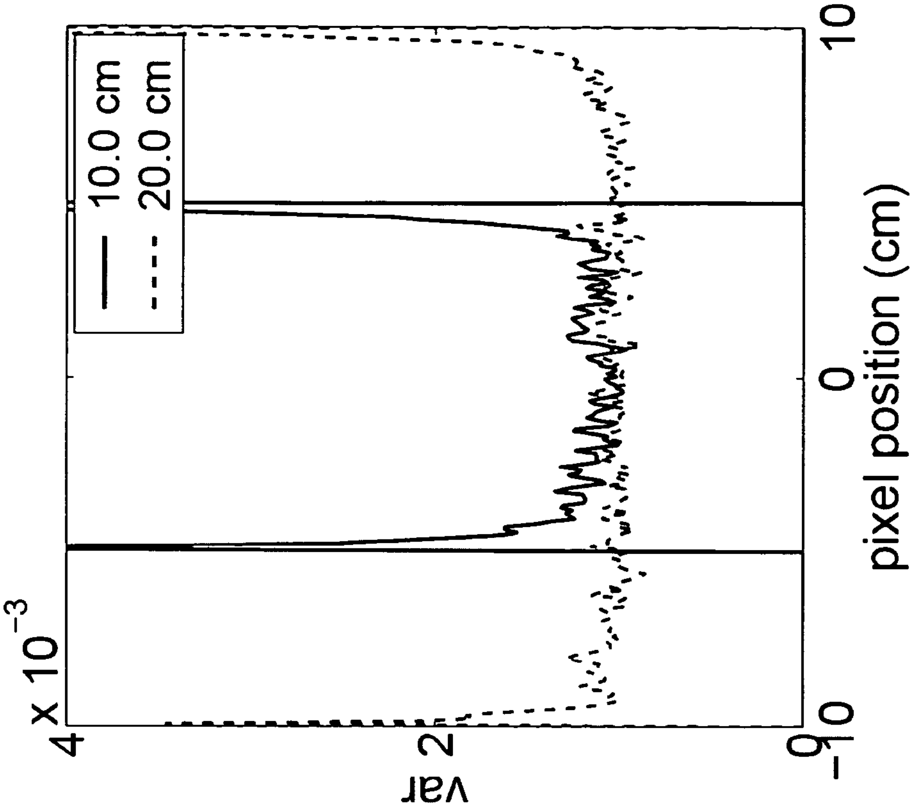
FIGS. 42*a-b* depict the variances of the chord-image obtained by use of the BPF methodology (FIG. 42*a*) and MDFBP methodology (FIG. 42*b*) for two different reconstruction segments with $L_{AB}$=10.0 cm (solid line) and 20.0 cm (dashed line).
Figure 42A:
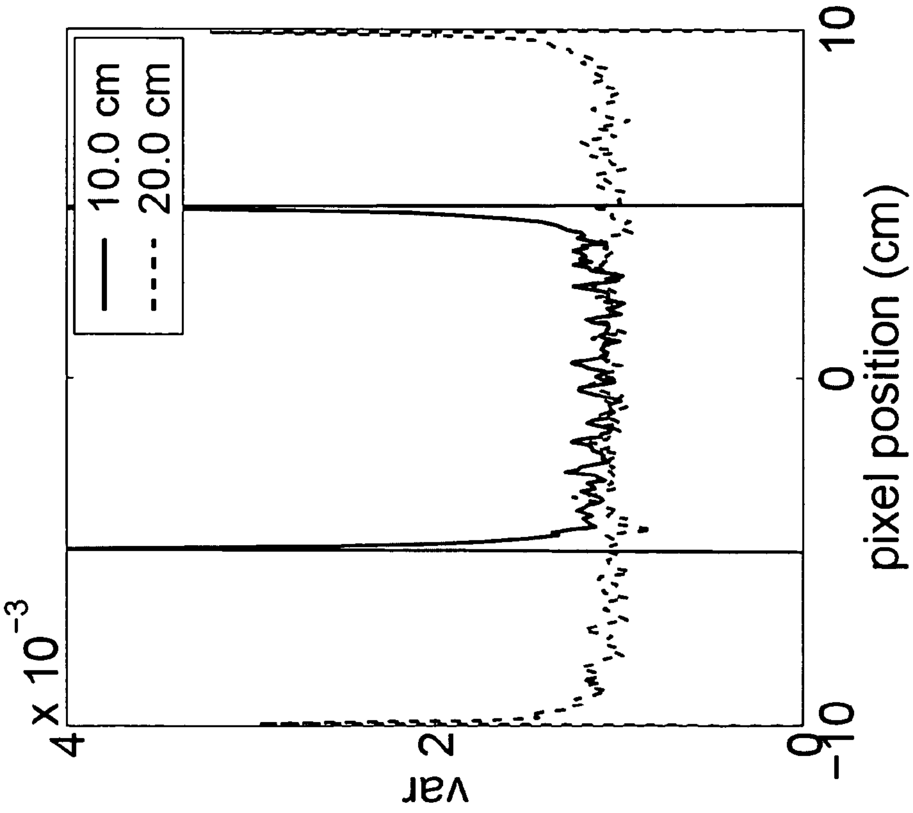

Numerical studies of the noise properties of the BPF and MDFBP methodologies are also shown by use of 500 sets of noisy data described above. As an example, FIGS. 42A-B depict the variances of the chord-image obtained by use of the BPF methodology (FIG. 42A) and MDFBP methodology (FIG. 42B) for two different reconstruction segments with $L_{AB}$=10.0 cm (solid line) and 20.0 cm (dashed line). The results in FIGS. 42A-B clearly support the conclusion that, in terms of chord-image variance, the noise properties of the BPF and MDFBP methodologies are similar to each other.

Figure 43D:
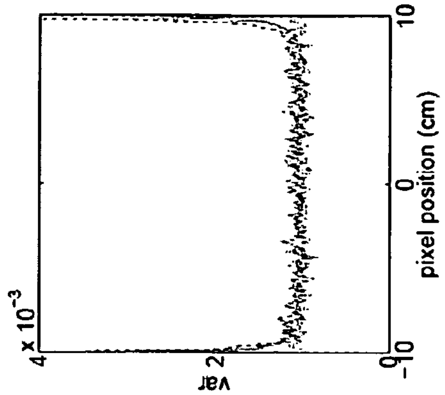
FIG. 43*d* shows the variance profiles on the dashed lines depicted in FIGS. 43*a-c*, (i.e., on a chord) with the solid line in FIG. 43*d* indicating the variance of the BPF along the dashed line in FIG. 43*a*, the dashed line in FIG. 43*d* indicating the variance of the MDFBP along the dashed line in FIG. 43*b*, and the dotted line in FIG. 43*d* indicating the variance of the FBP along the dashed line in FIG. 43*c*.
Figure 43C:
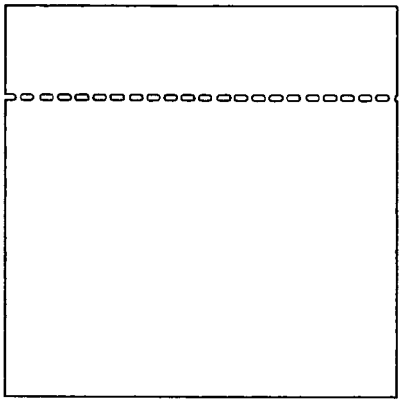
FIGS. 43*a-c* show the empirical variance images that were computed using the noisy images. Specifically, empirical variance images within the field of view obtained by use of the BPF (FIG. 43*a*), MDFBP (FIG. 43*b*), and FBP (FIG. 43*c*) methodologies from parallel-beam data without truncations.
Figure 43B:
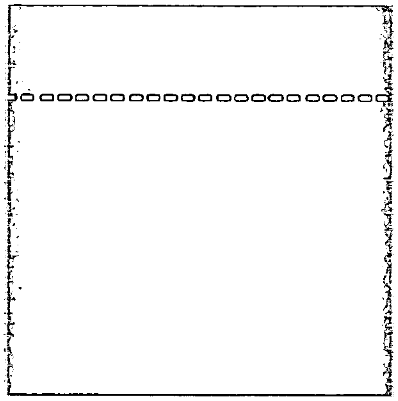
Figure 43A:
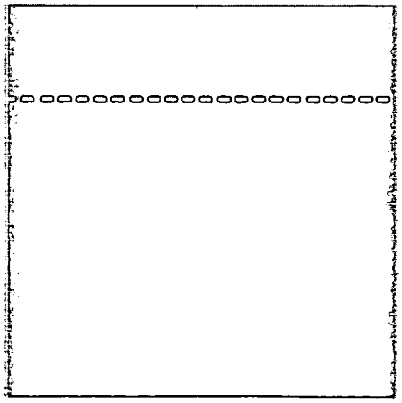

As discussed above, the FBP methodology cannot reconstruct exactly images from truncated data. Therefore, the noise properties of the FBP methodology are presented below from parallel-beam data without truncations. For the purpose of comparison, reconstruction results of the BPF and MDFBP methodologies are also included from the same non-truncated data. Using the numerical phantom in FIG. 40A and the Gaussian noise model described above, 500 noisy data sets were generated containing no truncations from which 500 noisy images were obtained through the image reconstruction on chords covering the object support by use of each of the BPF, MDFBP, and FBP methodologies. Using these noisy images, empirical variance images were computed, which are shown in FIGS. 43A-C. Specifically, empirical variance images within the field of view obtained by use of the BPF (FIG. 43A), MDFBP (FIG. 43B), and FBP (FIG. 43C) methodologies from parallel-beam data without truncations. For the purpose of displaying the details in the central (i.e., low variance) regions, a logarithmic scale is applied to the variance images. The display window is [−3.5, −2.5]. FIG. 43D also shows the variance profiles on the dashed lines depicted in FIGS. 43A-C, (i.e., on a chord) with the solid line in FIG. 43D indicating the variance of the BPF along the dashed line in FIG. 43A, the dashed line in FIG. 43D indicating the variance of the MDFBP along the dashed line in FIG. 43B, and the dotted line in FIG. 43D indicating the variance of the FBP along the dashed line in FIG. 43C. It can be observed from FIG. 43D that the image variances obtained with the three methodologies are similar and that the only difference comes at the extreme ends of the shown reconstruction segments. The BPF and MDFBP methodologies show a significant increase in the image variance at both ends of the profile. The reason for this may be that the reconstruction segment was taken to be the width of the image array, and the pre-factor for the finite Hilbert transform in Eqs. (B-4) and (B-7) has a singularity at the ends of the reconstruction segment. In practical situations, this pre-factor is of little consequence because the reconstruction segment can be selected slightly larger to avoid the singular behavior; furthermore, because the singularity goes as the −½ power, its effect is evident only very close to the endpoints of the reconstruction segment.

Figure 40C:
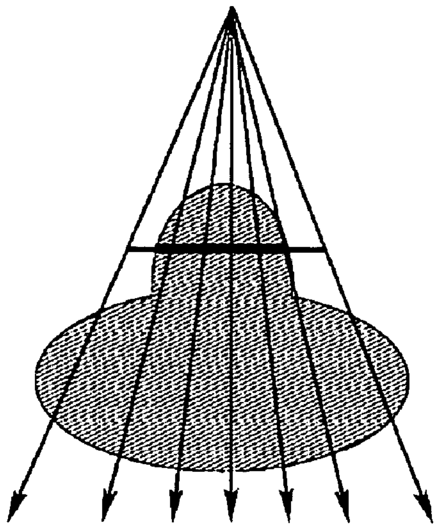

Using the numerical phantom in FIG. 40A and the fan-beam configuration in FIG. 40C, the 2D fan-beam, noiseless projection data at 512 views uniformly over [−π, π] is calculated. Each projection contains 256 bins spanning 40.0 cm. The distance between the source and the center-of-rotation is 20.0 cm with a fan angle of 90°. A short focal length is used to demonstrate the noise properties in the peripheral regions of the reconstructed images. 10,000 sets of noisy data are subsequently generated by adding to the noiseless data uncorrelated Gaussian noise, whose standard deviation is 1.74% of the maximum value in the noiseless data. The reconstruction segments were investigated with four $L_{AB}$=7.8 cm, 10.0 cm, 14.1 cm, and 20.0 cm. It can be observed in FIG. 40C that the length of the support segment is 5.5 cm, which is shorter than the four reconstruction segments. Therefore, the image on this chord may be reconstructed exactly by use of data determined by these reconstruction segments, respectively. One may also conclude from FIG. 40C that data determined by the first three reconstruction segments, which are shorter than the maximum dimension (about 15.6 cm) of the object support, are truncated.

Figures 44A, 44B, 44C:
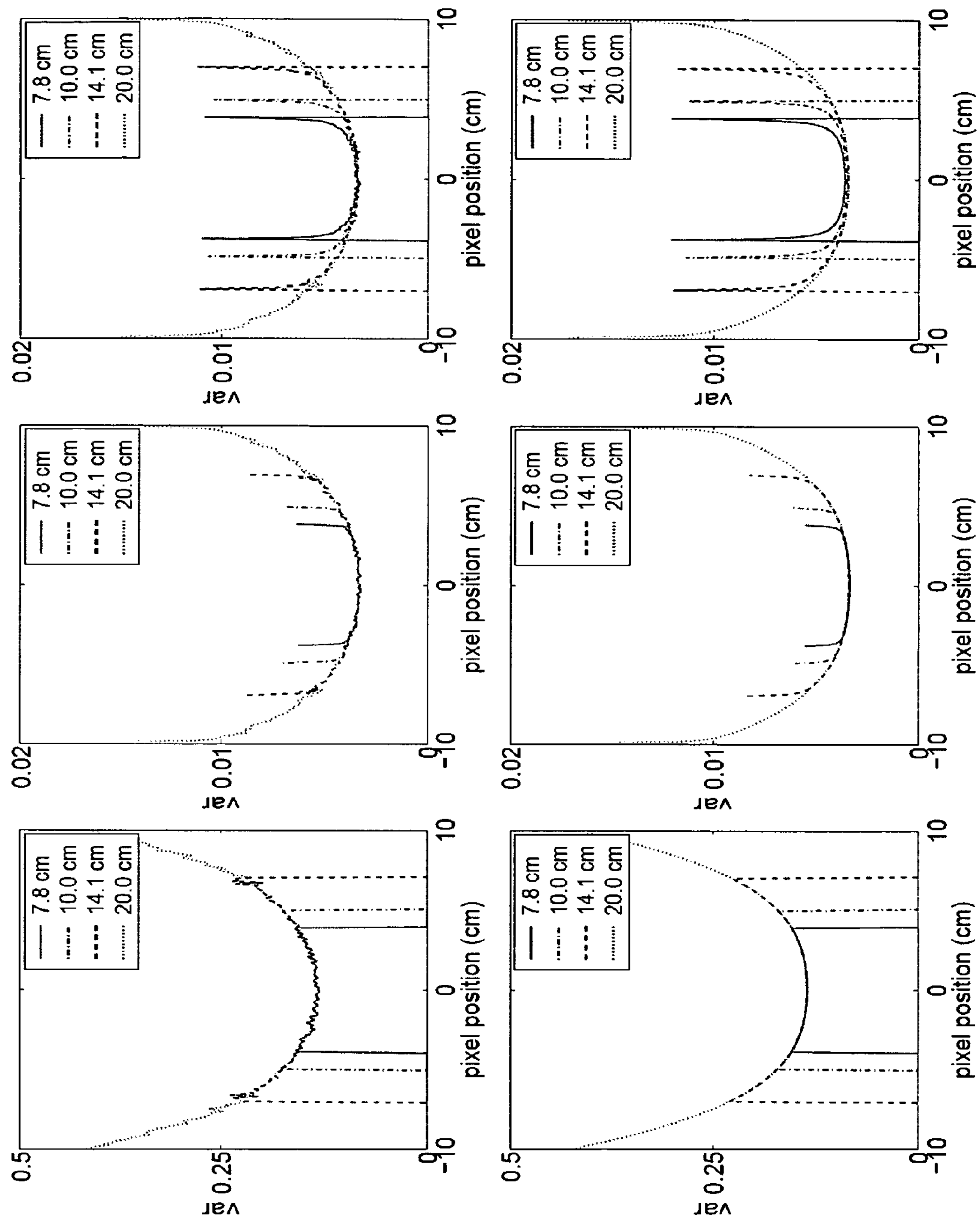
FIGS. 44*a-c* show graphs of empirical (upper row) and theoretical (lower row) variances of $g(x_c, s_a, s_b)$ (FIG. 44*a*), $\tilde{f}(x_c, s_a, s_b)$ (FIG. 44*b*), and $f_c(x_c, s_a, s_b)$ (FIG. 44*c*) obtained on four reconstruction segments with $L_{AB}$=7.8 cm, 10.0 cm, 14.1 cm, and 20.0 cm, respectively, from fan-beam data.

From the 10,000 sets of noisy data, Eqs. (B-4), (B-5), and (B-6) are used to calculate 10,000 noisy $f_c(x_c, s_a, s_b)$, $\tilde{f}(x_c, s_a, s_b)$, and $g(x_c, s_a, s_b)$, respectively. FIGS. 44A-C show graphs of empirical (upper row) and theoretical (lower row) variances of $g(x_c, s_a, s_b)$ (FIG. 44A), $\tilde{f}(x_c, s_a, s_b)$ (FIG. 44B) and $f_c(x_c, s_a, s_b)$ (FIG. 44*c*) obtained on four reconstruction segments with $L_{AB}$=7.8 cm, 10.0 cm, 14.1 cm, and 20.0 cm, respectively, from fan-beam data. Based upon these reconstructions, the corresponding empirical variances may be computed, which are shown in the upper row of FIGS. 44A-C. The result of the empirical variances of $g(x_c, s_a, s_b)$ in the upper row of FIG. 44A indicates that the empirical variance of $g(x_c, s_a, s_b)$ is spatially varying on the chord. From this empirical result, $c(x_c)$ is estimated, as shown in the lower row of FIG. 44A, which is subsequently used in Eqs. (B-12) and (B-13) for computing the theoretical variances of $\tilde{f}(x_c, s_a, s_b)$ and $f_c(x_c, s_a, s_b)$ for the fan-beam case. In the lower row of FIGS. 44A-C, the theoretical results are shown for the four different reconstruction segments described above. It may be observed that that the theoretical and empirical results agree quite well with each other, indicating that Eq. (B-12) provides an adequate theoretical description of the image variance on the chord for the fan-beam case as well.

Again, from these results, observations similar to those for the parallel-beam case can be made for the fan-beam case. For example, as FIG. 44C shows, the shorter the reconstruction segment, the higher the chord-image variances. This is because the second term in Eq. (B-12) increases as $L_{AB}$ (i.e., $(x_A-x_c)(x_c-x_B)$) decreases. The implication of this result is that there may be a real gain in terms of dose reduction by using a short reconstruction segment, because data required to reconstruct an image on this reconstruction segment is less than that required by using a longer reconstruction segment, which can result in the reduction of dose delivery to the object.

Figure 45B:
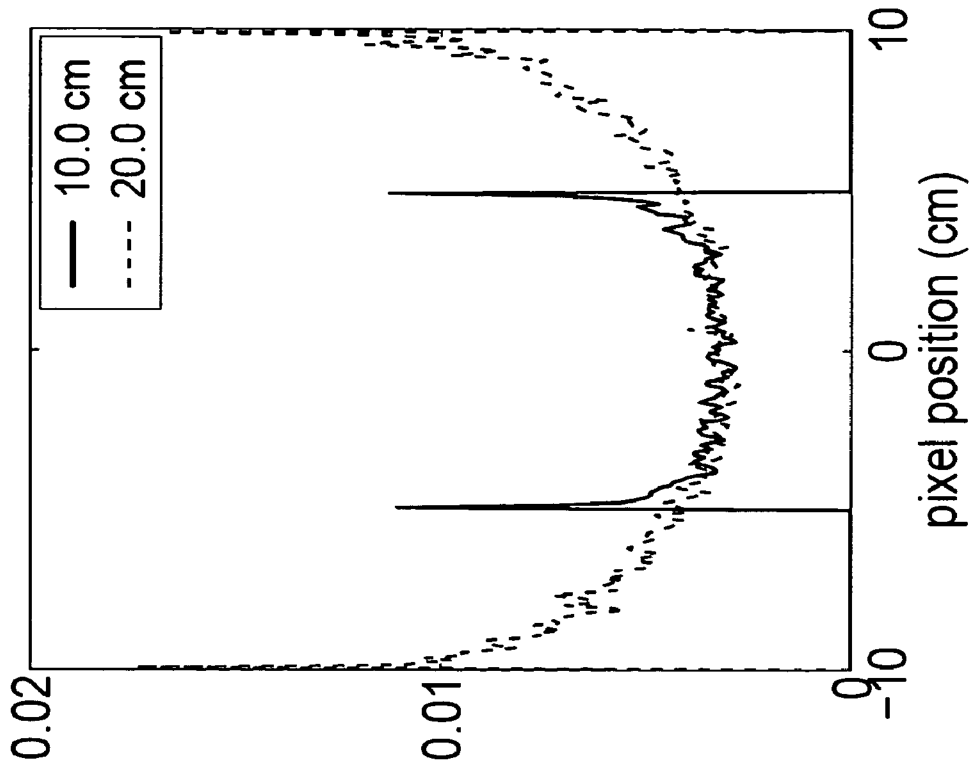
FIGS. 45*a-b* depict the image variances on the chord, as indicated in FIG. 40, obtained by use of the BPF methodology (FIG. 45*a*) and MDFBP methodology (FIG. 45*b*) from the 500 sets of noisy data described above for two different reconstruction segments with $L_{AB}$=10.0 cm and 20.0 cm.
Figure 45A:
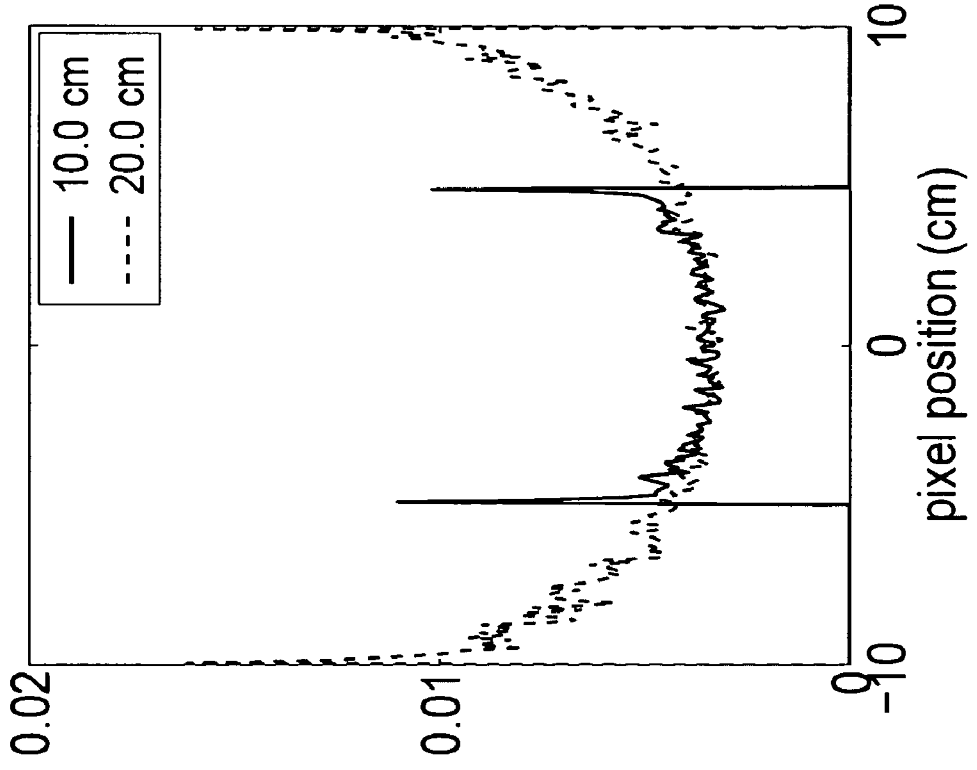

Numerical studies of the noise properties of the MDFBP methodology by use of the noisy fan-beam data were also performed. These results indicate that the noise properties of the MDFBP methodology is similar to those of the BPF methodology. As an example, FIGS. 45A-B depict the image variances on the chord, as indicated in FIG. 40, obtained by use of the BPF methodology (FIG. 45A) and MDFBP methodology (FIG. 45B) from the 500 sets of noisy data described above for two different reconstruction segments with $L_{AB}$=10.0 cm and 20.0 cm. From the results in FIGS. 45A-B, one can observe that, in terms of image variance, the noise properties of the BPF and MDFBP methodologies are similar to each other.

Figure 46B:
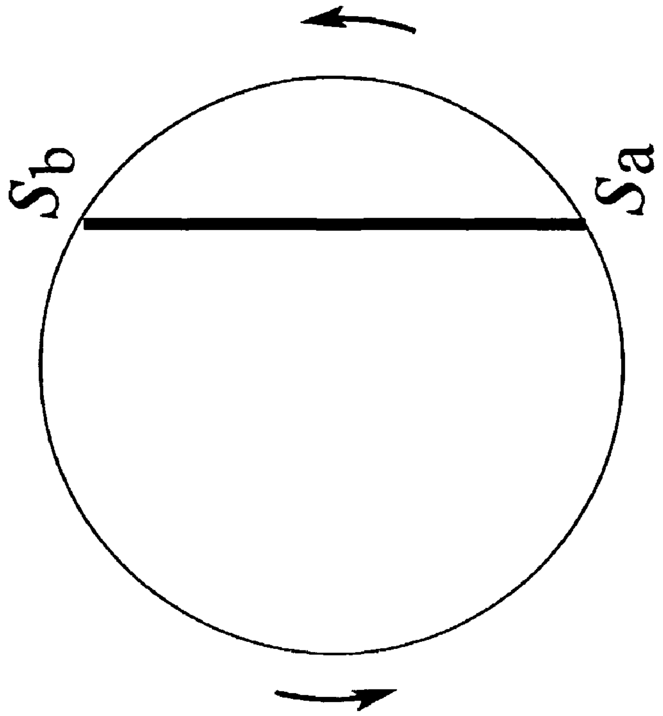
FIG. 46*b* depicts the right-side trajectory (solid line) and left-side trajectory (solid line) of the chord (thick line) specified by $s_a$ and $s_b$. The scanning configuration in FIG. 46*b* corresponds to a full, fan-beam scan.
Figure 46A:
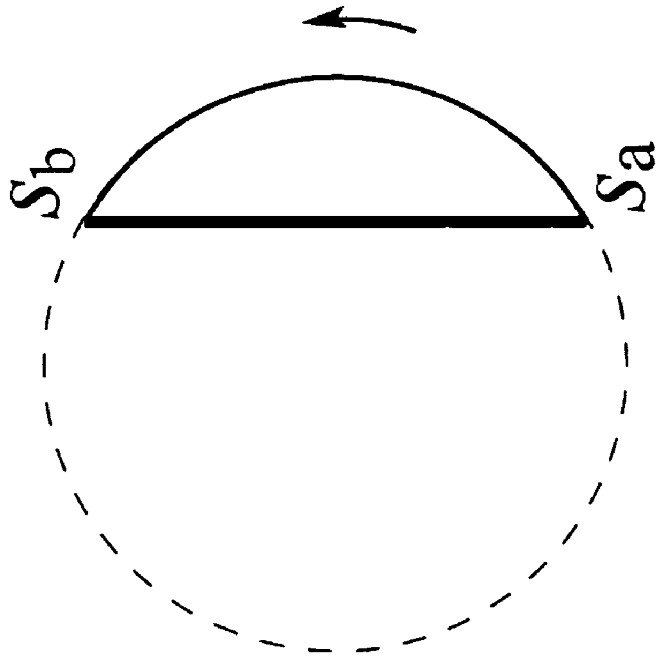
FIG. 46*a* depicts the right-side trajectory (solid line) of the chord (thick line) specified by $s_a$ and $s_b$.

The FBP methodology cannot reconstruct exactly images from truncated fan-beam data. Therefore, the noise properties of the FBP reconstruction are evaluated from non-truncated fan-beam data. For the purpose of comparison, reconstruction results of the BPF and MDFBP methodologies from the same data sets are also included. Using the numerical phantom in FIG. 40A and the Gaussian noise model described above, 500 sets of noisy fan-beam data are generated containing no truncations at 512 views uniformly covering 2π. For a given chord specified by $s_a$ and $s_b$, one can reconstruct its image from data acquired over the right-side trajectory (i.e., $s\epsilon[s_a, s_b]$), as shown in FIG. 46A. Specifically, FIG. 46A depicts the right-side trajectory (solid line) of the chord (thick line) specified by $s_a$ and $s_b$. Conversely, one may also reconstruct the chord image from data acquired with both right-side trajectory (i.e., $s\epsilon[s_a, s_b]$) and left-side trajectory (i.e., $s\epsilon[s_b, s_a]$), as shown in FIG. 46B. Specifically, FIG. 46B depicts the right-side trajectory (solid line) and left-side trajectory (solid line) of the chord (thick line) specified by $s_a$ and $s_b$. The scanning configuration in FIG. 46B corresponds to a full, fan-beam scan. In chord-based image reconstruction, the image area may be decomposed into chords parallel to the vertical direction with the source scanning from $s_a$ to $s_b$ and then from $s_b$ to $s_a$ as shown in FIGS. 46A-B.

Figure 47C:
FIGS. 47*a-c* show the variance images obtained by assembling the chord-image variances, for the BPF (FIG. 47*a*), MDFBP (FIG. 47*b*) and FBP (FIG. 47*c*) methodologies, respectively.
Figure 47B:
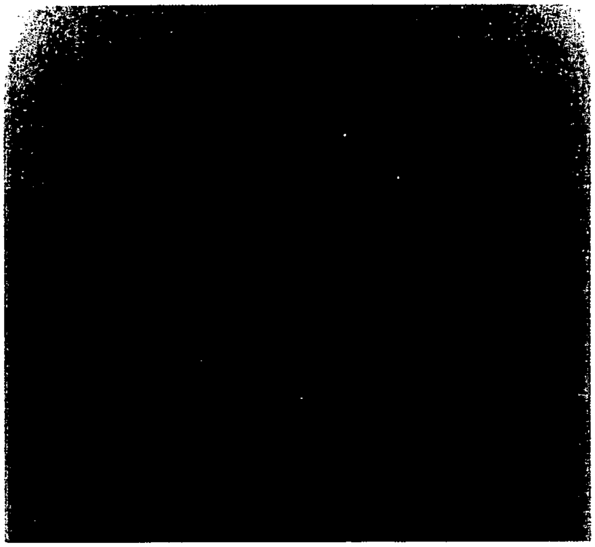
Figure 47A:
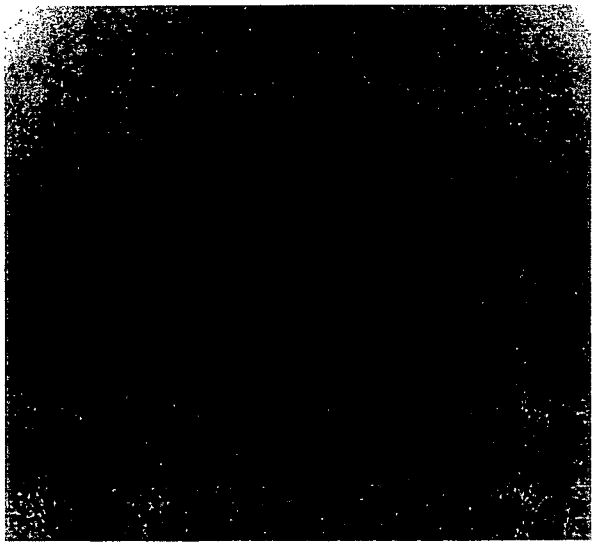
Figure 48A:
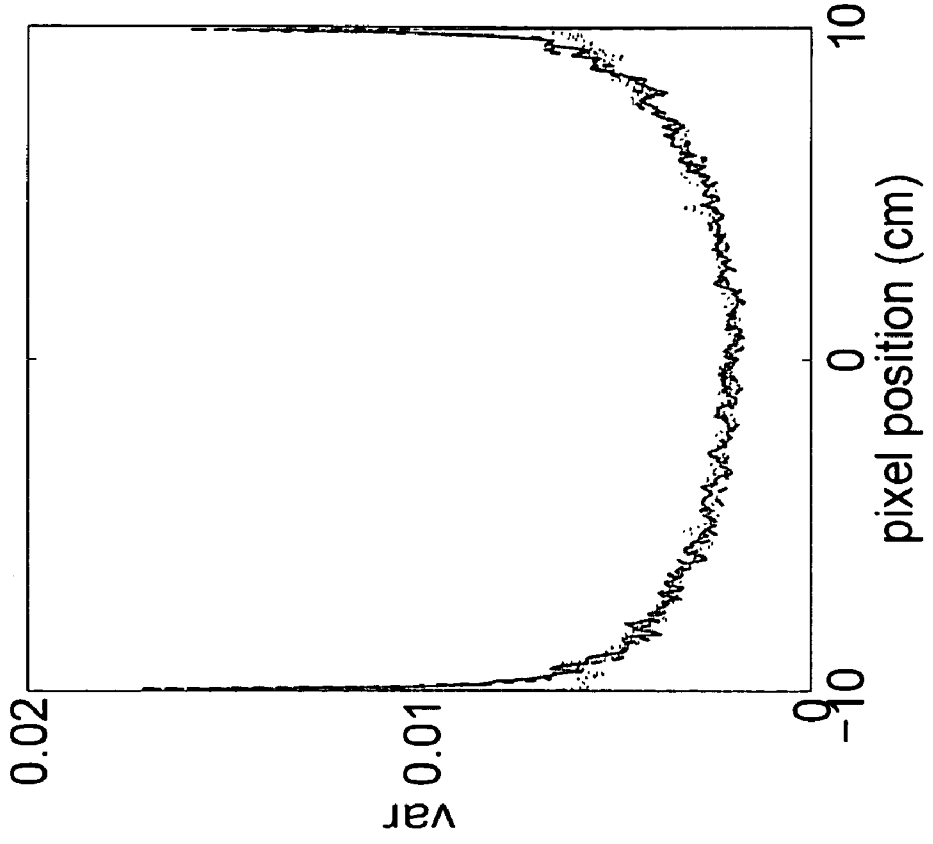
FIGS. 48*a-b* depict variance profiles along the central vertical (i.e., on a chord specified by $s_a=-\pi/2$ and $s_b=\pi/2$) (FIG. 48*a*) and horizontal (FIG. 48*b*) lines in the variance images shown in FIGS. 47*a-c*, obtained by the BPF (solid line), MDFBP (dashed line), and FBP (dotted line) methodologies.
Figure 48B:
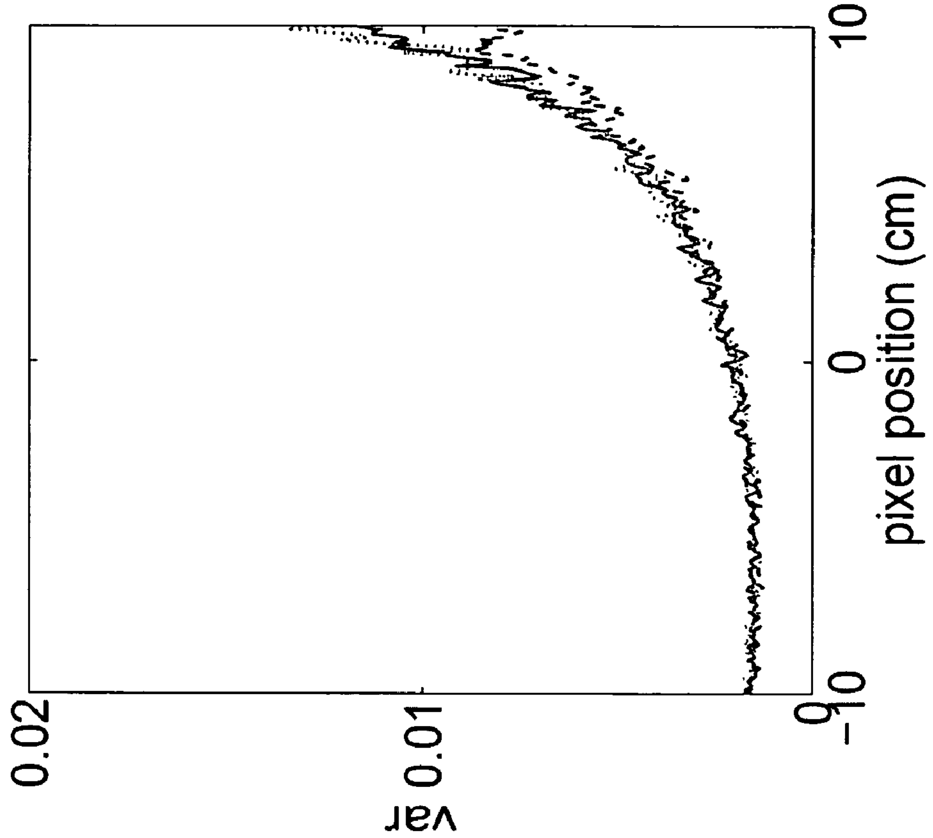

For each chord in the set covering the image area, the images may first be reconstructed by use of the BPF, MDFBP, and FBP methodologies from the 500 sets of noisy data acquired over the right-side trajectory specified by $s \in [s_a, s_b]$. Subsequently, the empirical chord-image variances may be computed from these noisy reconstructions. By assembling the chord-image variances, the variance images may be obtained, which are shown in FIGS. 47A-C, for the BPF (FIG. 47A), MDFBP (FIG. 47B) and FBP (FIG. 47C) methodologies, respectively. FIGS. 48A-B depict variance profiles along the central vertical (i.e., on a chord specified by $s_a=-\pi/2$ and $s_b=\pi/2$) (FIG. 48A) and horizontal (FIG. 48B) lines in the variance images shown in FIGS. 47A-C, obtained by the BPF (solid line), MDFBP (dashed line), and FBP (dotted line) methodologies. As seen above, the variance increases as the position along the chord nears the source trajectory. There appears, however, to be little difference between the three methodologies. Furthermore, these variance images have similar properties; the chords on the right part have higher and more non-uniform image variance than those on the left part in the image area. Comparing the middle point of each of the vertical chords in FIG. 48B does, however, reveal that some difference of the MDFBP result from the BPF and FBP results in the peripheral region. This difference may be attributed to a different mathematical data weighting before the back-projection step in the MDFBP methodology is performed. Further, this difference may only be seen for the extreme periphery of the imaging area. For most practical situations the three methodologies perform virtually the same in terms of image variance.

The variance for chords decreasing on the left of the variance image is investigated. One may contend that this decreasing trend may be because the scanning trajectory being on the right side, chords on the left of the variance image are reconstructed with a longer scanning trajectory. Thus, more data may be used in reconstructing chords covering the left part of the variance image. This explanation is, however, incorrect. First, there is a slight upturn in the variance for the chords on the extreme left of the variance image, which runs counter to this trend. Second, it can be demonstrated that the amount of data going into the chord reconstruction does not necessarily increase as the scanning trajectory increases. Through the examination of the specific case of comparing a left- and right-side scans of an off-center vertical chord, the data usage in left-side and right-side scans is identical, because the larger scanning trajectory for the one case is offset by a larger magnification factor in the other case. The cause of the behavior of the variance may be spatially dependent weighting factors such as the $1/|\vec{r}-\vec{r}_0(\lambda)|$ factor in the BPF, MDFBP, and FBP methodologies.

Figure 49A:
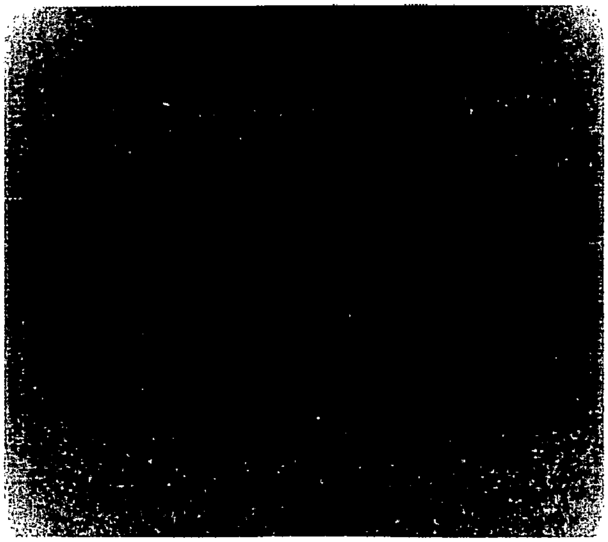
FIG. 49*a-c* show variance of images of the full scan obtained by use of the BPF (FIG. 49*a*), MDFBP (FIG. 49*b*), and FBP (FIG. 49*c*) methodologies from fan-beam data acquired over the right-side and left-side trajectories.
Figure 49B:
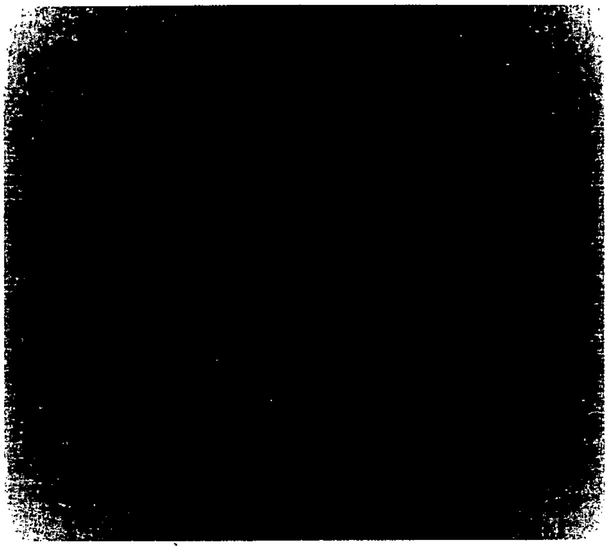
Figure 49C:
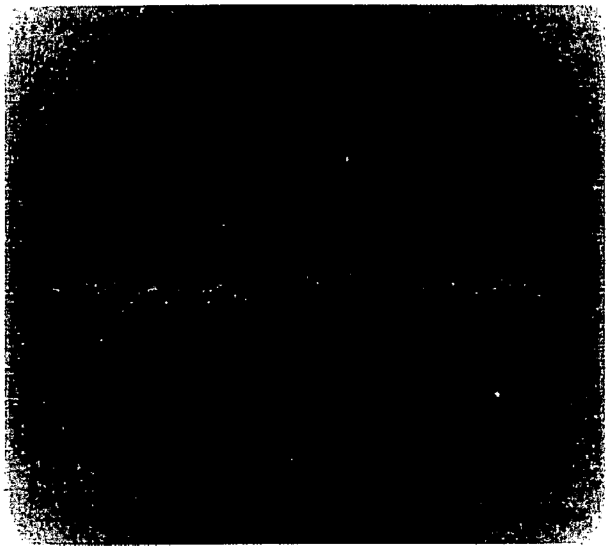
Figure 50A:
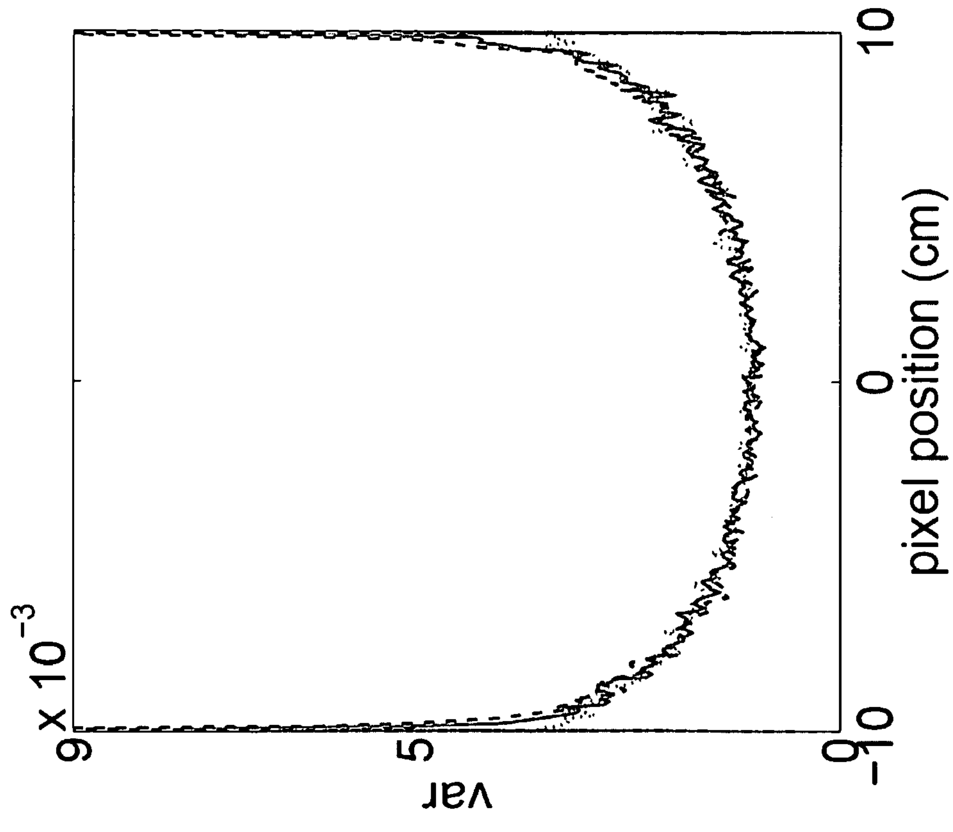
FIG. 50 shows variance profiles along the central vertical (FIG. 50*a*) and horizontal (FIG. 50*b*) lines in variance images shown in FIGS. 49*a-c*, obtained by the BPF (solid line), MDFBP (dashed line), and FBP (dotted line) methodologies.
Figure 50B:
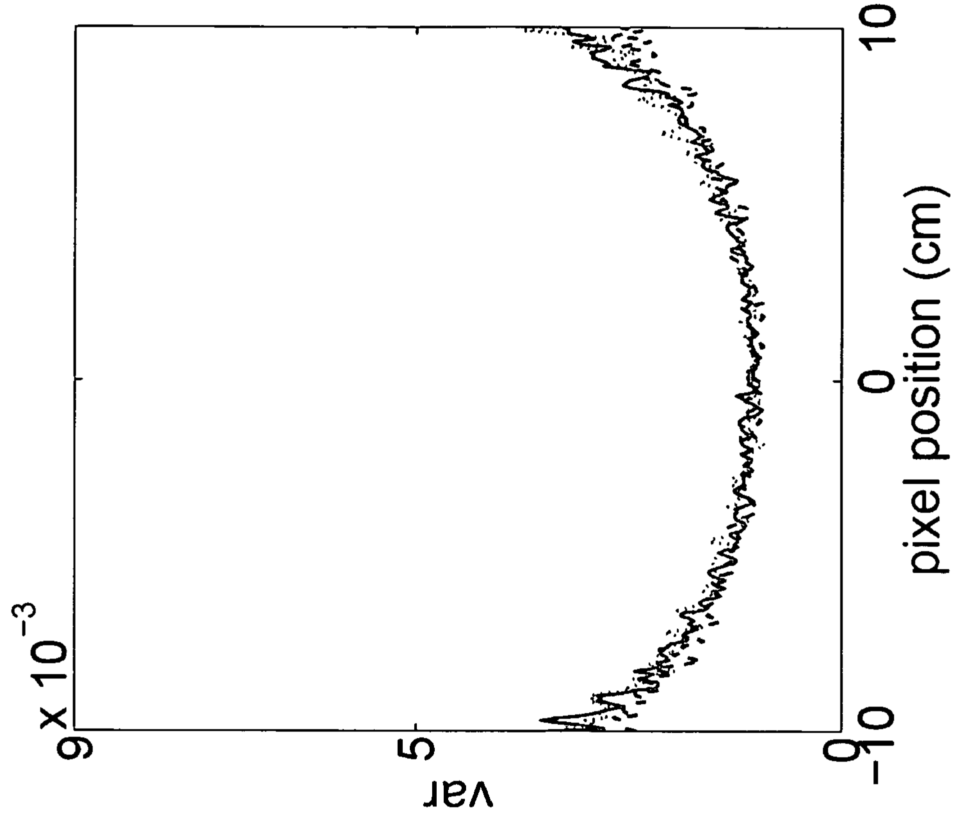

For a given chord specified by $s_a$ and $s_b$, when full scan data are available, one can reconstruct two chord images by use of data acquired with the right-side and left-side trajectories, as shown in FIGS. 46A-B and then obtain a final chord image by averaging the two chord images. FIG. 49A-C show variance of images of the full scan obtained by use of the BPF (FIG. 49A), MDFBP (FIG. 49B), and FBP (FIG. 49C) methodologies from fan-beam data acquired over the right-side and left-side trajectories. For the purpose of displaying the details in the central (i.e., low variance) regions, a logarithmic scale is applied to the variance images. The display window is [−3.0, −1.7]. FIG. 50A shows variance profiles along the central vertical (FIG. 50A) and horizontal (FIG. 50B) lines in variance images shown in FIGS. 49A-C, obtained by the BPF (solid line), MDFBP (dashed line), and FBP (dotted line) methodologies.

The BPF, MDFBP, and FBP methodologies may yield exact image reconstruction on a chord specified by $s_a$ and $s_b$ so long as the support segment on the chord is illuminated by the x-ray beam at the projection views $s \in [s_a, s_b]$, because these methodologies require data only on the fan-beam projections of the support segment. From the perspective of the methodologies, the reconstruction of a chord image from cone-beam data is identical to that of a chord image from fan-beam data except that the orientations of the fan-beam planes at different views remains unchanged in 2D fan-beam case, whereas the orientations of the fan-beam-illumination planes in the cone-beam case with a non-planar trajectory will generally vary from view to view. Despite the variation in the illumination plane, the properties of chord images in a cone-beam case may be similar to that of chord images in a fan-beam case, which were discussed above.

Figure 51B:
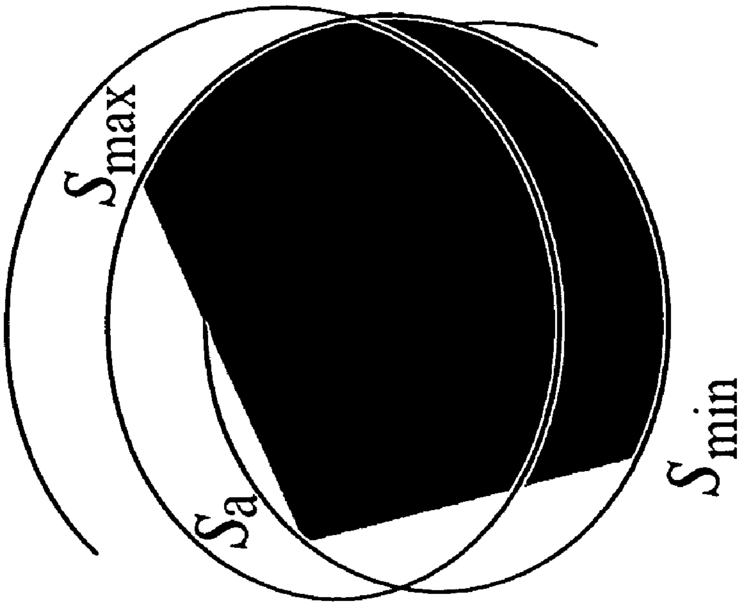
FIG. 51*b* depicts surfaces generated in the imaging volume by concatenating π-line segments specified by $s_a=-\pi$ and $s_b\in[-0.5\pi, 0.5\pi]$.
Figure 51A:
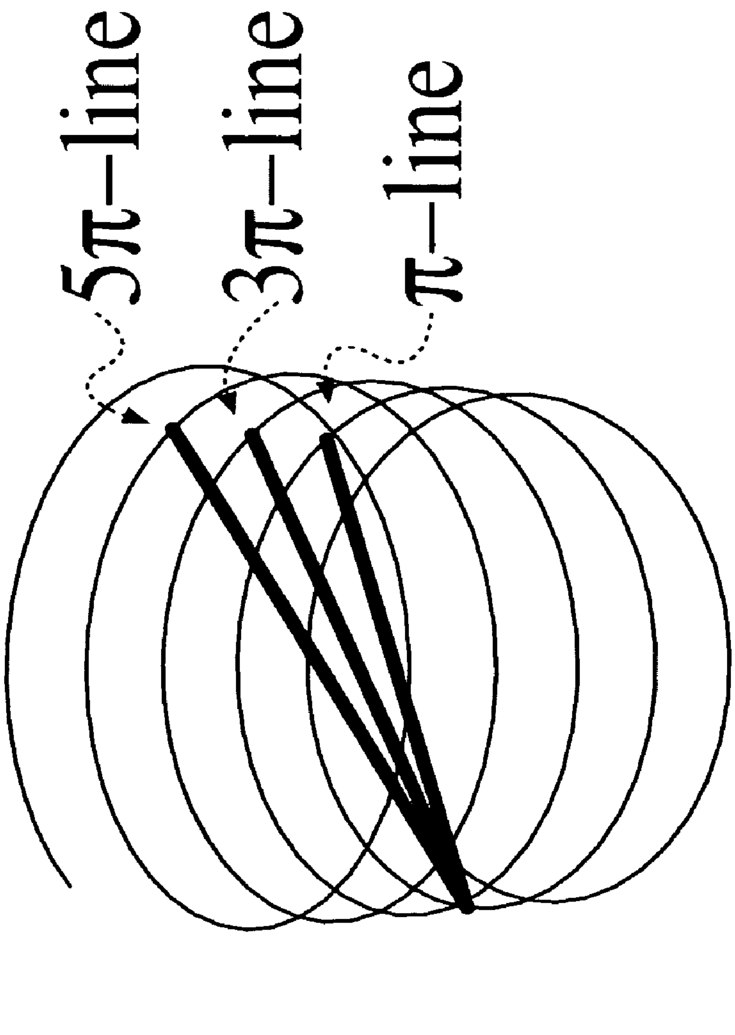
FIG. 51*a* depicts π-line, 3π-line, and 5π-line segments in a helical scan.

In the analysis of the noise properties of image reconstruction from cone-beam data, the helical trajectory is considered because it is the most widely used in clinical and industrial CT. FIG. 51A depicts π-line, 3π-line, and 5π-line segments in a helical scan. FIG. 51B depicts surfaces generated in the imaging volume by concatenating π-line segments specified by $s_a$ and $s_b \in [-0.5\pi, 0.5\pi]$. For a helical scan, the source trajectory may be described mathematically as $$\vec{r}_0(s) = \left(R\cos s,\ R\sin s,\ \frac{h}{2\pi}s\right),$$

where R is the source to center-of-rotation distance, and h indicates the helical pitch length. For a chord specified by $s_a$ and $s_b$, if $(n-1)\pi \leqq |s_b - s_a| \leqq (n+1)\pi$, where n is a positive odd integer, the chord is also referred to as an nπ-line segment, as shown in FIG. 51A. In particular, when n=1 and thus $0 \leqq |s_b - s_a| \leqq 2\pi$, the chord may be referred to as a π-line segment. In this analysis, image reconstruction is considered only on π-line segments since the imaging volume enclosed by the helix can be filled uniquely, completely by if π-line segments. In other words, any point in the imaging volume that is interior to the helix belongs to a unique or π-line segment. Thus, π-line segments can be used to form 3D images in a helical cone-beam scan.

The parameters of the helical cone-beam configuration may be as follows. The source to center-of-rotation distance is R=20.0 cm and the helical pitch is h=0.9 cm. The detector has 128×128 bins, and the fan- and cone-angles are 90° degrees. The noiseless data is determined from a uniform cylinder at 300 views uniformly distributed over [−π, π] and subsequently generated 500 sets of noisy data by adding Gaussian noise to the noiseless data. The standard deviation of Gaussian noise is chosen to be 1.56% of the maximum value of the noiseless data.

A curved surface in the helix volume can be formed by a set of π-line segments for which one end-point is fixed at $s_a$ and sweep the other endpoint over a range $s_b \in [s_{min}, s_{max}]$. In FIG. 51A, a curved surface is obtained by concatenating a set of π-line segments specified by $s_a=-\pi$ and $s_b \in [-0.5\pi, 0.5\pi]$. Using the 500 sets of noisy helical cone-beam data described above, 500 noisy images are reconstructed on the π-line surface by use of the BPF, MDFBP, and FBP methodologies. FIGS. 52A-D depict empirical variance images from these noisy images on the π-line surface shown in FIG. 51B obtained by use of the BPF (FIG. 52A), MDFBP (FIG. 52B), and FBP (FIG. 52C) methodologies. For the purpose of displaying the details in the central (i.e., low variance) regions, a logarithmic scale is applied to the variance images. The display window is [−3.5, −1.5].

Figure 52A:
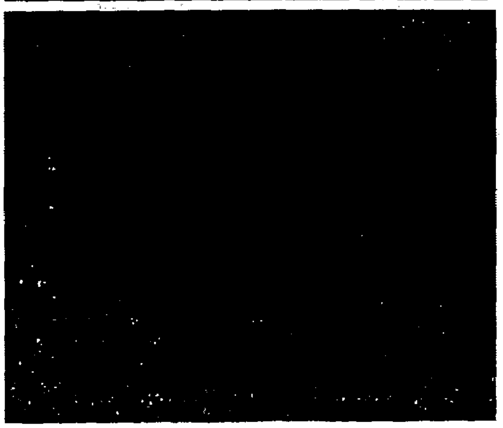
FIGS. 52*a-d* depict empirical variance images from these noisy images on the π-line surface shown in FIG. 51B obtained by use of the BPF (FIG. 52*a*), MDFBP (FIG. 52*b*), and FBP (FIG. 52*c*) methodologies.
Figure 52B:
Figure 52C:
Figure 52D:
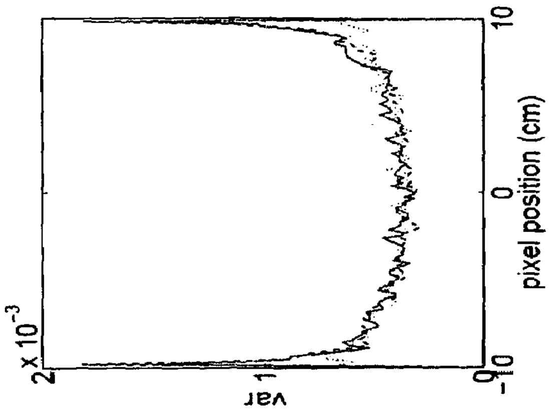

FIG. 52D depicts variances on the central vertical line segment, specified by $s_a=-\pi$ and $s_b=0$, obtained with the BPF (solid line), MDFBP (dashed line), and FBP (dotted line) methodologies, respectively. The image variances show the characteristics of fan-beam image variances observed in FIGS. 48A-B. Namely, the variance image on the π-line surface in FIG. 52 has a structure that is similar to the right-side scan fan-beam results discussed above; the images on π-line segments reconstructed from smaller helix segments tend to have higher and more non-uniform variances. The similarity with the fan-beam case is not surprising because the geometrical arrangement of the π-line with respect to its scanning trajectory is very similar to the relationship between the chords and corresponding fan-beam scanning trajectory. The only difference is that there is an out-of-plane bend to the helix segment.

Returning to the shape of the variance non-uniformity, one may attribute the high variance in the image periphery to the weighting factors multiplying the data derivatives before backprojection. As the methodologies are essentially the same for 2D and 3D image reconstruction, this conclusion is not surprising. In the 2D fan-beam cases, the variance non-uniformity and level is reduced by equally weighting reconstructions for both left and right side scans for each chord of the scanning circle. For the helical configuration, in a typical scan there may be some overscan for one, some or all of the chords comprising the volume. But the overscan part of the trajectory may not form a closed-loop so using the overscan data to reduce image variance is not as evident as the case of the circular scan. The overscan data may be utilized for non-closed trajectories for the purpose of reducing the impact of data noise on chord-based ROI-image reconstruction. Thus, in many situations, large data sets contain extraneous data that may not improve the image variance within a desired ROI, but may be utilized for other purposes, such as reducing the impact of data noise.

The following is the noise analysis of the weighted Hilbert transform over a finite interval. The weighted Hilbert transform constitutes a step in the chord-based BPF, MDFBP, and FBP methodologies. Consequently, the noise properties of these methodologies depend upon that of the weighted Hilbert transform. Let $\hat{f}(x)$ denote the weighted Hilbert transform of an input function g(x):

$$\hat{f}(x) = \frac{1}{a(x)}\int_{x_A}^{x_B} \frac{dx'}{x-x'} a(x')g(x'), \tag{B-14}$$

where $a(x)=\sqrt{(x_B-x)(x-x_A)}$. g(x) is assumed to be band-limited to $v_m$. Therefore, the Hilbert transform kernel $$\frac{1}{x}$$

may be replaced by $$h(x) = -\pi j\int_{-v_m}^{v_m} dv\,\mathrm{sgn}[v]e^{2\pi jvx} = \frac{2\sin^2(\pi v_m x)}{x}. \tag{B-15}$$

When the input function contains noise, g(x) and its weighted Hilbert transform $\hat{f}(x)$ may be interpreted as stochastic processes, which are denoted in boldface. The variance of $\hat{f}(x)$ may be written as:

$$\mathrm{Var}\{\hat{f}(x)\} = \frac{1}{a^2(x)} \int_{x_A}^{x_B} dx' \int_{x_A}^{x_B} dx'' h(x-x')a(x')h(x-x'')a(x'')\mathrm{Cov}\{g(x'), g(x'')\}, \tag{B-16}$$

where Cov{g(x'), g(x")} denotes the autocovariance of g(x').

g(x) is assumed to be an uncorrelated stochastic process, i.e., $$\mathrm{Cov}\{g(x'),g(x'')\}=c(x')\delta(x''-x'), \tag{B-17}$$

where c(x') is the variance of g(x'). Using Eq. (B-17) in Eq. (B-16), one obtains:

$$\mathrm{Var}\{\hat{f}(x)\} = \frac{1}{a^2(x)}\int_{x_A}^{x_B} dx' c(x')h^2(x-x')a^2(x'). \tag{B-18}$$

In numerical studies discussed above, $v_m=\frac{1}{2}\Delta x$ is used, where Δx denote the sample width of g(x).

As discussed above, an analysis of the noise properties of chord-based image reconstructions from parallel-, fan-, and cone-beam data is performed. One aspect of the analysis is to test whether or not the reduced illumination in designing a minimal data set for a particular ROI leads to a real reduction in exposure. The statistical properties of the ROI image reconstructed from noise realizations of the minimal data set may be compared with noise realizations of the full data set. Similar noise levels are used in both data sets, which are equivalent to modeling similar incident x-ray beam intensities. The results, using additive Gaussian noise in the data model, indicate that the resulting image variance is almost the same for images reconstructed from both data sets. Thus, the minimal data set for ROI reconstruction may lead to a significant overall dose reduction, because the body is exposed to less ionizing radiation in the reduced scan. Although this conclusion is demonstrated explicitly only for ROI scanning in 2D parallel-beam, it applies to other beams, such as the fan-beam and cone-beam cases, because of the similarity in reconstruction methodology. For fan-beam and cone-beam imaging, the noise properties of the extreme periphery of the imaging region are explored by investigating large fan- and cone-angles. Image variance non-uniformity may be caused by spatially dependent weighting factors in the chord-based reconstruction methodologies.

While Gaussian noise in the data model is used, other noise models may be used as well. Further, in seeking ways to reduce the impact of noise in volume imaging, schemes may be used to incorporate overscan data. The analysis discussed above may be directly applied to chord-based image reconstruction for general trajectories. Finally, the behavior of the ROI-reconstruction methodologies may be examined when other factors are included in the data model, such as x-ray polychromaticity and non-linear partial volume averaging.

4. Region of Interest Reconstruction from Truncated Data

The circular scanning trajectory has been widely used in computed tomography (CT) for data acquisition because it involves minimum hardware implementation complexity. It may be applied to a variety of applications, including micro-CT, dedicated breast CT, and radiotherapy CT. The circular cone-beam configuration may not, however, satisfy Tuy's sufficiency condition, and no stable methodology exists for exact reconstruction of three dimensional (3D) images from circular cone-beam projections of a longitudinally non-uniform object function. The so-called FDK (Feldkamp, Davis, Kress) methodology and other modifications have been developed for reconstructing approximately 3D images from circular cone-beam data. For a relatively small cone angle and certain object functions, these methodologies may yield images that are adequately accurate for some practical applications.

In imaging tasks involving micro-CT, dedicated breast CT, and radiotherapy MV and KV CT, it is not uncommon that the field of view (FOV) of the CT system is smaller than the support of the object function. Also, in these applications, one is often interested in information within a region of interest (ROI) of the subject; and, for the sake of reducing radiation dose delivered to the subject, one may intend to use a FOV that fully covers the ROI and that is otherwise considerably smaller than the subject. These situations may lead to transversely truncated projection data from which the existing methodologies generally yield images of the subject with severe artifacts. On the other hand, it is of practical significance to develop methodologies that can, from truncated circular cone-beam data, reconstruct ROI images with an accuracy comparable to that obtained from non-truncated data. The following discloses such methodologies for ROI-image reconstruction from circular cone-beam data containing transverse truncations.

A methodology, discussed above, discloses an exact image reconstruction on PI-lines from helical cone-beam data. This methodology, which is referred to as the backprojection-filtration (BPF) methodology, may reconstruct images by first computing the cone-beam backprojection of the data derivatives onto PI-lines and then performing a 1D filtering of the backprojection image along PI-lines. The BPF methodology may exactly reconstruct images by use of data less than that required by other existing filtered-backprojection (FBP)-based methodologies, such as Katsevich's methodology. The BPF methodology may reconstruct an ROI image within the subject from fan-beam data containing truncations, as discussed above.

Based upon the BPF methodology for helical cone-beam CT, an approximate BPF methodology is disclosed for 3D ROI-image reconstruction from circular cone-beam data containing truncations. This methodology, which is referred to as the BPF methodology for circular cone-beam CT, may reconstruct exactly an ROI image within the mid-plane and approximate ROI images within off-mid-planes and these ROI images may be free of truncation artifacts seen in images obtained with the FDK methodologies. Furthermore, this approximate BPF methodology may be generalized to exploit "redundant" information in data for further improving image quality. In addition to computer-simulation studies, the methodology is applied to reconstructing ROI images from circular cone-beam data acquired with a simulator-CT system for radiotherapy.

Figure 53:
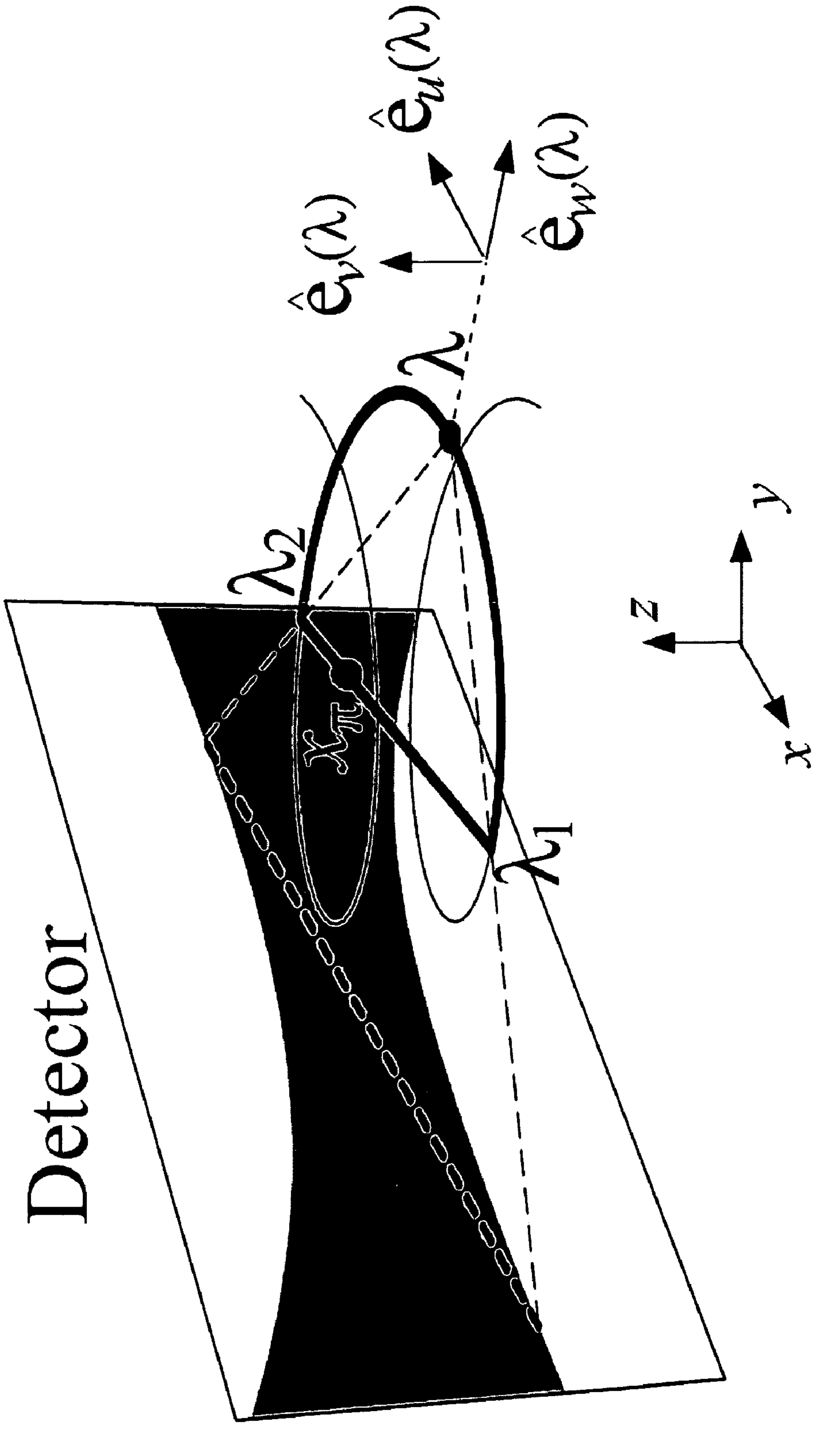
FIG. 53 is an illustration of the helical cone-beam scanning geometry and a PI-line segment.

In a helical cone-beam scan, the imaged object may be translated longitudinally while the x-ray source and detector rotate. Consider a coordinate system {x, y, z} that is fixed on the imaged object. FIG. 53 is an illustration of the helical cone-beam scanning geometry and a PI-line segment. A rotation-coordinate system whose origin may be fixed on the source point A is specified by three vectors $\hat{e}_u$, $\hat{e}_v$, and $\hat{e}_w$. From the perspective of the object, the source trajectory is a helix and can be written in the fixed-coordinate system as $$\vec{r}_0(\lambda) = \left(R\cos\lambda,\ R\sin\lambda,\ \frac{h}{2\pi}\lambda\right)^T, \tag{C-1}$$

where λ denotes the rotation angle of the x-ray source, R the distance from the source point to the rotation axis, and h the pitch of the helical trajectory, which may be defined as the translation distance of the imaged object during one turn of gantry rotation. The cylindrical volume enclosed by the helical trajectory may be referred to as the helix cylinder, and the support of the object function $f(\vec{r})$ is assumed to be within the helix cylinder.

A rotation-coordinate system is introduced whose origin is fixed on the source point. In the fixed-coordinate system, the three unit vectors of the rotation-coordinate system may be written as:

$$\hat{e}_u=(-\sin\lambda,\cos\lambda,0)^T$$

$$\hat{e}_v=(0,0,1)^T$$

$$\hat{e}_w=(\cos\lambda,\sin\lambda,0)^T. \tag{C-2}$$

Without loss of generality, a flat-panel detector is considered, which has a normal direction along $\hat{e}_w$ and is at a distance S from the source point. Any point on the detector may be specified by two parameters u and v. At angle λ, the cone-beam projection of the object function $f(\vec{r})$ at a point (u, v) on the detector may be expressed as:

$$P(u,v,\lambda)=\int_0^\infty ds f(\vec{r}_0(\lambda)+s\hat{\beta}), \tag{C-3}$$

where the unit vector $\hat{\beta}$ indicates the direction of the ray starting from source point $\vec{r}_0(\lambda)$ and passing through the point (u, v) on the detector and can be written as $$\hat{\beta} = \frac{1}{\sqrt{u^2+v^2+S^2}}[u\hat{e}_u(\lambda)+v\hat{e}_v(\lambda)-S\hat{e}_w(\lambda)]. \tag{C-4}$$

A PI-line may comprise a straight line intersecting with the helical trajectory at two points labeled by $\lambda_1$ and $\lambda_2$, where $|\lambda_2-\lambda_1|\leqq 2\pi$; and the segment on the PI-line within the helix cylinder may be referred to as the PI-line segment.

$$\hat{e}_\pi = \frac{\vec{r}_0(\lambda_2)-\vec{r}_0(\lambda_1)}{|\vec{r}_0(\lambda_2)-\vec{r}_0(\lambda_1)|} \tag{C-5}$$

denotes the direction of the PI-line segment and $x_\pi$ to index a point on the PI-line segment. $(x_\pi, \lambda_1, \lambda_2)$ may specify a unique point within the helix cylinder and any point within the helix cylinder can be uniquely described by $(x_\pi, \lambda_1, \lambda_2)$. Therefore, $\{x_\pi, \lambda_1, \lambda_2\}$ may be referred to as the PI-line coordinate system. For a point $\vec{r}$ within the helix cylinder, the relation between PI-line coordinates and $\vec{r}$ may be given by:

$$\vec{r} = \vec{r}_{c0} + x_\pi \hat{e}_\pi, \quad \text{(C-6)}$$

where $$\vec{r}_{c0} = \frac{\vec{r}_0(\lambda_1) + \vec{r}_0(\lambda_2)}{2}, \quad x_\pi \in (x_{\pi 1}, x_{\pi 2}),$$

and $x_{\pi 1}$ and $x_{\pi 2}$ denote the two end points of a PI-line segment. Moreover, we use $x_{s1}$ and $x_{s2}$ to denote the two end points of the intersection of the PI-line segment with the support of the object function. This intersection may be referred to as the support segment on the PI-line. Because the object function is enclosed completely within the helix cylinder, $[x_{\pi 1}, x_{\pi 2}] \supset [x_{s1}, x_{s2}]$.

The concept of PI-line segment plays a role in the development of methodologies for image reconstruction in helical cone-beam CT. A given point $\vec{r}$ within the helix may determine a unique PI-line segment and that the PI-line segments may completely fill the helix cylinder. Therefore, the image reconstruction within the helix cylinder may be equivalent to the image reconstruction on PI-line segments. Let $f_\pi(x_\pi, \lambda_1, \lambda_2)$ denote the image function on a PI-line segment, which may be reconstructed by use of the BPF methodology as:

$$f_\pi(x_\pi, \lambda_1, \lambda_2) = \frac{1}{2\pi^2}\frac{1}{\sqrt{(x_B - x_\pi)(x_\pi - x_A)}} + \left[\int_{x_A}^{x_B} \frac{dx'_\pi}{x_\pi - x'_\pi}\sqrt{(x_B - x'_\pi)(x'_\pi - x_A)} \times g_\pi(x'_\pi, \lambda_1, \lambda_2) + 2\pi P_0(u_\pi, v_\pi, \lambda_1)\right], \quad \text{(C-7)}$$

where $x_A$ and $x_B$ are any points satisfying $[x_{\pi 1}, x_{\pi 2}] \supset [x_A, x_B] \supset [x_{s1}, x_{s2}]$, the integral is to be considered as a Cauchy principal value, $(u_\pi, v_\pi)$ indicates the intersection of the PI-line on the detector, the constant term $P_0$ indicates the cone-beam projection of the object function along the PI-line, the backprojection image $g_\pi(x'_\pi, \lambda_1, \lambda_2)$ on the PI-line segment is determined by $$g_\pi(x'_\pi, \lambda_1, \lambda_2) = \int_{\lambda_1}^{\lambda_2} \frac{d\lambda}{|\vec{r} - \vec{r}_0(\lambda)|} \frac{d}{d\lambda} P(u, v, \lambda)\Big|_{\hat{\beta}}. \quad \text{(C-8)}$$

For given $(x'_\pi, \lambda_1, \lambda_2)$, $\vec{r}$ is determined by Eq. (C-6) and (u, v) are determined by $$u = \frac{S\vec{r}' \cdot \hat{e}_u(\lambda)}{R - \vec{r}' \cdot \hat{e}_w(\lambda)}, \text{ and } v = \frac{S\vec{r}' \cdot \hat{e}_v(\lambda)}{R - \vec{r}' \cdot \hat{e}_w(\lambda)}. \quad \text{(C-9)}$$

The BPF methodology may reconstruct the image on a PI-line segment by first backprojecting the data derivatives onto the PI-line segment e.g., the integration over $\lambda$ in Eq. (C-8)) and then performing a 1D filtering along the PI-line. (e.g., the integration over $x'_\pi$ in Eq. (C-7)).

For circular cone-beam CT, the physical source trajectory may be within a plane (e.g., the so-called mid-plane). Without loss of generality, the circular trajectory may be assumed to be within the plane at z=0 and thus may be expressed as:

$$\vec{r}_c(\lambda) = (R\cos\lambda, R\sin\lambda, 0)^T. \quad \text{(C-10)}$$

A PI-line intersecting two points on the trajectory may be defined meaningfully within the trajectory plane, e.g., the mid-plane. For an off-mid-plane (i.e., z≠0), however, no actual trajectory and, consequently, no actual PI-lines may exist. Therefore, the BPF methodology for helical cone-beam CT may not be applied directly to reconstructing images in off-mid-planes from circular cone-beam data.

Figure 54:
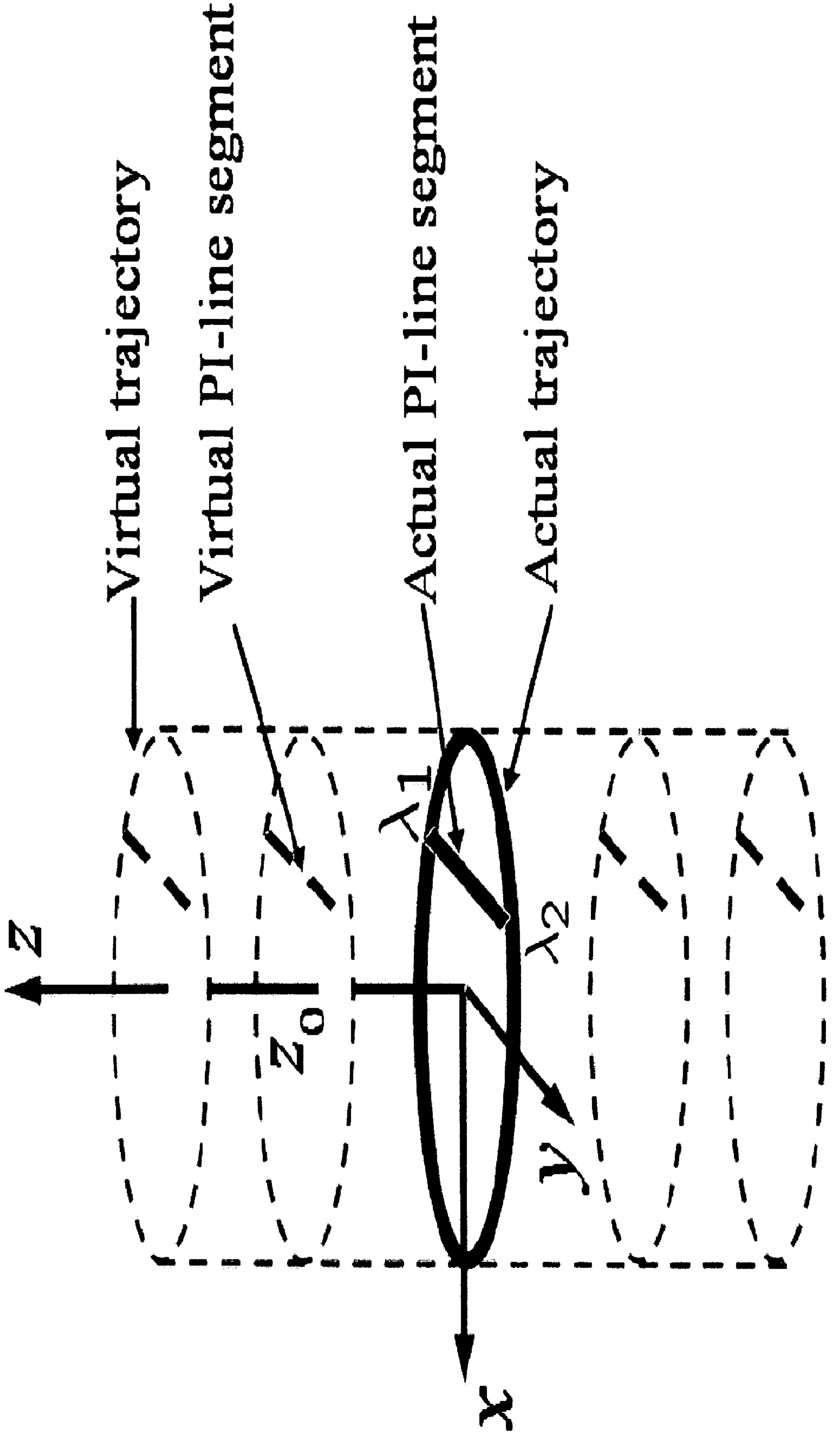
FIG. 54 is an illustration of the actual and virtual circular trajectories, and the actual and virtual PI-line segments.

In an attempt to derive an approximate BPF methodology for circular cone-beam CT, a virtual trajectory and virtual PI-line segments are disclosed. FIG. 54 is an illustration of the actual and virtual circular trajectories, and the actual and virtual PI-line segments. As illustrated in FIG. 54, a virtual circular trajectory within an off-mid-plane at z≠0 may use the z-axis as its central axis and may have a radius R identical to that of the actual circular trajectory in the plane at z=0. Thus, the collection of the actual and a stack of virtual circular trajectories within planes at different z may enclose a 3D cylindrical volume, which may be referred to as the virtual cylinder. A straight line segment connecting any two points on the actual circular trajectory at z=0 may be defined as an actual PI-line segment. Similarly, a straight line segment connecting any two points on a virtual circular trajectory at z≠0 may be defined as a virtual PI-line segment.

For a helical cone-beam scan, a point within the helix cylinder may be specified completely by three PI-line coordinates $(x_\pi, \lambda_1, \lambda_2)$ through Eq. (C-6), where $x_\pi$ indicates the location of the point on a PI-line segment specified by $(\lambda_1, \lambda_2)$. For the circular cone-beam scan, however, because the actual or virtual trajectory is within a plane, four PI-line parameters $(x_\pi, \lambda_1, \lambda_2, z_0)$ may be used to identify a point within the virtual cylinder. In addition to $x_\pi$, $\lambda_1$, and $\lambda_2$, the parameter $z_0$ may be used to indicate the plane that contains the actual or virtual trajectories. These PI-line coordinates are related to the fixed coordinates through:

$$\vec{r} = \vec{r}_{cl} + x_\pi \hat{e}_{\pi c}, \quad \text{(C-11)}$$

where $$\vec{r}_{cl} = \frac{\vec{r}_c(\lambda_2) + \vec{r}_c(\lambda_1)}{2} + z_0\hat{e}_v \quad \text{(C-12)}$$

$$\hat{e}_{\pi c} = \frac{\vec{r}_c(\lambda_2) - \vec{r}_c(\lambda_1)}{|\vec{r}_c(\lambda_2) - \vec{r}_c(\lambda_1)|}.$$

For simplicity of discussion below, an actual or a virtual PI-line segment is referred to below as a PI-line segment. Let $x_{\pi 1}$ and $x_{\pi 2}$ denote the two end points of a PI-line segment. Also, $x_{s1}$ and $x_{s2}$ are used to denote the two end points of the intersection of a PI-line segment % kith the support of the object function; and, this intersection is referred to as the support segment on the PI-line. Because the object function is enclosed completely within the virtual cylinder, we have $[x_{\pi 1}, x_{\pi 2}] \supset [x_{s1}, x_{s2}]$.

Below is a modified BPF methodology for circular cone-beam CT to reconstruct exact images on actual PI-line segments and approximate images on virtual PI-line segments. Let $f_{\pi c}(x_\pi, \lambda_1, \lambda_2, z_0)$ denote the image on a virtual PI-line segment when $z_0 \neq 0$ or the image on an actual PI-line segment when $z_0=0$. This modified BPF methodology for circular cone-beam CT may be expressed as:

$$f_{\pi c}(x_\pi, \lambda_1, \lambda_2, z_0) = \frac{1}{2\pi^2}\frac{1}{\sqrt{(x_B - x_\pi)(x_\pi - x_A)}} + \left[\int_{x_A}^{x_B} \frac{dx'_\pi}{x_\pi - x'_\pi} \sqrt{(x_B - x'_\pi)(x'_\pi - x_A)} \times g_{\pi c}(x'_\pi, \lambda_1, \lambda_2, z_0) + 2\pi P_{c0}\right], \quad \text{(C-13)}$$

where $x_A$ and $x_B$ are any points satisfying $[x_{\pi 1}, x_{\pi 2}] \supset [x_A, x_B] \supseteq [x_{s1}, x_{s2}]$, the integral is to be considered as a Cauchy principal value, the backprojection image on the PI-line segment may be expressed as:

$$g_{\pi c}(x'_\pi, \lambda_1, \lambda_2, z_0) = \int_{\lambda_1}^{\lambda_2} \frac{d\lambda}{|\vec{r}' - \vec{r}_0(\lambda)|} \frac{d}{d\lambda} P(u, v, \lambda)\bigg|_{\hat{\beta}}, \quad \text{(C-14)}$$

and the constant term $P_{c0}$ indicates the line integral of the object function along the PI-line. Note that $P_{c0}$ cannot be obtained from the data function $P(u, v, \lambda)$ when the PI-line is in an off-mid-plane ($z \neq 0$). Therefore, the following is used:

$$P_{c0} = \frac{P(u_1, v_1, \lambda_1) + P(u_2, v_2, \lambda_2)}{2} \quad \text{(C-15)}$$

to approximate the line integral of the object function along the PI-line, where $P(u_1, v_1, \lambda_1)$ and $P(u_2, v_2, \lambda_2)$ indicate the cone-beam projection of the point $$\left(\frac{x_{\pi 1} + x_{\pi 2}}{2}, \lambda_1, \lambda_2, z_0\right),$$

e.g., the central point on the PI-line segment, from view angle $\lambda_1$ and $\lambda_2$, respectively. In Eqs. (C-13) and (C-14) above, for a given $(x'_\pi, \lambda_1, \lambda_2, z_0)$, $\vec{r}$ is obtained by using Eq. (C-11), whereas $(u, v)$ may be determined through:

$$u = \frac{S\vec{r}' \cdot \hat{e}_u(\lambda)}{R - \vec{r}' \cdot \hat{e}_w(\lambda)}, \text{ and } v = \frac{Sz_0}{R - \vec{r}' \cdot \hat{e}_w(\lambda)}. \quad \text{(C-16)}$$

Comparison of Eqs. (C-7) and (C-13) indicates that the BPF methodology for circular cone-beam CT and helical cone-beam CT are formally identical. However, the constant terms and backprojection images in the two methodologies may be different.

Furthermore, the backprojection image in Eq. (C-14) may be re-expressed as:

$$g_{\pi c}(x'_\pi, \lambda_1, \lambda_2, z_0) = \int_{\lambda_1}^{\lambda_2} d\lambda \frac{S^2}{[R - \vec{r}' \cdot \hat{e}_w(\lambda)]^2} \times \frac{\partial}{\partial u}\left[\frac{R}{A} P(u, v, \lambda)\right] + \frac{P(u, v, \lambda)}{|\vec{r}' - \vec{r}_c(\lambda)|}\bigg|_{\lambda_1}^{\lambda_2}, \quad \text{(C-17)}$$

where $$A = \sqrt{u^2 + v^2 + S^2}. \quad \text{(C-18)}$$

In practical situations, the discrete samples on the detector are generally denser than those over a scanning trajectory. Therefore, Eq. (C-17) generally yields numerically a more accurate backprojection image than does Eq. (C-14).

Figure 55:
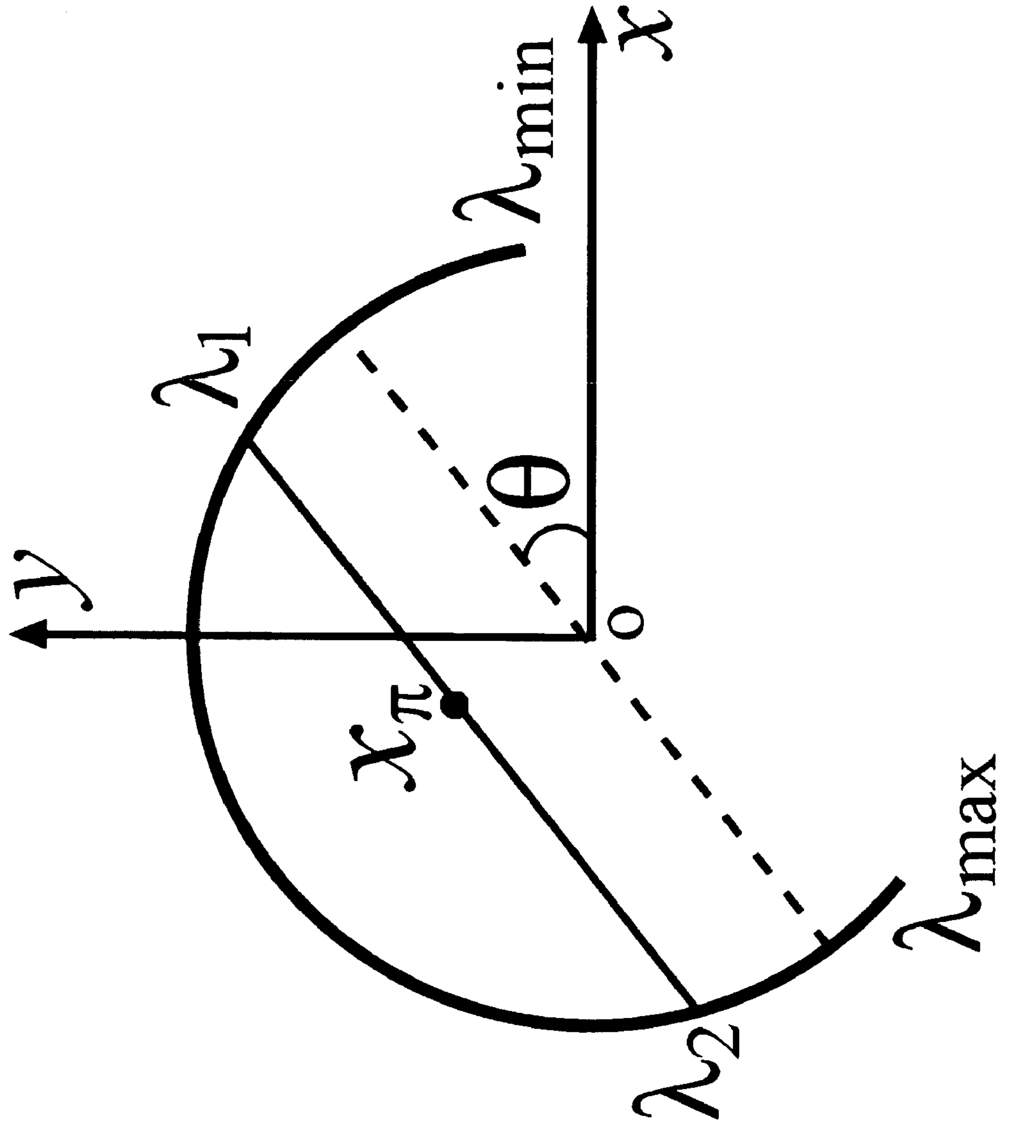
FIG. 55, illustrates the data acquired over the angular ranges $[\lambda_{min}, \lambda_1)$ and $(\lambda_2, \lambda_{max}]$ may constitute redundant information for image reconstruction on an actual PI-line segment specified by $\lambda_1$ and $\lambda_2$ in the mid-plane.
Figures 56A, 56B, 56C, 56D:
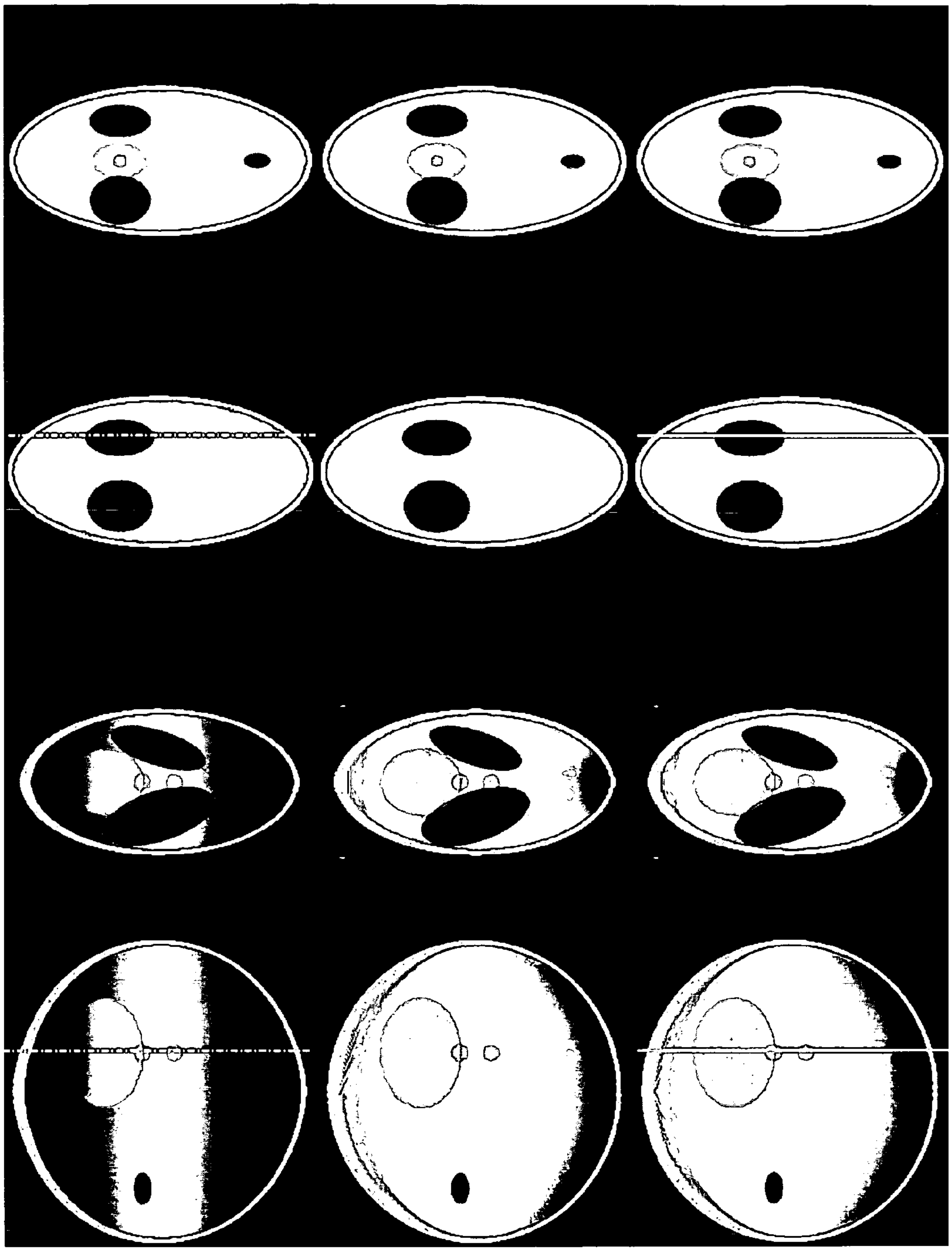
FIGS. 56*a-d* depict images within 2D slices in 3D images reconstructed by use of the FDK methodology (upper row), the BPF methodology in Eq. (C-17) (middle row), and the weighted BPF methodology in Eq. (C-19) (lower row), respectively, from non-truncated, noiseless cone-beam data generated with the Shepp-Logan phantom.

As described above, the BPF methodology reconstructs the image on a PI-line segment specified by $\lambda_1$ and $\lambda_2$ by use of data acquired over an angular range $[\lambda_1, \lambda_2]$. Let $[\lambda_{min}, \lambda_{max}]$ denote the total scanning angular range. Obviously, a PI-line segment that satisfies $[\lambda_1, \lambda_2] \subseteq [\lambda_{min}, \lambda_{max}]$ is reconstructible. Therefore, as shown in FIG. 55, data acquired over the angular ranges $[\lambda_{min}, \lambda_1)$ and $(\lambda_2, \lambda_{max}]$ may constitute redundant information for image reconstruction on an actual PI-line segment specified by $\lambda_1$ and $\lambda_2$ in the mid-plane. On the other hand, for a virtual PI-line specified by $\lambda_1$ and $\lambda_2$ in the off-mid-plane, the angular ranges $[\lambda_{min}, \lambda_1)$ and $(\lambda_2, \lambda_{max}]$ on the corresponding virtual trajectory do not generally contain truly redundant data information because no rays in the cone beam are within that off-mid-plane. However, data in the angular ranges $[\lambda_{min}, \lambda_1)$ and $(\lambda_2, \lambda_{max}]$ on a virtual trajectory may be treated as approximate redundant information. Below is presented a weighted BPF methodology that exploits the truly redundant information for actual PI-line segments in the mid-plane and the approximate redundant information for virtual PI-line segments in the off-mid-planes.

Following the strategy for exploiting data redundancy in fan-beam CT, a weighted BPF methodology is derived for exploiting data redundancy in circular cone-beam CT, which has a form identical to that of Eq. (C-13) except that the backprojection image should be replaced by $$g^{(\omega)}_{\pi c}(x'_\pi, \lambda_1, \lambda_2, z_0) = \int_{\lambda_{min}}^{\lambda_{max}} d\lambda \frac{S^2}{([R - \vec{r}' \cdot \hat{e}_w(\lambda)])^2} \times \frac{\partial}{\partial u}\left[\frac{R}{A}\omega(u, \lambda)P(u, v, \lambda)\right] + \frac{\omega(u, \lambda)P(u, v, \lambda)}{|\vec{r}' - \vec{r}_c(\lambda)|}\bigg|_{\lambda_{min}}^{\lambda_{max}}, \quad \text{(C-19)}$$

where the weighting function $\omega(u, \lambda)$ satisfies $$\omega(u, \lambda) - \omega\left(-u, \lambda + \pi - 2\arctan\frac{u}{S}\right) = 1. \quad \text{(C-20)}$$

Data redundancy may also be used for other types of beams in addition to fan beams discussed herein. Inspection of Eq. (C-20) shows that $\omega(u, \lambda)$ may be discontinuous in u and $\lambda$ and thus may prevent an accurate and stable numerical implementation of Eq. (C-19). In an attempt to avoid such a discontinuity in numerical implementation, without loss of generality, one may assume that, as shown in FIG. 55, a PI-line segment has an angle $\theta$ relative to the x-axis and that $\omega(u, \lambda)=H_0(u, \lambda)\omega_0(u, \lambda)$, where $\omega_0(u, \lambda)$ is a function satisfying:

$$\omega_0(u, \lambda) + \omega_0\left(-u, \lambda + \pi - 2\arctan\frac{u}{S}\right) = 1, \quad \text{(C-21)}$$

and function $H_0(u, \lambda)$ is given by $$H_0(u, \lambda) = \begin{Bmatrix} 1\lambda - \arctan\frac{u}{S}\big) \in (\theta, \theta+\pi) \\ -1\left(\lambda - \arctan\frac{u}{S}\right) \notin (\theta, \theta+\pi) \end{Bmatrix} \quad \text{(C-22)}$$

One can readily demonstrate that $\omega_0(u, \lambda)H_0(u, \lambda)$ satisfies Eq. (C-20). Below is shown that the weighted backprojection image in Eq. (C-19) may be rewritten as $$g_{\pi c}^{(\omega)}(x'_\pi, \lambda_1, \lambda_2, z_0) = \int_{\lambda_{min}}^{\lambda_{max}} d\lambda \frac{S^2}{\left[R - \vec{r}' \cdot \hat{e}_w(\lambda)\right]^2} H_0(u, \lambda) \times \frac{\partial}{\partial u}\left[\frac{R}{A}\omega_0(u, \lambda)P(u, v, \lambda)\right] + \frac{H_0(u, \lambda)\omega_0(u, \lambda)P(u, v, \lambda)}{|\vec{r}' - \vec{r}_c(\lambda)|}\Bigg|_{\lambda_{min}}^{\lambda_{max}} + \frac{2\omega_0(u, \lambda)P(u, v, \lambda)}{|\vec{r}' - \vec{r}_c(\lambda)|}\Bigg|_{\lambda_1}^{\lambda_2}. \quad \text{(C-23)}$$

It can be seen in Eq. (C-23) that, as long as $\omega_0(u, \lambda)$ is smooth, it is possible to compute accurately the derivative in the first term in Eq. (C-23). The result in Eq. (C-23) includes two boundary terms determined by the actual scanning angular range specified by $\lambda_{min}$ and $\lambda_{max}$ and by the angular range determined by $\lambda_1$ and $\lambda_2$ of a PI-line segment. For a full scan $\lambda_{min}=0$, $\lambda_{max}=2\pi$, the first boundary term vanishes, and only the second boundary term may remain. A smooth weighting function $\omega_0(u, \lambda)$ may be readily constructed in the case of a full-scan, a short-scan, or any scan with an angular range between a short-scan and a full-scan. However, when the scanning angular range is less than a short-scan, the construction of a smooth weighting function is not apparent.

A unique property of the proposed BPF methodologies is that they may, from circular cone-beam data containing transverse truncations, reconstruct ROI images with an accuracy comparable to that obtained from non-truncated circular cone-beam data.

For a PI-line segment specified by $\lambda_1$ and $\lambda_2$, as shown in Eq. (C-13), one needs knowledge of the backprojection only in $[x_A, x_B]$ for exact image reconstruction. Such knowledge may be obtained from data on the cone-beam projections of $[x_A, x_B]$ for $\lambda\in[\lambda_1, \lambda_2]$ (see Eq. (C-17)) or for $\lambda\in[\lambda_{min}, \lambda_{max}]$ (see Eq. (C-23)). Because $[x_{s1}, x_{s2}]\subseteq[x_A, x_B]$, one in effect may need data only on the cone-beam projections of the support segment. Therefore, as long as the support segment may be illuminated fully at $\lambda\in[\lambda_1, \lambda_2]$ or at $\lambda\in[\lambda_{min}, \lambda_{max}]$, sufficient data may be collected for computation of the backprojection image, even if the illumination at these views may not completely cover the entire object function (e.g., the projections are truncated). Therefore, an image on the PI-line segment free of data-truncation artifacts may be reconstructed.

A set of PI-line segments that completely fill in an ROI is considered. Without loss of generality, one assumes that the maximum angular range required by these PI-line segments is $[\lambda_{min}, \lambda_{max}]$. If the support segments on these PI-line segments may be fully illuminated for $\lambda\in[\lambda_{min}, \lambda_{max}]$, based upon the observation above, even if the FOV of the illumination is smaller than the actual size of the entire object support, (e.g., the projections are truncated,) one can reconstruct images on these PI-line segments and consequently the image within the ROI that are free of the impact of data truncation.

The following are quantitative studies to highlight and evaluate the above discussed methodologies by using both computer-simulation data and real-experimental data.

In the computer-simulation studies, a circular cone-beam configuration is considered in which the trajectory has a radius of 290 mm and a source-detector distance of 450 mm. Other beams and other radii may be used. A modified, low-contrast 3D Shepp-Logan phantom is used, which has an ellipsoidal support with radii of 49 mm, 98 mm and 90 mm along x-, y- and z-axes, respectively. As compared to the standard 3D Shepp-Logan phantom, this phantom has a shorter support along the x-axis and a longer support along the y-axis for demonstrating the transverse truncation effect. The detector plane consists of 256×256 elements each of which has an area of 1.3×1.3 $mm^2$. Non-truncated circular cone-beam data is generated at 300 projection views uniformly distributed over $2\pi$ and the transversely truncated data were obtained by setting the values in 35 bins on each side of the detector panel to zero. Noisy data is also generated by adding Gaussian noise to the noiseless data. In an attempt to show the low-contrast structures, the standard deviation of the Gaussian noise was selected to be about 0.063% of the maximum value of noiseless data. The proposed BPF methodologies for circular cone-beam CT were applied to these full and truncated data to reconstruct full and ROI images. To further compare the BPF methodologies with the FDK methodology when there is no truncation, we generated another circular cone-beam dataset with a disk phantom. The radius of the circular trajectory is 576 mm. The cone-angle is 20 degree with an FOV size of 200 mm.

FIGS. 56A-D depict images within 2D slices in 3D images reconstructed by use of the FDK methodology (upper row), the BPF methodology in Eq. (C-17) (middle row), and the weighted BPF methodology in Eq. (C-19) (lower row), respectively, from non-truncated, noiseless cone-beam data generated with the Shepp-Logan phantom. The images from the weighted BPF methodology were obtained using the complete $2\pi$ range of data with a weight of $$\frac{1}{2}.$$

Figure 57B:
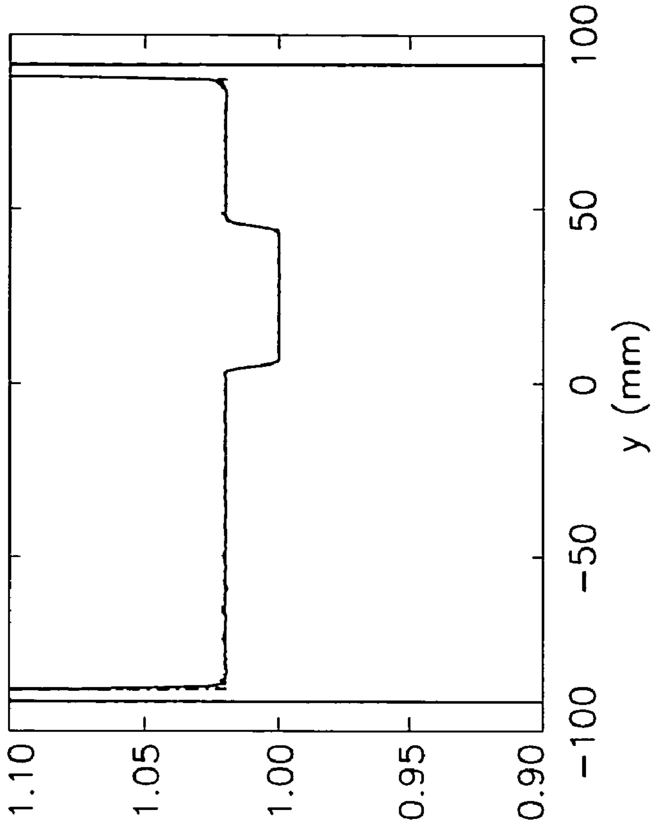
FIGS. 57*a-b* show image profiles obtained by use of the weighted BPF methodology in Eq. (C-19) (solid curve) and the FDK methodology (dashed-doted curve) on lines specified by x=0, y=25 mm (FIG. 57*a*); and x=17 mm, z=0 (FIG. 57*b*). For a comparison, the true profiles (dotted curves) are also plotted in FIGS. 57*a-b*.
Figure 57A:
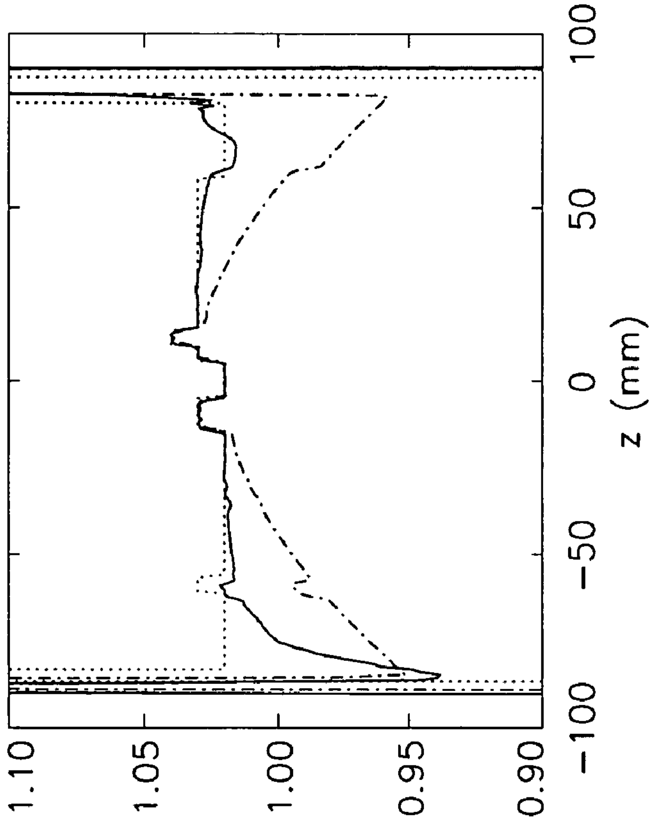

No smooth window was applied in all the reconstruction. FIGS. 56A-D represent images within planes at x=0 (FIG. 56A), y=25 mm (FIG. 56B), z=0 (FIG. 56C), and z=6.4 mm (FIG. 56D), respectively. The display window is [1.0, 1.04]. FIGS. 57A-B also show image profiles obtained by use of the weighted BPF methodology in Eq. (C-19) (solid curve) and the FDK methodology (dashed-dotted curve) on lines specified by x=0, y=25 mm (FIG. 57A); and x=17 mm, z=0 (FIG. 57B). For a comparison, the true profiles (dotted curves) are also plotted in FIGS. 57A-B.

Figures 58A, 58B, 58C, 58D:
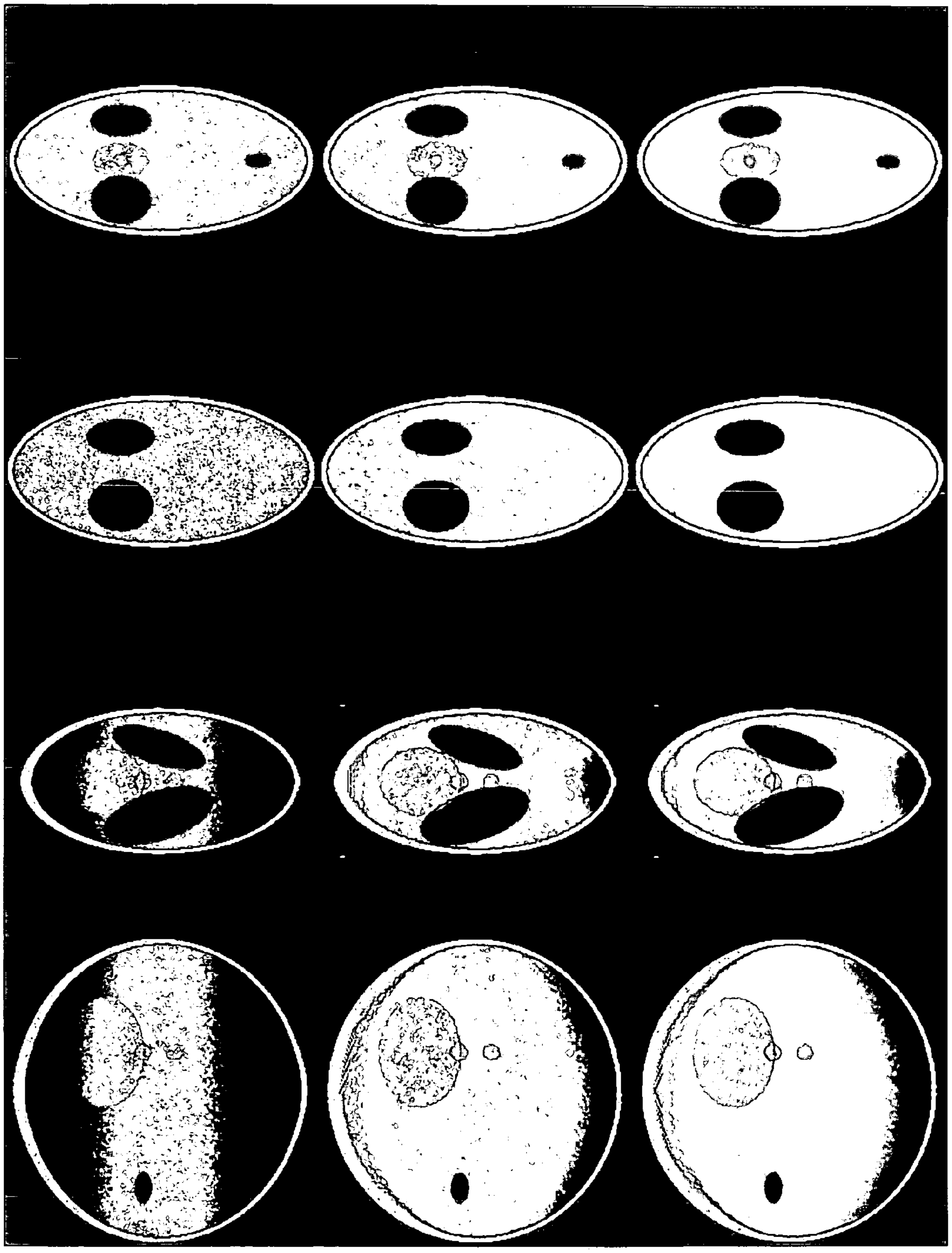
FIGS. 58*a-d* show images within 2D slices in 3D images reconstructed by use of the FDK methodology (upper row), the BPF methodology in Eq. (C-17) (middle row), and the weighted BPF methodology in Eq. (C-19) (lower row), respectively, from non-truncated, noisy cone-beam data generated with the Shepp-Logan phantom.

FIGS. 58A-D also show images within 2D slices in 3D images reconstructed by use of the FDK methodology (upper row), the BPF methodology in Eq. (C-17) (middle row), and the weighted BPF methodology in Eq. (C-19) (lower row), respectively, from non-truncated, noisy cone-beam data generated with the Shepp-Logan phantom. FIGS. 58A-D represent images within planes at x=0 (FIG. 58A), y=25 mm (FIG. 58B), z=0 (FIG. 58C), z=6.4 mm (FIG. 58D). The display window is [1.0, 1.04]. These results suggest that the weighted BPF methodology may exploit redundant information within data for suppression of image noise.

Figure 59:
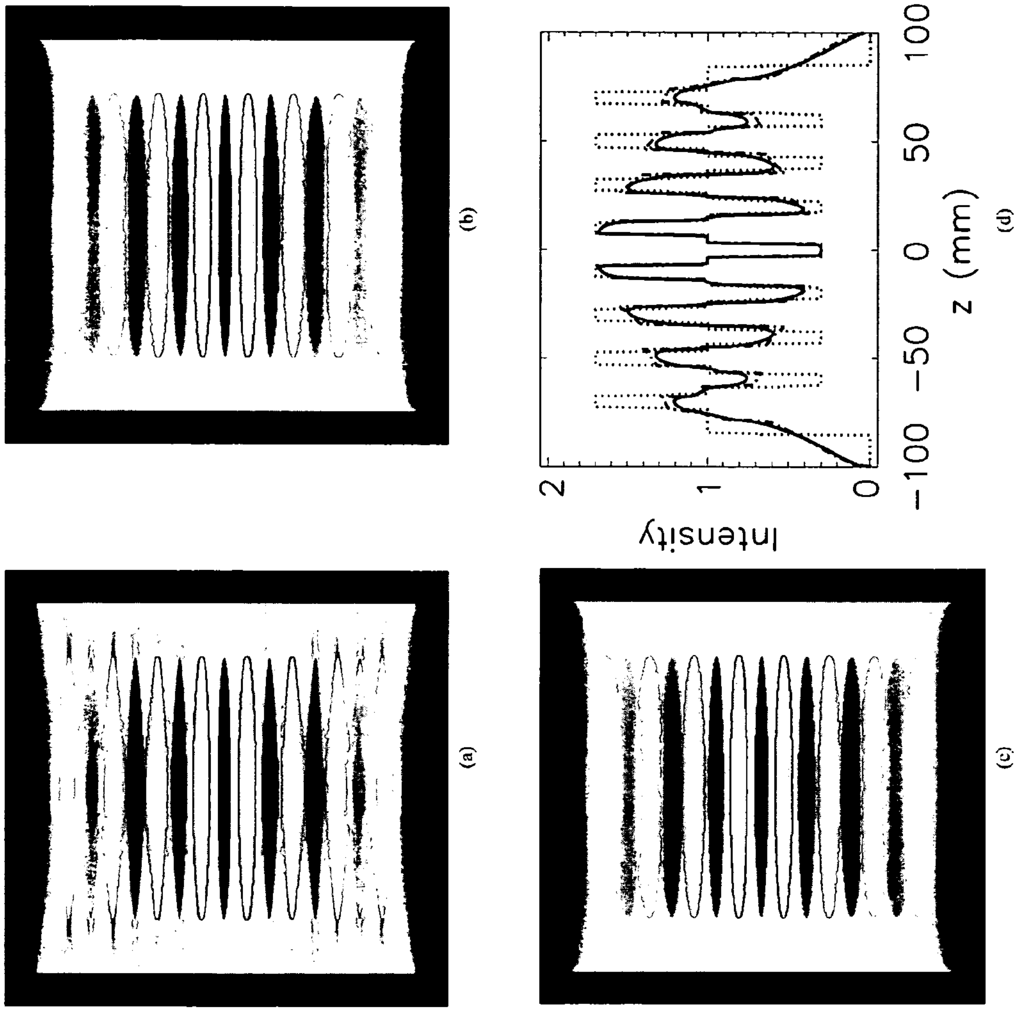
FIGS. 59*a-d* compare the reconstruction results from non-truncated data generated with the disk phantom. Sagittal slices (x=0) in the 3D images reconstructed by use of the FDK methodology (FIG. 59*a*), the BPF methodology in Eq. (C-17) (FIG. 59*b*), and the weighted BPF methodology in Eq. (C-19) (FIG. 59*c*) from noiseless data containing no truncation generated with a disk phantom.

FIGS. 59A-D compare the reconstruction results from non-truncated data generated with the disk phantom. Sagittal slices (x=0) in the 3D images reconstructed by use of the FDK methodology (FIG. 59A), the BPF methodology in Eq. (C-17) (FIG. 59B), and the weighted BPF methodology in Eq. (C-19) (FIG. 59C) from noiseless data containing no truncation generated with a disk phantom. The display window is [0, 2]. The profiles along central columns in FIG. 59A and FIG. 59C are plotted in FIG. 59D with dashed-dotted and solid curves, respectively. The corresponding true profile in the original disk phantom is also plotted with a dotted curve. It can be observed that the BPF methodologies perform differently from the FDK methodology in terms of shape distortion and intensity drop in the off-mid-plane.

Figures 60A, 60B, 60C, 60D:
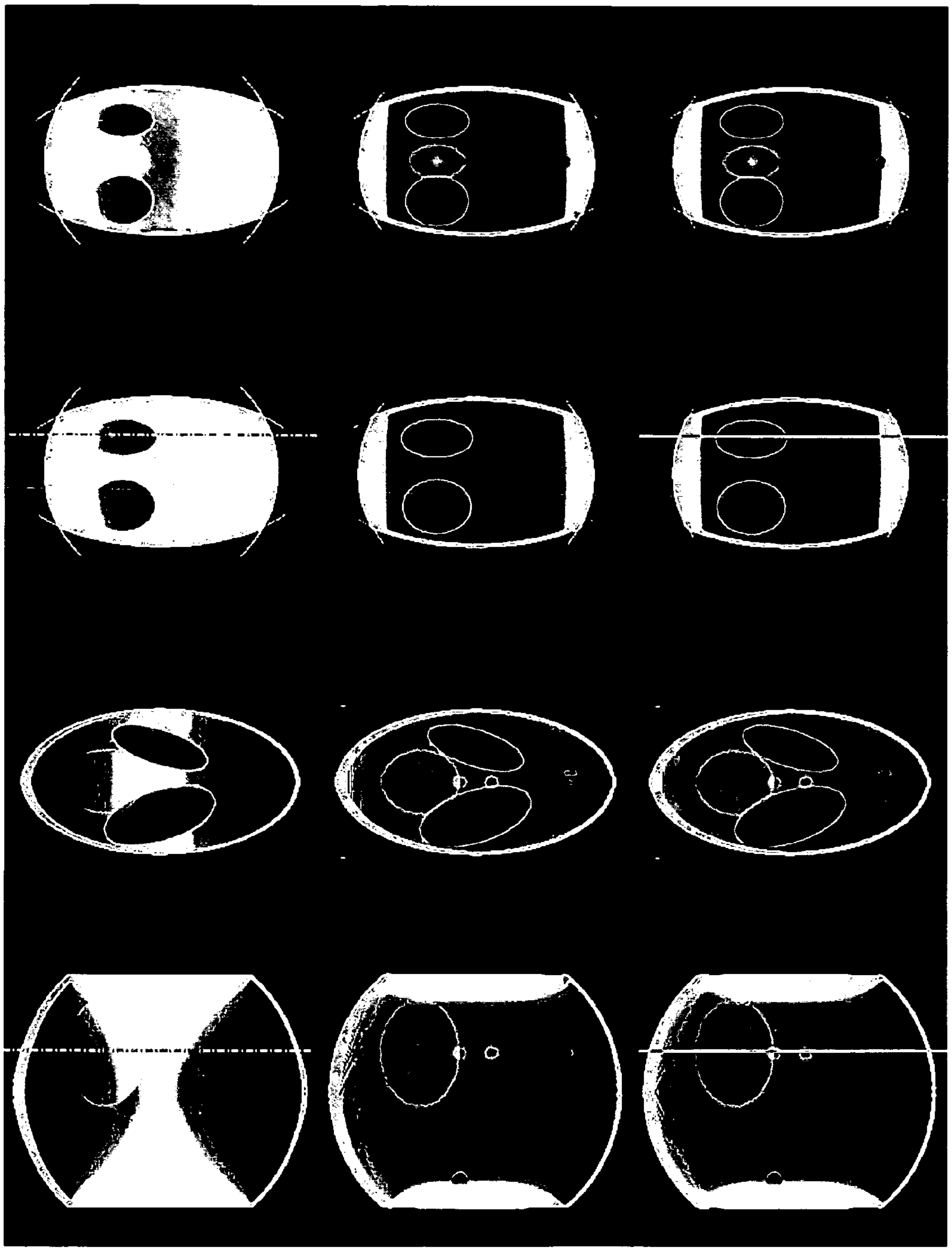
FIGS. 60*a-d* display ROI images reconstructed by using the FDK methodology (upper row), the BPF methodology in Eq. (C-17) (middle row), and the weighted BPF methodology in Eq. (C-19) (lower row), respectively, from truncated, noiseless cone-beam data.
Figure 61A:
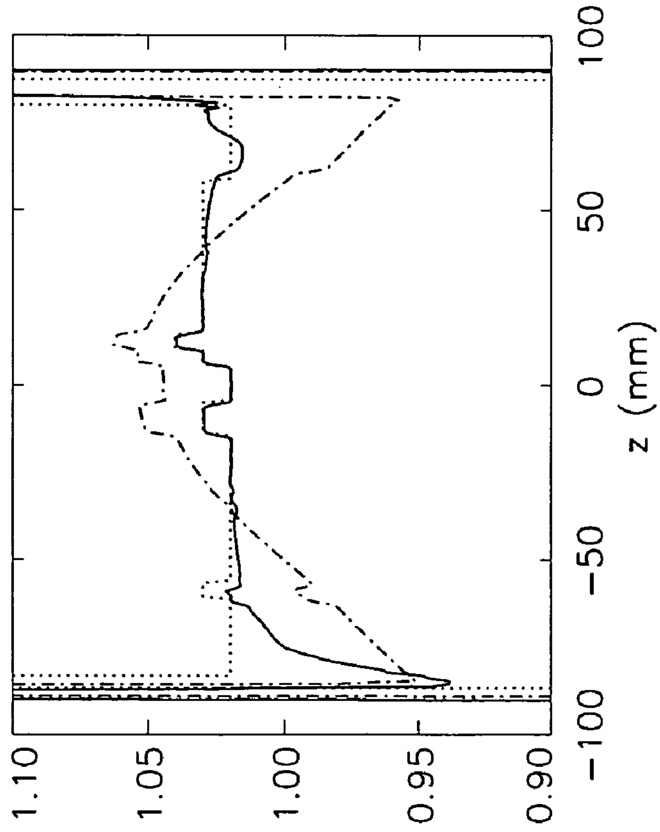
FIGS. 61*a-b* also show profiles in images displayed in FIGS. 60*a-c* along x=0, y=25 mm (FIG. 61*a*); and x=17 mm, z=0 (FIG. 61*b*).
Figure 61B:
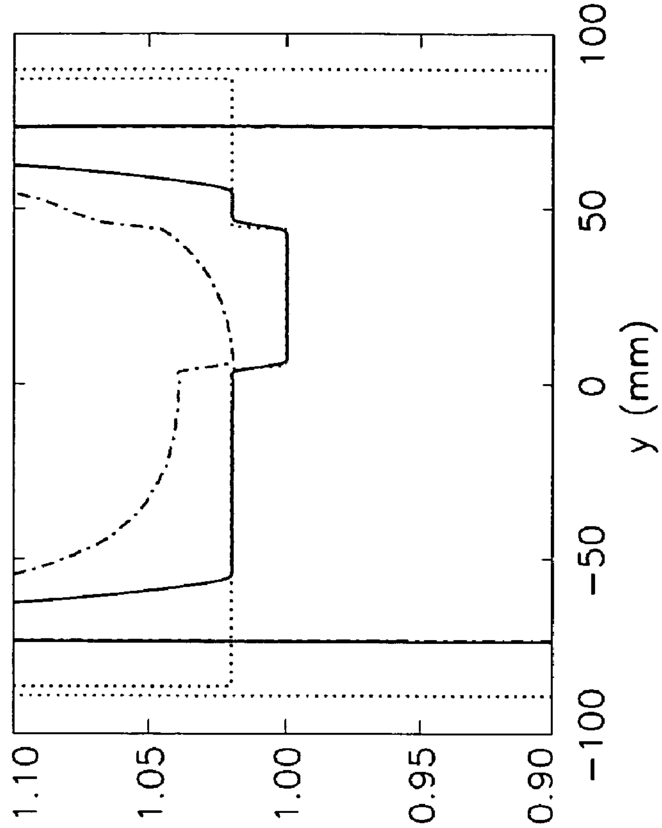

The described BPF methodologies may be applied to reconstructing ROI images from the computer simulated data containing truncations. FIGS. 60A-C display ROI images reconstructed by using the FDK methodology (upper row), the BPF methodology in Eq. (C-17) (middle row), and the weighted BPF methodology in Eq. (C-19) (lower row), respectively, from truncated, noiseless cone-beam data. FIGS. 60A-C represent images within planes at x=0 (FIG. 60A), y=25 mm (FIG. 60B), z=0 (FIG. 60C), z=6.4 mm (FIG. 60D). The display window is [1.0, 1.04]. FIGS. 61A-B also show profiles in images displayed in FIGS. 60A-C along x=0 y=25 mm (FIG. 61A); and x=17 mm, z=0 (FIG. 61B). The solid represents the results obtained by use of the weighted BPF methodology in Eq. (C-19) (solid curve) and the dashed-dotted curves represent the results obtained by the FDK methodology. For a comparison, the true profiles (dotted curve) are also plotted in FIGS. 61A-B. From these results, one can observe that data truncation may result in severe artifacts in images obtained with the FDK methodology. However, ROI images reconstructed by use of the proposed BPF methodologies may be free of truncation artifacts and may in fact be identical to the images within the same ROIs reconstructed by use of non-truncated data.

Figures 62A, 62B, 62C, 62D:
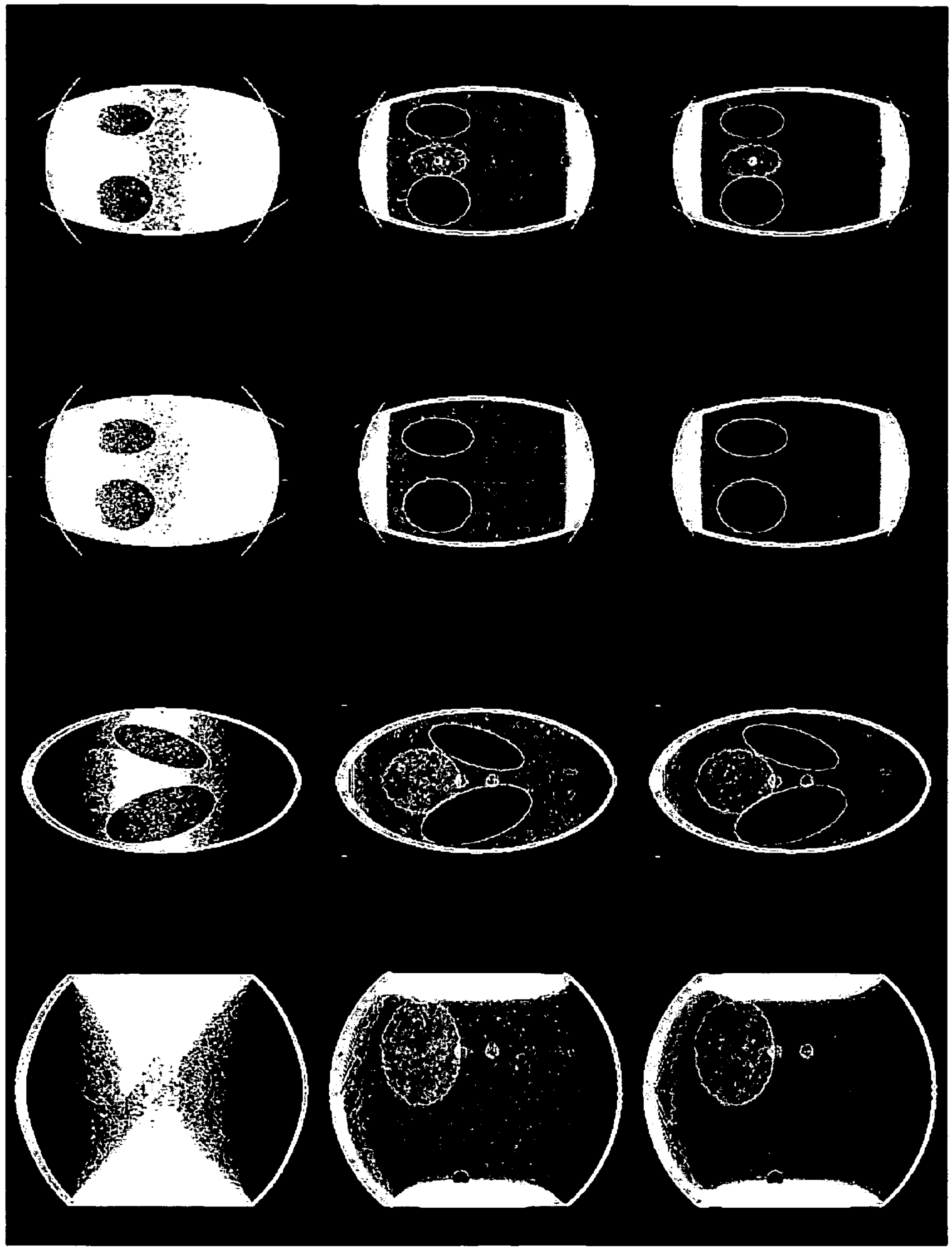
FIGS. 62*a-d* show ROI images reconstructed by using the FDK methodology (upper row), the BPF methodology in Eq. (C-17) (middle row), and the weighted BPF methodology in Eq. (C-19) (lower row), respectively, from truncated, noisy cone-beam data. Again.

FIGS. 62A-D show ROI images reconstructed by using the FDK methodology (upper row), the BPF methodology in Eq. (C-17) (middle row), and the weighted BPF methodology in Eq. (C-19) (lower row), respectively, from truncated, noisy cone-beam data. Again, FIGS. 62A-D represent images within planes at x=0 (FIG. 62A), y=25 mm (FIG. 62B), z=0 (FIG. 62C), z=6.4 mm (FIG. 62D). The display window is [1.0, 1.04]. It may be observed that data truncation may result in severe artifacts in images obtained with the FDK methodology. However, ROI images reconstructed by use of the proposed BPF methodologies may be free of truncation artifacts. The results also suggest that the weighted BPF methodology may exploit redundant information within data for suppression of image noise.

Analysis of the methodologies has been performed by using real data acquired with a simulator CT (Acuity, Varian Medical Systems) from a head phantom. The simulator cone-beam CT system for radiation therapy comprises a kV x-ray source, a patient couch, and an amorphous silicon flat-panel detector (Varian PaxScan 4030CB). It was operated for measurements at a source to isocenter distance of 996.3 mm and a source to detector distance of 1490.8 mm. The gantry may rotate in an angular range of ±185° and with isocenter accuracy less than 1 mm diameter when there is no accessory load. The rotation speed is up to 360° per minute. The detector has 2048×1536 pixels, each with a size of 0.194×0.194 $mm^2$. In our measurement, the detector was operated in a 2×2 rebinned mode and the data were stored as 16-bit values. The fan- and cone-angle are 15.2° and 11.4°, respectively, where the fan-angle is the angle in the mid-plane and cone-angle is the angle in the plane vertical to the mid-plane. Circular cone-beam data were collected from the head phantom at 683 projection views distributed over $2\pi$. In the original dataset, the head phantom was almost covered by the total FOV and truncated only in a very small peripheral region. In an effort to simulate a situation of data truncation, 227 columns of pixels in each side of the detector were manually set to zero. The numbers and equipment in this analysis are merely for illustrative purposes.

Figures 63A, 63B, 63C, 63D:
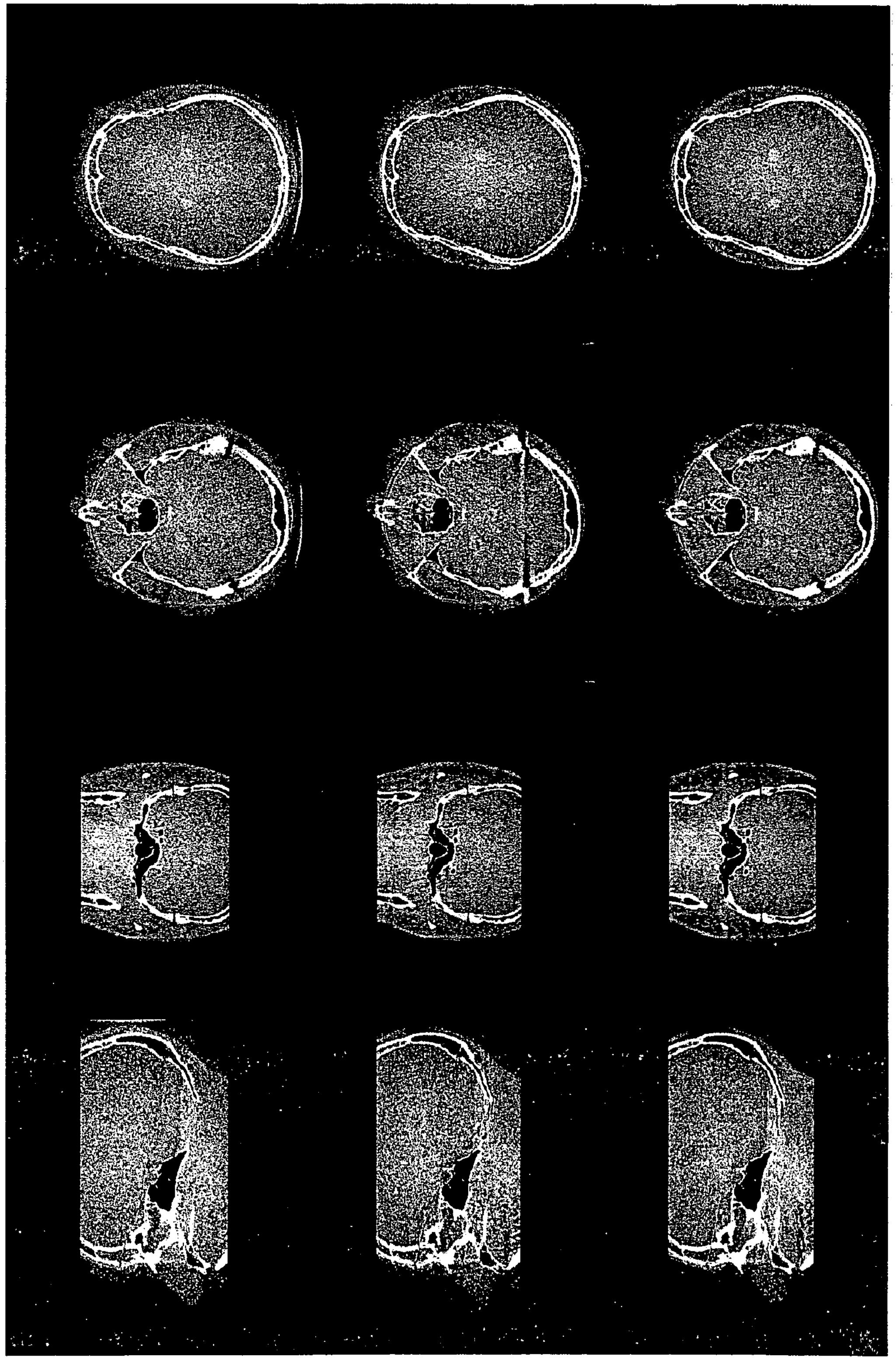
FIGS. 63*a-d* show images reconstructed from the original data by use of the FDK methodology (upper row), the BPF methodology in Eq. (C-17) (middle row), and the weighted BPF methodology in Eq. (C-19) (lower row), respectively.
Figure 64B:
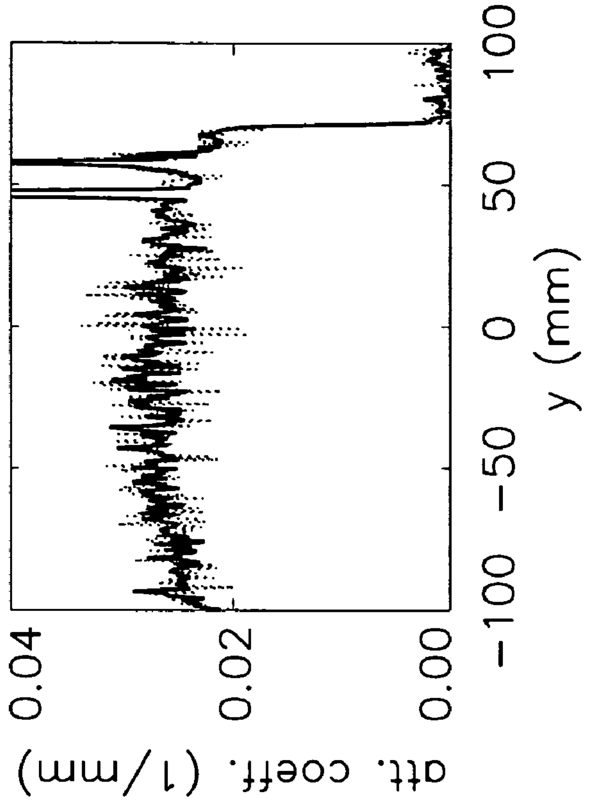
FIGS. 64*a-b* show profiles on lines specified (*a*) z=0, x=0 (FIG. 64*a*); and z=−33.8 mm, x=0 (FIG. 64*b*) in images displayed in FIG. 63 obtained by using the FDK methodology (dotted curve) and the weighted BPF methodology (solid curve).
Figure 64A:
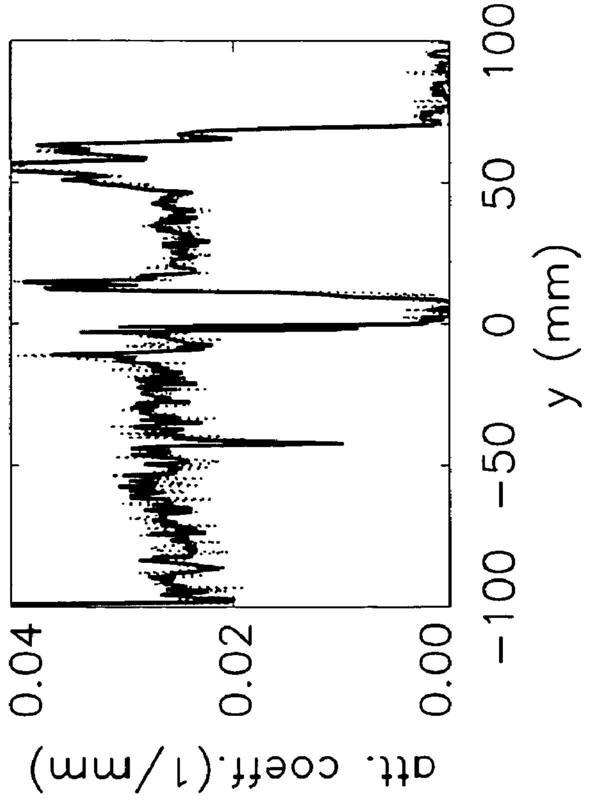

Both the original experimental data and the manually generated truncated data were used to reconstruct images. FIGS. 63A-D show images reconstructed from the original data by use of the FDK methodology (upper row), the BPF methodology in Eq. (C-17) (middle row), and the weighted BPF methodology in Eq. (C-19) (lower row), respectively. FIGS. 63A-D show the images within planes specified by x=0 (FIG. 63A), y=0 (FIG. 63B), z=0 (FIG. 63C), and z=−33.8 mm (FIG. 63D). The display window is [0.017, 0.030] $mm^{-1}$. The displayed FOV size is 251.0×251.0×125.5 $mm^3$. FIGS. 64A-B show profiles on lines specified (a) z=0, x=0 (FIG. 64A); and z=−33.8 mm, x=0 (FIG. 64B) in images displayed in FIG. 63 obtained by using the FDK methodology (dotted curve) and the weighted BPF methodology (solid curve). As can be seen from these results, in the situation of no truncation (almost), the three methodologies generate similar images except that their noise properties are different. The images obtained with the FDK methodology appear noisier than those obtained with our proposed two methodologies, but the resolution was not exactly matched either. Furthermore, the weighted BPF methodology generates images with lower noise level and less artifacts than does the BPF methodology because of the exploitation of the redundant information.

Figures 65A, 65B, 65C, 65D:
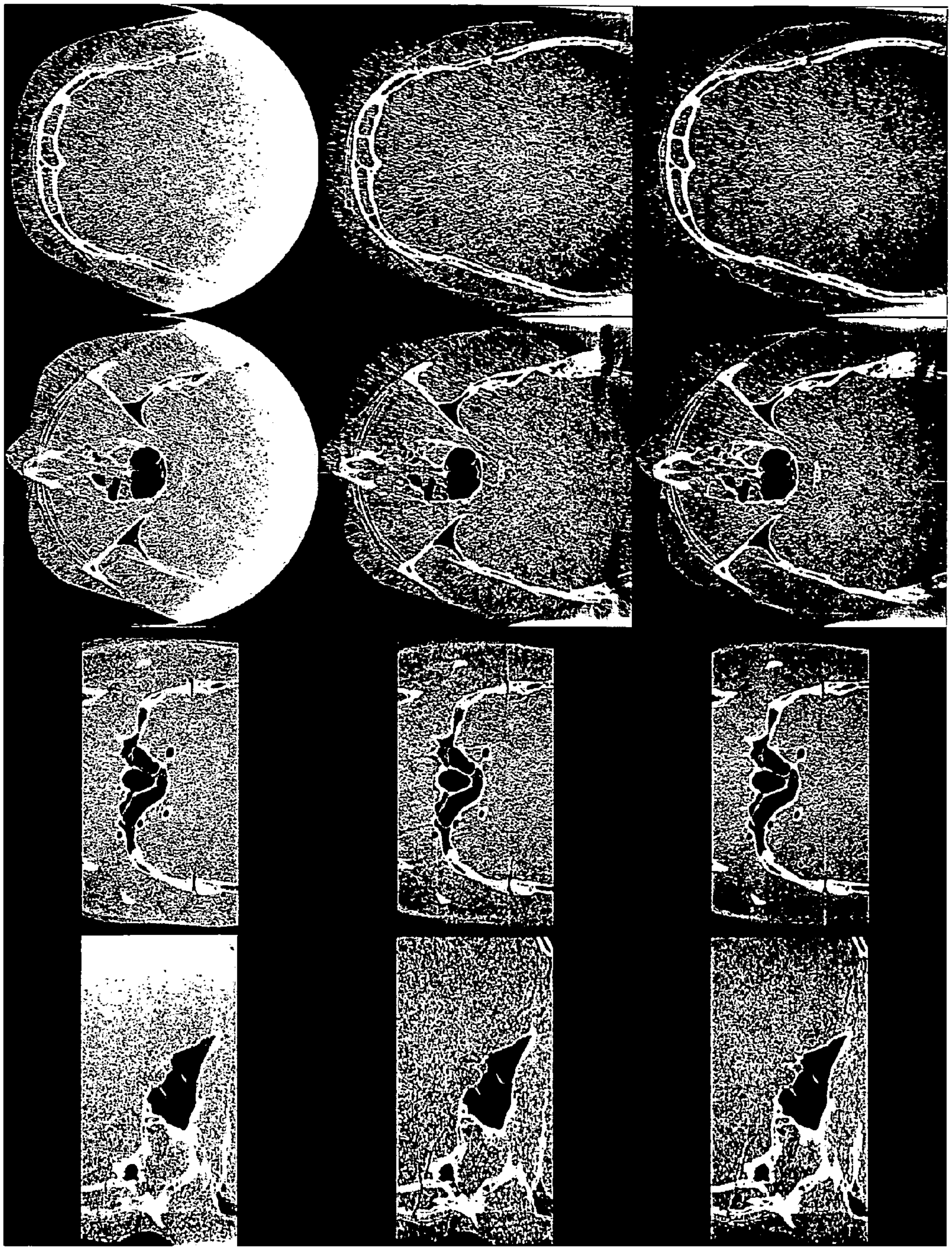
FIGS. 65*a-d* show images reconstructed from the generated truncated data by use of the FDK methodology (upper row), the BPF methodology in Eq. (C-17) (middle row), and the weighted BPF methodology in Eq. (C-19) (lower row).
Figure 66B:
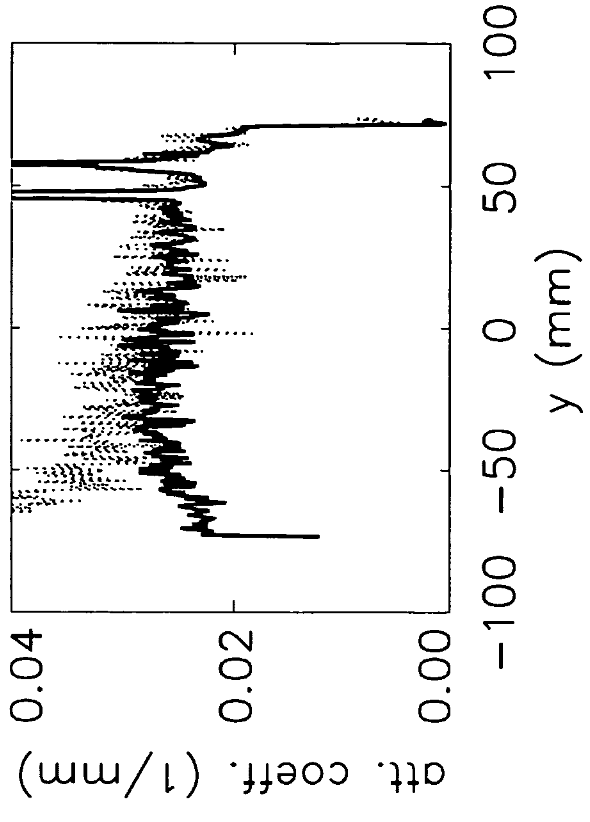
FIGS. 66*a-b* show profiles on lines specified by z=0, x=0 (FIG. 66A); and z=−33.8 mm, x=0 (FIG. 66*b*) in images displayed in FIG. 63 obtained by using the FDK methodology (dotted curve) and the weighted BPF methodology (solid curve).
Figure 66A:
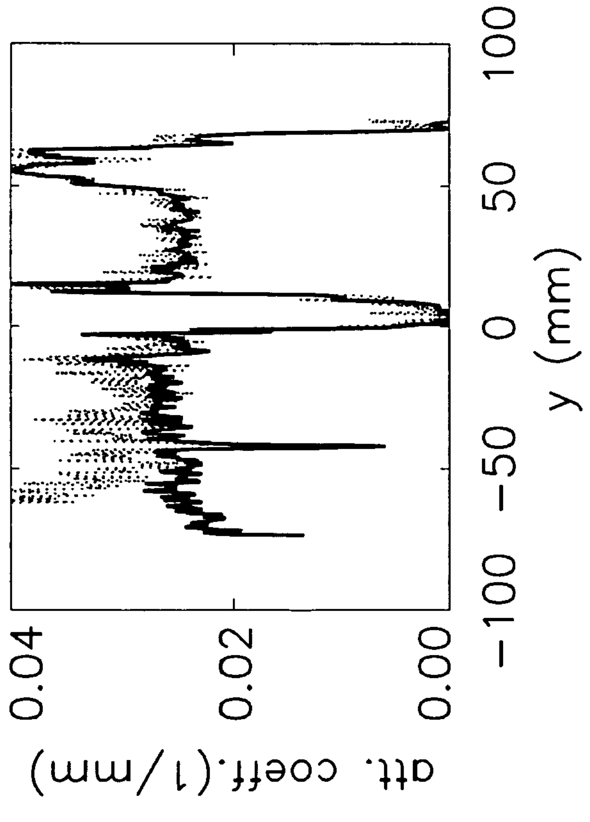

FIGS. 65A-D show images reconstructed from the generated truncated data by use of the FDK methodology (upper row), the BPF methodology in Eq. (C-17) (middle row), and the weighted BPF methodology in Eq. (C-19) (lower row). FIGS. 65A-D show the images within planes specified by x=0 (FIG. 65A), y=0 (FIG. 65B), z=0 (FIG. 65C), and z=−33.8 mm (FIG. 65D). The display window is [0.017, 0.030] $mm^{-1}$. The displayed FOV size is 147.4×147.4×73.7 $mm^3$. FIGS. 66A-B show profiles on lines specified by z=0, x=0 (FIG. 66A); and z=−33.8 mm, x=0 (FIG. 66B) in images displayed in FIG. 63 obtained by using the FDK methodology (dotted curve) and the weighted BPF methodology (solid curve).

Images displayed in FIG. 63 were obtained from data with almost no truncation; they may thus be considered as true images. Comparing results in FIGS. 65A-D and 66A-B with those in FIGS. 63A-D and 64A-B, one can observe that data truncation results in severe artifacts in images obtained with the FDK methodology. In contrast, ROI images reconstructed by use of the proposed BPF methodologies may be free of truncation artifacts.

In this present analysis, methodologies have been presented for image reconstruction from projection data acquired in circular cone-beam CT. These methodologies make use of the PI-line concept developed for exact image reconstruction in helical cone-beam CT. Image reconstruction on PI-lines allows for exact ROI image reconstruction from truncated data in the setting of a helical scan, Other beams may be used for exact ROI image reconstruction. The virtual PI-line concept allows for approximate image reconstruction for the imaging volume away from the mid-plane of the circular-scan orbit. The methodologies allow for ROI reconstruction from truncated data free (or substantially free) of the artifacts due to this truncation in the projection data.

Both the FDK and BPF methodologies may approximately reconstruct images from circular cone-beam data. The approximations invoked in the two methodologies are different, yielding different images within off-mid-planes. In the absence of data truncation, the differences between images obtained with the two methodologies appear to be dependent on several factors, such as cone angle, trajectory radius, and object structures. Approximations made in the FDK and BPF methodologies may differ from each other.

The virtual circular trajectories within planes parallel to the mid-plane were used to construct the virtual PI-lines. One may choose other types of virtual trajectories and the corresponding virtual chords. Because the BPF methodology for reconstructing chords of a general trajectory has been developed, one may readily apply it to reconstruct images on virtual chords. Specifically, image reconstruction may be performed for different types of virtual trajectories and virtual chords. In particular, one may identify the virtual trajectory and the conditions under which the identified trajectory performs more optimally than other possible virtual trajectories.

Further, there are significant practical benefits for the proposed BPF-based ROI-reconstruction methodologies for circular cone-beam CT. The methodologies may aid in scans where, due to detector size constraints, some views are truncated. For example, this may occur in chest scanning where the shoulders might be truncated for some views. Another apparent advantage of the proposed methodologies is the potential application to dose reduction. Oftentimes, clinicians may only be interested in viewing a small sub-volume of the patient. The methodologies presented here may allow the x-ray beam to be confined to exposing a smaller region of the body that includes the ROI. The reduced scanning angle of the ROI reconstruction methodologies for circular cone-beam CT can also reduce the required scanning time and radiation dose.

The following details the mathematics for the discontinuity in the weighted BPF methodology. Substitution of $\omega(u,\lambda)H_0(u,\lambda)\omega_0(u,\lambda)$ into Eq. (C-19) yields $$g_{\pi c}^{(\omega)}(x'_\pi,\lambda_1,\lambda_2,z_0) = \int_{\lambda_{min}}^{\lambda_{max}} d\lambda \frac{S^2}{\left[R-\vec{r}'\cdot\hat{e}_w(\lambda)\right]^2} H_0(u,\lambda)\times\frac{\partial}{\partial u}\left[\frac{R}{A}\omega_0(u,\lambda)P(u,v,\lambda)\right] + \int_{\lambda_{min}}^{\lambda_{max}} d\lambda \frac{S^2}{\left[R-\vec{r}\cdot\hat{e}_w(\lambda)\right]^2}\times\frac{R}{A}\omega_0(u,\lambda)P(u,v,\lambda) \tag{C-24}$$

-continued $$\frac{\partial}{\partial u}H_0(u,\lambda) + \left.\frac{\omega(u,\lambda)P(u,v,\lambda)}{\left|\vec{r}'-\vec{r}_c(\lambda)\right|}\right|_{\lambda_{min}}^{\lambda_{max}}$$

Eq. (C-23) may be written as:

$$H_0(u,\lambda) = \mathrm{sgn}\left(\sin\left(\lambda-\arctan\frac{u}{S}-\theta\right)\right), \tag{C-25}$$

and one may express the derivative of the $H_0(u,\lambda)$ function as:

$$\frac{\partial}{\partial u}[H_0(u,\lambda)] = -2\delta\left(\sin\left(\lambda-\arctan\frac{u}{S}-\theta\right)\right)\times\cos\left(\lambda-\arctan\frac{u}{S}-\theta\right)\cdot\frac{S}{u^2+S^2}. \tag{C-26}$$

Using the expression of Eq. (C-26), one may rewrite the second term in Eq. (C-24) as:

$$T_2 = -2\int_{\lambda_{min}}^{\lambda_{max}} d\lambda \frac{S^2}{\left[R-\vec{r}'\cdot\hat{e}_w(\lambda)\right]^2}\frac{R}{A}\omega_0(u,\lambda)\times P(u,v,\lambda)\,\delta\left(\sin\left(\lambda-\arctan\frac{u}{S}-\theta\right)\right)\times\cos\left(\lambda-\arctan\frac{u}{S}-\theta\right)\cdot\frac{S}{u^2+S^2}. \tag{C-27}$$

For a point $(x'_\pi, \lambda_1, \lambda_2, z_0)$, on the PI-line segment, $$\sin\left(\lambda-\arctan\frac{u}{S}-\theta\right) = 0$$

has two solutions, which are $\lambda_1$ and $\lambda_2$. Considering the property of the δ-function, one can re-express Eq. (C-27) as:

$$T_2 = -2\sum_{i=1}^{2}\frac{S^2}{\left[R-\vec{r}\cdot\hat{e}_w(\lambda_i)\right]^2}\frac{R}{A}\omega_0(u,\lambda_i)\,P(u,v,\lambda_i)\times\frac{\cos\left(\lambda-\arctan\frac{u}{S}-\theta\right)}{\left|\frac{d}{d\lambda}\sin\left(\lambda-\arctan\frac{u}{S}-\theta\right)\right|_{\lambda=\lambda_1}}\cdot\frac{S}{u^2+S^2}. \tag{C-28}$$

On the other hand, one may calculate:

$$\frac{du}{d\lambda} = \frac{d}{d\lambda}\frac{S\vec{r}'\cdot\hat{e}_u(\lambda)}{R-\vec{r}'\cdot\hat{e}_w(\lambda)} = \frac{u^2+S^2}{S} - \frac{SR}{R-\vec{r}'\cdot\hat{e}_w(\lambda)}. \tag{C-29}$$

Putting this result into Eq. (C-28) yields:

$$T_2 = -2\sum_{i=1}^{2} \frac{S^2}{\left[R - \vec{r}' \cdot \hat{e}_w(\lambda_i)\right]^2} \frac{R}{A} \omega_0(u, \lambda_i) P(u, v, \lambda_1) \times \frac{\mathrm{sgn}\left(\cos\left(\lambda_i - \arctan\frac{u}{S} - \theta\right)\right)}{\left|\frac{S}{u^2+S^2} \frac{SR}{R - \vec{r}\cdot\hat{e}_w(\lambda)}\right|_{\lambda=\lambda_i}} \cdot \frac{S}{u^2+S^2} = \left.\frac{2\omega_0(u, \lambda)P(u, v, \lambda)}{\left|\vec{r}' - \vec{r}_c(\lambda)\right|}\right|_{\lambda_1}^{\lambda_2}, \tag{C-30}$$

in which one invokes:

$$\cos\left(\lambda_1 - \arctan\frac{u}{S} - \theta\right) = 1 \qquad \cos\left(\lambda_2 - \arctan\frac{u}{S} - \theta\right) = -1. \tag{C-31}$$

Finally, replacing the second term of Eq. (C-24) with Eq. (C-30), one obtains Eq. (C-23).

5. Image Reconstruction within Regions of Interest from Truncated High-Dimensional Radon Transforms Methodologies have been developed for exact reconstruction of ROI-images from truncated high-dimensional Radon transforms. These methodologies may find significant applications in, for example, electron paramagnetic resonance imaging (EPRI), magnetic resonance spectral imaging (MRSI), and other imaging modalities. Specifically, the data function in CW EPRI (electron paramagnetic resonance imaging) or MRSI (magnetic resonance spectral imaging) can be interpreted as the nD Radon transform of the object function, where n can be up to four dimensions (a spectral dimension and three spatial dimensions). Therefore, the task of image reconstruction in EPRI may be tantamount to the task of image reconstruction from the Radon transform. In EPRI, data acquisition time is generally long if knowledge over the entire Radon-transform space has to be measured. On the other hand, one is often interested only in the image within a region of interest (ROI) in the imaged subject. If ROI images can be reconstructed from a subset of data in the Radon-transform space, one needs to acquire only that subset of data, thus substantially reducing the imaging time. In this aspect of the invention, a methodology has been developed for exact reconstruction of EPRI images within ROIs from the truncated Radon transform of n-dimensions. This methodology may also be applied to reconstructing images in any imaging modalities in which data can be related to Radon transforms.

6. Reconstruction of Singularities or Boundaries from Truncated Data Acquired with Trajectories of Arbitrary Shapes and Lengths In certain clinical and industrial imaging cases, one may be interested only in the spatial distributions of singularities within the imaged subject. Also, in many practical imaging applications, because of the physical constraints such as scanning time and geometries, one may acquire data that are severely truncated over trajectories of arbitrary shapes and lengths. Therefore, in these situations, it is not necessary or possible to reconstruct exact images from the acquired data. Methodologies have been developed which may obtain images of singularities or boundaries in the imaged subjects of n-dimensions, where n>=2. The methodologies may rely upon the unique backprojection-image function that may be computed from the aforementioned data, which contain certain information of the singularities within the imaged subjects.

7. Chord-Based Image Reconstruction with an at Least Partially Curved Detector

The following analyzes chord-based reconstruction for an at least partially curved detector. The source may comprise a cone-beam. Alternatively, other types of sources may be used. Cone-beam configurations are becoming widely adopted in modern computed tomography (CT) systems for increasing volume coverage, improving x-ray-tube utilization, and yielding isotropic spatial resolution. Methodologies may be used for exact image reconstruction from cone-beam projections acquired with a helical scanning trajectory. Unlike the previously proposed Radon-transform-based methodologies, these methodologies may invoke only one-dimensional (1D) filtration of the data derivative and reconstruct images directly from data without converting them into the Radon transform of the object function. In particular, as disclosed above, image reconstruction may be performed on PI-lines in helical cone-beam scans. Based upon this, the backprojection-filtration (BPF) methodology and the filtered-backprojection (FBP) methodology have been developed for image reconstruction on PI-lines from helical cone-beam data, as discussed above. The BPF methodology and the FBP methodology may be generalized to reconstruct images from cone-beam data acquired with general cone-beam trajectories. In addition to PI-lines, methodologies for image reconstruction may use M-lines. M-lines may comprise a line with one end of the line connected to the source trajectory and the other end is not connected to the source trajectory.

The BPF methodology may exactly reconstruct an image within a region of interest (ROI) from projection data containing both longitudinal and transverse truncations. On the other hand, the FBP-based methodologies cannot be applied to reconstructing exact ROI images from transversely truncated data because the methodologies invoke, at each view, 1D filtering that requires full knowledge of data. Another methodology is discussed above, which, like the existing FBP methodologies, invokes 1D filtering of the data derivative before its backprojection to the image space. However, because the data filtering may be carried out over a line segment of finite length on the detector, this methodology, like the BPF methodology, is capable of reconstructing exactly ROI images from data containing both longitudinal and transverse truncations. Therefore, to highlight the difference from the existing FBP-based methodologies, this methodology is referred to as the minimum-data FBP (MDFBP) methodology.

Clinical CT scanners generally use curved detectors for minimizing the scanner size and reducing the centrifugal force induced by the high speed rotation of the detector and X-ray tube. Katsevich's FBP methodology for a curved detector was developed. The chord-based BPF, MDFBP, and FBP methodologies may be used for a flat-panel detector. Further, the methodologies may be used, with modification, for a detector that is at least partially curved (such as a partially curved and partially straight or an entirely curved detector) so that they can be applied to data acquired by use of clinical CT scanners. In the following, the chord-based BPF, MDFBP, and FBP methodologies are derived for a curved detector.

The chord-based BPF, MDFBP, and FBP methodologies were developed for cone-beam CT with a flat-panel detector. For practical reasons, however, clinical CT scanners use curved detectors for data acquisition, preventing the applications of the current chord-based methodologies to reconstructing images directly from data acquired with a curved detector. These chord-based methodologies may be generalized so that they may be applied directly to cone-beam CT systems with curved detectors.

Figure 67:
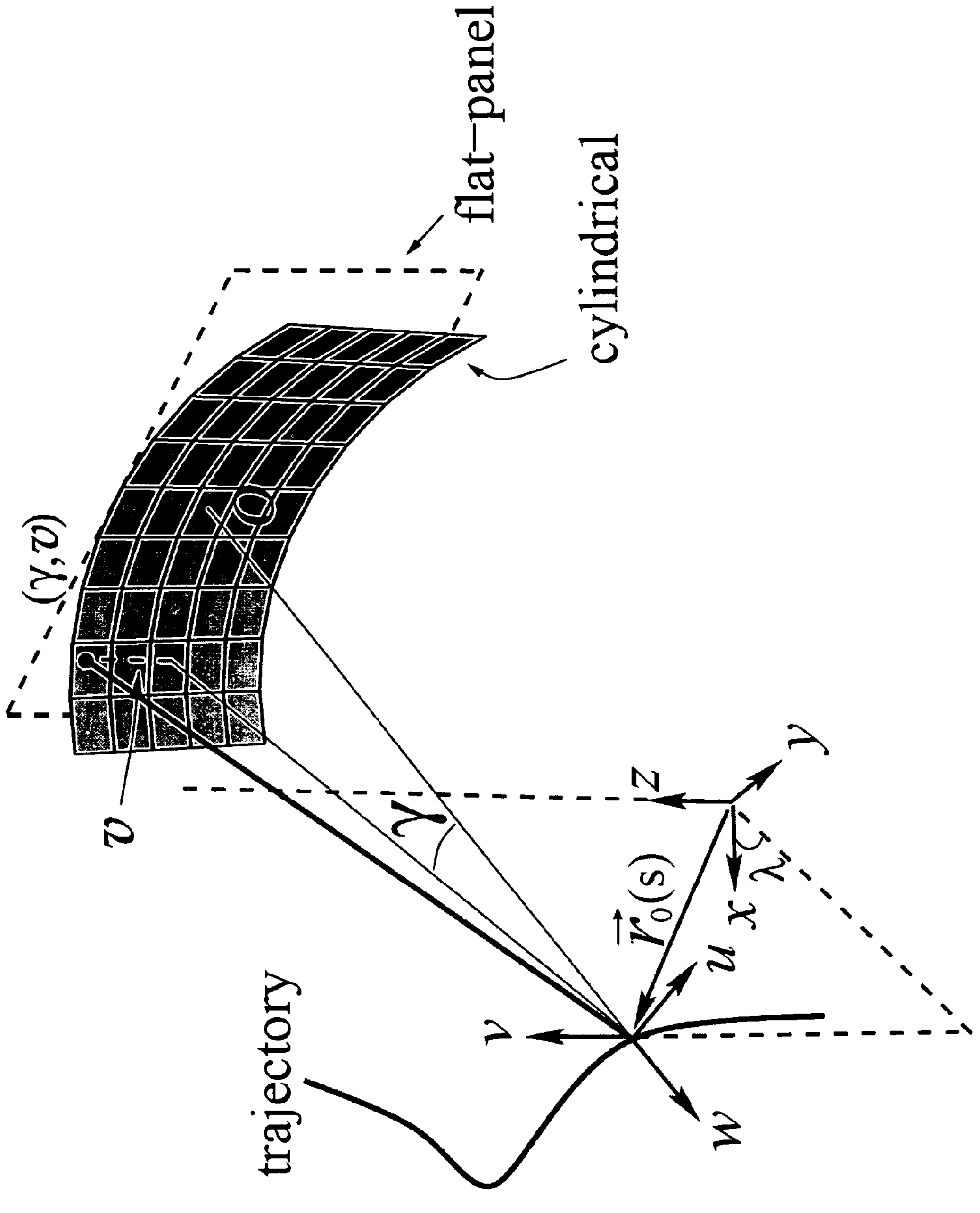
FIG. 67 depicts the scanning configuration with a curved detector (shaded surface) and a source over a general trajectory (thick curve).

The chord-based reconstruction methodologies may accommodate the general trajectory. FIG. 67 depicts the scanning configuration with a curved detector (shaded surface) and a source over a general trajectory (thick curve). Another type of detector may include a cylindrical type of detector. The rotation-coordinate system {u, v, w} has its origin on the source point $\vec{r}_0(s)$, its v-axis along the z-axis of the fixed-coordinate system {x, y, z} on the object, and its w-axis intersects perpendicularly the central point O of the curved detector. A source trajectory may thus be characterized by a three-dimensional (3D) vector, $\vec{r}_0(s)=(x(s), y(s), z(s))$, where x(s), y(s), and z(s) denote the x-, y-, and z-components of $\vec{r}_0(s)$ in the fixed-coordinate system, and s is a path-length parameter indicating the position of the x-ray source on the trajectory. Consider a ray from the source intersecting the curved detector (thick line), its projection line onto the u-w plane forms an angle γ with respect to the negative w-axis. The area enclosed by the dotted lines depicts a flat-panel detector, which is parallel to the u-v plane. The flat-panel and curved detectors may be assumed to share the same central point O. The angle λ is formed by the projection of vector $\vec{r}_0(s)$ onto the x-y plane with respect to the x-axis.

General trajectories may be divided into two categories: smooth trajectories and trajectories that have a finite number of kinks, where $d\vec{r}_0(s)/ds$ does not exist. In clinical CT, one example of a smooth trajectory is the general helical trajectory, which is mathematically expressed as $$\vec{r}_0(s) = \left(R_0(s)\cos(s),\ R_0(s)\sin(s)\cos(\phi),\ \frac{h_0(s)}{2\pi} + R_0(s)\sin(s)\sin(\phi)\right), \qquad \text{(D-1)}$$

in which, the rotation axis is assumed to coincide with the z-axis. This general helical trajectory may have a variable pitch $$\frac{dh_0(s)}{ds},$$

a variable radius $R_0(s)$ (e.g., the distance between the source and rotation axis), and a tilted angle ϕ. The circle-line trajectory, which may be an easy implementation trajectory with kinks, can be expressed in terms of path length as follows:

$$\vec{r}_0(s) = \begin{cases} (R,\ s\sin(\alpha),\ s\cos(\alpha)) & s \le 0 \\ (R\cos(s/R),\ R\sin(s/R),\ 0) & 0 < s < 2\pi R \\ (R,\ (s-2\pi R)\sin(\alpha),\ (s-2\pi R)\cos(\alpha)) & s \ge 2\pi R(2) \end{cases} \qquad \text{(D-2)}$$

where R indicates the radius of the circle, and the line is a radians from vertical in the y-z plane.

FIG. 67 depicts a cone-beam configuration with a curved detector that is used in a clinical CT scanner. In additional to the fixed-coordinate system, a rotation-coordinate system {u, v, w} is also introduced whose origin is fixed on the source point. In the fixed-coordinate system, the three unit vectors of the rotation-coordinate system may be written as:

$$\hat{e}_u=(\lambda)=(-\sin\lambda,\cos\lambda,0)^T$$

$$\hat{e}_v(\lambda)=(0,0,1)^T$$

$$\hat{e}_w=(\lambda)=(\cos\lambda,\sin\lambda,0)^T, \qquad \text{(D-3)}$$

where the superscript T denotes a matrix transpose, and λ is determined by $$\sin\lambda = \frac{y(s)}{\sqrt{x(s)^2 + y(s)^2}}$$

or $$\cos\lambda = \frac{x(s)}{\sqrt{x(s)^2 + x(s)^2}}.$$

Clearly, the v-axis is parallel to the z-axis. The w-axis is assumed to intersect the curved detector at its central point O and is perpendicular to a plane tangential to the curved detector at the central point O. For a point $\vec{r}$ in the image space, its components $u_0$, $v_0$ and $w_0$ along the u-, v- and w-axes of the rotation-coordinate system may be written as:

$$u_0=(\vec{r}-\vec{r}_0(s))\cdot\hat{e}_u(\lambda)$$

$$v_0=(\vec{r}-\vec{r}_0(s))\cdot\hat{e}_v(\lambda)$$

$$w_0=(\vec{r}-\vec{r}_0(s))\cdot\hat{e}_w(\lambda). \qquad \text{(D-4)}$$

In the following, a curved detector is considered that resembles those used in clinical scanners. The curved detector may be at least partly curved (with a flat portion) or may be entirely curved. The curved detector may be interpreted as a part of a cylindrical surface, which is focused on the source point. Therefore, in this situation, one may use two parameters γ and v to specify a point of interest on the curved detector, where γ denotes the angle formed by the negative w-axis and the projection line, onto the u-w plane, of the ray connecting the point of interest and the source point, and v indicates the distance, along the v-axis, between the point of interest and the central point O of the curved detector. In the rotation-coordinate system, a point of interest (γ, v) on the curved detector may be expressed as:

$$(u_c,v_c,w_c)=(S(s)\sin\gamma,v,-S(s)\cos\gamma), \qquad \text{(D-5)}$$

where S(s) denotes the distance from the x-ray source to the central point O of the curved detector for view s. It should be noted that γ is a signed angle, as shown in FIG. 67, and satisfies $\gamma\in[-\gamma_m, \gamma_m]$, where $\gamma_m$ indicates the half-fan angle in the u-w plane subtended by the curved detector.

The cone-beam projection of the object function $f(\vec{r})$ along a ray passing through a point $\vec{r}$ may be written as:

$$D(\vec{r}_0(s),\hat{\beta})=\int_0^\infty dt f(\vec{r}_0(s)+t\hat{\beta}), \qquad \text{(D-6)}$$

where the ray direction $\hat{\beta}$ is given by $$\hat{\beta} = \frac{\vec{r} - \vec{r}_0(s)}{|\vec{r} - \vec{r}_0(s)|}. \quad \text{(D-7)}$$

Using Eqs. (D-3), (D-4), and (D-5), one may show that this ray intersects the curved detector at a point (γ, v):

$$\gamma - \tan^{-1}\frac{(\vec{r} - \vec{r}_0(s)) \cdot \hat{e}_u(\lambda)}{(\vec{r} - \vec{r}_0(s)) \cdot \hat{e}_w(\lambda)} \quad \text{(D-8)}$$

and $$v = -S(s)\frac{(\vec{r} - \vec{r}_0(s)) \cdot \hat{e}_v(\lambda)}{(\vec{r} - \vec{r}_0(s)) \cdot \hat{e}_w(\lambda)}\cos\gamma.$$

The chord-based methodologies discussed above may be applied to a flat-panel detector (such as a partially flat panel detector or a fully flat panel detector). Without loss of generality, one may assume that the flat-panel detector, as shown in FIG. 67, is parallel to the u-v plane of the rotation-coordinate system and that its central point coincides with that of the curved detector. Let $(u_f, v_f, w_f)$ denote the point at which the ray with a direction $\hat{\beta}$ intersects the flat-panel detector. It may be shown that:

$$u_f = -\frac{(\vec{r} - \vec{r}_0(s)) \cdot \hat{e}_u(\lambda)}{(\vec{r} - \vec{r}_0(s)) \cdot \hat{e}_w(\lambda)}S(s) \quad \text{(D-9)}$$

$$v_f = -\frac{(\vec{r} - \vec{r}_0(s)) \cdot \hat{e}_v(\lambda)}{(\vec{r} - \vec{r}_0(s)) \cdot \hat{e}_w(\lambda)}S(s)$$

$$w_f = -S(s).$$

Let $P_c(s, \gamma, v)$ and $P_f(s, u_f, v_f)$ denote the projections of the object function $f(\vec{r})$ onto the curved and flat-panel detectors. Comparison of Eqs. (D-8) and (D-9) thus indicates that, when $$\gamma = \tan^{-1}\frac{u_f}{S(s)} \quad \text{(D-10)}$$

and $$v = v_f\cos\gamma,$$

the projections of the object function onto the curved and flat-panel detectors are identical, i.e., $$P_c(s,\gamma,v) = P_f(s,u_f,v_f) = D(\vec{r}_0(s),\hat{\beta}). \quad \text{(D-11)}$$

The result in Eqs. (D-10) and (D-11) reveals the relationship between projections on the curved and flat-panel detectors; and, as discussed in more detail below, it may provide the basis for the derivation of the chord-based reconstruction methodologies for a curved detector.

Figure 68:
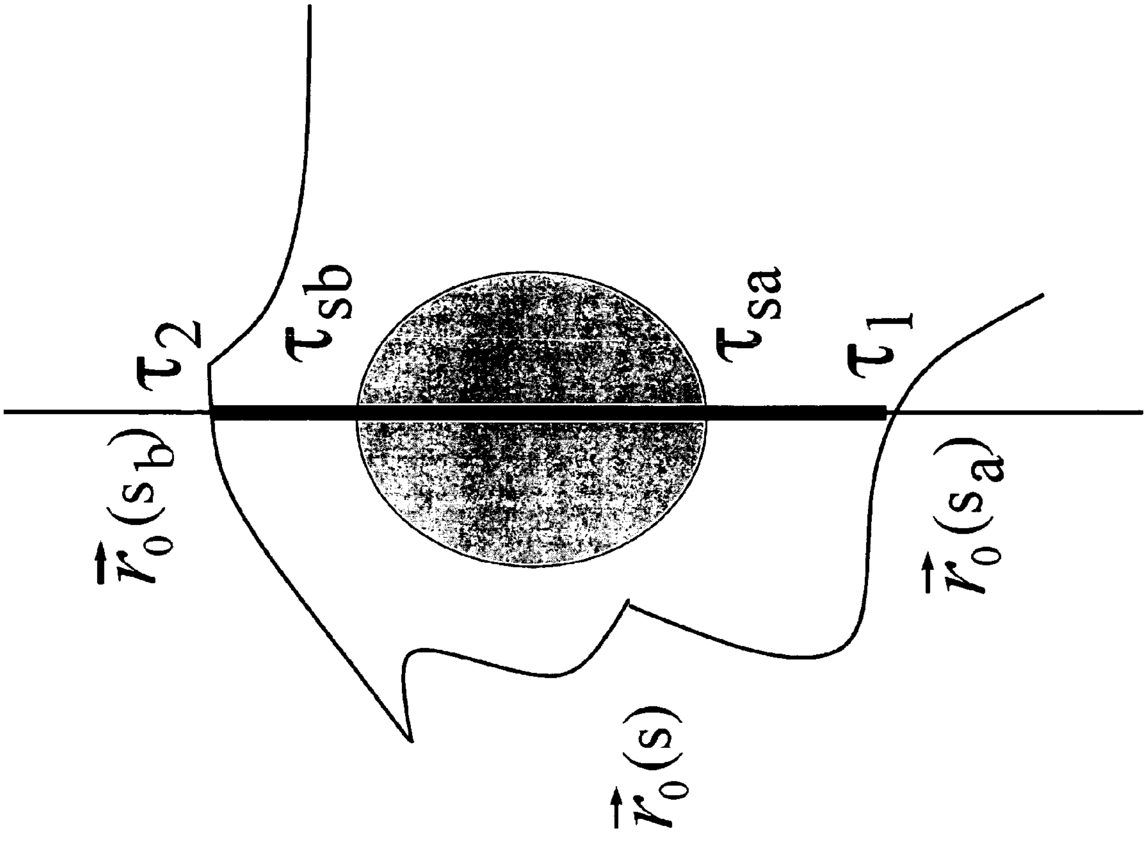
FIG. 68 illustrates an example of a chord-line, chord, and support segment for a general scanning trajectory.

Chords may be used in our chord-based reconstruction methodologies. FIG. 68 illustrates an example of a chord-line, chord, and support segment for a general scanning trajectory. A chord-line may be a straight line connecting any two points, $\vec{r}_0(s)$ and $\vec{r}_0(s_b)$, on the trajectory; the chord may be referred to as the segment of the chord-line between $\vec{r}_0(s_a)$ and $\vec{r}_0(s_b)$; and the support segment may be the portion of the chord within the support of the object function (shaded circular area). $\tau_1$ and $\tau_2$ may be used to denote the two endpoints of the chord and $\square_{sa}$ and $\square_{sb}$ to denote the two endpoints of the support segment on the chord. Because the trajectory never intersects the object support, $[\tau_{sa}, \tau_{sb}] \subset [\tau_1, \tau_2]$.

The trajectory, such as that shown in FIG. 68, may have a finite number of kinks at which its derivatives $d\vec{r}_0(s)/ds$ may not exist. Without loss of generality, one assumes $s_b > s_a$. Using the explanations for chord and the endpoints of the chord, for any point on the chord, its coordinate may be written as:

$$\vec{r} = \vec{r}_0(s_a) + \tau_c\hat{e}_c, \quad \text{(D-12)}$$

where $\tau_c \in [\tau_1, \tau_2]$, and the direction of the chord is defined as $$\hat{e}_c = \frac{\vec{r}_0(s_b) - \vec{r}_0(s_a)}{|\vec{r}_0(s_b) - \vec{r}_0(s_a)|}. \quad \text{(D-13)}$$

As displayed in FIG. 68, let $\tau_{sa}$ and $\tau_{sb}$ denote the two endpoints of the intersection of a chord with the support of the object function; and such an intersection may be referred to as the support segment. Because the trajectory under consideration may not intersect with the object, the support segment may be shorter than the corresponding chord, i.e., $[\tau_{sa}, \tau_{sb}] \subset [\tau_1, \tau_2]$.

For a chord determined by $s_a$ and $s_b$, the trajectory segment between $s_a$ and $s_b$ may have a finite number of kinks at which the derivative $d\vec{r}_0(s)/ds$ does not exist. Without loss of generality, the trajectory between $s_a$ and $s_b$ may assumed to contain N kinks at $s_i$, where i=2, 3 . . . , N+1, $s_1=s_a$, and $s_{N+2}=s_b$. The chord-based methodologies for a flat-panel detector are summarized below.

With regard to the BPF methodology for a flat-panel detector, image reconstruction is considered on a chord specified by $s_a$ and $s_b$. A ray that coincides with the chord may originate from a source point at either $s_a$ or $s_b$. When the ray is from $s_a$, $u_{fa}$ and $v_{fa}$ is used to denote its intersection with the flat-panel detector. The BPF methodology may reconstruct $f(\vec{r})$ on the chord by first backprojecting the data derivative, followed by filtering the backprojection image over the chord; and it can be expressed as:

$$f_c(\tau_c, s_a, s_b) = \frac{1}{2\pi}\frac{1}{\sqrt{(\tau_B - \tau_c)(\tau_c - \tau_A)}} \times \left[\int_R \frac{d\tau'_c}{\tau_c - \tau'_c}\Pi_c(\tau'_c)\sqrt{(\tau_B - \tau'_c)(\tau'_c - \tau_A)}\, g(\tau'_c, s_a, s_b) + 2\pi P_f(s_a, u_{fa}, v_{fa})\right], \quad \text{(D-14)}$$

where $$g(\tau_c, s_a, s_b) = \sum_{i=1}^{N+1}\int_{s_i}^{s_{i+1}} ds \frac{\mathrm{sgn}(-\hat{\beta} \cdot \hat{e}_w)}{|\vec{r}(\tau_c) - \vec{r}_0(s)|}\frac{\partial}{\partial s}P_f(s, u_f, v_f)\bigg|_{\hat{\beta}}, \quad \text{(D-15)}$$

$\tau_A$ and $\tau_B$ are two pre-selected parameters satisfying $[\tau_{sa}, \tau_{sb}] \subseteq [\tau_A, \tau_B] \subset [\tau_1, \tau_2]$, and $\Pi_c(\tau'_c)$ is the rect function, which is given by $$\Pi_c(\tau'_c) = \begin{cases} 1 & \text{if } \tau'_c \in [\tau_A, \tau_B](16) \\ 0 & \text{otherwise.} \end{cases} \tag{D-16}$$

The coordinate $\tau_c$ of a point on the chord is related to $\vec{r}$ through Eq. (D-12) and subsequently related to $(u_f, v_f)$ through Eq. (D-9), and the term $P_f(s_a, u_{fa}, v_{fa})$ may denote the known projection of the object function over the chord at view $s_a$. The BPF methodology may reconstruct exactly images by use of data less than can any existing methodologies. In this sense, the BPF methodology may require minimum data for exact image reconstruction. Furthermore, because the function $\Pi_c(\tau'_c)$ has a support $[\tau_A, \tau_B]$, which satisfies $[\tau_A, \tau_B] \supseteq [\tau_{sa}, \tau_{sb}]$ and can thus be selected as tight as $[\tau_{sa}, \tau_{sb}]$, the filtering step in Eq. (D-14) may require knowledge of projection data only over the support segment, i.e., $\tau_c \in [\tau_{sa}, \tau_{sb}]$, thus allowing the BPF methodology to reconstruct exactly ROI images from projection data containing longitudinal and/or transverse truncations. Conversely, the FBP-based methodologies cannot reconstruct exactly any ROI images from data containing transverse truncations.

Based upon the BPF methodology in which the backprojection of the data derivative is performed prior to the filtering of the backprojection image, a methodology may be derived in which the data derivative is filtered over the detector along a line-segment prior to its backprojection onto the chord. This methodology may be obtained by switching the order of the backprojection step (e.g., the integration over s in Eq. (D-15)) and the filtering step (e.g., the integration over $\tau'_c$ in Eq. (D-14)) and may be expressed as:

$$f_c(\tau_c, s_a, s_b) = \sum_{i=1}^{N+1} \int_{s_i}^{s_{i+1}} ds[w_2(u_B - u_c) + w_1(u_c - u_A)] \times \left[ \int_R \frac{du'_c}{u_c - u'_c} P_\Pi(u'_c, s_a, s_b) + 2\pi P_f(s_a, u_{fa}, v_{fa}) \right], \tag{D-17}$$

where $$P_\Pi(u'_c, s_a, s_b) = \frac{\sqrt{(\tau_B - \tau'_c)(\tau'_c - \tau_A)}}{w_2(u_B - u'_c) + w_1(u'_c - u_A)} \frac{\prod_c(\tau'_c)}{|\vec{r}' - \vec{r}_0(s)|} \operatorname{sgn}(-\hat{\beta} \cdot \hat{e}_w) \frac{\partial}{\partial s} P_f(s, u_f, v_f)_{\hat{\beta}}, \tag{D-18}$$

Figure 69:
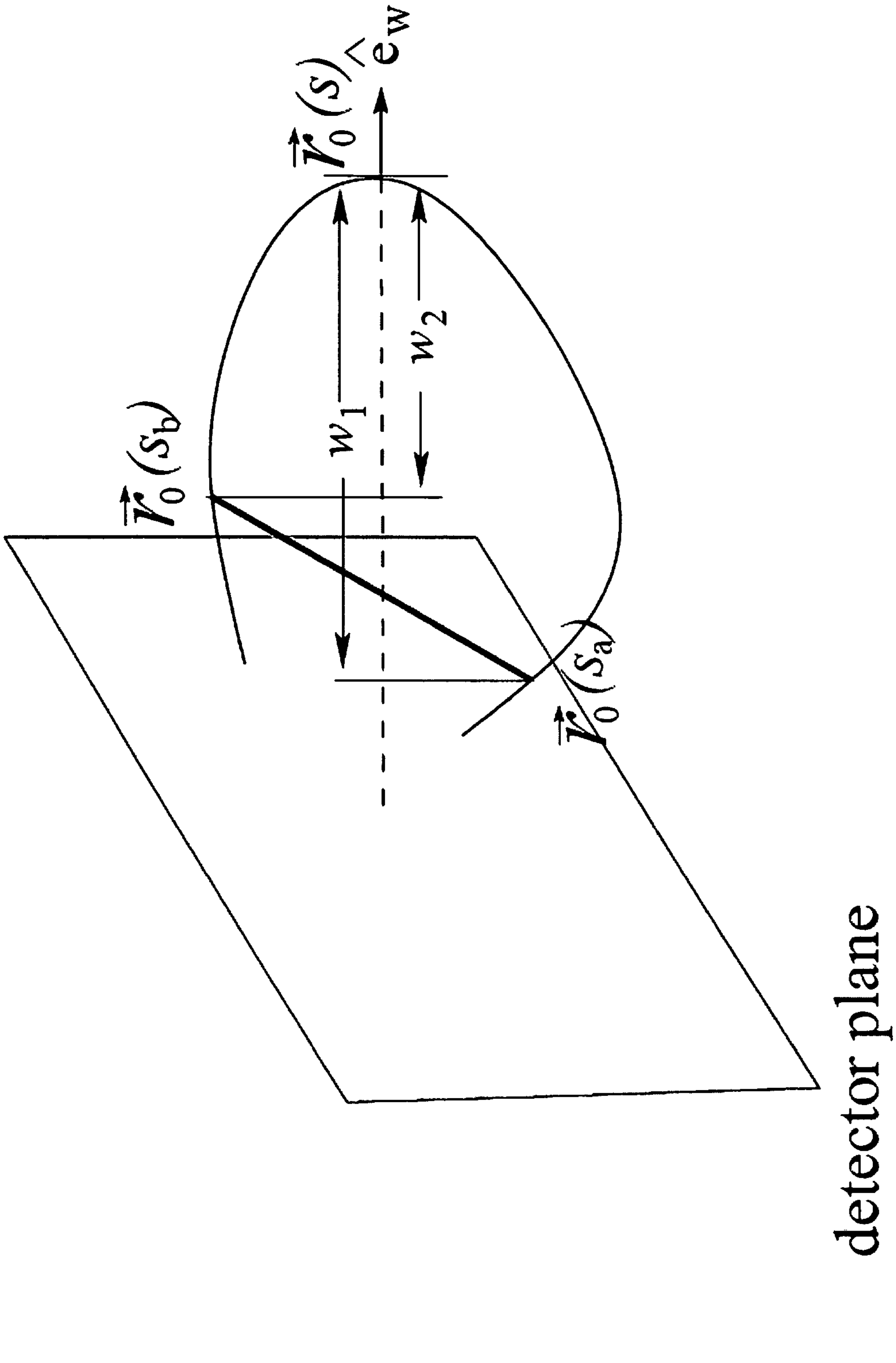
FIG. 69 illustrates switching the order of the backprojection step.

$w_1$ and $w_2$ are the projections of vectors $-[\vec{r}_0(s_a) - \vec{r}_0(s)]$ and $-[\vec{r}_0(s_b) - \vec{r}_0(s)]$ onto the direction $\hat{e}_w$, as shown in FIG. 69. For each source position s, $w_1$ and $w_2$ may be calculated by:

$$w_1 = -[\vec{r}_0(s_a) - \vec{r}_0(s)] \cdot \hat{e}_w$$

$$w_2 = -[\vec{r}_0(s_b) - \vec{r}_0(s)] \cdot \hat{e}_w. \tag{D-19}$$

Figure 70:
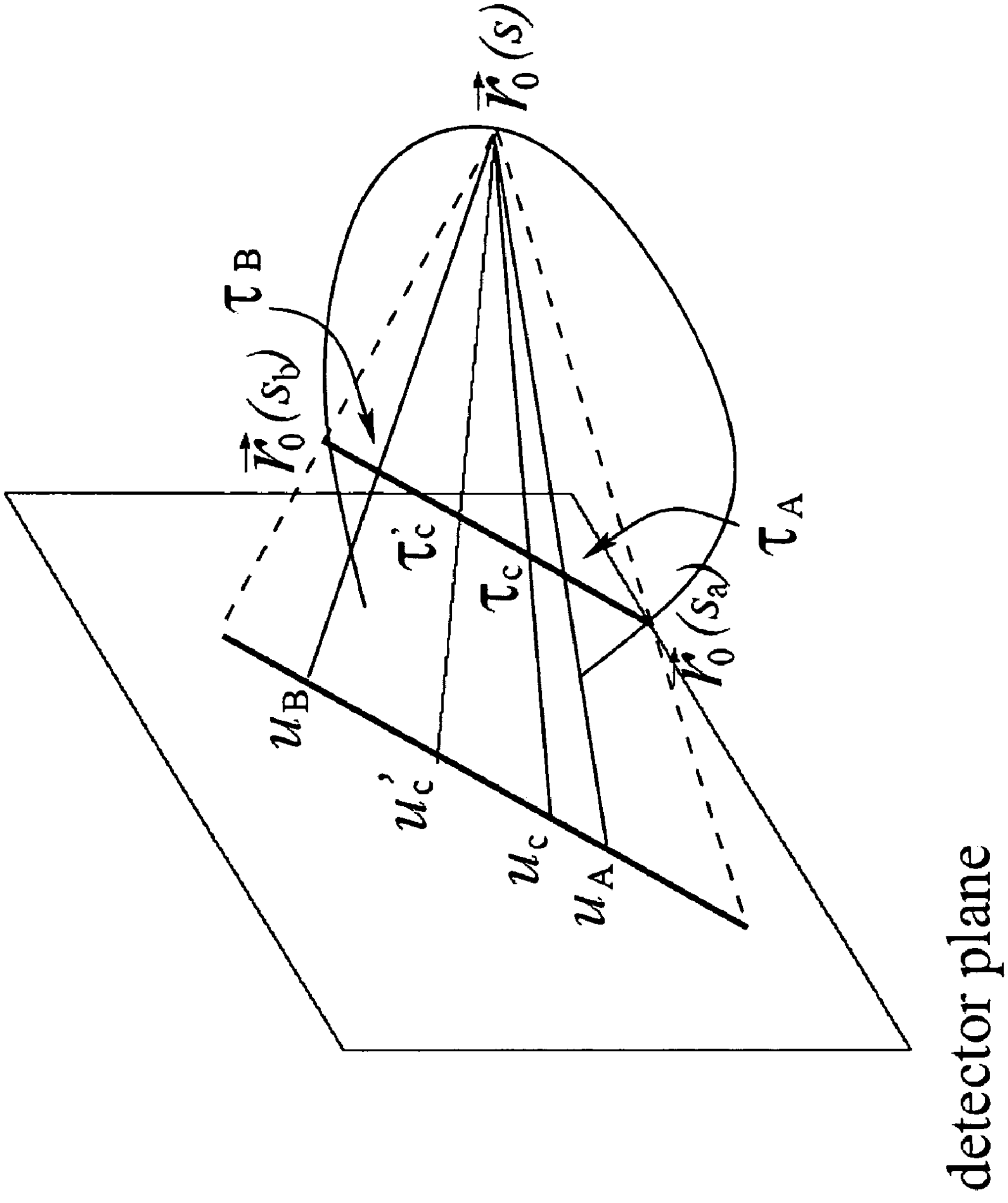
FIG. 70 illustrates the cone-beam projections of points on a chord. The variables $u_c$, $u_c$, $u_A$, and $u_B$ denote the cone-beam projections of chord points $\tau_c$, $\tau_c$, $\tau_A$, and $\tau_B$ onto the detector.

The variables $u_c$, $u'_c$, $u_A$, and $u_B$ denote the cone-beam projections of $\tau_c$, $\tau'_c$, $\tau_A$, and $\tau_B$ onto the detector as shown in FIG. 4. For any point $\tau$ on the chord, its cone-beam projection u onto the detector can be written as $$u = \frac{w_2(\tau - \tau_1)}{w_1(\tau_2 - \tau) + w_2(\tau - \tau_1)}, \tag{D-20}$$

where $\tau_1$ and $\tau_2$ denote the endpoints of the chord. FIG. 70 illustrates the cone-beam projections of points on a chord. The variables $u_c$, $u_c$, $u_A$, and $u_B$ denote the cone-beam projections of chord points $\tau_c$, $\tau_c$, $\tau_A$, and $\tau_B$ onto the detector. For example, for point $\tau_c$ shown in FIG. 70, its cone-beam projection $u_c$ on the detector may be obtained by replacing $\tau$ with $\tau_c$ in Eq. (D-20).

As shown in Eq. (D-17), similar to the existing FBP-based methodologies, this methodology performs data-derivative filtering (i.e., the integration over $u'_c$) prior to its backprojection (i.e., the integration over s). Because this methodology was derived from the BPF methodology, it can also reconstruct exact images from minimum data and can accommodate exact ROI-image reconstruction from projection data containing truncations. Therefore, the methodology may be referred to as the minimum-data filtered-backprojection (MDFBP) methodology. This reflects, on one hand, its minimum-data aspect and, on the other hand, its operation-order similarity to the existing FBP-based methodologies.

An FBP methodology may also be used for image reconstruction on a chord from cone-beam projections, which may be written as:

$$f_c(\tau_c, s_a, s_b) = \frac{1}{2\pi^2} \sum_{i=1}^{N+1} \int_{s_i}^{s_{i+1}} ds \frac{S(s)}{(\vec{r} - \vec{r}_0(s)) \cdot \hat{e}_w(\lambda)} \int_R \frac{du'_c}{u_c - u'_c} \frac{1}{|\vec{r}' - \vec{r}_0(s)|} \frac{\partial}{\partial s} P_f(s, u_f, v_f) \bigg|_{\hat{\beta}}, \tag{D-21}$$

where $u_c$ indicates the cone-beam projection, onto the detector, of a point $\tau_c$ on the chord and is determined by replacing $\tau$ with $\tau_c$ in Eq. (D-20).

It may be observed in Eq. (D-21) that the chord-based FBP methodology reconstructs the image by first filtering the data derivative (e.g., the integration over $u_c$) and then backprojecting the filtered data onto the chord (e.g., the integration over s). As the filtering is carried out over the projection of the entire chord-line, similar to other existing FBP-based methodologies, the chord-based FBP methodology cannot exactly reconstruct ROI images from data containing transverse truncations.

As Eqs. (D-14), (D-17), and (D-21) show, the chord-based BPF, MDFBP, and FBP methodologies may involve the computation of the data derivative $$\frac{\partial}{\partial s} P_f(s, u_f, v_f) \bigg|_{\hat{\beta}}.$$

Using Eqs. (D-9) and (D-11), the data derivative may be re-expressed in terms of the flat-panel-detector coordinates:

$$\frac{\partial}{\partial s}P_f(s,u_f,v_f)\Big|_{\hat\beta} = \frac{dP_f(s,u_f,v_f)}{ds}\Big|_{\vec r} + \left[\frac{d\vec r_0(s)}{ds}\cdot\hat e_u(\lambda) + \frac{u_f}{S(s)}\frac{d\vec r_0(s)}{ds}\cdot\hat e_w(\lambda)\right]\frac{A(u_f,v_f)}{|\vec r-\vec r_0(s)|}\frac{\partial P_f(s,u_f,v_f)}{\partial u_f} + \left[\frac{d\vec r_0(s)}{ds}\cdot\hat e_v(\lambda) + \frac{v_f}{S(s)}\frac{d\vec r_0(s)}{ds}\cdot\hat e_w(\lambda)\right]\frac{A(u_f,v_f)}{|\vec r-\vec r_0(s)|}\frac{\partial P_f(s,u_f,v_f)}{\partial v_f}, \tag{D-22}$$

where $A(u_f, v_f)=\sqrt{u_f^2+v_f^2+S(s)^2}$. Therefore, using Eq. (D-22) in Eqs. (D-14), (D-17), and (D-21), the final forms of the BPF, MDFBP, and FBP methodologies for a flat-panel detector may be obtained. A benefit of rewriting the data derivative in terms of the flat-panel-detector coordinates $u_f$ and $v_f$ is that it may improve the numerical stability of the reconstruction methodologies.

The chord-based BPF, MDFBP, and FBP methodologies may be obtained for a curved detector by re-expressing the data derivative $$\frac{\partial}{\partial s}D(\vec r_0(s),\hat\beta)\Big|_{\hat\beta}$$

in terms of the curved-detector coordinates. Again, using Eq. (D-11), one obtains $$\frac{dP_f(s,u_f,v_f)}{ds}\Big|_{\vec r} = \frac{dP_c(s,\gamma,v)}{ds}\Big|_{\vec r} \tag{D-23}$$

$$\frac{\partial P_f(s,u_f,v_f)}{\partial u_f} = \frac{\partial P_c(s,\gamma,v)}{\partial\gamma}\frac{\partial\gamma}{\partial u_f} + \frac{\partial P_c(s,\gamma,v)}{\partial v}\frac{\partial v}{\partial u_f}$$

$$\frac{\partial P_f(s,u_f,v_f)}{\partial v_f} = \frac{\partial P_c(s,\gamma,v)}{\partial\gamma}\frac{\partial\gamma}{\partial v_f} + \frac{\partial P_c(s,\gamma,v)}{\partial v}\frac{\partial v}{\partial v_f}.$$

Based upon Eq. (D-10), one can show that $$\frac{\partial\gamma}{\partial u_f} = \frac{\cos^2\gamma}{S(s)} \tag{D-24}$$

$$\frac{\partial v}{\partial u_f} = -\frac{v}{S(s)}\sin\gamma\cos\gamma$$

$$\frac{\partial\gamma}{\partial v_f} = 0$$

$$\frac{\partial v}{\partial v_f} = \cos\gamma.$$

Using Eq. (D-24) in Eq. (D-23) yields $$\frac{dP_f(s,u_f,v_f)}{ds}\Big|_{\vec r} = \frac{dP_c(s,\gamma,v)}{ds}\Big|_{\vec r} \tag{D-25}$$

$$\frac{\partial P_f(s,u_f,v_f)}{\partial u_f} = \frac{\partial P_c(s,\gamma,v)}{\partial\gamma}\frac{\cos^2\gamma}{S(s)} - \frac{\partial P_c(s,\gamma,v)}{\partial v}\frac{v}{S(s)}\sin\gamma\cos\gamma$$

$$\frac{\partial P_f(s,u_f,v_f)}{\partial v_f} = \frac{\partial P_c(s,\gamma,v)}{\partial v}\cos\gamma.$$

Substituting Eq. (D-25) into Eq. (D-22), the data derivative may be re-expressed in terms of the curved-detector coordinates as:

$$\frac{\partial}{\partial s}P_f(s,u_f,v_f)\Big|_{\hat\beta} \equiv P_c'(s,\gamma,v) = \frac{dP_c(s,\gamma,v)}{ds}\Big|_{\vec r} + \left[\frac{d\vec r_0(s)}{ds}\cdot\hat e_u(s) + \tan\gamma\cdot\frac{d\vec r_0(s)}{ds}\cdot\hat e_w(s)\right]\frac{A'(\gamma,v)}{|\vec r-\vec r_0(s)|}\times\left[\frac{\partial P_c(s,\gamma,v)}{\partial\gamma}\frac{\cos^2\gamma}{S(s)} - \frac{\partial P_c(s,\gamma,v)}{\partial v}\frac{v}{S(s)}\sin\gamma\cos\gamma\right] + \left[\frac{d\vec r_0(s)}{ds}\cdot\hat e_v(s) + \frac{v}{S(s)\cos\gamma}\cdot\frac{d\vec r_0(s)}{ds}\cdot\hat e_w(s)\right]\frac{A'(\gamma,v)}{|\vec r-\vec r_0(s)|}\times\frac{\partial P_c(s,\gamma,v)}{\partial v}\cos\gamma, \tag{D-26}$$

where $$A'(\gamma,v) = \frac{\sqrt{S^2(s)+v^2}}{\cos\gamma}.$$

With regard to the BPF methodology for a curved detector, for a given point $\tau'_c$ on a chord specified by $s_a$ and $s_b$, one may determine its projection onto the curved detector for a source point at $s\in[s_a, s_b]$. Specifically, substituting $\vec r'$, which is obtained by use of $\tau'_c$ in Eq. (D-12), into Eq. (D-8), one may obtain the coordinates $\gamma'_c$ and $v'_c$ of the projection of $\tau'_c$ on the curved detector. Therefore, the backprojection image may be re-expressed as:

$$g(\tau'_c, s_a, s_b) = g_c(\gamma'_c, v'_c, s_a, s_b) = \sum_{i=1}^{N+1}\int_{s_i}^{s_{i+1}} ds\frac{\text{sgn}(-\hat\beta\cdot\hat e_w)}{|\vec r(\tau'_c)-\vec r_0(s)|}P_c'(s,\gamma'_c,v'_c), \tag{D-27}$$

where $P'_c(s, \gamma'_c, v'_c)$ is given by Eq. (D-26).

Also, a ray that coincides with a chord specified by $s_a$ and $s_b$ may be from a source point at either $\vec r_0(s_a)$ or $\vec r_0(s_b)$ on the trajectory. Let $\gamma_a$ and $v_a$ denote the intersecting point of this ray on the curved detector. Therefore:

$$D(\vec r_0(s_a),\hat e_c)=P_c(s_a,\gamma_a,v_a). \tag{D-28}$$

Finally, using Eqs. (D-27) and (D-28) in Eq. (D-14) yields the BPF methodology for a curved detector:

$$f_c(\tau_c, s_a, s_b) = \frac{1}{2\pi} \frac{1}{\sqrt{(\tau_B - \tau_c)(\tau_c - \tau_A)}} \times \left[ \int_R \frac{d\tau'_c}{\tau_c - \tau'_c} \prod_c (\tau'_c) \sqrt{(\tau_B - \tau'_c)(\tau'_c - \tau_A)} \, g_c(\gamma_c, v_c, s_a, s_b) + 2\pi P_c(s_a, \gamma_a, v_a) \right]. \tag{D-29}$$

With the MDFBP methodology for a curved detector, for given $u_c$ and $s \in [s_a, s_b]$ in Eq. (D-18), one may use Eq. (D-21) to determine $\tau_c$ on a chord specified by $s_a$ and $s_b$. As discussed above, for the point $\tau_c$, one may subsequently determine its cone-beam projection ($\gamma_c$, $v_c$) on the curved detector. Therefore, using this result and Eqs. (D-27) and (D-29) in Eqs. (D-18) and (D-19), we obtain the MDFBP methodology for a curved detector as $$f_c(\tau_c, s_a, s_b) = \sum_{i=1}^{N+1} \int_{s_i}^{s_{i+1}} ds [w_2(u_B - u_c) + w_1(u_c - u_A)] \times \left[ \int_R \frac{du'_c}{u_c - u'_c} P_\Pi(u'_c, s_a, s_b) + 2\pi P_c(s_a, \gamma_a, v_a) \right], \tag{D-30}$$

where $$P_\Pi(u'_c, s_a, s_b) = \frac{\sqrt{(\tau_B - \tau'_c)(\tau'_c - \tau_A)}}{w_2(u_B - u'_c) + w_1(u'_c - u_A)} \frac{\prod_c (\tau'_c)}{\left|\vec{r}' - \vec{r}_0(s)\right|} \operatorname{sgn}(-\hat{\beta} \cdot \hat{e}_w) P'_c(s, \gamma_c, v_c), \tag{D-31}$$

in which $P'_c(s, \gamma_c, v_c)$ is given by Eq. (D-26).

With the FBP methodology for a curved detector, as discussed above, for given $u_c$ and $s \in [s_a, s_b]$ in Eq. (D-21), one may determine the corresponding ($\gamma_c$, $v_c$) on the curved detector. Therefore, using this result and Eq. (D-26) in Eq. (D-21), the FBP methodology for a curved detector may comprise:

$$f_c(\tau_c, s_a, s_b) = \frac{1}{2\pi^2} \sum_{i=1}^{N+1} \int_{s_i}^{s_{i+1}} ds \frac{S(s)}{(\vec{r} - \vec{r}_0(s)) \cdot \hat{e}_w(\lambda)} \int_R \frac{du'_c}{u_c - u'_c} \frac{1}{\left|\vec{r}' - \vec{r}_0(s)\right|} P'_c(s, \gamma_c, v_c), \tag{D-32}$$

where $P'_c(s, \gamma_c, v_c)$ is given by Eq. (D-27).

The chord-based BPF methodology in Eq. (D-29), the MDFBP methodology in Eq. (D-30), and the FBP methodology in Eq. (D-32), respectively, may be implemented for a curved detector. Such an implementation enables performing numerical studies to validate and evaluate the derived chord-based methodologies. In the numerical studies, different scanning trajectories are considered to show the versatility of the methodologies.

The chord-based methodologies described above may reconstruct images on chords. One may obtain the final image by converting the chord images onto the Cartesian grids (or other coordinate system). For a general scanning trajectory $\vec{r}_0(s)$, we use $\vec{r}_0(s_{min})$ and $\vec{r}_0(s_{max})$ to denote its starting and ending points. The projections $P_c(s_i, \gamma, v)$ are assumed to be measured at M source positions $s_i$ uniformly distributed over $[s_{min}, s_{max}]$. Namely $s_i = s_{min} + (i-1)\Delta s$, where $$\Delta s = \frac{(s_{\max} - s_{\min})}{M - 1}.$$

For a source position $s_i$, the reconstruction is considered on a chord connecting $\vec{r}_0(s_i)$ and $\vec{r}_0(s_j)$, where $s_i < s_j \leqq s_{max}$. It can readily be estimated that there are $$\frac{M(M-1)}{2}$$

such chords. In the reconstruction, chords are only considered that intersect the field of view (FOV). Alternatively, other chords may be used in addition to the intersecting chords. These intersecting chords form only a subset of the $$\frac{M(M-1)}{2}$$

chords. The number of reconstructed chords are given in each numerical study below.

In the first computer-simulation study, cone-beam data is generated from a 3D Shepp-Logan phantom by using a helical trajectory configuration, which is specified by a radius R=57.0 cm, a pitch h=12.8 cm, and a source-to-central-axis distance S=100.5 cm. The simulated data include projections at 1300 views which may be uniformly distributed over $s \in [-\pi, \pi]$. The curved detector may comprise 256 rows each of which includes 512 detector elements with a size of 0.07 cm×0.07 cm. Therefore, the half-fan angle $\gamma_m$ subtended by the curved detector is 10.1 degrees. Historically, in a helical scan, a chord-line and the corresponding chord, which are specified by $s_a$ and $s_b$ satisfying $|s_a - s_b| \leqq 2\pi$, may also be referred to as a PI-line and the corresponding PI-line segment. The BPF, MDFBP, and FBP methodologies may be applied to reconstructing images on PI-lines from the helical cone-beam data acquired with a curved detector. Images on about 105,558 PI-line segments were reconstructed, each of which contains 512 points within the FOV.

Figure 71C:
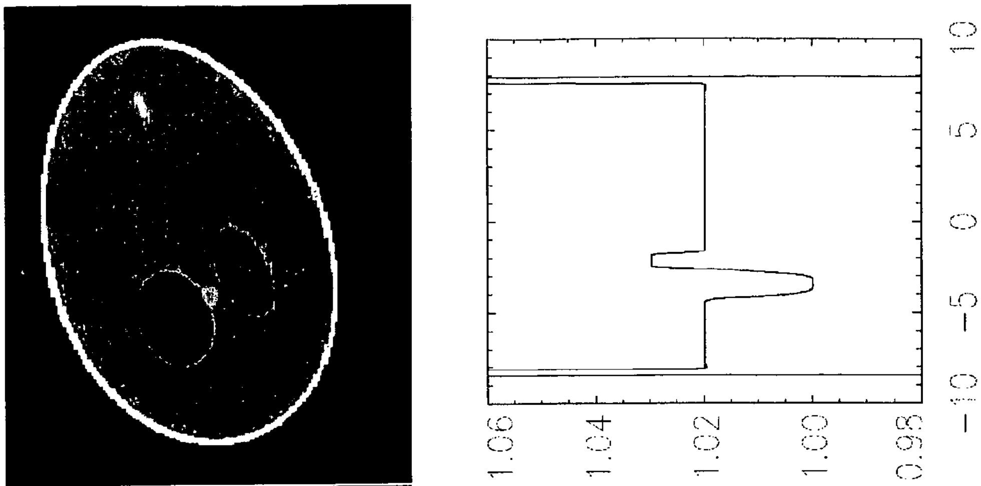
FIGS. 71*a-c* show images (upper row) displayed on a set of PI-line segments reconstructed by use of the BPF (FIG. 71*a*), MDFBP (FIG. 71*b*), and FBP (FIG. 71*c*) methodologies for a curved detector. The lower row shows the image profiles on a PI-line, specified by $s_a=-0.65\pi$ and $s_b=0.35\pi$, reconstructed by use of the BPF (FIG. 71*a*), MDFBP (FIG. 71*b*), and FBP (FIG. 71*c*) methodologies, respectively, for a curved detector.
Figure 71B:
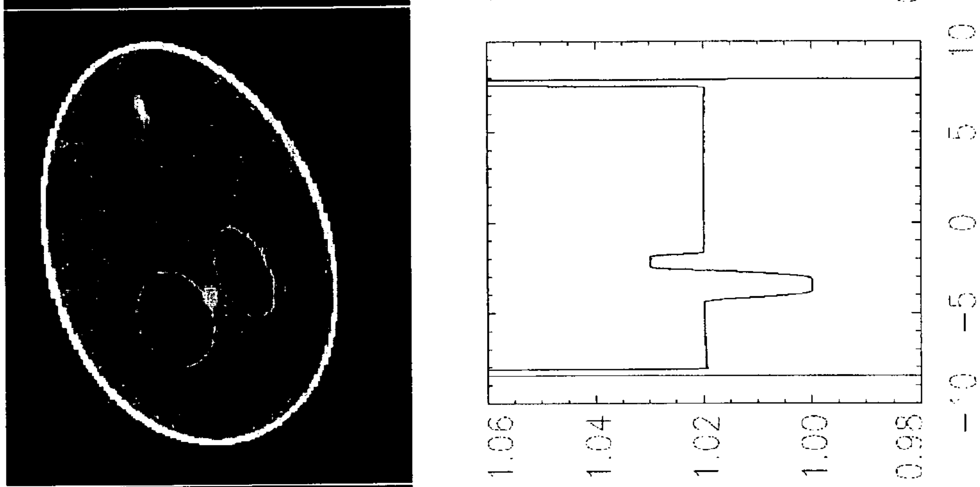
Figure 71A:
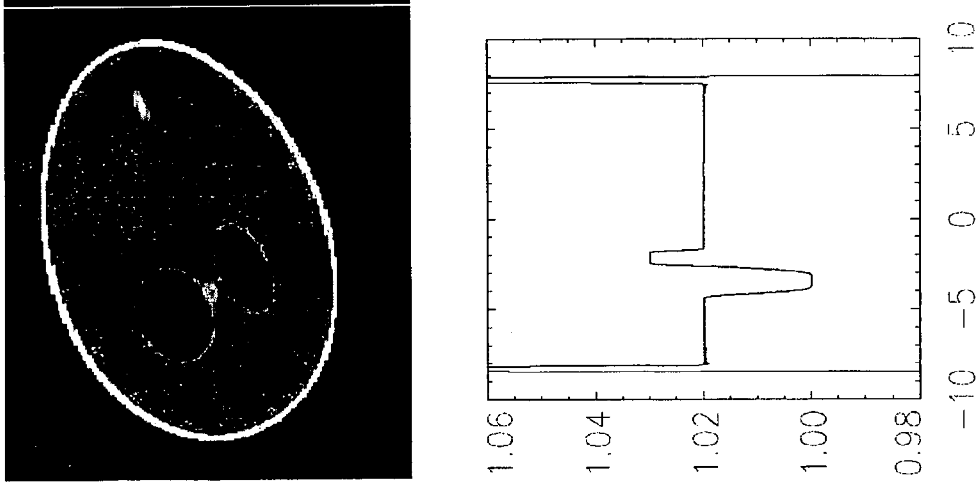

In the upper row of FIGS. 71A-C, images are displayed on a set of PI-line segments reconstructed by use of the BPF (FIG. 71A), MDFBP (FIG. 71B), and FBP (FIG. 71C) methodologies for a curved detector. In each of these images, the horizontal axis indicates the coordinate $\tau_c$ on a PI-line, whereas the vertical axis shows a stack of PI-lines specified by $s_a = -0.65\pi$ and $s_b \in [0.24\pi, 0.46\pi]$. The display window [1.0, 1.04] was chosen to demonstrate the low-contrast features in the reconstructed images. In order to show quantitatively the reconstruction accuracy, the lower row of FIGS. 71A-C shows the image profiles on a PI-line, specified by $s_a = -0.65\pi$ and $s_b = 0.35\pi$, reconstructed by use of the BPF (FIG. 71A), MDFBP (FIG. 71B), and FBP (FIG. 71C) methodologies, respectively, for a curved detector.

Figures 72A, 72B, 72C:
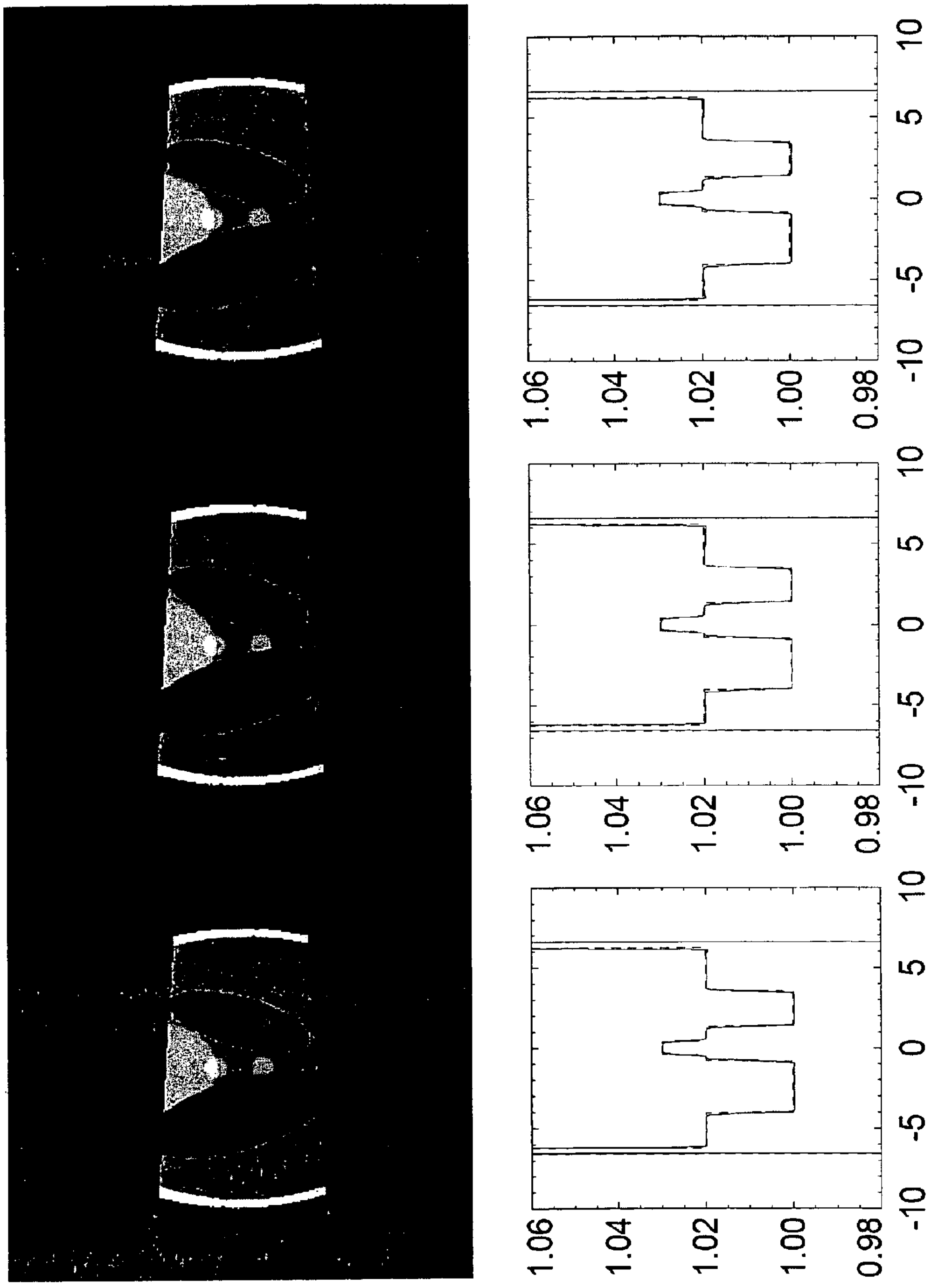
FIGS. 72*a-c* show how images in the fixed-coordinate system may be readily converted from PI-line images. The upper row displays the images in the 2D plane y=−2.5 cm, which were converted from PI-line images reconstructed by use of the BPF (FIG. 72*a*), MDFBP (FIG. 72*b*), and FBP (FIG. 72*c*) methodologies, respectively. In the lower row of FIGS. 72*a-c*, image profiles are displayed on a line specified by z=0.8 cm in the corresponding images in the upper row.

These images in the upper row of FIGS. 71A-C appear to be "distorted" because they are not displayed in the fixed-coordinate system. Images in the fixed-coordinate system may be readily converted from PI-line images. As shown in FIGS. 72A-C, the upper row displays the images in the 2D plane y=−2.5 cm, which were converted from PI-line images reconstructed by use of the BPF (FIG. 72A), MDFBP (FIG. 72B), and FBP (FIG. 72C) methodologies, respectively. Again, the display window is [1.0, 1.04]. In the lower row of FIGS. 72A-C, image profiles are displayed on a line specified by z=0.8 cm in the corresponding images in the upper row. For comparison, the corresponding true profile (dashed line) is also plotted. The horizontal axis of the lower row of FIGS. 72A-C has a unit of cm. It can be seen that, in the absence of noise, the BPF, MDFBP, and FBP methodologies for a curved detector yield virtually identical images that agree well with the original image.

Figures 73A, 73B, 73C:
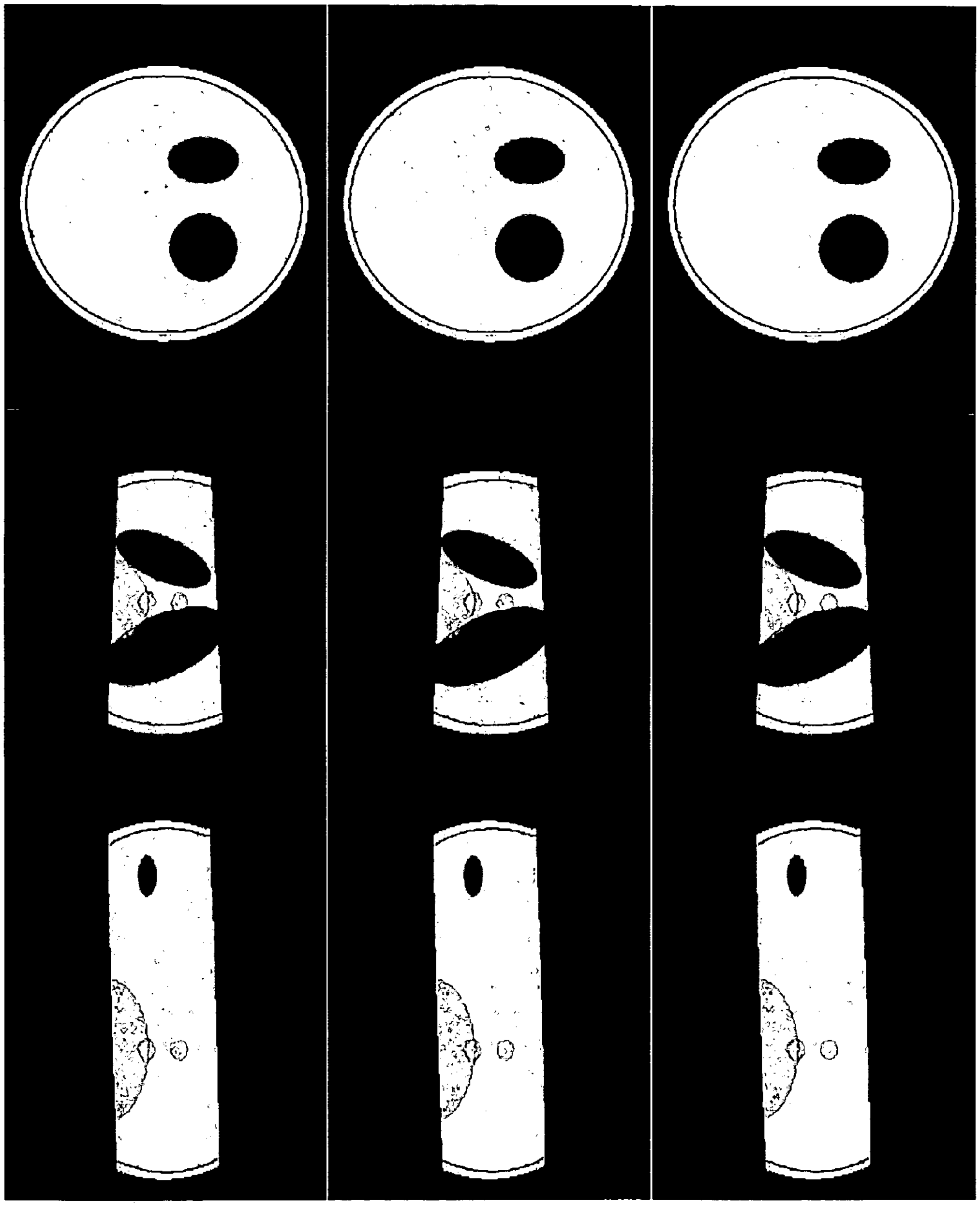
FIGS. 73*a-c* shows reconstructed images from the noisy data by use of the BPF (upper row), MDFBP (middle row), and FBP (lower row) methodologies for a curved detector.

Image reconstruction is also performed by use of the BPF, MDFBP, and FBP methodologies from noisy data that were generated by addition to the noiseless data, which have been used for obtaining the results above, Gaussian noise with a standard deviation that is 0.14% of the maximum value of noiseless data. The Gaussian noise is used merely for illustrative purposes. A standard deviation is used because it is comparable to the lowest contrast level in the 3D Shepp-Logan phantom subject to reconstruction. As shown in FIGS. 73A-C, images were reconstructed from the noisy data by use of the BPF (upper row), MDFBP (middle row), and FBP (lower row) methodologies for a curved detector. FIGS. 73A-C display the images within the sagittal (x=0 cm) (FIG. 73A), coronal (y=−2.5 cm) (FIG. 73B), and transverse (z=0 cm) (FIG. 73C) slices. It may be observed that the images obtained with these methodologies appear slightly different, suggesting that the methodologies in their discrete forms respond differently to data noise.

Figures 74A, 74B, 74C:
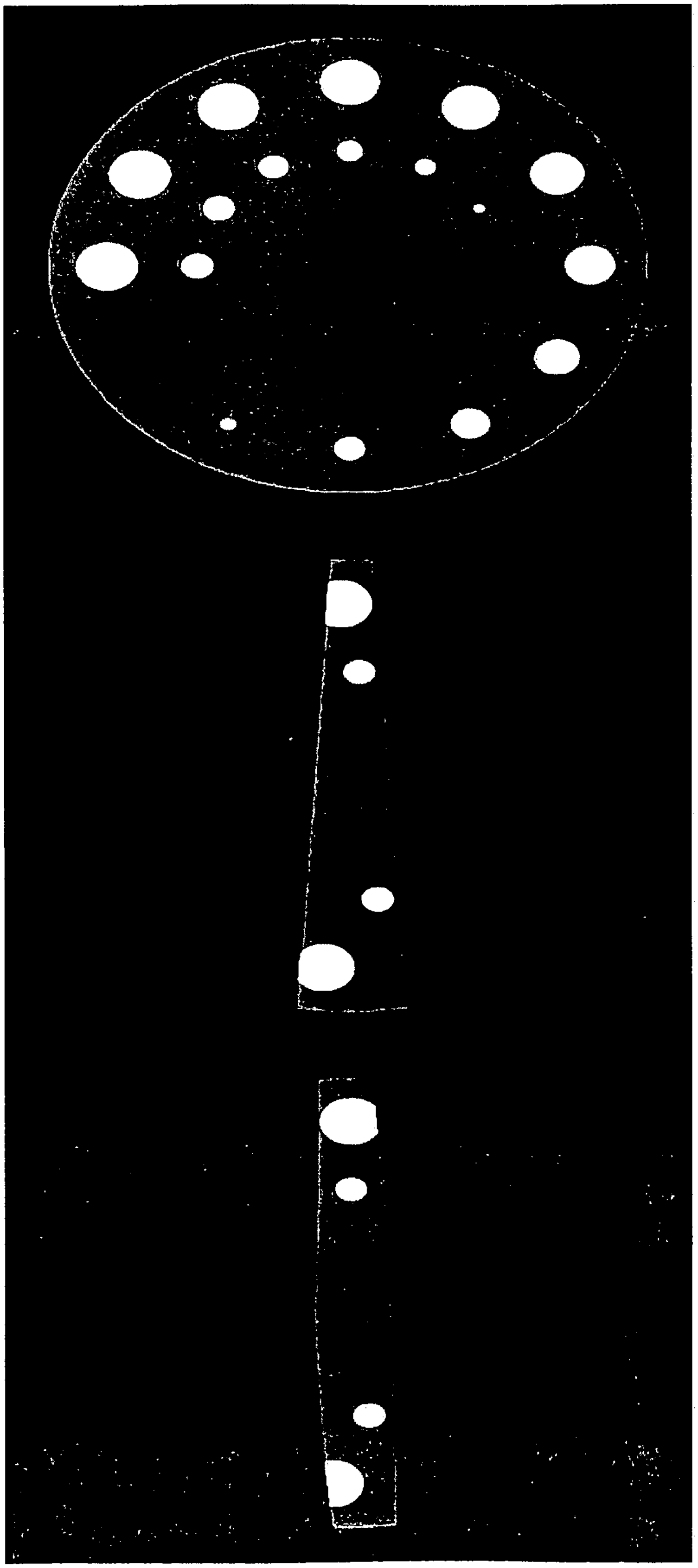
FIG. 74*a-c* display images in 2D planes within the coronal, the saggital, and transaxial slices reconstructed by use of the derived BPF methodology.

We also applied the chord-based methodologies to reconstructing images for the Clock phantom. In the analysis, a curved detector is used comprising 256 rows each of which includes 1536 detector elements with a size of 0.07 cm×0.07 cm. Cone-beam data was generated from the Clock phantom by using a helical configuration described above. The data set includes projections acquired at 1200 views uniformly distributed over s∈[−π, π]. The curved detector is placed at 5=100.5 cm, and it has a half-fan angle $\gamma_m$=30 degrees. About 321,201 PI-line segments were used, each of which contains 512 points within the FOV. FIG. 74A-C display images in 2D planes within the coronal (x=0 cm, FIG. 74A), the saggital (y=0 cm, FIG. 74B), and transaxial slices (z=0 cm, FIG. 74C) reconstructed by use of the derived BPF methodology. The display window is [0.9, 1.1]. Results similar to those in FIGS. 74A-C were also obtained by use of the MDFBP and FBP methodologies.

As discussed above, the BPF, MDFBP, and FBP methodologies for a curved detector may be applied to reconstructing images for general, non-helical source trajectories. Therefore, in addition to the analysis described above for a helical trajectory, studies were also conducted in which the methodologies for a curved detector were applied to reconstructing images for non-helical trajectories. Below, the results are shown for the analysis for a circle-line trajectory, which may find important applications in C-arm CT imaging and radiation-therapy imaging. In the following, only the results reconstructed by the BPF methodology are shown. The results for other methodologies may also be shown.

Figure 75B:
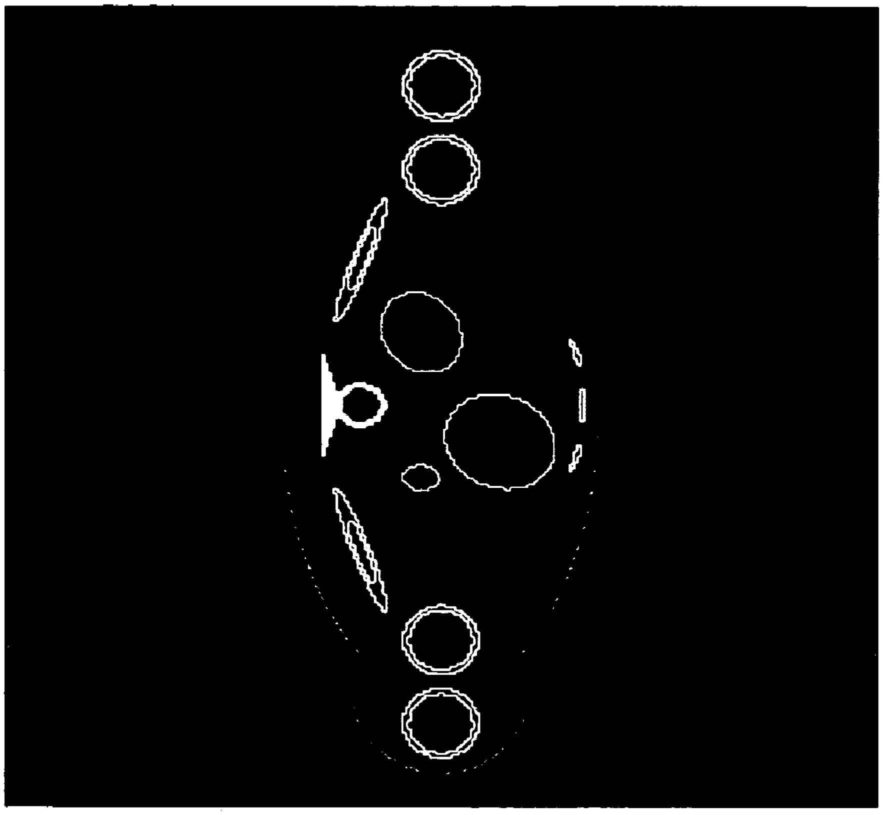
FIG. 75B displays the transverse slice of the 3D torso at Z=0.17 cm.
Figure 75A:
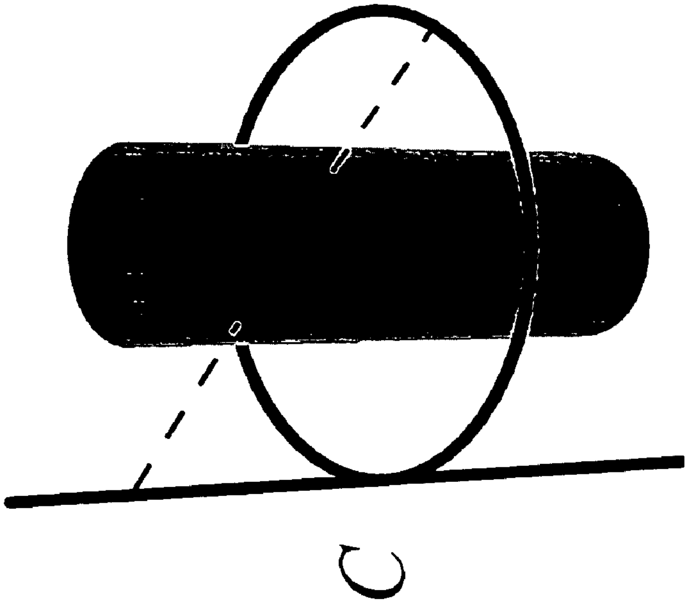
FIG. 75*a* shows the circle-line trajectory may comprise a circle-trajectory component with a radius R=57.0 cm and a line-trajectory component with a length L=31.31 cm.

As shown in FIG. 75A, the circle-line trajectory may comprise a circle-trajectory component with a radius R=57.0 cm and a line-trajectory component with a length L=31.31 cm. Without loss of generality, the line-trajectory component may be assumed to be perpendicular to the plane containing the circle-trajectory component; and its middle point C may intersect with the circle-trajectory component. Using the circle-line trajectory, cone-beam data is generated for a curved detector at 600 projection views that are distributed uniformly over the line-trajectory component and at 1542 projection views that are distributed uniformly over the circle-trajectory component, respectively. The curved detector used is identical to that described above. In this case, images are reconstructed only on chords that intersect both the line and circular trajectories. Therefore, about 87,600 chords were used each of which contains 512 points within the FOV. A 3D torso phantom is created that includes objects of ellipsoidal, cylindrical, and cone shapes for simulating the shoulders, heart, spine, and other organs within the body. FIG. 75B displays the transverse slice of the 3D torso at z=0.17 cm. The display window is [1.0, 2.5].

FIGS. 76A-B display the images within the plane of the circle-trajectory component reconstructed by use of the BPF methodology without noise (FIG. 76A) and with noise (FIG. 76B) for a curved detector. Using the noiseless data generated from the 3D torso phantom above as the means, noisy data may be generated by adding Gaussian noise with a standard deviation that is 1.5% of the maximum value of noiseless data. Furthermore, FIG. 76C shows the profiles along the lines specified by y=−0.26 cm and z=0.17 cm. For comparison, FIG. 76*c* also includes the true profiles as solid curves. It can be observed that the BPF methodology may accurately reconstruct images from the data acquired with a curved detector over a general, non-helical trajectory. Similar results may be obtained by use of the MDFBP and FBP methodologies, though not shown here.

The reconstructed images above demonstrate qualitatively the properties of the methodologies under discussion. Below, the spatial-resolution and noise properties are quantitatively investigated. The modulation transfer function (MTF) has been used for characterizing the spatial-resolution properties of a linear shift-invariant system. However, images reconstructed by use of the methodologies in their discrete forms are not, in general, shift-invariant transforms of the original image to be recovered. Therefore, the MTF may not meaningfully be applied to describing the spatial-resolution properties of images reconstructed by use of the methodologies in their discrete forms. Instead, the average modulus Fourier transform (AMFT), which reflects the Fourier content at a specific location within a reconstructed image, is used. The AMFT is a spatially dependent quantity that is defined as the modulus of the 2D discrete Fourier transform of the reconstruction of a point-like image averaged over the polar angle in the 2D Fourier space of the reconstructed image.

Figure 77C:
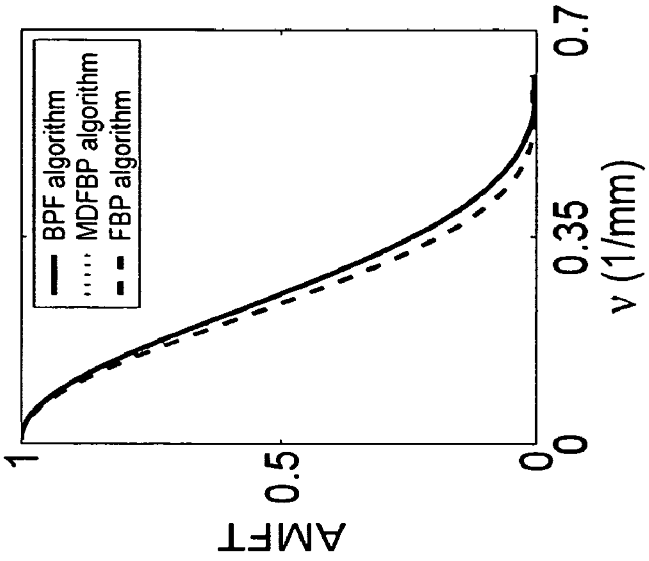
FIGS. 77*a-c* display the AMFTs within planes specified by x=0 cm (FIG. 77*a*), y=0 cm (FIG. 77*b*), and z=0 cm (FIG. 77*b*), respectively, obtained with the BPF (solid), MDFBP (dotted), and the FBP (dashed) methodologies for curved detectors.
Figure 77B:
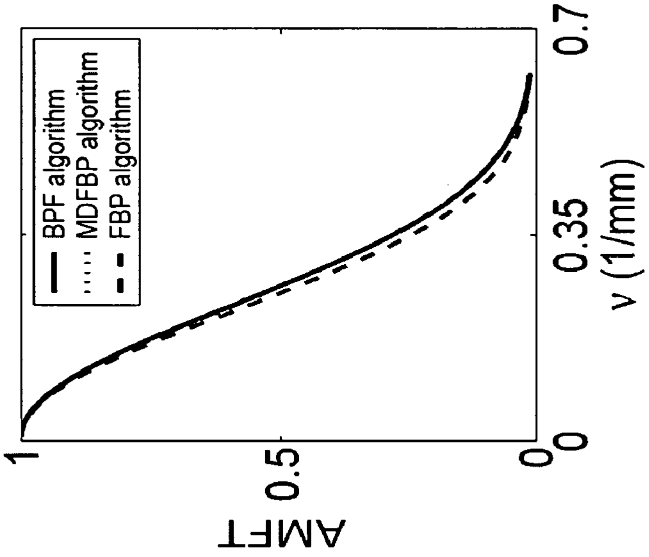
Figure 77A:
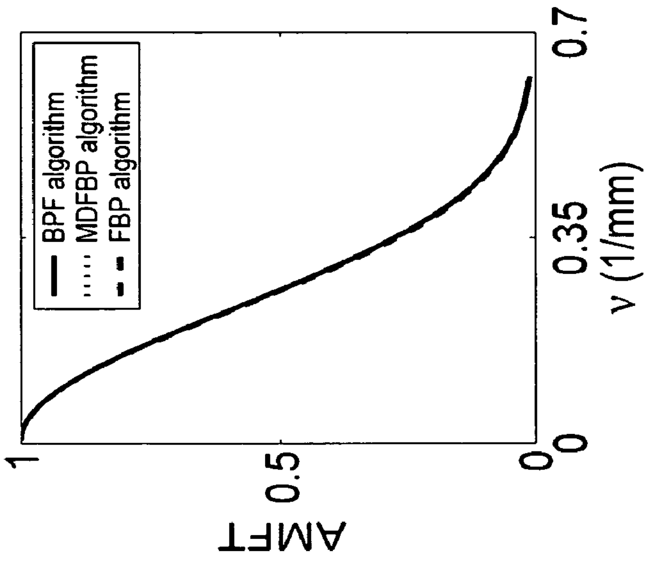
Figure 78A:
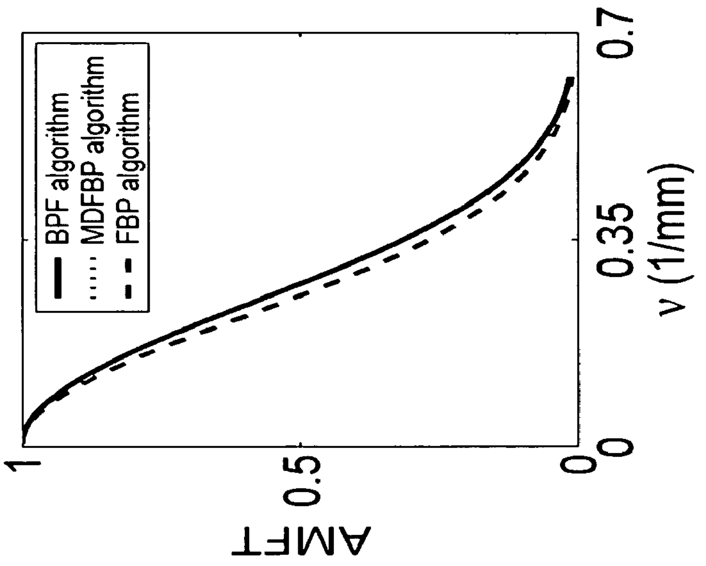
FIGS. 78*a-c* display the AMFTs within planes specified by x=5 cm (FIG. 78*a*), y=0 cm (FIG. 78*b*), and z=0 cm (FIG. 78*c*), respectively, obtained with the BPF (solid), MDFBP (dotted), and the FBP (dashed) methodologies for curved detectors.
Figure 78B:
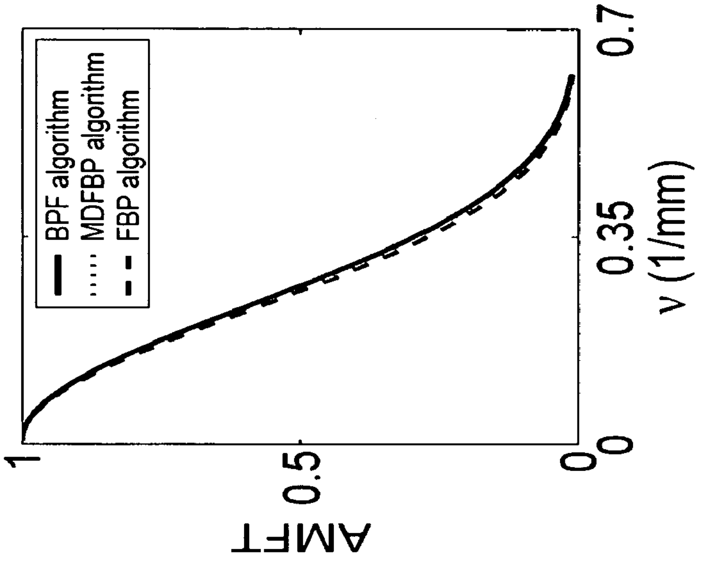
Figure 78C:
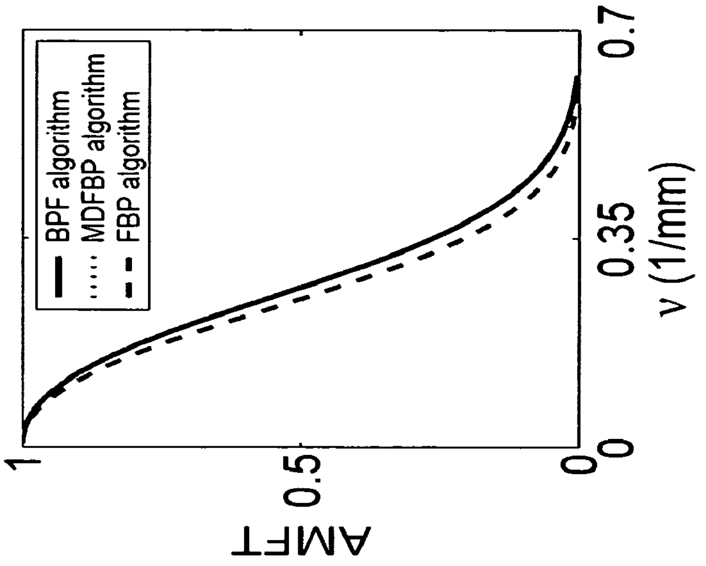

In the resolution study, cone-beam data were from a point-like phantom with a helical configuration specified by a radius R=50.0 cm, a pitch h=32.0 cm, and a source-to-central-axis distance S=50.0 cm. A curved detector was used comprising 256 rows each of which has 256 detector elements with a size of 0.2 cm×0.2 cm and forming a half-fan angle $\gamma_m$=30°. The data set includes projections acquired at 300 views uniformly distributed over s∈[−π, π]. In an attempt to have a set of PI-line segments so that they can provide a dense coverage of the point-like object. The interval [−π, π] is divided equally into 9,000 sub-intervals. In this analysis, the two reconstructions are investigated when the point-like object was placed at (0, 0, 0) (i.e., the center of the FOV) and (5, 0, 0), respectively. For the first case, each of $s_i$, i=1, 2, . . . , 300 uniformly distributed over [−0.538π, −0.471π], is selected as the starting point of PI-line segments. For each starting point $s_i$, each of $s_j$, j=1, 2, . . . , 166, uniformly distributed over [$s_i$+0.981π, $s_i$+1.018π], also selected as the ending point of a PI-line segment. Therefore, about 49,800 PI-line segments were used for reconstructing the point-like object at the center of the FOV. For the second case, each of $s_i$, i=1, 2, . . . , 270, uniformly distributed over [−0.498π, −0.445π], is selected as the starting point of PI-line segments. For each starting point $s_i$, each of $s_j$, j=1, 2, . . . , 300, uniformly distributed over $[s_i+0.906\pi, s_i+0.973\pi]$, is also selected as the ending point of a PI-line segment. Therefore, about 81,000 PI-line segments were used for this case. In each case, from images reconstructed on these PI-line segments, data is interpolated at their ends from the appropriate measurements. From the reconstructed images by use of the methodologies described, the AMFTs within the coronal, sagittal, and transaxial slices, respectively were calculated. The AMFTs were first determined for a point-like image near the center of the image space. FIGS. 77A-C display the AMFTs within planes specified by x=0 cm (FIG. 77A), y=0 cm (FIG. 77B), and z=0 cm (FIG. 77C), respectively, obtained with the BPF (solid), MDFBP (dotted), and the FBP (dashed) methodologies for curved detectors. It may be observed that the AMFTs obtained with the BPF and MDFBP methodologies virtually coincide with each other. On the other hand, the AMFT of the FBP methodology is slightly lower than that of the BPF and MDFBP methodologies, suggesting that images reconstructed by use of the BPF and MDFBP methodologies may have higher spatial resolution than the FBP methodology. In an effort to show the spatial-resolution difference at different locations within the image space, the AMFTs were also determined for a point-like image at x=5 cm on the x-axis. FIGS. 78A-C display the AMFTs within planes specified by x=5 cm (FIG. 78A), y=0 cm (FIG. 78B), and z=0 cm (FIG. 78C), respectively, obtained with the BPF (solid), MDFBP (dotted), and the FBP (dashed) methodologies for curved detectors. Again, the AMFTs obtained with the BPF and MDFBP methodologies are virtually the same, whereas the AMFT of the FBP methodology is slightly lower than that of the BPF and MDFBP methodologies. It may also be observed that the AMFT results for the two distinct locations are different, indicating that the resolution properties in the reconstructed images are spatially varying.

The noise properties of the three methodologies in their discrete forms were also analyzed numerically. The helical trajectory described above was used to generate noiseless cone-beam data from a uniform cylinder phantom of radius 12.5 cm at 300 views uniformly distributed over $s\epsilon[-\pi, \pi]$. The curved detector that includes 128 rows each of which has 128 detector elements with a size of 0.4 cm×0.4 cm forms a half-fan angle $\gamma_m$=30°. For this geometry, 14,100 chords were reconstructed, and for each chord 128 points within the FOV were computed. In the analysis, 500 sets of noisy data were used, which were obtained by adding to the noiseless data uncorrelated Gaussian noise with a standard deviation that is 1.25% of the maximum projection value. From these noisy data sets, the three methodologies were used to reconstruct 500 noisy images from which we subsequently computed empirical image variances.

The methodologies under discussion may first reconstruct images on chords before converting them into the Cartesian grid (or other coordinate system). Therefore, the image variances on chords were first determined. In particular, FIGS. 79A-C display the image variances on a set of chords, specified by $s_a=-\pi$ and $$s_b \in \left[-\frac{\pi}{3}, \frac{\pi}{3}\right],$$

obtained by use of the BPF (FIG. 79A), MDFBP (FIG. 79B), and FBP (FIG. 79C) methodologies, respectively. Each horizontal line in each panel of FIGS. 79A-C may represent a chord, with the lower the horizontal line, the smaller the value of $s_b-s_a$. For example, the bottom and top horizontal lines in each of FIGS. 79A-C represent the first and last chords that are specified by $s_b-s_a=2\pi/3$ and $4\pi/3$, respectively. Also, FIG. 80A shows the image variances on a chord represented by the central horizontal line from FIGS. 79A-C obtained by use of the BPF (solid), MDFBP (dotted), and FBP (dashed) methodologies, respectively. Furthermore, FIG. 80B shows the image variances across the different chords (i.e., along the central vertical line in FIGS. 79A-C) obtained by use of the BPF (solid), MDFBP (dotted), and FBP (dashed) methodologies, respectively. The above results indicate that image variances are generally non-uniform along a chord and across chords. Of note, the smaller the value of $s_b-s_a$, the higher the image variances on chords specified by $s_b-s_a$. This behavior of the image variances across chords may be caused by the spatially dependent weighting factors such as the $1/|\vec{r}-\vec{r}_0(s)|$ in the methodologies.

Once the chord images are reconstructed, the final images are determined by converting them onto the Cartesian grids. The variances in the final images may depend upon the interpolation schemes that are used for the image conversion. Two interpolation schemes were investigated in image conversion. For a voxel specified by (x, y, z) on the Cartesian grids, with a size of ΔxΔyΔz, the chords intersecting with this voxel are determined. In general, the voxel at different locations may have different number of intersecting chords. On each of these intersecting chords, the two points are identified that are closest to the center of the voxel. In the first interpolation scheme, the average image values are computed on the identified points from all of the intersecting chords with distance weights and the average value to the voxel is assigned. In the second scheme, the point on the intersecting chords, which is closest to the voxel, is identified and the image value on this chord point is chosen as the image value on the voxel. Because of the averaging process invoked in the first interpolation scheme, the image variances obtained with the first scheme may be generally lower than those obtained with the second interpolation scheme.

FIGS. 81A-C show image variances computed from images on the Cartesian grid converted from chord images by use of the first interpolation scheme. The image variances within 2D slices specified by x=−2.2 cm (FIG. 81A), y=−4.4 cm (FIG. 81B), and z=0 cm (FIG. 81C) are calculated from the reconstructed images obtained with the BPF (upper row), MDFBP (middle row), and FBP (lower row) methodologies for a helical scan. FIGS. 82A-C display image variances obtained by using the BPF (solid), MDFBP (dotted), and FBP (dashed) methodologies on lines (in FIGS. 81A-C) specified by x=−2.2 cm and y=−4.4 cm (FIG. 82A), x=−2.2 cm and z=0 cm (FIG. 82B), and y=−4.4 cm and z=0 cm (FIG. 82C). Similarly, FIGS. 83A-C show image variances computed from images on the Cartesian grid converted from chord images by use of the second interpolation scheme. The image variance within 2D slices specified by x=−2.2 cm (FIG. 83A), y=−4.4 cm (FIG. 83B), and z=0 cm (FIG. 83C) is calculated from the reconstructed images obtained with the BPF (upper row), MDFBP (middle row), and FBP (lower row) methodologies for a helical scan. FIGS. 84A-C depict image variances obtained by using the BPF (solid), MDFBP (dotted), and FBP (dashed) methodologies on lines (in FIGS. 83A-C) specified by x=−2.2 cm and y=4.4 cm (FIG. 84A), x=−2.2 cm and z=0 cm (FIG. 84B), and y=−4.4 cm and z=0 cm (FIG. 84C). From these results, one can see that the image variances obtained by use of the first interpolation scheme are lower than those obtained by use of the second interpolation. These results demonstrated that the noise properties of the final images on the Cartesian grid may depend not only upon the methodologies that reconstruct the chord images but also upon the interpolation schemes that convert the chord images onto the Cartesian grid.

Chord-based methodologies, including the BPF, MDFBP, and FBP methodologies, may be used for exact image reconstruction from cone-beam data acquired over helical and other source trajectories. These methodologies reconstruct images within an ROI or the entire object-support through reconstructing images on individual chords that compose the ROI or the entire object-support. The benefits offered by the methodologies include the easy identification of a reconstructible ROI for a given data set or of the sufficient cone-beam data for a given ROI to be reconstructed. Further, the BPF and MDFBP methodologies can exactly reconstruct an ROI image from data containing transverse truncations. These chord-based methodologies may be applied for cone-beam data acquired with a flat-panel detector.

In general, clinical CT systems may be equipped with curved detectors for increasing scanning speed, reducing gantry size, and possibly lowering detection cross-talks. Therefore, the chord-based methodologies may be modified to be used to reconstruct images for a clinical CT system that uses a curved detector for acquiring cone-beam data. Specifically, using the geometric relationship between the curved and flat-panel detectors, the chord-based methodologies may be generalized so that they are directly applicable to CT systems with curved detectors. Numerical studies were also conducted to validate and evaluate the chord-based methodologies for a curved detector. In these studies, cone-beam data, including transversely truncated data, were generated for a curved detector from numerical phantoms by use of the helical and circle-line trajectories. From the generated data, images were reconstructed by use of the derived BPF, MDFBP, and FBP methodologies for a curved detector. Quantitative results in these studies demonstrate that the derived chord-based methodologies for a curved detector can accurately reconstruct images. In particular, the BPF and MDFBP methodologies for a curved detector may exactly reconstruct ROI images from transversely truncated data.

The BPF methodology has a computational advantage over the MDFBP and FBP methodologies. Consider the image reconstruction within a 3D volume filled by M chords from data at N projection views. Based upon Eqs. (D-30), (D-31), and (D-33), it can be observed that the computational loads in the backprojections of the three methodologies are comparable. However, because the BPF methodology performs filtering along each chord, it may invoke M filterings along the M intersecting chords. On the other hand, for each view, the chord-based MDFBP and FPB methodologies may perform M filterings along the cone-beam projections of the M intersecting chords, and they may generally invoke N×M filterings.

Based upon the approach described above, one may also generalize the chord-based methodologies that may be used to reconstruct images from data acquired by use of detectors with shapes different from that of the curved or flat-panel detectors. Thus, any shape detector that is partly or fully curved, partly or fully flat, etc. such as such as a spherically shaped detector. Also, it is of theoretical as well as practical significance to compare the chord-based methodologies for curved detectors with the existing methodologies such as Katsevich's methodologies for curved detectors.

8. 3D Pet Image Reconstruction

Positron emission tomography (PET) is a powerful biomedical imaging modality that may provide in vivo molecular imaging with quantitative accuracy. Although PET imaging was introduced more than four decades ago, the technology is evolving rapidly in both instrumentation and reconstruction. One important development in the last decade is the introduction of three-dimensional (3D) PET imaging. Image reconstruction in 3D PET, which is considerably more challenging than that in 2D PET, may be achieved by use of analytic, iterative, or hybrid methods. The reprojection (3DRP) method and the Fourier rebinning (FORE) methodologies, followed by 2D filtered backprojection (2D FBP), are two popular approaches for yielding analytic 3D PET reconstruction. The FORE+2D FBP methodologies can produce images with a quantitative accuracy comparable to, and yet computationally more efficient than the 3DRP method, which is often regarded as the gold standard in analytic 3D PET reconstruction. As a result, FORE-based methodologies are becoming widely accepted for clinical use. Currently, the FORE methodologies are formulated for use with ring-based PET systems. Although an extension to panel-based PET systems has been reported, in general the extension of the FORE methodologies to work with the native coordinates of non-circular PET systems is not a trivial task, and one often derives approximate, analytic methodologies. In comparison with analytic methods, iterative methods can produce quantitatively improved PET images. Unfortunately, they are too computationally demanding to use in routine applications without utilization of specialized computation hardware. Hybrid methods attempt to achieve a reasonable compromise between image quality and computation cost. In one approach, the 3D PET data are first rebinned by use of the FORE methodologies to generate 2D direct-slice data. The direct-slice data are then reconstructed by use of 2D iterative methods. Overall, the field of 3D PET image reconstruction is far from mature; it is an area that requires improvements in methodology and in theoretical understanding.

The following discloses an analytic approach to achieving exact (or substantially exact) 3D PET image reconstruction by extending the chord-based reconstruction approach for x-ray cone-beam tomography (XCBT). This approach is an worthwhile alternative to existing exact analytic 3D PET reconstruction methods, can provide several practically important advantages over the existing methods, and generate theoretical insights into the 3D PET reconstruction problem, as discussed below. As previously mentioned, an advantage of the new analytic reconstruction approach is that it may work with PET systems with general geometry. This approach may be applied directly to reconstructing images for conventional ring-based PET systems, as well as non-conventional PET systems, such as the rectangular PET system that is made of four flat-panel detectors or made of curved-panel detectors. This approach is applied to reconstructing images in the rectangular PET system for demonstrating the unique features of the approach. In addition, other panel-based clinical PET systems may also exist, and the use of detector panel may enable building high-throughput clinical PET systems, application-specific PET imagers, and high-performance small-animal PET scanners. The methodology development discussed is relevant to such panel-based PET systems as well.

The approach for analytic 3D PET reconstruction is based on the chord-based reconstruction approach. The following is an analysis using a specific chord-based reconstruction approach, namely the chord-based x-ray cone-beam tomography reconstruction approach. Other types of chord-based reconstruction approaches may be used.

In x-ray cone-beam imaging, the source-detector assembly, comprising a single x-ray point source and a 2D detector, may move around the image function, denoted by $f(\vec{r})$, during scanning. Without loss of generality, one can assume a flat detector or a curved detector in the derivation. The following analysis focuses on a flat detector; however, a curved detector may be used. The movement of the assembly may be specified by the trajectory of the source, which will be denoted as $\vec{r}_s(\lambda)$, where λ is the path length parameterizing the trajectory. The orientation of the assembly, on the other hand, may be identified by the orientation of the detector. Let $\hat{u}_d(\lambda)$ and $\hat{v}_d(\lambda)$ denote two orthonormal basis vectors attached to the detector, and $(u_d, v_d)$ the coordinates of a point on the detector with respect to this local coordinate system. In addition, the origin of this detector-coordinate system is denoted by $\vec{r}_d(\lambda)$. The vector $\hat{w}_d(\lambda)=\vec{r}_d(\lambda)-\vec{r}_s(\lambda)/|\vec{r}_d(\lambda)-\vec{r}_s(\lambda)|$ is assumed to be perpendicular to the detector face, and the distance between the source and the detector is S. Using these definitions, the cone-beam data acquired at λ may be expressed mathematically as:

$$P(u_d,v_d,\lambda)=\int_0^\infty dt f(\vec{r}_s(\lambda)+t\hat{\beta}(u_d,v_d,\lambda)), \quad \text{(E-1)}$$

where the unit vector $\hat{\beta}(u_d, v_d, \lambda)$ denotes the direction from the source to the point $(u_d, v_d)$ on the detector. Consider a source trajectory $\vec{r}_s(\lambda)$ for $\lambda\in[\lambda_{min}, \lambda_{max}]$, where $\lambda_{min}$ and $\lambda_{max}$ indicate the starting and end points of the trajectory. One may connect two distinct points $\vec{r}_s(\lambda_a)$ and $\vec{r}_s(\lambda_b)$ on the trajectory, where $\lambda_{min}\leqq\lambda_a<\lambda_b\leqq\lambda_{max}$, to form a line segment. Such a line segment, denoted as $C(\lambda_a, \lambda_b)$, may be called a chord of the trajectory $\vec{r}_s(\lambda)$. The chord line $\overline{C}(\lambda_a, \lambda_b)$, on the other hand, refers to the line that contains the chord $C(\lambda_a, \lambda_b)$.

Given a chord line $\overline{C}(\lambda_a, \lambda_b)$, one can define $$\vec{r}'(x)=x\,\vec{r}_s(\lambda_a)+(1-x)\,\vec{r}_s(\lambda_b),\ -\infty<x<\infty, \quad \text{(E-2)}$$

so that $g(x)=f(\vec{r}')$ is the 1D restriction of the image function onto $\overline{C}(\lambda_a, \lambda_b)$. The point $\vec{r}'(x)$ may be projected onto the local detector coordinates $u'_d(x, \lambda)$ and $v'_d(x, \lambda)$ when the source is at the position $\vec{r}_s(\lambda)$, thus resulting in:

$$u'_d(x,\lambda)=\frac{(\vec{r}'(x)-\vec{r}_s(\lambda))\cdot\hat{u}_d(\lambda)}{(\vec{r}'(x)-\vec{r}_s(\lambda))\cdot\hat{w}_d(\lambda)}S \text{ and} \quad \text{(E-3)}$$

$$v'_d(x,\lambda)=\frac{(\vec{r}'(x)-\vec{r}_s(\lambda))\cdot\hat{v}_d(\lambda)}{(\vec{r}'(x)-\vec{r}_s(\lambda))\cdot\hat{w}_d(\lambda)}S.$$

The functional dependences of the quantities such as $\vec{r}'$, $\vec{r}_s$, $u'_d$, $v'_d$, and $\hat{\beta}$ may be implicitly assumed for notational simplicity. Let $g_H(x)$ denote the Hilbert transform of g(x), and define the modified data function $$P_m(u_d, v_d, \lambda) \quad \text{(E-4)}$$

as

-continued $$P_m(u_d, v_d, \lambda) = -\left[\frac{d\vec{r}_s}{d\lambda}\cdot\hat{\beta}\right]P(u_d, v_d, \lambda)+A(u_d, v_d)\left\{\left(\frac{d\vec{r}_s}{d\lambda}, \hat{u}_d\right)\frac{\partial}{\partial u_d}+\left(\frac{d\vec{r}_s}{d\lambda}, \hat{v}_d\right)\frac{\partial}{\partial v_d}\right\}P(u_d, v_d\lambda),$$

where $A(u_d, v_d)$ is the distance between the source and the point $(u_d, v_d)$ on the detector. It has been shown that $$g_H(x)=\frac{1}{\pi}\int_{\lambda_a}^{\lambda_b} d\lambda\frac{1}{|\vec{r}-\vec{r}_s'|^2}P_m(u'_d, v'_d, \lambda)+\left.\frac{P(u'_d, v'_d, \lambda)}{|\vec{r}-\vec{r}_s|}\right|_{\lambda=\lambda_a}^{\lambda_b}. \quad \text{(E-5)}$$

Therefore, within a constant, the backprojection image on a chord line may be the Hilbert transform of the image function on the chord line. Consequently, one may recover the image function on the chord line by computing the inverse Hilbert transform of Eq. (E-5).

Several important observations have been made based on the above results. First, Eq. (E-5) may be valid for continuous source trajectories that are piecewise $C^1$ smooth, e.g., connected trajectories that contain only a finite number of non-differentiable points (such points are called kinks below). Therefore, the resulting reconstruction methodologies may have general applicability, not limited to any specific system configuration and not requiring a smooth source trajectory. Second, the image function on a given line may be obtained from data measured by using any piecewise $C^1$ smooth source trajectory that intersects with the line. This finding allows one to design various imaging configurations for achieving exact reconstruction within given regions of interest (ROIs). Third, the computation of the modified data function may involve only local operations (scaling and derivative). Consequently, the local projection data of a chord line (e.g., an open set that may contain the projection data of the chord line) may be sufficient for obtaining exact reconstruction on the chord line. The fourth observation is related to the fact that image functions of practical interest have compact supports. The theorem of the finite Hilbert transform states that the Hilbert transform of a compact 1D function evaluated on its support interval contains sufficient information for complete recovery of the function inside the support interval. Moreover, closed-form formulas for achieving this recovery are available. As a consequence of this theorem and the fact that the reconstruction for a chord line requires only the local data function, non-trivial truncations to the data function may occur without affecting the evaluations of Eq. (E-5) over certain finite support intervals of the image function. The above observations have significant practical implications for imaging, including CT imaging. For example, it may enable a targeted ROI imaging strategy in which one employs variable radiation apertures and vintage source trajectories for minimizing scan time and avoiding unnecessary radiation exposure. Several specific examples of this targeted ROI imaging may be possible by use of the chord-based XCBT reconstruction approach.

Using Eq. (E-5) and the inverse finite Hilbert transform, three chord-based XCBT methodologies may be developed previously for reconstructing compactly-supported image functions. In the present example, only the so-called BPF methodology for 3D PET image reconstruction is analyzed. However, other chord-based methodologies (including minimum-data FBP and filtered-backprojection (FBP)) may also be extended to reconstruct PET images. Using Eq. (E-2), a chord may be specified by the parameter range $x \in [0, 1]$. Let $x_{s_1}$ and $x_{s_2}$ denote the intersection of the chord and the object support. By assumption, we have $[x_{s_1}, x_{s_2}] \subset [0, 1]$. In the BPF methodology, the image function $f(\vec{r})$ over the interval $[x_A, x_B]$ on the chord $C(\lambda_a, \lambda_b)$, which satisfies $[x_{s_1}, x_{s_2}] \subset [x_A, x_B] \subset [0, 1]$, is computed as the sum of two components as $$f(\vec{r}\,') = \frac{f_{bp}(\vec{r}\,') + f_{bc}(\vec{r}\,')}{2\pi^2\sqrt{(x_B - x)(x - x_A)}},\ x \in [x_A, x_B]. \tag{E-6}$$

The term $f_{bp}(\vec{r}\,')$, derived from the backprojection of the modified data function and inverting the finite Hilbert transform, may be given by:

$$f_{bp}(\vec{r}\,') = \int_{x_A}^{x_B} \frac{dx'}{x - x'}\sqrt{(x_B - x')(x' - x_A)} \int_{\lambda_a}^{\lambda_b} d\lambda \frac{P_m(u_d', v_d', \lambda)}{|\vec{r}\,' - \vec{r}_s|^2}. \tag{E-7}$$

On the other hand, the term $f_{bc}(\vec{r}\,')$ may be determined by a single projection measurement:

$$f_{bc}(\vec{r}\,') = \left[\frac{\pi\sqrt{(2l - x_B)(2l - x_A)}}{2l - x} + \frac{\pi\sqrt{x_B x_A}}{x}\right] P(u_{d0}, v_{d0}, \lambda_a), \tag{E-8}$$

where $l = |\vec{r}_s(\lambda_b) - \vec{r}_s(\lambda_a)|/2$, and $u_{d0}$ and $v_{d0}$ are $u'_d$ and $v'_d$ obtained at $\lambda = \lambda_a$.

Analytic PET reconstruction methodologies are conventionally derived by consideration of the parallel-beam projection geometry. However, PET data may also be organized as effective cone-beam data as follows. In PET, a pair of detection elements may define a line of response (LOR), which is typically defined as the line connecting the center of the front faces of the two detection elements. Assuming ideal spatial resolution and ignoring factors such as attenuation, scatter, and randoms, PET measurements may then provide line integrals of the activity distribution along the LORs provided by a scanner. In comparison, the line integrals in cone-beam imaging are defined by the lines connecting the point source to elements in the 2D detector. Therefore, one may treat an arbitrary detection element in PET as the "source" in cone-beam imaging with the other detection elements as detectors. By appropriately selecting a set of detection elements to serve as the source, one may then create an effective source trajectory from PET data, thus reformulating the PET data into "cone-beam" data. Consequently, the chord-based XCBT reconstruction approach can be applied to achieving exact reconstruction on chords of the chosen effective source trajectory.

Because the chord-based XCBT reconstruction approach may work with general continuous source trajectories, exact reconstruction methodologies may be derived for general PET system configurations. In addition, as indicated by Eqs. (E-4) and (E-6)-(E-8), the resulting methodologies may generate images directly from projection data, without requiring intermediate steps such as reprojection and rebinning in other analytic 3D PET reconstruction methods.

As mentioned above, the reconstruction approach may be directly applicable to the conventional circular PET configuration. Recently, there is also a growing interest in using flat-panel detectors for building PET systems. Therefore, applications of the chord-based reconstruction approach to exact image reconstruction for a rectangular PET system that is made of four flat-panel detectors are illustrated (shown schematically in FIGS. 85A-C). The LORs generated by this configuration do not conveniently occur at the native coordinates assumed in existing analytic methods developed for cylindrical PET systems. Although data may be interpolated, this process generally degrades the resulting image resolution and shall be avoided whenever possible—a consideration that is especially relevant for small-animal PET imaging.

Figure 1A:
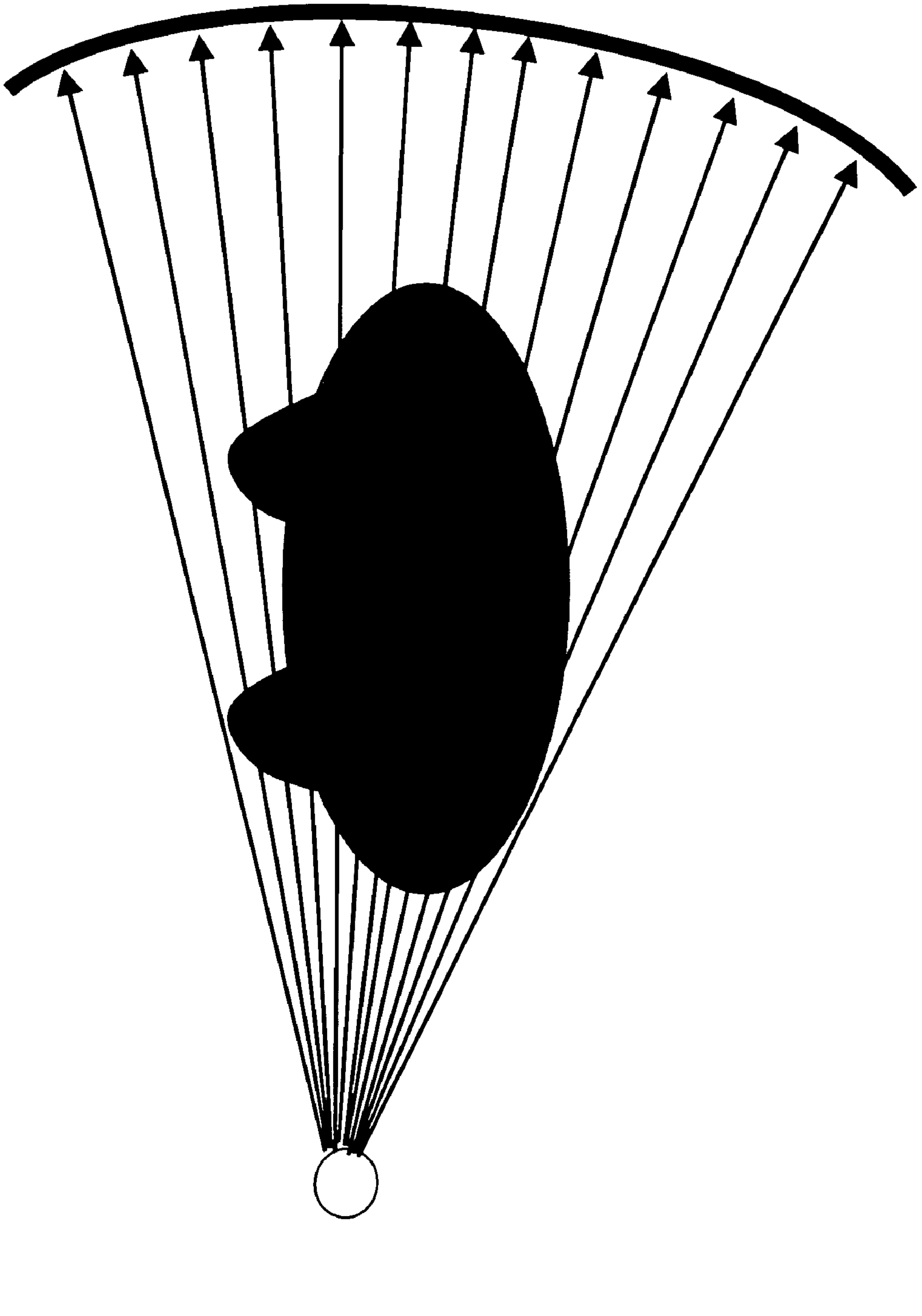
FIGS. 1*a* and 1*b* show two cross-sections of a source, object, and detector when scanning a torso to acquire data for use in imaging using an FBP methodology.

FIGS. 85A-C illustrate the reformulation of PET data into XCBT data. For simplicity, a 2D PET is first illustrated with a square configuration as shown in FIG. 1*a* in which we obtain fan-beam projections with the virtual source moving along the square detector-ring of the 2D PET system. Specifically, FIG. 85A illustrates two examples of fan-beam projections generated by grouping the LORs associated with a given detection element (designated as A or B in FIG. 85A) in a 2D rectangular PET system. By artificially advancing the detection element along the detector faces (indicated by arrows in FIG. 85A), an effective source trajectory may be obtained. Clearly, in this case there exists only one effective source trajectory (disregarding possible differences in the direction and speed). The selection of effective source trajectories in the 3D case, however, is no longer unique: there may exist an infinite number of ways for connecting paths on the four flat-panel detectors of the system. FIG. 85B illustrates an effective source trajectory formed by connected line segments on adjacent panel detectors. FIG. 85B depicts a 3D rectangular PET system comprising four flat-panel detectors, wherein the effective source trajectory is not unique and any connected path defined on the detector faces is valid. As an example, FIG. 85B shows the trajectory obtained by projecting a helical path onto the detectors. Thus, as one can observe, this effective trajectory may form a square helical configuration; the pitch of the helical path may be varied for obtaining different trajectories. FIG. 85C shows an additional effective source trajectory, denoted as 3h1v, in which the virtual source moves horizontally on three panel detectors before moving up vertically. Because of the rectangular geometry of the PET system, both trajectories contain kinks at the junctions of the panel detectors. Although unusual, the presence of kinks does not pose technical difficulty in the chord-based XCBT reconstruction approach since they may be naturally handled by the backprojection operation in Eq. (E-7).

The BPF methodology may be applied for 3D PET reconstruction by using the square helical and 3h1v trajectories shown in FIGS. 85B and 85C. The axis of the four-panel PET system may be aligned with the z-axis, and $R_0$ may denote the distance between the panel and the axis.

Without loss of generality, one may parameterize a square helical trajectory as $$\vec{r}_s(\lambda) = \begin{cases} (R_0, 2R_0\lambda - R_0, h\lambda)^T & \lambda \in [0, 1), \\ (-2R_0\lambda + 3R_0, R_0, h\lambda)^T & \lambda \in [1, 2), \\ (-R_0, -2R_0\lambda, +5R_0, h\lambda)^T & \lambda \in [2, 3), \\ (2R_0\lambda - 7R_0, R_0, h\lambda)^T & \lambda \in [3, 4), \end{cases} \quad \text{(E-9)}$$

where h may be analogous to the pitch in the conventional helical trajectory. Specifically, Eq. (E-9) may define one revolution of the trajectory around the z-axis that axially advances a distance of 4h. Below, a virtual flat detector that is $2R_0$ away from the source is assumed. The movement of the source-detector assembly may contain four linear translations as given by Eq. (E-9) above. More or fewer linear translations may be used. For example, instead of a cube, as depicted in FIGS. 85B-C, an enclosure with a cross section of a pentagon, hexagon, etc. may be used, so that five or six sided. Any number of sides may be used. For example, the number of sides may approach infinity to obtain a circular cross section (such as a cylinder or a sphere in 3D). At λ=1, 2, 3, the assembly rotates 90° so that the virtual detector is parallel to either the xz- or yz-plane, Thus, one can define:

$$\hat{u}_d(\lambda) = \begin{cases} (0, -1, 0)^T & \lambda \in [0, 1), \\ (1, 0, 0)^T & \lambda \in [1, 2), \\ (0, 1, 0)^T & \lambda \in [2, 3), \\ (-1, 0, 0)^T & \lambda \in [3, 4), \end{cases} \quad \text{(E-10)}$$

and $\hat{v}_d(\lambda) = (0, 0, 1)^T, \lambda \in [0, 4)$.

In addition, $A(u_d, v_d) = \sqrt{u_d^2 + v_d^2 + 4R_0^2}$, and the unit vector $\hat{\beta}(u_d, v_d, \lambda)$ is equal to:

$$\hat{\beta}(u_d, v_d, \lambda) = \begin{cases} \frac{1}{A(u_d v_d)}(-2R_0, -u_d, v_d)^T & \lambda \in [0, 1), \\ \frac{1}{A(u_d v_d)}(u_d, -2R_0, v_d)^T & \lambda \in [1, 2), \\ \frac{1}{A(u_d v_d)}(2R_0, u_d, v_d)^T & \lambda \in [2, 3), \\ \frac{1}{A(u_d v_d)}(-u_d, 2R_0, v_d)^T & \lambda \in [3, 4). \end{cases} \quad \text{(E-11)}$$

Consequently, the modified projection data given by Eq. (E-4) may be computed by using $$\begin{aligned} P_m(u_d, v_d, \lambda) &= -\frac{-2R_0u_d + hv_d}{A(u_d, v_d)} P(u_d, v_d, \lambda) + \\ & A(u_d, v_d)\left\{-2R_0\frac{\partial}{\partial u_d} + h\frac{\partial}{\partial v_d}\right\}P(u_d, v_d, \lambda) \\ &= \left\{-2R_0\frac{\partial}{\partial u_d} + h\frac{\partial}{\partial v_d}\right\}P'(u_d, v_d, \lambda), \end{aligned} \quad \text{(E-12)}$$

where $P'(u_d, v_d, \lambda) = A(u_d, v_d)P(u_d, v_d, \lambda)$.

For the 3h1v trajectory, one may similarly define:

$$\vec{r}_s(\lambda) = \begin{cases} (R_0, -R_0 + 2R_0\lambda, 0,)^T & \lambda \in [0, 1), \\ (-2R_0\lambda + 3R_0, R_0, 0)^T & \lambda \in [1, 2), \\ (-R_0, -2R_0\lambda + 5R_0, 0)^T & \lambda \in [2, 3), \\ (-R_0, -R_0, h\lambda)^T & \lambda \in [3, 4), \end{cases} \quad \text{(E-13)}$$

with the virtual source-detector assembly containing four linear translations and two 90° rotations at λ=2, 3. In this case, $A(u_d, v_d)$ and $\hat{v}_d(\lambda)$ are the same as above. On the other hand, there is:

$$\hat{u}_d(\lambda) = \begin{cases} (0, -1, 0)^T & \lambda \in [0, 1), \\ (1, 0, 0)^T & \lambda \in [1, 2), \\ (0, 1, 0)^T & \lambda \in [2, 4), \end{cases} \quad \text{(E-14)}$$

$$\text{and } \hat{\beta}(u_d, v_d, \lambda) = \begin{cases} \frac{(-2R_0, -u_d, v_d)^T}{A(u_d v_d)} & \lambda \in [0, 1), \\ \frac{(u_d, -2R_0, v_d)^T}{A(u_d v_d)} & \lambda \in [1, 2), \\ \frac{(2R_0, u_d, v_d)^T}{A(u_d v_d)} & \lambda \in [3, 4). \end{cases}$$

It therefore follows that:

$$P_m(u_d, v_d, \lambda) = \begin{cases} -2R_0\frac{\partial}{\partial u_d}P'(u_d, v_d, \lambda) & \lambda \in [0, 3), \\ h\frac{\partial}{\partial v_d}P'(u_d, v_d, \lambda) & \lambda \in [3, 4). \end{cases} \quad \text{(E-15)}$$

The virtual detector assumed in the above formulations is not entirely identical to the actual panel detectors in the rectangular PET system. However, it is not difficult to see that there exists a simple geometric relationship between them. In the implementation, the LORs of the PET measurements may be identified on the coordinate system of the virtual cone-beam imaging configuration, generating non-uniformly sampled data in the virtual cone-beam geometry. The partial derivatives in Eqs. (E-12) and (E-15), and the backprojection in Eq. (E-7) may then be computed, by using their discrete approximations. There need not be data interpolations in this process.

Chord-based reconstruction methodologies may guarantee exact reconstruction on chords. Therefore, in order to reconstruct a volume of interest, one may select an effective source trajectory such that every point in the volume may be passed by at least one chord of the trajectory. Or, the chords may be sufficiently dense such that every voxel in the volume will have at least one chord passing through it. It may be seen that, using the 3h1v trajectory, the reconstructible volume may the pentahedral volume of which the vertices are the two end points and three kinks of the trajectory. The reconstructible volume with a square helical trajectory, on the other hand, may be less obvious. It has been shown previously that the π-line segments of a conventional helical trajectory, which, in terms of our definition, are chords of which the two end points are spaced within one square helical revolution, may completely fill the cylindrical volume enclosed by the trajectory. This set of special chords may be referred to as the one-turn chords. Below, it is shown that one-turn chords of a square helical trajectory may also completely fill the square prism enclosed by the trajectory. However, unlike the case with the conventional helical trajectory, for a square helical trajectory, multiple one-turn chords may pass through a point within the square prism.

Numerical studies were performed to demonstrate the effectiveness of the chord-based reconstruction methodologies described above. The projection data was simulated for a four-panel PET system with $R_0$=26.5 cm when imaging a 3D Shepp-Logan phantom. The square helical trajectory was considered with one revolution with 4h=8.1 cm, and the 3h1v trajectory with h=5.8 cm. The Shepp-Logan phantom may be made of ellipsoids; therefore, by assuming idealized detection (e.g., factors such as detector blurring and subjection attenuation may be ignored), noiseless projection data were analytically calculated. 1024 projections, i.e., 1024 source positions, uniformly distributed on the source trajectories were generated. A noisy projection dataset was also generated by introducing Poisson noise to the analytically calculated noiseless dataset. The maximum value of the mean event count of this noisy dataset is 100.

FIGS. 86A-B and 87A-C show the images of the Shepp-Logan phantom reconstructed by use of the chord-based BFP methodology from noiseless data (FIG. 86A) and from noisy data (FIG. 86B) for the square helical trajectory. Images in FIGS. 86A-B were obtained on a sample set of one-turn chords specified by a fixed $\lambda_a$ and $1 \leqq \lambda_b < 3$. From Eq. (E-9), one may see that this set of one-turn chords spans a 2D surface that is made of two non-coplanar planes joining at the chord given by $\lambda_b$=2. When displayed on the chord coordinates, the resulting images therefore exhibit an apparent folding at this joining chord. After reconstructing on all one-turn chords of the trajectory, the results are converted onto the usual Cartesian coordinate system, yielding the results shown in FIGS. 87A-C.

Figure 86B:
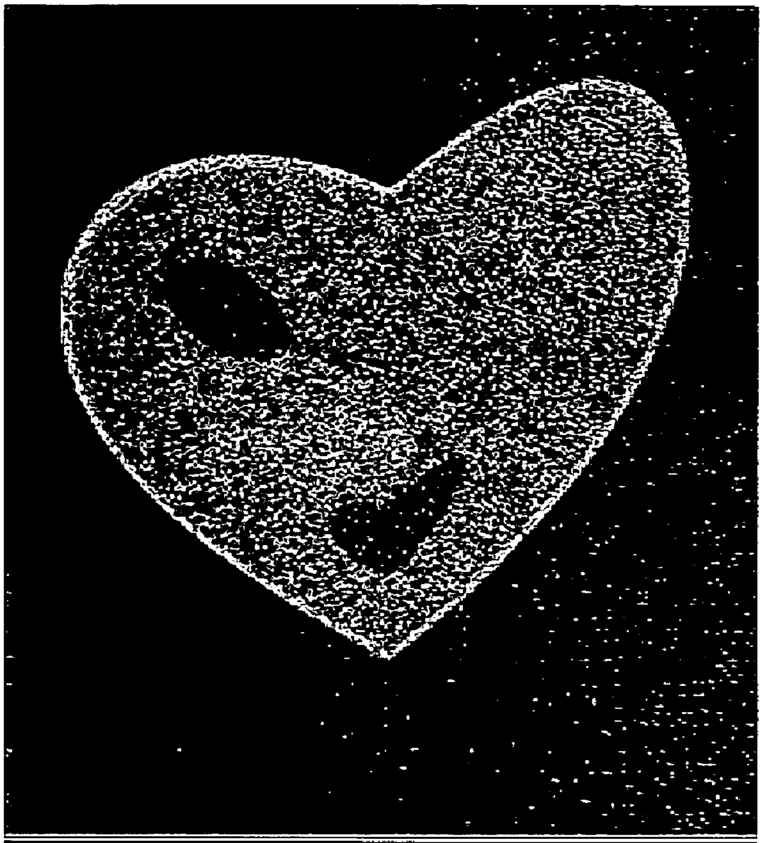
Figure 86A:
Figures 87A, 87B, 87C:
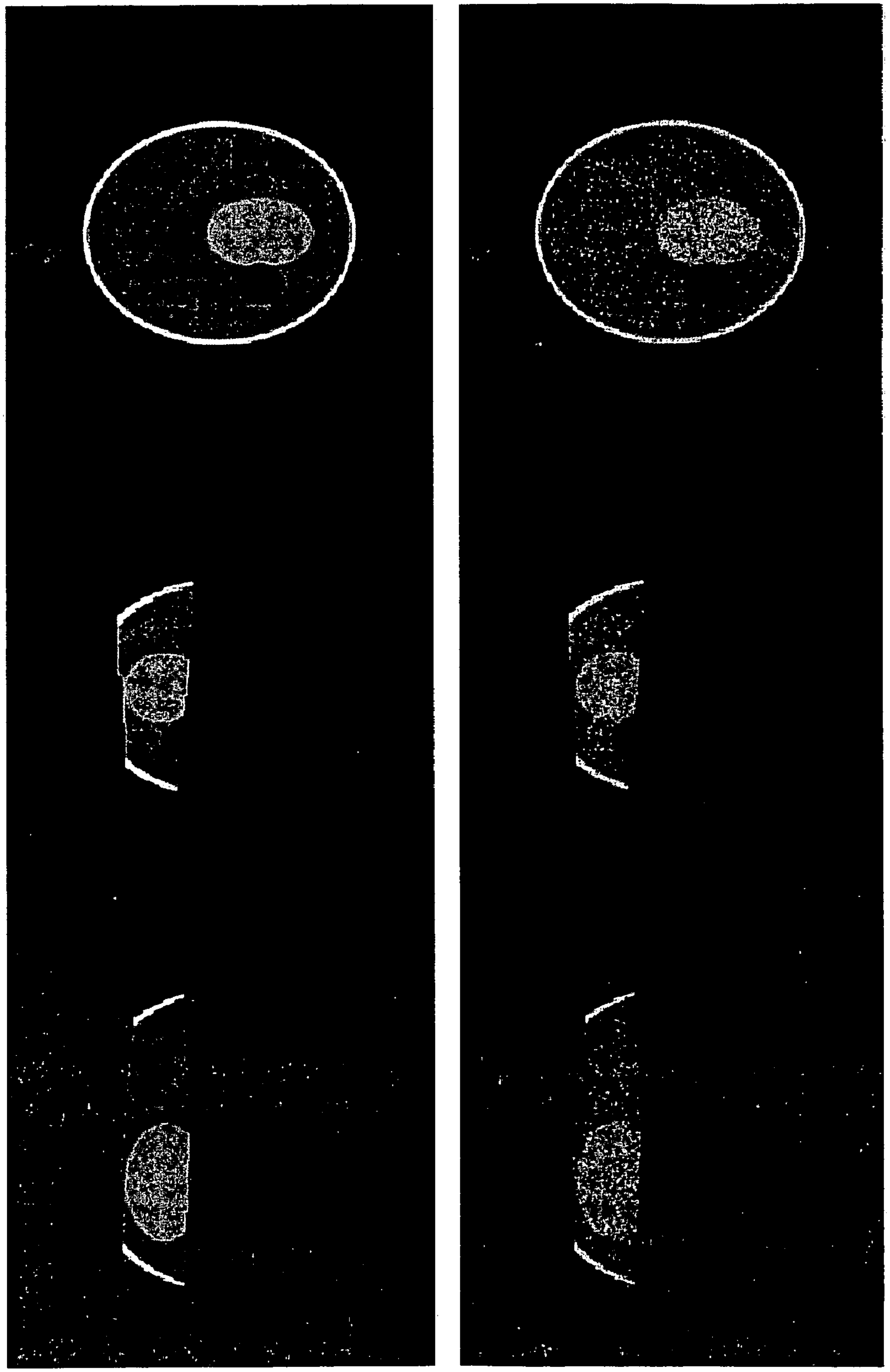

FIGS. 87A-C illustrate images of numerical Shepp-Logan phantom reconstructed by use of the BPF algorithm from noiseless (upper row) and noisy (lower row) data with the square helical trajectory. FIGS. 87A-C show 2D image slices obtained on the sagittal plane at x=0 cm (FIG. 87A), on the coronal plane at y=−2.7 cm (FIG. 87B), and on the transaxial plane at z=1.5 cm (FIG. 87C), respectively. These images are in good agreement with the original Shepp-Logan phantom. In the noiseless result shown in FIGS. 87A-C, no image artifacts are observed and fine structures in the phantom are adequately recovered. The noisy results in FIGS. 86A-B and 87A-C also show subjectively acceptable image quality.

In FIGS. 88A-B, images of the numerical Shepp-Logan phantom on a set of chords reconstructed by use of the BPF algorithm from noiseless data (FIG. 88A) and noisy data (FIG. 88B) derived for the 3h1v trajectory are shown. In FIGS. 88A-B, every horizontal line in the images represents a chord specified with a fixed $\lambda_a$ and $3 \leqq \lambda_b < 4$, with $\lambda_b$ increasing from the bottom to the top of the image. These images appear distorted because they are displayed on the chord coordinates. Specifically, this chord set may define a single triangular plane and the resulting images obtained on the chord do not display the apparent folding as seen in FIGS. 86A-B.

FIGS. 89A-C illustrate images of a numerical Shepp-Logan phantom reconstructed by use of the BPF algorithm from noiseless (upper row) and noisy (lower row) data with the 3h1v trajectory. FIGS. 89A-C are 2D image slices obtained on the sagittal plane at x=0 cm (FIG. 89A), on the coronal plane at y=−2.7 cm (FIG. 89B), and on the transaxial plane at z=0.7 cm (FIG. 89C). These images are in good agreement with the original Shepp-Logan phantom. Good image quality is also observed for images obtained from noisy data. Thus, the reconstructed images from noiseless data shown in FIGS. 89A-C again indicate that fine and low-contrast structures in the phantom may be adequately recovered by the methodology when applied to noiseless data. When applied to noisy data, the results in FIGS. 88A-B and 89A-C also show suitable statistical properties. The reconstructible volume with the 3h1v trajectory may be different from that with the square helical trajectory; this is reflected by the differences between the reconstructed regions shown in FIGS. 87A-C and 89A-C.

The present analysis discloses an analytic approach for achieving exact image reconstruction in 3D PET by considering PET data as effective cone-beam projections so that the chord-based XCBT approach may be applied to the resulting effective cone-beam data. A 3D rectangular PET system that is made of four flat-panel detectors was specifically considered. Other configurations are contemplated. No exact analytic reconstruction methodologies have been developed to work with the native data coordinates of such a rectangular PET system. The numerical results indicate that the resulting methodologies are accurate and appear not to deleteriously respond to data noise.

In comparison with the existing analytic 3D PET reconstruction methodologies, the present approach has four properties. First, as above, one may readily derive exact reconstruction methodologies to work with the native data coordinates in general PET system geometries, including panel-based PET systems. In addition, these methodologies may directly reconstruct images from PET data, without requiring intermediate steps such as reprojection or rebinning. Second, this reconstruction approach offers a substantial degree of freedom in how an image volume can be reconstructed. For example, one may employ different sets of chord (called chord sets) to fill the volume. In addition, there exist multiple possibilities in defining the effective source trajectories for a given chord set. Different selections of the chord set and effective source trajectories may lead to different reconstruction methodologies. Third, only the local data function is needed for reconstructing the image on a chord. The combination of the second and third properties suggest that different portions of the data function may be employed by different methodologies for reconstructing an image volume. Fourth, the existence of closed-form formulas for inverse finite Hilbert transform, in combination with the third property, may enable targeted ROI reconstruction for compact image functions.

The above-discussed properties may result in several practically important advantages of the reconstruction approach over existing methodologies. The first advantage is related to the ability in dealing with defective detection elements. In iterative methods, defective measurements may be removed from consideration in reconstruction, therefore reducing or minimizing their negative impacts to the image quality. This is not the case with existing analytic reconstruction methodologies. Consequently, defective measurements typically lead to deleterious artifacts in analytically reconstructed PET images. With the present approach, one may exploit the freedom, in the selection of chord sets and effective source trajectories, and the local data properties observed above to avoid using defective measurements in reconstruction. Similar considerations also suggest the second advantage of the methodologies: they may be better in handling certain missing data problems such as those due to the gaps between panel or block detectors. The third advantage derives from its targeted ROI reconstruction capability. This feature may be utilized to reduce the reconstruction volume, and thus the reconstruction time, in certain applications in which one is interested only in selected portions of the image (such as the heart in cardiac studies). In targeted ROI image reconstruction, one may reject a substantial amount of measurement for reconstruction. This may help reduce the scatter fraction in the targeted ROI.

The reconstruction approach may have important theoretical value as well. The above-observed freedom in obtaining different reconstruction methodologies that may in principle employ different portions of the data function for reconstructing an image volume is a surprising finding. Of note are how the noise properties of the reconstructed images in a volume are affected by the selection of the chord set and effective source trajectories (e.g., how the magnitude and characteristics of the image noise are affected by the change in the pitch of the square helical trajectory.) For reducing image noise, it may be useful to form weighted sums of the images on a given chord that are obtained by use of different effective source trajectories.

The following is an analysis of the square helical trajectory discussed above. The square helical trajectory may be parameterized as:

$$\begin{cases} \vec{r}_s(\lambda) = & (R_0,\ 2R_0\lambda - R_0,\ h\lambda)^T & \lambda \in [0, 1), \\ \vec{r}_s(\lambda) = & (-2R_0\lambda + 3R_0,\ R_0,\ h\lambda)^T & \lambda \in [1, 2), \\ \vec{r}_s(\lambda) = & (-R_0,\ -2R_0\lambda + 5R_0,\ h\lambda)^T & \lambda \in [2, 3), \\ \vec{r}_s(\lambda) = & (2R_0\lambda - 7R_0,\ -R_0,\ h\lambda)^T & \lambda \in [3, 4), \\ \vec{r}_s(\lambda) = & (R_0,\ 2R_0\lambda - 9R_0,\ h\lambda)^T & \lambda \in [4, 5), \\ \vec{r}_s(\lambda) = & (-2R_0\lambda + 11R_0,\ R_0,\ h\lambda)^T & \lambda \in [5, 6), \\ \ldots & \ldots & \ldots \end{cases} \quad \text{(E-16)}$$

$\lambda_a$ and $\lambda_b$ may be used to denote the intersecting points of a chord with the trajectory. Any point (x, y, z) on the chord satisfies:

$$x = x_s(\lambda_a) + l[x_s(\lambda_b) - x_s(\lambda_a)],$$

$$y = y_s(\lambda_a) + l[y_s(\lambda_b) - y_s(\lambda_a)],$$

$$z = z_s(\lambda_a) + l[z_s(\lambda_b) - z_s(\lambda_a)], \quad \text{((E-17)}$$

where $\vec{r}_s(\lambda) = (x_s(\lambda), y_s(\lambda), z_s(\lambda))^T$ and $0<l<1$ is a parameter indicating the position along the chord. Below it is shown that a special set of chords, which intersect the trajectory within one turn, i.e., with $|\lambda_b - \lambda_a| \leqq 4$, may completely fill the volume of the square prism formed by the four flat-panel detectors. For convenience, this special set of chords is referred to as the one-turn chords.

Consider a straight line L that is within the square prism and that is also parallel to the central axis of the square prism. It is first shown that line L can be completely filled by its intersections with a subset of the one-turn chords. Without loss of generality, one may assume that the distance between line L and the flat-panel detector on which the trajectory segment specified by $\lambda \in [0, 1)$ situates is shorter than the distances between line L and the other three flat-panel detectors. $x_0$ and $y_0$ are used to denote the x- and y-coordinates of line L. FIG. 90 illustrates a transverse section of the square prism. Line L, shown as a solid dot with coordinates $(x_0, y_0)$ within the x-y plane, is parallel to the central axis of the square prism and is closest to the flat-panel detector at $x=R_0$. As shown in FIG. 90, because line L is assumed to be closest to the flat-panel detector on which the trajectory segment specified by $\lambda \in [0, 1)$ situates, we have that $x_0 \geqq 0$ and $|y_0| \leqq x_0$.

The intersections of the one-turn chords with line L are investigated by varying λ from 0 to 4 and demonstrate that these intersections occupy continuously a portion of line L with a length of 4h. Let $\lambda_a$ and $\lambda_b$ depict the starting and ending points of a one-turn chord that intersects line L. Therefore, using $x_0$ and $y_0$ in the first two equations of Eq. (E-17), one can determine the relationship between $\lambda_a$ and $\lambda_b$. Applying it to the third equation in Eq. (E-17), one can subsequently derive the z-coordinate, $z_0(\lambda_a)$, of an intersection on line L as a function of $\lambda_a$, which is given in column one of Table 1.

One-turn chords formed by the trajectory segments on two adjacent flat-panel detectors may be within the same plane. Therefore, some of these one-turn chords intersect line L at the same point, implying that the volume within the square prism is not uniquely filled by the one-turn chords. However, the square prism volume may completely be filled by one-turn chords.

Based upon the result in Table 1, one may show that the intersections between a subset of one-turn chords and line L may completely fill line L. FIG. 91 is a plot of $z_0(\lambda_a)$ for $0<\lambda_a<4$. For simplicity, h and $R_0$ have been assumed to be one. Line L is specified by $x_0=0.5$ and $y_0=0.2$. In particular, the results in column one of Table 1, which are also displayed in FIG. 91, indicate that $z_0(\lambda_a)$ is a continuous function of $\lambda_a$. Furthermore, by adding respectively the results in columns one and two of Table 1, one may observe that a length of 4h on line L is filled completely by its intersections with a subset of one-turn chords specified by $0<\lambda_a \leqq 4$. Therefore, line L may completely be filled by a subset of one-turn chords. Moreover, the proof described above may readily be generalized to show that any straight line, which is within the square prism and parallel to the central axis of the square prism, may completely be filled by a subset of one-turn chords. Finally, because the square prism volume may completely be filled by a set of the straight lines each of which can be filled by its intersections with the one-turn chords, the square prism volume may completely be filled by the one-turn chords.

TABLE 1

The z-coordinate, $z_0(\lambda_a)$, on line L as a function of $\lambda_a$.

| $z_0(\lambda_a)$ | $\lambda_a$ | sign ($dz_0/d\lambda_a$) |
|---|---|---|
| $\frac{h}{2R_0}[y_0 - x_0 + 2R_0]$ | $0 \le \lambda_a < \frac{y_0 + x_0}{x_0 + R_0}$ | 0 |
| $\frac{h}{2R_0}[2(x_0 + R_0)\lambda_a - 3x_0 - y_0 + 2R_0]$ | $\frac{y_0 + x_0}{x_0 + R_0} \le \lambda_a < \frac{y_0 + R_0}{x_0 + R_0}$ | + |
| $\frac{h}{2R_0}\left[x_0 + y_0 - \frac{4(y_0 + R_0)}{\lambda_a} + 8R_0\right]$ | $\frac{y_0 + R_0}{x_0 + R_0} \le \lambda_a < 1$ | + |
| $\frac{h}{2R_0}[2(y_0 + R_0)\lambda_a + x_0 - 5y_0 + 2R_0]$ | $1 \le \lambda_a < \frac{-x_0 + R_0}{y_0 + R_0} + 1$ | + |
| $\frac{h}{2R_0}\left[-x_0 + y_0 + \frac{4(x_0 - R_0)}{\lambda_a - 1} + 10R_0\right]$ | $\frac{-x_0 + R_0}{y_0 + R_0} + 1 \le \lambda_a < 2$ | + |
| $\frac{h}{2R_0}[2(-x_0 + R_0)\lambda_a + 7x_0 + y_0 + 2R_0]$ | $2 \le \lambda_a < 3$ | + |

TABLE 1-continued

The z-coordinate, $z_0(\lambda_a)$, on line L as a function of $\lambda_a$.

| $z_0(\lambda_a)$ | $\lambda_a$ | sign ($dz_0/d\lambda_a$) |
|---|---|---|
| $\frac{h}{2R_0}[y_0 + x_0 + 8R_0]$ | $3 \le \lambda_a < \frac{x_0 - R_0}{-y_0 + R_0} + 4$ | 0 |
| $\frac{h}{2R_0}[2(-y_0 + R_0)\lambda_a - x_0 + 9y_0 + 2R_0]$ | $\frac{x_0 - R_0}{-y_0 + R_0} + 4 \le \lambda_a < 4$ | + |

Alternatively, a new analytic methodology is disclosed for image reconstruction from data acquired in PET systems with cylindrical and/or panel-based configurations by generalizing our x-ray cone-beam reconstruction techniques. Because the source trajectory may be any continuous path that is piecewise smooth (as discussed above), the methodologies discussed above may be applied to work with the native data coordinates of cylindrical and/or panel-based PET systems, without requiring interpolation of the data onto certain preferred coordinates. Therefore, one source of resolution loss in the conventional analytic PET reconstruction may be eliminated. In addition, because the techniques allow exact ROI reconstruction from reduced data that satisfy certain conditions, the reconstruction problems due to failed detection elements and detector gaps may be avoided for certain ROIs. Being analytic, the performance of these methods, such as image noise characteristics and spatial resolution, may also be analytically studied. Furthermore, the new techniques may be powerful for investigating the idea of modular design in which a PET system's configuration is flexible for yielding optimized performance under varying imaging conditions. In this case, the concepts developed in the methodologies discussed above may allow one to examine whether a given configuration can generate exact reconstructions for prescribed ROIs, before reconstruction is performed. Given an imaging task, one can therefore develop suitable configurations for use and select among those that can meet certain conditions, such as maximized sensitivity.

9. ROI-Image Reconstructions from Data Acquired with a Straight-Line Source Trajectory As disclosed above, there have been several methodology developments in image reconstruction for cone-beam computed tomography (CT). In particular, the backprojection-filtration (BPF) method allowed the possibility of 3D ROI reconstruction from a minimum projection data set in helical, cone-beam CT, because it provided a means to reconstruct volume images from data that is truncated longitudinally and transversely on the detector. The same methodology may be applied to apply to cone-beam CT with general x-ray source trajectories. The BPF methodology has also been adapted to the image reconstruction on so-called "M-lines" which offer even more flexibility on the scanning trajectory, and the BPF methodology has been derived from Tuy's formula. The BPF general methodology may apply to trajectories that do not satisfy Tuy's condition. One of these trajectories is presented below; namely, a volume image reconstruction methodology is derived for projection data acquired for an x-ray source moving on a straight line.

Image reconstruction from a straight-line trajectory may have many applications including medical imaging, such as tomosynthesis, and industrial or security scanning. Theoretically, the straight-line trajectory violates Tuy's sufficiency condition: any plane containing a point in the imaging ROI should intersect the source trajectory. For the straight-line trajectory there are some planes that intersect the imaging ROI, but, that do not intersect the source trajectory.

Below, a BPF methodology is disclosed for straight-line image reconstruction. The methodology may become exact in the limit that the source trajectory line segment goes to infinite length. A computer simulated phantom and test configuration is described to demonstrate the straight-line scan for different trajectory lengths. As the methodology is approximate, numerical results are compared with the widely used circular scanning trajectory.

The straight-line scanning configuration is quite flexible and can be executed physically in many ways. In medical imaging applications, the subject may remain stationary and the x-ray source may be translated by the patient; for industrial or security scanning, it may be desirable to fix the x-ray source and have the subject move on a straight-line; and for micro CT scanning, one could translate the x-ray source along a radial line while rotating the subject in such a way that the product of the source-to-rotation center distance, $R(\theta)$, and the sine of the subject angle, $\sin\theta$ remains constant. Without loss of generality, the straight-line source trajectory may move in the y=0 plane along the x-axis at a fixed height h in the z-direction:

$$\vec{r}_0(s)=(s,0,h). \tag{F-1}$$

The object function $f(\vec{r})$ may be compactly supported, and the trajectory does not intersect with the object support. For the standard BPF methodology, the image space is decomposed into chords of the scanning trajectory and the volume image is obtained chord-by-chord. Obviously, this concept may require some modification for the straight-line trajectory, because all chords of this trajectory lie on the same line. Also, the detector may be positioned relative to the source as discussed above.

The chord-lines upon which the straight-line BPF methodology yield the image are parallel to the trajectory. They may still be called chords and the intersection of the chords with the object support are support segments. An individual chord is identified by the vector $\vec{d}_0=(0, y_c, z_c)$. Thus, the expression specifying a point on an image chord is $$\vec{r}_c(x)=(x,0,0)+\vec{d}_0, \tag{F-2}$$

where x indicates the position along the chord.

The BPF methodology may entail a back-projection of the transmission data onto the chords of interest followed by a 1D filtering along the chords. The present analysis does not specify a particular geometry for the detector, and the detector-independent data function is written as $$D(s,x)=\int_0^\infty dt f[\vec{r}_0(s)+t\hat{\beta}(x)], \tag{F-3}$$

where the unit vector, $$\hat{\beta}(x)=\frac{\vec{r}_c(x)-\vec{r}_0(s)}{|\vec{r}_c(x)-\vec{r}_0(s)|}, \tag{F-4}$$

points from the x-ray source to the point $\vec{r}_c(x)$ in the image space.

The back-projection part of the methodology yields an intermediate image function $g_L(x)$ on the chord $\vec{r}_c(x)$, $$g_L(x) = \int_{-L}^{L} ds \frac{1}{|\vec{r}_c(x) - \vec{r}_0(s)|} \frac{\partial}{\partial_q} D(q, x)\bigg|_{q=s}. \quad \text{(F-5)}$$

The parameter L may specify the length of the line scan (2L). For a particular detector configuration, the equivalent back-projection formula may be obtained as described above. It can be shown that as L goes to infinity, $g_L(x)$ approaches the Hilbert transform of the image function along the chord, $f[\vec{r}_c(x)]$. The following filtration step is designed to invert the Hilbert transform, which would give the true object function when L approaches infinity.

The inversion of the Hilbert transform is complicated by the fact that in practical situations one does not have complete information of $g_L(x)$, which is in general not compactly supported along the chord. There are, however, inversion formulas for the case where a function's Hilbert transform is known on a finite segment larger than the support of the function. One of these formulas is applied here:

$$f_L(x) = \frac{1}{2\pi} \sqrt{\frac{x - x_a}{x_b - x}} \int_{x_a}^{x_b} dx' \frac{1}{x - x'} \sqrt{\frac{x_b - x'}{x' - x_a}} g_L(x'), \quad \text{(F-6)}$$

where the segment $[x_a x_b]$ contains the support segment. As L approaches infinity, $f_L(x)$ approaches the true image function $f[\vec{r}_c(x)]$ on the chord of interest.

Cone-beam image reconstruction for the straight-line trajectory configuration is investigated by looking at line trajectories of two different lengths and comparing also to circular cone-beam scanning.

FIG. 92 shows one type of non-straight source trajectory (shown as the curved line in FIG. 92). As shown, a chord may be drawn through the object (shown as the shaded region). FIG. 93 shows a straight source trajectory (the straight line in FIG. 93) with $\vec{r}_0$. The chord segments are also shown in FIG. 93. FIG. 94 further shows a segment for the source trajectory, designated as −L to L, with s being identified as one position for the source. Further, FIG. 94 shows a chord segment $x_a$ to $x_b$, with a point along the chord designated as x. As discussed above, as L goes to infinity, $g_L(x)$ approaches the Hilbert transform of the image function along the chord, $f[\vec{r}_c(x)]$. FIG. 95A depicts the dimensions of a long and short line trajectory, with L=61.3 cm for the long line trajectory and L=30.7 cm for the short line trajectory. Shown in FIG. 95B is a circular cone-beam scan, with a radius of 20 cm, so that the circumference of the circle shown in FIG. 95B is the same length as the long line scan depicted in FIG. 95A.

Figure 96B:
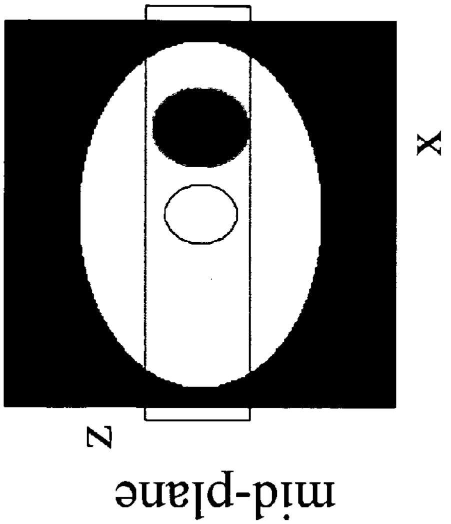
Figure 96C:
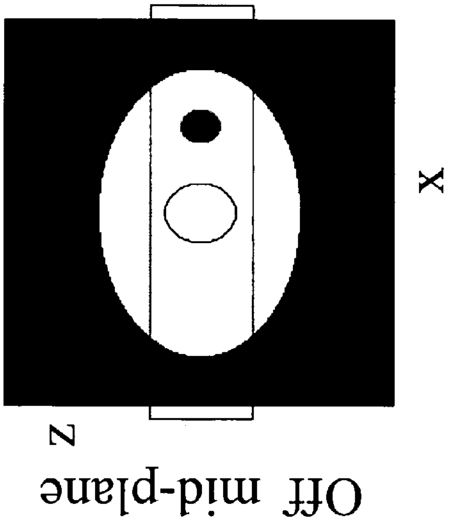
Figure 96A:
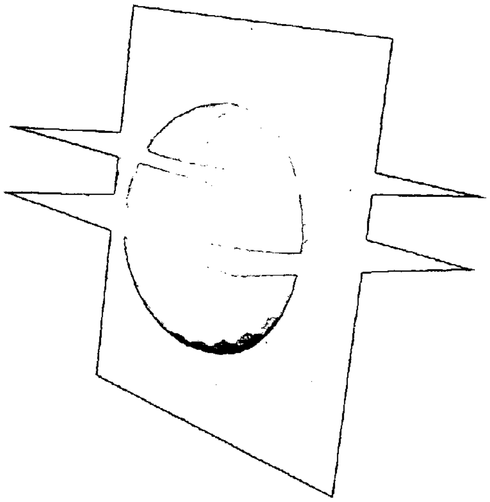
Figure 96D:
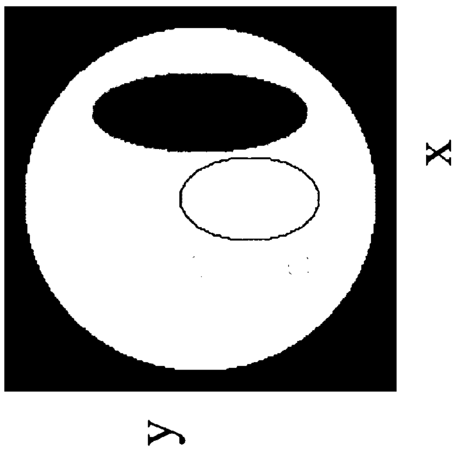

FIG. 96A is a schematic of the phantom with circular and line trajectories. The "in" plane slice, labeled a, "off"-plane slice, b, and a trans-axial slice c, are displayed in FIGS. 96B-D. "In" and "off" refer to the plane of the circular trajectory. Specifically, FIGS. 96B-D are slices of the computer-simulated phantom displayed in a gray scale window of [0.8, 1.2]: in-plane slice y=0 (FIG. 96B), off-plane slice y=5 cm (FIG. 96C), and trans-axial slice z=0 (FIG. 96D). The rectangles indicate the regions where the comparisons will be made with the reconstructed images in subsequent figures.

To test the reconstruction methodologies, the ellipsoidal computer generated phantom shown in FIGS. 96A-D is used. As can be seen, the line and circular trajectories are performed in the x-z plane. The image reconstruction results are compared for the regions indicated in FIGS. 96B-D for the y=0 plane (in-plane) and the y=5 cm plane (off-plane). Note that the line trajectory does not have "in-" and "off-" plane, because any of the chords described by Eq. (F-2) lie in a plane with the line trajectory. The terminology refers to the circular scan, where one may expect exact results for in-plane reconstruction versus approximate results for off-plane reconstruction. As shown below, these methodologies may reconstruct the image line-by-line, so that image reconstruction may be performed from data acquired with a straightline source.

For the line trajectory, the results for line trajectories are examined for two different lengths: a short line, L=30.7 cm and a long line L=61.3 cm (recall that the total scanning line length is actually 2L). The trajectories may pass rather close to the object h=7 cm for this simulation.

The image reconstruction results for the short-line and long-line scans are shown in FIGS. 97-105. FIGS. 97A-D show the mid-plane results, with FIG. 97A being the true reconstructed slice, and FIGS. 97B, 97C, and 97D being the reconstructed slices based on the short line trajectory, long line trajectory, and circular scan trajectory, respectively. The gray scale window is [0.8, 1.2]. FIGS. 98A-D show the off mid-plane results, with FIG. 98A being the true reconstructed slice, and FIGS. 98B, 98C, and 98D being the reconstructed slice based on the short line trajectory, long line trajectory, and circular scan trajectory respectively.

FIG. 99A is a true reconstructed slice for the off mid-plane profile (identical to FIG. 98A). FIGS. 99B-D represent the corresponding profiles for the short line trajectory, long line trajectory, and circular scan trajectory, respectively, for a horizontal line in the middle of the images, y=0, z=0. The solid curve is the reconstructed profile and the dashed curve represents the true phantom values.

For the short scan, mid-plane, FIG. 100A is identical to FIG. 97B, with an additional upper and a lower horizontal line through the images, and corresponding profiles for the lines in FIG. 100B and FIG. 100C, respectively. The solid curve is the reconstructed profile and the dashed curve represents the true phantom values. For the long scan, mid-plane, FIG. 101A is identical to FIG. 97C, with an additional upper and a lower horizontal line through the images, and corresponding profiles for the lines in FIG. 101B and FIG. 101C, respectively. The solid curve is the reconstructed profile and the dashed curve represents the true phantom values. For the circular scan, mid-plane, FIG. 102A is identical to FIG. 97D, with an additional upper and a lower horizontal line through the images, and corresponding profiles for the lines in FIG. 102B and FIG. 102C, respectively. The solid curve is the reconstructed profile and the dashed curve represents the true phantom values.

Figures 103A, 103B, 103C:
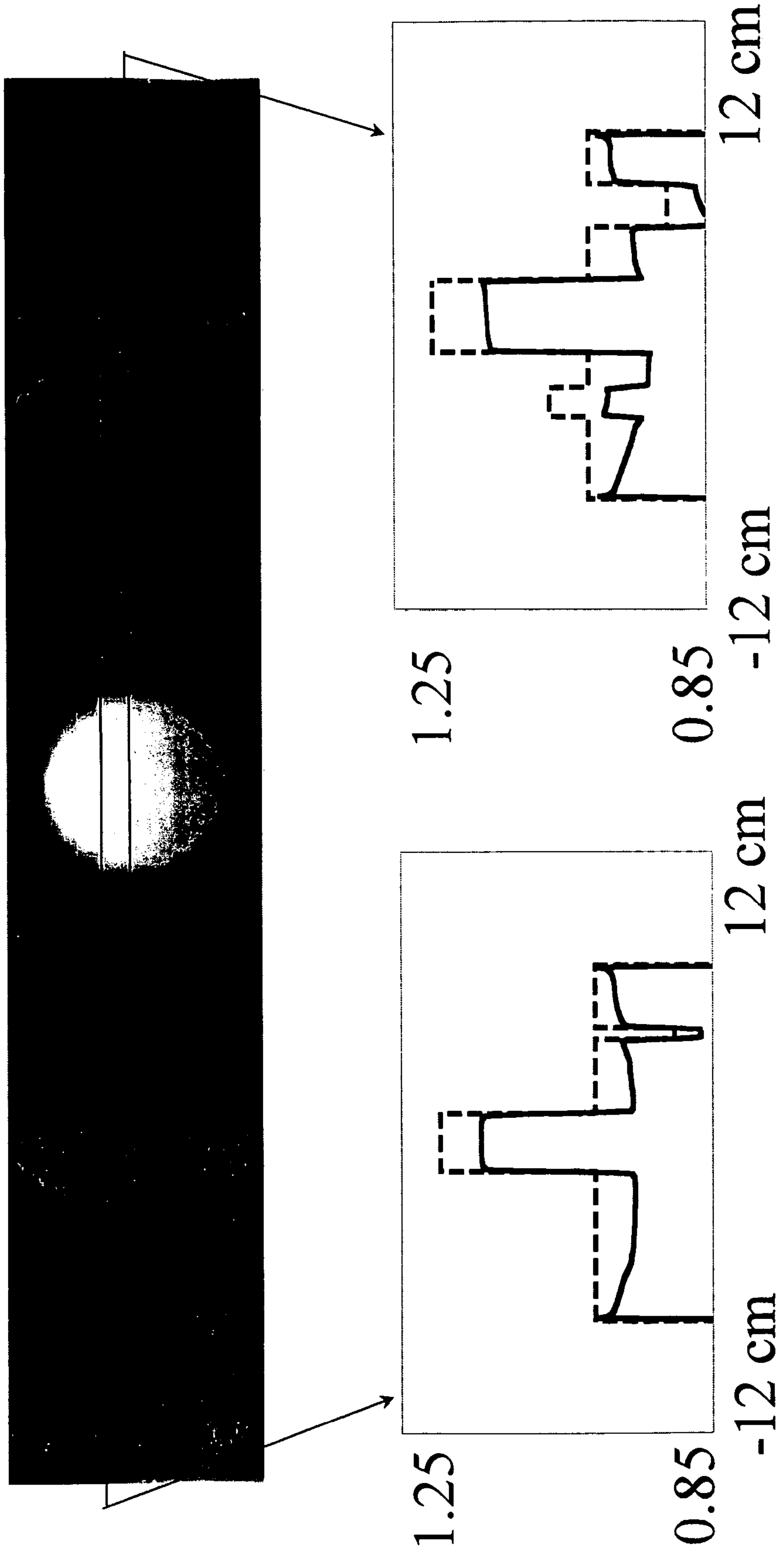
Figures 104A, 104B, 104C:
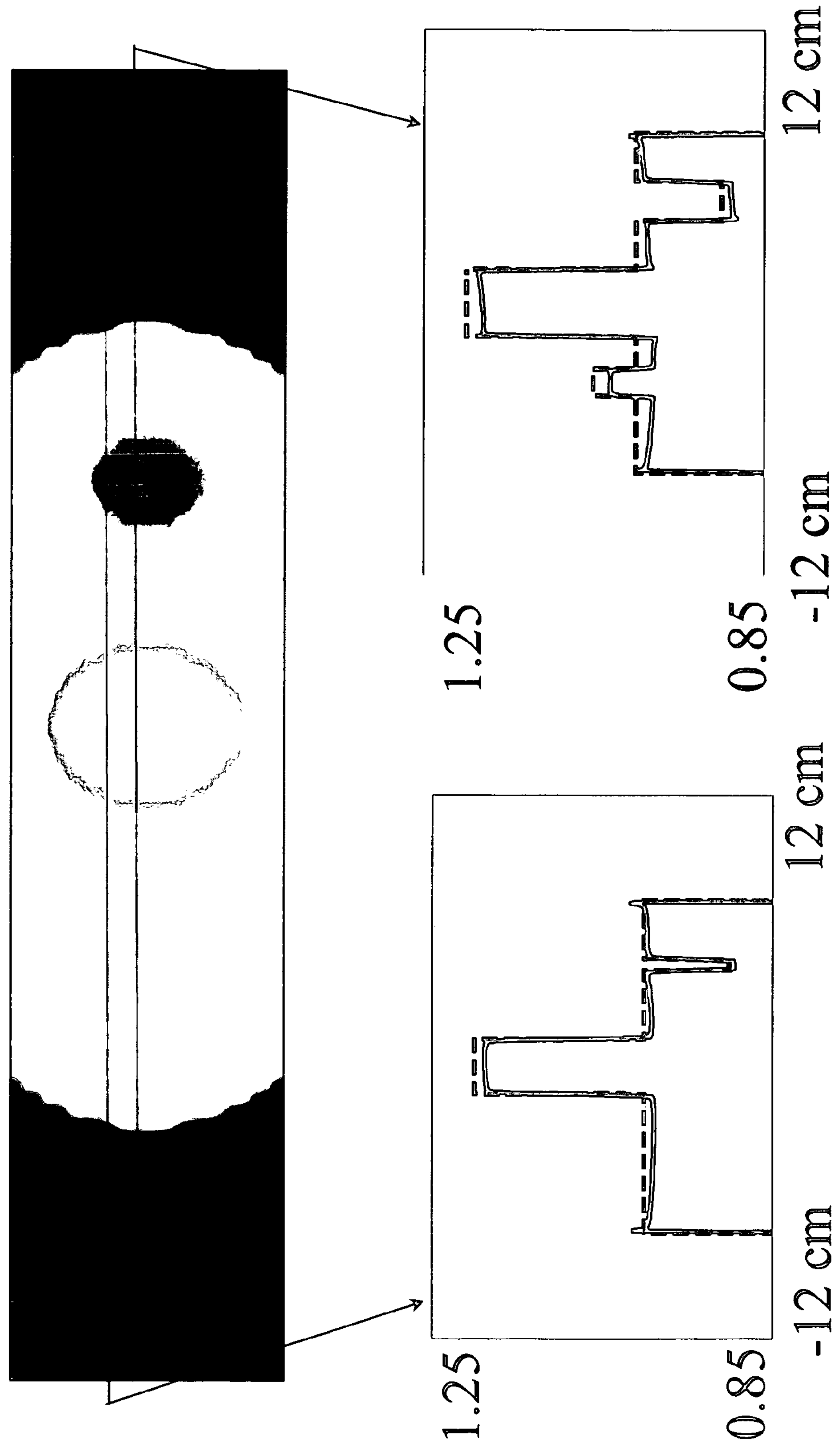
Figures 105A, 105B, 105C:
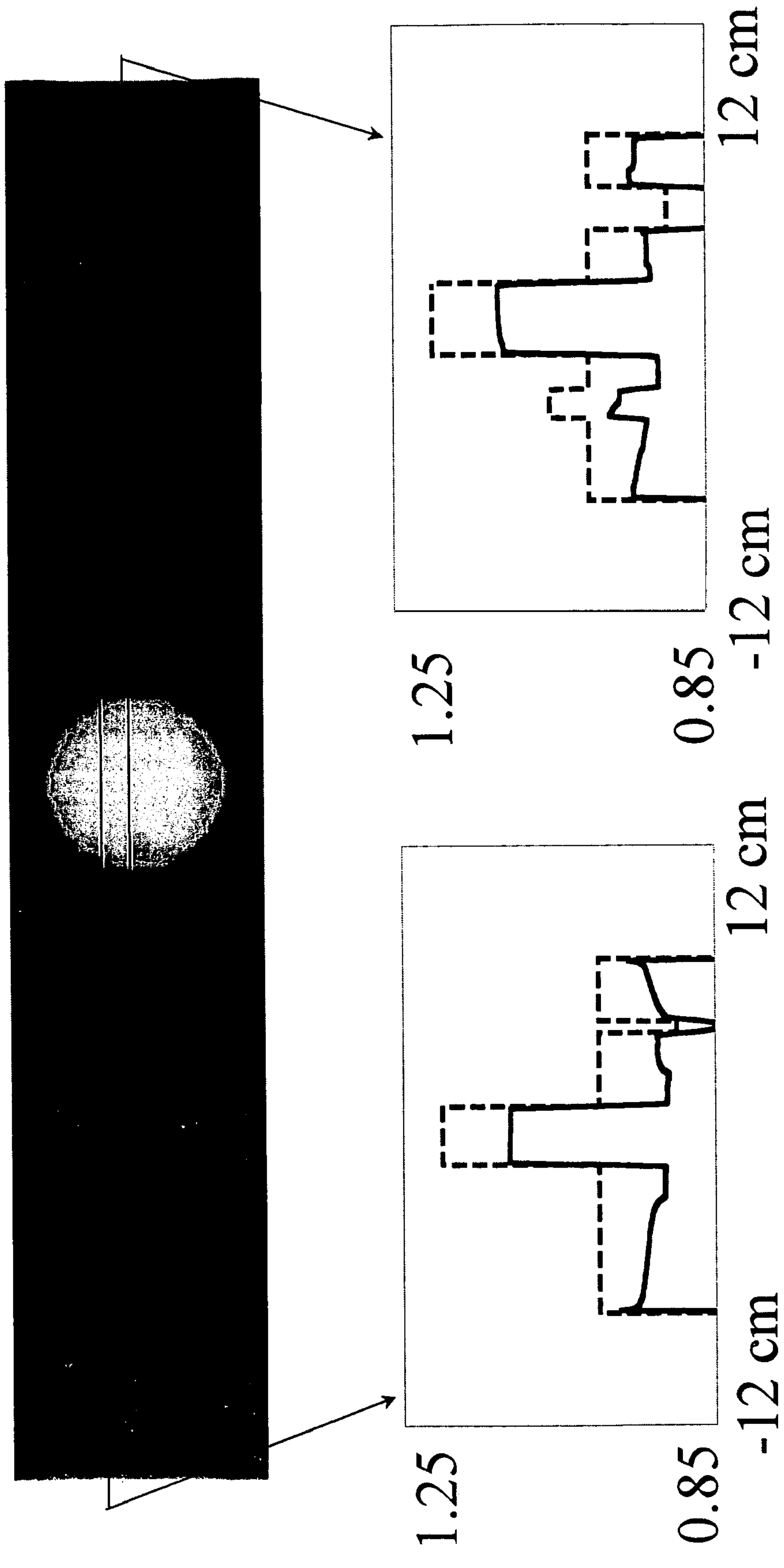

For the short scan, off-plane, FIG. 103A is identical to FIG. 98B, with an additional upper and a lower horizontal line through the images, and corresponding profiles for the lines in FIG. 103B and FIG. 103C, respectively. The solid curve is the reconstructed profile and the dashed curve represents the true phantom values. For the long scan, off-plane, FIG. 104A is identical to FIG. 98C, with an additional upper and a lower horizontal line through the images, and corresponding profiles for the lines in FIG. 104B and FIG. 104C, respectively. The solid curve is the reconstructed profile and the dashed curve represents the true phantom values. For the circular scan, off-plane, FIG. 105A is identical to FIG. 98D, with an additional upper and a lower horizontal line through the images, and corresponding profiles for the lines in FIG. 105B and FIG. 105C, respectively. The solid curve is the reconstructed profile and the dashed curve represents the true phantom values.

The results for the long-line configuration show greater accuracy than those of the short-line scan. For both line trajectories the agreement with the true function values is slightly better for the y=0 plane than the y=5 cm plane. This point is seen most clearly in comparing the image profiles, which give an idea of the quantitative accuracy of the reconstruction methodologies. As detailed below, the reason for the decrease in accuracy for the off-plane image is primarily due to the fact that the image chords comprising the off-plane are further away from the line-trajectory than the chords of the in-plane image.

For image reconstruction with the circular trajectory, the image volume is filled with the same set of chords used for the straight-line trajectories, specified by Eq. (F-2). The parameterization of the trajectories differs:

$$\vec{r}_0^{(circ)}(s)=R(\cos s, 0, \sin s), \tag{F-7}$$

where R is the radius of the trajectory. The back-projection formula for the circular trajectory differs slightly; the limits of the s-integration are modified so that the endpoints of the back-projection arc are co-linear with the in-plane chords and lie in a z=const plane together with off-plane chords:

$$g^{(circ)}(x) = \int_{\alpha}^{\pi-\alpha} ds \frac{1}{\left|\vec{r}_c(x) - \vec{r}_0^{(circ)}(s)\right|} \frac{\partial}{\partial_q} D(q, x) \Bigg|_{q=s}. \tag{F-8}$$

The angle $\alpha$ is $$\alpha = \sin^{-1}\frac{z_c}{R}. \tag{F-9}$$

According to the BPF theory, the image reconstruction for in-plane chords is exact, because these line segments coincide with the chords of the trajectory. The off-plane chords, on the other hand, may yield only approximate results; these chords may be termed "virtual chords".

The filtration step remains the same as in the straight-line trajectory case. For the purpose of comparison, R=20 cm is chosen so that the circle circumference is the same as the length of the long-line trajectory. Both the circular scan and long-line scan are discretized with 500 view angles each.

The circular cone-beam image reconstruction results are shown in FIGS. 102A-C and 105A-C. The in-plane image shows no perceptible artifacts, but the off-plane image has quite a bit of distortion. In particular, in examining the image profiles, there is a substantial drop in the reconstructed values as compared to the true values. The off-plane results of both linear trajectories are clearly superior to that of the circular trajectory for the present phantom.

The reason for the various results on the performance of the line and circular scans may be understood from the BPF theory. The BPF formulas may provide exact image reconstruction for the points on chords of the scanning trajectory. When the BPF equations are applied to line segments that do not coincide with a chord of the scanning trajectory, the reconstruction results are approximate. But it is clear that the image reconstruction could be made exact by adding segments to the scanning trajectory in such a way as to connect with the image-space line segment of interest. The validity of the approximation increases as the contribution of these extra trajectory segments decreases. In fact, it can be shown that the contribution from these segments is approximately proportional to the angular length of the each extra segment as viewed from the points along the image-space line segment. The approximation is illustrated schematically in FIG. 106; the difference, e.g., $g_L(x)-g(x)$, is proportional to $\gamma$. Specifically, FIG. 106 shows a diagram of approximation made by the chord reconstruction methodologies for "incomplete" trajectories. The solid thin line represents the actual source trajectory, and the thick solid line as a chord in the image space. The dotted arcs represent possible completions of the trajectory necessary for exact reconstruction of the image on the shown chord. The angle $\gamma=\gamma_1+\gamma_2$ is the total angular interval of the missing parts of the trajectory as viewed from the image point x. So that, the error in the back-projection image may be approximately proportional to $\gamma$.

Focusing on the middle off-plane chord, specified by $d_0=(0, 5, 0)$, the angle $\gamma$ may be computed at x=0 for the short-line, long-line and circular trajectories and $\gamma$=0.33, 0.16, and 0.49 radians, respectively, is obtained. By this analysis, it is clear that the circular trajectory makes the largest error of the three scans for the y=5 cm plane.

The foregoing analyzed 3D image reconstruction for cone-beam CT from a straight-line source trajectory. From the theoretical point of view this trajectory is interesting because it does not satisfy Tuy's condition; yet it may yield an arbitrarily accurate 3D image from a very low-dimensional trajectory.

From the application point of view, this scanning configuration is very rich. In medical imaging, the straight-line trajectory may lead to useful approximate image reconstruction methodologies for breast tomosynthesis where the detector is fixed and the source scans over a limited arc. Modification to a line segment scan is easy to implement. Other medical applications such as therapy imaging, and imaging for screening may benefit from this configuration. The straight-line trajectory could be very useful in industrial or security scanning. Due to the symmetry of the configuration, the x-ray source may be fixed with the object translating by, the object may be fixed with the source sweeping by, or both the source and object may translate relative to one another. The straight-line configuration for cone-beam CT tomography may substantially simplify scanning hardware and improve the efficiency in terms of objects scanned per unit time.

Alternatively, a bracket scan may be used for the trajectory of the source relative to the object. One example of the bracket scan is depicted in FIG. 107. As shown, the edges of the scan are perpendicular (or approximately perpendicular). Alternatively, the edges may form an angle with the long portion of the scan to form an angle less than 180° on the left side and greater than 180° on the right side. To retain the in-plane exactness of the circular scan while maintaining the improved accuracy of off-plane reconstruction by the straight-line scan, one may perform the bracket scan. The total length of the scan may be the same as the circular and long straight-line scans depicted in FIGS. 95A-B.

For the bracket scan, mid-plane, FIG. 108A shows the reconstructed slice based on the bracket line trajectory, with an additional upper and a lower horizontal line through the images, and corresponding profiles for the lines in FIG. 108B and FIG. 108C, respectively. The solid curve is the reconstructed profile and the dashed curve represents the true phantom values. For the bracket scan, off-plane, FIG. 109A shows the reconstructed slice based on the bracket line trajectory, with an additional upper and a lower horizontal line through the images, and corresponding profiles for the lines in FIG.

109B and FIG. 109C, respectively. The solid curve is the reconstructed profile and the dashed curve represents the true phantom values.

As discussed above, the source and/or object may move relative to one another to generate the source trajectory. For example, the source may move and the object may be stationary, the source may be stationary and the object may move, or the source and object may move. Further, any trajectory may be generated using one or more sources. For example, the bracket scan shown in FIG. 107 has three piecewise continuous sections (a long section and two short sections). One source may be moved along each of the three sections. Alternatively, three sources may move, one along each of the three sections. Or, one source may move along two of the three sections and a second source may move along the third section. Thus, any trajectory may be subdivided so that one or more sources may traverse the trajectory.

10. ROI-Image Reconstruction from Motion-Contaminated Data

Object motion represents one of the greatest obstacles towards obtaining diagnostic quality images of the cardiac and respiratory organs. As a result, efficient means of handling motion-contaminated projection data are needed. Current algorithms for cardiac and respiratory imaging, though varied, are fundamentally based on filtered back-projection (FBP) methods, which require more than half of the full scan projection data in order to produce an image at a given plane. Furthermore, since most of the projection data contribute to the formation of each voxel within the image space, motion artifacts in one region of the object may preclude the exact reconstruction of another portion of the object that is stationary.

The backprojection filtration methodologies (BPF) and minimum-data filtered backprojection (MFBP), discussed above, which are fundamentally different from FBP methods, may handle motion-contaminated projection data more effectively. In particular, the BPF and MFBP methodologies are capable of reconstructing specific regions of interest (ROI) of an object with less than the amount of data required to reconstruct the entire image. In addition, depending on the object and acquisition geometries, motion artifacts from one region of the object may not necessarily affect the ability to produce exact reconstructions of another portion of the object. As a result, BPF and MDFBP methodologies may be used to reconstruct images from motion-contaminated projection data.

10.1 ROI-Image Reconstruction from Motion-Contaminated Data Using Weighted Backprojection Filtration Methodology In computed tomography (CT), motion artifacts may represent a major obstacle towards obtaining diagnostic quality images of the cardiac and respiratory organs. Since reconstruction methodologies generally assume that the objects being imaged are stationary, cardiac and/or respiratory motion during data acquisition may lead to inconsistencies in the projection data. These inconsistencies may manifest themselves as streaks, blurs, positional changes, or general anatomical distortions that may mislead a physician who is attempting to make an accurate clinical diagnosis. For example, coronary artery stenoses may be difficult to detect in images contaminated by cardiac motion. Respiratory motion may prevent the accurate delineation of a tumor volume needed for radiation treatment planning.

Developing innovative methods for obtaining accurate image reconstructions from motion-contaminated data may be difficult. In cardiac imaging, reconstructing images at predefined cardiac phases combined with ECG-correlated gating have been commonly used for reducing motion artifacts. In respiratory imaging, techniques involving breath-holds or respiratory gating from four-dimensional data sets have shown promise in improving image quality. Many of these methods are based upon the assumption that image quality can be improved through the reduction of motion-contamination in the data used for image reconstruction.

Methodologies may be used for fan-beam and cone-beam CT. For the fan-beam case, many of these methodologies have capabilities which cannot be realized by the conventional fan-beam filtered backprojection (FFBP) methodology. For example, methodologies are capable of reconstructing exact region-of-interest (ROI) images with less data than that required to reconstruct the entire reconstruction field-of-view (FOV) by use of the FFBP methodology. These methodologies can reconstruct an ROI image from a reduced-scan angular range, which is smaller than the short-scan angular range of $\pi$ plus the fan angle needed by the FFBP methodology. Reconstructing ROI images from motion-contaminated reduced-scan data may be effective in suppressing motion artifacts. However, the amount by which the reduced-scan angular range can be shortened is dependent on the spatial location of the object of interest within the FOV. For a central organ such as the heart, the reduced-scan angular range cannot be shortened substantially, since an angular range greater than $\pi$ still is needed for the entire heart to be visualized. As a result, motion artifacts may not be adequately suppressed.

In order to further decrease the reduced-scan angular range, the projection data may be acquired with the patient positioned off-center within the FOV. Although the data may become truncated if a portion of the patient extends outside of the FOV, methodologies which are capable of handling reduced-scan data with truncations are available, as discussed above. Such methodologies include the PI-line-based backprojection filtration (BPF) and minimum data filtered backprojection (MDFBP) methodologies. The BPF and MDFBP methodologies therefore may be used to further decrease the amount of motion-contaminated data needed to reconstruct an image containing a central organ such as the heart.

The results indicate that the use of the original BPF and MDFBP methodologies for reconstructing ROI images from motion-contaminated data may result in streaks, which may occur in the direction of the PI-line segments used to reconstruct the image. These motion-induced streaks can be suppressed by use of the weighted BPF (WBPF) and weighted MDFBP methodologies, which exploit the redundancies in the fan-beam data. More specifically, reconstructions using short-scan data can allow for substantial suppression of these streaks, whereas those using reduced-scan data can allow for partial suppression. As a result, the weighted methodologies may be used for reconstructing ROI images from motion-contaminated fan-beam data. In addition, since the WBPF and the weighted MDFBP methodologies are mathematically equivalent, and because the former is computationally more efficient than the latter, the following analysis focuses the application of the WBPF methodology for reconstructing ROI images from motion-contaminated data using examples from cardiac imaging.

The following describes the fan-beam scanning configuration, the conventional FFBP methodology, and the WBPF methodology.

Figure 1B:
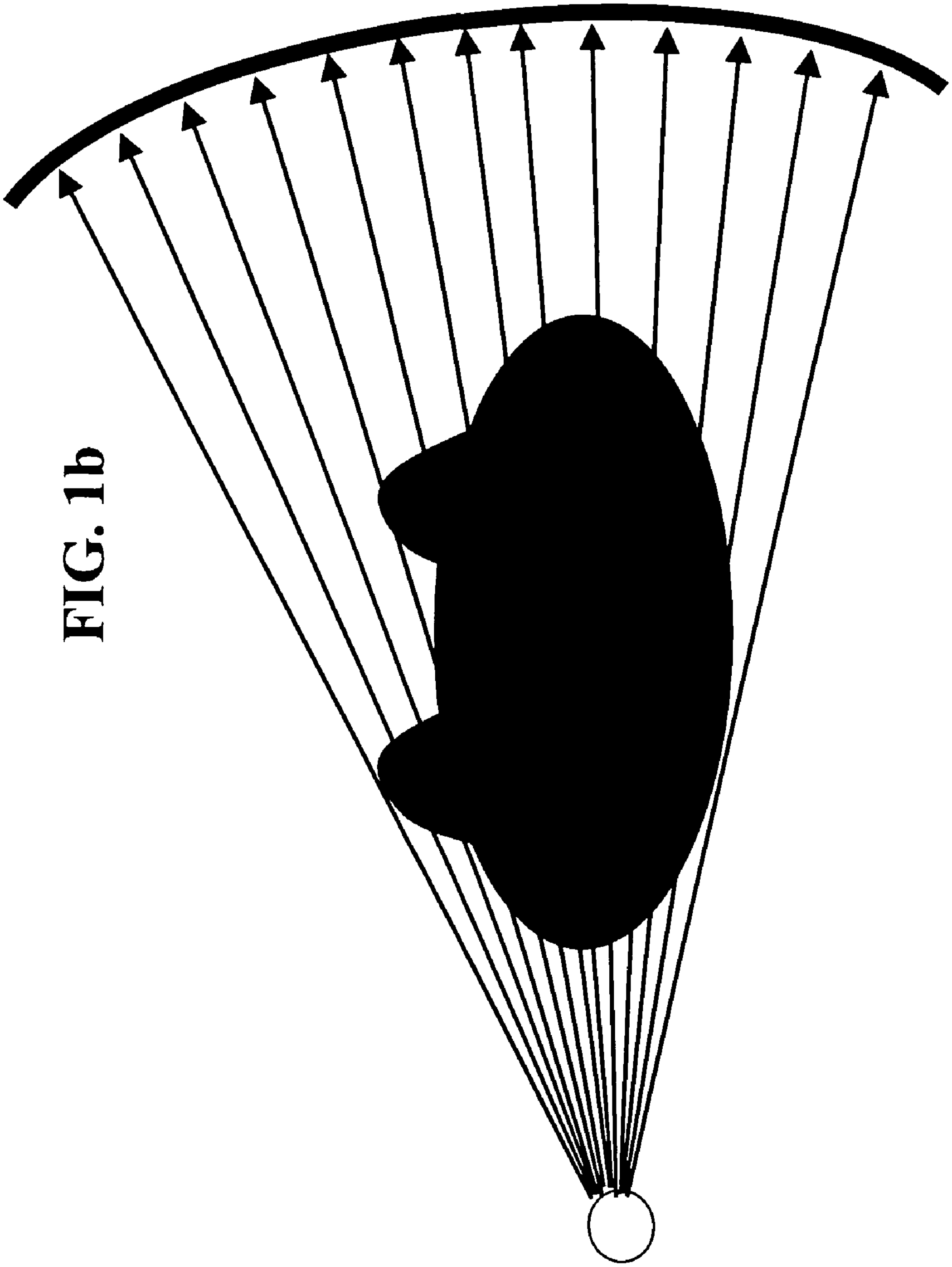
Figure 110B:
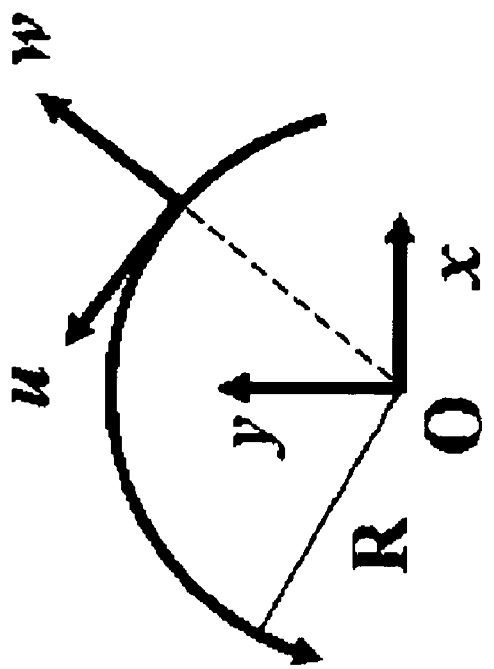
Figure 110A:
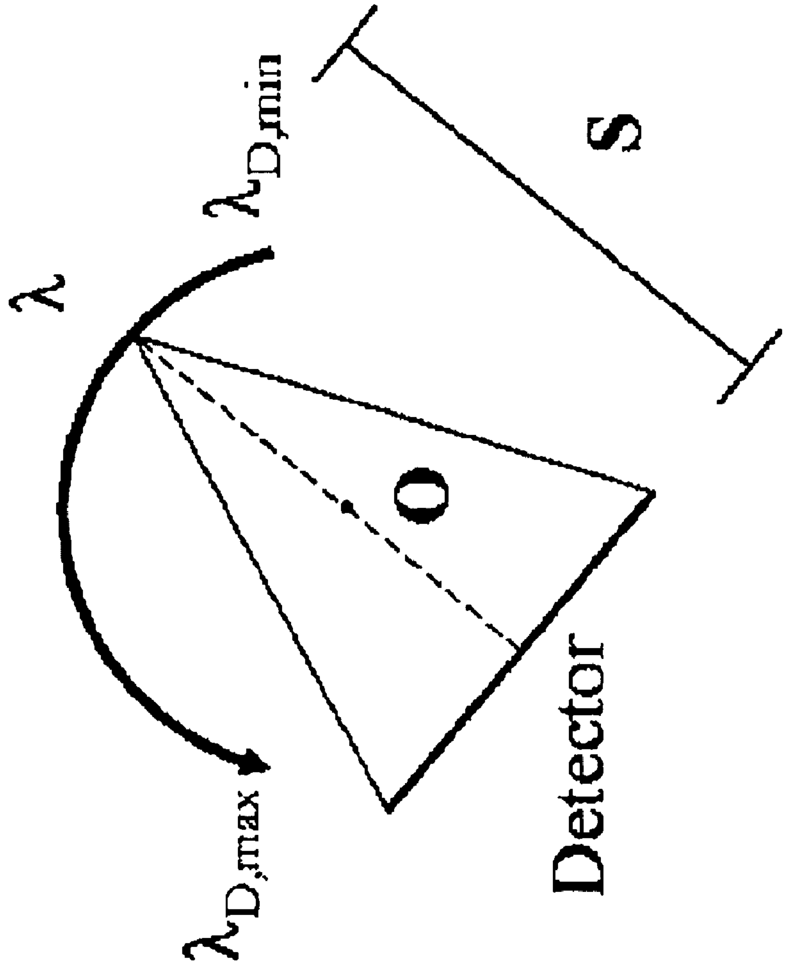

The simulations conducted use the traditional fan-beam geometry with a circular source trajectory. In terms of the stationary coordinate system {x, y} fixed on the source's center-of-rotation O, the circular trajectory $r_0(\lambda)$ can be written as $$r_0(\lambda)=(R\cos\lambda, R\sin\lambda)^t, \quad \text{(G-1)}$$

where R denotes the radius of the circular trajectory and λ indicates the scanning angle. FIGS. 110A-B illustrate the fan-beam geometry with a circular source trajectory. FIG. 110A illustrates the trajectory covers a scanning angular range $\lambda\in[\lambda_{D,min}, \lambda_{D,max}]$. The distance from the source to the center of the line detector may be represented by S. The source's center-of-rotation may be represented by O. As shown in FIG. 1(*a*), this source trajectory, whose endpoints are mapped out by angles $\lambda_{D,min}$ and $\lambda_{D,max}$, encloses a compact support $\Omega_R$ containing the two-dimensional image $f(r)$. The radius of the object support is assumed to be smaller than R. In other words, the trajectory may never intersect the object support.

A rotating coordinate system {u, w} whose origin is fixed on the source trajectory $r_0(\lambda)$ is also defined. FIG. 110B illustrates the origin of the stationary coordinate system {x, y} fixed on O. The origin of the rotating coordinate system {u, w} is defined on the circular source trajectory of radius R. The unit vectors of this rotating coordinate system, as depicted in FIG. 110B, may be expressed in terms of the fixed coordinate system as $$\hat{e}_u(\lambda)=(-\sin\lambda, \cos\lambda)^T,$$

$$\hat{e}_w(\lambda)=(\cos\lambda, \sin\lambda)^T. \quad \text{(G-2)}$$

It can be shown that the fixed and rotating coordinate systems are related through $$x=-u\sin\lambda+(w+R)\cos\lambda,$$

$$y=u\cos\lambda+(w+R)\sin\lambda. \quad \text{(G-3)}$$

The line detector located a distance S from the source is oriented parallel to $\hat{e}_u$ for all scanning angles λ. A point on the detector $u_d$ can be related to u in the rotating coordinate system by $$u_d = -\frac{S}{w}u. \quad \text{(G-4)}$$

Fan-beam projections of the two-dimensional image at a particular scanning angle λ and a detector position $u_d$ can be expressed as $$P(u_d,\lambda)=\int_0^\infty dl f(r_0(\lambda)+l\hat{\beta}), \quad \text{(G-5)}$$

where $\hat{\beta}$ denotes the direction of the ray from the source to a specific detector position $u_d$, and $A(u_d)$ represents the distance between the source and this detector position. $\hat{\beta}$ and $A(u_d)$ can be determined by $$\hat{\beta} = \frac{1}{A(u_d)}[u_d\hat{e}_u(\lambda) - S\hat{e}_w(\lambda)], \quad \text{(G-6)}$$

$$A(u_d) = \sqrt{u_d^2 + S^2}. \quad \text{(G-7)}$$

As shown in FIG. 110A, the data is assumed to be acquired along the source trajectory specified by $r_0(\lambda)$.

The conventional FFBP methodology for reconstructing images from fan-beam data, which are obtained using the geometry described above, can be expressed as follows $$f(r) = \int_{\lambda_{R,\min}}^{\lambda_{R,\max}} d\lambda U^{-2}(r,\lambda)\int_{-\infty}^{\infty} du_d\left(\frac{R}{A(u_d)}\right) \quad \text{(G-8)}$$

$$xP(u_d,\lambda)\omega_{FFBP}(u_d,\lambda)h(u_d'-u_d),$$

where $$U(r,\lambda) = \frac{R - r\cdot\hat{e}_u(\lambda)}{S}, \quad \text{(G-9)}$$

and $h(u_d)=\int_{-\infty}^{\infty}dv|v|e^{j2\pi vu_d}$ is the spatial representation of the ramp filter |v|. $\lambda_{R,min}$ and $\lambda_{R,max}$ represent the respective minimum and maximum limits of the angular reconstruction interval used for acquiring $f(r)$. When $\lambda_{R,max}-\lambda_{R,min}=2\pi$, full-scan data are used. When $\lambda_{R,max}-\lambda_{R,min}=\pi+\gamma_{fan}$, where $\gamma_{fan}$ is the fan-angle, short-scan data are used. Furthermore, $\omega_{FFBP}(u_d, \lambda)$ represents the weighting function for the FFBP methodology as written above. This weighting function satisfies the fan-beam data redundancy condition $$\omega_{FFBP}(u_d,\lambda)+\omega_{FFBP}[-u_d,\lambda+\pi-2\arctan(u_d/S)]=1, \text{ if } \lambda\in[\lambda_{R,min},\lambda_{R,max}],$$

$$\omega_{FFBP}(u_d,\lambda)=0, \text{ if } \lambda\notin[\lambda_{R,min},\lambda_{R,max}]. \quad \text{(G-10)}$$

When full-scan projection data are used, $\omega_{FFBP}(u_d, \lambda)$ can be set to 0.5.

The BPF methodology may reconstruct images on PI-line segments without exploiting the redundant information in the fan-beam data. Alternatively, the WBPF methodology may exploit these data redundancies.

Figures 111A, 111B, 111C, 111D:
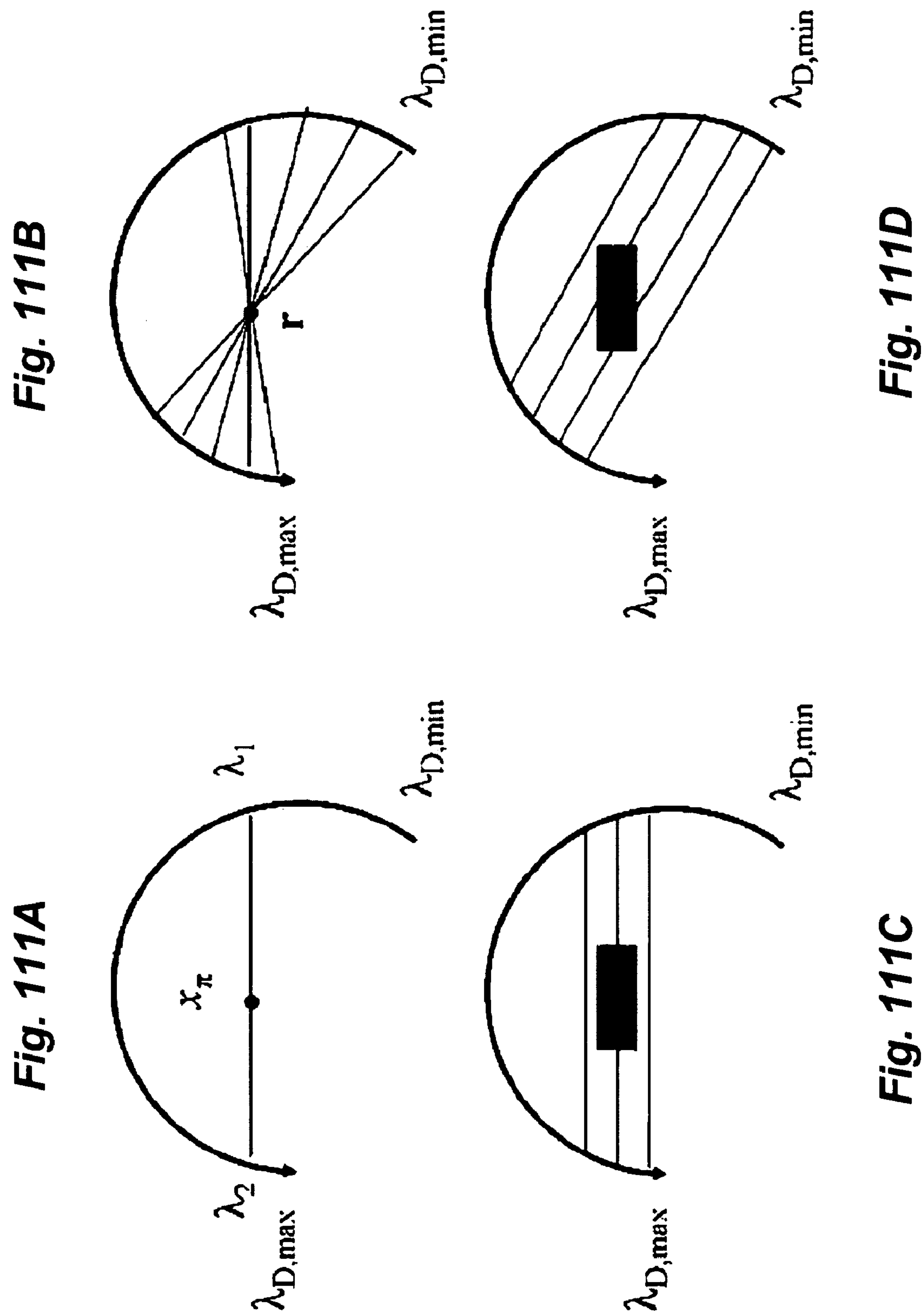

FIGS. 111A-D illustrate PI-line segments. FIG. 111A illustrates a PI-line segment connecting scanning angles specified by $\lambda_1$ and $\lambda_2$ on the source trajectory. A point on this PI-line segment can be specified by $x_\pi$. For the fan-beam case, a PI-line segment may comprise a straight line segment connecting two points labeled by scanning angles $\lambda_1$ and $\lambda_2$ on the source trajectory, as shown in FIG. 111A. The direction of the PI-line segment may be defined as $$\hat{e}_\pi = \frac{r_0(\lambda_2) - r_0(\lambda_1)}{|r_0(\lambda_2) - r_0(\lambda_1)|}. \quad \text{(G-11)}$$

Points on a PI-line segment are specified by a parameter $x_\pi$, which is related to the spatial vector r through $$r = \frac{r_0(\lambda_1) + r_0(\lambda_2)}{2} + x_\pi\hat{e}_\pi, \quad \text{(G-12)}$$

where $x_\pi\in[x_{\pi1}, x_{\pi2}]$, and $x_{\pi1}$ and $x_{\pi2}$ denote the two endpoints of the PI-line segment. A point r can be specified in terms of PI-line coordinates $\{x_\pi, \lambda_1, \lambda_2\}$.

Since all PI-line segments lie within the same two-dimensional plane, an infinite number of PI-line segments can cross each point r, as shown in FIG. 111B. Furthermore, because images are reconstructed on PI-line segments crossing a specific ROI, an infinite number of ROI images containing the same object can be reconstructed simply by changing the orientation of the PI-line segments. FIGS. 111C-D illustrate two different orientations of parallel PI-line segments that can be used to reconstruct ROI images containing the solid rectangle from data acquired with a source trajectory specified by $r_0(\lambda)$, with $\lambda\in[\lambda_{D,min}, \lambda_{D,max}]$.

Let $f_\pi(x_\pi, \lambda_1, \lambda_2)$ denote the image on a PI-line segment. Also, let $x_{\pi\lambda 1}$ and $x_{\pi\lambda 2}$ denote the two ends of this segment's support, whereby $f_\pi(x_\pi, \lambda_1, \lambda_2)=0$ for $x_\pi \notin [x_{\pi\lambda 1}, x_{\pi\lambda 2}]$. One may assume that $[x_{\pi\lambda 1}, x_{\pi\lambda 2}] \subseteq [x_{\pi 1}, x_{\pi 2}]$. The BPF methodology for fan-beam scans may be written as follows $$f_\pi(x_\pi, \lambda_1, \lambda_2) = \frac{1}{2\pi^2}\frac{1}{\sqrt{(x_{\pi\lambda 2} - x'_\pi)(x'_\pi - x_{\pi\lambda 1})}} \times \left[\int_{x_{\pi\lambda 1}}^{x_{\pi\lambda 2}} dx'_\pi \frac{\sqrt{(x_{\pi\lambda 2} - x_\pi)(x_\pi - x_{\pi\lambda 1})}}{(x_\pi - x'_\pi)} \times g_\pi(x'_\pi, \lambda_1, \lambda_2) + 2\pi D(r_0(\lambda_1), \hat{e}_\pi)\right], \quad \text{(G-13)}$$

where $x_\pi \in [x_{\pi\lambda 1}, x_{\pi\lambda 2}]$ and $D(r_0(\lambda_1), \hat{e}_\pi)$ is the projection of the ray coinciding with the PI-line segment $(\lambda_1, \lambda_2)$. The backprojection term $g(x'_\pi, \lambda_1, \lambda_2)$ may be obtained from $P(u'_d, \lambda)$ as $$g_\pi(x'_\pi, \lambda_1, \lambda_2) = \int_{\lambda_1}^{\lambda_2} d\lambda \frac{S^2}{[R - r' \cdot \hat{e}_w(\lambda)]^2} \frac{\partial}{\partial u'_d} \times \left(\frac{R}{A(u'_d)} P(u'_d, \lambda)\right) + \left.\frac{P(u'_d, \lambda)}{|r' - r_0(\lambda)|}\right|_{\lambda}^{\lambda_2}, \quad \text{(G-14)}$$

where $r'=(x', y')^T$ can be determined through Eq. G-12 and $u'_d$ can be determined by Eqns. G-3 and G-4. $[\lambda_1, \lambda_2]$ represents the angular reconstruction interval required for obtaining the PI-line segment image, $f_\pi(x_\pi, \lambda_1, \lambda_2)$.

As stated earlier, ROI images may be reconstructed by identifying the PI-line segments that cross the desired ROI. Once $f_\pi(x_\pi, \lambda_1, \lambda_2)$ is obtained for all PI-line segments crossing the ROI, these PI-line segment images can be re-expressed in terms of Cartesian coordinates {x, y} using Eq. G-12. In this way, the image $f(r)$ can be obtained.

The WBPF methodology, which may exploit the inherent redundancies in fan-beam data, has been derived from the BPF methodology. This weighted methodology differs from the original BPF methodology in two respects. First, the data $P(u_d, \lambda)$ may need to be multiplied by the weighting function $\omega_{WBPF}(u_d, \lambda)$ prior to backprojection. The WBPF weighting function may be written as $$\omega_{WBPF}(u_d,\lambda)+\omega_{WBPF}[-u_d,\lambda+\pi-2\arctan(u_d/S)]=1, \text{ if } \lambda\in[\lambda_{R,min},\lambda_{R,max}],$$

$$\omega_{WBPF}(u_d,\lambda)=0, \text{ if } \lambda\notin[\lambda_{R,min},\lambda_{R,max}]. \quad \text{(G-15)}$$

Second, since the WBPF methodology reconstructs an image $f_\pi^{(w)}(x_\pi, \lambda_1, \lambda_2)$ on the PI-line segment specified by $(\lambda_1, \lambda_2)$ using an expanded angular reconstruction interval $[\lambda_{R,min}, \lambda_{R,max}] \supseteq [\lambda_1, \lambda_2]$, the weighted data may need to be backprojected across this expanded angular interval. Therefore, the backprojection term may be written as:

$$g_\pi^{(w)}(x'_\pi, \lambda_1, \lambda_2) = \int_{\lambda_{R,\min}}^{\lambda_{R,\max}} d\lambda \frac{S^2}{[R - r' \cdot \hat{e}_w(\lambda)]^2} \frac{\partial}{\partial u'_d} \times \left(\frac{R}{A(u'_d)} \omega_{WBPF}(u'_d, \lambda) P(u'_d, \lambda)\right) + \left.\frac{\omega_{WBPF}(u'_d, \lambda) P(u'_d, \lambda)}{|r' - r_0(\lambda)|}\right|_{\lambda_{R,\min}}^{\lambda_{R,\max}}. \quad \text{(G-16)}$$

Figure 112B:
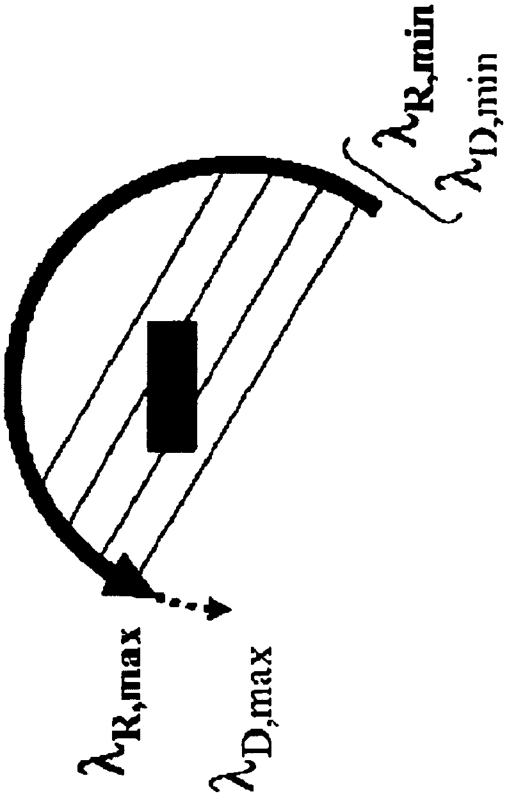
Figure 112A:
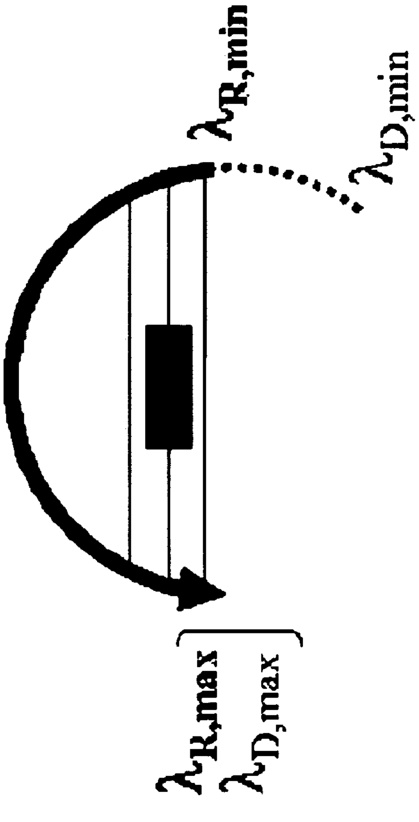

The limits of the angular reconstruction interval $\lambda_{R,min}$ and $\lambda_{R,max}$ may correspond to the type of weighting function $\omega_{WBPF}(u_d, \lambda)$ used for reconstruction. A full-scan weighting function requires that $\lambda_{R,max}-\lambda_{R,min}=2\pi$, whereas a short-scan weighting function requires that $\lambda_{R,max}-\lambda_{R,min}=\pi+\gamma_{fan}$. When $\lambda_{R,max}-\lambda_{R,min}<\pi+\gamma_{fan}$, the WBPF methodology may necessitate a reduced-scan weighting function that satisfies Eq. G-15. FIGS. 112A-B illustrate ROI reconstruction using redundant data, depicting two different angular reconstruction intervals used by the WBPF methodology for reconstructing ROI images containing the solid rectangle (which may act as an object). The thick regions of the source trajectory are used to highlight the angular reconstruction intervals, whose limits are defined by $[\lambda_{R,min}, \lambda_{R,max}]$. The dotted regions of the source trajectory are used to highlight portions of the available projection data $[\lambda_{D,min}, \lambda_{D,max}]$ that are not used. Other angular reconstruction intervals are also possible.

Two data sufficiency conditions for reconstructing an image on a PI-line segment have been identified. The first condition is concerned with whether the angular reconstruction interval is sufficient to reconstruct the image on the PI-line segment specified by $\lambda_1$ and $\lambda_2$. For the WBPF methodology, all scanning angles within the angular reconstruction interval $[\lambda_{R,min}, \lambda_{R,max}]$ may be required for reconstructing this PI-line segment image. The second condition is concerned with sufficient object illumination at each projection view.

FIG. 113 is a schematic illustrating the data sufficiency conditions for obtaining an exact reconstruction of an image on a PI-line segment specified by $\lambda_1$ and $\lambda_2$ using the WBPF methodology. The angular reconstruction interval $[\lambda_{R,min}, \lambda_{R,max}]$ is highlighted on the source trajectory. The projection range $u_d \in [u_{d1}, u_{d2}]$ for a depicted scanning angle $\lambda$ is highlighted on the detector array. The reconstruction FOV is enclosed by the dashed circle. As shown in FIG. 113, since $x_{\pi\lambda 1}$ and $x_{\pi\lambda 2}$ denote the two ends of the PI-line segment's support, $u_{d1}$ and $u_{d2}$ can represent their fan-beam projections on the detector. For a given $\lambda$, the set of detector points $u_d \in [u_{d1}, u_{d2}]$ represents the projection range of the PI-line segment's support on the detector.

As long as the projection ranges $u_d \in [u_{d1}, u_{d2}]$ are available over all $\lambda \in [\lambda_{R,min}, \lambda_{R,max}]$, an exact reconstruction of the image on the PI-line segment specified by $\lambda_1$ and $\lambda_2$ may be obtained using the WBPF methodology. Since data residing outside of the projection ranges are not used, the WBPF methodology is capable of reconstructing the PI-line segment image from truncated data, which are obtained when the entire object is not completely illuminated over all necessary scanning views.

Although the data sufficiency conditions for the weighted MDFBP methodology are similar to those for the WBPF methodology, the conventional FFBP methodology requires that the entire reconstruction FOV is illuminated over all necessary scanning views. As a result, the FFBP methodology does not allow for exact reconstructions from truncated data.

Approaches for reconstructing images from motion-contaminated data are analyzed below. In particular, phase-interval image reconstruction and retrospective gating are analyzed.

The temporal phase of an object undergoing periodic motion can be defined as $\phi \in [0, 1]$. A temporal phase of zero refers to the state of the object at the beginning of its temporal cycle, whereas a temporal phase of one refers to the state of the object at the end of its temporal cycle. All other temporal phases falling between zero and one refer to the state of the object after a fraction of its temporal cycle has passed. For the case of the cardiac cycle, the temporal phase variable $\phi$ essentially is equivalent to the percent R-R interval. The R-peak is assigned a phase $\phi=0$. Lower values of $\phi$ refer to the heart in systole and higher values of $\phi$ refer to the heart in diastole.

Phase-interval image reconstruction simply refers to the reconstruction of the entire FOV using short-scan data obtained over selected phase intervals. Usually, these intervals are selected over phases of reduced motion in order to obtain a higher quality reconstruction. For example, in the case of cardiac imaging, data acquired during phases corresponding to diastole often produce reconstructions with less motion artifact.

In order to reconstruct an image, the angular reconstruction interval $[\lambda_{R,min}, \lambda_{R,max}]$ corresponding to the selected phase interval $[\phi_{R,min}, \lambda_{R,max}]$ may need to be obtained. The following relation, which relates the gantry angle $\lambda$ to a specific temporal phase of the object $\phi$, may be used for determining $\lambda_{R,min}$ and $\lambda_{R,max}$ $$\lambda = \lambda_{D,\min} \pm 2\pi(\phi - \phi_{D,\min})\left(\frac{T_C}{RT}\right), \tag{G-17}$$

where $\lambda_{D,min}$ refers to the gantry angle at the start of data acquisition, $\phi_{D,min}$ is the temporal phase at the start of data acquisition, $T_C$ refers to the time needed for one complete temporal cycle, and RT is the gantry rotation time. The addition operator is used when the gantry rotates in the counter-clockwise direction, and the subtraction operator is used when the gantry rotates in the clockwise direction. When the angular reconstruction interval is defined, the angular range $\Delta\lambda_R=\lambda_{R,max}-\lambda_{R,min}$ can be determined. From this variable, the percent of full-scan data, PFSD, used for reconstruction may be defined as:

$$PFSD = \frac{\Delta\lambda_R}{2\pi}. \tag{G-18}$$

The phase interval range $\Delta\phi_R=\phi_{R,max}-\phi_{R,min}$, which represents the fraction of the temporal cycle used for reconstruction, can be determined from the following expression $$\Delta\phi_R = \pm\frac{RT}{T_C}\left(\frac{\Delta\lambda_R}{2\pi}\right). \tag{G-19}$$

As seen from this expression, $\Delta\phi_R$ is directly proportional to $\Delta\lambda_R$ for non-gated reconstructions. The addition and subtraction operators for this equation are used in the same manner as that described for Eq. G-17.

If an image is to be reconstructed from short-scan data, $\Delta\lambda_R$ equals $\pi+\gamma_{fan}$. The selected phase interval $[\phi_{R,min}, \phi_{R,max}]$ therefore should be adjusted accordingly if $\Delta\lambda_R$ is not sufficient for short-scan reconstruction. Once the data corresponding to the angular reconstruction interval are obtained, either the FFBP or the WBPF methodology can be used to reconstruct the entire image.

Since $\Delta\lambda_R$ is fixed for short-scan data, $\Delta\phi_R$ for an object with a constant cycle time $T_C$ cannot be changed. However, $\Delta\phi_R$ still may be decreased for objects with certain cycle times through the use of retrospective gating, which nullifies the relationship shown in Eq. G-19.

Retrospective gating extracts two or more segments from a data set acquired over multiple temporal cycles. The union of the angular reconstruction intervals for these segments must span an angular range of at least $\pi+\gamma_{fan}$ to ensure sufficient data for short-scan reconstruction. In addition, the temporal phase intervals for these segments must overlap so that the overall phase interval range $\Delta\phi_R$ can be decreased. The manner in which these two conditions can be fulfilled depends on the degree to which the object cycle time is synchronized to the gantry rotation time. When the gantry rotation time is completely synchronized with the object cycle time, such as when RT=0.4 s and $T_C$=0.8 s (heart rate HR=75 bpm), these conditions cannot be fulfilled to any extent, and $\Delta\phi_R$ cannot be decreased. On the other hand, complete desynchronization of these two variables, such as when RT=0.4 s and $T_C$=0.91 s (HR=66 bpm), allows for $\Delta\phi_R$ to be reduced by almost 50% for the case of two-segment gating.

The extracted segments then are combined to form the gated short-scan data set. In order to reduce data inconsistencies due to gating, a weighted average of the extracted segments with overlapping scanning angles is performed. The resulting data set then is reconstructed with either the FFBP or the WBPF methodology.

The following discusses phase-interval ROI reconstruction with the option for off-center positioning using the WBPF methodology. The following further describes how the average temporal resolution of these ROIs can be calculated.

Similar to phase-interval image reconstruction with the FFBP methodology, phase-interval ROI reconstruction with the WBPF methodology may require the selection of an angular reconstruction interval $[\lambda_{R,min}, \lambda_{R,max}]$ corresponding to the desired phase interval $[\phi_{R,min}, \lambda_{R,max}]$. However, since the WBPF methodology allows for ROI reconstruction from reduced-scan data, the angular range $\Delta\lambda_R$ and the PFSD may be smaller than their corresponding values for short-scan reconstructions with either methodology. The smaller $\Delta\lambda_R$ also allows for a decrease in the phase interval range $\Delta\phi_R$, as shown in Eq. G-19, for the case of ungated data. As a result, the WBPF methodology can be used to decrease the fraction of the temporal cycle in the data used for reconstruction.

The amount by which $\Delta\lambda_R$ can be decreased depends on the spatial location of the object within the reconstruction FOV.

Figure 114B:
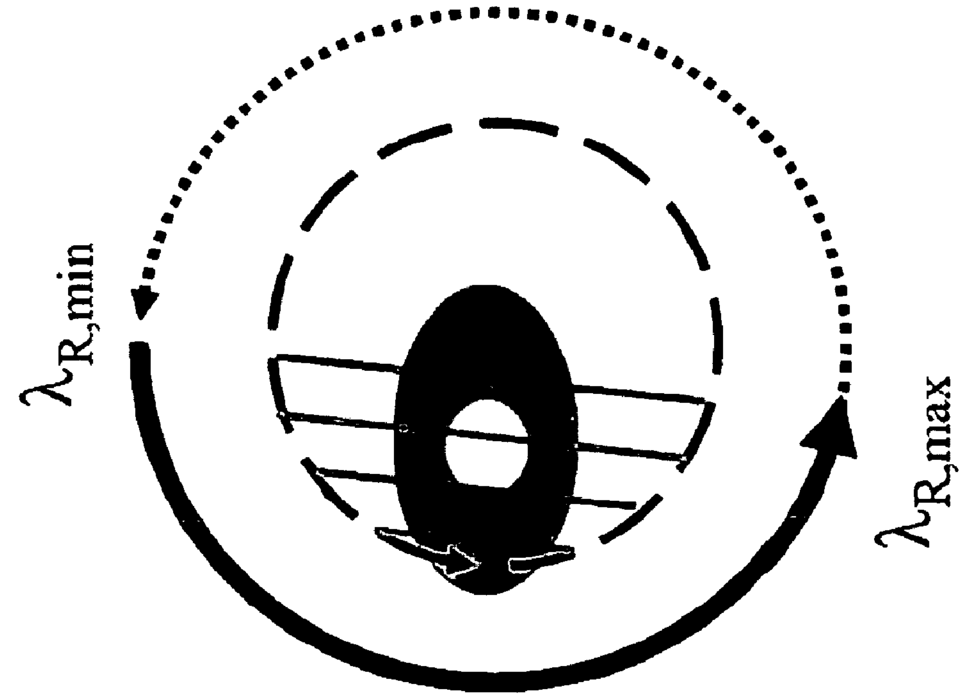
Figure 114A:
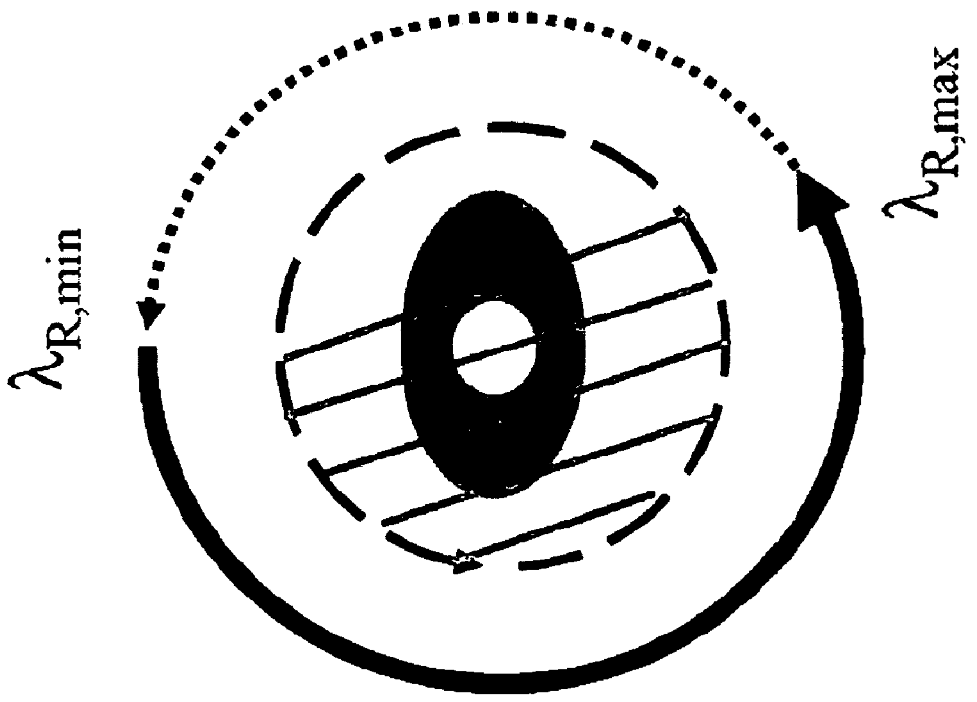

FIGS. 114A-B illustrate the effect of off-center positioning on the angular range $\Delta\lambda_R$. FIG. 114A depicts an ellipse positioned in the center of the reconstruction FOV (dashed inner circle). In its central region, the ellipse contains a lighter component that undergoes continuous motion. The thick solid portion of the outer circle represents the angular reconstruction interval needed to reconstruct the lighter component. The thin dotted portion corresponds to the data interval not used for reconstruction. The parallel lines across the ROI represent support sections of the defined PI-line segments. For this configuration, $\Delta\lambda_R>\pi$ and PFSD>50%. FIG. 114B depicts the same elliptical object shown in FIG. 114A, shifted towards one side of the FOV. For this geometric configuration, $\Delta\lambda_R<\pi$ and PFSD<50%. Note that the PI-line segments crossing the lighter component have support endpoints which do not intersect any portion of the object. Images on these PI-line segment supports may be reconstructed without truncation artifacts.

As stated above, in order to reconstruct an ROI image of an object located in the center of the FOV such as the heart, the reconstruction interval still must span an angular interval $\Delta\lambda_R>\pi$, as shown by the schematic in FIG. 114A. Otherwise portions of the desired object may not be available in the reconstructed image.

In this case, the PFSD remains above 50%. In order to further reduce the angular range required for reconstructing the ROI image, the object can be shifted to one side. Thus, the object previously positioned in the center of the FOV now becomes located towards the edge of the FOV, as shown in FIG. 114B. If projection data are acquired with this off-center configuration, an ROI image of an object such as the heart now can be reconstructed with an angular range $\Delta\lambda_R<\pi$, a PFSD<50%, and a smaller $\Delta\phi_R$. Thus, the potential decrease in $\Delta\phi_R$ from using reduced-scan data can be enhanced with off-center object positioning. Combining off-center positioning with retrospective gating may allow for an even further reduction in $\Delta\phi_R$, as long as the data segments used for constructing the gated data set are selected based on the degree of overlap between their respective phase intervals.

Positioning the object off-center may lead to truncations in the projection data. However, as discussed above, the WBPF methodology is capable of handling truncated data. In most cases, careful positioning of the PI-line segment supports, as shown in FIG. 114B, may ensure that truncation artifacts do not contaminate the reconstructed image of the off-center object.

The absolute temporal resolution is a parameter commonly used for assessing the amount of temporal information contributing to the formation of an image. This parameter may be derived from the phase sensitivity profile PSP(x, y), a distribution showing the weighted contribution of data from different temporal phases used for reconstructing a pixel within the image. The PSP(x, y) specifically may take into account the values of the weighting function $\omega_{FFBP}(u_d, \lambda)$ or $\omega_{WBPF}(u_d, \lambda)$ corresponding to the spatial location of this pixel as well as changes to this distribution from retrospective gating. The full width at tenth maximum $FWTM_{PSP}(x, y)$ of this phase sensitivity profile is labeled as an empirical measure of the fraction of the temporal cycle contributing to the formation of this pixel. The absolute temporal resolution of the pixel $T_i(x, y)$ then is calculated by multiplying $FWTM_{PSP}(x, y)$ by $T_C$.

The absolute temporal resolution often may be calculated only for the central pixel within the FOV. This value then represents the absolute temporal resolution of the entire image. However, since ROI reconstructions often not including the central pixel within the FOV are performed in this study, and the weighting functions for reduced-scan data are different from those for short-scan data, calculating the absolute temporal resolution contributing to the central pixel would not be meaningful. Instead, $T_i(x, y)$ is computed for all pixels within the available ROI following reconstruction. The mean of these values is calculated to obtain the $\overline{T}_{ROI}$, the average temporal resolution defined over an ROI. This pixel-specific approach for obtaining $\overline{T}_{ROI}$ is similar to a proposed voxel-based approach for calculating the temporal resolution of a reconstructed volume. A smaller $\overline{T}_{ROI}$ represents an improved temporal resolution, since the motion-contaminated data used for reconstructing the ROI image was obtained over a smaller temporal span.

The performance of the WBPF methodology may be evaluated in reconstructing ROI images from motion-contaminated data, which were generated by using the modified FORBILD phantom and the NCAT phantom.

Figure 115B:
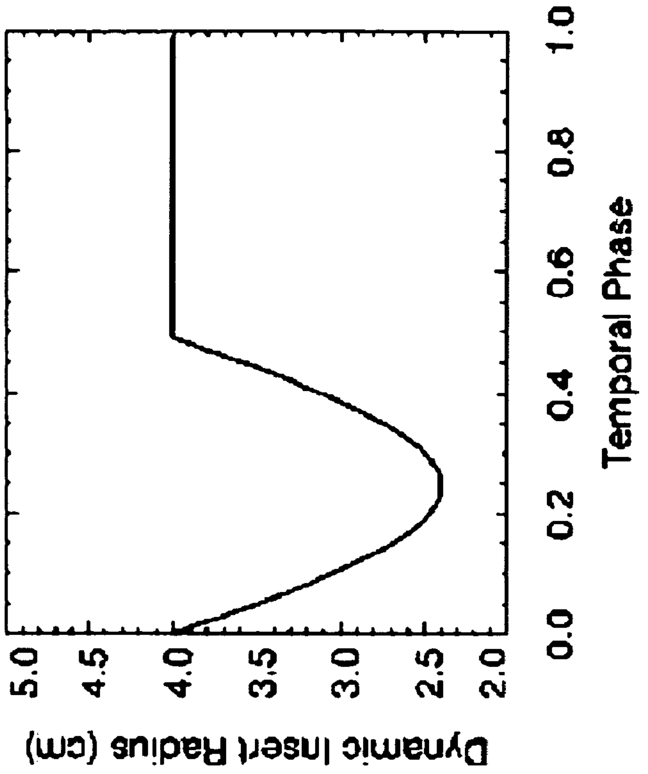
Figure 115A:
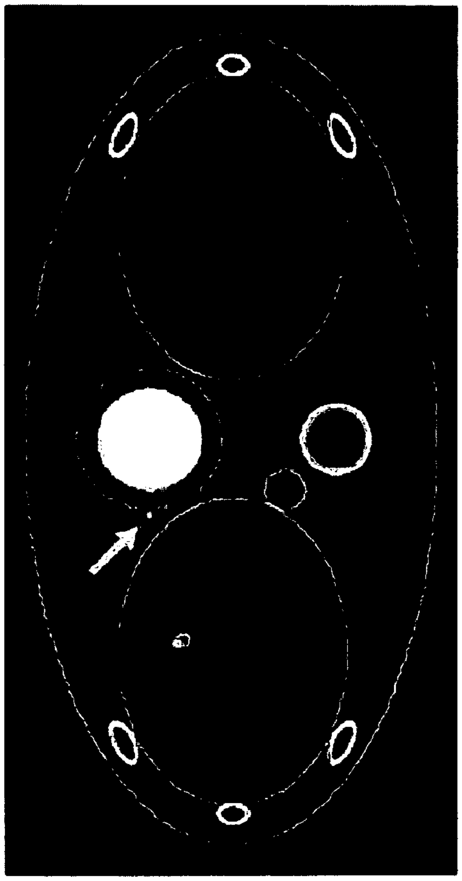

A two-dimensional FORBILD phantom representing the human thorax was sized so that it spanned 40 cm in width and 20 cm in height. FIG. 115A illustrates a modified FORBILD phantom with dynamic cardiac insert. The white arrow points to a high contrast circle representing a coronary plaque within the cardiac insert (L: 50 HU/W: 400 HU). FIG. 115B illustrates a temporal phase profile for the radius of the entire cardiac insert. As shown in FIG. 115A, this phantom was modified to include a dynamic cardiac insert. In particular, the cardiac insert was composed of three concentric circles representing an outer epicardial layer, a middle myocardial layer, and an inner ventricular cavity. A high contrast circle representing a coronary plaque was placed in the outer epicardial layer. The dynamic cardiac insert underwent in-plane contractile motion during 50% of its temporal cycle in a manner shown in FIG. 115B. This insert remained in its stationary state during the remainder of its temporal cycle.

The simulations involving the modified FORBILD phantom provide insights into how motion-contaminated data can be used for reconstructing ROI images with the WBPF methodology. However, in order to demonstrate how the WBPF methodology might perform in more clinically realistic situations, in which the entire data set is contaminated by the continuous beating motion of the heart, simulations also were performed with the NCAT phantom. This phantom not only provides anatomical information of the human torso, but also models cardiac and respiratory movements. For the case of projection imaging, the NCAT phantom yields four-dimensional attenuation maps, which can be used to assess how reconstruction methodologies might perform when handling actual clinical data.

The NCAT phantom was used to generate two-dimensional attenuation maps through the lower portion of the heart at 32 temporal phases equally-spaced throughout one cardiac cycle. Respiratory motion was not implemented. Alternatively, respiratory motion may be implemented. The spatial resolution was 0.2 mm/pixel. Two coronary plaques, one in the left anterior descending (LAD) artery and another in the left circumflex (LCX) artery, were added to the attenuation maps at all temporal phases. Although these plaques underwent three-dimensional motion, both plaques were present in the plane of interest at temporal phases $\phi\epsilon[0, 0.125]\cup[0.438, 1]$. Since the fan-beam data used for all reconstructions shown below were obtained during those temporal phases, it can be assumed that both plaques, while undergoing motion, did not disappear from the plane of interest. The LAD and LCX plaques therefore serve as a qualitative benchmark for assessing how the FFBP and WBPF methodologies handle motion-contaminated data. An example of a NCAT attenuation map with the LAD and LCX plaques at a temporal phase of 0.75 can be seen in FIG. 116. Specifically, FIG. 116 depicts an attenuation map generated from the NCAT phantom at mid-to-late diastole ($\phi$=0.75). A thin white arrow points to high-contrast plaque in the left circumflex (LCX) artery. A thick white arrow points to high-contrast plaque in the left anterior descending (LAD) artery (L: 50 HU/W: 400 HU).

TABLE 2

Acquisition and reconstruction parameters with corresponding figure designations for the modified FORBILD phantom.

| Methodology | Acquisition Type PFSD | No noise (60 bpm) FIG. | Noise (60 bpm) FIG. | Off-center 5 cm (60 bpm) FIG. | Off-center 15 cm (66 bpm) FIG. | Expanded phantom (60 bpm) FIG. |
|---|---|---|---|---|---|---|
| FFBP | 64.5% | 118A | 118C | 120A | 121A | 122C |
| WBPF | 64.5% | 118B | 118D | | | 122D |
| WBPF | 53.0% | 119B | 119D | | | |
| WBPF | 50.0% | 119A | 119C | 120B | | |
| WBPF | 45.0% | | | | 121B | |

All projection data sets for the modified FORBILD phantom were acquired with the same circular fan-beam geometry and line detector array. In particular, a 57 cm radius for the circular trajectory, a 104 cm source-to-detector distance, and a 50 cm reconstruction FOV were used. The one-dimensional detector contained 512 detector elements, each with a bin size of 1.09 mm when scaled to isocenter. For this geometry, the PFSD necessary for short-scan acquisitions was 64.5%.

Data were acquired with a starting gantry angle of $-0.5\pi$, a starting temporal phase of 0.5, and a gantry rotation time of 1.0 s. The gantry was set to rotate in a counter-clockwise direction. Images containing the FOV were reconstructed on a 512×512 matrix. All reconstructions were displayed with a level and window of 50 HU and 400 HU respectively. Table 2 depicts acquisition and reconstruction parameters, as well as their corresponding figure numbers, for these simulations.

In the following, a full-scan data set of the modified FORBILD phantom beating at 60 bpm was acquired with the parameters described above. The portion of the data obtained with scanning angles $\lambda\in[-0.5\pi, 0.5\pi]$ was free from all motion-contamination, whereas the portion from $[0.5\pi, 1.5\pi]$ contained motion-induced inconsistencies. FIG. 117 illustrates a difference sinogram (scanning angle $\lambda$ versus detector bin $u_d$) highlighting regions of motion-induced inconsistencies in the data acquired from the modified FORBILD phantom. The dashed line separates motion-contaminated regions obtained with $\lambda\in[0.5\pi, 1.5\pi]$ from motion-free regions acquired with $\lambda\in[-0.5\pi, 0.5\pi]$. This difference sinogram was obtained by subtracting the motion-contaminated data set acquired over temporal phases $\phi\in[0.5, 1.5]$ from the motion-free data set obtained at =0.5. The individual data sets were acquired using the parameters described above.

Two sets of FFBP and WBPF reconstructions were obtained from motion-contaminated short-scan data with $\lambda\in[-0.5\pi, 0.79\pi]$. The first set was obtained from noiseless data, and the second set was acquired from noisy data. For the second set, Gaussian noise with a standard deviation of 0.3% of the maximum value of the noiseless data was added. This standard deviation was chosen to ensure that the coronary plaque in the outer epicardial layer was visible in the noisy FFBP reconstruction acquired from the motion-free data set described above.

Figure 118A:
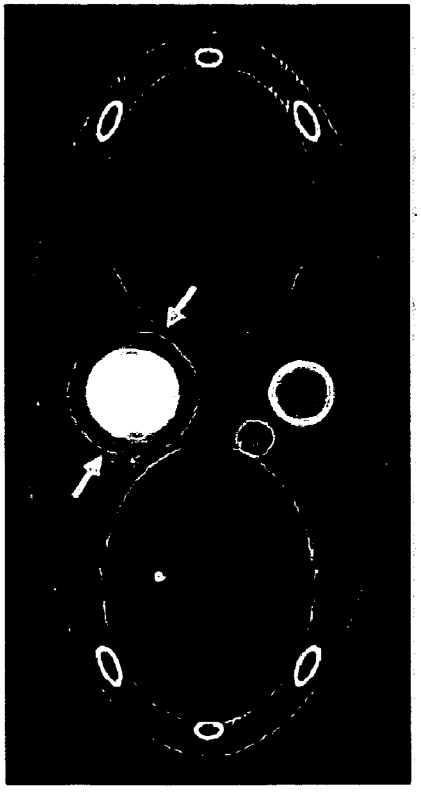
Figure 118B:
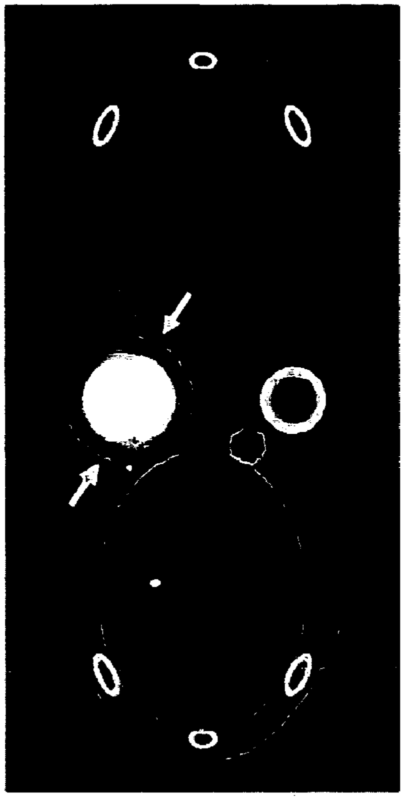
Figure 118C:
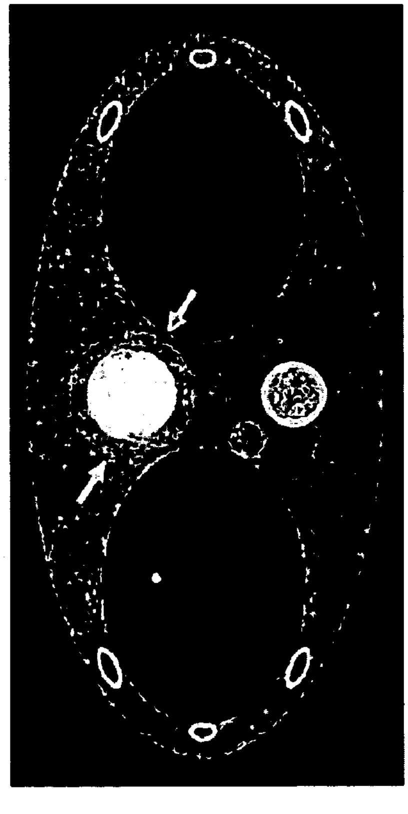
Figure 118D:
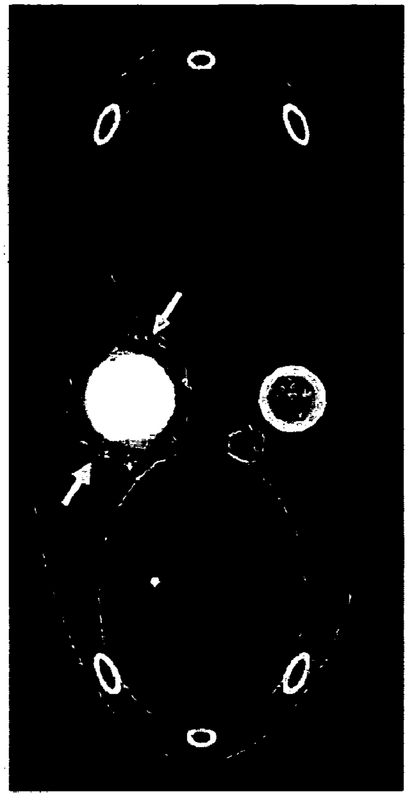

FIGS. 118A-D illustrate the phase-interval image reconstruction for the modified FORBILD phantom. FFBP (FIG. 118A) and WBPF (FIG. 118B) illustrate reconstructions from the motion-contaminated data described in FIG. 117 using short-scan data (PFSD=64.5%) from $[-0.5\pi, 0.79\pi]$. FIG. 118C and FIG. 118D are corresponding FFBP and WBPF reconstructions with added Gaussian noise, respectively. Gaussian noise with a standard deviation of 0.3% of the maximum value of the noiseless data was added to the noiseless data prior to reconstruction. For all reconstructions, $\bar{T}_{ROI}$=583 ms. Arrows point to motion artifacts along the edges of the dynamic insert (L: 50 HU/W: 400 HU). As seen in FIGS. 118A-D, the motion artifacts along the edges of the dynamic insert in the four reconstructions appeared rather similar to one another. The average temporal resolutions for all reconstructions were 583 ms.

Figure 119B:
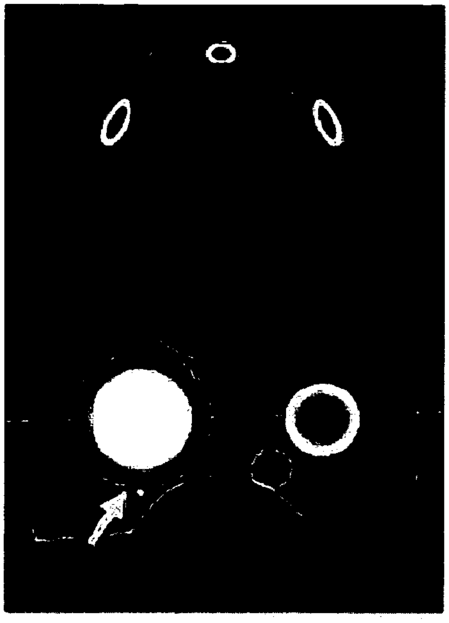

Four phase-interval ROI reconstructions for the modified FORBILD phantom using the WBPF methodology then were performed. The results are shown in FIGS. 119A-D. FIG. 119A depicts the WBPF reconstruction from the motion-contaminated dataset described in FIG. 117 using reduced-scan data (PFSD=50%) from $[-0.5\pi, 0.5\pi]$, with $\bar{T}_{ROI}$=473 ms. Since the data used for this reconstruction were not contaminated by motion, the resultant reconstruction shown in FIG. 119A was free of motion artifacts. This reconstruction included only the right half of the cardiac insert. FIG. 119B depicts the WBPF reconstruction using this same data set (PFSD=53%) from $[-0.5\pi, 0.56\pi]$, with $\bar{T}_{ROI}$=492 ms. Thus, this second reconstruction used 53% of the full-scan data. The additional 3% of motion-contaminated data was sufficient for reconstructing the entire cardiac insert, as shown in FIG. 119B. The entire cardiac insert is visible, and less motion artifact is present in this reconstruction than that present in the short-scan reconstruction shown in FIG. 118B.

Figure 119D:
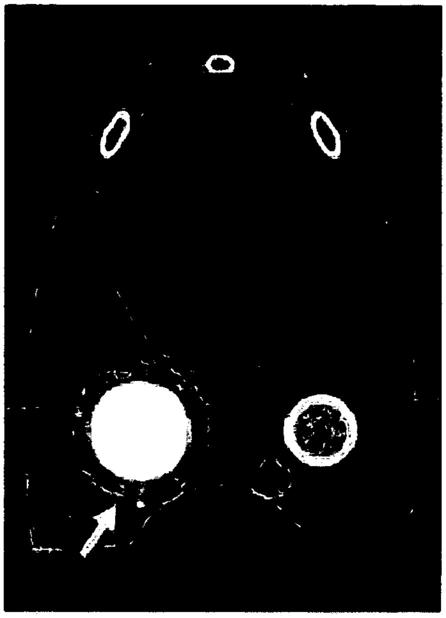
Figure 119A:
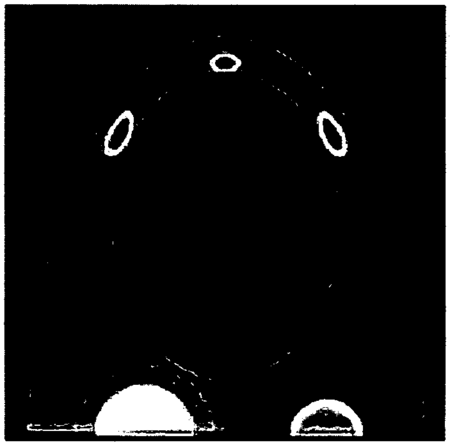
Figure 119C:
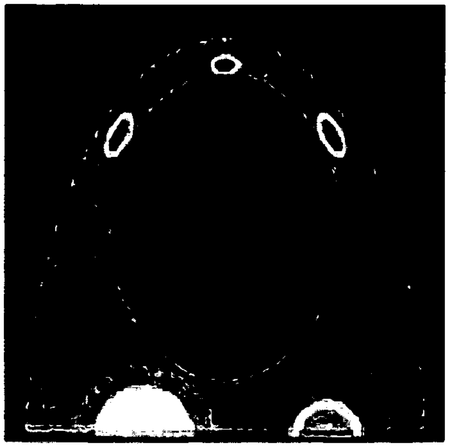

The reconstructions of FIGS. 119A-B were repeated with Gaussian noise added to the noiseless data to produce FIGS. 119C-D. Gaussian noise with a standard deviation of 0.3% of the maximum value of the noiseless data was added to the noiseless data prior to reconstruction. In FIG. 119B and FIG. 119D, the white arrow points to motion artifacts along the edges of the cardiac insert (L: 50 HU/W: 400 HU).

Phase-interval ROI reconstruction allowed for the entire cardiac insert to be reconstructed with less motion-contaminated data than that required to reconstruct the entire image. By using data with less motion-contamination, the resulting reduced-scan reconstruction shown in FIG. 119B exhibited less motion artifact and improved image quality than its corresponding short-scan reconstruction shown in FIG. 118B. In addition, the temporal resolution of the reduced-scan reconstruction improved approximately 16% from 583 ms for the short-scan reconstruction to 492 ms for this reduced-scan reconstruction.

In order to obtain an exact reconstruction of the entire cardiac insert with the heart rate fixed at 60 bpm, the modified FORBILD phantom was re-positioned 5 cm to the right of the gantry's isocenter. A full-scan data set was acquired with the parameters described above. Motion contaminated regions of the projection data spanned scanning angles $\lambda\in[0.5\pi, 1.5\pi]$.

Reconstructions were performed with the FFBP and WBPF methodologies. The FFBP methodology required short-scan data from [−0.5π, 0.79π].

Figure 120B:
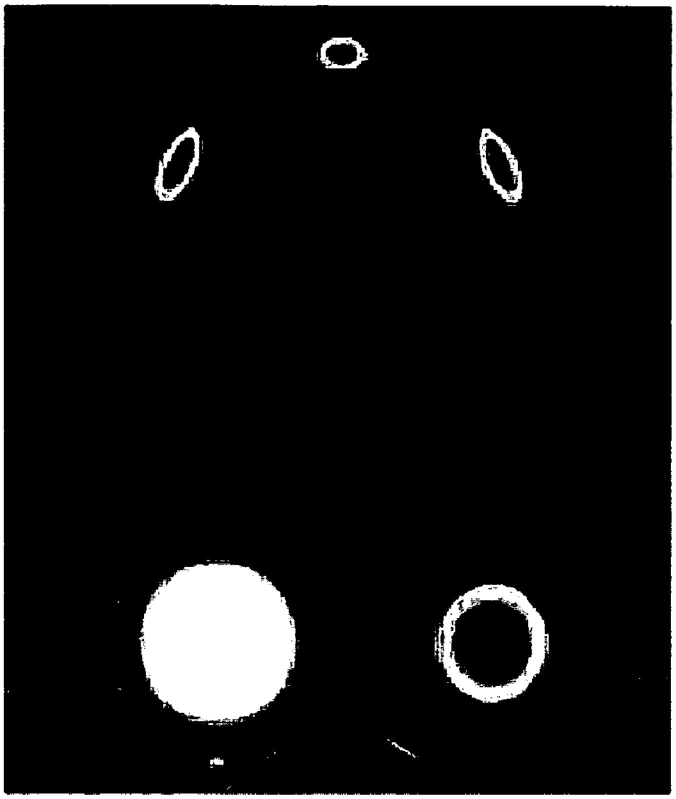
Figure 120A:
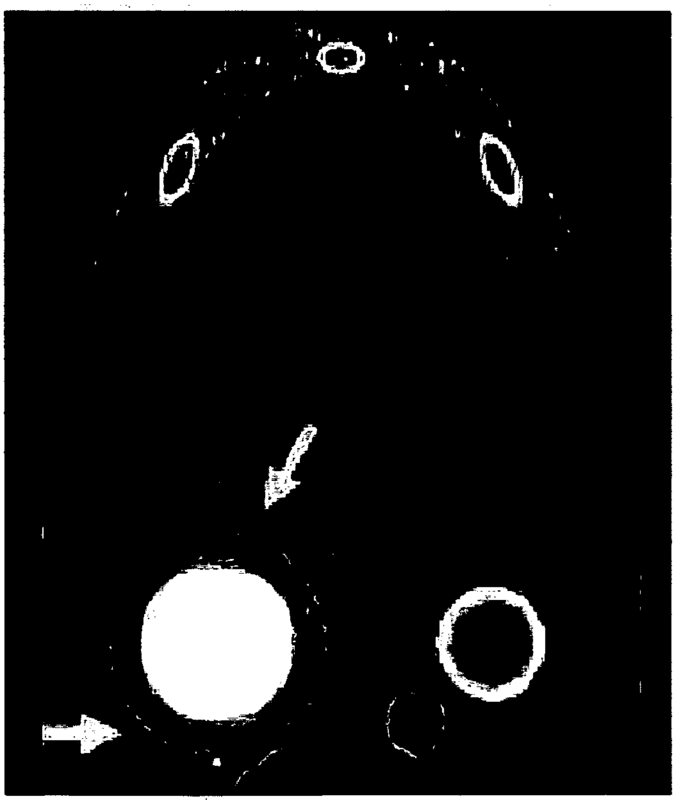

FIGS. 120 A-B depict phase-interval ROI reconstruction with off-center positioning using non-truncated data. The modified FORBILD phantom with a heart rate of 60 bpm as before was shifted 5 cm towards the right, and data were acquired with the parameters described above. Motion-contaminated data ranged from [0.5π, 1.5π]. The FFBP reconstruction in FIG. 120A used short-scan data from [−0.5π, 0.79π], with $\bar{T}_{ROI}$=562 ms. Arrows point to motion artifacts at the edges of the dynamic insert. The WBPF reconstruction in FIG. 120B used reduced-scan data (PFSD=50%) acquired from [−0.5π, 0.5π], with $\bar{T}_{ROI}$=473 ms. For both reconstructions, $\bar{T}_{ROI}$ was calculated over the ROI recovered with an angular reconstruction interval spanning [−0.5π, 0.5π] (L: 50 HU/W: 400 HU).

The use of motion-contaminated data segments resulted in motion artifacts, as depicted by the white arrows in the FFBP reconstruction shown in FIG. 120A. On the other hand, the WBPF methodology, which used motion-free reduced-scan data (PFSD=50%) from [−0.5π, 0.5π], was able to produce a reconstruction of the entire dynamic insert that was not contaminated by motion artifacts, as shown in FIG. 120B. No motion artifacts were present because the reduced-scan data used for reconstructing this ROI image did not contain any motion-induced inconsistencies. Thus, the WBPF methodology's capability of reconstructing ROI images from reduced-scan data allowed for the scanning configuration to be altered so that an image containing the entire ROI could be reconstructed without using any motion-contaminated data. The temporal resolution of this reconstruction was 473 ms.

In order to obtain an exact reconstruction of an ROI that contains the entire cardiac insert with the heart rate fixed at 66 bpm, the phantom was re-positioned 15 cm to the right of the gantry's isocenter. Data were acquired with the acquisition parameters described above. Since the phantom extended outside of the reconstruction FOV, the data contained truncations over a portion of the acquired scanning views. Motion-contaminated regions of the truncated data spanned scanning angles λ∈[0.41π, 1.5π] at this heart rate.

Figure 121B:
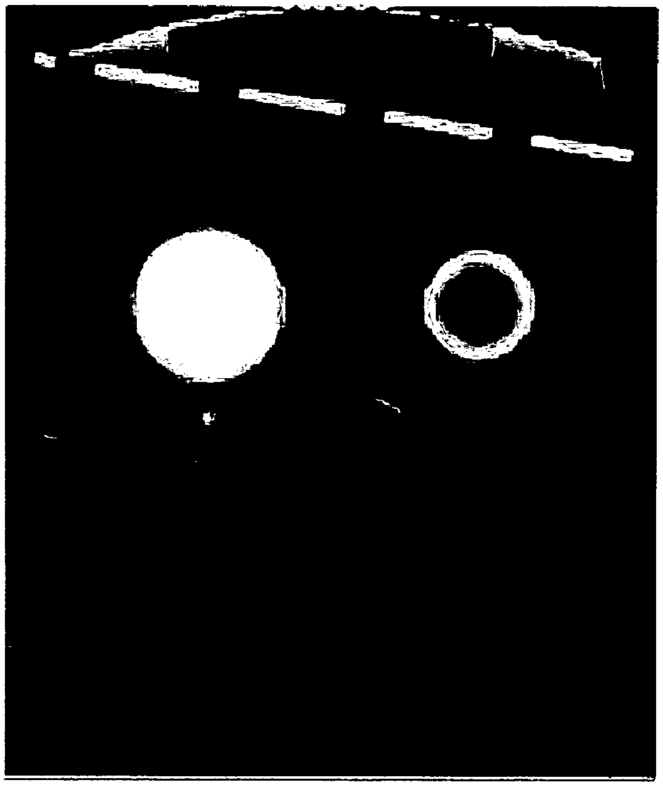
Figure 121A:
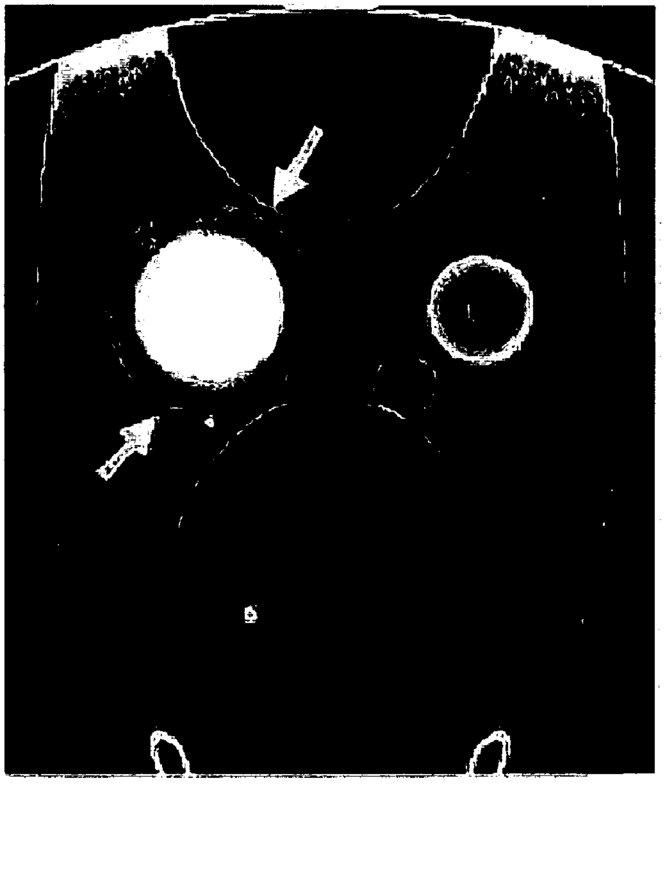

An FFBP reconstruction using short-scan data from [−0.5π, 0.79π] and a WBPF reconstruction using reduced-scan data (PFSD=45%) from [−0.5π, 0.4π] were performed. FIGS. 121A-B illustrate the phase-interval ROI reconstruction with off-center positioning using truncated data. The modified FORBILD phantom with a heart rate of 66 bpm was shifted 15 cm towards the right, and data were acquired with the parameters described above. Motion-contaminated data ranged from [0.41π, 1.5π]. The FFBP reconstruction in FIG. 121A used short-scan data from [−0.5π, 0.79π], with $\bar{T}_{ROI}$=555 ms. This reconstruction contains not only motion artifacts as denoted by the white arrows but also truncation artifacts resulting from the phantom extending beyond the FOV. The WBPF reconstruction in FIG. 121B used reduced-scan data (PFSD=45%) from [−0.5π, 0.4π] , with $\bar{T}_{ROI}$=432 ms. This reconstruction is free from both motion and truncation artifacts in the region to the left of the white dashed line, as no motion-contaminated data were used to reconstruct this ROI image. For both reconstructions, $\bar{T}_{ROI}$ was calculated over the ROI recovered with an angular reconstruction interval spanning [−0.5π, 0.4π] (L: 50 HU/W: 400 HU). Thus, compared to the $\bar{T}_{ROI}$ of 473 ms for the 5 cm off-center WBPF reconstruction shown in FIG. 120B, the 15 cm off-center WBPF reconstruction had a $\bar{T}_{ROI}$ of 432 ms.

Figures 122A, 122B, 122C, 122D:
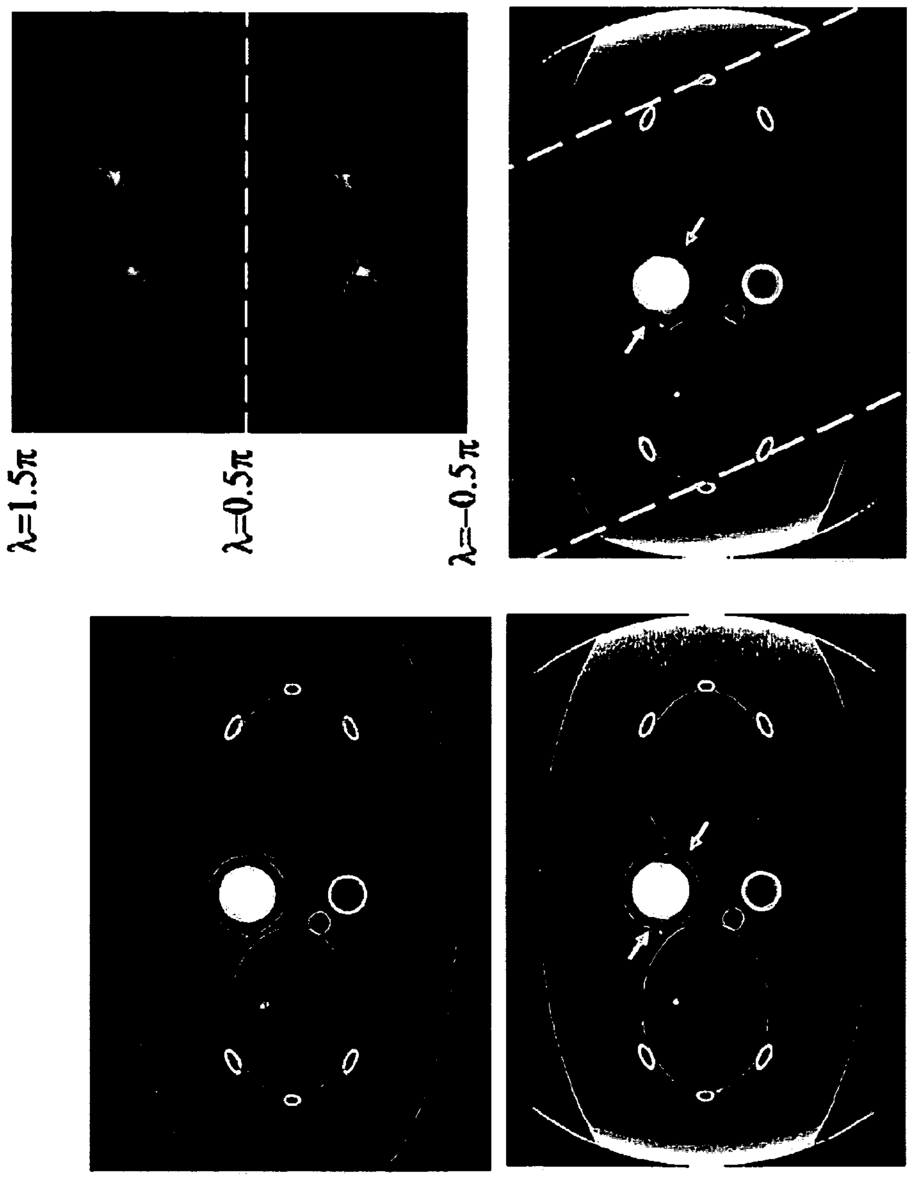

FIGS. 122A-D illustrate morphology of motion artifacts in reconstructions from truncated data. FIG. 122A illustrates a modified FORBILD phantom with its outer ellipse expanded by 50% so that its lateral dimensions exceeded the 50 cm FOV. All other parameters of the dynamic phantom remained unchanged. In order to evaluate whether truncations in a projection data set affect the morphology of motion artifacts, the phantom was modified by expanding the dimensions of the outer ellipse by 50% so that its lateral dimensions extended beyond the 50 cm FOV, as shown in FIG. 122A. All other phantom parameters, including the spatial and temporal characteristics of the dynamic insert, remained the same as the previously described normal-sized phantom. The expanded phantom was centered within the FOV and its heart rate was set to 60 bpm. Projection data of the expanded phantom were acquired with acquisition parameters described above. FIG. 122B illustrates motion-contaminated data set with truncations. The dashed line separates the motion-contaminated region [0.5π, 1.5π] from the motion-free region [−0.5π, 0.5π]. Thus, the resulting data depicted in FIG. 122B contained truncations over a portion of scanning angles.

Images of the expanded phantom were reconstructed with the FFBP and WBPF methodologies using short-scan data with scanning angles λ∈[−0.5π, 0.79π]. FIGS. 122C-D illustrate FFBP and WBPF reconstructions, respectively, of the expanded phantom using short-scan data from [−0.5π, 0.79π], resulting in $\bar{T}_{ROI}$=583 ms. Motion artifacts are denoted by the white arrows. In FIG. 122D, the region between the dashed white lines is free of truncation artifacts. Thus, the FFBP reconstruction in FIG. 122C contained both truncation and motion artifacts, whereas the WBPF reconstruction in FIG. 122D contained only motion artifacts in the region around the cardiac insert. As seen in FIGS. 122C and 122D, the motion artifacts in both expanded phantom reconstructions appeared similar to the motion artifacts in the reconstructions of the normal-sized phantom shown in FIGS. 118A and 118B, respectively. This visual assessment supports that truncations in this data set may not have a substantial effect on the morphology of motion artifacts in the reconstructed images.

TABLE 3

Acquisition and reconstruction parameters with corresponding figure designations for the NCAT phantom.

| Methodology | Acquisition Type PFSD | No noise (60 bpm) FIG. | Noise (60 bpm) FIG. | Off-center (60 bpm) FIG. | Gating (66 bpm) FIG. | Gating plus off-center (66 bpm) FIG. |
|---|---|---|---|---|---|---|
| FFBP | 64.5% | 123A | 123C | 124A | 125C | 125E |
| WBPF | 64.5% | 123B | 123D | | 125D | |
| WBPF | 45.0% | | | 124B | | 125F |

All projection datasets were acquired with the same circular fan-beam geometry and line detector array. In particular, fan-beam data were acquired using a 57 cm radius for the circular trajectory, a 104 cm source-to-detector distance, and a 50 cm reconstruction FOV. A one-dimensional detector with 1024 detector elements, each with a bin size of 0.54 mm when scaled to isocenter, was used. For this geometry, the PFSD necessary for short-scan acquisitions was 64.5%.

Datasets were acquired with starting gantry angle fixed at 1.5π, the starting temporal phase set at 0.75 (mid-to-late diastole), and the gantry rotation time set to 0.4 s. The gantry was set to rotate in a clockwise direction, which was the opposite of the counter-clockwise direction used for the modified FORBILD phantom described above. Images containing the FOV were reconstructed on a 1024×1024 matrix. All reconstructions were displayed with a level and window of 50 HU and 400 HU respectively. Table 3 depicts acquisition and reconstruction parameters, as well as their corresponding figure numbers, for the simulations involving the NCAT phantom.

A full-scan data set of the NCAT phantom beating at 60 bpm was acquired with the parameters described above. Two sets of FFBP and WBPF reconstructions were obtained with short-scan data from [0.21π, 1.5π]. The first set was obtained from noiseless data, and the second set was acquired from noisy data. For the second set, Gaussian noise with a standard deviation of 0.1% of the maximum value of the noiseless data was added. This standard deviation was chosen to ensure that both LAD and LCX plaques were visible in a FFBP reconstruction acquired from noisy motion-free data obtained at a temporal phase of 0.75.

Figures 123A, 123B, 123C, 123D:
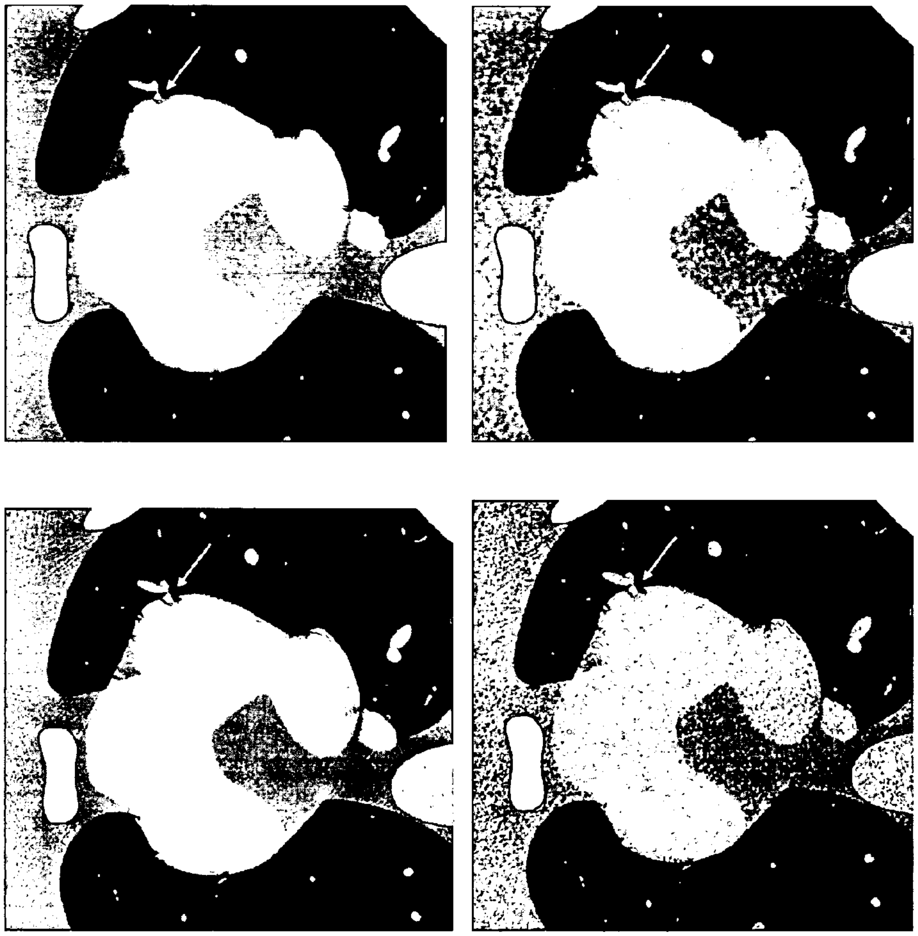

FIGS. 123A-D illustrate phase-interval image reconstruction for the NCAT phantom. Projection data of the NCAT phantom beating at 60 bpm were acquired with the parameters described above. FIGS. 123A-B illustrate respective FFBP and WBPF reconstructions using short-scan data from [0.21π, 1.5π], with $\overline{T}_{ROI}$=234 ms. FIGS. 123C-D illustrate corresponding FFBP and WBPF reconstructions from noisy data. Gaussian noise with a standard deviation of 0.1% of the maximum value of the noiseless data was added.

As seen in FIG. 123, the motion artifacts in all four reconstructions appeared rather similar. In fact, neither the LAD nor LCX plaques could be seen in any reconstruction. However, the motion artifact resulting from the ventricular wall coming into contact with a structure within the lung could be seen in all reconstructions.

In order to improve the quality of the reconstructions shown in FIG. 123 without adjusting the starting temporal phase, methods of reducing the average temporal resolution of the reconstruction may be applied. Since the 0.4 s gantry rotation time and the 1.0 s cardiac cycle time at 60 bpm are synchronous, ECG-correlated gating cannot be used for improving the average temporal resolution of this reconstruction. In addition, the modest improvements in temporal resolution from phase-interval ROI reconstruction using more than half of the full-scan data may not be sufficient to see reductions in motion artifacts due to the fast gantry rotation time with respect to the cardiac cycle time. However, as shown in the demonstrations involving the modified FORBILD phantom, combining phase-interval ROI reconstruction with off-center positioning of the NCAT phantom may be a viable option for reducing the PFSD to an extent that motion artifacts can be suppressed rather noticeably.

As a result, the NCAT phantom was shifted 18 cm to the left of isocenter, and a full-scan data set was acquired with the parameters described above. Two reconstructions were obtained from this data set. The first was an FFBP reconstruction using short-scan data from [0.21π, 1.5π], and the second was a WBPF reconstruction using reduced-scan data (PFSD=45%) from [0.6π, 1.5π].

Figure 124B:
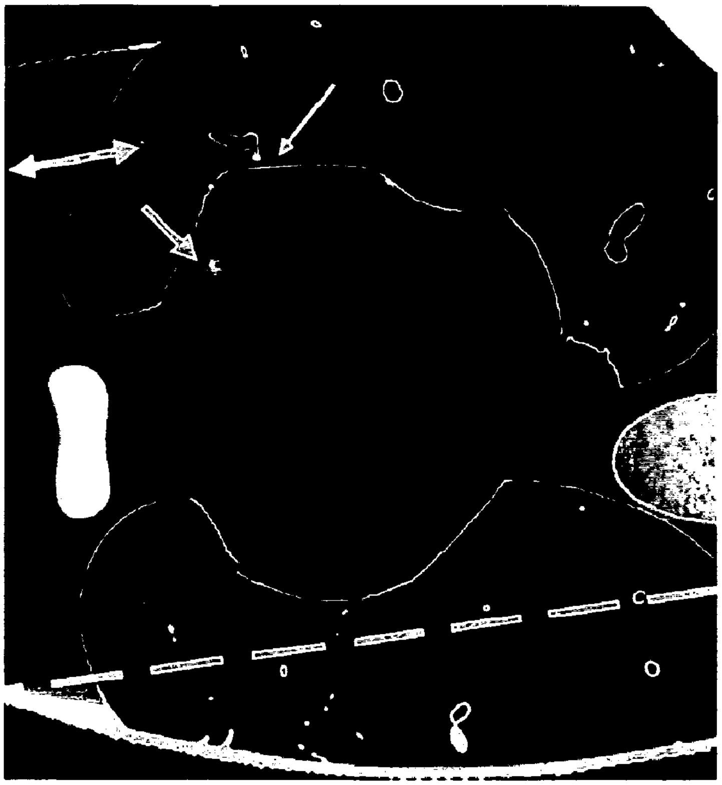
Figure 124A:

FIGS. 124A-B illustrate phase-interval ROI reconstruction with off-center positioning using non-gated data with truncations. The phantom with a heart rate of 60 bpm was shifted 18 cm towards the left, and a full-scan data set was acquired with the parameters described above. The FFBP reconstruction in FIG. 124A used short data from [0.21π, 1.5π] with $\overline{T}_{ROI}$=222 ms. This reconstruction contains truncation artifacts. The WBPF reconstruction in FIG. 124B used reduced-scan data (PFSD=45.%) from [0.6π, 1.5π], with $\overline{T}_{ROI}$=173 ms. This reconstruction is free from truncation artifacts in the region to the right of the white dashed line. A white double-sided arrow lies parallel to a motion-induced streak along a PI-line segment tangent to the edges of the moving heart. For both reconstructions, $\overline{T}_{ROI}$ was calculated over the ROI recovered with an angular reconstruction interval spanning [0.6π, 1.5π] The thick white arrow points to the LAD plaque.

Although the LAD plaque can be seen quite clearly in both FFBP and WBPF reconstructions shown in FIG. 124, the motion artifact resulting from the ventricular wall coming into contact with an adjacent pulmonary structure is much less evident in the WBPF reconstruction. Specifically, the thin white arrow points to a motion artifact, which is less evident in FIG. 124B than in FIG. 124A. Phase-interval ROI reconstruction with off-center positioning may be successful in suppressing this motion artifact. The average temporal resolution for the WBPF reconstruction was 173 ms. However, the WBPF reconstruction also included a motion-induced streak along some PI-line segments located tangent to the edges of the moving heart. The endpoints of these PI-line segments were located near the boundaries of the angular reconstruction interval.

In order to allow for two-segment retrospective gating, the NCAT heart rate was increased to 66 bpm. At a gantry rotation time of 0.4 s, a substantial improvement in temporal resolution can be obtained by gating at this heart rate. The phantom was centered within the FOV, and a data set was obtained over three cardiac cycles with the parameters described above. The FFBP and WBPF methodologies were used to reconstruct four images from this data set.

Figure 125A:
Figure 125B:
Figure 125C:
Figure 125D:

FIGS. 125A-F illustrate phase-interval ROI reconstruction using gated data. The NCAT heart rate was increased to 66 bpm, and a data set was acquired with the parameters described above. FIGS. 125A-B illustrate respective FFBP and WBPF reconstructions using nongated short-scan data from [0.21π, 1.5π], with $\overline{T}_{ROI}$=234 ms. FIGS. 125C-D illustrate respective FFBP and WBPF reconstructions from two-segment retrospectively-gated short-scan data from [0.21π, 1.5π], with $\overline{T}_{ROI}$=121 ms. Thus, two reconstructions were obtained without gating, as shown in FIGS. 125A and 125B, and two were obtained with two-segment retrospective gating, as shown in FIGS. 125C and 125D. Retrospective gating allowed for a 48% reduction in $\overline{T}_{ROI}$ from 234 ms to 121 ms. When compared to the ungated reconstructions, the motion artifact resulting from the collision of the left ventricular wall with the pulmonary structure was suppressed in both gated reconstructions.

Figure 125E:
Figure 125F:
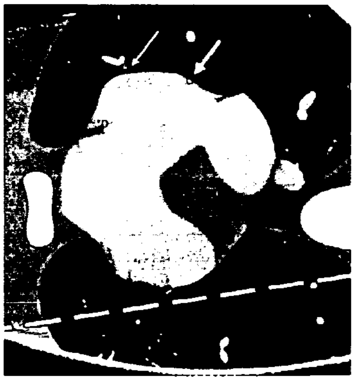

In order to examine how phase-interval ROI reconstruction with off-center positioning would perform with retrospectively-gated data, the phantom was shifted 18 cm to the left of isocenter and a data set was obtained over three cardiac cycles with the same parameters as those used above. FIGS. 125E-F illustrate the NCAT phantom was shifted 18 cm laterally prior to data acquisition. Respective short-scan FFBP (PFSD=64.5% $\overline{T}_{ROI}$=113 ms, [0.21π, 1.5π]) and reduced-scan WBPF (PFSD=45%, $\overline{T}_{ROI}$=111 ms, [0.6π, 1.5π]) reconstructions following two-segment gating were performed. Gating parameters were selected based on the amount of data used for reconstruction. In particular, for each PFSD, the segments used for constructing the gated data set were almost equally-sized. The slight difference in segment sizes was implemented to account for the small angular overlap commonly used for suppressing gating in homogeneities.

For both reconstructions, $\overline{T}_{ROI}$ was calculated over the ROI recovered with an angular reconstruction interval spanning [0.6π, 1.5π] In FIG. 125F, the region to the right of the white dashed line is free of truncation artifacts. In all images, the thick white arrow points to the LCX plaque, which is most apparent in FIG. 125F. The thin white arrow points to a motion artifact resulting from the ventricular wall coming into contact with an adjacent structure. Thus, in both FFBP and WBPF reconstructions shown in FIGS. 125E and 125F, the LCX plaque was visible and the motion artifact between the left ventricular wall and the adjacent pulmonary structure was suppressed. The LCX plaque in the WBPF reconstruction shown in FIG. 125F was more apparent than the LCX plaque in all other reconstructions shown in this figure. This was partly due to the $\overline{T}_{ROI}$ of 111 ms as well as the lack of truncation artifacts in the region covering the heart.

Since the WBPF methodology may reconstruct ROI images from reduced-scan data, the temporal resolutions of the ROI images can vary depending on the amount of data used for a given gantry rotation time. In order to determine how the average ROI temporal resolution varies with respect to the amount of data used in the presence and absence of retrospective gating, $\overline{T}_{ROI}$ values were calculated at PFSD s of 45%, 50%, 53%, 56%, 60% and 64.5% without and with retrospective gating. A 1024×1024 matrix containing a 50 cm reconstruction FOV was used. A gantry rotation time of 0.4 s and an object cycle time of 0.91 s (HR=66 bpm) were assumed. For each PFSD, gating parameters were selected so that the two segments used for constructing the gated data set were almost equally-sized. The slight difference in segment sizes was implemented to account for the small angular overlap commonly used for suppressing gating inhomogeneities. $\overline{T}_{ROI}$ was calculated over the entire ROI available following reconstruction.

Figures 126A, 126B:
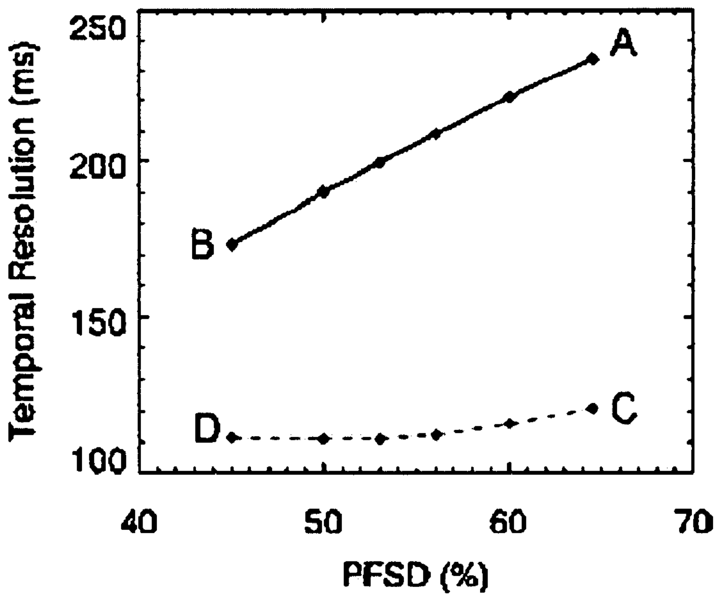

FIGS. 126A-B illustrate $\overline{T}_{ROI}$ calculations for ungated and gated reconstructions. Lower $\overline{T}_{ROI}$ values correspond to improved temporal resolutions. FIG. 126A graphs $\overline{T}_{ROI}$ versus PFSD for a 0.4 s gantry rotation time. The dark solid line represents $\overline{T}_{ROI}$ for ungated data. The light dashed line represents $\overline{T}_{ROI}$ for gated data (two-segment gating at 66 bpm). For each PFSD, the $\overline{T}_{ROI}$ was calculated over the entire ROI available following reconstruction. FIG. 126B illustrates a chart depicting relevant reconstruction parameters for the labeled points shown in FIG. 126A. For ungated data, the reduced-scan reconstruction with a PFSD of 45% allowed for a 25.8% decrease in $\overline{T}_{ROI}$ when compared to that of the short-scan reconstruction. This substantial improvement in $\overline{T}_{ROI}$ with a lower PFSD was part of a consistent trend, as seen in FIGS. 126A-B. For gated data, the trend between $\overline{T}_{ROI}$ and PFSD s seemed much less pronounced. Reduced-scan reconstruction with a PFSD of 45% allowed for only a 7.9% reduction in $\overline{T}_{ROI}$ when compared to that of a short-scan reconstruction. This result demonstrates that gating may not be as effective for improving the temporal resolution of a reduced-scan reconstruction as it may be for a short-scan reconstruction. This phenomenon may be due in part to the different weighting functions used for short-scan and reduced-scan reconstructions.

The usefulness of reconstructing ROI images from motion-contaminated fan-beam data with the WBPF methodology has been demonstrated. In particular, the WBPF methodology's capabilities of reconstructing ROI images from reduced-scan data containing truncations may be exploited to reduce the amount of motion-contaminated data used for ROI reconstruction. Also, phase-interval ROI reconstruction with the option of off-center positioning may be used to reduce motion artifacts and improve the average temporal resolution of the ROI image in numerical simulations involving the modified FORBILD and NCAT phantoms.

The improvements in temporal resolution from exploiting the WBPF methodology's capabilities are particularly noteworthy. As seen in FIG. 126, a consistently decreasing trend between the average temporal resolution of the ROI, $\overline{T}_{ROI}$, and the percent of full-scan data, PFSD, used for reconstruction can be observed for ungated data. When compared to the short-scan reconstruction, the reduced-scan reconstruction using 45% of the full-scan data resulted in a 25.8% improvement in temporal resolution. Although this trend seems much less profound for gated data, potential improvements in image quality still can be seen. For example, despite the slight 7.9% improvement in temporal resolution from using the reduced-scan data (PFSD=45%) gated at 66 bpm, the LCX plaque is delineated most clearly in the gated reduced-scan reconstruction shown in FIG. 125F.

In terms of the applications for cardiac imaging, the WBPF methodology may be used for patients who cannot benefit from ECG-correlated gating. Given the strong relationship between $\overline{T}_{ROI}$ and PFSD for ungated data, phase-interval ROI reconstruction potentially may allow for better delineation of critical structures in patients with arrhythmia, variable heart rates, or heart rates that synchronize with the rotation of the gantry. The WBPF methodology also may be used for reconstructing images from larger patients. Even if the patient extends beyond the FOV without and with off-center patient positioning, the WBPF methodology can provide a reconstruction of the heart that is potentially free of truncation artifacts.

For example, suppose a part of the object is moving during the scan (1 minute over 2π), during a ½ minute, the object may not be moving (therefore during this ½ minute, the data does not have motion artifacts). Previous methodologies required use of the entire scan. Cardiac imaging, in which the heart is in motion for a portion of the scan, is one application of this technique.

The WBPF methodology is not limited to reconstructing images from motion-contaminated data for cardiac imaging. This methodology may also be used for certain respiratory imaging applications, such as four-dimensional CT. If temporally-correlated projection data are obtained in an axial cine mode, in which data are obtained over one slice before progressing to the next, the WBPF methodology may be used to reconstruct ROI images using full-scan, short-scan, or even reduced-scan data. Since the lungs are not in the center of the reconstruction FOV, reduced-scan data requiring less than 50% of the full-scan data can be used to reconstruct either the right or left lung without re-positioning the patient within the FOV. Potential motion artifacts also may be suppressed.

The present analysis of the WBPF methodology focused on certain aspects for reconstructing ROI images from motion-contaminated data. First, only visual assessments were used to analyze the morphology of motion artifacts in the reconstructed images. Alternatively, a quantitative analysis of motion artifacts may be performed to compare how motion artifacts appear in WBPF and FFBP reconstructions. Second, phase-interval ROI reconstruction with off-center positioning which may affect the resolution and noise properties of the imaged object may also be performed. Cardiac CT chest exams may be used to rule out additional life-threatening illnesses such as pulmonary embolism, aortic dissection, and an aortic aneurysm, and these techniques may improve a physician's ability to diagnose these additional illnesses.

The WBPF or other BPF-derived methodologies may further be used for reconstructing ROI images from motion-contaminated cone-beam data. The analysis may likewise be readily extended to circular cone-beam data, and to other trajectories.

10.2 ROI Reconstruction of Motion-Contaminated Data Using Chord-Based Reconstruction Methodologies Chord-based methodologies may be used for reconstructing 2D or 3D images (such as cardiac images) from motion-contaminated data (including motion-contaminated fan-beam data). Chord-based reconstruction methodologies may play an essential role in methods for reconstructing two-dimensional (2D) or three-dimensional (3D) cardiac images. The following includes numerical simulations involving 2D images reconstructed from fan-beam data. Similarly, reconstruction of 3D images may be achieved from cone-beam data, even though reconstruction of 3D images may add a layer of complexity. In the fan-beam studies, the susceptibilities of chord-based methodologies are evaluated using different amounts of projection data to motion artifacts. The following analyzes the capabilities of chord-based methodologies, including on backprojection filtration (BPF), to be used in order to improve the quality of images reconstructed from non-gated and ECG-gated data. These capabilities, which may comprise reconstructing ROI images from reduced-scan data containing truncations, may allow for the usage of less motion-contaminated data and the acquisition of images with reduced motion artifacts.

Since circular and low-pitch helical cone-beam scans are commonly used for acquiring the projection data needed for reconstructing a 3D image containing the heart, strategies for reconstructing images from cone-beam data using chord-based methodologies may be developed. However, two issues may be addressed. First, since streak artifacts may appear along the chords used to reconstruct the image, methods of incorporating overscan data, or data in excess of the minimum amount, may be analyzed. Second, if phase-correlated data with or without ECG-gating are used for the helical cone-beam case, the continuous 3D volume may be reconstructed from a fragmented helix. Approximate chord-based methodologies may address both issues, so that entire 3D volumes of acceptable image quality can be obtained. Numerical studies involving the NCAT phantom may be used to analyze the methodologies Basic third-generation CT scanners may have a single x-ray source and a single detector rotating on opposite sides of the gantry. The source may provide divergent x-rays in a fan-beam configuration, and the detector, which contains a single row of detector elements, may measure the attenuated projections of the divergent x-rays that have passed through the reconstruction field-of-view (FOV) containing the object. Since the source may progress in a circular trajectory about the object, a circular fan-beam dataset may be acquired for reconstructing a 2D cross-sectional image of the object. By interspersing multiple circular fan-beam scans with incremental table translations, sufficient data may be obtained for reconstructing a 3D image of the object. Although high quality volumetric images of the object may be obtained through this step-and-shoot method, the required scan time for acquiring the necessary 3D dataset may be too long for this technique to be used efficiently and effectively for diagnostic screening applications.

Two recent technological advances have allowed for 3D datasets to be obtained in a more timely fashion. The first is the development of the helical source trajectory in the late 1980's. Since the helical source trajectory comprises translating the patient couch while the gantry is rotating, sufficient data may be obtained for reconstructing a 3D volume in a much shorter period of time. The second is the development and commercialization of multi-detector CT (MDCT) scanners in the late 1990's. Since these scanners use multiple detector rows, the overall X-ray collimation in the axial direction (parallel to the direction of translation for the patient couch) may be increased dramatically, and data may be obtained from divergent X-rays in a cone-beam configuration. For a circular source trajectory, data from a single gantry rotation can be used to reconstruct a 3D volume approximately due to the presence of data obtained above and below the plane of the source trajectory. For a helical source trajectory, the larger X-ray collimation can further increase the distance that the table translates per gantry rotation. As a result, datasets that can be used to reconstruct an even larger 3D volume can be obtained in a shorter period of time. As the number of detector rows have increased from 4 to 64, the performance of MDCT scanners have improved dramatically with respect to spatial resolution, temporal resolution, and scan time. The increased number of detector rows has allowed for the axial spatial resolution to improve from 1.0 mm to approximately 0.4 mm. As a result, the spatial resolution of an individual voxel has become nearly isotropic, such that the resolution of this voxel in the axial direction is almost equivalent to its resolutions in the transverse directions. The decrease in gantry rotation time from 500 ms to 330 ms for a single gantry rotation has allowed for a corresponding improvement in temporal resolution from 250 ms to 165 ms when images are reconstructed using a short-scan (also known as half-scan) data interval. These technological advancements have been especially beneficial for applications involving cardiac imaging, since the scan time for a complete cardiac acquisition has decreased from 40 s to 10 s.

Further improvements in temporal resolution may be achieved with the recently introduced dual-source CT (DSCT) scanners, which have two source-detector pairs located 90° from one another. DSCT scanners with a gantry rotation time of 330 ms have a temporal resolution of 83 ms when images are reconstructed using a short-scan data interval.

The recent technological advances in MDCT have revolutionized cardiac imaging. Faster gantry rotation times, increased numbers of detector rows, and the development of reconstruction methodologies incorporating ECG-correlated gating have allowed for the generation of high quality images containing the entire 3D volume of the heart from scan times lasting much less than the time needed for a single breath-hold. In many cases, the spatial and temporal resolutions of the reconstructed images are sufficient for the delineation of calcified and non-calcified coronary plaques. As a result, MDCT represents an emerging modality for applications such as coronary calcium scoring and coronary angiography.

However, even with faster gantry rotation times, increased numbers of detector rows, and efficient methods for ECG-correlated gating, image quality from cardiac MDCT often suffers from motion artifacts. These motion artifacts appear because the projection data needed for reconstructing a cross-sectional image of the heart are not obtained within a small enough time window. In other words, temporal resolutions are not sufficient for "freezing" the motion of the heart, and the inconsistencies in the projection data are pronounced enough such that streaks, blurs, positional changes, or general anatomical distortions may become easily discernible in the reconstructed images. In order to provide a sense of the temporal resolution needed in order to produce an image relatively free of motion artifacts, X-ray angiography (XRA), the gold standard for coronary angiography, boasts a temporal resolution of around 20 ms. Although 64-slice scanners with gantry rotation times of 330 ms and reconstruction methodologies incorporating two-segment retrospective gating are capable of producing images with temporal resolutions between 83-165 ms depending on the heart rate of the patient, these temporal resolutions still may be significantly greater than the temporal resolution of XRA. DSCT scanners can be used to close this gap in temporal resolution, as DSCT scanners with a gantry rotation time of 330 ms and reconstruction methodologies incorporating two-segment retrospective gating can produce images with temporal resolutions between 41.5 ms and 83 ms depending on the heart rate of the patient.

For MDCT and DSCT scanners, motion artifacts may corrupt the reconstructed image to such an extent that coronary segments sometimes no longer can be evaluated for potential lesions. As a result, physicians must spend a great deal of time searching for the optimal cardiac phases needed for assessing a particular coronary artery for a given patient. In addition, studies have shown that motion artifacts represent a major reason that the diagnostic performance of MDCT has not reached that of invasive coronary angiography for the detection of stenotic coronary lesions, especially for patients with higher heart rates. Motion artifacts also have been shown to affect the accuracy and reproducibility of coronary artery calcium scores. Finally, the development of innovative computer-aided schemes for quantitatively assessing coronary lesions has been hindered by the degradation in image quality caused by motion artifacts.

Significant efforts have been placed on developing strategies for handling motion-contaminated data and improving the quality of reconstructed images. For example, alternative methods for cardiac gating based on center-of-mass calculations and volumetric data have been proposed. These approaches are based on the observation that cardiac motion is not described completely by ECG signals and can be analyzed by other methods. Automated methods for determining the optimal phase intervals for image re-construction and interpretation also have been developed. These automated methods may prove useful, as clinical studies have shown that the optimal phases for visualizing coronary arteries often differ depending on the spatial locations of the arteries and the heart rate of the patient. Moreover, as stated above, the process of finding optimal cardiac phases for each artery may be very time-consuming. Proposed approaches include one based on determining the 3D velocities of coronary landmarks and another based on creating motion maps by computing similarity metrics between successively reconstructed low-resolution images. The motion map method is potentially promising, as a clinical study has shown that the phases selected using this method demonstrated an 85% agreement with those obtained manually using observers.

The recent advances in MDCT technologies also have encouraged the development of novel reconstruction methodologies. Many of these methodologies have capabilities that cannot be realized by the conventional fan-beam filtered backprojection (FFBP) methodology, the circular cone-beam methodology developed by Feldkamp, Davis, and Kress (FDK), and helical cone-beam methodologies based on linear interpolation (LI). For example, super short-scan methodologies were developed capable of reconstructing an ROI image from reduced-scan fan-beam data, which span an angular range shorter than the $\pi$ plus fan angle needed by the FFBP methodology.

The methodologies discussed above may produce exact 2D or 3D reconstructions from helical cone-beam data. Since these methodologies reconstruct images on PI-line segments, which may be chords that fill a cylindrical 3D volume enclosed by the helical source trajectory, they may be referred to as chord-based methodologies. The chord-based backprojection filtration (BPF) and minimum-data filtered backprojection (MD-FBP) methodologies are unique in that in many cases, they can produce exact ROI reconstructions from projection data containing truncations. Although the chord-based filtered backprojection (FBP) methodology cannot handle truncated data exactly, its established mathematical equivalence to the cone-beam FDK methodology may offer this methodology theoretical and practical significance. All three methodologies also may be capable of reconstructing images from reduced-scan fan-beam and circular cone-beam data.

Due to their unique capabilities, many of these methodologies may find useful applications in cardiac imaging. For the fan-beam case, current cardiac reconstruction methodologies may require data spanning a short-scan angular interval. Image temporal resolution may be improved for both ungated and gated projection datasets by using the backprojection filtration (BPF) methodology, whose capability of reconstructing ROI images from reduced-scan data allows for less motion-contaminated data to be used. For the helical cone-beam case, current cardiac reconstruction methodologies may be based on approximate methods such as LI or the 3D backprojection of filtered data onto the Cartesian coordinate system. The latter methodologies are referred to as FDK-based methodologies. Methods based on exact methodologies may produce images which are less susceptible to cone-beam artifacts, especially as detectors with an increased number of rows are developed.

Understanding and analyzing how chord-based methodologies respond to motion-contaminated fan-beam data is beneficial in developing strategies for reconstructing 2D or 3D images of the heart. For example, analyzing the susceptibilities of these methodologies to motion artifacts may provide assistance as to which methodologies may be used and amounts of projection data may be used for reconstructing a 2D or 3D volume. Moreover, since BPF-based methodologies may handle reduced-scan fan-beam data with truncations in an exact fashion, assessments of whether these unique capabilities may be exploited in cardiac imaging may assist in further understanding the advantages that these methodologies may have in reconstructing images from motion-contaminated data.

Since most cardiac acquisition protocols involve obtaining cone-beam datasets from circular or low pitch helical trajectories, methods for acquiring images from these motion-contaminated datasets using chord-based methodologies may be needed. The following analyzes modifications to the chord-based methodologies in the following manners. First, overscan data may be incorporated in circular cone-beam and helical cone-beam reconstructions so that motion-induced streak artifacts may be suppressed. Second, strategies may be developed for reconstructing images from fragmented low-pitch helical trajectories so that entire image volumes may be reconstructed from phase-correlated data.

The studies described below involve the use of chord-based methodologies for reconstructing images from motion-contaminated data. Since all studies involve using the same set of reconstruction methodologies and phantoms, these entities are introduced first. Descriptions of the studies then follow.

The helical source trajectory may be defined as $$\vec{r}_0(\lambda) = \left(R\cos\lambda,\ R\sin\lambda,\ \frac{h}{2\pi}\lambda\right)^T,$$

where λ is the scanning angle, R represents the focal length, and h represents the pitch. If h=0, a circular source trajectory can be obtained. A rotating coordinate system with unit vectors $\hat{e}_u=(-\sin\lambda, \cos\lambda, 0)^T$, $\hat{e}_v=(0, 0, 1)^T$ and $\hat{e}_w=(\cos\lambda, \sin\lambda, 0)^T$ can be defined with respect to the source trajectory. A flat-panel detector parallel to the u-v plane may be located a distance S from the source. For the cone-beam case, the projection data at a detector bin (u, v) and a scanning angle λ may be given by:

$$P(u,v,\lambda)=\int_0^{\infty} dl f(\vec{r}_0(\lambda)+l\hat{\beta}), \quad \text{(H-1)}$$

where $\hat{\beta}$ denotes the direction of the ray from the source to a specific detector position (u, v), and A(u, v) represents the distance between the source and this detector position. $\hat{\beta}$ and A(u, v) may be determined by:

$$\hat{\beta} = \frac{1}{A(u)}[u\hat{e}_u(\lambda) + v\hat{e}_v(\lambda) - S\hat{e}_w(\lambda)], \quad \text{(H-2)}$$

$$A(u, v) = \sqrt{u^2 + v^2 + S^2}. \quad \text{(H-3)}$$

As stated above, a circular source trajectory can be obtained by setting the pitch to zero. If the cone-angle remains non-zero, Eqs. H-1-H-3 may be used to describe a circular cone-beam scanning configuration. By setting the cone-angle to zero and considering detector measurements only in the mid-plane at v=0, a circular fan-beam configuration may be obtained.

The conventional FFBP methodology may be used for reconstructing images from an angular interval $[\lambda_{R,min}, \lambda_{R,max}]$ spanning a full-scan angular range $\Delta\lambda_R=\lambda_{R,max}-\lambda_{R,min}=2\pi$ or a short-scan angular range $\Delta\lambda_R=\pi+\gamma_{fan}$, where $\gamma_{fan}$ is the fan angle. Once the angular range is determined, the percent of full-scan data (PFSD) required for reconstructing an image may be obtained from the expression $$PFSD = \frac{\Delta\lambda_R}{2\pi}.$$

The conventional FFBP methodology may require a projection data weighting function ω(u, λ) satisfying the fan-beam data redundancy condition ω(u, λ)+ω(u', λ')=1 if $\lambda\in[\lambda_{R,min}, \lambda_{R,max}]$ and ω(u, λ)=0 if $\lambda\notin[\lambda_{R,min}, \lambda_{R,max}]$. (u', λ') are coordinates used for representing the conjugate projections of (u, λ), and are defined as u'=−u and λ'=λ+π−2 arctan(u/S) for the flat-panel detector geometry described above. The weighting function used for reconstructing images from full-scan data is ω(u, λ)=0.5.

Chord-based reconstruction methodologies such as the FBP, BPF, and MD-FBP methodologies may reconstruct images on chords, which connect two points corresponding to scanning angles $(\lambda_1, \lambda_2)$ on a given source trajectory. The direction of an individual chord can be expressed as $$\hat{e}_\pi = \frac{\vec{r}_0(\lambda_2) - \vec{r}_0(\lambda_1)}{|\vec{r}_0(\lambda_1) - \vec{r}_0(\lambda_2)|},$$

and a point on the chord can be specified by $x_\pi$, where $x_\pi\in[x_{\pi 1}, x_{\pi 2}]$, and $x_{\pi 1}$ and $x_{\pi 2}$ denote the two endpoints of the chord. The three parameters $(x_\pi, \lambda_1, \lambda_2)$, which serve as chord coordinates, are related to the spatial vector $\vec{r}$ by the following expression $$\vec{r} = \frac{\vec{r}_0(\lambda_1) - \vec{r}_0(\lambda_2)}{2} + x_\pi\hat{e}_\pi. \quad \text{(H-4)}$$

Figure 138A:
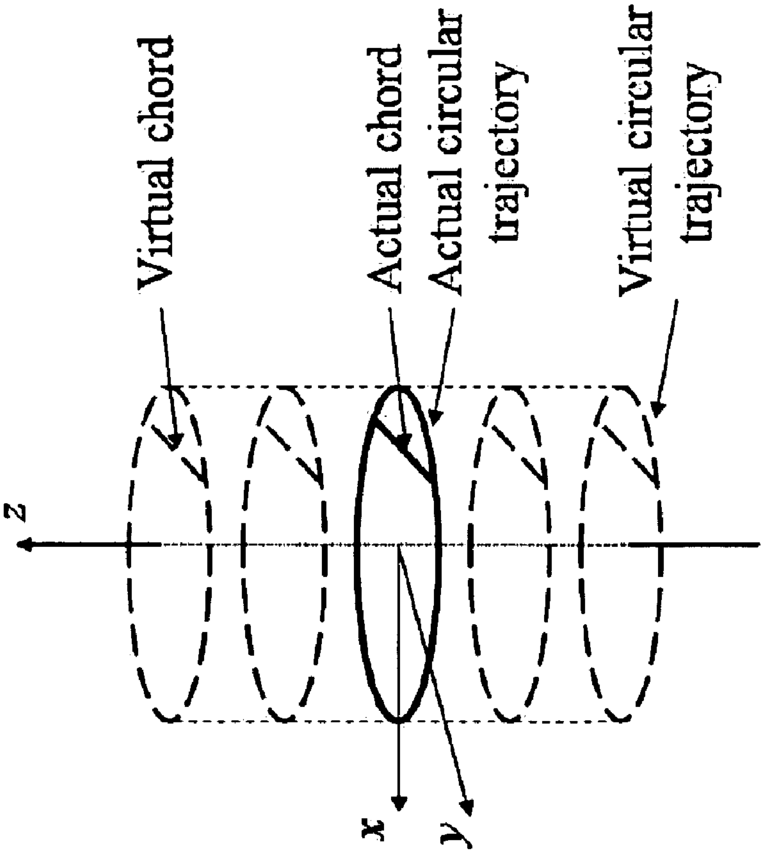

Chords may be defined depending on the source trajectory that is used. For the circular fan-beam case, chords may be defined using various configurations such as the parallel (angular orientation α) (see FIG. 127A), the converging (angle of convergence $\lambda_C$) (see FIG. 127B), and the intersecting configurations (point $\vec{r}$) (see FIG. 127C). These same configurations may be used for the circular cone-beam case, although virtual circular trajectories and virtual chords parallel to those in the actual source trajectory may used, as shown in FIG. 138A.

The helical cone-beam case may not allow for this type of flexibility in defining chord configurations. The reason is that chords on which images are reconstructed are PI-line segments, which satisfy the following condition $|\lambda_2-\lambda_1|\leqq 2\pi$. Every point $\vec{r}$ within the helix cylinder, which is the cylindrical volume enclosed by the trajectory, may be associated with a unique PI-line segment, and these PI-line segments may completely fill the helix cylinder. Due to the unique association between each point $\vec{r}$ within the helix cylinder and a particular PI-line segment, two different PI-line segments may not be used to reconstruct images on the same point. In order to ensure that images on enough PI-line segments are reconstructed to obtain a continuous volume, images on converging PI-line segments may be reconstructed as the angle of convergence is incrementally increased. The resulting images then may be re-interpolated onto a Cartesian coordinate system using Eq. H-4.

Let $f_\pi(x_\pi, \lambda_1, \lambda_2)$ denote the image on a chord $(\lambda_1, \lambda_2)$. Also, let $x_{\pi\lambda 1}$ and $x_{\pi\lambda 2}$ denote the two endpoints of the support section for this chord, whereby $f_\pi(x_\pi, \lambda_1, \lambda_2)=0$ for $x_\pi\notin[x_{\pi\lambda 1}, x_{\pi\lambda 2}]$. One may assume that this support section is contained within the actual chord, such that $[x_{\pi\lambda 1}, x_{\pi\lambda 2}]\subseteq[x_{\pi 1}, x_{\pi 2}]$. The chord-based FBP methodology involves taking the angular derivative of the projection data $$\left[\frac{dP(u', v', \lambda)}{d\lambda}\right]_{\hat{\beta}},$$

filtering the geometrically weighted data derivative along the cone-beam projection of the chord on the detector, and then performing a geometrically weighted backprojection of the filtered data onto the actual chord. The methodology can be implemented as follows:

$$f_\pi(x_\pi, \lambda_1, \lambda_2) = \frac{1}{2\pi^2} \int_{\lambda_1}^{\lambda_2} d\lambda \frac{A(u,v)}{|\vec{r} - \vec{r}_0(\lambda)|} \quad \text{(H-5)}$$

$$\int_{-\infty}^{\infty} \frac{du'_\pi}{u_\pi - u'_\pi} \frac{1}{|\vec{r}' - \vec{r}_0(\lambda)|}$$

$$\left[\frac{dP(u',v',\lambda)}{d\lambda}\right]_{\hat{\beta}}$$

where $u_\pi$ represents coordinates along the cone-beam projection of the chord $(\lambda_1, \lambda_2)$ on the detector.

The chord-based BPF methodology for reconstructing an image $f_\pi(x_\pi, \lambda_1, \lambda_2)$ on the chord $(\lambda_1, \lambda_2)$ may involve taking the angular derivative of the projection data $$\left[\frac{dP(u',v',\lambda)}{d\lambda}\right]_{\hat{\beta}},$$

calculating the geometrically weighted cone-beam backprojection image $$g_\pi(x'_\pi, \lambda_1, \lambda_2) = \int_{\lambda_1}^{\lambda_2} \frac{d\lambda}{|\vec{r}' - \vec{r}_0(\lambda)|} \left[\frac{dP(u',v',\lambda)}{d\lambda}\right]_{\hat{\beta}}, \quad \text{(H-6)}$$

and then performing an inverse Hilbert transform of $g_\pi(x'_\pi, \lambda_1, \lambda_2)$ to obtain $f_\pi(x_\pi, \lambda_1, \lambda_2)$. The inverse Hilbert transform may be implemented by filtering the backprojected data along the chord in the manner shown below $$f_\pi(x'_\pi, \lambda_1, \lambda_2) = \quad \text{(H-7)}$$

$$\frac{1}{2\pi^2} \frac{1}{\sqrt{(x_{\pi\lambda 2} - x_\pi)(x_\pi - x_{\pi\lambda 1})}}$$

$$\times \left[\int_{x_{\pi\lambda 1}}^{x_{\pi\lambda 2}} dx'_\pi \frac{\sqrt{(x_{\pi\lambda 2} - x'_\pi)(x'_\pi - x_{\pi\lambda 1})}}{(x_\pi - x'_\pi)} x g_\pi(x'_\pi, \lambda_1, \lambda_2) + \right.$$

$$\left. 2\pi D(\vec{r}_0(\lambda_1), \vec{r}_0(\lambda_2))\right],$$

where $x_\pi \in [x_{\pi\lambda 1}, x_{\pi\lambda 2}]$ and $D(\vec{r}_0(\lambda_1), \vec{r}_0(\lambda_2))$ is the projection of the ray coinciding with the chord $(\lambda_1, \lambda_2)$. Unlike the chord-based FBP methodology, the chord-based BPF methodology is capable of reconstructing images exactly from truncated data in certain cases. BPF methodologies are also capable of reconstructing images on chords from parallel and fan-parallel data.

The chord-based MD-FBP methodology is a methodology which involves the same order of operations as those for the chord-based FBP methodology. However, the MD-FBP methodology is also capable of reconstructing images exactly from truncated data in a manner similar to that for the BPF methodology. The MD-FBP methodology can be derived directly from the BPF methodology.

Suppose that a full-scan projection dataset for a circular fan-beam scan is obtained. An image on a chord $(\lambda_1, \lambda_2)$ may be reconstructed from two different segments of this full-scan dataset: minimum standard data with angles $\lambda \in [\lambda_1, \lambda_2]$ and minimum opposing data with angles $\lambda \notin [\lambda_1, \lambda_2]$, $f_{STD}(x_\pi, \lambda_1, \lambda_2)$ and $f_{OPP}(x_\pi, \lambda_1, \lambda_2)$ represent images obtained by using minimum standard and minimum opposing data, respectively. Although the angular reconstruction intervals required for obtaining these two images often differ, these images should be equivalent for projection datasets that are free of inconsistencies.

The angular interval required to reconstruct an image on a chord $(\lambda_1, \lambda_2)$ may also depend on the location of the chord with respect to the circular FOV. For example, a chord crossing the edge of the FOV may require more or less data than a chord crossing the center of the FOV depending on whether minimum standard or minimum opposing data are used. Since multiple chords may be required to reconstruct an image containing an entire ROI, different portions of the ROI may have different data requirements. As a result, the PFSD may be labeled as variable for ROI images reconstructed using chord-based methodologies. Note that these observations also apply to the virtual chords used in circular cone-beam scans.

For the circular fan-beam and circular cone-beam configurations, weighted variants of the chord-based FBP, BPF, and MD-FBP methodologies are mathematically equivalent to their respective original chord-based methodologies for the continuous case. These methodologies may incorporate overscan data, or data in excess of the minimum angular interval $[\lambda_1, \lambda_2]$ for reconstructing an image on a chord $(\lambda_1, \lambda_2)$. By using an expanded angular reconstruction interval $[\lambda_{R,min}, \lambda_{R,max}] \supseteq [\lambda_1, \lambda_2]$, these weighted methodologies may be used to improve noise properties. In addition, these methodologies may handle motion-contaminated data differently than the original chord-based methodologies.

The three weighted methodologies may entail that the backprojection step is extended over the expanded angular interval $[\lambda_{R,min}, \lambda_{R,max}]$. In addition, these methodologies may entail the usage of a projection data weighting function $\omega(u, \lambda)$, which satisfies the well-known fan-beam redundancy condition given below:

$$\omega(u,\lambda) \pm \omega(u',\lambda') = 1 \text{ if } \lambda \in [\lambda_{R,min}, \lambda_{R,max}], \quad (7)$$

$$\omega(u,\lambda) = 0 \text{ if } \lambda \notin [\lambda_{R,min}, \lambda_{R,max}]. \quad \text{(H-8)}$$

where a positive sign is used for the chord-based FBP methodology, and a negative sign is used for the chord-based BPF and MD-FBP methodologies. The weighting function $\omega(u, \lambda)$ also may correspond with the expanded angular interval $[\lambda_{R,min}, \lambda_{R,max}]$ used for reconstruction. A full-scan weighting function entails that $\Delta\lambda_R = 2\pi$, whereas a short-scan weighting function entails that $\Delta\lambda_R = \pi + \gamma_{fan}$. When $\Delta\lambda_R < \pi + \gamma_{fan}$, the WBPF methodology includes a reduced-scan weighting function. As with the conventional FFBP methodology, the percent of full-scan data PFSD needed for reconstructing an image using weighted chord-based methodologies may be obtained from the expression $$PFSD = \frac{\Delta\lambda_B}{2\pi}.$$

The weighted chord-based methodologies may use the same full-scan ($\omega(u, \lambda) = 0.5$) and short-scan (Parker's and alternative) weighting functions as those described for the conventional FFBP methodology. Reduced-scan weighting functions can be derived from both types of short-scan weighting functions.

For the circular fan-beam case, the three weighted chord-based methodologies may be mathematically equivalent to the conventional FFBP methodology for full-scan and short-scan datasets. The chord-based FBP methodology also is equivalent to the FDK methodology for the circular cone-beam case when datasets covering a full-scan or short-scan angular intervals are used. For each of the established equivalencies described above, $f_{FULL}(x_\pi, \lambda_1, \lambda_2)$, the image obtained over a full-scan interval is an average of $f_{STD}(x_\pi, \lambda_1, \lambda_2)$ and $f_{OPP}(x_\pi, \lambda_1, \lambda_2)$, which represent the images obtained over the minimum standard and minimum opposing angular intervals, respectively.

Since all phantoms described below have an object that undergoes periodic motion, the temporal phase $\phi \in [0, 1]$ can be used to describe the state of the object at a given point in time. A temporal phase of zero refers to the state of the object at the beginning of its temporal cycle, whereas a temporal phase of one refers to the state of the object at the end of its temporal cycle. All other temporal phases falling between zero and one refer to the state of the object after a fraction of its temporal cycle has passed. For the case of the cardiac cycle, the temporal phase variable $\phi$ essentially is equivalent to the percent R-R interval. The R-peak is assigned a phase $\phi=0$. Lower values of $\phi$ refer to the heart in systole and higher values of $\phi$ refer to the heart in diastole.

The uniform circular phantom may comprise an outer circle and an inner circle with respective diameters of 40 cm and 15 cm. Their respective attenuation values are 1.0 and 2.0 units. The inner circle may be programmed to undergo contractile motion in a sinusoidal fashion at three different diameter amplitudes: −2 cm, −6 cm, and −12 cm. One complete temporal cycle corresponds to one full period of sinusoidal motion.

The uniform elliptical phantom may comprise an outer circle with a 40 cm diameter and an attenuation value of 1.0 unit, as well as an inner ellipse with a 15 cm major axis, a 7.5 cm minor axis, and an attenuation value of 2.0 units. The inner ellipse may be programmed to undergo two different types of motion: rotational motion in a sinusoidal fashion at amplitudes of 30, 60, and 90 degrees about its central point, and translational motion in a sinusoidal fashion at amplitudes of 1, 5, and 10 cm. For both rotational and translational cases, one complete temporal cycle corresponds to one full period of sinusoidal motion.

Figure 129B:
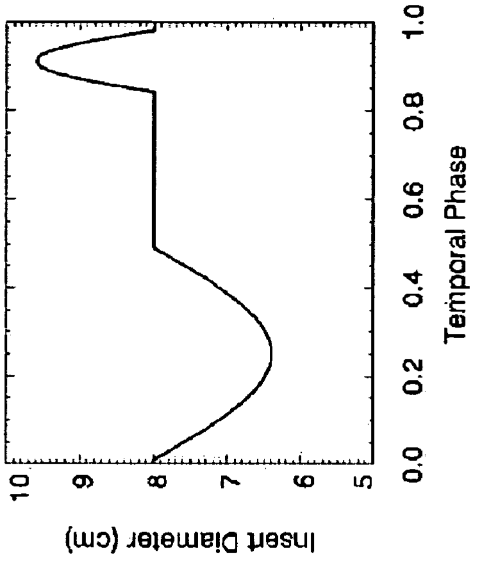
Figure 129A:
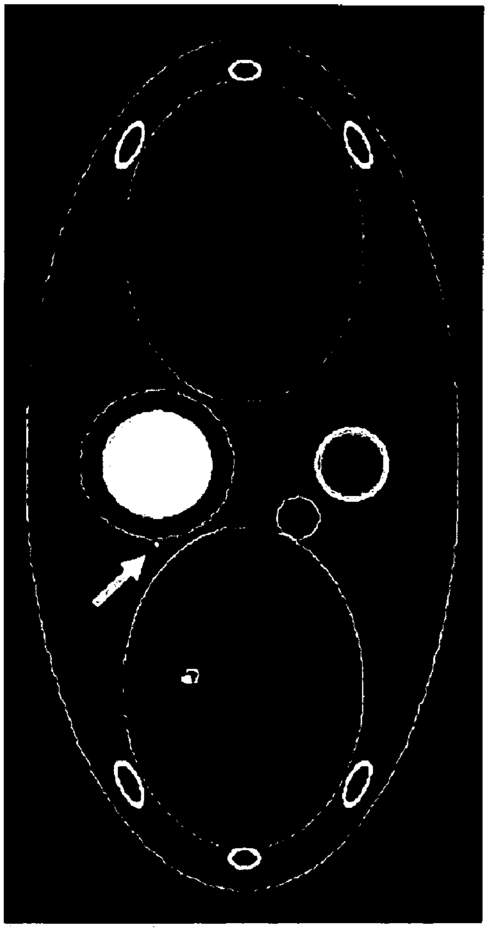

The modified FORBILD phantom is a 2-D digital phantom that contains an 8 cm diameter dynamic cardiac insert undergoing contractile motion. FIG. 129A illustrates a modified FORBILD phantom with dynamic cardiac insert. The white arrow in FIG. 129A points to an added high contrast circle representing a coronary plaque or calcification within the cardiac insert (L: 50 HU/W: 400 HU). A sample temporal trajectory of the diameter of the entire cardiac insert over one complete temporal phase for the diameter of the entire cardiac insert is shown in FIG. 129B. For this trajectory, the dynamic insert undergoes contractile motion during the first half of its temporal cycle.

The NCAT phantom is a digital phantom capable of producing a temporal series of 3D-attenuation maps modeling either cardiac motion, respiratory motion, or both types of motion. Phantoms may be generated at user-specified spatial resolutions and temporal intervals. In addition, calcified coronary plaques may be added to multiple locations around the heart. These plaques may move according to motion of the heart. An example of the NCAT phantom with coronary plaques in the left anterior descending (LAD) and left circumflex (LCX) is shown in FIG. 130. Specifically, FIG. 130 depicts an attenuation map generated from the NCAT phantom at a spatial resolution of 0.2 mm/pixel and a temporal phase in mid-to-late diastole ($\phi=0.75$).

Studies involving both approximate and exact reconstruction methodologies of the Katsevich type have shown that data covering the minimum angular interval (minimum data) necessary for reconstructing an image may lead to more pronounced motion artifacts. However, when data covering an overscan angular range (overscan data) are included, these motion artifacts may be suppressed. The following analysis evaluates whether similar observations may be made by using chord-based reconstruction methodologies for the fan-beam case, in which overscan data may be referred to as redundant data.

Figure 128B:
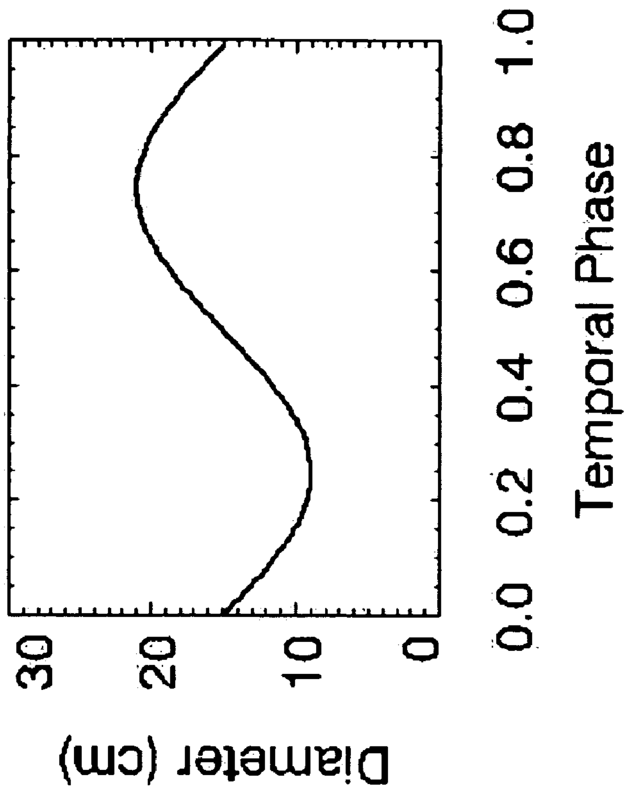
Figure 128A:
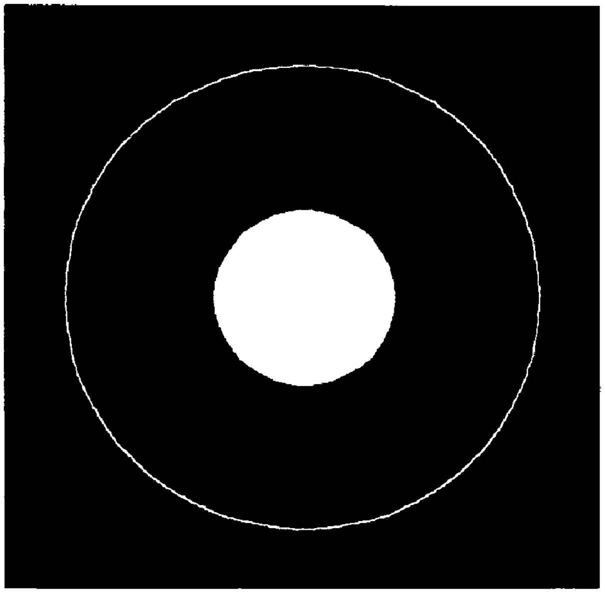

Results are presented for the uniform circular phantom contracting with an amplitude of −6 cm in diameter. The temporal trajectory for this phantom is shown in FIGS. 128A-B, whereby FIG. 128A depicts a uniform circular phantom (L: 1 HU/W: 1 HU) and FIG. 128B plots a sample temporal phase profile for the diameter of the inner circle, which undergoes sinusoidal contractile motion with an amplitude of −6 cm. Although simulation studies were also performed for amplitudes of −2 cm and −12 cm, the results of these studies mirror those for the −6 cm amplitude case shown below.

Three sets of full-scan projection data were obtained for the uniform circular phantom over scanning angles $\lambda \in [-\pi, \pi]$. The first dataset S was obtained from the phantom fixed at a temporal phase $\phi=0$. The second and third datasets were obtained as the phantom undervent contractile motion according to the temporal trajectory shown in FIG. 128B. These datasets, labeled A and B, were obtained from temporal phases $\phi \in [0, 0.25]$ and $\phi \in [0, 0.50]$, respectively. For all three datasets, the following four reconstructions were obtained: chord-based FBP reconstructions using standard, opposing, and full-scan data and a conventional FFBP reconstruction using full-scan data. Vertical chords and vertical coordinate systems were used for the chord-based FBP and conventional FFBP reconstructions, respectively.

Figure 131A:
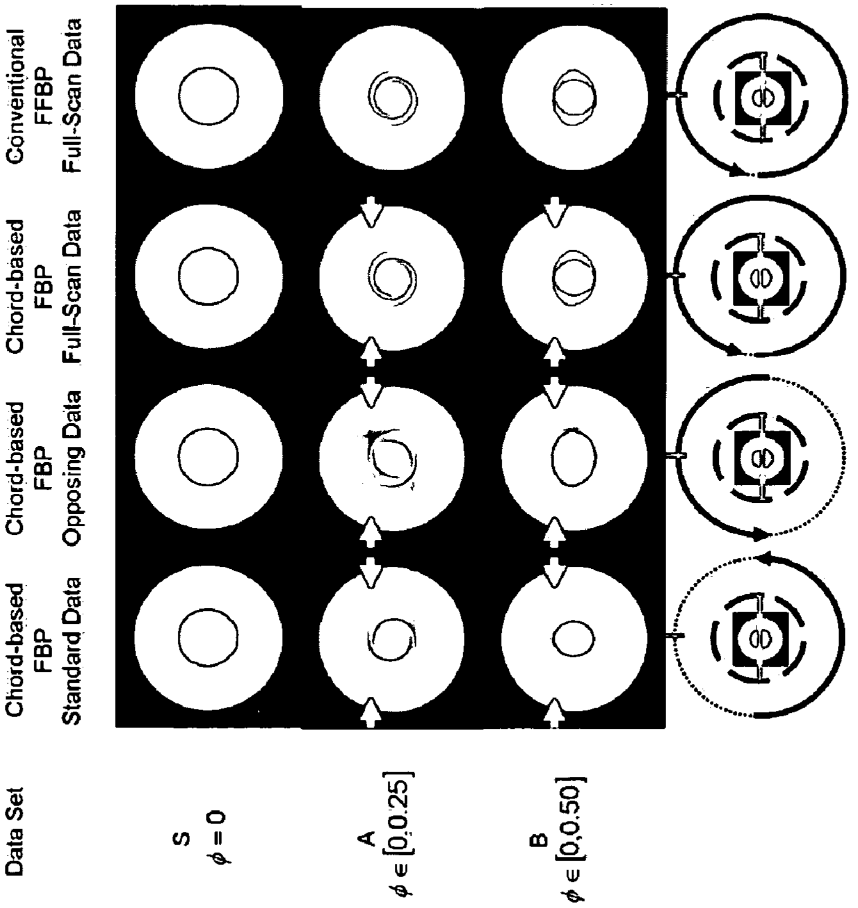
Figure 131B:
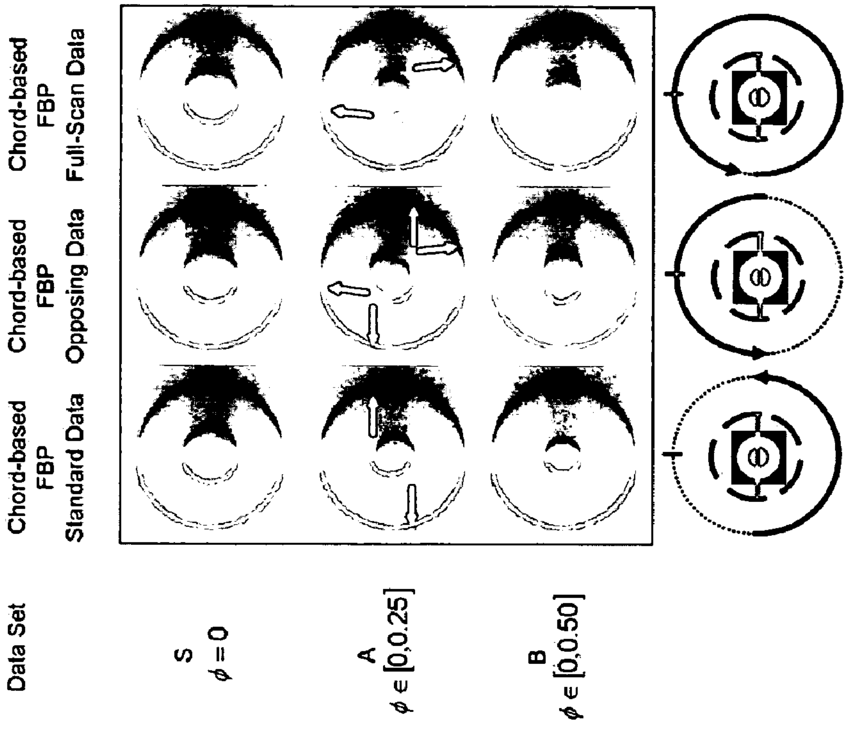

FIG. 131A depicts minimum data and full-scan reconstructions of the uniform circular phantom contracting at an amplitude of −6 cm diameter using a vertical chord orientation. Arrows point to chords whose profiles are plotted in FIGS. 132A-B (L: 1 HU/W: 2 HU). FIG. 131B depicts corresponding backprojection images for the images shown in FIG. 131A. Backprojection images were obtained by using Eq. H-6. Arrows point away from the incompletions in the elliptical structures that correspond to high attenuation artifacts in FIG. 131A. In FIGS. 131A-B, the left column lists the different temporal phases that are present during the acquisition of each of the three full-scan datasets S, A, and B. These temporal phases correspond to the phases of the temporal trajectory shown in FIG. 128B. The top row shows the reconstruction methodologies used to obtain images from each dataset.

As seen in FIG. 131A, motion-induced streak artifacts are visible along the chords used for reconstruction in the standard and opposing images shown in dataset A. These artifacts are especially prominent for chords tangent to the edge of the contracting circular phantom. These artifacts are not seen in the standard and opposing images for dataset B, and also are not seen in any of the full-scan reconstructions shown for both datasets A and B. In fact, for a given dataset, the full-scan reconstructions obtained with the chord-based FBP and conventional FFBP methodologies exhibit rather similar motion artifacts.

Figure 132A:
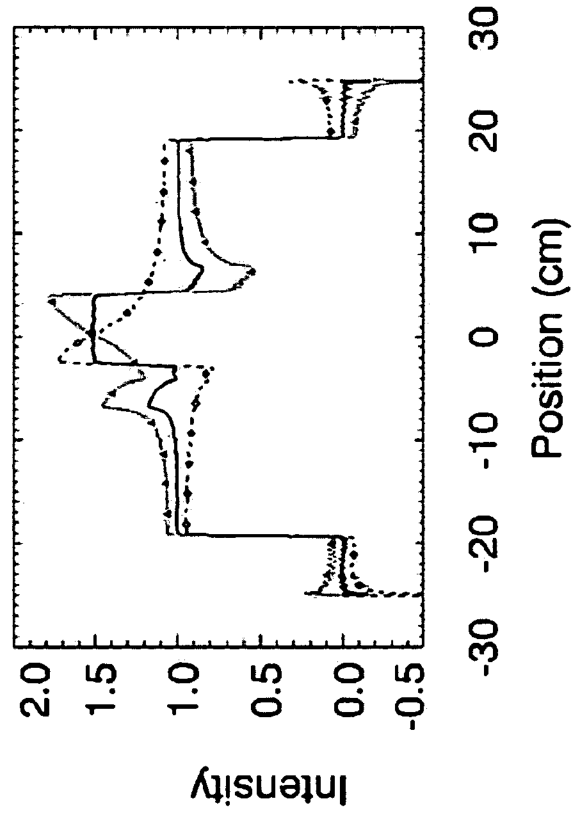
Figure 132B:
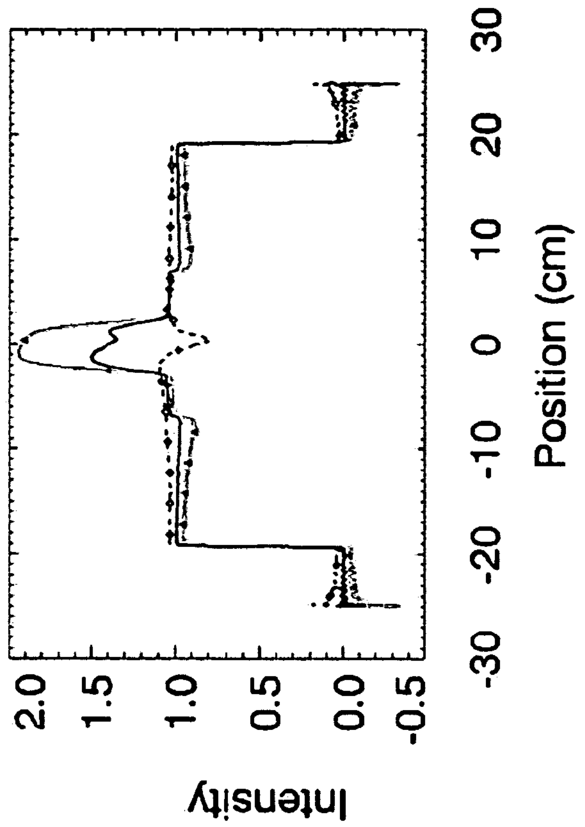

Profiles were plotted along the same vertical chord near the edge of the contracting phantom for each of the vertical chord-based reconstructions obtained using datasets A and B, as shown by the white arrows in FIG. 131A. FIGS. 132A-B depicts profiles involving vertical chord-based reconstructions obtained from datasets A (FIG. 132A) and B (FIG. 132B). For FIGS. 132A-B, images are plotted along the same chord tangent to the edges of the contracting ellipses. Arrows pointing to the chords on which these profiles are plotted are shown in FIG. 131A. In FIGS. 132A-B, the dark solid lines represent profiles obtained using full-scan data; the dark dashed lines represent profiles obtained using minimum standard data; and the light dashed line represents profiles obtained using minimum opposing data.

As seen in FIGS. 132A-B, the full-scan profiles appear to be averages of their corresponding standard and opposing profiles for both datasets. This phenomenon is consistent with the analysis above since chord images reconstructed using full-scan data can be obtained by averaging the chord images obtained with standard and opposing data, as discussed above. However, the standard and opposing profiles behave differently in each dataset. For dataset A, the standard profile tends to exhibit a negative deviation from the full-scan profile over most of the left half of the image and a positive deviation over most of the right half of the image. For dataset B, the standard profile tends to exhibit a positive deviation from the full-scan profile over most of both halves of the image. Since motion-induced streak artifacts are much more apparent in the standard and opposing chord-based reconstructions obtained from dataset A, a chord image which has positive and negative deviations from the full-scan profile on opposite sides of the image is associated as exhibiting a motion-induced streak artifact. Even though the standard and opposing profiles from dataset B are not considered as exhibiting these types of artifacts, these profiles still manage deviate noticeably from the full-scan profile in dataset B.

For each dataset, intermediate backprojection images then were obtained over standard, opposing, and full-scan intervals using Eq. H-6. As shown in FIG. 131B, the edges of complete elliptical structures may be delineated in all three backprojection images obtained from datasets S and B. However, in dataset A, the edges of a complete elliptical structure cannot be delineated in any of the images. By comparing the backprojection images for dataset A in FIG. 131B and the corresponding reconstructed images in FIG. 131A, one can see that the incompletions in the elliptical structures within the backprojection images correspond to high attenuation portions of the motion-induced streak artifacts in standard and opposing reconstructions as well as the high attenuation portions of the fan-beam artifacts in the opposing and full-scan reconstructions. These fan-beam artifacts, which are due to inconsistencies in the projection data at scanning angles $-\pi$ and $\pi$, also are present in the fan-beam FFBP reconstructions as well. From the results of these studies and additional simulations, one may associate the presence of motion-induced streak artifacts and fan-beam artifacts with incompletions in the structure of a moving object in the backprojection image.

The chord-based BPF and MD-FBP methodologies also were used to reconstruct images from datasets S, A, and B using vertical chords. In general, motion artifacts including motion-induced streak artifacts follow the same pattern as those seen in the chord-based FBP reconstructions. However, the BPF and MD-FBP methodologies demonstrate an increased susceptibility to these artifacts, especially in regions near the opposite ends of the reconstructed chords (data not shown). This increased susceptibility may be due to both methodologies using the factor $$\frac{1}{\sqrt{(x_{\pi\lambda 2}-x_\pi)(x_\pi-x_{\pi\lambda 1})}},$$

as shown in Eq. H-7 or the BPF methodology. For points $x_\pi$ reconstructed near the endpoints of the PI-line support segment $[x_{\pi\lambda 1}, x_{\pi\lambda 2}]$, this factor becomes numerical unstable, and this numerical instability seems to increase in the presence of motion-induced inconsistencies in the data.

In order to determine how motion artifacts appear in reconstructions using reduced-scan and short-scan data, the chord-based FBP, BPF, and MD-FBP methodologies were used to reconstruct images from the datasets described above using reduced-scan data with PFSD=48.5%, reduced-scan data with PFSD=51.5%, and short-scan data (PFSD=64.5%). These images were reconstructed on vertical chords. Images also were reconstructed using the conventional FFBP methodology with short-scan data. The angular intervals used for all reconstructions were centered around an angle $\lambda=0$. Parker's and the alternative weighting functions were used to reconstruct two separate images for each reduced-scan and short-scan configuration.

Figure 133B:
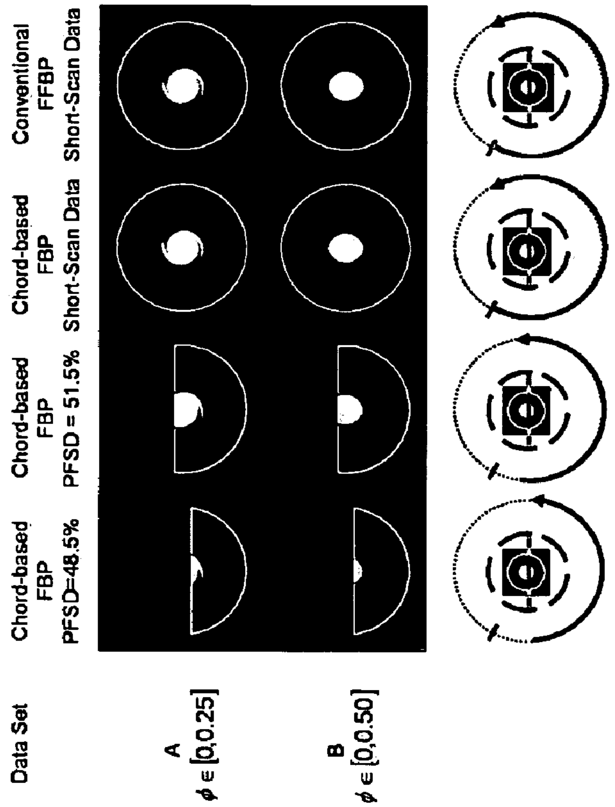
Figure 133A:
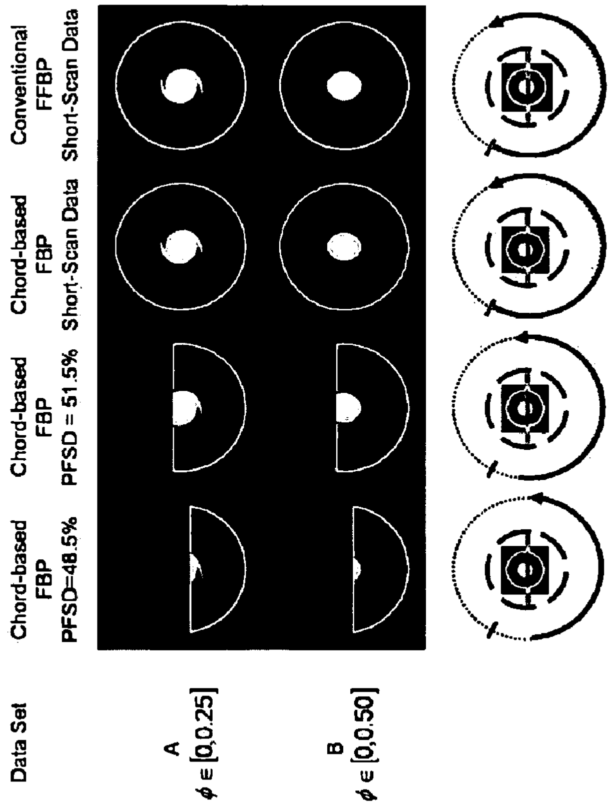

FIGS. 133A-B depict reduced-scan and short-scan chord-based FBP reconstructions of the uniform circular phantom using vertical chords from full-scan datasets A ($\phi\in[0, 0.25]$) and B ($\phi\in[0, 0.50]$). The weighting functions used to obtain the reconstructions are Parker's weighting function in FIG. 133A and the alternative weighting function in FIG. 133B (L: 1 HU/W: 2 HU). For images obtained from dataset A ($\phi\in[0, 0.25]$), the reduced-scan reconstruction with PFSD=48. 5% exhibit motion-induced streak artifacts similar to those present in the reconstruction obtained using standard data, as shown in FIG. 131A. However, as the amount of data used for reconstruction is increased, these motion-induced streak artifacts begin to curve about the center-of-rotation such that they morph into the types of motion artifacts seen in the short-scan reconstructions. On the other hand, the reduced-scan reconstructions obtained from dataset B ($\phi\in[0, 0.50]$) do not exhibit motion-induced streak artifacts. This result is not surprising, given that the standard reconstructions from this dataset also do not exhibit motion-induced streak artifacts.

The specific weighting function used for reconstructing an image also has an influence on the morphology of the motion artifacts produced. As shown in FIG. 133B short-scan reconstructions using the alternative weighting function exhibit more straight wispy artifacts.

The same studies performed using the uniform circular phantom undergoing contractile motion also were conducted with the uniform elliptical phantom undergoing translational and rotational motion. Although the data are not presented here, the same conclusions drawn for the studies involving the uniform circular phantom also may be drawn for the uniform elliptical phantom undergoing both types of motions.

An extended dataset of the NCAT phantom was obtained with a gantry rotation time of 0.4 s, a heart rate of 60 bpm, a starting gantry angle of $-\pi$, and a starting temporal phase set at the beginning of systole ($\phi=0$). Data were acquired over three heart beats. Gaussian noise with the standard deviation equivalent to the number of detected photons for each detector element was added to the extended dataset. The number of incident photons was $1.0*10^6$ photons/detector element. A full-scan dataset spanning gantry angles $\lambda\in[-\pi, \pi]$ and obtained during systolic temporal phases $\phi\in[0.0, 0.4]$ was extracted from this extended dataset. The chord-based FBP, BPF, and MD-FBP methodologies were used to reconstruct images using standard data, opposing data, full-scan data, short-scan data (PFSD=64.5%), and reduced-scan data using PFSD's of 56%, 51.5%, and 48.5%. All angular reconstruction intervals were centered on $\lambda=-0.355\pi$. Images were reconstructed on parallel chords oriented obliquely at an angle $\alpha$ of 26.1° from the horizontal axis.

Figure 134B:
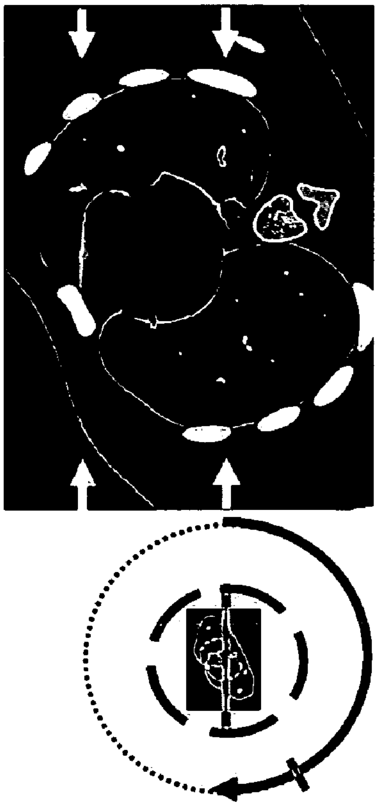
Figure 134D:
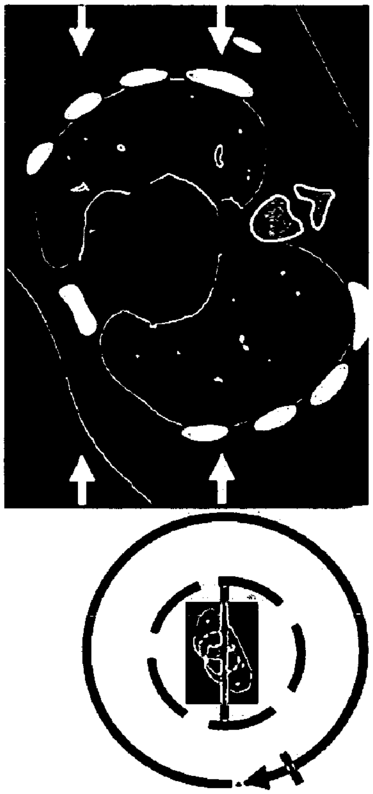
Figure 134A:
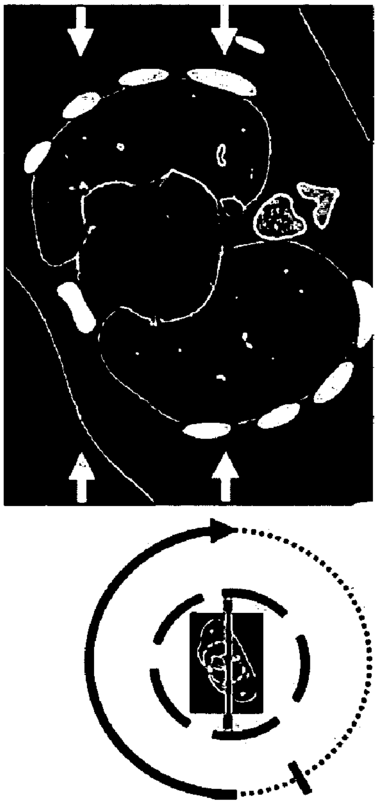
Figure 134C:
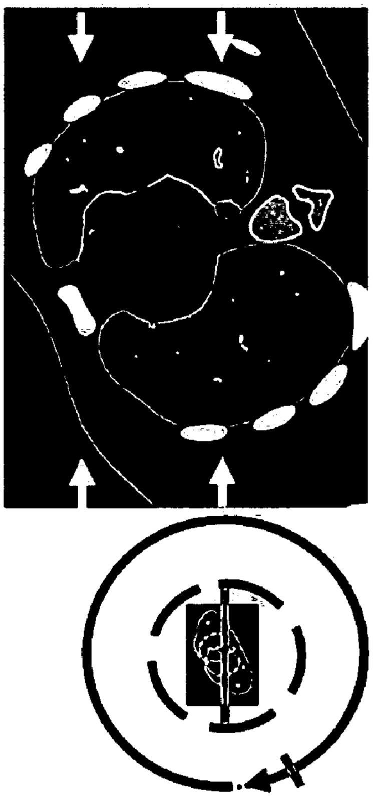

FIGS. 134A-D depict minimum data and full-scan reconstructions of the NCAT phantom from noisy data acquired during early systole $\phi\in[0, 0.4]$. Chord-based FBP reconstructions are shown using minimum standard data (FIG. 134A), minimum opposing data (FIG. 134B), and full-scan data (FIG. 134C). FIG. 134D depicts conventional FFBP reconstruction using full-scan data. In FIGS. 134A-C, images are shown along the oblique chords ($\alpha$=26.1°) used for reconstruction. In FIG. 134D, the image has been reconstructed on a rotated Cartesian coordinate system. In all images, arrows point to chords tangent to the edges of the moving heart. In FIGS. 134A-B, images on these chords contain visible motion-induced streak artifacts. In FIGS. 134B-D, artifacts in the lateral direction across the phantom may be due to inconsistencies in the data at scanning angles of $-\pi$ and $\pi$ (L: 50 HU/W: 400 HU).

As seen in the chord-based FBP reconstructions using standard and opposing data shown in FIGS. 134A-B, motion-induced streak artifacts can be seen along the oblique chords tangent to the edges of the beating heart. These artifacts can be delineated even in the presence of noise. However, these artifacts may be suppressed when full-scan data are used for reconstruction. Note that the full-scan chord-based FBP and conventional FFBP reconstructions in FIGS. 134C-D exhibit similar motion artifacts.

Figure 135A:
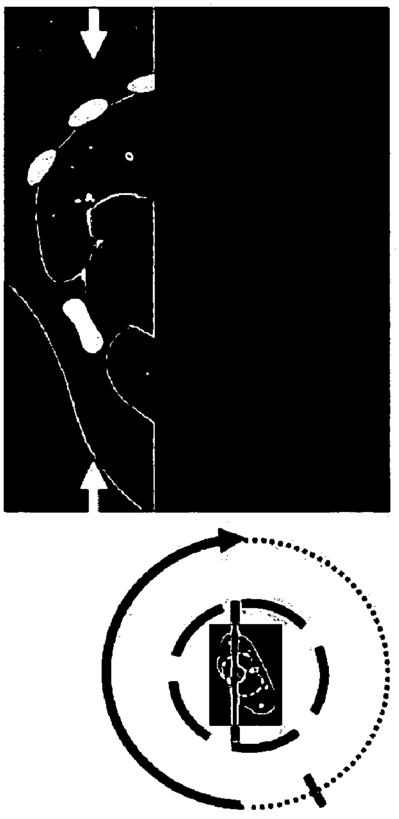
Figure 135B:
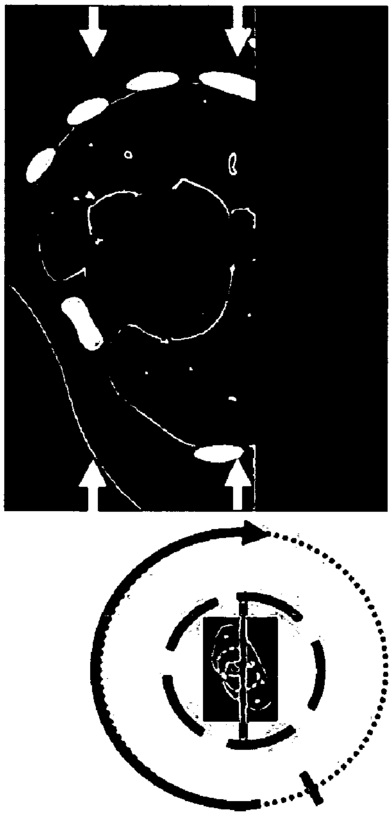
Figure 135C:
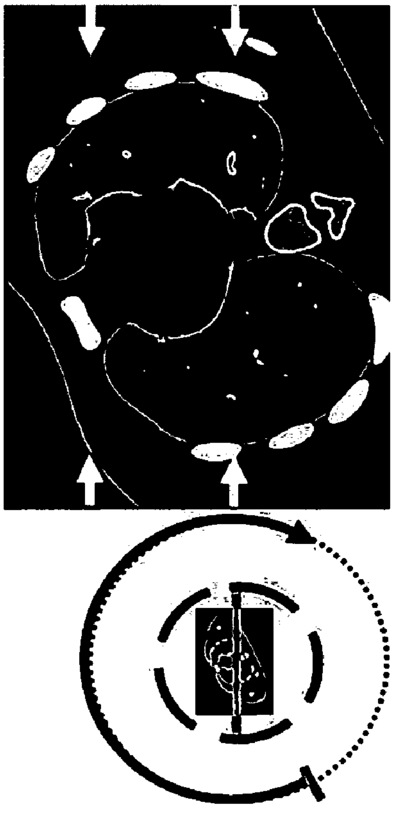
Figure 135D:
Figure 136A:
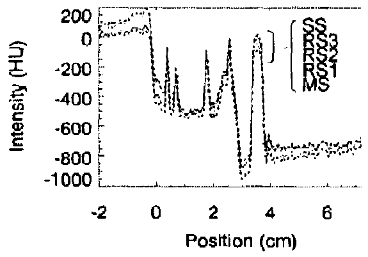

FIGS. 135A-D depict reduced-scan and short-scan reconstructions of the NCAT phantom from noisy data acquired during early systole $\phi\in[0, 0.4]$. Chord-based FBP reconstruction are shown using reduced-scan data with PFSD=48.5% (FIG. 135A), reduced-scan data with PFSD=51.5% (FIG. 135B), and short-scan data (PFSD=64.5%) (FIG. 135C). FIG. 135D depicts conventional FFBP reconstruction using short-scan data. In FIGS. 135A-C, images are shown along the oblique chords ($\alpha$=26.1°) used for reconstruction. In FIG. 135D, the image has been reconstructed on a rotated Cartesian coordinate system. In all images, arrows point to chords tangent to the edges of the moving heart. In FIGS. 135A-B, images on these chords contain visible motion-induced streak artifacts (L: 50 HU/W: 400 HU). Motion-induced streak artifacts can be seen in the reduced-scan reconstructions shown in FIGS. 135A-B. As more data are used for reconstruction, these artifacts become suppressed such that they are no longer visible in the short-scan reconstruction shown in FIG. 135C. This trend may be better appreciated by examining profiles for the same oblique chord tangent to the anterior portion of the heart, as shown in FIG. 136A. For the short-scan reconstructions obtained using the chord-based FBP and the conventional FFBP methodologies, as shown in FIGS. 134C-D, the motion artifacts seem rather similar to one another.

The chord-based FBP, BPF, and MD-FBP methodologies may produce similar types of motion artifacts for reconstructions using standard, full-scan, reduced-scan data (PFSD=48.5%), and short-scan data. For all reconstruction methodologies, the profiles of the same chord tangent to the anterior edge of the beating heart essentially overlap one another over the central portion of the chord and match one another very closely across the length of the entire chord (data not shown). The chord-based FBP, BPF, and MD-FBP methodologies may perform more consistently with one another for the NCAT phantom than they do for the uniform circular phantom possibly because the motion of the beating heart is not as great in magnitude as the motion of the contracting phantom.

The short-scan and reduced reconstructions discussed above were obtained from a full-scan dataset acquired during systolic temporal phases $\phi\in[0.0, 0.4]$. The profiles of these alternative reconstructions for a chord tangent to the edge of the left ventricle, as labeled by the bottom thick arrow depicted in FIG. 135A, are shown in FIG. 136A.

Figure 136B:
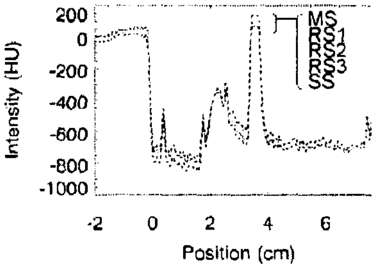
Figure 136C:
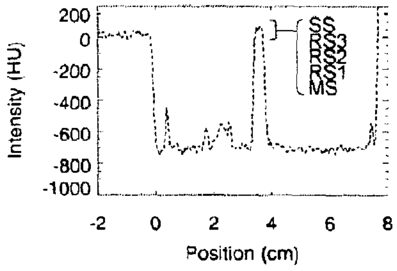
Figure 136D:
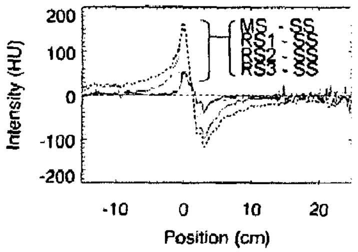
Figure 136E:
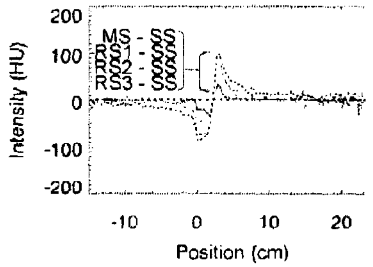
Figure 136F:
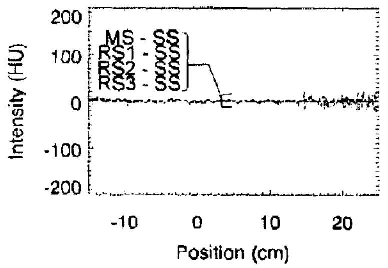

FIGS. 136A-F illustrate the dependency of motion-induced streak artifacts on cardiac phase. FIGS. 136A-C depict profiles along oblique chords ($\alpha$=26.1°) tangent to the anterior edge of the left ventricle from full-scan data acquired during systolic temporal phases $\phi\in[0.0, 0.4]$ (FIG. 136A), diastolic phases $\phi\in[0.6, 1.0]$ (FIG. 136B), and a stationary phase $\phi$=0.7 (FIG. 136C). The location of the chord using the dataset from systole is depicted by the bottom white arrow in FIG. 135A. FIGS. 136D-F depict difference profiles obtained by subtracting the short-scan profiles labeled as SS from the other respective profiles for data acquired during systolic phases (FIG. 136D), diastolic phases (FIG. 136E), and a stationary temporal phase (FIG. 136F). PFSD refers to the percent of motion-contaminated data used for reconstruction.

The same set of reconstructions with the same oblique orientation ($\alpha$=26.1°) were performed with two full-scan datasets acquired from diastolic temporal phases $\phi\in[0.6, 1.0]$ and a stationary temporal phase at $\phi$=0.7. Profiles for reconstructed images from these two datasets along the same oblique chord tangent to the anterior edge of the contracted left ventricle are shown in FIGS. 136B-C, respectively. As seen in both systolic and diastolic profiles, a good separation may be seen between the chord images obtained with different amounts of data even in the presence of noise in the data. In order to evaluate the magnitude of the chord separations for all data sets, the profiles obtained using short-scan data were subtracted from the other four profiles obtained from their respective systolic, diastolic, or stationary datasets. The difference profiles for chord images acquired from all datasets are shown in FIGS. 136D-F. The chord images corresponding to the systolic dataset achieve a much better separation than those corresponding to the diastolic dataset. Almost no separation can be seen in chord images corresponding to the stationary dataset. These results indicate that there is more motion-contamination in the systolic dataset than the diastolic dataset.

The weighted backprojection filtration (WBPF) methodology using data redundancy has capabilities that make this methodology applicable to reconstructing images from motion-contaminated projection data. First, the WBPF methodology is capable of reconstructing ROI images from reduced-scan fan-beam data, which have less data than the short-scan data necessary to reconstruct the entire FOV. Second, this methodology may reconstruct ROI images from truncated data.

The results of simulation studies demonstrate how the unique capabilities of the WBPF methodology may be exploited to reduce the amount of motion-contaminated data used for reconstruction. In particular, examples involving the modified FORBILD and NCAT phantoms are used to illustrate how off-center phantom positioning combined with phase-interval ROI reconstruction can result in the suppression of motion artifacts seen in short-scan FFBP reconstructions. In terms of temporal resolution, reduced-scan reconstruction with 45% of a full-scan dataset may be used to improve the temporal resolution of a short-scan reconstruction by 25.8% if ungated data are used. For data gated at 66 beats per minute, reduced-scan reconstruction with 45% of a full-scan dataset can be used to improve the temporal resolution of a short-scan reconstruction by 7.9%. The studies indicate that the WBPF methodology demonstrates the ability to reconstruct quality 2D and 3D cardiac images from motion-contaminated fan-beam data.

Figure 137A:
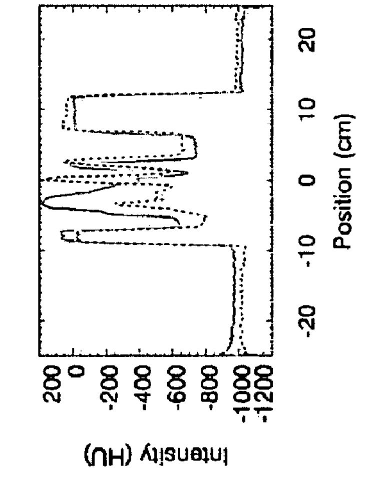
Figure 137B:
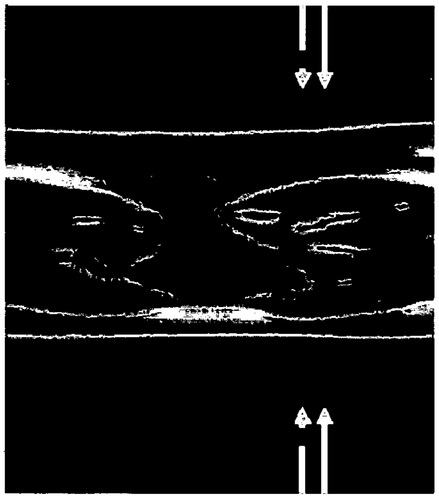
Figure 137C:
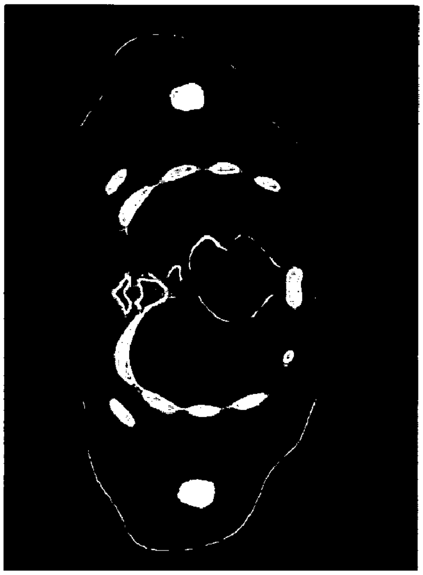

Motion-induced streak artifacts may also appear when chord-based methodologies are used to reconstruct images from helical cone-beam data. The BPF methodology was used to reconstruct a 3D volume of the NCAT phantom beating at 60 bpm from helical cone-beam data acquired at a high pitch of 15 cm/revolution during systolic temporal phases $\phi \in [0.0, 0.4]$ over scanning angles $\lambda \in [-\pi, \pi]$. A 0.4 s gantry rotation time was used. FIGS. 137A-C illustrate a helical cone-beam reconstruction of the dynamic NCAT phantom by use of the BPF methodology. FIG. 137A illustrates profiles along two chords tangent to the left ventricle of the heart. The thin solid line and thick dashed lines refer to chords with chord coordinates ($-0.51\pi$, $0.454\pi$) and ($-0.51\pi$, $0.448\pi$), respectively. FIG. 137B depicts reconstructed images on converging chords. All chords converge to $\lambda_C = -0.51\pi$. The solid line and dashed lines refer to chords with chord coordinates ($-0.51\pi$, $0.454\pi$) and ($-0.51\pi$, $0.448\pi$), respectively. FIG. 137C depicts a reconstructed image at a transverse slice through the heart (L: 50 HU/W: 400 HU). Thus, FIG. 137A shows profiles along two chords converging to the same point on the source trajectory ($\lambda_C$–$0.51\pi$) and located tangent to the same edge of the moving heart, as shown by the arrows on the chord image in FIG. 137B. The differing baseline values of the two profiles indicate that motion-induced streak artifacts may also exist along these chords. Since the 3D image is obtained following interpolation of the reconstructed chord images, the streak artifacts become smeared throughout the entire volume. The resulting image of a transverse slice through the heart suffers from curved streak artifacts extending from the moving object, as shown in FIG. 137C.

The following involves using variants or alternatives of the same chord-based reconstruction methodologies as those described above.

The modified FORBILD and the dynamic NCAT phantoms, which have been used previously, may also be used. In addition, the alternative methodologies may be used with a clinical 64-slice MDCT scanner.

Further, methods for reconstructing 3D images from motion-contaminated circular cone-beam and low-pitch helical cone-beam datasets may be performed. These methods involve incorporating overscan data in order to allow for the suppression of motion-induced streak artifacts in both circular and helical cone-beam reconstructions. In addition, a method for reconstructing continuous 3D images from fragmented helical cone-beam data may be used.

For the circular cone-beam configuration, actual chords only exist within the plane of the source trajectory. In order to reconstruct an entire volume by use of chord-based methodologies, virtual circular trajectories and virtual chords may be defined above and below the actual scanning trajectory.

Figure 138B:
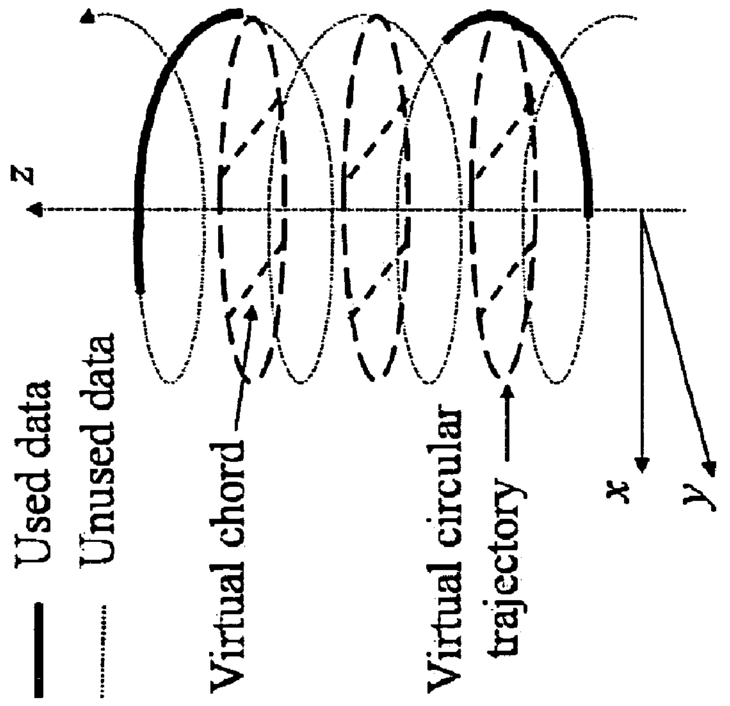

FIG. 138A shows how actual and virtual chords may be defined for circular cone-beam scans. FIG. 138B shows virtual chords for a fragmented helical cone-beam configuration. The helix may become fragmented when phase-correlated reconstruction is performed. Since the two available data segments shown in FIG. 138B span less than a short-scan angular interval, as is commonly the case in ECG-gated data, data from these segments may need to be combined in order to reconstruct images on the virtual chords between these segments.

The chord-based weighted FBP (WFBP) and WBPF methodologies may be used to reconstruct images from motion-contaminated circular cone-beam data. Although both chord-based methodologies allow for overscan weighting, these methodologies have different advantages when reconstructing images from circular cone-beam data. The advantage of the WFBP methodology is that it does not require calculation of the $D(\vec{r}_0(\lambda_1), \vec{r}_0(\lambda_2))$ term, which is the projection of the ray coinciding with the chord ($\lambda_1$, $\lambda_2$) and must be approximated for reconstructing images on virtual chords. The WBPF methodology, on the other hand, is capable of reconstructing images from data containing truncations. This methodology also is more computationally efficient. Both methodologies may use actual and virtual chords oriented in a parallel configuration based on the orientation of the actual chord ($\lambda_{min}$, $\lambda_{max}$), whose endpoints span a short-scan angular interval. Short-scan weighting functions may be used so that overscan data are included and motion-induced streak artifacts are suppressed. Images may be reconstructed from ungated and gated datasets.

Computer simulation studies may be used to validate the alternative methods for reconstructing images from motion-contaminated circular cone-beam data acquired from the NCAT phantom with calcified plaques placed in the left anterior descending (LAD) artery and left circumflex (LCX) arteries. A heart rate of 66 bpm and a gantry rotation time of 0.4 s will be used. Four sets of short-scan data will be prepared. The first is an ungated dataset acquired during diastole. The second is a gated dataset also acquired during diastole. Noise following Poisson statistics may be added to both datasets in order to generate the third and fourth sets. The number of incident photons per detector element may be set to $1.0 \times 10^6$. The WFBP and WBPF methodologies may be used to reconstruct 3D images from all four datasets. The FDK methodology also may be used to reconstruct images from all four datasets. Images may be compared in terms of the ability to delineate key cardiac structures, the presence of motion artifacts, and the presence of cone-beam artifacts.

As seen in FIG. 137C, reconstructing images from motion-contaminated helical cone-beam data using chord-based methodologies without incorporating overscan data may lead to images with curved streak artifacts. However, the motion-induced streak artifacts in the converging chord image shown in FIG. 137B are linear and appear similar to those in the unweighted fan-beam chord-based FBP reconstruction shown in FIG. 135A. The streak artifacts in these chord images may be suppressed simply by applying overscan weighting prior to reconstruction. Further, the curved streaks seen in the final reconstructed image may be suppressed.

For the case of non phase-correlated reconstructions, in which data from the entire helix are available, the WFBP and WBPF methodologies may be used in conjunction with short-scan weighting functions for reconstructing images from low-pitch helical cone-beam acquisitions. Although the use of overscan data may compromise the exactness of these methodologies and possibly introduce cone-beam artifacts in the reconstructions, these artifacts may not be very pronounced due to the low helical pitches commonly used in cardiac MDCT.

The applications of the WFBP and WBPF methodologies to helical cone-beam datasets require modifications to the existing weighted methodologies, which were originally intended for handling circular fan-beam data. First, a converging chord configuration commonly used in helical cone-beam reconstructions may be used. (See FIG. 127B). Second, a short-scan weighting function may be applied to each set of converging chords at every convergence angle $\lambda_c$ needed to obtain the 3D volume. Since the weighting function may use data from scanning angles [$\lambda_{min}$, $\lambda_{max}$], the boundary angles $\lambda_{min}$ and $\lambda_{max}$ may need to be defined. Thus, the convergence angle $\lambda_c$ as $\lambda_{min}$ and $\lambda_c+\pi+\gamma_{fan}$ as $\lambda_{max}$ may be used.

The WBPF methodology demonstrates very favorable qualities in reconstructing images from non phase-correlated helical cone-beam data. First, the WBPF methodology is much more computationally efficient than the WFBP methodology, as only one filtration step is needed for reconstructing an image on a single chord. The WFBP methodology, on the other hand, requires filtrations along the weighted cone-beam projections of the chord at each angle within the short-scan interval [$\lambda_{min}$, $\lambda_{max}$]. Second, the WBPF methodology can handle datasets with truncations. Finally, since data are available for the term $D(\vec{r}_0(\lambda_1), \vec{r}_0(\lambda_2))$ for each chord image, this term does not need to be approximated with this methodology.

To validate the proposed methodology, three sets of projection data may be obtained from the NCAT phantom with relative pitches of 0.15, 0.3, and 0.5. A heart rate of 66 bpm and a gantry rotation time of 0.4 s may be used. Three additional datasets may be generated by adding the same type of Poisson noise as that used in Sec. 12 to each dataset. The cone-beam WBPF methodology as well as a FDK-based methodology may be used to reconstruct images from all six datasets. Images may be assessed with regard to the presence of motion-induced streak artifacts, cardiac motion artifacts, clear delineation of cardiac structures, and cone-beam artifacts.

In phase-correlated reconstruction without or with ECG-gating, 3D images of the entire heart may be reconstructed from data spanning a specific R-R interval. Since much of the acquired data are not used, low pitch helical cone-beam scans may be required to ensure that sufficient data exist in order to obtain a 3D reconstruction of acceptable quality. Applying exact methodologies to phase-correlated data may be a challenging task, since these methodologies may need to reconstruct a continuous volume from essentially a fragmented helix. Moreover, an exact reconstruction of the entire volume is not possible according to Tuy's condition. However, a methodology based on Katsevich's methodology has been proposed for cardiac imaging.

The WFBP and WBPF methodologies may be applied to phase-correlated low-pitch helical cone-beam data. As shown in FIG. 138B, virtual circular trajectories may be positioned along the fragmented helix, and virtual chords oriented in the parallel configuration may be defined on these virtual trajectories. The angular configuration of these chords may be defined according to the locations of the available data segments on the fragmented helix. If segments span at least a short-scan angular interval of $\pi$ plus the fan angle, data from these segments can be used to reconstruct virtual chords above and below these segments. If segments span less than the short-scan angular interval, as is commonly the case in ECG-gated data, data from two consecutive segments must be used to reconstruct images on virtual chords between these segments, as shown in FIG. 138B. All virtual chords may be oriented parallel to the chord ($\lambda_{min}$, $\lambda_{max}$), whose endpoints are defined by the short-scan angular interval used for both ungated and gated datasets.

The WFBP and WBPF methodologies may not be exact, as overscan data and virtual chords are used. In fact, the WBPF methodology may require an additional approximation, in that the term $D(\vec{r}_0(\lambda_1), \vec{r}_0(\lambda_2))$ may not be available for any of the reconstructed chord images. The WFBP methodology, however, is similar to other FDK-based methodologies, which involve the 3D backprojection of filtered data onto the image coordinate system. As a result, this methodology may be no more susceptible to cone-beam artifacts as these reported methodologies. Although the WFBP and WBPF methodologies may not demonstrate as favorable detector utilization properties as some of these methodologies, innovative weighting schemes may be developed so that potentially equivalent detector utilization may be achieved.

Computer simulation studies may be performed to validate the alternative methodologies. The helical cone-beam WFBP and WBPF methodologies may be used to reconstruct images from phase-correlated datasets obtained from the three noiseless and three noisy helical cone-beam datasets, as discussed above. Images may also be reconstructed with a FDK-based methodology. All images may be reconstructed using non-gated and gated data corresponding to a diastolic phase interval. Images may be assessed with regard to the clear delineation of cardiac structures, the presence of motion-induced streak artifacts, cardiac motion artifacts, and cone-beam artifacts.

11. Rebinning Reconstruction Approaches in Helical and Non-Helical Cone-Beam CT

The spatially-variant weighting factor involved in methodologies for image reconstruction from divergent-beam data may significantly amplify data noise and aliasing artifacts, especially in the peripheral region of the field of view (FOV) when the focal length is small and the divergent angle is large. This effect can generate highly non-uniform noise level in reconstructed images, which may impede the image utilities for detection/classification tasks. In particular, because many potentially useful applications of these newly developed methodologies, discussed above, may involve the ROI imaging and the ROI may be located in the peripheral region of the FOV, the effect of the weighting factor is even more severe. Exact methodologies may be used with improved noise properties for helical or circular cone-beam CT, which reconstructs images by first rebinning the helical cone-beam data into the parallel beam data and then reconstructing images from the rebinned data. These methodologies retain the properties of the existing helical cone-beam methodologies in that they also requires only minimum data and can address the problem of exact ROI reconstruction from truncated data. One advantage of this methodologies over the existing methodologies is that it has improved noise properties because of the elimination of the weighting factor. The proposed methodologies may not yield images containing artifacts that may otherwise appear in images obtained with the existing methodologies when the divergent angle is large.

12. ROI-Image Reconstruction from Data Acquired with Perturbed Trajectories without Mechanical Recalibration of the Trajectories In designing CT scanning systems, great care is taken to align the hardware so that the x-ray source spot executes the trajectory demanded by the reconstruction methodology, for example, a helical trajectory. It is known that deviations from the ideal trajectory shape may cause artifacts in the reconstructed images for existing reconstruction methodologies. Because the methodologies discussed above may offer great flexibility in the x-ray source trajectory, the x-ray source need not be precisely aligned to any particular trajectory. The scanning trajectory can deviate from the programmed trajectory as long as the deviation is known. The proposed methodology may be able to perform accurate image reconstruction from the perturbed trajectory. This potential to perform accurate image reconstruction from the perturbed trajectory is particularly important for C-arm devices where the control of the source trajectory might not be as precise as for helical CT scanners.

13. ROI-Image Reconstruction from Data Acquired with Reverse Helical And/or Reverse Non-Helical Trajectories 13.1 In many imaging situations, due to the physical and mechanical constraints, the moving (e.g., rotation) direction of the scanning source and detector may be changed or reversed, while the motion (e.g., translation) of the imaged subject remains unchanged. Therefore, these imaging cases involve data acquisition with reverse helical and reverse non-helical trajectories. One application of the reversed helical and non-helical trajectories is in medical applications, such as radiation therapy, or in industrial applications, such as scanning an object, where the rotation extent of the onboard imager is seriously restricted by the treatment or scanning system. Therefore, a large, rapid volume coverage in this situation can be accomplished by use of the reversed trajectories. For example, the reverse scanning configurations may be used in cone-beam imaging and its application to radiation therapy. Further, the methodologies discussed above for ROI-image reconstruction from data acquired with a reversed trajectory may be applied to data acquired from the reverse scanning configuration. This may be used in instances where the imager cannot rotate more than a fixed number of times (such as one rotation). Further, the trajectory may be a combination of a forward (such as a helical or non-helical forward trajectory) and a reverse trajectory (such as a helical or non-helical reverse trajectory).

Computed tomography (CT) is one of the dominant imaging techniques for image-guided radiation therapy (IGRT). With the advance of detector technology, cone-beam CT (CBCT) has become available in a LINAC treatment system either using MV-treatment beam or using kV-source mounted on a LINAC. Use of a large flat panel detector allows the acquisition of volumetric image data from a circular scanning of the gantry. However, a circular trajectory does not provide sufficient data for exact reconstruction of volume images. The commonly used FDK algorithm and its variations can produce only approximate 3D images.

π-line-based backprojection-filtration (BPF) and minimum data filtered backprojection (MDFBP) methodologies have been developed for helical scanning trajectories and for general scanning trajectories. Important features of those methodologies are the exactness of the 3D image reconstruction on π-lines/chords and the flexibility in terms of data truncation. In many imaging applications, it is desirable to extend the length of a helical trajectory for increasing its longitudinal coverage. Diagnostic CT achieves this goal through the use of slip-ring technology, which allows the X-ray source to rotate continuously by multiple turns in one direction. The LINAC-mounted imager, however, can not rotate continuously and must reverse the rotation direction after each turn. Therefore, to extend the longitudinal coverage, one can maintain the couch translation during the gantry's reverse rotations, resulting in a scanning trajectory that we refer to as a reverse helix. The following explores numerically the reconstructible images for the reverse helical trajectory with our chord-based CBCT reconstruction algorithm.

The chord-based methodologies are disclosed above. The 3D Shepp-Logan phantom was used with a chord-based BPF algorithm. The BPG algorithm may first compute the cone-beam backprojections of the data derivatives onto chord segments and then reconstruct the image by invoking a 1D shift-varying filtration of the cone-beam backprojections over chord segments. Any scanning trajectory may be used. Examples of scanning trajectories considered are as follows.

The reverse helical trajectory, a schematic of which is shown in FIG. 139A may be parameterized as:

$$\vec{r}_0(\lambda) = \left(R_0\cos\lambda,\ R_0\sin\lambda,\ \frac{h}{2\pi}\lambda\right) \quad \lambda \in [-2\pi, 0) \qquad \text{I-(1)}$$

$$\vec{r}_0(\lambda) = \left(R_0\cos(-\lambda),\ R_0\sin(-\lambda),\ \frac{h}{2\pi}\lambda\right) \quad \lambda \in [0, 2\pi)$$

where $R_0$ and h indicate the radius and the pitch length, respectively, and λ is an angular parameter.

The reverse helical trajectory with a line segment between two helices, a schematic of which is shown in FIG. 139B may be parameterized as:

$$\vec{r}_0(\lambda) = \left(R_0\cos\lambda,\ R_0\sin\lambda,\ \frac{h}{2\pi}\lambda\right) \quad \lambda \in [-3\pi, -\pi) \qquad \text{I-(2)}$$

$$\vec{r}_0(\lambda) = \left(-R_0 0,\ \frac{h}{2\pi}\lambda\right) \quad \lambda \in [-\pi, \pi,)$$

$$\vec{r}_0(\lambda) = \left(R_0\cos(-\lambda),\ R_0\sin(-\lambda),\ \frac{h}{2\pi}\lambda\right) \quad \lambda \in [\pi, 3\pi,)$$

The reverse helical trajectory with a long line segment connecting the end points of the helices, a schematic of which is shown in FIG. 139C may be parameterized as:

$$\vec{r}_0(\lambda) = \left(R_0\cos\lambda,\ R_0\sin\lambda,\ \frac{h}{2\pi}\lambda\right) \quad \lambda \in [-2\pi, 0) \qquad \text{I-(3)}$$

$$\vec{r}_0(\lambda) = \left(R_0\cos(-\lambda),\ R_0\sin(-\lambda),\ \frac{h}{2\pi}\lambda\right) \quad \lambda \in [0, 2\pi,)$$

$$\vec{r}_0(\lambda) = \left(R_0 0,\ \frac{h}{2\pi}(4\pi - \lambda)\right) \quad \lambda \in [2\pi, 6\pi,)$$

Helical scan parameters used in reverse helical trajectory are: R=97.0 cm, h=13.5 cm and S=153.0 cm, where S represents the source-to-detector distance. The support of the phantom is an ellipsoid that fits within a cylinder of radius 26.0 cm. FIG. 140A-C shows slices of the reconstructed volume obtained for the reverse helical trajectory with π-line based BPF algorithm with FIG. 140A-C showing the sagittal, coronal and trans-axial slices of the reconstructed Shepp-Logan phantom, respectively. The gray scale display range is [1.0, 1.04].

A narrow gray scale may be used for the low contrast objects to be visible. FIGS. 141A-C show slice images of the reconstructed volume obtained for the reverse helical trajectory with chord-based BPF algorithm corresponding to the same slice positions with those in FIG. 140A-C. FIG. 141A-C showing the sagittal, coronal and trans-axial slices of the reconstructed Shepp-Logan phantom, respectively. π-line may be defined as a line connecting two points on the helical trajectory of which angular difference is within 2π. The angular difference of two points of a chord on the reverse helical trajectory is within 4π. It is the middle gap in the reconstructed volume to address. In addition to the reconstructible volume when using π-lines, more volume can be filled in the middle gap using chords. The upper-limit for the allowable helical pitch size in practical situations when using chord-based BPG methodologies is smaller than when we use π-line-based BPF algorithm because of the longer longitudinal length of a chord segment than a π-line segment.

Helical scan parameters used in line plus reverse helical trajectory I are: R=97.0 cm, h=8.9 cm and S=153.0 cm. FIGS. 142A-C show slices of the reconstructed volume obtained for the line plus reverse helical trajectory I. FIG. 142A-C showing the sagittal, coronal and trans-axial slices of the reconstructed Shepp-Logan phantom, respectively. The volume of the middle gap in the reconstructed image is reduced but still substantially large. The angular difference of two points of a chord on the line plus reverse helical trajectory I is within $4\pi$. Helical scan parameters used in line plus reverse helical trajectory II are: R=97.0 cm, h=10.8 cm and S=153.0 cm. FIGS. 143A-C show slices of the reconstructed volume obtained for the line plus reverse helical trajectory II. FIG. 143A-C showing the sagittal, coronal and trans-axial slices of the reconstructed Shepp-Logan phantom, respectively. The middle gap in the reconstructed image is completely removed. The angular difference of two points of a chord on the line plus reverse helical trajectory II is either between 0 and $2\pi$ or between $4\pi$ and $6\pi$.

Since the reverse helical scanning trajectory has a volume inside a support cylinder where there is no $\pi$-line passing through, the image may not be reconstructed completely using $\pi$-line-based exact BPF algorithm. However, the irreconstructible volume may be reduced by using chords and by employing a line segment in between the reverse helices of the trajectory. The irreconstructible volume may be removed by adding a line segment connecting two end-points of the reverse helical trajectory. While the improvement of the reconstructible volume in the middle gap is remarkable, the chord-based algorithm with modified trajectories has a disadvantage of narrower allowable range of the scanning helical pitch size than $\pi$-line based algorithm, with helical trajectory. This is because the longitudinal length of a chord segment, which may not be truncated at any view from a source position on the trajectory between two points making the chord, is longer than that of a $\pi$-line segment. However, this is believed to have significance not only in a theoretical perspective but also in clinical aspects. For example, a region-of-interest (ROI) imaging can be efficiently obtained by employing the line plus reverse helical trajectory II, of which helices are just long enough to cover the ROI.

13.2 In this following, the asymmetric reconstructible image volume for a cone-beam CT (CBCT) with a single-turn helical scanning trajectory using a PI-line based algorithm is addressed. Maximum helical pitch size that allows no data truncation is determined for a given detector size and scanning geometry. An optimization process to reconstruct the maximum volumes of the targeted regions-of-interest (ROI's) in terms of phase angle of the helical scanning is introduced. A practical issue of achieving various phase angles for a linear accelerator (LINAC) gantry whose rotation is bounded is raised, and a bi-reversal technique to make it possible is proposed.

The LINAC-mounted CBCT imager may yield accurate image acquisition of a patient before, during, and after treatment sessions. Because its integration with the treatment system is relatively new, the on-board imager currently uses a circular trajectory, which does not provide sufficient data for exact reconstruction of volume images. The commonly used FDK algorithm and its variations can produce only approximate 3D images. Moreover the FDK algorithm is sensitive to data truncation problems. PI-line based backprojection-filtration (BPF) and minimum data filtered backprojection (MDFBP) methodologies have been developed for helical scanning trajectories and for general scanning trajectories. The important features of those methodologies are the exactness of the 3D image reconstruction on PI-lines/chords and the flexibility in terms of data truncation. These features of the new methodologies motivated applications to the CBCT image reconstruction for the purpose of image-guided radiation therapy (IGRT). An experimental phantom image has been acquired with a single turn helical trajectory and presented a promising result.

In the following, the asymmetry in the shape of the reconstructible volume is addressed with PI-line based methodologies for a single-turn helical trajectory and present how to maximize the reconstructible volume of targeted ROI's by maximizing the pitch size and by optimizing the phase angle of the helix. A numerical phantom was used in the study and no transverse data truncation was assumed throughout the work since the presence of the transverse truncation does not directly affect the essence of the work.

The BPF algorithm first computes the cone-beam backprojections of the data derivatives onto PI-line segments and then reconstructs the image by invoking a 1D shift-varying filtration of the cone-beam backprojections over PI-line segments. It is well known that any ROI within a helical support cylinder can be filled completely by PI-line segments if we have an infinitely long helical scanning trajectory along the axial axis. However, the volume filled by PI-line segments for a single-turn helical trajectory is not simply a cylinder with the same height as the helical pitch. This work originates from the observation that the reconstructible volume of a CBCT image for a single-turn helical trajectory with a PI-line based algorithm has an asymmetric shape as shown in FIGS. 144A-C. Specifically, the reconstructible volume by PI-line based algorithm for a single-turn helical trajectory at an angle of 0° (FIG. 144A), 45° (FIG. 144B), and 90° (FIG. 144C) are shown. The ellipsoid represents an object to be imaged.

For a given set of helical scanning parameters such as radius of the helix, distance from the rotation axis to the detector plane, and size of the detector, the maximum helical pitch that allows no data truncation can be determined. FIGS. 145A and 145B illustrate how the maximum pitch is determined from a given geometry. A 2W×2W square detector is assumed. R is the radius of the helical trajectory, S is the distance from the source to the detector, and r is the radius of the cylindrical support containing the object in it. The support cylinder was chosen to fit the FOV size of the scanning system. The points on the helical trajectory can be parameterized by an angular parameter $\lambda$ as $$\vec{r}_0(\lambda) = \left(R\cos\lambda,\ R\sin\lambda,\ \frac{H}{2\pi}\lambda\right). \qquad \text{Eq. (J-1)}$$

One can easily show that the helical pitch, H, must satisfy the following condition for all the PI-line segments between $\lambda_b$ and $\lambda_t$ to be projected onto the detector plane without data truncation.

$$H \le \frac{4\pi SRW}{(W^2 + S^2)(\lambda_0 - \lambda_b)} \qquad \text{Eq. (J-2)}$$

The reconstructible volume may be considered to be enclosed by two surfaces, one of which is the set of PI-line segments originating from the start source-point of the trajectory and the other of which is the set of PI-line segments originating from the end source-point of the trajectory. After creating 3D voxel-grids, we can easily calculate the volume of a specific targeted ROI by counting the number of voxels enclosed by those two surfaces. A numerical phantom similar to the 3D Shepp-Logan phantom was used. Its dimension and the contained objects were modified so that one can illuminate the optimization procedure better. Most of the time, the treatment target is aligned to be at the isocenter of the LINAC treatment system in radiation therapy. This convention was followed by fixing the centered object, presumably a tumor site, in the phantom at the origin of the coordinate system. The reconstructible volume may be optimized of pre-selected targeted ROI's by varying the phase angle of the helical trajectory. FIG. 146A illustrates how phase angle is defined as the angle between the fixed X-Y frame and the moving x-y frame in which the helical scan starts from its negative x-axis. Two objects in the phantom purposely designed to illuminate the phase angle dependency were selected.

In order to achieve variable phase angles for the CBCT imager mounted to the LINAC gantry, a bi-reversal technique is proposed which employs reversal of the gantry rotation together with reversing the couch translation after a free running of the couch by the helical pitch with the gantry motion frozen. This may be necessary since the gantry rotation is physically limited to a single turn with fixed angular boundaries. The idea is illustrated in FIG. 146B. Mathematically, it means that Eq. (J-3) is equivalent to Eq. (J-4) when $\lambda'=2\pi-\lambda$ is satisfied.

$$\vec{r}_0(\lambda') = \left(R\cos\lambda', -R\sin\lambda', \frac{H}{2\pi}(2\pi-\lambda')\right) \quad \lambda' \in [0, 2\pi-\phi) \qquad \text{Eq. (J-3)}$$

$$\vec{r}_0(\lambda) = \left(R\cos\lambda, R\sin\lambda, \frac{H}{2\pi}\lambda\right) \quad \lambda \in [\phi, 2\pi) \qquad \text{Eq. (J-4)}$$

The computer-simulation studies are presented that demonstrate image reconstruction with the BPF algorithm. Helical scan parameters used in the helical trajectory are: R=97.0 cm, H=41.6 cm and S=153.0 cm. The phantom fits within a cylinder of radius 26.0 cm. FIG. 147A shows the fraction of the reconstructible volumes of two targeted ROI's as a function of phase angle. The darker object in FIG. 147B is the object 1, and the brighter one is object 2. The optimum phase angle in this case was chosen to be 2.42 rad. FIGS. 147B-D show 2D slices of the reconstructed volumes; top row for the optimized phase angle and bottom row for the phase angle giving the minimum reconstructible volumes. It is clearly shown that targeted ROI's can be reconstructed maximally by choosing optimum phase angle of the helical scanning trajectory.

The phase angle dependent reconstructible volume in a CBCT for a single-turn helical trajectory with PI-line based algorithm was addressed and a novel approach named bi-reversal technique was proposed to apply for IGRT. Bi-reversal technique may also be used to produce a two-turn helical trajectory. The bi-reversal technique may contribute significantly to extending the capability of a LINAC-mounted CBCT imaging system. In addition to phase angle, tilted helical trajectory can produce various shapes of reconstructible volume for a single-turn helix. Depending on the positions of targeted ROI's, the tilt angle may need to be considered in the optimization process. However, a tilted helical trajectory generally needs a larger FOV than an untilted one. Moreover, the interplay between tilt angle and phase angle is complicated, which makes the optimization process more difficult. To provide accurate guidance of radiation therapy, the system must be immune to geometric errors originating from the image acquisition process. A circular trajectory appears to have an advantage in this regard for IGRT because it does not require precise patient translation.

It is intended that the foregoing detailed description be regarded as illustrative, rather than limiting, and that it be understood that the following claims, including all equivalents, are intended to define the scope of this invention.

The invention claimed is:

1. A method of imaging at least a part of a region of interest (ROI) comprising:

moving a source relative to the ROI in a trajectory, virtual chords intersecting and filling the ROI, the virtual chords not intersecting the trajectory;

collecting data from at least one sensor as the source moves relative to the ROI; and generating a substantially exact reconstruction of the ROI using the virtual chords based on the data collected, wherein the substantially exact reconstruction is derived from a mathematically exact transformation from data space into image space.

2. The method of claim 1, where the trajectory is a substantially straight line.

3. The method of claim 2, where generating a substantially exact reconstruction comprises:

calculating image densities on the virtual chords from the collected data; and constructing an image based on the image densities.

4. The method of claim 3, where the virtual chords are parallel to the source trajectory.

5. The method of claim 4, where the virtual chords are parallel to the source trajectory along at least one dimension; and where the image densities for points on the virtual chords that are outside of the trajectory along the dimension are zero.

6. The method of claim 2, where the source is stationary and the ROI moves in the straight line.

7. The method of claim 2, where the ROI is stationary and the source moves in the straight line.

8. The method of claim 2, where the source and the ROI both move relative to one another in the straight line.

9. A method of imaging at least a part of a region of interest (ROI) in an off-plane to a trajectory comprising:

moving a source relative to the ROI in a trajectory, the trajectory being at least one of non-continuous or non-closed, the trajectory defining a first plane and the ROI being transected by a second plane, the second plane being off of the first plane;

collecting data from at least one sensor as the source moves relative to the ROI; and generating a substantially exact reconstruction of the ROI based on the data collected, wherein the substantially exact reconstruction is derived from a mathematically exact transformation from data space into image space.

10. The method of claim 9, where the trajectory is piecewise continuous.

11. The method of claim 9, where the trajectory comprises a non-closed bracket.

12. The method of claim 9, where generating a substantially exact reconstruction comprises:

decomposing the at least a part of the ROI into chords; and reconstructing the at least a part of the ROI based on the chords.

13. The method of claim 9, where the first plane and second plane are parallel to one another.

14. The method of claim 9, where the first plane and second plane are not coincident with one another.

15. A method of imaging at least a part of a region of interest (ROI) in an off-plane to a trajectory comprising:

moving a source relative to the ROI in a trajectory, the trajectory defining a first plane and the ROI being transected by a second plane, the second plane being off of the first plane;

collecting data from at least one sensor as the source moves relative to the ROI; and generating a substantially exact reconstruction of the ROI using virtual chords based on the data collected, wherein the substantially exact reconstruction is derived from a mathematically exact transformation from data space into image space.

16. The method of claim 15, wherein the ROI is 2-dimensional.

17. The method of claim 15, wherein the ROI is 3-dimensional.

18. The method of claim 15, wherein generating a substantially exact reconstruction comprises:

backprojecting based on the collected data to generate an intermediate density distribution; and filtering the intermediate density distribution to create a substantially exact image of the ROI.

19. The method of claim 15, wherein the data is collected from a curved detector.

20. A system of imaging at least a part of a region of interest (ROI), the system comprising:

at least one source for illuminating the ROI;

at least one motor to control at least one of the source or the ROI in order to move the source relative to the ROI in a trajectory;

at least one sensor to acquire data at least partly when the source and the ROI move relative to one another; and at least one processor configured to:

control the motor in order to move the source relative to the ROI in a trajectory, virtual chords intersecting and filling the ROI, the virtual chords not intersecting the trajectory;

receive data from the at least one sensor, the at least one sensor collecting the data as the source moves relative to the ROI; and generate a substantially exact reconstruction of the ROI using the virtual chords based on the data received, wherein the substantially exact reconstruction is derived from a mathematically exact transformation from data space into image space.

21. The method of claim 2, where, in generating the substantially exact reconstruction of the ROI, the straight line trajectory is assumed to be infinite relative to the ROI.

22. The method of claim 1, where the trajectory comprises a finite length; and where, in generating the substantially exact reconstruction of the ROI, missing data is assigned a predetermined value, the missing data comprising data which would have been collected if the trajectory was longer.

23. The method of claim 22, where the predetermined value is zero.

* * * * *